United States Patent
Brooks et al.

(10) Patent No.: US 12,230,378 B2
(45) Date of Patent: *Feb. 18, 2025

(54) SYSTEMS AND METHODS FOR COORDINATING MANUFACTURING OF CELLS FOR PATIENT-SPECIFIC IMMUNOTHERAPY

(71) Applicant: Iovance Biotherapeutics, Inc., San Carlos, CA (US)

(72) Inventors: Anne Brooks, Downingtown, PA (US); Steve Macrides, West Chester, PA (US); Kristin Lanzi, San Francisco, CA (US)

(73) Assignee: Iovance Biotherapeutics, Inc., San Carlos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/357,360

(22) Filed: Jun. 24, 2021

(65) Prior Publication Data

US 2021/0407639 A1 Dec. 30, 2021

Related U.S. Application Data

(63) Continuation of application No. 17/238,092, filed on Apr. 22, 2021.

(Continued)

(51) Int. Cl.
*G16H 20/00* (2018.01)
*A61K 35/13* (2015.01)
(Continued)

(52) U.S. Cl.
CPC .............. *G16H 20/00* (2018.01); *A61K 35/13* (2013.01); *A61K 39/4611* (2023.05);
(Continued)

(58) Field of Classification Search
CPC ........ G16H 10/60; G16H 20/00; G16H 80/00; A61K 35/13; G06Q 10/083; G06Q 10/0832
(Continued)

(56) References Cited

U.S. PATENT DOCUMENTS

| 7,943,743 B2 | 5/2011 | Korman et al. |
| 8,008,449 B2 | 8/2011 | Korman et al. |

(Continued)

FOREIGN PATENT DOCUMENTS

| EP | 3601533 B1 * | 2/2021 | ........... A01N 1/0284 |
| WO | WO 2013/057500 A1 | 4/2013 | |

(Continued)

OTHER PUBLICATIONS

Heimann, Andreas; Elongated T Cell Expansion by Utilizing IL7 and IL15 Leads to Increased T Cell Yield While Preserving Tem/Tsem Characteristics Feasible for Adoptive T Cell Therapy; Freie Universitaet Berlin (Germany), ProQuest Dissertations Publishing, 2020. 28539109. (Year: 2020).*

(Continued)

*Primary Examiner* — Hiep V Nguyen
(74) *Attorney, Agent, or Firm* — Morgan, Lewis & Bockius LLP

(57) ABSTRACT

A method for coordinating the manufacturing of an expanded cell therapy product for a patient may include receiving a cell order request to expand the cell therapy product for the patient; generating a patient-specific identifier or cell order identifier associated with the cell order request; and initiating a process to expand the cell therapy product from at least some of a solid tumor obtained from the patient. If acceptance parameters for the expansion cell therapy product do not meet certain acceptance criteria at a second time point subsequent to a first time point in the (Continued)

expansion process, it is determined whether re-performing the expansion of the cell therapy product using the cell expansion technique is possible from the first time point based on the acceptance parameters at the second time point. If such re-performing the expansion is possible, patient treatment events that use the expanded cell therapy product are rescheduled.

19 Claims, 29 Drawing Sheets

Specification includes a Sequence Listing.

Related U.S. Application Data

(60) Provisional application No. 63/159,806, filed on Mar. 11, 2021, provisional application No. 63/155,711, filed on Mar. 2, 2021, provisional application No. 63/013,942, filed on Apr. 22, 2020.

(51) Int. Cl.
| | |
|---|---|
| *A61K 39/00* | (2006.01) |
| *C12N 5/0783* | (2010.01) |
| *C12N 5/09* | (2010.01) |
| *G06Q 10/0832* | (2023.01) |
| *G16H 10/60* | (2018.01) |
| *G16H 80/00* | (2018.01) |

(52) U.S. Cl.
CPC ........ *A61K 39/4644* (2023.05); *C12N 5/0638* (2013.01); *C12N 5/0693* (2013.01); *G06Q 10/0832* (2013.01); *G16H 10/60* (2018.01); *G16H 80/00* (2018.01)

(58) Field of Classification Search
USPC .......................................................... 705/3
See application file for complete search history.

(56) References Cited

U.S. PATENT DOCUMENTS

| | | | |
|---|---|---|---|
| 8,034,334 B2 | 10/2011 | Dudley et al. | |
| 9,074,185 B2 | 7/2015 | Dudley et al. | |
| 9,844,569 B2 | 12/2017 | Gros et al. | |
| 2003/0099643 A1* | 5/2003 | June | C07K 16/00 435/372 |
| 2003/0175242 A1* | 9/2003 | Gruenberg | G16H 20/10 705/2 |
| 2003/0235908 A1* | 12/2003 | Berenson | C07K 16/2878 435/372 |
| 2005/0106717 A1 | 5/2005 | Wilson et al. | |
| 2007/0204497 A1* | 9/2007 | de la Huerga | B65C 9/46 283/67 |
| 2011/0052530 A1 | 3/2011 | Dudley et al. | |
| 2011/0136228 A1 | 6/2011 | Vera et al. | |
| 2012/0244133 A1 | 9/2012 | Rosenberg et al. | |
| 2013/0102075 A1 | 4/2013 | Vera et al. | |
| 2013/0115617 A1 | 5/2013 | Wilson | |
| 2014/0377739 A1 | 12/2014 | Welch et al. | |
| 2015/0175966 A1 | 6/2015 | Vera et al. | |
| 2016/0010058 A1 | 1/2016 | Gros et al. | |
| 2016/0208216 A1 | 7/2016 | Vera et al. | |
| 2016/0215262 A1 | 7/2016 | Powell | |
| 2017/0044496 A1 | 2/2017 | Sarnaik et al. | |
| 2017/0051252 A1* | 2/2017 | Morgan | C12N 15/86 |
| 2017/0081635 A1 | 3/2017 | Sarnaik et al. | |
| 2017/0107490 A1 | 4/2017 | Maeurer | |
| 2017/0152478 A1 | 6/2017 | Rosenberg et al. | |
| 2018/0325954 A1 | 11/2018 | Wardell et al. | |

FOREIGN PATENT DOCUMENTS

| | | | |
|---|---|---|---|
| WO | WO 2013/088147 A1 | 6/2013 | |
| WO | WO 2013/173835 A1 | 11/2013 | |
| WO | WO 2013/188427 A1 | 12/2013 | |
| WO | WO 2015/189357 A1 | 12/2015 | |
| WO | WO 2016/053338 A1 | 4/2016 | |
| WO | WO 2016/096903 A1 | 6/2016 | |
| WO | WO 2018/081473 A1 | 5/2018 | |
| WO | WO-2019055896 A1 * | 3/2019 | ......... A61K 39/0011 |

OTHER PUBLICATIONS

Besser et al., "Minimally Cultured or Selected Autologous Tumor-infiltrating Lymphocytes After a Lympho-depleting Chemotherapy Regimen in Metastatic Melanoma Patients"; J Immunother 32, 415-423 (2009).

Besser, et al., "Adoptive Transfer of Tumor-Infiltrating Lymphocytes inPatients with Metastatic Melanoma: Intent-to-Treat Analysis and Efficacy after Failure to Prior Immunotherapies"; Clin Cancer Res, 19(17):0F1-0F9 (2013).

Donia M, et al.. Simplified protocol for clinical-grade tumor-infiltrating lymphocyte manufacturing with use of the Wave bioreactor. Cytotherapy. Aug. 2014;16(8):1117-20.

Donia, et al., "Characterization and Comparison of 'Standard' and 'Young' Tumour—Infiltrating Lymphocytes for Adoptive Cell Therapy at a Danish Translational Research Institution"; Scandinavian Journal of Immunology, 75, 157-157 (2012).

Dudley et al., "Adoptive Cell Transfer Following Non-Myeloablative but Lymphodepleting Chemotherapy for the Treatment of Patients with Refractory Metastatic Melanoma", J. Clin. Oncol. Apr. 2005, 23(10), 2346-57.

Dudley et al., "Generation of Tumor-Infiltrating Lymphocyte Cultures for Use in Adoptive Transfer Therapy for Melanoma Patients," J Immunother., 2003: 26(4): 332-342.

Dudley, et al., "Cancer Regression and Autoimmunity in Patients After Clonal Repopulation with Antitumor Lymphocytes", Science, Oct. 2002, 298, 850-54.

He et al., "Ex vivo expansion of tumor-infiltrating lymphocytes from nasopharyngeal carcinoma patients for adoptive immunotherapy," Chinese Journal of Cancer, vol. 31, No. 6, Jun. 5, 2012.

Hopewell, E. et al: "Tumor-infiltrating lymphocytes: Streamlining a complex manufacturing process", Cytotherapy, vol. 21, No. 3, Nov. 30, 2018 (Nov. 30, 2018), pp. 307-314.

International Search Report and Written Opinion dated Jun. 28, 2021 for International Application No. PCT/US2021/028709, 18 pages.

International Search Report and Written Opinion for International Patent Application No. PCT/US2018/012633 dated May 25, 2018, 14 pages.

Jin et al., "Simplified method of the growth of human tumor infiltrating lymphocytes in gas-permiable flasks to Nos. needed for patient treatment", J. Immunotherapy, 2012, 35:283-292.

Levine, B. et al: "Global Manufacturing of Car T Cell Therapy", Molecular Therapy—Methods & Clinical Development, vol. 4, Mar. 4, 2017 (Mar. 4, 2017), pp. 92-101.

Li et al. MART-1-specific melanoma tumor-infiltrating lymphocytes maintaining CD28 expression have improved survival and expansion capability following antigenic restimulation in vitro. J Immunol. Jan. 1, 2010;184(1):452-65.

Robbins, et al., "Cutting Edge: Persistence of Transferred Lymphocyte Clonotypes Correlates with Cancer Regression in Patients Receiving Cell Transfer Therapy"; J. Immunol 2004; 173, 7125-7130.

Rosenberg SA, Dudley ME. "Adoptive cell therapy for the treatment of patients with metastatic melanoma", Curr Opin Immunol. Apr. 2009;21(2):233-40.

Rosenberg, "IL-2: The First Effective Immunotherapy for Human Cancer," The Journal of Immunology, col. 192, No. 12, Jun. 6, 2014.

Sadeghi, et al., "Rapid expansion of T cells: Effects of culture and cryopreservation and improtance of short-term cell recovery", Acta Oncologica 2013, 52, 978-986.

(56) References Cited

OTHER PUBLICATIONS

Somerville RP, et al., "Clinical scale rapid expansion of lymphocytes for adoptive cell transfer therapy in the WAVE® bioreactor", J Transl Med. Apr. 4, 2012;10:69.
Tran et al., "Minimally Cultured tumor-infiltrating lymphocytes display optimal characteristics for adoptive cell therapy", J. Immunother., Oct. 2008; 31(8), 742-751.
Ye et al.; Engineered artificial antigen presenting cells facilitate direct and efficient expansion of tumor infiltrating lymphocytes Journal of Translational Medicine 2011, 9:131.
U.S. Appl. No. 17/238,092, filed Apr. 22, 2021.
U.S. Appl. No. 17/357,393, filed Jun. 24, 2021.
U.S. Appl. No. 17/519,065, filed Nov. 4, 2021; and.
U.S. Appl. No. 17/570,195, filed Jan. 6, 2022.
International Preliminary Report on Patentability dated Oct. 25, 2022 for International Application No. PCT/US2021/028709>.

* cited by examiner

Process GEN 3: about 14-18 days from Steps A - E

STEP A
Obtain Patient Tumor Sample
(optionally can be frozen before Step B)

STEP B
Priming First Expansion
(physical fragmentation of up to 60 fragments per container grown for about 1 days to 7/8 days with media comprising IL-2, OKT-3, and optionally antigen-presenting feeder cells)

STEP C
Priming First Expansion to Rapid Second Expansion Transition
(Step B TILs directly move to Step D on day 7/8)

STEP D
Rapid Second Expansion
(TILs grown in growth media medium comprising IL-2, OKT-3, and 2X antigen-presenting feeder cells; Days 10-11 scale up and add additional IL-2)

STEP E
Harvest TILS from Step D

STEP F
Final Formulation and/or Transfer to Infusion Bag
(optionally cryopreserve)

FIG. 2A

| Process 2A: about 22 days from Steps A - E | Process GEN 3: about 14-18 days from Steps A - E |
|---|---|
| STEP A<br>Obtain Patient Tumor Sample<br>(optionally can be frozen before Step B;<br>optionally tumor sample can be a core/small biopsy) | STEP A<br>Obtain Patient Tumor Sample<br>(optionally can be frozen before Step B) |
| STEP B<br>First Expansion<br>(physical fragmentation to at least 40 fragments per container grown for about 3 days to 14 days with media comprising IL-2) | STEP B<br>Priming First Expansion<br>(physical fragmentation of up to 60 fragments per container grown for about 1 days to 7/8 days with media comprising IL-2, OKT-3, and optionally antigen-presenting feeder cells) |
| STEP C<br>First Expansion to Second Expansion Transition<br>(Step B TILs directly move to Step D, optionally on Step B day 11) | STEP C<br>Priming First Expansion to Rapid Second Expansion Transition<br>(Step B TILs directly move to Step D on day 7/8) |
| STEP D<br>Second Expansion<br>(TILs grown in growth media medium comprising IL-2, OKT-3, and antigen-presenting feeder cells in a closed container) | STEP D<br>Rapid Second Expansion<br>(TILs grown in growth media medium comprising IL-2, OKT-3, and 2X antigen-presenting feeder cells; Days 10-11 scale up and add additional IL-2) |
| STEP E<br>Harvest TILS from Step D<br>(TILs harvested via closed system) | STEP E<br>Harvest TILS from Step D |
| STEP F<br>Final Formulation and/or Transfer to Infusion Bag<br>(optionally cryopreserve) | STEP F<br>Final Formulation and/or Transfer to Infusion Bag<br>(optionally cryopreserve) |

FIG. 2B

| Embodiment GEN 3.0: about 14-18 days from Steps A - E | Embodiment GEN 3.1 control: about 14-18 days from Steps A - E | Embodiment GEN 3.1 Test/F: about 14-18 days from Steps A - E |
|---|---|---|
| STEP A Obtain Patient Tumor Sample (optionally can be frozen before Step B) | STEP A Obtain Patient Tumor Sample (optionally can be frozen before Step B) | STEP A Obtain Patient Tumor Sample (optionally can be frozen before Step B) |
| STEP B Priming First Expansion (physical fragmentation of up to 60 fragments per container grown for about 1 days to 7/8 days with media comprising IL-2) | STEP B Priming First Expansion (physical fragmentation of up to 60 fragments per container grown for about 1 days to 7/8 days with media comprising IL-2, and OKT-3) | STEP B Priming First Expansion (physical fragmentation of up to 60 fragments per container grown for about 1 days to 7/8 days with media comprising IL-2, OKT-3, and antigen-presenting feeder cells) |
| STEP C Priming First Expansion to Rapid Second Expansion Transition (Step B TILs directly move to Step D on day 7/8) | STEP C Priming First Expansion to Rapid Second Expansion Transition (Step B TILs directly move to Step D on day 7/8) | STEP C Priming First Expansion to Rapid Second Expansion Transition (Step B TILs directly move to Step D on day 7/8) |
| STEP D Rapid Second Expansion (TILs grown in growth media medium comprising IL-2, OKT-3, and antigen-presenting feeder cells; Days 10-11 scale up and add additional IL-2) | STEP D Rapid Second Expansion (TILs grown in growth media medium comprising IL-2, OKT-3, and 2X antigen-presenting feeder cells; Days 10-11 scale up and add additional IL-2) | STEP D Rapid Second Expansion (TILs grown in growth media medium comprising IL-2, OKT-3, and 2X antigen-presenting feeder cells; Days 10-11 scale up and add additional IL-2) |
| STEP E Harvest TILS from Step D | STEP E Harvest TILS from Step D | STEP E Harvest TILS from Step D |
| STEP F Final Formulation and/or Transfer to Infusion Bag (optionally cryopreserve) | STEP F Final Formulation and/or Transfer to Infusion Bag (optionally cryopreserve) | STEP F Final Formulation and/or Transfer to Infusion Bag (optionally cryopreserve) |

FIG. 2C

| # | Label Type & Barcode Type | Quantity | Description |
|---|---|---|---|
| 1 | Tumor Shipper | 1 | Label needed to ship raw materials from the center to plant |
| 2 | Tumor Media Bottle | 1 | Label for the bottle that the raw material will be placed in for storage during the shipment to plant |
| 3 | In Process | 11 | Labels needed for Day 0, Day 11, and Day 16 Flasks and Batch Record |
| 4 | Day 22 - Bag 1 | 2 | Labels needed for Final Product Bag 1 and Cassette 1 |
| 5 | Day 22 - Bag 2 | 2 | Labels needed for Final Product Bag 2 and Cassette 2 |
| 6 | Day 22 - Bag 3 | 2 | Labels needed for Final Product Bag 3 and Cassette 3 |
| 7 | Day 22 - Bag 4 | 2 | Labels needed for Final Product Bag 4 and Cassette 4 |
| 8 | Day 22 - Batch | 1 | Label needed for Day 22 Batch Record |
| 9 | TIL Shipper | 1 | Label needed to ship final product from plant to the center |

FIG. 3H

| Home | Tumor Procurement Module | Resources |

[ Print TPF ] [ Transfer Ownership ] [ Remove Ownership ]

Details

∨ General

| | |
|---|---|
| TPF Owner | Leonard Brown |
| TPF Status | Complete |
| Hospital Patient ID | CPMC-STP-01 |
| Patient Name | Spags T Patient 01 |
| Date Of Birth | 01/01/1990 |
| COI Number | 202101002A |
| Lot Number | STP-LOT-01 |
| TIL Center Name | California Pacific Medical Center |
| Indication | Metastatic Melanoma |
| Resection Date | 04/07/2021 |
| Notes | |

∨ Screen 1 Check Materials

| | |
|---|---|
| Sterile Transfer Pipettes, Quantity = 4 | ☐ |
| Parafilm, Quantity = 6 | ☐ |
| Transport Bags w/Absorbent Sheets, Quantity = 1 | ☐ |
| Label Sheet with Tumor Bottle Label and Shipper Box Label | ☐ |
| Specimen Washing Containers, Quantity = 4, Serial # / Lot # | Done |
| Specimen Washing Containers - Expiration Date | 04/30/2021 |
| Temperature Monitor, Quantity = 1, Serial # / Lot # | Done |
| Temperature Monitor - Expiration Date | 04/30/2021 |

FIG. 3K

| Home | Tumor Procurement Module | Resources | | |
|---|---|---|---|---|
| | | Print TPF | Transfer Ownership | Remove Ownership |

Details

∨ General

| | |
|---|---|
| TPF Owner | Leonard Brown |
| TPF Status | Complete |
| Hospital Patient ID | CPMC-STP-01 |
| Patient Name | Spags T Patient 01 |
| Date Of Birth | 01/01/1990 |
| COI Number | 202101002A |
| Lot Number | STP-LOT-01 |
| TIL Center Name | California Pacific Medical Center |
| Indication | Metastatic Melanoma |
| Resection Date | 04/07/2021 |
| Notes | |

∨ Screen 1 Check Materials

| | |
|---|---|
| Sterile Transfer Pipettes, Quantity = 4 | ☑ |
| Parafilm, Quantity = 6 | ☑ |
| Transport Bags w/Absorbent Sheets, Quantity = 1 | ☑ |
| Label Sheet with Tumor Bottle Label and Shipper Box Label | ☑ |
| Specimen Washing Containers, Quantity = 4, Serial # / Lot # | Done |
| Specimen Washing Containers - Expiration Date | 04/30/2021 |
| Temperature Monitor, Quantity = 1, Serial # / Lot # | Done |
| Temperature Monitor - Expiration Date | 04/30/2021 |

FIG. 3L

| | |
|---|---|
| Specimen Washing Containers - Expiration Date | 04/30/2021 |
| Temperature Monitor, Quantity = 1, Serial # / Lot # | Done |
| Temperature Monitor - Expiration Date | 04/30/2021 |
| NanoCool, Quantity = 1 - Serial # / Lot # | Done |
| NanoCool - Expiration Date | 04/30/2021 |
| HBSS, Quantity = 1 - Serial # / Lot # | Done |
| HBSS - Expiration Date | 04/30/2021 |
| Gentamicin, Quantity = 1 - Serial # / Lot # | Done |
| Gentamicin - Expiration Date | 04/30/2021 |
| Amphotericin B, Quantity = 1 - Serial # / Lot # | Done |
| Amphotericin B - Expiration Date | 04/30/2021 |
| HypoThermosol, Quantity = 1 - Serial # / Lot # | Done |
| HypoThermosol - Expiration Date | 04/30/2021 |

⌄ Screen 1 Prepare Materials

| | |
|---|---|
| The Amphotericin B bottle has been removed from the freezer and defrosted. | ☑ |
| The Gentamicin bottle has been removed from the refrigerator. | ☑ |
| The amount of 0.5 mL of Amphotericin B and 0.5 mL of Gentamicin have been added to the HypoThermosol bottle. The remaining Amphotericin B and Gentamicin provided by Iovance should be discarded. | ☑ |
| Iovance provided label has been verified and applied to the HypoThermosol bottle. Verify patient details against hospital records. Specimen bottle labels: Patient ID, COI #, DOB | ☑ |

⌄ Screen 1 Approval

| | |
|---|---|
| Screen 1 Confirmation | ☑ |
| Screen 1 Confirmed By | Leonard Brown |
| Screen 1 Verification | ☑ |

FIG. 3M

| | |
|---|---|
| Screen 1 Confirmation | ☑ |
| ⌄ Screen 1 Confirmed By | Leonard Brown |
| Screen 1 Verification | ☑ |
| Screen 1 Verified By | Cal Pacific TPV |

Screen 2 Tumor Procurement Details

| | |
|---|---|
| Media transported to OR by | Done |
| Media received in OR by | Done |
| Name of Surgeon performing Tumor Procurement | Done |
| Time first Tumor procured (24 hr-hhmm) | 04/07/2021 03:00 |
| Time last Tumor procured (24 hr-hhmm) | 04/07/2021 03:00 |
| # of lesions procured | 1 |
| Location(s) of lesions procured | |

| LOCATION NAME |
|---|
| Done |

| | |
|---|---|
| Has the ideal amount of viable tumor of at least 1.5 cm, but no more than 4.0 cm in diameter (aggregate) for TIL isolation/manufacturing been obtained? | Yes |
| Was an intraoperative frozen section or biopsy of tumor taken to confirm presence of malignant cells? | Yes |
| Ensure that the tumor has been washed 3 times in HBSS | ☑ |
| ⌄ Confirm that the Hospital Patient ID and COI match with the labels and Tumor Tissue Procurement Form | ☑ |
| Time Last Tumor is placed in HypoThermosol (24 hr-hhmm) | 04/07/2021 03:00 |

Screen 2 Tumor Containment Details

| | |
|---|---|
| Ensure the tumor is placed in the 100 mL specimen bottle containing the HypoThermosol/Gentamicin/Amphotericin B solution (at 2-8 C) with the lid tightly closed and wrapped in parafilm | ☑ |
| Ensure the pre-printed tumor specimen label has been affixed to the | ☑ |

FIG. 3N

| | |
|---|---|
| Ensure the tumor is placed in the 100 mL specimen bottle containing the HypoThermosol/Gentamicin/Amphotericin B solution (at 2-8 C) with the lid tightly closed and wrapped in parafilm | ☑ |
| Ensure the pre-printed tumor specimen label has been affixed to the specifmen bottle with the required and verified information | ☑ |
| Ensure the specimen bottle has been placed in the transport bag with absorbent pads and sealed | ☑ |
| If available, document the DIN (Donation Identification Number): | N/A |

∨ Screen 2 Approval

| | |
|---|---|
| Screen 2 Confirmation | ☑ |
| Screen 2 Confirmed By | Leonard Brown |
| Screen 2 Verification | ☑ |
| Screen 2 Verified By | Cal Pacific TPV |

∨ Screen 3 Tumor Packout Details

| | |
|---|---|
| Ensure the 2 Cooling Engines in the NanoCool been activated (Represented by the Light Blue "NanoCool" Logo) - Typically takes 5 minutes to fully activate | ☑ |
| Verify the temperature monitor matches with the serial # and expiry captured in section 1 of this form | ☑ |
| Ensure the temperature monitor has been activated and affix the temperature monitor to the transport bag containing the tumor specimen | ☑ |
| Ensure the transport bag containing the specimen bottle is placed in the NanoCool | ☑ |
| Ensure to check and affix the shipper box labels from the printed label sheet to the outer side of the NanoCool | ☑ |
| Ensure the Correct Courier Bill of Lading (BOL) has been securely affixed to the outside of the NanoCool. Note: The Correct BOL utilizes a reference number that will match the COI number of the Patient Specimen and COI Number captured on this form. | ☑ |
| Ensure the NanoCool has been sealed with tamper evident tape | ☑ |

FIG. 3O

Screen 3 Tumor Packout Details

| | |
|---|---|
| Ensure the 2 Cooling Engines in the NanoCool been activated (Represented by the Light Blue "NanoCool" Logo) - Typically takes 5 minutes to fully activate | ☑ |
| Verify the temperature monitor matches with the serial # and expiry captured in section 1 of this form | ☑ |
| Ensure the temperature monitor has been activated and affix the temperature monitor to the transport bag containing the tumor specimen | ☑ |
| Ensure the transport bag containing the specimen bottle is placed in the NanoCool | ☑ |
| Ensure to check and affix the shipper box labels from the printed label sheet to the outer side of the NanoCool | ☑ |
| Ensure the Correct Courier Bill of Lading (BOL) has been securely affixed to the outside of the NanoCool. Note: The Correct BOL utilizes a reference number that will match the COI number of the Patient Specimen and COI Number captured on this form. | ☑ |
| Ensure the NanoCool has been sealed with tamper evident tape | ☑ |
| Time NanoCool Packing was completed (24 hr-hhmm) | 04/07/2021 00:00 |

Screen 3 Approval

| | |
|---|---|
| Screen 3 Confirmation | ☑ |
| Screen 3 Confirmed By | Leonard Brown |
| Screen 3 Verification | ☑ |
| Screen 3 Verified By | Cal Pacific TPV |

TPF Files

Upload Scanned TPF

[ ⬆ Upload Files ]  [ Or drop files ]

FIG. 3P

Process Development

| Step | Process-1C | Process-2A | Impact |
|---|---|---|---|
| 1 | 4 Fragments/10 G-Rex 10-21 Days | 40 Fragments/1-G-Rex 100 CS- (x2?) 11 Days | Increases Tumor Sample/Container, Shortens Culture, Reduces Steps, Amenable To Closed System |
| 2 | PreREP Freeze-> Testing -> Thaw- ~Day 27- >40e6TIL | Direct To REP- Day 11- <200e6 | Shorten Process, Reduces Steps, Eliminates Testing |
| 3 | 36 G-Rex 100-~Day 30 >5e6TIL - Split ~Day 36 | 4-5 G-Rex 500CS- TIL- Split Day 16 | Reduces Steps, Closed System, Shorter REP |
| 4 | Harvest Day ~43+ Harvesting By Centrifugation | Harvest Day 22 LOVO-Automated Cell Washer | Reduces Steps, Automated Closed System |
| 5 | Fresh Product-Hypothermosol-Single Infusion Bag | Cryopreserved Product-CS10 In $LN_2$, Multiple Aliquots | Shipping Flexibility, Patient Scheduling, Easier Release Testing, Global Trials |
| 6 | 43+ Day Process Time | 22 Day Process Time | Turnaround To Patient, Clean Room Throughput, COGs |

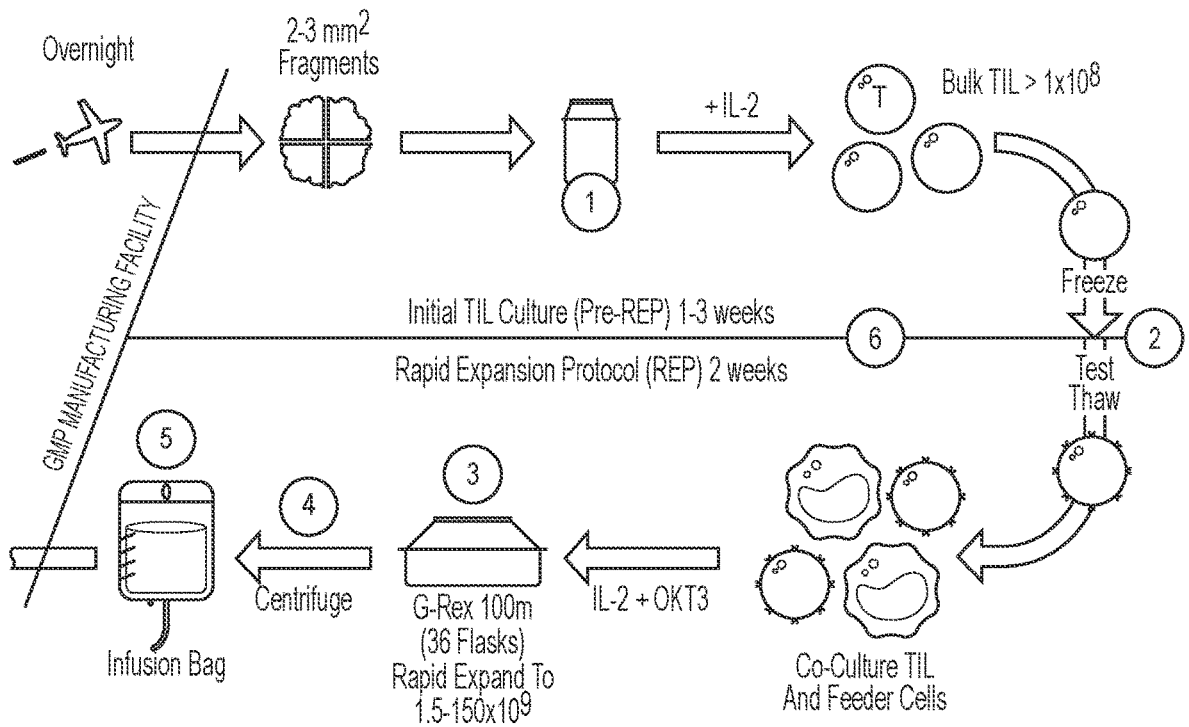

FIG. 6

Process 2A: about 22 days from Steps A - E

1. STEP A

Obtain Patient Tumor Sample

2. STEP B

Fragmentation and First Expansion 3 days to 14 days

3. STEP C

First Expansion to Second Expansion Transition

No Storage and Closed System

4. STEP D

Second Expansion

IL-2, OKT-3, and antigen-presenting feeder cells

Closed System

5. STEP E

Harvest TILS from Step D

Closed System

6. STEP F

Final Formulation and/or Transfer to Infusion Bag (optionally cryopreserve)

FIG. 9

| Process 1C: 43 - 55 Days for Steps A - E | Process 2A: About 22 Days from Steps A - E |
|---|---|
| 1. Step A<br>Obtain Patient Tumor Sample | 1. Step A<br>Obtain Patient Tumor Sample |
| 2. Step B<br>Fragmentation and First Expansion<br>11 days to 21 days | 2. Step B<br>Fragmentation and First Expansion<br>3 days to 14 days |
| 3. Step C<br>First Expansion to Second Expansion Transition<br>Optional Storage until Selection | 3. Step C<br>First Expansion to Second Expansion Transition<br>No Storage and Closed System |
| 4. Step D<br>Second Expansion<br>IL-2, OKT-3, antigen-presenting feeder cells<br>Optionally repeat one or more times | 4. Step D<br>Second Expansion<br>IL-2, OKT-3, antigen-presenting feeder cells<br>Closed System |
| 5. Step E<br>Harvest TILS from Step D | 5. Step E<br>Harvest TILS from Step D<br>Closed System |
| 6. Step F<br>Final Formulation and/or Transfer to Infusion Bag | 6. Step F<br>Final Formulation and/or Transfer to Infusion Bag<br>(optional cryopreserve) |

FIG. 10

| Process Step | Process 1C Embodiment | Process 2A Embodiment | Advantages |
|---|---|---|---|
| Pre-REP | • 4 fragments per 10 GREX-10 flasks<br>• 11-21 day duration | • 40 fragments per 1 GREX-100M flask<br>• 11 day duration | • Increased tumor fragments per flask<br>• Shortened culture time<br>• Reduced number of steps<br>• Amenable to closed system |
| Pre-REP to REP Transition | • Pre-REP TIL are frozen until phenotyped for selection then thawed to proceed to the REP (~day 30)<br>• REP requires >40x$10^6$ TIL | • Pre-REP TIL directly move to REP on day 11<br>• REP requires 25-200x$10^6$ TIL | • Shortened pre-REP-to-REP process<br>• Reduced number of steps<br>• Eliminated phenotyping selection<br>• Amenable to closed system |
| REP | • 6 GREX-100M flasks on REP day 0<br>• 5x$10^6$ TIL and 5x$10^8$ PBMC feeders per flask on REP day 0<br>• Split to 18-36 flasks on REP day 7<br>• 14 day duration | • 1 GREX-500M flask on day 11<br>• 25-200x$10^6$ TIL and 5x$10^9$ PBMC feeders on day 11<br>• Split to ≤ 6 GREX-500M flasks on day 16<br>• 11 day duration | • Reduced number of steps<br>• Shorter REP duration<br>• Closed system transfer of TIL between flasks<br>• Closed system media exchanges |
| Harvest | • TIL harvested via centrifugation | • TIL harvested via LOVO automated cell washing system | • Reduced number of steps<br>• Automated cell washing<br>• Closed system<br>• Reduced loss of product during wash |
| Final Formulation | • Fresh product in Hypothermosol<br>• Single infusion bag<br>• Limited shipping stability | • Cryopreserved product in PlasmaLyte-A + 1% HSA and CS10 stored in $LN_2$<br>• Multiple aliquots<br>• Longer shipping stability | • Shipping flexibility<br>• Flexible patient scheduling<br>• More timely release testing |
| Overall Estimated Process Time | • 43-55 days | • 22 days | • Faster turnaround to patient |

FIG. 11

SEQUENCE LISTING

```
<160> NUMBER OF SEQ ID NOS: 237

<210> SEQ ID NO 1
<211> LENGTH: 450
<212> TYPE: PRT
<213> ORGANISM: Artificial Sequence
<220> FEATURE:
<223> OTHER INFORMATION: Synthetic Muromonab heavy chain

<400> SEQUENCE: 1

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
```

```
            50                  55                  60
Lys Asp Lys Ala Thr Leu Thr Thr Asp Lys Ser Ser Thr Ala Tyr
 65                  70                  75                  80

Met Gln Leu Ser Ser Leu Thr Ser Glu Asp Ser Ala Val Tyr Tyr Cys
                     85                  90                  95

Ala Arg Tyr Tyr Asp Asp His Tyr Cys Leu Asp Tyr Trp Gly Gln Gly
                100                 105                 110

Thr Thr Leu Thr Val Ser Ser Ala Lys Thr Thr Ala Pro Ser Val Tyr
                115                 120                 125

Pro Leu Ala Pro Val Cys Gly Gly Thr Thr Gly Ser Ser Val Thr Leu
130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Thr Ser Ser
                180                 185                 190

Thr Trp Pro Ser Gln Ser Ile Thr Cys Asn Val Ala His Pro Ala Ser
                195                 200                 205

Ser Thr Lys Val Asp Lys Lys Ile Glu Pro Arg Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
450

<210> SEQ ID NO 2
```

```
<211> LENGTH: 213
<212> TYPE: PRT
<213> ORGANISM: Artificial Sequence
<220> FEATURE:
<223> OTHER INFORMATION: Synthetic Muromonab light chain

<400> SEQUENCE: 2

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

Asn Trp Tyr Gln Gln Lys Ser Gly Thr Ser Pro Lys Arg Trp Ile Tyr
            35                  40                  45

Asp Thr Ser Lys Leu Ala Ser Gly Val Pro Ala His Phe Arg Gly Ser
        50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn Arg Ala Asp Thr Ala Pro
            100                 105                 110

Thr Val Ser Ile Phe Pro Pro Ser Glu Gln Leu Thr Ser Gly Gly
            115                 120                 125

Ala Ser Val Val Cys Phe Leu Asn Asn Phe Tyr Pro Lys Asp Ile Asn
130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210

<210> SEQ ID NO 3
<211> LENGTH: 134
<212> TYPE: PRT
<213> ORGANISM: Artificial Sequence
<220> FEATURE:
<223> OTHER INFORMATION: Synthetic recombinant human IL-2 (rhIL-2)

<400> SEQUENCE: 3

Met Ala Pro Thr Ser Ser Ser Thr Lys Lys Thr Gln Leu Gln Leu Glu
1               5                   10                  15

His Leu Leu Leu Asp Leu Gln Met Ile Leu Asn Gly Ile Asn Asn Tyr
            20                  25                  30

Lys Asn Pro Lys Leu Thr Arg Met Leu Thr Phe Lys Phe Tyr Met Pro
        35                  40                  45

Lys Lys Ala Thr Glu Leu Lys His Leu Gln Cys Leu Glu Glu Glu Leu
    50                  55                  60

Lys Pro Leu Glu Glu Val Leu Asn Leu Ala Gln Ser Lys Asn Phe His
65                  70                  75                  80

Leu Arg Pro Arg Asp Leu Ile Ser Asn Ile Asn Val Ile Val Leu Glu
                85                  90                  95

Leu Lys Gly Ser Glu Thr Thr Phe Met Cys Glu Tyr Ala Asp Glu Thr
```

```
                    100                 105                 110

Ala Thr Ile Val Glu Phe Leu Asn Arg Trp Ile Thr Phe Cys Gln Ser
            115                 120                 125

Ile Ile Ser Thr Leu Thr
            130

<210> SEQ ID NO 4
<211> LENGTH: 132
<212> TYPE: PRT
<213> ORGANISM: Artificial Sequence
<220> FEATURE:
<223> OTHER INFORMATION: Synthetic Aldesleukin

<400> SEQUENCE: 4

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
        130

<210> SEQ ID NO 5
<211> LENGTH: 133
<212> TYPE: PRT
<213> ORGANISM: Artificial Sequence
<220> FEATURE:
<223> OTHER INFORMATION: Synthetic IL-2 form

<400> SEQUENCE: 5

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125
```

Ile Ser Thr Leu Thr
    130

<210> SEQ ID NO 6
<211> LENGTH: 303
<212> TYPE: PRT
<213> ORGANISM: Artificial Sequence
<220> FEATURE:
<223> OTHER INFORMATION: Synthetic Nemvaleukin alfa

<400> SEQUENCE: 6

Ser Lys Asn Phe His Leu Arg Pro Arg Asp Leu Ile Ser Asn Ile Asn
1               5                   10                  15

Val Ile Val Leu Glu Leu Lys Gly Ser Glu Thr Thr Phe Met Cys Glu
            20                  25                  30

Tyr Ala Asp Glu Thr Ala Thr Ile Val Glu Phe Leu Asn Arg Trp Ile
        35                  40                  45

Thr Phe Ser Gln Ser Ile Ile Ser Thr Leu Thr Gly Gly Ser Ser Ser
    50                  55                  60

Thr Lys Lys Thr Gln Leu Gln Leu Glu His Leu Leu Leu Asp Leu Gln
65                  70                  75                  80

Met Ile Leu Asn Gly Ile Asn Asn Tyr Lys Asn Pro Lys Leu Thr Arg
                85                  90                  95

Met Leu Thr Phe Lys Phe Tyr Met Pro Lys Lys Ala Thr Glu Leu Lys
            100                 105                 110

His Leu Gln Cys Leu Glu Glu Glu Leu Lys Pro Leu Glu Glu Val Leu
        115                 120                 125

Asn Leu Ala Gln Gly Ser Gly Gly Ser Glu Leu Cys Asp Asp Asp
    130                 135                 140

Pro Pro Glu Ile Pro His Ala Thr Phe Lys Ala Met Ala Tyr Lys Glu
145                 150                 155                 160

Gly Thr Met Leu Asn Cys Glu Cys Lys Arg Gly Phe Arg Arg Ile Lys
                165                 170                 175

Ser Gly Ser Leu Tyr Met Leu Cys Thr Gly Asn Ser Ser His Ser Ser
            180                 185                 190

Trp Asp Asn Gln Cys Gln Cys Thr Ser Ser Ala Thr Arg Asn Thr Thr
        195                 200                 205

Lys Gln Val Thr Pro Gln Pro Glu Glu Gln Lys Glu Arg Lys Thr Thr
    210                 215                 220

Glu Met Gln Ser Pro Met Gln Pro Val Asp Gln Ala Ser Leu Pro Gly
225                 230                 235                 240

His Cys Arg Glu Pro Pro Pro Trp Glu Asn Glu Ala Thr Glu Arg Ile
                245                 250                 255

Tyr His Phe Val Val Gly Gln Met Val Tyr Tyr Gln Cys Val Gln Gly
            260                 265                 270

Tyr Arg Ala Leu His Arg Gly Pro Ala Glu Ser Val Cys Lys Met Thr
        275                 280                 285

His Gly Lys Thr Arg Trp Thr Gln Pro Gln Leu Ile Cys Thr Gly
    290                 295                 300

<210> SEQ ID NO 7
<211> LENGTH: 452
<212> TYPE: PRT
<213> ORGANISM: Artificial Sequence
<220> FEATURE:
<223> OTHER INFORMATION: Synthetic IL-2 form

<400> SEQUENCE: 7

-continued

```
Met Asp Ala Met Lys Arg Gly Leu Cys Cys Val Leu Leu Cys Gly
1               5                   10                  15

Ala Val Phe Val Ser Ala Arg Arg Pro Ser Gly Arg Lys Ser Ser Lys
            20                  25                  30

Met Gln Ala Phe Arg Ile Trp Asp Val Asn Gln Lys Thr Phe Tyr Leu
            35                  40                  45

Arg Asn Asn Gln Leu Val Ala Gly Tyr Leu Gln Gly Pro Asn Val Asn
50                  55                  60

Leu Glu Glu Lys Ile Asp Val Val Pro Ile Glu Pro His Ala Leu Phe
65                  70                  75                  80

Leu Gly Ile His Gly Gly Lys Met Cys Leu Ser Cys Val Lys Ser Gly
                85                  90                  95

Asp Glu Thr Arg Leu Gln Leu Glu Ala Val Asn Ile Thr Asp Leu Ser
            100                 105                 110

Glu Asn Arg Lys Gln Asp Lys Arg Phe Ala Phe Ile Arg Ser Asp Ser
        115                 120                 125

Gly Pro Thr Thr Ser Phe Glu Ser Ala Ala Cys Pro Gly Trp Phe Leu
        130                 135                 140

Cys Thr Ala Met Glu Ala Asp Gln Pro Val Ser Leu Thr Asn Met Pro
145                 150                 155                 160

Asp Glu Gly Val Met Val Thr Lys Phe Tyr Phe Gln Glu Asp Glu Ser
                165                 170                 175

Gly Ser Gly Gly Ala Ser Ser Glu Ser Ser Ala Ser Ser Asp Gly Pro
            180                 185                 190

His Pro Val Ile Thr Glu Ser Arg Ala Ser Ser Glu Ser Ala Ser
            195                 200                 205

Ser Asp Gly Pro His Pro Val Ile Thr Glu Ser Arg Glu Pro Lys Ser
210                 215                 220

Ser Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
        290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
        370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415
```

```
Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
        450

<210> SEQ ID NO 8
<211> LENGTH: 16
<212> TYPE: PRT
<213> ORGANISM: Artificial Sequence
<220> FEATURE:
<223> OTHER INFORMATION: Synthetic mucin domain polypeptide

<400> SEQUENCE: 8

Ser Glu Ser Ser Ala Ser Ser Asp Gly Pro His Pro Val Ile Thr Pro
1               5                   10                  15

<210> SEQ ID NO 9
<211> LENGTH: 130
<212> TYPE: PRT
<213> ORGANISM: Artificial Sequence
<220> FEATURE:
<223> OTHER INFORMATION: Synthetic recombinant human IL-4 (rhIL-4)

<400> SEQUENCE: 9

Met His Lys Cys Asp Ile Thr Leu Gln Glu Ile Ile Lys Thr Leu Asn
1               5                   10                  15

Ser Leu Thr Glu Gln Lys Thr Leu Cys Thr Glu Leu Thr Val Thr Asp
            20                  25                  30

Ile Phe Ala Ala Ser Lys Asn Thr Thr Glu Lys Glu Thr Phe Cys Arg
        35                  40                  45

Ala Ala Thr Val Leu Arg Gln Phe Tyr Ser His His Glu Lys Asp Thr
    50                  55                  60

Arg Cys Leu Gly Ala Thr Ala Gln Gln Phe His Arg His Lys Gln Leu
65                  70                  75                  80

Ile Arg Phe Leu Lys Arg Leu Asp Arg Asn Leu Trp Gly Leu Ala Gly
                85                  90                  95

Leu Asn Ser Cys Pro Val Lys Glu Ala Asn Gln Ser Thr Leu Glu Asn
            100                 105                 110

Phe Leu Glu Arg Leu Lys Thr Ile Met Arg Glu Lys Tyr Ser Lys Cys
        115                 120                 125

Ser Ser
    130

<210> SEQ ID NO 10
<211> LENGTH: 153
<212> TYPE: PRT
<213> ORGANISM: Artificial Sequence
<220> FEATURE:
<223> OTHER INFORMATION: Synthetic recombinant human IL-7 (rhIL-7)

<400> SEQUENCE: 10

Met Asp Cys Asp Ile Glu Gly Lys Asp Gly Lys Gln Tyr Glu Ser Val
1               5                   10                  15

Leu Met Val Ser Ile Asp Gln Leu Leu Asp Ser Met Lys Glu Ile Gly
            20                  25                  30

Ser Asn Cys Leu Asn Asn Glu Phe Asn Phe Phe Lys Arg His Ile Cys
        35                  40                  45

Asp Ala Asn Lys Glu Gly Met Phe Leu Phe Arg Ala Ala Arg Lys Leu
```

```
                        50                  55                  60

Arg Gln Phe Leu Lys Met Asn Ser Thr Gly Asp Phe Asp Leu His Leu
 65                  70                  75                  80

Leu Lys Val Ser Glu Gly Thr Thr Ile Leu Leu Asn Cys Thr Gly Gln
                     85                  90                  95

Val Lys Gly Arg Lys Pro Ala Ala Leu Gly Glu Ala Gln Pro Thr Lys
                100                 105                 110

Ser Leu Glu Glu Asn Lys Ser Leu Lys Glu Gln Lys Lys Leu Asn Asp
            115                 120                 125

Leu Cys Phe Leu Lys Arg Leu Leu Gln Glu Ile Lys Thr Cys Trp Asn
        130                 135                 140

Lys Ile Leu Met Gly Thr Lys Glu His
145                 150

<210> SEQ ID NO 11
<211> LENGTH: 115
<212> TYPE: PRT
<213> ORGANISM: Artificial Sequence
<220> FEATURE:
<223> OTHER INFORMATION: Synthetic recombinant human IL-15 (rhIL-15)

<400> SEQUENCE: 11

Met Asn Trp Val Asn Val Ile Ser Asp Leu Lys Lys Ile Glu Asp Leu
 1               5                  10                  15

Ile Gln Ser Met His Ile Asp Ala Thr Leu Tyr Thr Glu Ser Asp Val
                20                  25                  30

His Pro Ser Cys Lys Val Thr Ala Met Lys Cys Phe Leu Leu Glu Leu
            35                  40                  45

Gln Val Ile Ser Leu Glu Ser Gly Asp Ala Ser Ile His Asp Thr Val
        50                  55                  60

Glu Asn Leu Ile Ile Leu Ala Asn Asn Ser Leu Ser Ser Asn Gly Asn
 65                  70                  75                  80

Val Thr Glu Ser Gly Cys Lys Glu Cys Glu Glu Leu Glu Glu Lys Asn
                 85                  90                  95

Ile Lys Glu Phe Leu Gln Ser Phe Val His Ile Val Gln Met Phe Ile
            100                 105                 110

Asn Thr Ser
        115

<210> SEQ ID NO 12
<211> LENGTH: 132
<212> TYPE: PRT
<213> ORGANISM: Artificial Sequence
<220> FEATURE:
<223> OTHER INFORMATION: Synthetic recombinant human IL-21 (rhIL-21)

<400> SEQUENCE: 12

Met Gln Asp Arg His Met Ile Arg Met Arg Gln Leu Ile Asp Ile Val
 1               5                  10                  15

Asp Gln Leu Lys Asn Tyr Val Asn Asp Leu Val Pro Glu Phe Leu Pro
                20                  25                  30

Ala Pro Glu Asp Val Glu Thr Asn Cys Glu Trp Ser Ala Phe Ser Cys
            35                  40                  45

Phe Gln Lys Ala Gln Leu Lys Ser Ala Asn Thr Gly Asn Asn Glu Arg
        50                  55                  60

Ile Ile Asn Val Ser Ile Lys Lys Leu Lys Arg Lys Pro Pro Ser Thr
 65                  70                  75                  80
```

```
Asn Ala Gly Arg Arg Gln Lys His Arg Leu Thr Cys Pro Ser Cys Asp
                85                  90                  95

Ser Tyr Glu Lys Lys Pro Pro Lys Glu Phe Leu Glu Arg Phe Lys Ser
            100                 105                 110

Leu Leu Gln Lys Met Ile His Gln His Leu Ser Ser Arg Thr His Gly
        115                 120                 125

Ser Glu Asp Ser
    130

<210> SEQ ID NO 13
<211> LENGTH: 153
<212> TYPE: PRT
<213> ORGANISM: Artificial Sequence
<220> FEATURE:
<223> OTHER INFORMATION: Synthetic IL-2

<400> SEQUENCE: 13

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150

<210> SEQ ID NO 14
<211> LENGTH: 133
<212> TYPE: PRT
<213> ORGANISM: Artificial Sequence
<220> FEATURE:
<223> OTHER INFORMATION: Synthetic IL-2 mutein

<400> SEQUENCE: 14

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Ala Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95
```

```
Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 15
<211> LENGTH: 133
<212> TYPE: PRT
<213> ORGANISM: Artificial Sequence
<220> FEATURE:
<223> OTHER INFORMATION: Synthetic IL-2 mutein

<400> SEQUENCE: 15

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Tyr Met Pro Lys
        35                  40                  45

Lys Ala Thr Glu Leu Lys His Leu Gln Cys Leu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 16
<211> LENGTH: 145
<212> TYPE: PRT
<213> ORGANISM: Artificial Sequence
<220> FEATURE:
<223> OTHER INFORMATION: Synthetic HCDR1_IL-2

<400> SEQUENCE: 16

Gly Phe Ser Leu Ala Pro Thr Ser Ser Ser Thr Lys Lys Thr Gln Leu
1               5                   10                  15

Gln Leu Glu His Leu Leu Leu Asp Leu Gln Met Ile Leu Asn Gly Ile
            20                  25                  30

Asn Asn Tyr Lys Asn Pro Lys Leu Thr Ala Met Leu Thr Phe Lys Phe
        35                  40                  45

Tyr Met Pro Lys Lys Ala Thr Glu Leu Lys His Leu Gln Cys Leu Glu
    50                  55                  60

Glu Glu Leu Lys Pro Leu Glu Glu Val Leu Asn Leu Ala Gln Ser Lys
65                  70                  75                  80

Asn Phe His Leu Arg Pro Arg Asp Leu Ile Ser Asn Ile Asn Val Ile
                85                  90                  95

Val Leu Glu Leu Lys Gly Ser Glu Thr Thr Phe Met Cys Glu Tyr Ala
            100                 105                 110

Asp Glu Thr Ala Thr Ile Val Glu Phe Leu Asn Arg Trp Ile Thr Phe
```

```
                115                 120                 125
Cys Gln Ser Ile Ile Ser Thr Leu Thr Ser Thr Ser Gly Met Ser Val
        130                 135                 140

Gly
145

<210> SEQ ID NO 17
<211> LENGTH: 16
<212> TYPE: PRT
<213> ORGANISM: Artificial Sequence
<220> FEATURE:
<223> OTHER INFORMATION: Synthetic HCDR2

<400> SEQUENCE: 17

Asp Ile Trp Trp Asp Asp Lys Lys Asp Tyr Asn Pro Ser Leu Lys Ser
1               5                   10                  15

<210> SEQ ID NO 18
<211> LENGTH: 10
<212> TYPE: PRT
<213> ORGANISM: Artificial Sequence
<220> FEATURE:
<223> OTHER INFORMATION: Synthetic HCDR3

<400> SEQUENCE: 18

Ser Met Ile Thr Asn Trp Tyr Phe Asp Val
1               5                   10

<210> SEQ ID NO 19
<211> LENGTH: 141
<212> TYPE: PRT
<213> ORGANISM: Artificial Sequence
<220> FEATURE:
<223> OTHER INFORMATION: Synthetic HCDR1_IL-2 kabat

<400> SEQUENCE: 19

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Ala Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Ser Thr Ser Gly Met Ser Val Gly
    130                 135                 140

<210> SEQ ID NO 20
<211> LENGTH: 16
<212> TYPE: PRT
<213> ORGANISM: Artificial Sequence
<220> FEATURE:
<223> OTHER INFORMATION: Synthetic HCDR2 kabat
```

```
<400> SEQUENCE: 20

Asp Ile Trp Trp Asp Asp Lys Asp Tyr Asn Pro Ser Leu Lys Ser
1               5                   10                  15

<210> SEQ ID NO 21
<211> LENGTH: 10
<212> TYPE: PRT
<213> ORGANISM: Artificial Sequence
<220> FEATURE:
<223> OTHER INFORMATION: Synthetic HCDR3 kabat

<400> SEQUENCE: 21

Ser Met Ile Thr Asn Trp Tyr Phe Asp Val
1               5                   10

<210> SEQ ID NO 22
<211> LENGTH: 142
<212> TYPE: PRT
<213> ORGANISM: Artificial Sequence
<220> FEATURE:
<223> OTHER INFORMATION: Synthetic HCDR1_IL-2 clothia

<400> SEQUENCE: 22

Gly Phe Ser Leu Ala Pro Thr Ser Ser Thr Lys Lys Thr Gln Leu
1               5                   10                  15

Gln Leu Glu His Leu Leu Leu Asp Leu Gln Met Ile Leu Asn Gly Ile
                20                  25                  30

Asn Asn Tyr Lys Asn Pro Lys Leu Thr Ala Met Leu Thr Phe Lys Phe
            35                  40                  45

Tyr Met Pro Lys Lys Ala Thr Glu Leu Lys His Leu Gln Cys Leu Glu
    50                  55                  60

Glu Glu Leu Lys Pro Leu Glu Glu Val Leu Asn Leu Ala Gln Ser Lys
65                  70                  75                  80

Asn Phe His Leu Arg Pro Arg Asp Leu Ile Ser Asn Ile Asn Val Ile
                85                  90                  95

Val Leu Glu Leu Lys Gly Ser Glu Thr Thr Phe Met Cys Glu Tyr Ala
            100                 105                 110

Asp Glu Thr Ala Thr Ile Val Glu Phe Leu Asn Arg Trp Ile Thr Phe
        115                 120                 125

Cys Gln Ser Ile Ile Ser Thr Leu Thr Ser Thr Ser Gly Met
    130                 135                 140

<210> SEQ ID NO 23
<211> LENGTH: 5
<212> TYPE: PRT
<213> ORGANISM: Artificial Sequence
<220> FEATURE:
<223> OTHER INFORMATION: Synthetic HCDR2 clothia

<400> SEQUENCE: 23

Trp Trp Asp Asp Lys
1               5

<210> SEQ ID NO 24
<211> LENGTH: 10
<212> TYPE: PRT
<213> ORGANISM: Artificial Sequence
<220> FEATURE:
<223> OTHER INFORMATION: Synthetic HCDR3 clothia

<400> SEQUENCE: 24

Ser Met Ile Thr Asn Trp Tyr Phe Asp Val
```

<210> SEQ ID NO 25
<211> LENGTH: 143
<212> TYPE: PRT
<213> ORGANISM: Artificial Sequence
<220> FEATURE:
<223> OTHER INFORMATION: Synthetic HCDR1_IL-2 IMGT

<400> SEQUENCE: 25

Gly Phe Ser Leu Ala Pro Thr Ser Ser Thr Lys Lys Thr Gln Leu
1               5                   10                  15

Gln Leu Glu His Leu Leu Leu Asp Leu Gln Met Ile Leu Asn Gly Ile
            20                  25                  30

Asn Asn Tyr Lys Asn Pro Lys Leu Thr Ala Met Leu Thr Phe Lys Phe
        35                  40                  45

Tyr Met Pro Lys Lys Ala Thr Glu Leu Lys His Leu Gln Cys Leu Glu
    50                  55                  60

Glu Glu Leu Lys Pro Leu Glu Glu Val Leu Asn Leu Ala Gln Ser Lys
65                  70                  75                  80

Asn Phe His Leu Arg Pro Arg Asp Leu Ile Ser Asn Ile Asn Val Ile
                85                  90                  95

Val Leu Glu Leu Lys Gly Ser Glu Thr Thr Phe Met Cys Glu Tyr Ala
            100                 105                 110

Asp Glu Thr Ala Thr Ile Val Glu Phe Leu Asn Arg Trp Ile Thr Phe
        115                 120                 125

Cys Gln Ser Ile Ile Ser Thr Leu Thr Ser Thr Ser Gly Met Ser
    130                 135                 140

<210> SEQ ID NO 26
<211> LENGTH: 7
<212> TYPE: PRT
<213> ORGANISM: Artificial Sequence
<220> FEATURE:
<223> OTHER INFORMATION: Synthetic HCDR2 IMGT

<400> SEQUENCE: 26

Ile Trp Trp Asp Asp Lys Lys
1               5

<210> SEQ ID NO 27
<211> LENGTH: 12
<212> TYPE: PRT
<213> ORGANISM: Artificial Sequence
<220> FEATURE:
<223> OTHER INFORMATION: Synthetic HCDR3 IMGT

<400> SEQUENCE: 27

Ala Arg Ser Met Ile Thr Asn Trp Tyr Phe Asp Val
1               5                   10

<210> SEQ ID NO 28
<211> LENGTH: 253
<212> TYPE: PRT
<213> ORGANISM: Artificial Sequence
<220> FEATURE:
<223> OTHER INFORMATION: Synthetic VH

<400> SEQUENCE: 28

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ala Pro Thr

```
                20                  25                  30
Ser Ser Ser Thr Lys Lys Thr Gln Leu Gln Leu Glu His Leu Leu Leu
            35                  40                  45

Asp Leu Gln Met Ile Leu Asn Gly Ile Asn Asn Tyr Lys Asn Pro Lys
        50                  55                  60

Leu Thr Ala Met Leu Thr Phe Lys Phe Tyr Met Pro Lys Lys Ala Thr
65                  70                  75                  80

Glu Leu Lys His Leu Gln Cys Leu Glu Glu Leu Lys Pro Leu Glu
                85                  90                  95

Glu Val Leu Asn Leu Ala Gln Ser Lys Asn Phe His Leu Arg Pro Arg
                100                 105                 110

Asp Leu Ile Ser Asn Ile Asn Val Ile Val Leu Glu Leu Lys Gly Ser
            115                 120                 125

Glu Thr Thr Phe Met Cys Glu Tyr Ala Asp Glu Thr Ala Thr Ile Val
        130                 135                 140

Glu Phe Leu Asn Arg Trp Ile Thr Phe Cys Gln Ser Ile Ile Ser Thr
145                 150                 155                 160

Leu Thr Ser Thr Ser Gly Met Ser Val Gly Trp Ile Arg Gln Pro Pro
                165                 170                 175

Gly Lys Ala Leu Glu Trp Leu Ala Asp Ile Trp Trp Asp Asp Lys Lys
                180                 185                 190

Asp Tyr Asn Pro Ser Leu Lys Ser Arg Leu Thr Ile Ser Lys Asp Thr
            195                 200                 205

Ser Lys Asn Gln Val Val Leu Lys Val Thr Asn Met Asp Pro Ala Asp
        210                 215                 220

Thr Ala Thr Tyr Tyr Cys Ala Arg Ser Met Ile Thr Asn Trp Tyr Phe
225                 230                 235                 240

Asp Val Trp Gly Ala Gly Thr Thr Val Thr Val Ser Ser
                245                 250

<210> SEQ ID NO 29
<211> LENGTH: 533
<212> TYPE: PRT
<213> ORGANISM: Artificial Sequence
<220> FEATURE:
<223> OTHER INFORMATION: Synthetic Heavy chain

<400> SEQUENCE: 29

Gln Met Ile Leu Asn Gly Ile Asn Asn Tyr Lys Asn Pro Lys Leu Thr
1               5                   10                  15

Ala Met Leu Thr Phe Lys Phe Tyr Met Pro Lys Lys Ala Thr Glu Leu
            20                  25                  30

Lys His Leu Gln Cys Leu Glu Glu Leu Lys Pro Leu Glu Glu Val
        35                  40                  45

Leu Asn Leu Ala Gln Ser Lys Asn Phe His Leu Arg Pro Arg Asp Leu
50                  55                  60

Ile Ser Asn Ile Asn Val Ile Val Leu Glu Leu Lys Gly Ser Glu Thr
65                  70                  75                  80

Thr Phe Met Cys Glu Tyr Ala Asp Glu Thr Ala Thr Ile Val Glu Phe
                85                  90                  95

Leu Asn Arg Trp Ile Thr Phe Cys Gln Ser Ile Ile Ser Thr Leu Thr
                100                 105                 110

Ser Thr Ser Gly Met Ser Val Gly Trp Ile Arg Gln Pro Pro Gly Lys
            115                 120                 125

Ala Leu Glu Trp Leu Ala Asp Ile Trp Trp Asp Asp Lys Lys Asp Tyr
```

```
            130                 135                 140
Asn Pro Ser Leu Lys Ser Arg Leu Thr Ile Ser Lys Asp Thr Ser Lys
145                 150                 155                 160

Asn Gln Val Val Leu Lys Val Thr Asn Met Asp Pro Ala Asp Thr Ala
                165                 170                 175

Thr Tyr Tyr Cys Ala Arg Ser Met Ile Thr Asn Trp Tyr Phe Asp Val
            180                 185                 190

Trp Gly Ala Gly Thr Thr Val Thr Val Ser Ser Ala Ser Thr Lys Gly
        195                 200                 205

Pro Ser Val Phe Pro Leu Ala Pro Ser Ser Lys Ser Thr Ser Gly Gly
    210                 215                 220

Thr Ala Ala Leu Gly Cys Leu Val Lys Asp Tyr Phe Pro Glu Pro Val
225                 230                 235                 240

Thr Val Ser Trp Asn Ser Gly Ala Leu Thr Ser Gly Val His Thr Phe
                245                 250                 255

Pro Ala Val Leu Gln Ser Ser Gly Leu Tyr Ser Leu Ser Ser Val Val
            260                 265                 270

Thr Val Pro Ser Ser Ser Leu Gly Thr Gln Thr Tyr Ile Cys Asn Val
        275                 280                 285

Asn His Lys Pro Ser Asn Thr Lys Val Asp Lys Arg Val Glu Pro Lys
    290                 295                 300

Ser Cys Asp Lys Thr His Thr Cys Pro Pro Cys Pro Ala Pro Glu Leu
305                 310                 315                 320

Leu Gly Gly Pro Ser Val Phe Leu Phe Pro Pro Lys Pro Lys Asp Thr
                325                 330                 335

Leu Met Ile Ser Arg Thr Pro Glu Val Thr Cys Val Val Val Ala Val
            340                 345                 350

Ser His Glu Asp Pro Glu Val Lys Phe Asn Trp Tyr Val Asp Gly Val
        355                 360                 365

Glu Val His Asn Ala Lys Thr Lys Pro Arg Glu Glu Gln Tyr Asn Ser
    370                 375                 380

Thr Tyr Arg Val Val Ser Val Leu Thr Val Leu His Gln Asp Trp Leu
385                 390                 395                 400

Asn Gly Lys Glu Tyr Lys Cys Lys Val Ser Asn Lys Ala Leu Ala Ala
                405                 410                 415

Pro Ile Glu Lys Thr Ile Ser Lys Ala Lys Gly Gln Pro Arg Glu Pro
            420                 425                 430

Gln Val Tyr Thr Leu Pro Pro Ser Arg Glu Glu Met Thr Lys Asn Gln
        435                 440                 445

Val Ser Leu Thr Cys Leu Val Lys Gly Phe Tyr Pro Ser Asp Ile Ala
    450                 455                 460

Val Glu Trp Glu Ser Asn Gly Gln Pro Glu Asn Tyr Lys Thr Thr
465                 470                 475                 480

Pro Pro Val Leu Asp Ser Asp Gly Ser Phe Phe Leu Tyr Ser Lys Leu
                485                 490                 495

Thr Val Asp Lys Ser Arg Trp Gln Gln Gly Asn Val Phe Ser Cys Ser
            500                 505                 510

Val Met His Glu Ala Leu His Asn His Tyr Thr Gln Lys Ser Leu Ser
        515                 520                 525

Leu Ser Pro Gly Lys
    530

<210> SEQ ID NO 30
```

```
<211> LENGTH: 10
<212> TYPE: PRT
<213> ORGANISM: Artificial Sequence
<220> FEATURE:
<223> OTHER INFORMATION: Synthetic LCDR1 kabat

<400> SEQUENCE: 30

Lys Ala Gln Leu Ser Val Gly Tyr Met His
1               5                   10

<210> SEQ ID NO 31
<211> LENGTH: 7
<212> TYPE: PRT
<213> ORGANISM: Artificial Sequence
<220> FEATURE:
<223> OTHER INFORMATION: Synthetic LCDR2 kabat

<400> SEQUENCE: 31

Asp Thr Ser Lys Leu Ala Ser
1               5

<210> SEQ ID NO 32
<211> LENGTH: 9
<212> TYPE: PRT
<213> ORGANISM: Artificial Sequence
<220> FEATURE:
<223> OTHER INFORMATION: Synthetic LCDR3 kabat

<400> SEQUENCE: 32

Phe Gln Gly Ser Gly Tyr Pro Phe Thr
1               5

<210> SEQ ID NO 33
<211> LENGTH: 6
<212> TYPE: PRT
<213> ORGANISM: Artificial Sequence
<220> FEATURE:
<223> OTHER INFORMATION: Synthetic LCDR1 chothia

<400> SEQUENCE: 33

Gln Leu Ser Val Gly Tyr
1               5

<210> SEQ ID NO 34
<211> LENGTH: 3
<212> TYPE: PRT
<213> ORGANISM: Artificial Sequence
<220> FEATURE:
<223> OTHER INFORMATION: Synthetic LCDR2 chothia

<400> SEQUENCE: 34

Asp Thr Ser
1

<210> SEQ ID NO 35
<211> LENGTH: 6
<212> TYPE: PRT
<213> ORGANISM: Artificial Sequence
<220> FEATURE:
<223> OTHER INFORMATION: Synthetic LCDR3 chothia

<400> SEQUENCE: 35

Gly Ser Gly Tyr Pro Phe
1               5

<210> SEQ ID NO 36
<211> LENGTH: 106
```

```
<212> TYPE: PRT
<213> ORGANISM: Artificial Sequence
<220> FEATURE:
<223> OTHER INFORMATION: Synthetic VL

<400> SEQUENCE: 36

Asp Ile Gln Met Thr Gln Ser Pro Ser Thr Leu Ser Ala Ser Val Gly
1               5                   10                  15

Asp Arg Val Thr Ile Thr Cys Lys Ala Gln Leu Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys
            100                 105

<210> SEQ ID NO 37
<211> LENGTH: 213
<212> TYPE: PRT
<213> ORGANISM: Artificial Sequence
<220> FEATURE:
<223> OTHER INFORMATION: Synthetic Light chain

<400> SEQUENCE: 37

Asp Ile Gln Met Thr Gln Ser Pro Ser Thr Leu Ser Ala Ser Val Gly
1               5                   10                  15

Asp Arg Val Thr Ile Thr Cys Lys Ala Gln Leu Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 38
<211> LENGTH: 583
<212> TYPE: PRT
<213> ORGANISM: Artificial Sequence
<220> FEATURE:
<223> OTHER INFORMATION: Synthetic Light chain

<400> SEQUENCE: 38

```
Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ala Pro Thr
            20                  25                  30

Ser Ser Ser Thr Lys Lys Thr Gln Leu Gln Leu Glu His Leu Leu Leu
        35                  40                  45

Asp Leu Gln Met Ile Leu Asn Gly Ile Asn Asn Tyr Lys Asn Pro Lys
    50                  55                  60

Leu Thr Arg Met Leu Thr Ala Lys Phe Tyr Met Pro Lys Lys Ala Thr
65                  70                  75                  80

Glu Leu Lys His Leu Gln Cys Leu Glu Glu Glu Leu Lys Pro Leu Glu
                85                  90                  95

Glu Val Leu Asn Leu Ala Gln Ser Lys Asn Phe His Leu Arg Pro Arg
            100                 105                 110

Asp Leu Ile Ser Asn Ile Asn Val Ile Val Leu Glu Leu Lys Gly Ser
        115                 120                 125

Glu Thr Thr Phe Met Cys Glu Tyr Ala Asp Glu Thr Ala Thr Ile Val
130                 135                 140

Glu Phe Leu Asn Arg Trp Ile Thr Phe Cys Gln Ser Ile Ile Ser Thr
145                 150                 155                 160

Leu Thr Ser Thr Ser Gly Met Ser Val Gly Trp Ile Arg Gln Pro Pro
                165                 170                 175

Gly Lys Ala Leu Glu Trp Leu Ala Asp Ile Trp Trp Asp Asp Lys Lys
            180                 185                 190

Asp Tyr Asn Pro Ser Leu Lys Ser Arg Leu Thr Ile Ser Lys Asp Thr
        195                 200                 205

Ser Lys Asn Gln Val Val Leu Lys Val Thr Asn Met Asp Pro Ala Asp
    210                 215                 220

Thr Ala Thr Tyr Tyr Cys Ala Arg Ser Met Ile Thr Asn Trp Tyr Phe
225                 230                 235                 240

Asp Val Trp Gly Ala Gly Thr Thr Val Thr Val Ser Ser Ala Ser Thr
                245                 250                 255

Lys Gly Pro Ser Val Phe Pro Leu Ala Pro Ser Ser Lys Ser Thr Ser
            260                 265                 270

Gly Gly Thr Ala Ala Leu Gly Cys Leu Val Lys Asp Tyr Phe Pro Glu
        275                 280                 285

Pro Val Thr Val Ser Trp Asn Ser Gly Ala Leu Thr Ser Gly Val His
    290                 295                 300

Thr Phe Pro Ala Val Leu Gln Ser Ser Gly Leu Tyr Ser Leu Ser Ser
305                 310                 315                 320

Val Val Thr Val Pro Ser Ser Ser Leu Gly Thr Gln Thr Tyr Ile Cys
                325                 330                 335

Asn Val Asn His Lys Pro Ser Asn Thr Lys Val Asp Lys Arg Val Glu
            340                 345                 350

Pro Lys Ser Cys Asp Lys Thr His Thr Cys Pro Pro Cys Pro Ala Pro
        355                 360                 365
```

Glu Leu Leu Gly Gly Pro Ser Val Phe Leu Phe Pro Pro Lys Pro Lys
            370                 375                 380

Asp Thr Leu Met Ile Ser Arg Thr Pro Glu Val Thr Cys Val Val Val
385                 390                 395                 400

Ala Val Ser His Glu Asp Pro Glu Val Lys Phe Asn Trp Tyr Val Asp
            405                 410                 415

Gly Val Glu Val His Asn Ala Lys Thr Lys Pro Arg Glu Glu Gln Tyr
            420                 425                 430

Asn Ser Thr Tyr Arg Val Val Ser Val Leu Thr Val Leu His Gln Asp
            435                 440                 445

Trp Leu Asn Gly Lys Glu Tyr Lys Cys Lys Val Ser Asn Lys Ala Leu
            450                 455                 460

Ala Ala Pro Ile Glu Lys Thr Ile Ser Lys Ala Lys Gly Gln Pro Arg
465                 470                 475                 480

Glu Pro Gln Val Tyr Thr Leu Pro Pro Ser Arg Glu Glu Met Thr Lys
            485                 490                 495

Asn Gln Val Ser Leu Thr Cys Leu Val Lys Gly Phe Tyr Pro Ser Asp
            500                 505                 510

Ile Ala Val Glu Trp Glu Ser Asn Gly Gln Pro Glu Asn Asn Tyr Lys
            515                 520                 525

Thr Thr Pro Pro Val Leu Asp Ser Asp Gly Ser Phe Phe Leu Tyr Ser
530                 535                 540

Lys Leu Thr Val Asp Lys Ser Arg Trp Gln Gln Gly Asn Val Phe Ser
545                 550                 555                 560

Cys Ser Val Met His Glu Ala Leu His Asn His Tyr Thr Gln Lys Ser
            565                 570                 575

Leu Ser Leu Ser Pro Gly Lys
            580

<210> SEQ ID NO 39
<211> LENGTH: 213
<212> TYPE: PRT
<213> ORGANISM: Artificial Sequence
<220> FEATURE:
<223> OTHER INFORMATION: Synthetic Light chain

<400> SEQUENCE: 39

Asp Ile Gln Met Thr Gln Ser Pro Ser Thr Leu Ser Ala Ser Val Gly
1               5                   10                  15

Asp Arg Val Thr Ile Thr Cys Lys Ala Gln Leu Ser Val Gly Tyr Met
            20                  25                  30

His Trp Tyr Gln Gln Lys Pro Gly Lys Ala Pro Lys Leu Leu Ile Tyr
            35                  40                  45

Asp Thr Ser Lys Leu Ala Ser Gly Val Pro Ser Arg Phe Ser Gly Ser
        50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
            85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

```
Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
        210

<210> SEQ ID NO 40

<400> SEQUENCE: 40

000

<210> SEQ ID NO 41

<400> SEQUENCE: 41

000

<210> SEQ ID NO 42

<400> SEQUENCE: 42

000

<210> SEQ ID NO 43

<400> SEQUENCE: 43

000

<210> SEQ ID NO 44

<400> SEQUENCE: 44

000

<210> SEQ ID NO 45

<400> SEQUENCE: 45

000

<210> SEQ ID NO 46

<400> SEQUENCE: 46

000

<210> SEQ ID NO 47

<400> SEQUENCE: 47

000

<210> SEQ ID NO 48

<400> SEQUENCE: 48

000
```

```
<210> SEQ ID NO 49
<400> SEQUENCE: 49
000

<210> SEQ ID NO 50
<400> SEQUENCE: 50
000

<210> SEQ ID NO 51
<400> SEQUENCE: 51
000

<210> SEQ ID NO 52
<400> SEQUENCE: 52
000

<210> SEQ ID NO 53
<400> SEQUENCE: 53
000

<210> SEQ ID NO 54
<400> SEQUENCE: 54
000

<210> SEQ ID NO 55
<400> SEQUENCE: 55
000

<210> SEQ ID NO 56
<400> SEQUENCE: 56
000

<210> SEQ ID NO 57
<400> SEQUENCE: 57
000

<210> SEQ ID NO 58
<400> SEQUENCE: 58
000

<210> SEQ ID NO 59
<400> SEQUENCE: 59
000

<210> SEQ ID NO 60
```

```
<400> SEQUENCE: 60
000

<210> SEQ ID NO 61
<400> SEQUENCE: 61
000

<210> SEQ ID NO 62
<400> SEQUENCE: 62
000

<210> SEQ ID NO 63
<400> SEQUENCE: 63
000

<210> SEQ ID NO 64
<400> SEQUENCE: 64
000

<210> SEQ ID NO 65
<400> SEQUENCE: 65
000

<210> SEQ ID NO 66
<400> SEQUENCE: 66
000

<210> SEQ ID NO 67
<400> SEQUENCE: 67
000

<210> SEQ ID NO 68
<400> SEQUENCE: 68
000

<210> SEQ ID NO 69
<400> SEQUENCE: 69
000

<210> SEQ ID NO 70
<400> SEQUENCE: 70
000

<210> SEQ ID NO 71
<400> SEQUENCE: 71
```

000

<210> SEQ ID NO 72
<400> SEQUENCE: 72
000

<210> SEQ ID NO 73
<400> SEQUENCE: 73
000

<210> SEQ ID NO 74
<400> SEQUENCE: 74
000

<210> SEQ ID NO 75
<400> SEQUENCE: 75
000

<210> SEQ ID NO 76
<400> SEQUENCE: 76
000

<210> SEQ ID NO 77
<400> SEQUENCE: 77
000

<210> SEQ ID NO 78
<400> SEQUENCE: 78
000

<210> SEQ ID NO 79
<400> SEQUENCE: 79
000

<210> SEQ ID NO 80
<400> SEQUENCE: 80
000

<210> SEQ ID NO 81
<400> SEQUENCE: 81
000

<210> SEQ ID NO 82
<400> SEQUENCE: 82
000

-continued

<210> SEQ ID NO 83

<400> SEQUENCE: 83

000

<210> SEQ ID NO 84

<400> SEQUENCE: 84

000

<210> SEQ ID NO 85

<400> SEQUENCE: 85

000

<210> SEQ ID NO 86

<400> SEQUENCE: 86

000

<210> SEQ ID NO 87

<400> SEQUENCE: 87

000

<210> SEQ ID NO 88

<400> SEQUENCE: 88

000

<210> SEQ ID NO 89

<400> SEQUENCE: 89

000

<210> SEQ ID NO 90

<400> SEQUENCE: 90

000

<210> SEQ ID NO 91

<400> SEQUENCE: 91

000

<210> SEQ ID NO 92

<400> SEQUENCE: 92

000

<210> SEQ ID NO 93

<400> SEQUENCE: 93

000

```
<210> SEQ ID NO 94
<400> SEQUENCE: 94
000

<210> SEQ ID NO 95
<400> SEQUENCE: 95
000

<210> SEQ ID NO 96
<400> SEQUENCE: 96
000

<210> SEQ ID NO 97
<400> SEQUENCE: 97
000

<210> SEQ ID NO 98
<400> SEQUENCE: 98
000

<210> SEQ ID NO 99
<400> SEQUENCE: 99
000

<210> SEQ ID NO 100
<400> SEQUENCE: 100
000

<210> SEQ ID NO 101
<400> SEQUENCE: 101
000

<210> SEQ ID NO 102
<400> SEQUENCE: 102
000

<210> SEQ ID NO 103
<400> SEQUENCE: 103
000

<210> SEQ ID NO 104
<400> SEQUENCE: 104
000

<210> SEQ ID NO 105
```

```
<400> SEQUENCE: 105

000

<210> SEQ ID NO 106

<400> SEQUENCE: 106

000

<210> SEQ ID NO 107

<400> SEQUENCE: 107

000

<210> SEQ ID NO 108

<400> SEQUENCE: 108

000

<210> SEQ ID NO 109

<400> SEQUENCE: 109

000

<210> SEQ ID NO 110

<400> SEQUENCE: 110

000

<210> SEQ ID NO 111

<400> SEQUENCE: 111

000

<210> SEQ ID NO 112

<400> SEQUENCE: 112

000

<210> SEQ ID NO 113

<400> SEQUENCE: 113

000

<210> SEQ ID NO 114

<400> SEQUENCE: 114

000

<210> SEQ ID NO 115

<400> SEQUENCE: 115

000

<210> SEQ ID NO 116

<400> SEQUENCE: 116
```

000

<210> SEQ ID NO 117
<400> SEQUENCE: 117
000

<210> SEQ ID NO 118
<400> SEQUENCE: 118
000

<210> SEQ ID NO 119
<400> SEQUENCE: 119
000

<210> SEQ ID NO 120
<400> SEQUENCE: 120
000

<210> SEQ ID NO 121
<400> SEQUENCE: 121
000

<210> SEQ ID NO 122
<400> SEQUENCE: 122
000

<210> SEQ ID NO 123
<400> SEQUENCE: 123
000

<210> SEQ ID NO 124
<400> SEQUENCE: 124
000

<210> SEQ ID NO 125
<400> SEQUENCE: 125
000

<210> SEQ ID NO 126
<400> SEQUENCE: 126
000

<210> SEQ ID NO 127
<400> SEQUENCE: 127
000

-continued

<210> SEQ ID NO 128
<400> SEQUENCE: 128
000

<210> SEQ ID NO 129
<400> SEQUENCE: 129
000

<210> SEQ ID NO 130
<400> SEQUENCE: 130
000

<210> SEQ ID NO 131
<400> SEQUENCE: 131
000

<210> SEQ ID NO 132
<400> SEQUENCE: 132
000

<210> SEQ ID NO 133
<400> SEQUENCE: 133
000

<210> SEQ ID NO 134
<400> SEQUENCE: 134
000

<210> SEQ ID NO 135
<400> SEQUENCE: 135
000

<210> SEQ ID NO 136
<400> SEQUENCE: 136
000

<210> SEQ ID NO 137
<400> SEQUENCE: 137
000

<210> SEQ ID NO 138
<400> SEQUENCE: 138
000

<210> SEQ ID NO 139

```
<400> SEQUENCE: 139
000

<210> SEQ ID NO 140
<400> SEQUENCE: 140
000

<210> SEQ ID NO 141
<400> SEQUENCE: 141
000

<210> SEQ ID NO 142
<400> SEQUENCE: 142
000

<210> SEQ ID NO 143
<400> SEQUENCE: 143
000

<210> SEQ ID NO 144
<400> SEQUENCE: 144
000

<210> SEQ ID NO 145
<400> SEQUENCE: 145
000

<210> SEQ ID NO 146
<400> SEQUENCE: 146
000

<210> SEQ ID NO 147
<400> SEQUENCE: 147
000

<210> SEQ ID NO 148
<400> SEQUENCE: 148
000

<210> SEQ ID NO 149
<400> SEQUENCE: 149
000

<210> SEQ ID NO 150
<400> SEQUENCE: 150
```

000

<210> SEQ ID NO 151

<400> SEQUENCE: 151

000

<210> SEQ ID NO 152

<400> SEQUENCE: 152

000

<210> SEQ ID NO 153

<400> SEQUENCE: 153

000

<210> SEQ ID NO 154

<400> SEQUENCE: 154

000

<210> SEQ ID NO 155

<400> SEQUENCE: 155

000

<210> SEQ ID NO 156

<400> SEQUENCE: 156

000

<210> SEQ ID NO 157

<400> SEQUENCE: 157

000

<210> SEQ ID NO 158
<211> LENGTH: 440
<212> TYPE: PRT
<213> ORGANISM: Artificial Sequence
<220> FEATURE:
<223> OTHER INFORMATION: Synthetic nivolumab heavy chain

<400> SEQUENCE: 158

```
Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95
```

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440

<210> SEQ ID NO 159
<211> LENGTH: 214
<212> TYPE: PRT
<213> ORGANISM: Artificial Sequence
<220> FEATURE:
<223> OTHER INFORMATION: Synthetic nivolumab light chain

<400> SEQUENCE: 159

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 160
<211> LENGTH: 113
<212> TYPE: PRT
<213> ORGANISM: Artificial Sequence
<220> FEATURE:
<223> OTHER INFORMATION: Synthetic nivolumab variable heavy chain

<400> SEQUENCE: 160

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
 50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser

<210> SEQ ID NO 161
<211> LENGTH: 107
<212> TYPE: PRT
<213> ORGANISM: Artificial Sequence
<220> FEATURE:

<223> OTHER INFORMATION: Synthetic nivolumab variable light chain

<400> SEQUENCE: 161

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys
            100                 105

<210> SEQ ID NO 162
<211> LENGTH: 5
<212> TYPE: PRT
<213> ORGANISM: Artificial Sequence
<220> FEATURE:
<223> OTHER INFORMATION: Synthetic nivolumab heavy chain CDR1

<400> SEQUENCE: 162

Asn Ser Gly Met His
1               5

<210> SEQ ID NO 163
<211> LENGTH: 17
<212> TYPE: PRT
<213> ORGANISM: Artificial Sequence
<220> FEATURE:
<223> OTHER INFORMATION: Synthetic nivolumab heavy chain CDR2

<400> SEQUENCE: 163

Val Ile Trp Tyr Asp Gly Ser Lys Arg Tyr Tyr Ala Asp Ser Val Lys
1               5                   10                  15

Gly

<210> SEQ ID NO 164
<211> LENGTH: 4
<212> TYPE: PRT
<213> ORGANISM: Artificial Sequence
<220> FEATURE:
<223> OTHER INFORMATION: Synthetic nivolumab heavy chain CDR3

<400> SEQUENCE: 164

Asn Asp Asp Tyr
1

<210> SEQ ID NO 165
<211> LENGTH: 11
<212> TYPE: PRT
<213> ORGANISM: Artificial Sequence
<220> FEATURE:
<223> OTHER INFORMATION: Synthetic nivolumab light chain CDR1

<400> SEQUENCE: 165

Arg Ala Ser Gln Ser Val Ser Ser Tyr Leu Ala
1               5                   10

<210> SEQ ID NO 166
<211> LENGTH: 7
<212> TYPE: PRT
<213> ORGANISM: Artificial Sequence
<220> FEATURE:
<223> OTHER INFORMATION: Synthetic nivolumab light chain CDR2

<400> SEQUENCE: 166

Asp Ala Ser Asn Arg Ala Thr
1               5

<210> SEQ ID NO 167
<211> LENGTH: 9
<212> TYPE: PRT
<213> ORGANISM: Artificial Sequence
<220> FEATURE:
<223> OTHER INFORMATION: Synthetic nivolumab light chain CDR3

<400> SEQUENCE: 167

Gln Gln Ser Ser Asn Trp Pro Arg Thr
1               5

<210> SEQ ID NO 168
<211> LENGTH: 447
<212> TYPE: PRT
<213> ORGANISM: Artificial Sequence
<220> FEATURE:
<223> OTHER INFORMATION: Synthetic pembrolizumab heavy chain

<400> SEQUENCE: 168

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val

```
              225                 230                 235                 240
      Phe Leu Phe Pro Pro Lys Pro Lys Asp Thr Leu Met Ile Ser Arg Thr
                      245                 250                 255

Pro Glu Val Thr Cys Val Val Val Asp Val Ser Gln Glu Asp Pro Glu
                      260                 265                 270

Val Gln Phe Asn Trp Tyr Val Asp Gly Val Glu Val His Asn Ala Lys
                      275                 280                 285

Thr Lys Pro Arg Glu Glu Gln Phe Asn Ser Thr Tyr Arg Val Val Ser
                      290                 295                 300

Val Leu Thr Val Leu His Gln Asp Trp Leu Asn Gly Lys Glu Tyr Lys
      305                 310                 315                 320

Cys Lys Val Ser Asn Lys Gly Leu Pro Ser Ser Ile Glu Lys Thr Ile
                      325                 330                 335

Ser Lys Ala Lys Gly Gln Pro Arg Glu Pro Gln Val Tyr Thr Leu Pro
                      340                 345                 350

Pro Ser Gln Glu Glu Met Thr Lys Asn Gln Val Ser Leu Thr Cys Leu
                      355                 360                 365

Val Lys Gly Phe Tyr Pro Ser Asp Ile Ala Val Glu Trp Glu Ser Asn
      370                 375                 380

Gly Gln Pro Glu Asn Asn Tyr Lys Thr Thr Pro Pro Val Leu Asp Ser
      385                 390                 395                 400

Asp Gly Ser Phe Phe Leu Tyr Ser Arg Leu Thr Val Asp Lys Ser Arg
                      405                 410                 415

Trp Gln Glu Gly Asn Val Phe Ser Cys Ser Val Met His Glu Ala Leu
                      420                 425                 430

His Asn His Tyr Thr Gln Lys Ser Leu Ser Leu Ser Leu Gly Lys
                      435                 440                 445

<210> SEQ ID NO 169
<211> LENGTH: 218
<212> TYPE: PRT
<213> ORGANISM: Artificial Sequence
<220> FEATURE:
<223> OTHER INFORMATION: Synthetic pembrolizumab light chain

<400> SEQUENCE: 169

Glu Ile Val Leu Thr Gln Ser Pro Ala Thr Leu Ser Leu Ser Pro Gly
      1               5                   10                  15

Glu Arg Ala Thr Leu Ser Cys Arg Ala Ser Lys Gly Val Ser Thr Ser
                      20                  25                  30

Gly Tyr Ser Tyr Leu His Trp Tyr Gln Gln Lys Pro Gly Gln Ala Pro
                      35                  40                  45

Arg Leu Leu Ile Tyr Leu Ala Ser Tyr Leu Glu Ser Gly Val Pro Ala
                      50                  55                  60

Arg Phe Ser Gly Ser Gly Ser Gly Thr Asp Phe Thr Leu Thr Ile Ser
      65                  70                  75                  80

Ser Leu Glu Pro Glu Asp Phe Ala Val Tyr Tyr Cys Gln His Ser Arg
                      85                  90                  95

Asp Leu Pro Leu Thr Phe Gly Gly Gly Thr Lys Val Glu Ile Lys Arg
                      100                 105                 110

Thr Val Ala Ala Pro Ser Val Phe Ile Phe Pro Pro Ser Asp Glu Gln
                      115                 120                 125

Leu Lys Ser Gly Thr Ala Ser Val Val Cys Leu Leu Asn Asn Phe Tyr
                      130                 135                 140

Pro Arg Glu Ala Lys Val Gln Trp Lys Val Asp Asn Ala Leu Gln Ser
```

```
                145                 150                 155                 160
Gly Asn Ser Gln Glu Ser Val Thr Glu Gln Asp Ser Lys Asp Ser Thr
                    165                 170                 175
Tyr Ser Leu Ser Ser Thr Leu Thr Leu Ser Lys Ala Asp Tyr Glu Lys
                    180                 185                 190
His Lys Val Tyr Ala Cys Glu Val Thr His Gln Gly Leu Ser Ser Pro
                195                 200                 205
Val Thr Lys Ser Phe Asn Arg Gly Glu Cys
                210                 215

<210> SEQ ID NO 170
<211> LENGTH: 120
<212> TYPE: PRT
<213> ORGANISM: Artificial Sequence
<220> FEATURE:
<223> OTHER INFORMATION: Synthetic pembrolizumab variable heavy chain

<400> SEQUENCE: 170

Gln Val Gln Leu Val Gln Ser Gly Val Glu Val Lys Lys Pro Gly Ala
1               5                   10                  15
Ser Val Lys Val Ser Cys Lys Ala Ser Gly Tyr Thr Phe Thr Asn Tyr
                20                  25                  30
Tyr Met Tyr Trp Val Arg Gln Ala Pro Gly Gln Gly Leu Glu Trp Met
            35                  40                  45
Gly Gly Ile Asn Pro Ser Asn Gly Gly Thr Asn Phe Asn Glu Lys Phe
        50                  55                  60
Lys Asn Arg Val Thr Leu Thr Thr Asp Ser Ser Thr Thr Thr Ala Tyr
65                  70                  75                  80
Met Glu Leu Lys Ser Leu Gln Phe Asp Asp Thr Ala Val Tyr Tyr Cys
                85                  90                  95
Ala Arg Arg Asp Tyr Arg Phe Asp Met Gly Phe Asp Tyr Trp Gly Gln
                100                 105                 110
Gly Thr Thr Val Thr Val Ser Ser
            115                 120

<210> SEQ ID NO 171
<211> LENGTH: 111
<212> TYPE: PRT
<213> ORGANISM: Artificial Sequence
<220> FEATURE:
<223> OTHER INFORMATION: Synthetic pembrolizumab variable light chain

<400> SEQUENCE: 171

Glu Ile Val Leu Thr Gln Ser Pro Ala Thr Leu Ser Leu Ser Pro Gly
1               5                   10                  15
Glu Arg Ala Thr Leu Ser Cys Arg Ala Ser Lys Gly Val Ser Thr Ser
                20                  25                  30
Gly Tyr Ser Tyr Leu His Trp Tyr Gln Gln Lys Pro Gly Gln Ala Pro
            35                  40                  45
Arg Leu Leu Ile Tyr Leu Ala Ser Tyr Leu Glu Ser Gly Val Pro Ala
        50                  55                  60
Arg Phe Ser Gly Ser Gly Ser Gly Thr Asp Phe Thr Leu Thr Ile Ser
65                  70                  75                  80
Ser Leu Glu Pro Glu Asp Phe Ala Val Tyr Tyr Cys Gln His Ser Arg
                85                  90                  95
Asp Leu Pro Leu Thr Phe Gly Gly Gly Thr Lys Val Glu Ile Lys
                100                 105                 110
```

```
<210> SEQ ID NO 172
<211> LENGTH: 5
<212> TYPE: PRT
<213> ORGANISM: Artificial Sequence
<220> FEATURE:
<223> OTHER INFORMATION: Synthetic pembrolizumab heavy chain CDR1

<400> SEQUENCE: 172

Asn Tyr Tyr Met Tyr
1               5

<210> SEQ ID NO 173
<211> LENGTH: 16
<212> TYPE: PRT
<213> ORGANISM: Artificial Sequence
<220> FEATURE:
<223> OTHER INFORMATION: Synthetic pembrolizumab heavy chain CDR2

<400> SEQUENCE: 173

Gly Ile Asn Pro Ser Asn Gly Gly Thr Asn Phe Asn Glu Lys Phe Lys
1               5                   10                  15

<210> SEQ ID NO 174
<211> LENGTH: 11
<212> TYPE: PRT
<213> ORGANISM: Artificial Sequence
<220> FEATURE:
<223> OTHER INFORMATION: Synthetic pembrolizumab heavy chain CDR3

<400> SEQUENCE: 174

Arg Asp Tyr Arg Phe Asp Met Gly Phe Asp Tyr
1               5                   10

<210> SEQ ID NO 175
<211> LENGTH: 15
<212> TYPE: PRT
<213> ORGANISM: Artificial Sequence
<220> FEATURE:
<223> OTHER INFORMATION: Synthetic pembrolizumab light chain CDR1

<400> SEQUENCE: 175

Arg Ala Ser Lys Gly Val Ser Thr Ser Gly Tyr Ser Tyr Leu His
1               5                   10                  15

<210> SEQ ID NO 176
<211> LENGTH: 7
<212> TYPE: PRT
<213> ORGANISM: Artificial Sequence
<220> FEATURE:
<223> OTHER INFORMATION: Synthetic pembrolizumab light chain CDR2

<400> SEQUENCE: 176

Leu Ala Ser Tyr Leu Glu Ser
1               5

<210> SEQ ID NO 177
<211> LENGTH: 9
<212> TYPE: PRT
<213> ORGANISM: Artificial Sequence
<220> FEATURE:
<223> OTHER INFORMATION: Synthetic pembrolizumab light chain CDR3

<400> SEQUENCE: 177

Gln His Ser Arg Asp Leu Pro Leu Thr
1               5
```

```
<210> SEQ ID NO 178
<211> LENGTH: 451
<212> TYPE: PRT
<213> ORGANISM: Artificial Sequence
<220> FEATURE:
<223> OTHER INFORMATION: Synthetic durvalumab heavy chain

<400> SEQUENCE: 178
```

| | | | | | | | | | | | | | | |
|---|---|---|---|---|---|---|---|---|---|---|---|---|---|---|
|Glu|Val|Gln|Leu|Val|Glu|Ser|Gly|Gly|Gly|Leu|Val|Gln|Pro|Gly|Gly|
|1| | | |5| | | | |10| | | | |15|

Ser Leu Arg Leu Ser Cys Ala Ala Ser Gly Phe Thr Phe Ser Arg Tyr
                20                  25                  30

Trp Met Ser Trp Val Arg Gln Ala Pro Gly Lys Gly Leu Glu Trp Val
            35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Trp Phe Gly Glu Leu Ala Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Phe Glu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu

```
                370                 375                 380
Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
    450

<210> SEQ ID NO 179
<211> LENGTH: 265
<212> TYPE: PRT
<213> ORGANISM: Artificial Sequence
<220> FEATURE:
<223> OTHER INFORMATION: Synthetic durvalumab light chain

<400> SEQUENCE: 179

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
                20                  25                  30

Trp Met Ser Trp Val Arg Gln Ala Pro Gly Lys Gly Leu Glu Trp Val
                35                  40                  45

Ala Asn Glu Ile Val Leu Thr Gln Ser Pro Gly Thr Leu Ser Leu Ser
        50                  55                  60

Pro Gly Glu Arg Ala Thr Leu Ser Cys Arg Ala Ser Gln Arg Val Ser
65                  70                  75                  80

Ser Ser Tyr Leu Ala Trp Tyr Gln Gln Lys Pro Gly Gln Ala Pro Arg
                85                  90                  95

Leu Leu Ile Tyr Asp Ala Ser Ser Arg Ala Thr Gly Ile Pro Asp Arg
                100                 105                 110

Phe Ser Gly Ser Gly Ser Gly Thr Asp Phe Thr Leu Thr Ile Ser Arg
                115                 120                 125

Leu Glu Pro Glu Asp Phe Ala Val Tyr Tyr Cys Gln Gln Tyr Gly Ser
    130                 135                 140

Leu Pro Trp Thr Phe Gly Gln Gly Thr Lys Val Glu Ile Lys Arg Thr
145                 150                 155                 160

Val Ala Ala Pro Ser Val Phe Ile Phe Pro Pro Ser Asp Glu Gln Leu
                165                 170                 175

Lys Ser Gly Thr Ala Ser Val Val Cys Leu Leu Asn Asn Phe Tyr Pro
                180                 185                 190

Arg Glu Ala Lys Val Gln Trp Lys Val Asp Asn Ala Leu Gln Ser Gly
                195                 200                 205

Asn Ser Gln Glu Ser Val Thr Glu Gln Asp Ser Lys Asp Ser Thr Tyr
        210                 215                 220

Ser Leu Ser Ser Thr Leu Thr Leu Ser Lys Ala Asp Tyr Glu Lys His
225                 230                 235                 240

Lys Val Tyr Ala Cys Glu Val Thr His Gln Gly Leu Ser Ser Pro Val
                245                 250                 255

Thr Lys Ser Phe Asn Arg Gly Glu Cys
                260                 265
```

```
<210> SEQ ID NO 180
<211> LENGTH: 121
<212> TYPE: PRT
<213> ORGANISM: Artificial Sequence
<220> FEATURE:
<223> OTHER INFORMATION: Synthetic durvalumab variable heavy chain

<400> SEQUENCE: 180

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Trp Phe Gly Glu Leu Ala Phe Asp Tyr Trp Gly
            100                 105                 110

Gln Gly Thr Leu Val Thr Val Ser Ser
        115                 120

<210> SEQ ID NO 181
<211> LENGTH: 108
<212> TYPE: PRT
<213> ORGANISM: Artificial Sequence
<220> FEATURE:
<223> OTHER INFORMATION: Synthetic durvalumab variable light chain

<400> SEQUENCE: 181

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Trp Thr Phe Gly Gln Gly Thr Lys Val Glu Ile Lys
            100                 105

<210> SEQ ID NO 182
<211> LENGTH: 5
<212> TYPE: PRT
<213> ORGANISM: Artificial Sequence
<220> FEATURE:
<223> OTHER INFORMATION: Synthetic durvalumab heavy chain CDR1

<400> SEQUENCE: 182

Arg Tyr Trp Met Ser
1               5

<210> SEQ ID NO 183
```

-continued

```
<211> LENGTH: 17
<212> TYPE: PRT
<213> ORGANISM: Artificial Sequence
<220> FEATURE:
<223> OTHER INFORMATION: Synthetic durvalumab heavy chain CDR2

<400> SEQUENCE: 183

Asn Ile Lys Gln Asp Gly Ser Glu Lys Tyr Tyr Val Asp Ser Val Lys
1               5                   10                  15
Gly

<210> SEQ ID NO 184
<211> LENGTH: 12
<212> TYPE: PRT
<213> ORGANISM: Artificial Sequence
<220> FEATURE:
<223> OTHER INFORMATION: Synthetic durvalumab heavy chain CDR3

<400> SEQUENCE: 184

Glu Gly Gly Trp Phe Gly Glu Leu Ala Phe Asp Tyr
1               5                   10

<210> SEQ ID NO 185
<211> LENGTH: 12
<212> TYPE: PRT
<213> ORGANISM: Artificial Sequence
<220> FEATURE:
<223> OTHER INFORMATION: Synthetic durvalumab light chain CDR1

<400> SEQUENCE: 185

Arg Ala Ser Gln Arg Val Ser Ser Ser Tyr Leu Ala
1               5                   10

<210> SEQ ID NO 186
<211> LENGTH: 7
<212> TYPE: PRT
<213> ORGANISM: Artificial Sequence
<220> FEATURE:
<223> OTHER INFORMATION: Synthetic durvalumab light chain CDR2

<400> SEQUENCE: 186

Asp Ala Ser Ser Arg Ala Thr
1               5

<210> SEQ ID NO 187
<211> LENGTH: 9
<212> TYPE: PRT
<213> ORGANISM: Artificial Sequence
<220> FEATURE:
<223> OTHER INFORMATION: Synthetic durvalumab light chain CDR3

<400> SEQUENCE: 187

Gln Gln Tyr Gly Ser Leu Pro Trp Thr
1               5

<210> SEQ ID NO 188
<211> LENGTH: 420
<212> TYPE: PRT
<213> ORGANISM: Artificial Sequence
<220> FEATURE:
<223> OTHER INFORMATION: Synthetic avelumab  heavy chain

<400> SEQUENCE: 188

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
```

```
                    20                  25                  30
        Ile Met Met Trp Val Arg Gln Ala Pro Gly Lys Gly Leu Glu Trp Val
                    35                  40                  45

Ser Ser Ile Tyr Pro Ser Gly Gly Ile Thr Phe Tyr Ala Asp Thr Val
            50                  55                  60

Lys Gly Arg Phe Thr Ile Ser Arg Asp Asn Ser Lys Asn Thr Leu Tyr
        65                  70                  75                  80

Leu Gln Met Asn Ser Leu Arg Ala Glu Asp Thr Ala Val Tyr Tyr Cys
                        85                  90                  95

Ala Arg Ile Lys Leu Gly Thr Val Thr Val Asp Tyr Trp Gly Gln
                        100                 105                 110

Gly Thr Leu Val Thr Val Ser Ser Ala Ser Thr Lys Gly Pro Ser Val
                        115                 120                 125

Phe Pro Leu Ala Pro Ser Ser Lys Ser Thr Ser Gly Gly Thr Ala Ala
                        130                 135                 140

Leu Gly Cys Leu Val Lys Asp Tyr Phe Pro Glu Pro Val Thr Val Ser
        145                 150                 155                 160

Trp Asn Ser Gly Ala Leu Thr Ser Gly Val His Thr Phe Pro Ala Val
                        165                 170                 175

Leu Gln Ser Ser Gly Leu Tyr Ser Leu Ser Ser Val Val Thr Val Pro
                        180                 185                 190

Ser Ser Ser Leu Gly Thr Gln Thr Tyr Ile Cys Asn Val Asn His Lys
                    195                 200                 205

Pro Ser Asn Thr Lys Val Asp Lys Lys Val Glu Pro Lys Ser Cys Asp
                    210                 215                 220

Lys Thr His Thr Cys Pro Pro Cys Pro Ala Pro Glu Leu Leu Gly Gly
        225                 230                 235                 240

Pro Ser Val Phe Leu Phe Pro Pro Lys Pro Lys Asp Thr Leu Met Ile
                        245                 250                 255

Ser Arg Thr Pro Glu Val Thr Cys Val Val Val Asp Val Ser His Glu
                        260                 265                 270

Asp Pro Glu Val Lys Phe Asn Trp Tyr Val Asp Gly Val Glu Val His
                        275                 280                 285

Asn Ala Lys Thr Lys Pro Arg Glu Glu Gln Tyr Asn Ser Thr Tyr Arg
                        290                 295                 300

Val Val Ser Val Leu Thr Val Leu His Gln Asp Trp Leu Asn Gly Lys
        305                 310                 315                 320

Glu Tyr Lys Cys Lys Val Ser Asn Lys Ala Leu Pro Ala Pro Ile Glu
                        325                 330                 335

Lys Thr Ile Ser Lys Ala Lys Gly Gln Pro Arg Glu Pro Gln Val Tyr
                        340                 345                 350

Thr Leu Pro Pro Ser Arg Asp Glu Leu Thr Lys Asn Gln Val Ser Leu
                        355                 360                 365

Thr Cys Leu Val Lys Gly Phe Tyr Pro Ser Asp Ile Ala Val Glu Trp
                        370                 375                 380

Glu Ser Asn Gly Gln Pro Glu Asn Asn Tyr Lys Thr Thr Pro Pro Val
        385                 390                 395                 400

Leu Asp Ser Asp Gly Ser Phe Phe Leu Tyr Ser Lys Leu Thr Val Asp
                        405                 410                 415

Lys Ser Arg Trp
                        420

<210> SEQ ID NO 189
```

```
<211> LENGTH: 216
<212> TYPE: PRT
<213> ORGANISM: Artificial Sequence
<220> FEATURE:
<223> OTHER INFORMATION: Synthetic avelumab light chain

<400> SEQUENCE: 189
```

| | | | | | | | | | | | | | | | |
|---|---|---|---|---|---|---|---|---|---|---|---|---|---|---|---|
| Gln | Ser | Ala | Leu | Thr | Gln | Pro | Ala | Ser | Val | Ser | Gly | Ser | Pro | Gly | Gln |
| 1 | | | | 5 | | | | | 10 | | | | | 15 | |
| Ser | Ile | Thr | Ile | Ser | Cys | Thr | Gly | Thr | Ser | Ser | Asp | Val | Gly | Gly | Tyr |
| | | | 20 | | | | | 25 | | | | | 30 | | |
| Asn | Tyr | Val | Ser | Trp | Tyr | Gln | Gln | His | Pro | Gly | Lys | Ala | Pro | Lys | Leu |
| | | | 35 | | | | | 40 | | | | | 45 | | |
| Met | Ile | Tyr | Asp | Val | Ser | Asn | Arg | Pro | Ser | Gly | Val | Ser | Asn | Arg | Phe |
| | | 50 | | | | | 55 | | | | | 60 | | | |
| Ser | Gly | Ser | Lys | Ser | Gly | Asn | Thr | Ala | Ser | Leu | Thr | Ile | Ser | Gly | Leu |
| 65 | | | | | 70 | | | | | 75 | | | | | 80 |
| Gln | Ala | Glu | Asp | Glu | Ala | Asp | Tyr | Tyr | Cys | Ser | Ser | Tyr | Thr | Ser | Ser |
| | | | | 85 | | | | | 90 | | | | | 95 | |
| Ser | Thr | Arg | Val | Phe | Gly | Thr | Gly | Thr | Lys | Val | Thr | Val | Leu | Gly | Gln |
| | | | 100 | | | | | 105 | | | | | 110 | | |
| Pro | Lys | Ala | Asn | Pro | Thr | Val | Thr | Leu | Phe | Pro | Pro | Ser | Ser | Glu | Glu |
| | | | 115 | | | | | 120 | | | | | 125 | | |
| Leu | Gln | Ala | Asn | Lys | Ala | Thr | Leu | Val | Cys | Leu | Ile | Ser | Asp | Phe | Tyr |
| | 130 | | | | | 135 | | | | | 140 | | | | |
| Pro | Gly | Ala | Val | Thr | Val | Ala | Trp | Lys | Ala | Asp | Gly | Ser | Pro | Val | Lys |
| 145 | | | | | 150 | | | | | 155 | | | | | 160 |
| Ala | Gly | Val | Glu | Thr | Thr | Lys | Pro | Ser | Lys | Gln | Ser | Asn | Asn | Lys | Tyr |
| | | | | 165 | | | | | 170 | | | | | 175 | |
| Ala | Ala | Ser | Ser | Tyr | Leu | Ser | Leu | Thr | Pro | Glu | Gln | Trp | Lys | Ser | His |
| | | | 180 | | | | | 185 | | | | | 190 | | |
| Arg | Ser | Tyr | Ser | Cys | Gln | Val | Thr | His | Glu | Gly | Ser | Thr | Val | Glu | Lys |
| | | | 195 | | | | | 200 | | | | | 205 | | |
| Thr | Val | Ala | Pro | Thr | Glu | Cys | Ser | | | | | | | | |
| | 210 | | | | | 215 | | | | | | | | | |

```
<210> SEQ ID NO 190
<211> LENGTH: 120
<212> TYPE: PRT
<213> ORGANISM: Artificial Sequence
<220> FEATURE:
<223> OTHER INFORMATION: Synthetic avelumab variable heavy chain

<400> SEQUENCE: 190
```

| | | | | | | | | | | | | | | | |
|---|---|---|---|---|---|---|---|---|---|---|---|---|---|---|---|
| Glu | Val | Gln | Leu | Leu | Glu | Ser | Gly | Gly | Gly | Leu | Val | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Phe | Thr | Phe | Ser | Ser | Tyr |
| | | | 20 | | | | | 25 | | | | | 30 | | |
| Ile | Met | Met | Trp | Val | Arg | Gln | Ala | Pro | Gly | Lys | Gly | Leu | Glu | Trp | Val |
| | | | 35 | | | | | 40 | | | | | 45 | | |
| Ser | Ser | Ile | Tyr | Pro | Ser | Gly | Gly | Ile | Thr | Phe | Tyr | Ala | Asp | Thr | Val |
| | | 50 | | | | | 55 | | | | | 60 | | | |
| Lys | Gly | Arg | Phe | Thr | Ile | Ser | Arg | Asp | Asn | Ser | Lys | Asn | Thr | Leu | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Ala | Arg | Ile | Lys | Leu | Gly | Thr | Val | Thr | Thr | Val | Asp | Tyr | Trp | Gly | Gln |

```
                100             105             110
Gly Thr Leu Val Thr Val Ser Ser
        115             120

<210> SEQ ID NO 191
<211> LENGTH: 110
<212> TYPE: PRT
<213> ORGANISM: Artificial Sequence
<220> FEATURE:
<223> OTHER INFORMATION: Synthetic avelumab variable light chain

<400> SEQUENCE: 191

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu
            100                 105                 110

<210> SEQ ID NO 192
<211> LENGTH: 5
<212> TYPE: PRT
<213> ORGANISM: Artificial Sequence
<220> FEATURE:
<223> OTHER INFORMATION: Synthetic avelumab heavy chain CDR1

<400> SEQUENCE: 192

Ser Tyr Ile Met Met
1               5

<210> SEQ ID NO 193
<211> LENGTH: 17
<212> TYPE: PRT
<213> ORGANISM: Artificial Sequence
<220> FEATURE:
<223> OTHER INFORMATION: Synthetic avelumab heavy chain CDR2

<400> SEQUENCE: 193

Ser Ile Tyr Pro Ser Gly Gly Ile Thr Phe Tyr Ala Asp Thr Val Lys
1               5                   10                  15

Gly

<210> SEQ ID NO 194
<211> LENGTH: 11
<212> TYPE: PRT
<213> ORGANISM: Artificial Sequence
<220> FEATURE:
<223> OTHER INFORMATION: Synthetic avelumab heavy chain CDR3

<400> SEQUENCE: 194

Ile Lys Leu Gly Thr Val Thr Thr Val Asp Tyr
1               5                   10

<210> SEQ ID NO 195
```

```
<211> LENGTH: 14
<212> TYPE: PRT
<213> ORGANISM: Artificial Sequence
<220> FEATURE:
<223> OTHER INFORMATION: Synthetic avelumab light chain CDR1

<400> SEQUENCE: 195

Thr Gly Thr Ser Ser Asp Val Gly Gly Tyr Asn Tyr Val Ser
1               5                   10

<210> SEQ ID NO 196
<211> LENGTH: 7
<212> TYPE: PRT
<213> ORGANISM: Artificial Sequence
<220> FEATURE:
<223> OTHER INFORMATION: Synthetic avelumab light chain CDR2

<400> SEQUENCE: 196

Asp Val Ser Asn Arg Pro Ser
1               5

<210> SEQ ID NO 197
<211> LENGTH: 10
<212> TYPE: PRT
<213> ORGANISM: Artificial Sequence
<220> FEATURE:
<223> OTHER INFORMATION: Synthetic avelumab light chain CDR3

<400> SEQUENCE: 197

Ser Ser Tyr Thr Ser Ser Ser Thr Arg Val
1               5                   10

<210> SEQ ID NO 198
<211> LENGTH: 448
<212> TYPE: PRT
<213> ORGANISM: Artificial Sequence
<220> FEATURE:
<223> OTHER INFORMATION: Synthetic atezolizumab heavy chain

<400> SEQUENCE: 198

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175
```

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Ala Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 199
<211> LENGTH: 214
<212> TYPE: PRT
<213> ORGANISM: Artificial Sequence
<220> FEATURE:
<223> OTHER INFORMATION: Synthetic atezolizumab light chain

<400> SEQUENCE: 199

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
            85                  90                  95

```
Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 200
<211> LENGTH: 118
<212> TYPE: PRT
<213> ORGANISM: Artificial Sequence
<220> FEATURE:
<223> OTHER INFORMATION: Synthetic atezolizumab variable heavy chain

<400> SEQUENCE: 200

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ala
        115

<210> SEQ ID NO 201
<211> LENGTH: 108
<212> TYPE: PRT
<213> ORGANISM: Artificial Sequence
<220> FEATURE:
<223> OTHER INFORMATION: Synthetic atezolizumab variable light chain

<400> SEQUENCE: 201

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
```

```
                  50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Leu Tyr His Pro Ala
                 85                  90                  95

Thr Phe Gly Gln Gly Thr Lys Val Glu Ile Lys Arg
            100                 105

<210> SEQ ID NO 202
<211> LENGTH: 10
<212> TYPE: PRT
<213> ORGANISM: Artificial Sequence
<220> FEATURE:
<223> OTHER INFORMATION: Synthetic atezolizumab heavy chain CDR1

<400> SEQUENCE: 202

Gly Phe Thr Phe Ser Asp Ser Trp Ile His
 1               5                  10

<210> SEQ ID NO 203
<211> LENGTH: 18
<212> TYPE: PRT
<213> ORGANISM: Artificial Sequence
<220> FEATURE:
<223> OTHER INFORMATION: Synthetic atezolizumab heavy chain CDR2

<400> SEQUENCE: 203

Ala Trp Ile Ser Pro Tyr Gly Gly Ser Thr Tyr Tyr Ala Asp Ser Val
 1               5                  10                  15

Lys Gly

<210> SEQ ID NO 204
<211> LENGTH: 9
<212> TYPE: PRT
<213> ORGANISM: Artificial Sequence
<220> FEATURE:
<223> OTHER INFORMATION: Synthetic atezolizumab heavy chain CDR3

<400> SEQUENCE: 204

Arg His Trp Pro Gly Gly Phe Asp Tyr
 1               5

<210> SEQ ID NO 205
<211> LENGTH: 11
<212> TYPE: PRT
<213> ORGANISM: Artificial Sequence
<220> FEATURE:
<223> OTHER INFORMATION: Synthetic atezolizumab light chain CDR1

<400> SEQUENCE: 205

Arg Ala Ser Gln Asp Val Ser Thr Ala Val Ala
 1               5                  10

<210> SEQ ID NO 206
<211> LENGTH: 7
<212> TYPE: PRT
<213> ORGANISM: Artificial Sequence
<220> FEATURE:
<223> OTHER INFORMATION: Synthetic atezolizumab light chain CDR2

<400> SEQUENCE: 206

Ser Ala Ser Phe Leu Tyr Ser
 1               5
```

<210> SEQ ID NO 207
<211> LENGTH: 9
<212> TYPE: PRT
<213> ORGANISM: Artificial Sequence
<220> FEATURE:
<223> OTHER INFORMATION: Synthetic atezolizumab light chain CDR3

<400> SEQUENCE: 207

Gln Gln Tyr Leu Tyr His Pro Ala Thr
1               5

<210> SEQ ID NO 208
<211> LENGTH: 225
<212> TYPE: PRT
<213> ORGANISM: Artificial Sequence
<220> FEATURE:
<223> OTHER INFORMATION: Synthetic ipilimumab heavy chain

<400> SEQUENCE: 208

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His
225

<210> SEQ ID NO 209
<211> LENGTH: 215
<212> TYPE: PRT
<213> ORGANISM: Artificial Sequence
<220> FEATURE:
<223> OTHER INFORMATION: Synthetic ipilimumab light chain

<400> SEQUENCE: 209

Glu Ile Val Leu Thr Gln Ser Pro Gly Thr Leu Ser Leu Ser Pro Gly
1               5                   10                  15

```
Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 210
<211> LENGTH: 118
<212> TYPE: PRT
<213> ORGANISM: Artificial Sequence
<220> FEATURE:
<223> OTHER INFORMATION: Synthetic ipilimumab variable heavy chain

<400> SEQUENCE: 210

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser
        115

<210> SEQ ID NO 211
<211> LENGTH: 108
<212> TYPE: PRT
<213> ORGANISM: Artificial Sequence
```

```
<220> FEATURE:
<223> OTHER INFORMATION: Synthetic ipilimumab variable light chain

<400> SEQUENCE: 211

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

<210> SEQ ID NO 212
<211> LENGTH: 8
<212> TYPE: PRT
<213> ORGANISM: Artificial Sequence
<220> FEATURE:
<223> OTHER INFORMATION: Synthetic ipilimumab heavy chain CDR1

<400> SEQUENCE: 212

Gly Phe Thr Phe Ser Ser Tyr Thr
1               5

<210> SEQ ID NO 213
<211> LENGTH: 10
<212> TYPE: PRT
<213> ORGANISM: Artificial Sequence
<220> FEATURE:
<223> OTHER INFORMATION: Synthetic ipilimumab heavy chain CDR2

<400> SEQUENCE: 213

Thr Phe Ile Ser Tyr Asp Gly Asn Asn Lys
1               5                   10

<210> SEQ ID NO 214
<211> LENGTH: 11
<212> TYPE: PRT
<213> ORGANISM: Artificial Sequence
<220> FEATURE:
<223> OTHER INFORMATION: Synthetic ipilimumab heavy chain CDR3

<400> SEQUENCE: 214

Ala Arg Thr Gly Trp Leu Gly Pro Phe Asp Tyr
1               5                   10

<210> SEQ ID NO 215
<211> LENGTH: 7
<212> TYPE: PRT
<213> ORGANISM: Artificial Sequence
<220> FEATURE:
<223> OTHER INFORMATION: Synthetic ipilimumab light chain CDR1

<400> SEQUENCE: 215

Gln Ser Val Gly Ser Ser Tyr
1               5
```

-continued

```
<210> SEQ ID NO 216
<211> LENGTH: 3
<212> TYPE: PRT
<213> ORGANISM: Artificial Sequence
<220> FEATURE:
<223> OTHER INFORMATION: Synthetic ipilimumab light chain CDR2

<400> SEQUENCE: 216

Gly Ala Phe
1

<210> SEQ ID NO 217
<211> LENGTH: 9
<212> TYPE: PRT
<213> ORGANISM: Artificial Sequence
<220> FEATURE:
<223> OTHER INFORMATION: Synthetic ipilimumab light chain CDR3

<400> SEQUENCE: 217

Gln Gln Tyr Gly Ser Ser Pro Trp Thr
1               5

<210> SEQ ID NO 218
<211> LENGTH: 451
<212> TYPE: PRT
<213> ORGANISM: Artificial Sequence
<220> FEATURE:
<223> OTHER INFORMATION: Synthetic tremelimumab heavy chain

<400> SEQUENCE: 218

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Arg Gly Ala Thr Leu Tyr Tyr Tyr Tyr Gly Met
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Asn Phe Gly Thr Gln Thr Tyr Thr Cys
        195                 200                 205

Asn Val Asp His Lys Pro Ser Asn Thr Lys Val Asp Lys Thr Val Glu
    210                 215                 220

Arg Lys Cys Cys Val Glu Cys Pro Pro Cys Pro Ala Pro Pro Val Ala
225                 230                 235                 240
```

```
Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Phe
    290                 295                 300

Arg Val Val Ser Val Leu Thr Val Val His Gln Asp Trp Leu Asn Gly
305                 310                 315                 320

Lys Glu Tyr Lys Cys Lys Val Ser Asn Lys Gly Leu Pro Ala Pro Ile
                325                 330                 335

Glu Lys Thr Ile Ser Lys Thr Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 219
<211> LENGTH: 214
<212> TYPE: PRT
<213> ORGANISM: Artificial Sequence
<220> FEATURE:
<223> OTHER INFORMATION: Synthetic tremelimumab light chain

<400> SEQUENCE: 219

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Ser Tyr
            20                  25                  30

Leu Asp Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Thr Pro Phe
                85                  90                  95

Thr Phe Gly Pro Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 220
<211> LENGTH: 167
<212> TYPE: PRT
<213> ORGANISM: Artificial Sequence
<220> FEATURE:
<223> OTHER INFORMATION: Synthetic tremelimumab variable heavy chain

<400> SEQUENCE: 220

Gly Val Val Gln Pro Gly Arg Ser Leu Arg Leu Ser Cys Ala Ala Ser
1               5                   10                  15

Gly Phe Thr Phe Ser Ser Tyr Gly Met His Trp Val Arg Gln Ala Pro
            20                  25                  30

Gly Lys Gly Leu Glu Trp Val Ala Val Ile Trp Tyr Asp Gly Ser Asn
        35                  40                  45

Lys Tyr Tyr Ala Asp Ser Val Lys Gly Arg Phe Thr Ile Ser Arg Asp
    50                  55                  60

Asn Ser Lys Asn Thr Leu Tyr Leu Gln Met Asn Ser Leu Arg Ala Glu
65                  70                  75                  80

Asp Thr Ala Val Tyr Tyr Cys Ala Arg Asp Pro Arg Gly Ala Thr Leu
                85                  90                  95

Tyr Tyr Tyr Tyr Tyr Gly Met Asp Val Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His
            165

<210> SEQ ID NO 221
<211> LENGTH: 139
<212> TYPE: PRT
<213> ORGANISM: Artificial Sequence
<220> FEATURE:
<223> OTHER INFORMATION: Synthetic tremelimumab variable light chain

<400> SEQUENCE: 221

Pro Ser Ser Leu Ser Ala Ser Val Gly Asp Arg Val Thr Ile Thr Cys
1               5                   10                  15

Arg Ala Ser Gln Ser Ile Asn Ser Tyr Leu Asp Trp Tyr Gln Gln Lys
            20                  25                  30

Pro Gly Lys Ala Pro Lys Leu Leu Ile Tyr Ala Ala Ser Ser Leu Gln
        35                  40                  45

Ser Gly Val Pro Ser Arg Phe Ser Gly Ser Gly Ser Gly Thr Asp Phe
```

```
                    50                  55                  60
Thr Leu Thr Ile Ser Ser Leu Gln Pro Glu Asp Phe Ala Thr Tyr Tyr
 65                  70                  75                  80

Cys Gln Gln Tyr Tyr Ser Thr Pro Phe Thr Phe Gly Pro Gly Thr Lys
                 85                  90                  95

Val Glu Ile Lys Arg Thr Val Ala Ala Pro Ser Val Phe Ile Phe Pro
            100                 105                 110

Pro Ser Asp Glu Gln Leu Lys Ser Gly Thr Ala Ser Val Val Cys Leu
        115                 120                 125

Leu Asn Asn Phe Tyr Pro Arg Glu Ala Lys Val
    130                 135

<210> SEQ ID NO 222
<211> LENGTH: 10
<212> TYPE: PRT
<213> ORGANISM: Artificial Sequence
<220> FEATURE:
<223> OTHER INFORMATION: Synthetic tremelimumab heavy chain CDR1

<400> SEQUENCE: 222

Gly Phe Thr Phe Ser Ser Tyr Gly Met His
 1               5                  10

<210> SEQ ID NO 223
<211> LENGTH: 15
<212> TYPE: PRT
<213> ORGANISM: Artificial Sequence
<220> FEATURE:
<223> OTHER INFORMATION: Synthetic tremelimumab heavy chain CDR2

<400> SEQUENCE: 223

Val Ile Trp Tyr Asp Gly Ser Asn Lys Tyr Tyr Ala Asp Ser Val
 1               5                  10                  15

<210> SEQ ID NO 224
<211> LENGTH: 16
<212> TYPE: PRT
<213> ORGANISM: Artificial Sequence
<220> FEATURE:
<223> OTHER INFORMATION: Synthetic tremelimumab heavy chain CDR3

<400> SEQUENCE: 224

Asp Pro Arg Gly Ala Thr Leu Tyr Tyr Tyr Tyr Tyr Gly Met Asp Val
 1               5                  10                  15

<210> SEQ ID NO 225
<211> LENGTH: 11
<212> TYPE: PRT
<213> ORGANISM: Artificial Sequence
<220> FEATURE:
<223> OTHER INFORMATION: Synthetic tremelimumab light chain CDR1

<400> SEQUENCE: 225

Arg Ala Ser Gln Ser Ile Asn Ser Tyr Leu Asp
 1               5                  10

<210> SEQ ID NO 226
<211> LENGTH: 7
<212> TYPE: PRT
<213> ORGANISM: Artificial Sequence
<220> FEATURE:
<223> OTHER INFORMATION: Synthetic tremelimumab light chain CDR2

<400> SEQUENCE: 226
```

Ala Ala Ser Ser Leu Gln Ser
1               5

<210> SEQ ID NO 227
<211> LENGTH: 9
<212> TYPE: PRT
<213> ORGANISM: Artificial Sequence
<220> FEATURE:
<223> OTHER INFORMATION: Synthetic tremelimumab light chain CDR3

<400> SEQUENCE: 227

Gln Gln Tyr Tyr Ser Thr Pro Phe Thr
1               5

<210> SEQ ID NO 228
<211> LENGTH: 448
<212> TYPE: PRT
<213> ORGANISM: Artificial Sequence
<220> FEATURE:
<223> OTHER INFORMATION: Synthetic zalifrelimab heavy chain

<400> SEQUENCE: 228

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Gly Leu Met Gly Pro Phe Asp Ile Trp Gly Gln Gly Thr
            100                 105                 110

Met Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

```
Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 229
<211> LENGTH: 214
<212> TYPE: PRT
<213> ORGANISM: Artificial Sequence
<220> FEATURE:
<223> OTHER INFORMATION: Synthetic zalifrelimab light chain

<400> SEQUENCE: 229

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Tyr
            20                  25                  30

Leu Gly Trp Tyr Gln Gln Lys Pro Gly Gln Ala Pro Arg Leu Leu Ile
        35                  40                  45

Tyr Gly Ala Ser Thr Arg Ala Thr Gly Ile Pro Asp Arg Phe Ser Gly
50                  55                  60

Ser Gly Ser Gly Thr Asp Phe Thr Leu Thr Ile Thr Arg Leu Glu Pro
65                  70                  75                  80

Glu Asp Phe Ala Val Tyr Tyr Cys Gln Gln Tyr Gly Ser Ser Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

```
Phe Asn Arg Gly Glu Cys
    210

<210> SEQ ID NO 230
<211> LENGTH: 118
<212> TYPE: PRT
<213> ORGANISM: Artificial Sequence
<220> FEATURE:
<223> OTHER INFORMATION: Synthetic zalifrelimab variable heavy chain

<400> SEQUENCE: 230

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Gly Leu Met Gly Pro Phe Asp Ile Trp Gly Gln Gly Thr
            100                 105                 110

Met Val Thr Val Ser Ser
        115

<210> SEQ ID NO 231
<211> LENGTH: 107
<212> TYPE: PRT
<213> ORGANISM: Artificial Sequence
<220> FEATURE:
<223> OTHER INFORMATION: Synthetic zalifrelimab variable light chain

<400> SEQUENCE: 231

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Tyr
            20                  25                  30

Leu Gly Trp Tyr Gln Gln Lys Pro Gly Gln Ala Pro Arg Leu Leu Ile
        35                  40                  45

Tyr Gly Ala Ser Thr Arg Ala Thr Gly Ile Pro Asp Arg Phe Ser Gly
    50                  55                  60

Ser Gly Ser Gly Thr Asp Phe Thr Leu Thr Ile Thr Arg Leu Glu Pro
65                  70                  75                  80

Glu Asp Phe Ala Val Tyr Tyr Cys Gln Gln Tyr Gly Ser Ser Pro Trp
                85                  90                  95

Thr Phe Gly Gln Gly Thr Lys Val Glu Ile Lys
            100                 105

<210> SEQ ID NO 232
<211> LENGTH: 8
<212> TYPE: PRT
<213> ORGANISM: Artificial Sequence
<220> FEATURE:
<223> OTHER INFORMATION: Synthetic zalifrelimab heavy chain CDR1

<400> SEQUENCE: 232
```

```
Gly Phe Thr Phe Ser Ser Tyr Ser
1               5

<210> SEQ ID NO 233
<211> LENGTH: 8
<212> TYPE: PRT
<213> ORGANISM: Artificial Sequence
<220> FEATURE:
<223> OTHER INFORMATION: Synthetic zalifrelimab heavy chain CDR2

<400> SEQUENCE: 233

Ile Ser Ser Ser Ser Ser Tyr Ile
1               5

<210> SEQ ID NO 234
<211> LENGTH: 11
<212> TYPE: PRT
<213> ORGANISM: Artificial Sequence
<220> FEATURE:
<223> OTHER INFORMATION: Synthetic zalifrelimab heavy chain CDR3

<400> SEQUENCE: 234

Ala Arg Val Gly Leu Met Gly Pro Phe Asp Ile
1               5                   10

<210> SEQ ID NO 235
<211> LENGTH: 6
<212> TYPE: PRT
<213> ORGANISM: Artificial Sequence
<220> FEATURE:
<223> OTHER INFORMATION: Synthetic zalifrelimab light chain CDR1

<400> SEQUENCE: 235

Gln Ser Val Ser Arg Tyr
1               5

<210> SEQ ID NO 236
<211> LENGTH: 3
<212> TYPE: PRT
<213> ORGANISM: Artificial Sequence
<220> FEATURE:
<223> OTHER INFORMATION: Synthetic zalifrelimab light chain CDR2

<400> SEQUENCE: 236

Gly Ala Ser
1

<210> SEQ ID NO 237
<211> LENGTH: 9
<212> TYPE: PRT
<213> ORGANISM: Artificial Sequence
<220> FEATURE:
<223> OTHER INFORMATION: Synthetic zalifrelimab light chain CDR3

<400> SEQUENCE: 237

Gln Gln Tyr Gly Ser Ser Pro Trp Thr
1               5
```

SYSTEMS AND METHODS FOR COORDINATING MANUFACTURING OF CELLS FOR PATIENT-SPECIFIC IMMUNOTHERAPY

CROSS-REFERENCE TO RELATED APPLICATIONS

This application is a continuation of U.S. patent application Ser. No. 17/238,092, filed on Apr. 22, 2021, which claims priority to U.S. Provisional Application No. 63/013,942, filed on Apr. 22, 2020, U.S. Provisional Application No. 63/155,711, filed Mar. 2, 2021, and U.S. Provisional Application No. 63/159,806, filed Mar. 11, 2021, each of which is incorporated herein by reference in its entirety for all purposes.

BACKGROUND

Treatment of bulky, refractory cancers using adoptive transfer of tumor infiltrating lymphocytes (TILs) represents a powerful approach to therapy for patients with poor prognoses. Gattinoni, et al., *Nat. Rev. Immunol.* 2006, 6, 383-393. A large number of TILs are required for successful immunotherapy, and a robust and reliable process is needed for commercialization. This has been a challenge to achieve because of technical, logistical, and regulatory issues with cell expansion. IL-2-based TIL expansion followed by a "rapid expansion process" (REP) has become a preferred method for TIL expansion because of its speed and efficiency. Dudley, et al., *Science* 2002, 298, 850-54; Dudley, et al., *J. Clin. Oncol.* 2005, 23, 2346-57; Dudley, et al., *J. Clin. Oncol.* 2008, 26, 5233-39; Riddell, et al., *Science* 1992, 257, 238-41; Dudley, et al., *J. Immunother.* 2003, 26, 332-42. REP can result in a 1,000-fold expansion of TILs over a 14-day period, although it requires a large excess (e.g., 200-fold) of irradiated allogeneic peripheral blood mononuclear cells (PBMCs, also known as mononuclear cells (MNCs)), often from multiple donors, as feeder cells, as well as anti-CD3 antibody (OKT3) and high doses of IL-2. Dudley, et al., *J. Immunother.* 2003, 26, 332-42. TILs that have undergone an REP procedure have produced successful adoptive cell therapy following host immunosuppression in patients with melanoma.

BRIEF DESCRIPTION OF DRAWINGS

FIG. 2A shows the timeline for a GEN 3 process for TIL manufacturing.

FIG. 2B shows a comparison between a 2A process and an embodiment of a GEN 3 process for TIL manufacturing.

FIG. 2C shows a comparison between an embodiment of a GEN 3, an embodiment of a GEN 3.1 process, and an alternate embodiment of a GEN 3.1 process for TIL manufacturing.

FIG. 3H is a table showing various types of labels generated during the process of manufacturing cell therapy product in accordance with some embodiments.

FIGS. 3K-3P are representative screenshot images of tumor procurement forms in accordance with some embodiments.

FIG. 6 shows a comparison between the 1C process and an embodiment of the 2A process for TIL manufacturing.

FIG. 9 shows an exemplary Process 2A chart providing an overview of Steps A through F.

FIG. 10 shows a comparison table of Steps A through F from exemplary embodiments of process 1C and process 2A.

FIG. 11 shows a detailed comparison of an embodiment of process 1C and an embodiment of process 2A.

BRIEF DESCRIPTION OF THE SEQUENCE LISTING

Figure 1:
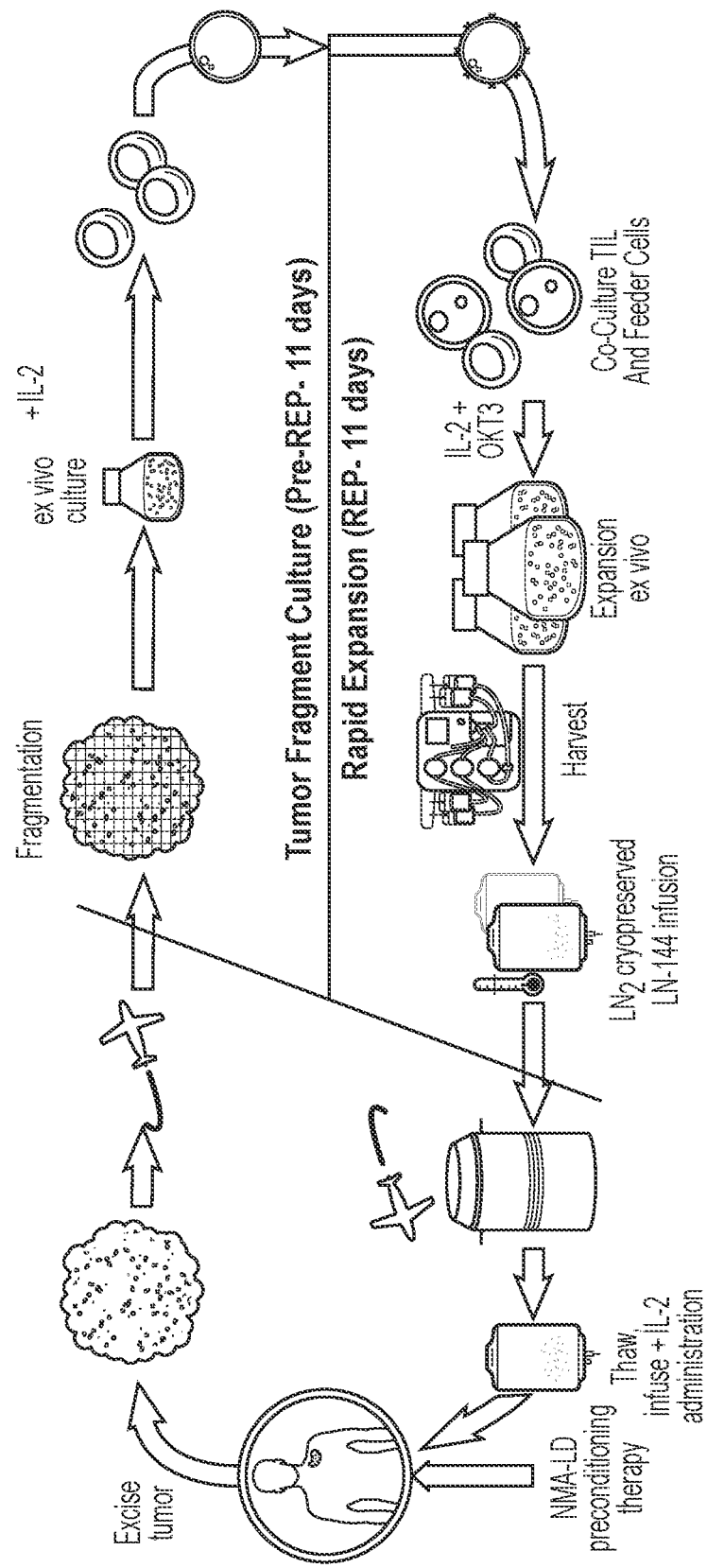
FIG. 1 schematically depicts various stages in a treatment of a patient using adoptive cell therapy using TILs including various steps for manufacturing allogenic TILs.

SEQ ID NO:1 is the amino acid sequence of the heavy chain of muromonab.

SEQ ID NO:2 is the amino acid sequence of the light chain of muromonab.

SEQ ID NO:3 is the amino acid sequence of a recombinant human IL-2 protein.

SEQ ID NO:4 is the amino acid sequence of aldesleukin.

SEQ ID NO:5 is an IL-2 form.

SEQ ID NO:6 is the amino acid sequence of nemvaleukin alfa.

SEQ ID NO:7 is an IL-2 form.

SEQ ID NO:8 is a mucin domain polypeptide.

SEQ ID NO:9 is the amino acid sequence of a recombinant human IL-4 protein.

SEQ ID NO:10 is the amino acid sequence of a recombinant human IL-7 protein.

SEQ ID NO:11 is the amino acid sequence of a recombinant human IL-15 protein.

SEQ ID NO:12 is the amino acid sequence of a recombinant human IL-21 protein.

SEQ ID NO:13 is an IL-2 sequence.

SEQ ID NO:14 is an IL-2 mutein sequence.

SEQ ID NO:15 is an TL-2 mutein sequence.

SEQ ID NO:16 is the HCDR1_IL-2 for IgG.IL2R67A.H1.
SEQ ID NO:17 is the HCDR2 for IgG.IL2R67A.H1.
SEQ ID NO:18 is the HCDR3 for IgG.IL2R67A.H1.
SEQ ID NO:19 is the HCDR1_IL-2 kabat for IgG.IL2R67A.H1.
SEQ ID NO:20 is the HCDR2 kabat for IgG.IL2R67A.H1.
SEQ ID NO:21 is the HCDR3 kabat for IgG.IL2R67A.H1.
SEQ ID NO:22 is the HCDR1_IL-2 clothia for IgG.IL2R67A.H1.
SEQ ID NO:23 is the HCDR2 clothia for IgG.IL2R67A.H1.
SEQ ID NO:24 is the HCDR3 clothia for IgG.IL2R67A.H1.
SEQ ID NO:25 is the HCDR1_IL-2 IMGT for IgG.IL2R67A.H1.
SEQ ID NO:26 is the HCDR2 IMGT for IgG.IL2R67A.H1.
SEQ ID NO:27 is the HCDR3 IMGT for IgG.IL2R67A.H1.
SEQ ID NO:28 is the $V_H$ chain for IgG.IL2R67A.H1.
SEQ ID NO:29 is the heavy chain for IgG.IL2R67A.H1.
SEQ ID NO:30 is the LCDR1 kabat for IgG.IL2R67A.H1.
SEQ ID NO:31 is the LCDR2 kabat for IgG.IL2R67A.H1.
SEQ ID NO:32 is the LCDR3 kabat for IgG.IL2R67A.H1.
SEQ ID NO:33 is the LCDR1 chothia for IgG.IL2R67A.H1.
SEQ ID NO:34 is the LCDR2 chothia for IgG.IL2R67A.H1.
SEQ ID NO:35 is the LCDR3 chothia for IgG.IL2R67A.H1.
SEQ ID NO:36 is a $V_L$ chain.
SEQ ID NO:37 is a light chain.
SEQ ID NO:38 is a light chain.
SEQ ID NO:39 is a light chain.
SEQ ID NO:40 is the amino acid sequence of human 4-1BB.
SEQ ID NO:41 is the amino acid sequence of murine 4-1BB.
SEQ ID NO:42 is the heavy chain for the 4-1BB agonist monoclonal antibody utomilumab (PF-05082566).
SEQ ID NO:43 is the light chain for the 4-1BB agonist monoclonal antibody utomilumab (PF-05082566).
SEQ ID NO:44 is the heavy chain variable region ($V_H$) for the 4-1BB agonist monoclonal antibody utomilumab (PF-05082566).
SEQ ID NO:45 is the light chain variable region ($V_L$) for the 4-1BB agonist monoclonal antibody utomilumab (PF-05082566).
SEQ ID NO:46 is the heavy chain CDR1 for the 4-1BB agonist monoclonal antibody utomilumab (PF-05082566).
SEQ ID NO:47 is the heavy chain CDR2 for the 4-1BB agonist monoclonal antibody utomilumab (PF-05082566).
SEQ ID NO:48 is the heavy chain CDR3 for the 4-1BB agonist monoclonal antibody utomilumab (PF-05082566).
SEQ ID NO:49 is the light chain CDR1 for the 4-1BB agonist monoclonal antibody utomilumab (PF-05082566).
SEQ ID NO:50 is the light chain CDR2 for the 4-1BB agonist monoclonal antibody utomilumab (PF-05082566).
SEQ ID NO:51 is the light chain CDR3 for the 4-1BB agonist monoclonal antibody utomilumab (PF-05082566).
SEQ ID NO:52 is the heavy chain for the 4-1BB agonist monoclonal antibody urelumab (BMS-663513).
SEQ ID NO:53 is the light chain for the 4-1BB agonist monoclonal antibody urelumab (BMS-663513).
SEQ ID NO:54 is the heavy chain variable region (VH) for the 4-1BB agonist monoclonal antibody urelumab (BMS-663513).
SEQ ID NO:55 is the light chain variable region (VL) for the 4-1BB agonist monoclonal antibody urelumab (BMS-663513).
SEQ ID NO:56 is the heavy chain CDR1 for the 4-1BB agonist monoclonal antibody urelumab (BMS-663513).
SEQ ID NO:57 is the heavy chain CDR2 for the 4-1BB agonist monoclonal antibody urelumab (BMS-663513).
SEQ ID NO:58 is the heavy chain CDR3 for the 4-1BB agonist monoclonal antibody urelumab (BMS-663513).
SEQ ID NO:59 is the light chain CDR1 for the 4-1BB agonist monoclonal antibody urelumab (BMS-663513).
SEQ ID NO:60 is the light chain CDR2 for the 4-1BB agonist monoclonal antibody urelumab (BMS-663513).
SEQ ID NO:61 is the light chain CDR3 for the 4-1BB agonist monoclonal antibody urelumab (BMS-663513).
SEQ ID NO:62 is an Fc domain for a TNFRSF agonist fusion protein.
SEQ ID NO:63 is a linker for a TNFRSF agonist fusion protein.
SEQ ID NO:64 is a linker for a TNFRSF agonist fusion protein.
SEQ ID NO:65 is a linker for a TNFRSF agonist fusion protein.
SEQ ID NO:66 is a linker for a TNFRSF agonist fusion protein.
SEQ ID NO:67 is a linker for a TNFRSF agonist fusion protein.
SEQ ID NO:68 is a linker for a TNFRSF agonist fusion protein.
SEQ ID NO:69 is a linker for a TNFRSF agonist fusion protein.
SEQ ID NO:70 is a linker for a TNFRSF agonist fusion protein.
SEQ ID NO:71 is a linker for a TNFRSF agonist fusion protein.
SEQ ID NO:72 is a linker for a TNFRSF agonist fusion protein.
SEQ ID NO:73 is an Fe domain for a TNFRSF agonist fusion protein.
SEQ ID NO:74 is a linker for a TNFRSF agonist fusion protein.
SEQ ID NO:75 is a linker for a TNFRSF agonist fusion protein.
SEQ ID NO:76 is a linker for a TNFRSF agonist fusion protein.
SEQ ID NO:77 is a 4-1BB ligand (4-1BBL) amino acid sequence.
SEQ ID NO:78 is a soluble portion of 4-1BBL polypeptide.
SEQ ID NO:79 is a heavy chain variable region ($V_H$) for the 4-1BB agonist antibody 4B4-1-1 version 1.
SEQ ID NO:80 is a light chain variable region ($V_L$) for the 4-1BB agonist antibody 4B4-1-1 version 1.
SEQ ID NO:81 is a heavy chain variable region ($V_H$) for the 4-1BB agonist antibody 4B4-1-1 version 2.
SEQ ID NO:82 is a light chain variable region ($V_L$) for the 4-1BB agonist antibody 4B4-1-1 version 2.
SEQ ID NO:83 is a heavy chain variable region ($V_H$) for the 4-1BB agonist antibody H39E3-2.

SEQ ID NO:84 is a light chain variable region (V$_L$) for the 4-1BB agonist antibody H39E3-2.

SEQ ID NO:85 is the amino acid sequence of human OX40.

SEQ ID NO:86 is the amino acid sequence of murine OX40.

SEQ ID NO:87 is the heavy chain for the OX40 agonist monoclonal antibody tavolixizumab (MEDI-0562).

SEQ ID NO:88 is the light chain for the OX40 agonist monoclonal antibody tavolixizumab (MEDI-0562).

SEQ ID NO:89 is the heavy chain variable region (V$_H$) for the OX40 agonist monoclonal antibody tavolixizumab (MEDI-0562).

SEQ ID NO:90 is the light chain variable region (V$_L$) for the OX40 agonist monoclonal antibody tavolixizumab (MEDI-0562).

SEQ ID NO:91 is the heavy chain CDR1 for the OX40 agonist monoclonal antibody tavolixizumab (MEDI-0562).

SEQ ID NO:92 is the heavy chain CDR2 for the OX40 agonist monoclonal antibody tavolixizumab (MEDI-0562).

SEQ ID NO:93 is the heavy chain CDR3 for the OX40 agonist monoclonal antibody tavolixizumab (MEDI-0562).

SEQ ID NO:94 is the light chain CDR1 for the OX40 agonist monoclonal antibody tavolixizumab (MEDI-0562).

SEQ ID NO:95 is the light chain CDR2 for the OX40 agonist monoclonal antibody tavolixizumab (MEDI-0562).

SEQ ID NO:96 is the light chain CDR3 for the OX40 agonist monoclonal antibody tavolixizumab (MEDI-0562).

SEQ ID NO:97 is the heavy chain for the OX40 agonist monoclonal antibody 11D4.

SEQ ID NO:98 is the light chain for the OX40 agonist monoclonal antibody 11D4.

SEQ ID NO:99 is the heavy chain variable region (V$_H$) for the OX40 agonist monoclonal antibody 11D4.

SEQ ID NO:100 is the light chain variable region (V$_L$) for the OX40 agonist monoclonal antibody 11D4.

SEQ ID NO:101 is the heavy chain CDR1 for the OX40 agonist monoclonal antibody 111D4.

SEQ ID NO:102 is the heavy chain CDR2 for the OX40 agonist monoclonal antibody 11D4.

SEQ ID NO:103 is the heavy chain CDR3 for the OX40 agonist monoclonal antibody 11D4.

SEQ ID NO:104 is the light chain CDR1 for the OX40 agonist monoclonal antibody 111D4.

SEQ ID NO:105 is the light chain CDR2 for the OX40 agonist monoclonal antibody 11D4.

SEQ ID NO:106 is the light chain CDR3 for the OX40 agonist monoclonal antibody 11D4.

SEQ ID NO:107 is the heavy chain for the OX40 agonist monoclonal antibody 18D8.

SEQ ID NO:108 is the light chain for the OX40 agonist monoclonal antibody 18D8.

SEQ ID NO:109 is the heavy chain variable region (V$_H$) for the OX40 agonist monoclonal antibody 18D8.

SEQ ID NO:110 is the light chain variable region (V$_L$) for the OX40 agonist monoclonal antibody 18D8.

SEQ ID NO:111 is the heavy chain CDR1 for the OX40 agonist monoclonal antibody 18D8.

SEQ ID NO:112 is the heavy chain CDR2 for the OX40 agonist monoclonal antibody 18D8.

SEQ ID NO:113 is the heavy chain CDR3 for the OX40 agonist monoclonal antibody 18D8.

SEQ ID NO: 114 is the light chain CDR1 for the OX40 agonist monoclonal antibody 18D8.

SEQ ID NO:115 is the light chain CDR2 for the OX40 agonist monoclonal antibody 18D8.

SEQ ID NO:116 is the light chain CDR3 for the OX40 agonist monoclonal antibody 18D8.

SEQ ID NO:117 is the heavy chain variable region (V$_H$) for the OX40 agonist monoclonal antibody Hu119-122.

SEQ ID NO:118 is the light chain variable region (V$_L$) for the OX40 agonist monoclonal antibody Hu119-122.

SEQ ID NO:119 is the heavy chain CDR1 for the OX40 agonist monoclonal antibody Hu119-122.

SEQ ID NO:120 is the heavy chain CDR2 for the OX40 agonist monoclonal antibody Hu119-122.

SEQ ID NO:121 is the heavy chain CDR3 for the OX40 agonist monoclonal antibody Hu119-122.

SEQ ID NO:122 is the light chain CDR1 for the OX40 agonist monoclonal antibody Hu119-122.

SEQ ID NO:123 is the light chain CDR2 for the OX40 agonist monoclonal antibody Hu119-122.

SEQ ID NO:124 is the light chain CDR3 for the OX40 agonist monoclonal antibody Hu119-122.

SEQ ID NO:125 is the heavy chain variable region (V$_H$) for the OX40 agonist monoclonal antibody Hu106-222.

SEQ ID NO:126 is the light chain variable region (V$_L$) for the OX40 agonist monoclonal antibody Hu106-222.

SEQ ID NO:127 is the heavy chain CDR1 for the OX40 agonist monoclonal antibody Hu106-222.

SEQ ID NO:128 is the heavy chain CDR2 for the OX40 agonist monoclonal antibody Hu106-222.

SEQ ID NO:129 is the heavy chain CDR3 for the OX40 agonist monoclonal antibody Hu106-222.

SEQ ID NO:130 is the light chain CDR1 for the OX40 agonist monoclonal antibody Hu106-222.

SEQ ID NO:131 is the light chain CDR2 for the OX40 agonist monoclonal antibody Hu106-222.

SEQ ID NO:132 is the light chain CDR3 for the OX40 agonist monoclonal antibody Hu106-222.

SEQ ID NO:133 is an OX40 ligand (OX40L) amino acid sequence.

SEQ ID NO:134 is a soluble portion of OX40L polypeptide.

SEQ ID NO:135 is an alternative soluble portion of OX40L polypeptide.

SEQ ID NO:136 is the heavy chain variable region (V$_H$) for the OX40 agonist monoclonal antibody 008.

SEQ ID NO:137 is the light chain variable region (V$_L$) for the OX40 agonist monoclonal antibody 008.

SEQ ID NO:138 is the heavy chain variable region (V$_H$) for the OX40 agonist monoclonal antibody 011.

SEQ ID NO:139 is the light chain variable region (V$_L$) for the OX40 agonist monoclonal antibody 011.

SEQ ID NO:140 is the heavy chain variable region (V$_H$) for the OX40 agonist monoclonal antibody 021.

SEQ ID NO:141 is the light chain variable region (V$_L$) for the OX40 agonist monoclonal antibody 021.

SEQ ID NO:142 is the heavy chain variable region (V$_H$) for the OX40 agonist monoclonal antibody 023.

SEQ ID NO:143 is the light chain variable region (V$_L$) for the OX40 agonist monoclonal antibody 023.

SEQ ID NO:144 is the heavy chain variable region (V$_H$) for an OX40 agonist monoclonal antibody.

SEQ ID NO:145 is the light chain variable region (V$_L$) for an OX40 agonist monoclonal antibody.

SEQ ID NO:146 is the heavy chain variable region (V$_H$) for an OX40 agonist monoclonal antibody.

SEQ ID NO:147 is the light chain variable region (V$_L$) for an OX40 agonist monoclonal antibody.

SEQ ID NO:148 is the heavy chain variable region (V$_H$) for a humanized OX40 agonist monoclonal antibody.

SEQ ID NO:149 is the heavy chain variable region ($V_H$) for a humanized OX40 agonist monoclonal antibody.

SEQ ID NO:150 is the light chain variable region ($V_L$) for a humanized OX40 agonist monoclonal antibody.

SEQ ID NO:151 is the light chain variable region ($V_L$) for a humanized OX40 agonist monoclonal antibody.

SEQ ID NO:152 is the heavy chain variable region ($V_H$) for a humanized OX40 agonist monoclonal antibody.

SEQ ID NO:153 is the heavy chain variable region ($V_H$) for a humanized OX40 agonist monoclonal antibody.

SEQ ID NO:154 is the light chain variable region ($V_L$) for a humanized OX40 agonist monoclonal antibody.

SEQ ID NO:155 is the light chain variable region ($V_L$) for a humanized OX40 agonist monoclonal antibody.

SEQ ID NO:156 is the heavy chain variable region ($V_H$) for an OX40 agonist monoclonal antibody.

SEQ ID NO:157 is the light chain variable region ($V_L$) for an OX40 agonist monoclonal antibody.

SEQ ID NO:158 is the heavy chain amino acid sequence of the PD-1 inhibitor nivolumab.

SEQ ID NO:159 is the light chain amino acid sequence of the PD-1 inhibitor nivolumab.

SEQ ID NO:160 is the heavy chain variable region ($V_H$) amino acid sequence of the PD-1 inhibitor nivolumab.

SEQ ID NO:161 is the light chain variable region ($V_L$) amino acid sequence of the PD-1 inhibitor nivolumab.

SEQ ID NO:162 is the heavy chain CDR1 amino acid sequence of the PD-1 inhibitor nivolumab.

SEQ ID NO:163 is the heavy chain CDR2 amino acid sequence of the PD-1 inhibitor nivolumab.

SEQ ID NO:164 is the heavy chain CDR3 amino acid sequence of the PD-1 inhibitor nivolumab.

SEQ ID NO:165 is the light chain CDR1 amino acid sequence of the PD-1 inhibitor nivolumab.

SEQ ID NO:166 is the light chain CDR2 amino acid sequence of the PD-1 inhibitor nivolumab.

SEQ ID NO:167 is the light chain CDR3 amino acid sequence of the PD-1 inhibitor nivolumab.

SEQ ID NO:168 is the heavy chain amino acid sequence of the PD-1 inhibitor pembrolizumab.

SEQ ID NO:169 is the light chain amino acid sequence of the PD-1 inhibitor pembrolizumab.

SEQ ID NO:170 is the heavy chain variable region ($V_H$) amino acid sequence of the PD-1 inhibitor pembrolizumab.

SEQ ID NO:171 is the light chain variable region ($V_L$) amino acid sequence of the PD-1 inhibitor pembrolizumab.

SEQ ID NO:172 is the heavy chain CDR1 amino acid sequence of the PD-1 inhibitor pembrolizumab.

SEQ ID NO:173 is the heavy chain CDR2 amino acid sequence of the PD-1 inhibitor pembrolizumab.

SEQ ID NO:174 is the heavy chain CDR3 amino acid sequence of the PD-1 inhibitor pembrolizumab.

SEQ ID NO:175 is the light chain CDR1 amino acid sequence of the PD-1 inhibitor pembrolizumab.

SEQ ID NO:176 is the light chain CDR2 amino acid sequence of the PD-1 inhibitor pembrolizumab.

SEQ ID NO:177 is the light chain CDR3 amino acid sequence of the PD-1 inhibitor pembrolizumab.

SEQ ID NO:178 is the heavy chain amino acid sequence of the PD-L1 inhibitor durvalumab.

SEQ ID NO:179 is the light chain amino acid sequence of the PD-L1 inhibitor durvalumab.

SEQ ID NO:180 is the heavy chain variable region ($V_H$) amino acid sequence of the PD-L1 inhibitor durvalumab.

SEQ ID NO:181 is the light chain variable region ($V_L$) amino acid sequence of the PD-L1 inhibitor durvalumab.

SEQ ID NO:182 is the heavy chain CDR1 amino acid sequence of the PD-L1 inhibitor durvalumab.

SEQ ID NO:183 is the heavy chain CDR2 amino acid sequence of the PD-L1 inhibitor durvalumab.

SEQ ID NO:184 is the heavy chain CDR3 amino acid sequence of the PD-L1 inhibitor durvalumab.

SEQ ID NO:185 is the light chain CDR1 amino acid sequence of the PD-L1 inhibitor durvalumab.

SEQ ID NO:186 is the light chain CDR2 amino acid sequence of the PD-L1 inhibitor durvalumab.

SEQ ID NO:187 is the light chain CDR3 amino acid sequence of the PD-L1 inhibitor durvalumab.

SEQ ID NO:188 is the heavy chain amino acid sequence of the PD-L1 inhibitor avelumab.

SEQ ID NO:189 is the light chain amino acid sequence of the PD-L1 inhibitor avelumab.

SEQ ID NO:190 is the heavy chain variable region ($V_H$) amino acid sequence of the PD-L1 inhibitor avelumab.

SEQ ID NO:191 is the light chain variable region ($V_L$) amino acid sequence of the PD-L1 inhibitor avelumab.

SEQ ID NO:192 is the heavy chain CDR1 amino acid sequence of the PD-L1 inhibitor avelumab.

SEQ ID NO:193 is the heavy chain CDR2 amino acid sequence of the PD-L1 inhibitor avelumab.

SEQ ID NO:194 is the heavy chain CDR3 amino acid sequence of the PD-L1 inhibitor avelumab.

SEQ ID NO:195 is the light chain CDR1 amino acid sequence of the PD-L1 inhibitor avelumab.

SEQ ID NO:196 is the light chain CDR2 amino acid sequence of the PD-L1 inhibitor avelumab.

SEQ ID NO:197 is the light chain CDR3 amino acid sequence of the PD-L1 inhibitor avelumab.

SEQ ID NO:198 is the heavy chain amino acid sequence of the PD-L1 inhibitor atezolizumab.

SEQ ID NO:199 is the light chain amino acid sequence of the PD-L1 inhibitor atezolizumab.

SEQ ID NO:200 is the heavy chain variable region ($V_H$) amino acid sequence of the PD-L1 inhibitor atezolizumab.

SEQ ID NO:201 is the light chain variable region ($V_L$) amino acid sequence of the PD-L1 inhibitor atezolizumab.

SEQ ID NO:202 is the heavy chain CDR1 amino acid sequence of the PD-L1 inhibitor atezolizumab.

SEQ ID NO:203 is the heavy chain CDR2 amino acid sequence of the PD-L1 inhibitor atezolizumab.

SEQ ID NO:204 is the heavy chain CDR3 amino acid sequence of the PD-L1 inhibitor atezolizumab.

SEQ ID NO:205 is the light chain CDR1 amino acid sequence of the PD-L1 inhibitor atezolizumab.

SEQ ID NO:206 is the light chain CDR2 amino acid sequence of the PD-L1 inhibitor atezolizumab.

SEQ ID NO:207 is the light chain CDR3 amino acid sequence of the PD-L1 inhibitor atezolizumab.

SEQ ID NO:208 is the heavy chain amino acid sequence of the CTLA-4 inhibitor ipilimumab.

SEQ ID NO:209 is the light chain amino acid sequence of the CTLA-4 inhibitor ipilimumab.

SEQ ID NO:210 is the heavy chain variable region ($V_H$) amino acid sequence of the CTLA-4 inhibitor ipilimumab.

SEQ ID NO:211 is the light chain variable region ($V_L$) amino acid sequence of the CTLA-4 inhibitor ipilimumab.

SEQ ID NO:212 is the heavy chain CDR1 amino acid sequence of the CTLA-4 inhibitor ipilimumab.

SEQ ID NO:213 is the heavy chain CDR2 amino acid sequence of the CTLA-4 inhibitor ipilimumab.

SEQ ID NO:214 is the heavy chain CDR3 amino acid sequence of the CTLA-4 inhibitor ipilimumab.

SEQ ID NO:215 is the light chain CDR1 amino acid sequence of the CTLA-4 inhibitor ipilimumab.

SEQ ID NO:216 is the light chain CDR2 amino acid sequence of the CTLA-4 inhibitor ipilimumab.

SEQ ID NO:217 is the light chain CDR3 amino acid sequence of the CTLA-4 inhibitor ipilimumab.

SEQ ID NO:218 is the heavy chain amino acid sequence of the CTLA-4 inhibitor tremelimumab.

SEQ ID NO:219 is the light chain amino acid sequence of the CTLA-4 inhibitor tremelimumab.

SEQ ID NO:220 is the heavy chain variable region ($V_H$) amino acid sequence of the CTLA-4 inhibitor tremelimumab.

SEQ ID NO:221 is the light chain variable region ($V_L$) amino acid sequence of the CTLA-4 inhibitor tremelimumab.

SEQ ID NO:222 is the heavy chain CDR1 amino acid sequence of the CTLA-4 inhibitor tremelimumab.

SEQ ID NO:223 is the heavy chain CDR2 amino acid sequence of the CTLA-4 inhibitor tremelimumab.

SEQ ID NO:224 is the heavy chain CDR3 amino acid sequence of the CTLA-4 inhibitor tremelimumab.

SEQ ID NO:225 is the light chain CDR1 amino acid sequence of the CTLA-4 inhibitor tremelimumab.

SEQ ID NO:226 is the light chain CDR2 amino acid sequence of the CTLA-4 inhibitor tremelimumab.

SEQ ID NO:227 is the light chain CDR3 amino acid sequence of the CTLA-4 inhibitor tremelimumab.

SEQ ID NO:228 is the heavy chain amino acid sequence of the CTLA-4 inhibitor zalifrelimab.

SEQ ID NO:229 is the light chain amino acid sequence of the CTLA-4 inhibitor zalifrelimab.

SEQ ID NO:230 is the heavy chain variable region ($V_H$) amino acid sequence of the CTLA-4 inhibitor zalifrelimab.

SEQ ID NO:231 is the light chain variable region ($V_L$) amino acid sequence of the CTLA-4 inhibitor zalifrelimab.

SEQ ID NO:232 is the heavy chain CDR1 amino acid sequence of the CTLA-4 inhibitor zalifrelimab.

SEQ ID NO:233 is the heavy chain CDR2 amino acid sequence of the CTLA-4 inhibitor zalifrelimab.

SEQ ID NO:234 is the heavy chain CDR3 amino acid sequence of the CTLA-4 inhibitor zalifrelimab.

SEQ ID NO:235 is the light chain CDR1 amino acid sequence of the CTLA-4 inhibitor zalifrelimab.

SEQ ID NO:236 is the light chain CDR2 amino acid sequence of the CTLA-4 inhibitor zalifrelimab.

SEQ ID NO:237 is the light chain CDR3 amino acid sequence of the CTLA-4 inhibitor zalifrelimab.

DETAILED DESCRIPTION

I. Introduction

Adoptive cell therapy utilizing TILs cultured ex vivo by the Rapid Expansion Protocol (REP) has produced successful adoptive cell therapy following host immunosuppression in patients with melanoma. For example, it has been found that in some cases, lymphodepletion prior to adoptive transfer of tumor-specific T lymphocytes plays a key role in enhancing treatment efficacy by eliminating regulatory T-cells and competing elements of the immune system ("cytokine sinks"). In some cases, the efficacy of the ACT may be increased by pre-treating the patient receiving the ACT with non-myeloablative chemotherapy prior to an infusion of TILs, e.g., 28-25 days prior to TIL infusion. It has also been found that an IL-2 treatment regimen following TIL infusion may improve the chances of success of the therapy. The timing and duration of these pre-infusion treatment and post-infusion treatment determines the ultimate efficacy of entire therapeutic regimen.

Thus, scheduling various treatment regimens depends on the timing and duration of TIL manufacturing process which itself is dependent on acceptance parameters for the final product. Current infusion acceptance parameters rely on readouts of the composition of TILs (e.g., CD28, CD8, or CD4 positivity) and on fold expansion and viability of the expanded TIL product (also referred to herein as a REP product). The fold expansion and viability of the REP product, in turn, depends on various parameters measured during the expansion process. Such variation in the output and timing of an acceptable REP product for infusion poses challenges in logistics of the transport of the tumor to the manufacturing facility, transfer of the REP product and the scheduling of various patient treatment events during the TIL manufacturing process.

Moreover, various parameters such as cell viability and cell count during different stages of the TIL manufacturing process determine the duration of subsequent stages so that an acceptable viability, numerical fold and final cell count is obtained at the end of the TIL manufacturing process.

In addition, it is important to keep track of the biological material from the time it is removed from the patient to the time it is infused into the patient, including throughout the TIL manufacturing process, to avoid manufacturing delays, mislabeling of material and misidentification of patient, and thereby improving patient safety.

The present disclosure provides a framework for coordinating manufacturing process of an expanded cell therapy product for a patient and the various patient treatment events by dynamically scheduling various patient treatment events based on various measured parameters during different stages of the manufacturing process.

For example, in an embodiment, a method for coordinating the manufacturing of expanded T-cells for a patient may include receiving, by a computing, a cell order request to expand T-cells for the patient; generating, by the computing device, a patient-specific identifier or cell-order identifier associated with the cell order request; and initiating a process to expand T-cells. The process to expand T-cells may include performing, at a clinical facility, a procedure on the patient to obtain T-cells from the patient and transferring the obtained T-cells to a manufacturing facility. After receiving the obtained T-cells at the manufacturing facility, patient treatment events are dynamically scheduled by a computing device. The dynamic scheduling is dependent on acceptance parameters in subsequently obtained expansion T-cells. Expansion of T-cells from at least some of the obtained T-cells using a cell expansion technique is initiated and acceptance parameters in the expansion T-cells are determined.

In another embodiment, a method for coordinating the manufacturing of an expanded cell therapy product for a patient may include receiving, by a computing device, a cell order request to expand the cell therapy product for the patient; generating, by the computing device, a patient-specific identifier including a cell order identifier associated with the cell order request; and initiating a process to expand the cell therapy product. The process to expand the cell therapy product may include performing, at a clinical facility, a procedure on the patient to obtain a solid tumor from the patient and transferring the obtained solid tumor to a manufacturing facility. After receiving the solid tumor at the manufacturing facility, the patient treatment events are dynamically scheduled by the computing device. The dynamic scheduling is dependent on acceptance parameters for subsequently obtained expansion cell therapy product. Expansion of the cell therapy product from at least some of the obtained solid tumor using a cell expansion technique is initiated and acceptance parameters for the expansion cell therapy product are determined at a first time point and at a second time point subsequent to the first time point. It is determined whether the acceptance parameters for the expansion cell therapy product meet certain acceptance criteria at the first time point and at the second time point. If the acceptance parameters at the first time point meet the acceptance criteria, the expansion of the cell therapy product is continued up to the second time point. If the acceptance parameters for the expansion cell therapy product do not meet the acceptance criteria at the second time point, it is determined whether re-performing the expansion of the cell therapy product using the cell expansion technique is possible from the first time point based on the acceptance parameters at the second time point. If re-performing the expansion is determined to be possible, the expansion of the cell therapy product from at least some of the cell therapy product obtained at the second time point using the cell expansion technique from the first time point. A time of completion of the expansion of the cell therapy product following the re-performing of the expansion of the cell therapy product from the first time point is estimated. The patient treatment events are rescheduled based on the estimated time of completion of the expansion of the cell therapy product and a timing of patient treatment events prior to or subsequent to an infusion of the expanded cell therapy product in the patient. The subsequent expansion of the cell therapy product is completed from the first time point.

The present disclosure additionally provides methods and systems for accurately tracking the biological material from the time it extracted from the patient until the time it is infused back in the patient. In particular, the methods and systems disclosed herein facilitate maintenance of a chain of identity and a chain of custody for the biological material.

For example, in an embodiment, a method of tracking a patient's biological material may include receiving a cell order request for manufacturing biological material for the patient. Upon receiving the cell order request, a computing device generates a patient-specific identifier associated with the cell order request. The patient-specific identifier may include one or more of a patient identifier, a cell request order identifier, an order code and a cell order lot number. The patient's biological material is then tracked during shipping the biological material from a clinical facility where the biological material is extracted from the patient to a manufacturing facility, at the manufacturing facility during the manufacturing process and during shipping the manufactured biological material from the manufacturing facility to a clinical facility where the manufactured biological material is and back to the clinical facility where the manufactured biological material is infused into the patient using the patient-specific identifier. The tracking may include recording, by the computing device, a tracking event at each step from the shipping and manufacturing processes. The record of the tracking events comprises a chain of custody of the patient's biological material.

Unless defined otherwise, all technical and scientific terms used herein have the same meaning as is commonly understood by one of skill in the art to which this invention belongs. All patents and publications referred to herein are incorporated by reference in their entireties.

The term "in vivo" refers to an event that takes place in a subject's body.

The term "in vitro" refers to an event that takes places outside of a subject's body. In vitro assays encompass cell-based assays in which cells alive or dead are employed and may also encompass a cell-free assay in which no intact cells are employed.

The term "ex vivo" refers to an event which involves treating or performing a procedure on a cell, tissue and/or organ which has been removed from a subject's body. Aptly, the cell, tissue and/or organ may be returned to the subject's body in a method of surgery or treatment.

The term "rapid expansion" means an increase in the number of antigen-specific TILs of at least about 3-fold (or 4-, 5-, 6-, 7-, 8-, or 9-fold) over a period of a week, more preferably at least about 10-fold (or 20-, 30-, 40-, 50-, 60-, 70-, 80-, or 90-fold) over a period of a week, or most preferably at least about 100-fold over a period of a week. A number of rapid expansion protocols are outlined below.

By "tumor infiltrating lymphocytes" or "TILs" herein is meant a population of cells originally obtained as white blood cells that have left the bloodstream of a subject and migrated into a tumor. TILs include, but are not limited to, $CD8^+$ cytotoxic T-cells (lymphocytes), Th1 and Th17 $CD4^+$ T-cells, natural killer cells, dendritic cells and M1 macrophages. TILs include both primary and secondary TILs. "Primary TILs" are those that are obtained from patient tissue samples as outlined herein (sometimes referred to as "freshly obtained" or "freshly isolated"), and "secondary TILs" are any TIL cell populations that have been expanded or proliferated as discussed herein, including, but not limited to bulk TILs and expanded TILs ("REP TILs" or "post-REP TILs"). TIL cell populations can include genetically modified TILs.

By "population of cells" (including TILs) herein is meant a number of cells that share common traits. In general, populations generally range from $1 \times 10^6$ to $1 \times 10^{10}$ in number, with different TIL populations comprising different numbers. For example, initial growth of primary TILs in the presence of IL-2 results in a population of bulk TILs of roughly $1 \times 10^8$ cells. REP expansion is generally done to provide populations of $1.5 \times 10^9$ to $1.5 \times 10^{10}$ cells for infusion. In some embodiments, REP expansion is done to provide populations of $2.3 \times 10^{10}$-$13.7 \times 10^{10}$.

By "cryopreserved TILs" herein is meant that TILs, either primary, bulk, or expanded (REP TILs), are treated and stored in the range of about −150° C. to −60° C. General methods for cryopreservation are also described elsewhere herein, including in the Examples. For clarity, "cryopreserved TILs" are distinguishable from frozen tissue samples which may be used as a source of primary TILs.

By "thawed cryopreserved TILs" herein is meant a population of TILs that was previously cryopreserved and then treated to return to room temperature or higher, including but not limited to cell culture temperatures or temperatures wherein TILs may be administered to a patient.

TILs can generally be defined either biochemically, using cell surface markers, or functionally, by their ability to infiltrate tumors and effect treatment. TILs can be generally categorized by expressing one or more of the following biomarkers: CD4, CD8, TCR αβ, CD27, CD28, CD56, CCR7, CD45Ra, CD95, PD-1, and CD25. Additionally, and alternatively, TILs can be functionally defined by their ability to infiltrate solid tumors upon reintroduction into a patient.

The term "cryopreservation media" or "cryopreservation medium" refers to any medium that can be used for cryopreservation of cells. Such media can include media comprising 7% to 10% DMSO. Exemplary media include CryoStor CS10, Hyperthermasol, as well as combinations thereof. The term "CS10" refers to a cryopreservation medium which is obtained from Stemcell Technologies or from Biolife Solutions. The CS10 medium may be referred to by the trade name "CryoStor® CS10". The CS10 medium is a serum-free, animal component-free medium which comprises DMSO.

The term "central memory T-cell" refers to a subset of T-cells that in the human are CD45R0+ and constitutively express CCR7 ($CCR7^{hi}$) and CD62L ($CD62^{hi}$). The surface phenotype of central memory T-cells also includes TCR, CD3, CD127 (IL-7R), and IL-15R. Transcription factors for central memory T-cells include BCL-6, BCL-6B, MBD2, and BMI1. Central memory T-cells primarily secret IL-2 and CD40L as effector molecules after TCR triggering. Central memory T-cells are predominant in the CD4 compartment in blood, and in the human are proportionally enriched in lymph nodes and tonsils.

The term "effector memory T-cell" refers to a subset of human or mammalian T-cells that, like central memory T-cells, are CD45R0+, but have lost the constitutive expression of CCR7 ($CCR7^{lo}$) and are heterogeneous or low for CD62L expression ($CD62L^{lo}$). The surface phenotype of central memory T-cells also includes TCR, CD3, CD127 (IL-7R), and IL-15R. Transcription factors for central memory T-cells include BLIMP1. Effector memory T-cells rapidly secret high levels of inflammatory cytokines following antigenic stimulation, including interferon-γ, IL-4, and IL-5. Effector memory T-cells are predominant in the CD8 compartment in blood, and in the human are proportionally enriched in the lung, liver, and gut. $CD8^+$ effector memory T-cells carry large amounts of perforin.

The term "closed system" refers to a system that is closed to the outside environment. Any closed system appropriate for cell culture methods can be employed with the methods of the present invention. Closed systems include, for example, but are not limited to closed G-containers. Once a tumor segment is added to the closed system, the system is not opened to the outside environment until the TILs are ready to be administered to the patient.

The terms "fragmenting," "fragment," and "fragmented," as used herein to describe processes for disrupting a tumor, includes mechanical fragmentation methods such as crushing, slicing, dividing, and morcellating tumor tissue as well as any other method for disrupting the physical structure of tumor tissue.

The term "fine needle aspirate" or FNA refers to a type of biopsy procedure that can be employed for sampling or diagnostic procedures, including tumor sampling, in which a sample is taken but the tumor is not removed or resected. In fine needle aspiration, a hollow needle, for example 25-18 gauge, is inserted into the tumor or into an area containing the tumor and fluid and cells (including tissue) are obtained for further analysis or expansion, as described herein. With an FNA, the cells are removed without preserving the histological architecture of the tissue cells. An FNA can comprise TILs. In some instances, a fine needle aspiration biopsy is performed using an ultrasound-guided fine needle aspiration biopsy needle. FNA needles are commercially available from Becton Dickinson, Covidien, and the like.

The term "core biopsy" or "core needle biopsy" refers to a type of biopsy procedure that can be employed for sampling or diagnostic procedures, including tumor sampling, in which a sample is taken but the tumor is not removed or resected. In a core biopsy, a hollow needle, for example 16-11 gauge, is inserted into the tumor or into an area containing the tumor and fluid and cells (including tissue) are obtained for further analysis or expansion, as described herein. With a core biopsy, the cells can be removed with some preservation of the histological architecture of the tissue cells, given the larger needle size as compared to a FNA. The core biopsy needle is generally of a gauge size that is able to preserve at least some portion of the histological architecture of the tumor. A core biopsy can comprise TILs. In some instances, a core needle biopsy is performed using a biopsy instrument, a vacuum-assisted core-needle biopsy instrument, a steretactically guided core-needle biopsy instrument, an ultrasound-guided core-needle biopsy instrument, an MRI-guided core-needle biopsy instrument commercially available from Bard Medical, Becton Dickinson, and the like.

The terms "peripheral blood mononuclear cells" and "PBMCs" refers to a peripheral blood cell having a round nucleus, including lymphocytes (T-cells, B cells, NK cells) and monocytes. When used as antigen-presenting cells (PBMCs are a type of antigen-presenting cell), the peripheral blood mononuclear cells are irradiated allogeneic peripheral blood mononuclear cells.

The terms "peripheral blood lymphocytes" and "PBLs" refer to T-cells expanded from peripheral blood. In some embodiments, PBLs are separated from whole blood or apheresis product from a donor. In some embodiments, PBLs are separated from whole blood or apheresis product from a donor by positive or negative selection of a T-cell phenotype, such as the T-cell phenotype of CD3+ CD45+.

The term "anti-CD3 antibody" refers to an antibody or variant thereof, e.g., a monoclonal antibody and including human, humanized, chimeric or murine antibodies which are directed against the CD3 receptor in the T-cell antigen receptor of mature T-cells. Anti-CD3 antibodies include OKT-3, also known as muromonab. Anti-CD3 antibodies also include the UHCT1 clone, also known as T3 and CD3ε. Other anti-CD3 antibodies include, for example, otelixizumab, teplizumab, and visilizumab.

The term "OKT-3" (also referred to herein as "OKT3") refers to a monoclonal antibody or biosimilar or variant thereof, including human, humanized, chimeric, or murine antibodies, directed against the CD3 receptor in the T-cell antigen receptor of mature T-cells, and includes commercially-available forms such as OKT-3 (30 ng/mL, MACS GMP CD3 pure, Miltenyi Biotech, Inc., San Diego, CA, USA) and muromonab or variants, conservative amino acid substitutions, glycoforms, or biosimilars thereof. The amino acid sequences of the heavy and light chains of muromonab are given in Table 1 (SEQ ID NO:1 and SEQ ID NO:2). A hybridoma capable of producing OKT-3 is deposited with the American Type Culture Collection and assigned the ATCC accession number CRL 8001. A hybridoma capable of producing OKT-3 is also deposited with European Collection of Authenticated Cell Cultures (ECACC) and assigned Catalogue No. 86022706.

TABLE 1

Amino acid sequences of muromonab.

| Identifier | Sequence (One-Letter Amino Acid Symbols) | |
|---|---|---|
| SEQ ID NO: 1<br>Muromonab heavy<br>chain | QVQLQQSGAE LARPGASVKM SCKASGYTFT RYTMHWVKQR PGQGLEWIGY INPSRGYTNY<br>NQKFKDKATL TTDKSSSTAY MQLSSLTSED SAVYYCARYY DDHYCLDYWG QGTTLTVSSA<br>KTTAPSVYPL APVCGGTTGS SVTLGCLVKG YFPEPVTLTW NSGSLSSGVH TFPAVLQSDL<br>YTLSSSVTVT SSTWPSQSIT CNVAHPASST KVDKKIEPRP KSCDKTHTCP PCPAPELLGG<br>PSVFLFPPKP KDTLMISRTP EVTCVVVDVS HEDPEVKFNW YVDGVEVHNA KTKPREEQYN<br>STYRVVSVLT VLHQDWLNGK EYKCKVSNKA LPAPIEKTIS KAKGQPREPQ VYTLPPSRDE<br>LTKNQVSLTC LVKGFYPSDI AVEWESNGQP ENNYKTTPPV LDSDGSFFLY SKLTVDKSRW<br>QQGNVFSCSV MHEALHNHYT QKSLSLSPGK | 60<br>120<br>180<br>240<br>300<br>360<br>420<br>450 |
| SEQ ID NO: 2<br>Muromonab light<br>chain | QIVLTQSPAI MSASPGEKVT MTCSASSSVS YMNWYQQKSG TSPKRWIYDT SKLASGVPAH<br>FRGSGSGTSY SLTISGMEAE DAATYYCQQW SSNPFTFGSG TKLEINRADT APTVSIFPPS<br>SEQLTSGGAS VVCFLNNFYP KDINVKWKID GSERQNGVLN SWTDQDSKDS TYSMSSTLTL<br>TKDEYERHNS YTCEATHKTS TSPIVKSFNR NEC | 60<br>120<br>180<br>213 |

The term "IL-2" (also referred to herein as "IL2") refers to the T cell growth factor known as interleukin-2 and includes all forms of IL-2 including human and mammalian forms, conservative amino acid substitutions, glycoforms, biosimilars, and variants thereof. IL-2 is described, e.g., in Nelson, *J. Immunol.* 2004, 172, 3983-88 and Malek, *Annu. Rev. Immunol.* 2008, 26, 453-79, the disclosures of which are incorporated by reference herein. The amino acid sequence of recombinant human IL-2 suitable for use in the invention is given in Table 2 (SEQ ID NO:3). For example, the term IL-2 encompasses human, recombinant forms of IL-2 such as aldesleukin (PROLEUKIN, available commercially from multiple suppliers in 22 million IU per single use vials), as well as the form of recombinant IL-2 commercially supplied by CellGenix, Inc., Portsmouth, NH, USA (CELL-GRO GMP) or ProSpec-Tany TechnoGene Ltd., East Brunswick, NJ, USA (Cat. No. CYT-209-b) and other commercial equivalents from other vendors. Aldesleukin (des-alanyl-1, serine-125 human IL-2) is a nonglycosylated human recombinant form of IL-2 with a molecular weight of approximately 15 kDa. The amino acid sequence of aldesleukin suitable for use in the invention is given in Table 2 (SEQ ID NO:4). The term IL-2 also encompasses pegylated forms of IL-2, as described herein, including the pegylated IL2 prodrug bempegaldesleukin (NKTR-214), pegylated human recombinant IL-2 as in SEQ ID NO:4 in which an average of 6 lysine residues are $N^6$ substituted with [(2,7-bis{[methylpoly(oxyethylene)]carbamoyl}-9H-fluoren-9-yl)methoxy]carbonyl), which is available from Nektar Therapeutics, South San Francisco, CA, USA, or which may be prepared by methods known in the art, such as the methods described in Example 19 of International Patent Application Publication No. WO 2018/132496 A1 or the method described in Example 1 of U.S. Patent Application Publication No. US 2019/0275133 A1, the disclosures of which are incorporated by reference herein. Bempegaldesleukin (NKTR-214) and other pegylated IL-2 molecules suitable for use in the invention are described in U.S. Patent Application Publication No. US 2014/0328791 A1 and International Patent Application Publication No. WO 2012/065086 A1, the disclosures of which are incorporated by reference herein. Alternative forms of conjugated IL-2 suitable for use in the invention are described in U.S. Pat. Nos. 4,766,106, 5,206,344, 5,089,261 and 4,902,502, the disclosures of which are incorporated by reference herein. Formulations of IL-2 suitable for use in the invention are described in U.S. Pat. No. 6,706,289, the disclosure of which is incorporated by reference herein.

In some embodiments, an IL-2 form suitable for use in the present invention is THOR-707, available from Synthorx, Inc. The preparation and properties of THOR-707 and additional alternative forms of IL-2 suitable for use in the invention are described in U.S. Patent Application Publication Nos. US 2020/0181220 A1 and US 2020/0330601 A1, the disclosures of which are incorporated by reference herein. In some embodiments, and IL-2 form suitable for use in the invention is an interleukin 2 (IL-2) conjugate comprising: an isolated and purified IL-2 polypeptide; and a conjugating moiety that binds to the isolated and purified IL-2 polypeptide at an amino acid position selected from K35, T37, R38, T41, F42, K43, F44, Y45, E61, E62, E68, K64, P65, V69, L72, and Y107, wherein the numbering of the amino acid residues corresponds to SEQ ID NO:5. In some embodiments, the amino acid position is selected from T37, R38, T41, F42, F44, Y45, E61, E62, E68, K64, P65, V69, L72, and Y107. In some embodiments, the amino acid position is selected from T37, R38, T41, F42, F44, Y45, E61, E62, E68, P65, V69, L72, and Y107. In some embodiments, the amino acid position is selected from T37, T41, F42, F44, Y45, P65, V69, L72, and Y107. In some embodiments, the amino acid position is selected from R38 and K64. In some embodiments, the amino acid position is selected from E61, E62, and E68. In some embodiments, the amino acid position is at E62. In some embodiments, the amino acid residue selected from K35, T37, R38, T41, F42, K43, F44, Y45, E61, E62, E68, K64, P65, V69, L72, and Y107 is further mutated to lysine, cysteine, or histidine. In some embodiments, the amino acid residue is mutated to cysteine. In some embodiments, the amino acid residue is mutated to lysine. In some embodiments, the amino acid residue selected from K35, T37, R38, T41, F42, K43, F44, Y45, E61, E62, E68, K64, P65, V69, L72, and Y107 is further mutated to an unnatural amino acid. In some embodiments, the unnatural amino acid comprises N6-azidoethoxy-L-lysine (AzK), N6-propargylethoxy-L-lysine (PraK), BCN-L-lysine, norbornene lysine, TCO-lysine, methyltetrazine lysine, allyloxycarbonyllysine, 2-amino-8-oxononanoic acid, 2-amino-8-oxooctanoic acid, p-acetyl-L-phenylalanine, p-azidomethyl-L-phenylalanine (pAMF), p-iodo-L-phenylalanine, m-acetylphenylalanine, 2-amino-8-oxononanoic acid, p-propargyloxyphenylalanine, p-propargyl-phenylalanine, 3-methyl-phenylalanine, L-Dopa, fluorinated phenylalanine, isopropyl-L-phenylalanine, p-azido-L-phenylalanine, p-acyl-L-phenylalanine, p-benzoyl-L-phenylalanine, p-bromophenylalanine, p-amino-L-phenylalanine, isopropyl-L-phenylalanine, O-allyltyrosine, O-methyl-L-tyrosine, O-4-allyl-L-tyrosine, 4-propyl-L-tyrosine, phosphonotyrosine, tri-O-acetyl-GlcNAcp-serine, L-phosphoserine, phosphonoserine, L-3-(2-naphthyl)alanine, 2-amino-3-((2-((3-(benzyloxy)-3-oxopropyl)amino)ethyl)selanyl)propanoic acid, 2-amino-3-(phenylselanyl)propanoic, or selenocysteine. In some embodiments, the IL-2 conjugate has a decreased affinity to IL-2 receptor α (IL-2Rα) subunit relative to a wild-type IL-2 polypeptide. In some embodiments, the decreased affinity is about 10%, 20%, 30%, 40%, 50%, 60%, 70%, 80%, 90%, 95%, 99%, or greater than 99% decrease in binding affinity to IL-2Ra relative to a wild-type IL-2 polypeptide. In some embodiments, the decreased affinity is about 1-fold, 2-fold, 3-fold, 4-fold, 5-fold, 6-fold, 7-fold, 8-fold, 9-fold, 10-fold, 30-fold, 50-fold, 100-fold, 200-fold, 300-fold, 500-fold, 1000-fold, or more relative to a wild-type IL-2 polypeptide. In some embodiments, the conjugating moiety impairs or blocks the binding of IL-2 with IL-2Rα. In some embodiments, the conjugating moiety comprises a water-soluble polymer. In some embodiments, the additional conjugating moiety comprises a water-soluble polymer. In some embodiments, each of the water-soluble polymers independently comprises polyethylene glycol (PEG), poly(propylene glycol) (PPG), copolymers of ethylene glycol and propylene glycol, poly (oxyethylated polyol), poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazolines (POZ), poly(N-acryloylmorpholine), or a combination thereof. In some embodiments, each of the water-soluble polymers independently comprises PEG. In some embodiments, the PEG is a linear PEG or a branched PEG. In some embodiments, each of the water-soluble polymers independently comprises a polysaccharide. In some embodiments, the polysaccharide comprises dextran, polysialic acid (PSA), hyaluronic acid (HA), amylose, heparin, heparan sulfate (HS), dextrin, or hydroxyethyl-starch (HES). In some embodiments, each of the water-soluble polymers independently comprises a glycan. In some embodiments, each of the water-soluble polymers independently comprises polyamine. In some embodiments, the conjugating moiety comprises a protein. In some embodiments, the additional conjugating moiety comprises a protein. In some embodiments, each of the proteins independently comprises an albumin, a transferrin, or a transthyretin. In some embodiments, each of the proteins independently comprises an Fc portion. In some embodiments, each of the proteins independently comprises an Fc portion of IgG. In some embodiments, the conjugating moiety comprises a polypeptide. In some embodiments, the additional conjugating moiety comprises a polypeptide. In some embodiments, each of the polypeptides independently comprises a XTEN peptide, a glycine-rich homoamino acid polymer (HAP), a PAS polypeptide, an elastin-like polypeptide (ELP), a CTP peptide, or a gelatin-like protein (GLK) polymer. In some embodiments, the isolated and purified IL-2 polypeptide is modified by glutamylation. In some embodiments, the conjugating moiety is directly bound to the isolated and purified IL-2 polypeptide. In some embodiments, the conjugating moiety is indirectly bound to the isolated and purified IL-2 polypeptide through a linker. In some embodiments, the linker comprises a homobifunctional linker. In some embodiments, the homobifunctional linker comprises Lomant's reagent dithiobis(succinimidylpropionate) DSP, 3'3'-dithiobis(sulfosuccinimidyl proprionate) (DTSSP), disuccinimidyl suberate (DSS), bis(sulfosuccinimidyl)suberate (BS), disuccinimidyl tartrate (DST), disulfosuccinimidyl tartrate (sulfo DST), ethylene glycobis (succinimidylsuccinate) (EGS), disuccinimidyl glutarate (DSG), N,N'-disuccinimidyl carbonate (DSC), dimethyl adipimidate (DMA), dimethyl pimelimidate (DMP), dimethyl suberimidate (DMS), dimethyl-3,3'-dithiobispropionimidate (DTBP), 1,4-di-(3'-(2'-pyridyldithio)propionamido)butane (DPDPB), bismaleimidohexane (BMH), aryl halide-containing compound (DFDNB), such as e.g. 1,5-difluoro-2,4-dinitrobenzene or 1,3-difluoro-4,6-dinitrobenzene, 4,4'-difluoro-3,3'-dinitrophenylsulfone (DFDNPS), bis-[β-(4-azidosalicylamido)ethyl]disulfide (BASED), formaldehyde, glutaraldehyde, 1,4-butanediol diglycidyl ether, adipic acid dihydrazide, carbohydrazide, o-toluidine, 3,3'-dimethylbenzidine, benzidine, α,α'-p-diaminodiphenyl, diiodo-p-xylene sulfonic acid, N,N'-ethylene-bis(iodoacetamide), or N,N'-hexamethylene-bis(iodoacetamide). In some embodiments, the linker comprises a heterobifunctional linker. In some embodiments, the heterobifunctional linker comprises N-succinimidyl 3-(2-pyridyldithio)propionate (sPDP), long-chain N-succinimidyl 3-(2-pyridyldithio)propionate (LC-sPDP), water-soluble-long-chain N-succinimidyl 3-(2-pyridyldithio) propionate (sulfo-LC-sPDP), succinimidyloxycarbonyl-α-methyl-α-(2-pyridyldithio)toluene (sMPT), sulfosuccinimidyl-6-[α-methyl-α-(2-pyridyldithio)toluamido]hexanoate (sulfo-LC-sMPT), succinimidyl-4-(N-maleimidomethyl)cyclohexane-1-carboxylate (sMCC), sulfosuccinimidyl-4-(N-maleimidomethyl)cyclohexane-1-carboxylate (sulfo-sMCC), m-maleimidobenzoyl-N-hydroxysuccinimide ester (MBs), m-maleimidobenzoyl-N-hydroxysulfosuccinimide ester (sulfo-MBs), N-succinimidyl(4-iodoacteyl)aminobenzoate (sIAB), sulfosuccinimidyl(4-iodoacteyl)aminobenzoate (sulfo-sIAB), succinimidyl-4-(p-maleimidophenyl)butyrate (sMPB), sulfosuccinimidyl-4-(p-maleimidophenyl)butyrate (sulfo-sMPB), N-(γ-maleimidobutyryloxy)succinimide ester (GMBs), N-(γ-maleimidobutyryloxy) sulfosuccinimide ester (sulfo-GMBs), succinimidyl 6-((iodoacetyl)amino) hexanoate (sIAX), succinimidyl 6-[6-(((iodoacetyl)amino) hexanoyl]amino]hexanoate (sIAXX), succinimidyl 4-(((iodoacetyl)amino)methyl)cyclohexane-1-carboxylate (sIAC), succinimidyl 6-(((((4-iodoacetyl)amino)methyl)cyclohexane-1-carbonyl)amino) hexanoate (sIACX), p-nitrophenyl iodoacetate (NPIA), carbonyl-reactive and sulfhydryl-reactive cross-linkers such as 4-(4-N-maleimidophenyl) butyric acid hydrazide (MPBH), 4-(N-maleimidomethyl) cyclohexane-1-carboxyl-hydrazide-8 (M2C2H), 3-(2-pyridyldithio)propionyl hydrazide (PDPH), N-hydroxysuccinimidyl-4-azidosalicylic acid (NHs-AsA), N-hydroxysulfosuccinimidyl-4-azidosalicylic acid (sulfo-NHs-AsA), sulfosuccinimidyl-(4-azidosalicylamido) hexanoate (sulfo-NHs-LC-AsA), sulfosuccinimidyl-2-(p-azidosalicylamido)ethyl-1,3'-dithiopropionate (sAsD), N-hydroxysuccinimidyl-4-azidobenzoate (HsAB), N-hydroxysulfosuccinimidyl-4-azidobenzoate (sulfo-HsAB), N-succinimidyl-6-(4'-azido-2'-nitrophenyl amino)hexanoate (sANPAH), sulfosuccinimidyl-6-(4'-azido-2'-nitrophenylamino)hexanoate (sulfo-sANPAH), N-5-azido-2-nitrobenzoyloxysuccinimide (ANB-NOs), sulfosuccinimidyl-2-(m-azido-o-nitrobenzamido)-ethyl-1,3'-dithiopropionate (sAND), N-succinimidyl-4(4-azidophenyl)1,3'-dithiopropionate (sADP), N-sulfosuccinimidyl(4-azidophenyl)-1,3'-dithiopropionate (sulfo-sADP), sulfosuccinimidyl 4-(p-azidophenyl)butyrate (sulfo-sAPB), sulfosuccinimidyl 2-(7-azido-4-methylcoumarin-3-acetamide)ethyl-1,3'-dithiopropionate (sAED), sulfosuccinimidyl 7-azido-4-methylcoumain-3-acetate (sulfo-sAMCA), p-nitrophenyl diazopyruvate (pNPDP), p-nitrophenyl-2-diazo-3,3,3-trifluoropropionate (PNP-DTP), 1-(p-azidosalicylamido)-4-

(iodoacetamido)butane (AsIB), N-[4-(p-azidosalicylamido) butyl]-3'-(2'-pyridyldithio) propionamide (APDP), benzophenone-4-iodoacetamide, p-azidobenzoyl hydrazide (ABH), 4-(p-azidosalicylamido)butylamine (AsBA), or p-azidophenyl glyoxal (APG). In some embodiments, the linker comprises a cleavable linker, optionally comprising a dipeptide linker. In some embodiments, the dipeptide linker comprises Val-Cit, Phe-Lys, Val-Ala, or Val-Lys. In some embodiments, the linker comprises a non-cleavable linker. In some embodiments, the linker comprises a maleimide group, optionally comprising maleimidocaproyl (mc), succinimidyl-4-(N-maleimidomethyl)cyclohexane-1-carboxylate (sMCC), or sulfosuccinimidyl-4-(N-maleimidomethyl)cyclohexane-1-carboxylate (sulfo-sMCC). In some embodiments, the linker further comprises a spacer. In some embodiments, the spacer comprises p-aminobenzyl alcohol (PAB), p-aminobenzyoxycarbonyl (PABC), a derivative, or an analog thereof. In some embodiments, the conjugating moiety is capable of extending the serum half-life of the IL-2 conjugate. In some embodiments, the additional conjugating moiety is capable of extending the serum half-life of the IL-2 conjugate. In some embodiments, the IL-2 form suitable for use in the invention is a fragment of any of the IL-2 forms described herein. In some embodiments, the IL-2 form suitable for use in the invention is pegylated as disclosed in U.S. Patent Application Publication No. US 2020/0181220 A1 and U.S. Patent Application Publication No. US 2020/0330601 A1. In some embodiments, the IL-2 form suitable for use in the invention is an IL-2 conjugate comprising: an IL-2 polypeptide comprising an N6-azidoethoxy-L-lysine (AzK) covalently attached to a conjugating moiety comprising a polyethylene glycol (PEG), wherein: the IL-2 polypeptide comprises an amino acid sequence having at least 80% sequence identity to SEQ ID NO:5; and the AzK substitutes for an amino acid at position K35, F42, F44, K43, E62, P65, R38, T41, E68, Y45, V69, or L72 in reference to the amino acid positions within SEQ ID NO:5. In some embodiments, the IL-2 polypeptide comprises an N-terminal deletion of one residue relative to SEQ ID NO:5. In some embodiments, the IL-2 form suitable for use in the invention lacks IL-2R alpha chain engagement but retains normal binding to the intermediate affinity IL-2R beta-gamma signaling complex. In some embodiments, the IL-2 form suitable for use in the invention is an IL-2 conjugate comprising: an IL-2 polypeptide comprising an N6-azidoethoxy-L-lysine (AzK) covalently attached to a conjugating moiety comprising a polyethylene glycol (PEG), wherein: the IL-2 polypeptide comprises an amino acid sequence having at least 90% sequence identity to SEQ ID NO:5; and the AzK substitutes for an amino acid at position K35, F42, F44, K43, E62, P65, R38, T41, E68, Y45, V69, or L72 in reference to the amino acid positions within SEQ ID NO:5. In some embodiments, the IL-2 form suitable for use in the invention is an IL-2 conjugate comprising: an IL-2 polypeptide comprising an N6-azidoethoxy-L-lysine (AzK) covalently attached to a conjugating moiety comprising a polyethylene glycol (PEG), wherein: the IL-2 polypeptide comprises an amino acid sequence having at least 95% sequence identity to SEQ ID NO:5; and the AzK substitutes for an amino acid at position K35, F42, F44, K43, E62, P65, R38, T41, E68, Y45, V69, or L72 in reference to the amino acid positions within SEQ ID NO:5. In some embodiments, the IL-2 form suitable for use in the invention is an IL-2 conjugate comprising: an IL-2 polypeptide comprising an N6-azidoethoxy-L-lysine (AzK) covalently attached to a conjugating moiety comprising a polyethylene glycol (PEG), wherein: the IL-2 polypeptide comprises an amino acid sequence having at least 98% sequence identity to SEQ ID NO:5; and the AzK substitutes for an amino acid at position K35, F42, F44, K43, E62, P65, R38, T41, E68, Y45, V69, or L72 in reference to the amino acid positions within SEQ ID NO:5.

In some embodiments, an IL-2 form suitable for use in the invention is nemvaleukin alfa, also known as ALKS-4230 (SEQ ID NO:6), which is available from Alkermes, Inc. Nemvaleukin alfa is also known as human interleukin 2 fragment (1-59), variant ($Cys^{125}$>$Ser^{51}$), fused via peptidyl linker ($^{61}GG^{61}$) to human interleukin 2 fragment (62-132), fused via peptidyl linker ($^{133}GSGGGS^{138}$) to human interleukin 2 receptor α-chain fragment (139-303), produced in Chinese hamster ovary (CHO) cells, glycosylated; human interleukin 2 (IL-2) (75-133)-peptide [$Cys^{125}$(51)>Ser]-mutant (1-59), fused via a G2 peptide linker (60-61) to human interleukin 2 (IL-2) (4-74)-peptide (62-132) and via a GSG3S peptide linker (133-138) to human interleukin 2 receptor α-chain (IL2R subunit alpha, IL2Rα, IL2RA) (1-165)-peptide (139-303), produced in Chinese hamster ovary (CHO) cells, glycoform alfa. The amino acid sequence of nemvaleukin alfa is given in SEQ ID NO:6. In some embodiments, nemvaleukin alfa exhibits the following post-translational modifications: disulfide bridges at positions: 31-116, 141-285, 184-242, 269-301, 166-197 or 166-199, 168-199 or 168-197 (using the numbering in SEQ ID NO:6), and glycosylation sites at positions: N187, N206, T212 using the numbering in SEQ ID NO:6. The preparation and properties of nemvaleukin alfa, as well as additional alternative forms of IL-2 suitable for use in the invention, is described in U.S. Patent Application Publication No. US 2021/0038684 A1 and U.S. Pat. No. 10,183,979, the disclosures of which are incorporated by reference herein. In some embodiments, an IL-2 form suitable for use in the invention is a protein having at least 80%, at least 90%, at least 95%, or at least 90% sequence identity to SEQ ID NO:6. In some embodiments, an IL-2 form suitable for use in the invention has the amino acid sequence given in SEQ ID NO:6 or conservative amino acid substitutions thereof. In some embodiments, an IL-2 form suitable for use in the invention is a fusion protein comprising amino acids 24-452 of SEQ ID NO:7, or variants, fragments, or derivatives thereof. In some embodiments, an IL-2 form suitable for use in the invention is a fusion protein comprising an amino acid sequence having at least 80%, at least 90%, at least 95%, or at least 90% sequence identity to amino acids 24-452 of SEQ ID NO:7, or variants, fragments, or derivatives thereof. Other IL-2 forms suitable for use in the present invention are described in U.S. Pat. No. 10,183,979, the disclosures of which are incorporated by reference herein. Optionally, in some embodiments, an IL-2 form suitable for use in the invention is a fusion protein comprising a first fusion partner that is linked to a second fusion partner by a mucin domain polypeptide linker, wherein the first fusion partner is IL-Rα or a protein having at least 98% amino acid sequence identity to IL-Rα and having the receptor antagonist activity of IL-Rα, and wherein the second fusion partner comprises all or a portion of an immunoglobulin comprising an Fc region, wherein the mucin domain polypeptide linker comprises SEQ ID NO:8 or an amino acid sequence having at least 90% sequence identity to SEQ TD NO:8 and wherein the half-life of the fusion protein is improved as compared to a fusion of the first fusion partner to the second fusion partner in the absence of the mucin domain polypeptide linker.

TABLE 2

Amino acid sequences of interleukins.

| Identifier | Sequence (One-Letter Amino Acid Symbols) | |
|---|---|---|
| SEQ ID NO: 3 recombinant human IL-2 (rhIL-2) | MAPTSSSTKK TQLQLEHLLL DLQMILNGIN NYKNPKLTRM LTFKFYMPKK ATELKHLQCL<br>EEELKPLEEV LNLAQSKNFH LRPRDLISNI NVIVLELKGS ETTFMCEYAD ETATIVEFLN<br>RWITFCQSII STLT | 60<br>120<br>134 |
| SEQ ID NO: 4 Aldesleukin | PTSSSTKKTQ LQLEHLLLDL QMILNGINNY KNPKLTRMLT FKFYMPKKAT ELKHLQCLEE<br>ELKPLEEVLN LAQSKNFHLR PRDLISNINV IVLELKGSET TFMCEYADET ATIVEFLNRW<br>ITFSQSIIST LT | 60<br>120<br>132 |
| SEQ ID NO: 5 IL-2 form | APTSSSTKKT QLQLEHLLLD LQMILNGINN YKNPKLTRML TFKFYMPKKA TELKHLQCLE<br>EELKPLEEVL NLAQSKNFHL RPRDLISNIN VIVLELKGSE TTFMCEYADE TATIVEFLNR<br>WITFCQSIIS TLT | 60<br>120<br>133 |
| SEQ ID NO: 6 Nemvaleukin alfa | SKNFHLRPFD LISNINVIVL ELKGSETTFM CEYADETATI VEFLNRWITF SQSIISTLTG<br>GSSSTKKTQL QLEHLLLDLQ MILNGINNYK NPKLTRMLTF KFYMPKKATE LKHLQCLEEE<br>LKPLEEVLNL AQGSGGGSEL CDDDPPEIPH ATFKAMAYKE GTMLNCECKR GFFFIKSGSL<br>YMLCTGNSSH SSWDNQCQCT SSATRNTTKQ VTPQPEEQKE RKTTEMQSPM QPVDQASLPG<br>HCREPPPWEN EATERIYHFV VGQMVYYQCV QGYRALHRGP AESVCKMTHG KTRWTQPQLI<br>CTG | 60<br>120<br>180<br>240<br>300<br>303 |
| SEQ ID NO: 7 IL-2 form | MDAMKRGLCC VLLLCGAVFV SARRPSGRKS SKMQAFRIWD VNQKTFYLRN NQLVAGYLQG<br>PNVNLEEKID VVPIEPHALF LGIHGGKMCL SCVKSGDETR LQLEAVNITD LSENRKQDKR<br>FAFIRSDSGP TTSFESAACP GWFLCTAMEA DQPVSLTNMP DEGVMVTKFY FQEDESGSGG<br>ASSESSASSD GPHPVITESR ASSESSASSD GPHPVITESR EPKSSDKTHT CPPCPAPELL<br>GGPSVFLPPP KPKDTLMISR TPEVTCVVVD VSHEDPEVKF NWYVDGVEVH NAKTKPREEQ<br>YNSTYRVVSV LTVLHQDWLN GKEYKCKVSN KALPAPIEKT ISKAKGQPRE PQVYTLPPSR<br>EEMTKNQVSL TCLVKGFYPS DIAVEWESNG QPENNYKTTP PVLDSDGSFF LYSKLTVDKS<br>RWQQGNVFSC SVMHEALHNH YTQKSLSLSP GK | 60<br>120<br>180<br>240<br>300<br>360<br>420<br>452 |
| SEQ ID NO: 8 musin domain polypeptide | SESSASSDGP HPVITP | 16 |
| SEQ ID NO: 9 recombinant human IL-4 (rhIL-4) | MHKCDITLQE IIKTLNSLTE QKTLCTELTV TDIFAASKNT TEKETFCRAA TVLRQFYSHH<br>EKDTRCLGAT AQQFHRHKQL IRFLKRLDRN LWGLAGLNSC PVKEANQSTL ENFLERLKTI<br>MREKYSKCSS | 60<br>120<br>130 |
| SEQ ID NO: 10 recombinant human IL-7 (rhIL-7) | MDCDIEGKDG KQYESVLMVS IDQLLDSMKE IGSNCLNNEF NFFKRHICDA NKEGMFLFRA<br>ARKLRQFLKM NSTGDFDLHL LKVSEGTTIL LNCTGQVKGR KPAALGEAQP TKSLEENKSL<br>KEQKKLNDLC FLKRLLQEIK TCWNKILMGT KEH | 60<br>120<br>153 |
| SEQ ID NO: 11 recombinant human IL-15 (rhIL-15) | MNWVNVISDL KKIEDLIQSM HIDATLYTES DVHPSCKVTA MKCFLLELQV ISLESGDASI<br>HDTVENLIIL ANNSLSSNGN VTESGCKECE ELEEKNIKEF LQSFVHIVQM FINTS | 60<br>115 |
| SEQ ID NO: 12 recombinant human IL-21 (rhIL-21) | MQDRHMIRMR QLIDIVDQLK NYVNDLVPEF LPAPEDVETN CEWSAFSCFQ KAQLKSANTG<br>NNERIINVSI KKLKRKPPST NAGRRQKHRL TCPSCDSYEK KPPKEFLERF KSLLQKMIHQ<br>HLSSRTHGSE DS | 60<br>120<br>132 |

In some embodiments, an IL-2 form suitable for use in the invention includes a antibody cytokine engrafted protein comprises a heavy chain variable region ($V_H$), comprising complementarity determining regions HCDR1, HCDR2, HCDR3; a light chain variable region ($V_L$), comprising LCDR1, LCDR2, LCDR3; and an IL-2 molecule or a fragment thereof engrafted into a CDR of the $V_H$ or the $V_L$, wherein the antibody cytokine engrafted protein preferentially expands T effector cells over regulatory T cells. In an embodiment, the antibody cytokine engrafted protein comprises a heavy chain variable region ($V_H$), comprising complementarity determining regions HCDR1, HCDR2, HCDR3; a light chain variable region ($V_L$), comprising LCDR1, LCDR2, LCDR3; and an IL-2 molecule or a fragment thereof engrafted into a CDR of the $V_H$ or the $V_L$, wherein the IL-2 molecule is a mutein, and wherein the antibody cytokine engrafted protein preferentially expands T effector cells over regulatory T cells. In an embodiment, the IL-2 regimen comprises administration of an antibody described in U.S. Patent Application Publication No. US 2020/0270334 A1, the disclosures of which are incorporated by reference herein. In an embodiment, the antibody cytokine engrafted protein comprises a heavy chain variable region ($V_H$), comprising complementarity determining regions HCDR1, HCDR2, HCDR3; a light chain variable region ($V_L$), comprising LCDR1, LCDR2, LCDR3; and an IL-2 molecule or a fragment thereof engrafted into a CDR of the $V_H$ or the $V_L$, wherein the IL-2 molecule is a mutein, wherein the antibody cytokine engrafted protein preferentially expands T effector cells over regulatory T cells, and wherein the antibody further comprises an IgG class heavy chain and an IgG class light chain selected from the group consisting of: a IgG class light chain comprising SEQ ID NO:39 and a IgG class heavy chain comprising SEQ ID NO:38; a IgG class light chain comprising SEQ ID NO:37 and a IgG class heavy chain comprising SEQ ID NO:29; a IgG class light chain comprising SEQ ID NO:39 and a IgG class heavy chain comprising SEQ ID NO:29; and a IgG class light chain comprising SEQ ID NO:37 and a IgG class heavy chain comprising SEQ ID NO:38.

In an embodiment, an IL-2 molecule or a fragment thereof is engrafted into HCDR1 of the $V_H$, wherein the IL-2 molecule is a mutein. In an embodiment, an IL-2 molecule or a fragment thereof is engrafted into HCDR2 of the $V_H$, wherein the IL-2 molecule is a mutein. In an embodiment, an IL-2 molecule or a fragment thereof is engrafted into HCDR3 of the $V_H$, wherein the IL-2 molecule is a mutein. In an embodiment, an IL-2 molecule or a fragment thereof is engrafted into LCDR1 of the $V_L$, wherein the IL-2 molecule is a mutein. In an embodiment, an IL-2 molecule or a fragment thereof is engrafted into LCDR2 of the $V_L$, wherein the IL-2 molecule is a mutein. In an embodiment, an IL-2 molecule or a fragment thereof is engrafted into LCDR3 of the $V_L$, wherein the IL-2 molecule is a mutein.

The insertion of the IL-2 molecule can be at or near the N-terminal region of the CDR, in the middle region of the CDR or at or near the C-terminal region of the CDR. In some embodiments, the antibody cytokine engrafted protein comprises an IL-2 molecule incorporated into a CDR, wherein the IL2 sequence does not frameshift the CDR sequence. In some embodiments, the antibody cytokine engrafted protein comprises an IL-2 molecule incorporated into a CDR, wherein the IL-2 sequence replaces all or part of a CDR sequence. The replacement by the IL-2 molecule can be the N-terminal region of the CDR, in the middle region of the CDR or at or near the C-terminal region the CDR. A replacement by the IL-2 molecule can be as few as one or two amino acids of a CDR sequence, or the entire CDR sequences.

In some embodiments, an IL-2 molecule is engrafted directly into a CDR without a peptide linker, with no additional amino acids between the CDR sequence and the IL-2 sequence. In some embodiments, an IL-2 molecule is engrafted indirectly into a CDR with a peptide linker, with one or more additional amino acids between the CDR sequence and the IL-2 sequence.

In some embodiments, the IL-2 molecule described herein is an IL-2 mutein. In some instances, the IL-2 mutein comprising an R67A substitution. In some embodiments, the IL-2 mutein comprises the amino acid sequence SEQ ID NO:14 or SEQ ID NO:15. In some embodiments, the IL-2 mutein comprises an amino acid sequence in Table 1 in U.S. Patent Application Publication No. US 2020/0270334 A1, the disclosure of which is incorporated by reference herein.

In an embodiment, the antibody cytokine engrafted protein comprises an HCDR1 selected from the group consisting of SEQ ID NO:16, SEQ ID NO:19, SEQ ID NO:22 and SEQ ID NO:25. In an embodiment, the antibody cytokine engrafted protein comprises an HCDR1 selected from the group consisting of SEQ ID NO:7, SEQ ID NO:10, SEQ ID NO:13 and SEQ ID NO:16. In an embodiment, the antibody cytokine engrafted protein comprises an HCDR1 selected from the group consisting of HCDR2 selected from the group consisting of SEQ ID NO:17, SEQ ID NO:20, SEQ ID NO:23, and SEQ ID NO:26. In an embodiment, the antibody cytokine engrafted protein comprises an HCDR3 selected from the group consisting of SEQ ID NO:18, SEQ ID NO:21, SEQ ID NO:24, and SEQ ID NO:27. In an embodiment, the antibody cytokine engrafted protein comprises a $V_H$ region comprising the amino acid sequence of SEQ ID NO:28. In an embodiment, the antibody cytokine engrafted protein comprises a heavy chain comprising the amino acid sequence of SEQ ID NO:29. In an embodiment, the antibody cytokine engrafted protein comprises a $V_L$ region comprising the amino acid sequence of SEQ ID NO:36. In an embodiment, the antibody cytokine engrafted protein comprises a light chain comprising the amino acid sequence of SEQ ID NO:37. In an embodiment, the antibody cytokine engrafted protein comprises a $V_H$ region comprising the amino acid sequence of SEQ ID NO:28 and a $V_L$ region comprising the amino acid sequence of SEQ ID NO:36. In an embodiment, the antibody cytokine engrafted protein comprises a heavy chain region comprising the amino acid sequence of SEQ ID NO:29 and a light chain region comprising the amino acid sequence of SEQ ID NO:37. In an embodiment, the antibody cytokine engrafted protein comprises a heavy chain region comprising the amino acid sequence of SEQ ID NO:29 and a light chain region comprising the amino acid sequence of SEQ ID NO:39. In an embodiment, the antibody cytokine engrafted protein comprises a heavy chain region comprising the amino acid sequence of SEQ ID NO:38 and a light chain region comprising the amino acid sequence of SEQ ID NO:37. In an embodiment, the antibody cytokine engrafted protein comprises a heavy chain region comprising the amino acid sequence of SEQ ID NO:38 and a light chain region comprising the amino acid sequence of SEQ ID NO:39. In an embodiment, the antibody cytokine engrafted protein comprises IgG.IL2F71A.H1 or IgG.IL2R67A.H1 of U.S. Patent Application Publication No. 2020/0270334 A1, or variants, derivatives, or fragments thereof, or conservative amino acid substitutions thereof, or proteins with at least 80%, at least 90%, at least 95%, or at least 98% sequence identity thereto. In an embodiment, the antibody components of the antibody cytokine engrafted protein described herein comprise immunoglobulin sequences, framework sequences, or CDR sequences of palivizumab. In some embodiments, the antibody cytokine engrafted protein described herein has a longer serum half-life that a wild-type IL-2 molecule such as, but not limited to, aldesleukin or a comparable molecule. In an embodiment, the antibody cytokine engrafted protein described herein has a sequence as set forth in Table 3.

TABLE 3

Sequences of exemplary palivizumab antibody-IL-2 engrafted proteins.

| Identifier | Sequence (One-Letter Amino Acid Symbols) | |
|---|---|---|
| SEQ ID NO: 13<br>IL-2 | MYRMQLLSCI ALSLALVTNS APTSSSTKKT QLQLEHLLLD LQMILNGINN YKNPKLTRML<br>TFKFYMPKKA TELKHLQCLE EELKPLEEVL NLAQSKNFHL RPRDLISNIN VIVLELKGSE<br>TTFMCEYADE TATIVEFLNR WITFCQSIIS TLT | 60<br>120<br>153 |
| SEQ ID NO: 14<br>IL-2 mutein | APTSSSTKKT QLQLEHLLLD LQMILNGINN YKNPKLTAML TFKFYMPKKA TELKHLQCLE<br>EELKPLEEVL NLAQSKNFHL RPRDLISNIN VIVLELKGSE TTFMCEYADE TATIVEFLNR<br>WITFCQSIIS TLT | 60<br>120<br>133 |

TABLE 3-continued Sequences of exemplary palivizumab antibody-IL-2 engrafted proteins.

| Identifier | Sequence (One-Letter Amino Acid Symbols) | |
|---|---|---|
| SEQ ID NO: 15 IL-2 mutein | APTSSSTKKT QLQLEHLLLD LQMILNGINN YKNPKLTRML TAKFYMPKKA TELKHLQCLE | 60 |
| | EELKPLEEVL NLAQSKNFHL RPRDLISNIN VIVLELKGSE TTFMCEYADE TATIVEFLNR | 120 |
| | WITFCQSIIS TLT | 133 |
| SEQ ID NO: 16 HCDR1_IL-2 | GFSLAPTSSS TKKTQLQLEH LLLDLQMILN GINNYKNPKL TAMLTEKEYM PKKATELKHL | 60 |
| | QCLEEELKPL EEVLNLAQSK NFHLRPRDLI SNINVIVLEL KGSETTFMCE YADETATIVE | 120 |
| | FLNRWITFCQ SIISTLTSTS GMSVG | 145 |
| SEQ ID NO: 17 HCDR2 | DIWWDDKKDY NPSLKS | 16 |
| SEQ ID NO: 18 HCDR3 | SMITNWYFDV | 10 |
| SEQ ID NO: 19 HCDR1_IL-2 kabat | APTSSSTKKT QLQLEHLLLD LQMILNGINN YKNPKLTAML TFKFYMPKKA TELKHLQCLE | 60 |
| | EELKPLEEVL NLAQSKNFHL RPRDLISNIN VIVLELKGSE TTFMCEYADE TATIVEFLNR | 120 |
| | WITFCQSIIS TLTSTSGMSV G | 141 |
| SEQ ID NO: 20 HCDR2 kabat | DIWWDDKKDY NPSLKS | 16 |
| SEQ ID NO: 21 HCDR3 kabat | SMITNWYFDV | 10 |
| SEQ ID NO: 22 HCDR1_IL-2 clothia | GFSLAPTSSS TKKTQLQLEH LLLDLQMILN GINNYKNPKL TAMLTEKEYM PKKATELKHL | 60 |
| | QCLEEELKPL EEVLNLAQSK NFHLRPRDLI SNINVIVLEL KGSETTFMCE YADETATIVE | 120 |
| | FLNRWITFCQ SIISTLTSTS GM | 142 |
| SEQ ID NO: 23 HCDR2 clothia | WWDDK | 5 |
| SEQ ID NO: 24 HCDR3 clothia | SMITNWYFDV | 10 |
| SEQ ID NO: 25 HCDR1_IL-2 IMGT | GFSLAPTSSS TKKTQLQLEH LLLDLQMILN GINNYKNPKL TAMLTEKEYM PKKATELKHL | 60 |
| | QCLEEELKPL EEVLNLAQSK NFHLRPRDLI SNINVIVLEL KGSETTFMCE YADETATIVE | 120 |
| | FLNRWITFCQ SIISTLTSTS GMS | 143 |
| SEQ ID NO: 26 HCDR2 IMGT | IWWDDKK | 7 |
| SEQ ID NO: 27 HCDR3 IMGT | ARSMITNWYF DV | 12 |
| SEQ ID NO: 28 VH | QVTLRESGPA LVKPTQTLTL TCTFSGFSLA PTSSSTKKTQ LQLEHLLLDL QMILNGINNY | 60 |
| | KNPKLTAMLT FKFYMPKKAT ELKHLQCLEE ELKPLEEVLN LAQSKNFHLR PRDLISNINV | 120 |
| | IVLELKGSET TFMCEYADET ATIVEFLNRW ITFCQSIIST LTSTSGMSVG WIRQPPGKAL | 180 |
| | EWLADIWWDD KKDYNPSLKS RLTISKDTSK NQVVLKVTNM DPADTATYYC ARSMITNWYF | 240 |
| | DVWGAGTTVT VSS | 253 |
| SEQ ID NO: 29 Heavy chain | QMILNGINNY KNPKLTAMLT FKFYMPKKAT ELKHLQCLEE ELKPLEEVLN LAQSKNFHLR | 60 |
| | PRDLISNINV IVLELKGSET TFMCEYADET ATIVEFLNRW ITFCQSIIST LTSTSGMSVG | 120 |
| | WIRQPPGKAL EWLADIWWDD KKDYNPSLKS RLTISKDTSK NQVVLKVTNM DPADTATYYC | 180 |
| | ARSMITNWYF DVWGAGTTVT VSSASTKGPS VFPLAPSSKS TSGGTAALGC LVKDYFPEPV | 240 |
| | TVSWNSGALT SGVHTFPAVL QSSGLYSLSS VVTVPSSSLG TQTYICNVNH KPSNTKVDKR | 300 |
| | VEPKSCDKTH TCPPCPAPEL LGGPSVFLFP PKPKDTLMIS RTPEVTCVVV AVSHEDPEVK | 360 |
| | FNWYVDGVEV HNAKTKPREE QYNSTYRVVS VLTVLHQDWL NGKEYKCKVS NKALAAPIEK | 420 |
| | TISKAKGQPR EPQVYTLPPS REEMTKNQVS LTCLVKGFYP SDIAVEWESN GQPENNYKTT | 480 |
| | PPVLDSDGSF FLYSKLTVDK SRWQQGNVFS CSVMHEALHN HYTQKSLSLS PGK | 533 |
| SEQ ID NO: 30 LCDR1 kabat | KAQLSVGYMH | 10 |
| SEQ ID NO: 31 LCDR2 kabat | DTSKLAS | 7 |
| SEQ ID NO: 32 LCDR3 kabat | FQGSGYPFT | 9 |
| SEQ ID NO: 33 LCDR1 chothia | QLSVGY | 6 |
| SEQ ID NO: 34 LCDR2 chothia | DTS | 3 |

TABLE 3-continued

Sequences of exemplary palivizumab antibody-IL-2 engrafted proteins.

| Identifier | Sequence (One-Letter Amino Acid Symbols) | |
|---|---|---|
| SEQ ID NO: 35<br>LCDR3 chothia | GSGYPF | 6 |
| SEQ ID NO: 36<br>VL | DIQMTQSPST LSASVGDRVT ITCKAQLSVG YMHWYQQKPG KAPKLLIYDT SKLASGVPSR<br>FSGSGSGTEF TLTISSLQPD DFATYYCFQG SGYPFTFGGG TKLEIK | 60<br>106 |
| SEQ ID NO: 37<br>Light chain | DIQMTQSPST LSASVGDRVT ITCKAQLSVG YMHWYQQKPG KAPKLLIYDT SKLASGVPSR<br>FSGSGSGTEF TLTISSLQPD DFATYYCFQG SGYPFTFGGG TKLEIKRTVA APSVFIFPPS<br>DEQLKSGTAS VVCLLNNFYP REAKVQWKVD NALQSGNSQE SVTEQDSKDS TYSLSSTLTL<br>SKADYEKHKV YACEVTHQGL SSPVTKSFNR GEC | 60<br>120<br>180<br>213 |
| SEQ ID NO: 38<br>Light chain | QVTLRESGPA LVKPTQTLTL TCTFSGFSLA PTSSSTKKTQ LQLEHLLLDL QMILNGINNY<br>KNPKLTRMLT AKFYMPKKAT ELKHLQCLEE ELKPLEEVLN LAQSKNFHLR PRDLISNINV<br>IVLELKGSET TFMCEYADET ATIVEFLNRW ITFCQSIIST LTSTSGMSVG WIRQPPGKAL<br>EWLADIWWDD KKDYNPSLKS RLTISKDTSK NQVVLKVTNM DPADTATYYC ARSMITNWYF<br>DVWGAGTTVT VSSASTKGPS VFPLAPSSKS TSGGTAALGC LVKDYFPEPV TVSWNSGALT<br>SGVHTFPAVL QSSGLYSLSS VVTVPSSSLG TQTYICNVNH KPSNTKVDKR VEPKSCDKTH<br>TCPPCPAPEL LGGPSVFLFP PKPKDTLMIS RTPEVTCVVV AVSHEDPEVK FNWYVDGVEV<br>HNAKTKPREE QYNSTYRVVS VLTVLHQDWL NGKEYKCKVS NKALAAPIEK TISKAKGQPR<br>EPQVYTLPPS REEMTKNQVS LTCLVKGFYP SDIAVEWESN GQPENNYKTT PPVLDSDGSF<br>FLYSKLTVDK SRWQQGNVFS CSVMHEALHN HYTQKSLSLS PGK | 60<br>120<br>180<br>240<br>300<br>360<br>420<br>480<br>540<br>583 |
| SEQ ID NO: 39<br>Light chain | DIQMTQSPST LSASVGDRVT ITCKAQLSVG YMHWYQQKPG KAPKLLIYDT SKLASGVPSR<br>FSGSGSGTEF TLTISSLQPD DFATYYCFQG SGYPFTFGGG TKLEIKRTVA APSVFIFPPS<br>DEQLKSGTAS VVCLLNNFYP REAKVQWKVD NALQSGNSQE SVTEQDSKDS TYSLSSTLTL<br>SKADYEKHKV YACEVTHQGL SSPVTKSFNR GEC | 60<br>120<br>180<br>213 |

The term "IL-4" (also referred to herein as "IL4") refers to the cytokine known as interleukin 4, which is produced by Th2 T cells and by eosinophils, basophils, and mast cells. IL-4 regulates the differentiation of naïve helper T cells (Th0 cells) to Th2 T cells. Steinke and Borish, *Respir. Res.* 2001, 2, 66-70. Upon activation by IL-4, Th2 T cells subsequently produce additional IL-4 in a positive feedback loop. IL-4 also stimulates B cell proliferation and class II MHC expression, and induces class switching to IgE and IgG₁ expression from B cells. Recombinant human IL-4 suitable for use in the invention is commercially available from multiple suppliers, including ProSpec-Tany TechnoGene Ltd., East Brunswick, NJ, USA (Cat. No. CYT-211) and ThermoFisher Scientific, Inc., Waltham, MA, USA (human IL-15 recombinant protein, Cat. No. Gibco CTP0043). The amino acid sequence of recombinant human IL-4 suitable for use in the invention is given in Table 2 (SEQ ID NO:9).

The term "IL-4" (also referred to herein as "IL4") refers to the cytokine known as interleukin 4, which is produced by Th2 T cells and by eosinophils, basophils, and mast cells. IL-4 regulates the differentiation of naïve helper T cells (Th0 cells) to Th2 T cells. Steinke and Borish, *Respir. Res.* 2001, 2, 66-70. Upon activation by IL-4, Th2 T cells subsequently produce additional IL-4 in a positive feedback loop. IL-4 also stimulates B cell proliferation and class II MHC expression, and induces class switching to IgE and IgG₁ expression from B cells. Recombinant human IL-4 suitable for use in the invention is commercially available from multiple suppliers, including ProSpec-Tany TechnoGene Ltd., East Brunswick, NJ, USA (Cat. No. CYT-211) and ThermoFisher Scientific, Inc., Waltham, MA, USA (human IL-15 recombinant protein, Cat. No. Gibco CTP0043). The amino acid sequence of recombinant human IL-4 suitable for use in the invention is given in Table 2 (SEQ ID NO:5).

The term "IL-7" (also referred to herein as "IL7") refers to a glycosylated tissue-derived cytokine known as interleukin 7, which may be obtained from stromal and epithelial cells, as well as from dendritic cells. Fry and Mackall, *Blood* 2002, 99, 3892-904. IL-7 can stimulate the development of T cells. IL-7 binds to the IL-7 receptor, a heterodimer consisting of IL-7 receptor alpha and common gamma chain receptor, which in a series of signals important for T cell development within the thymus and survival within the periphery. Recombinant human IL-7 suitable for use in the invention is commercially available from multiple suppliers, including ProSpec-Tany TechnoGene Ltd., East Brunswick, NJ, USA (Cat. No. CYT-254) and ThermoFisher Scientific, Inc., Waltham, MA, USA (human IL-15 recombinant protein, Cat. No. Gibco PHC0071). The amino acid sequence of recombinant human IL-7 suitable for use in the invention is given in Table 2 (SEQ ID NO:6).

The term "IL-15" (also referred to herein as "IL15") refers to the T cell growth factor known as interleukin-15 and includes all forms of IL-2 including human and mammalian forms, conservative amino acid substitutions, glycoforms, biosimilars, and variants thereof. IL-15 is described, e.g., in Fehniger and Caligiuri, *Blood* 2001, 97, 14-32, the disclosure of which is incorporated by reference herein. IL-15 shares β and γ signaling receptor subunits with IL-2. Recombinant human IL-15 is a single, non-glycosylated polypeptide chain containing 114 amino acids (and an N-terminal methionine) with a molecular mass of 12.8 kDa. Recombinant human IL-15 is commercially available from multiple suppliers, including ProSpec-Tany TechnoGene Ltd., East Brunswick, NJ, USA (Cat. No. CYT-230-b) and ThermoFisher Scientific, Inc., Waltham, MA, USA (human IL-15 recombinant protein, Cat. No. 34-8159-82). The amino acid sequence of recombinant human IL-15 suitable for use in the invention is given in Table 2 (SEQ ID NO:7).

The term "IL-21" (also referred to herein as "IL21") refers to the pleiotropic cytokine protein known as interleukin-21 and includes all forms of IL-21 including human and mammalian forms, conservative amino acid substitutions, glycoforms, biosimilars, and variants thereof. IL-21 is described, e.g., in Spolski and Leonard, *Nat. Rev. Drug. Disc.* 2014, 13, 379-95, the disclosure of which is incorporated by reference herein. IL-21 is primarily produced by natural killer T cells and activated human CD4+ T cells. Recombinant human IL-21 is a single, non-glycosylated polypeptide chain containing 132 amino acids with a molecular mass of 15.4 kDa. Recombinant human IL-21 is commercially available from multiple suppliers, including ProSpec-Tany TechnoGene Ltd., East Brunswick, NJ, USA (Cat. No. CYT-408-b) and ThermoFisher Scientific, Inc., Waltham, MA, USA (human IL-21 recombinant protein, Cat. No. 14-8219-80). The amino acid sequence of recombinant human IL-21 suitable for use in the invention is given in Table 2 (SEQ ID NO:8).

When "an anti-tumor effective amount", "a tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the tumor infiltrating lymphocytes (e.g., secondary TILs or genetically modified cytotoxic lymphocytes) described herein may be administered at a dosage of $10^4$ to $10^{11}$ cells/kg body weight (e.g., $10^5$ to $10^6$, $10^5$ to $10^{10}$, $10^5$ to $10^{11}$, $10^6$ to $10^{10}$, $10^6$ to $10^{11}$, $10^7$ to $10^{11}$, $10^7$ to $10^{10}$, $10^8$ to $10^{11}$, $10^8$ to $10^{10}$, $10^9$ to $10^{11}$, or $10^9$ to $10^{10}$ cells/kg body weight), including all integer values within those ranges. Tumor infiltrating lymphocytes (including in some cases, genetically modified cytotoxic lymphocytes) compositions may also be administered multiple times at these dosages. The tumor infiltrating lymphocytes (including in some cases, genetically modified cytotoxic lymphocytes) can be administered by using infusion techniques that are commonly known in immunotherapy (see, e.g., Rosenberg et al., *New Eng. J. of Med.* 319: 1676, 1988). The optimal dosage and treatment regime for a particular patient can readily be determined by one skilled in the art of medicine by monitoring the patient for signs of disease and adjusting the treatment accordingly.

The term "hematological malignancy", "hematologic malignancy" or terms of correlative meaning refer to mammalian cancers and tumors of the hematopoietic and lymphoid tissues, including but not limited to tissues of the blood, bone marrow, lymph nodes, and lymphatic system. Hematological malignancies are also referred to as "liquid tumors." Hematological malignancies include, but are not limited to, acute lymphoblastic leukemia (ALL), chronic lymphocytic lymphoma (CLL), small lymphocytic lymphoma (SLL), acute myelogenous leukemia (AML), chronic myelogenous leukemia (CML), acute monocytic leukemia (AMoL), Hodgkin's lymphoma, and non-Hodgkin's lymphomas. The term "B cell hematological malignancy" refers to hematological malignancies that affect B cells.

The term "solid tumor" refers to an abnormal mass of tissue that usually does not contain cysts or liquid areas. Solid tumors may be benign or malignant. The term "solid tumor cancer" refers to malignant, neoplastic, or cancerous solid tumors. Solid tumor cancers include, but are not limited to, sarcomas, carcinomas, and lymphomas, such as cancers of the lung, breast, prostate, colon, rectum, and bladder. The tissue structure of solid tumors includes interdependent tissue compartments including the parenchyma (cancer cells) and the supporting stromal cells in which the cancer cells are dispersed and which may provide a supporting microenvironment.

The term "liquid tumor" refers to an abnormal mass of cells that is fluid in nature. Liquid tumor cancers include, but are not limited to, leukemias, myelomas, and lymphomas, as well as other hematological malignancies. TILs obtained from liquid tumors may also be referred to herein as marrow infiltrating lymphocytes (MILs). TILs obtained from liquid tumors, including liquid tumors circulating in peripheral blood, may also be referred to herein as PBLs. The terms MIL, TIL, and PBL are used interchangeably herein and differ only based on the tissue type from which the cells are derived.

The term "microenvironment," as used herein, may refer to the solid or hematological tumor microenvironment as a whole or to an individual subset of cells within the microenvironment. The tumor microenvironment, as used herein, refers to a complex mixture of "cells, soluble factors, signaling molecules, extracellular matrices, and mechanical cues that promote neoplastic transformation, support tumor growth and invasion, protect the tumor from host immunity, foster therapeutic resistance, and provide niches for dominant metastases to thrive," as described in Swartz, et al., *Cancer Res.*, 2012, 72, 2473. Although tumors express antigens that should be recognized by T-cells, tumor clearance by the immune system is rare because of immune suppression by the microenvironment.

The term "dynamically scheduling," or "dynamic scheduling" as used herein, may refer to creating a flexible schedule for events to take place based on an outcome or result of one or more subsequent events. Thus, a scheduled date for an event, such as a patient treatment event, may be dynamically changed based on an outcome or a result of one or more manufacturing steps performed after scheduling the scheduled date, but before the event.

In an embodiment, the invention includes a method of treating a cancer with a population of TILs, wherein a patient is pre-treated with non-myeloablative chemotherapy prior to an infusion of TILs according to the invention. In some embodiments, the population of TILs may be provided wherein a patient is pre-treated with nonmyeloablative chemotherapy prior to an infusion of TILs according to the present invention. In an embodiment, the non-myeloablative chemotherapy is cyclophosphamide 60 mg/kg/d for 2 days (days 27 and 26 prior to TIL infusion) and fludarabine 25 mg/m²/d for 5 days (days 27 to 23 prior to TIL infusion). In an embodiment, after non-myeloablative chemotherapy and TIL infusion (at day 0) according to the invention, the patient receives an intravenous infusion of IL-2 intravenously at 720,000 IU/kg every 8 hours to physiologic tolerance.

Experimental findings indicate that lymphodepletion prior to adoptive transfer of tumor-specific T lymphocytes plays a key role in enhancing treatment efficacy by eliminating regulatory T-cells and competing elements of the immune system ("cytokine sinks"). Accordingly, some embodiments of the invention utilize a lymphodepletion step (sometimes also referred to as "immunosuppressive conditioning") on the patient prior to the introduction of the rTILs of the invention.

The terms "co-administration," "co-administering," "administered in combination with," "administering in combination with," "simultaneous," and "concurrent," as used herein, encompass administration of two or more active pharmaceutical ingredients (in a preferred embodiment of the present invention, for example, at least one potassium channel agonist in combination with a plurality of TILs) to a subject so that both active pharmaceutical ingredients and/or their metabolites are present in the subject at the same time. Co-administration includes simultaneous administration in separate compositions, administration at different times in separate compositions, or administration in a composition in which two or more active pharmaceutical ingredients are present. Simultaneous administration in separate compositions and administration in a composition in which both agents are present are preferred.

The term "effective amount" or "therapeutically effective amount" refers to that amount of a compound or combination of compounds as described herein that is sufficient to effect the intended application including, but not limited to, disease treatment. A therapeutically effective amount may vary depending upon the intended application (in vitro or in vivo), or the subject and disease condition being treated (e.g., the weight, age and gender of the subject), the severity of the disease condition, or the manner of administration. The term also applies to a dose that will induce a particular response in target cells (e.g., the reduction of platelet adhesion and/or cell migration). The specific dose will vary depending on the particular compounds chosen, the dosing regimen to be followed, whether the compound is administered in combination with other compounds, timing of administration, the tissue to which it is administered, and the physical delivery system in which the compound is carried.

The terms "treatment", "treating", "treat", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development or progression; and (c) relieving the disease, i.e., causing regression of the disease and/or relieving one or more disease symptoms. "Treatment" is also meant to encompass delivery of an agent in order to provide for a pharmacologic effect, even in the absence of a disease or condition. For example, "treatment" encompasses delivery of a composition that can elicit an immune response or confer immunity in the absence of a disease condition, e.g., in the case of a vaccine.

The term "heterologous" when used with reference to portions of a nucleic acid or protein indicates that the nucleic acid or protein comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source, or coding regions from different sources. Similarly, a heterologous protein indicates that the protein comprises two or more subsequences that are not found in the same relationship to each other in nature (e.g., a fusion protein).

The terms "sequence identity," "percent identity," and "sequence percent identity" (or synonyms thereof, e.g., "99% identical") in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences. Suitable programs to determine percent sequence identity include for example the BLAST suite of programs available from the U.S. Government's National Center for Biotechnology Information BLAST web site. Comparisons between two sequences can be carried using either the BLASTN or BLASTP algorithm. BLASTN is used to compare nucleic acid sequences, while BLASTP is used to compare amino acid sequences. ALIGN, ALIGN-2 (Genentech, South San Francisco, California) or MegAlign, available from DNASTAR, are additional publicly available software programs that can be used to align sequences. One skilled in the art can determine appropriate parameters for maximal alignment by particular alignment software. In certain embodiments, the default parameters of the alignment software are used.

As used herein, the term "variant" encompasses but is not limited to, proteins, antibodies or fusion proteins which comprise an amino acid sequence which differs from the amino acid sequence of a reference protein, antibody or fusion protein by way of one or more substitutions, deletions and/or additions at certain positions within or adjacent to the amino acid sequence of the reference antibody, protein, or fusion protein. The variant may comprise one or more conservative substitutions in its amino acid sequence as compared to the amino acid sequence of a reference antibody. Conservative substitutions may involve, e.g., the substitution of similarly charged or uncharged amino acids. The variant retains the ability to specifically bind to the antigen of the reference antibody, protein, or fusion protein. The term variant also includes pegylated antibodies or proteins.

By "tumor infiltrating lymphocytes" or "TILs" herein is meant a population of cells originally obtained as white blood cells that have left the bloodstream of a subject and migrated into a tumor. TILs include, but are not limited to, $CD8^+$ cytotoxic T-cells (lymphocytes), Th1 and Th17 $CD4^+$ T-cells, natural killer cells, dendritic cells and M1 macrophages. TILs include both primary and secondary TILs. "Primary TILs" are those that are obtained from patient tissue samples as outlined herein (sometimes referred to as "freshly obtained" or "freshly isolated"), and "secondary TILs" are any TIL cell populations that have been expanded or proliferated as discussed herein, including, but not limited to bulk TILs, expanded TILs ("REP TILs") as well as "reREP TILs" as discussed herein. reREP TILs can include for example second expansion TILs or second additional expansion TILs (such as, for example, those described in Step D of FIG. 2A and/or FIG. 9, including TILs referred to as reREP TILs).

TILs can generally be defined either biochemically, using cell surface markers, or functionally, by their ability to infiltrate tumors and effect treatment. TILs can be generally categorized by expressing one or more of the following biomarkers: CD4, CD8, TCR αβ, CD27, CD28, CD56, CCR7, CD45Ra, CD95, PD-1, and CD25. Additionally, and alternatively, TILs can be functionally defined by their ability to infiltrate solid tumors upon reintroduction into a patient. TILS may further be characterized by potency—for example, TILS may be considered potent if, for example, interferon (IFN) release is greater than about 50 pg/mL, greater than about 100 pg/mL, greater than about 150 pg/mL, or greater than about 200 pg/mL. TILS may be considered potent if, for example, interferon (IFNγ) release is greater than about 50 pg/mL, greater than about 100 pg/mL, greater than about 150 pg/mL, or greater than about 200 pg/mL, greater than about 300 pg/mL, greater than about 400 pg/mL, greater than about 500 pg/mL, greater than about 600 pg/mL, greater than about 700 pg/mL, greater than about 800 pg/mL, greater than about 900 pg/mL, greater than about 1000 pg/mL.

The terms "pharmaceutically acceptable carrier" or "pharmaceutically acceptable excipient" are intended to include any and all solvents, dispersion media, coatings, antibacterial and antifungal agents, isotonic and absorption delaying agents, and inert ingredients. The use of such pharmaceutically acceptable carriers or pharmaceutically acceptable excipients for active pharmaceutical ingredients is well known in the art. Except insofar as any conventional pharmaceutically acceptable carrier or pharmaceutically acceptable excipient is incompatible with the active pharmaceutical ingredient, its use in the therapeutic compositions of the invention is contemplated. Additional active pharmaceutical ingredients, such as other drugs, can also be incorporated into the described compositions and methods.

The terms "about" and "approximately" mean within a statistically meaningful range of a value. Such a range can be within an order of magnitude, preferably within 50%, more preferably within 20%, more preferably still within 10%, and even more preferably within 5% of a given value or range. The allowable variation encompassed by the terms "about" or "approximately" depends on the particular system under study, and can be readily appreciated by one of ordinary skill in the art. Moreover, as used herein, the terms "about" and "approximately" mean that dimensions, sizes, formulations, parameters, shapes and other quantities and characteristics are not and need not be exact, but may be approximate and/or larger or smaller, as desired, reflecting tolerances, conversion factors, rounding off, measurement error and the like, and other factors known to those of skill in the art. In general, a dimension, size, formulation, parameter, shape or other quantity or characteristic is "about" or "approximate" whether or not expressly stated to be such. It is noted that embodiments of very different sizes, shapes and dimensions may employ the described arrangements.

The transitional terms "comprising," "consisting essentially of," and "consisting of," when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All compositions, methods, and kits described herein that embody the present invention can, in alternate embodiments, be more specifically defined by any of the transitional terms "comprising," "consisting essentially of," and "consisting of."

II. TIL Manufacturing Processes (Embodiments of GEN3 Processes)

Without being limited to any particular theory, it is believed that the priming first expansion that primes an activation of T-cells followed by the rapid second expansion that boosts the activation of T-cells as described in the methods of the invention allows the preparation of expanded T-cells that retain a "younger" phenotype, and as such the expanded T-cells of the invention are expected to exhibit greater cytotoxicity against cancer cells than T-cells expanded by other methods. In particular, it is believed that an activation of T-cells that is primed by exposure to an anti-CD3 antibody (e.g., OKT-3), IL-2 and optionally antigen-presenting cells (APCs) and then boosted by subsequent exposure to additional anti-CD-3 antibody (e.g., OKT-3), IL-2 and APCs as taught by the methods of the invention limits or avoids the maturation of T-cells in culture, yielding a population of T-cells with a less mature phenotype, which T-cells are less exhausted by expansion in culture and exhibit greater cytotoxicity against cancer cells. In some embodiments, the step of rapid second expansion is split into a plurality of steps to achieve a scaling up of the culture by: (a) performing the rapid second expansion by culturing T-cells in a small scale culture in a first container, e.g., a G-REX 100MCS container, for a period of about 3 to 4 days, and then (b) effecting the transfer of the T-cells in the small scale culture to a second container larger than the first container, e.g., a G-REX 500MCS container, and culturing the T-cells from the small scale culture in a larger scale culture in the second container for a period of about 4 to 7 days. In some embodiments, the step of rapid expansion is split into a plurality of steps to achieve a scaling out of the culture by: (a) performing the rapid second expansion by culturing T-cells in a first small scale culture in a first container, e.g., a G-REX 100MCS container, for a period of about 3 to 4 days, and then (b) effecting the transfer and apportioning of the T-cells from the first small scale culture into and amongst at least 2, 3, 4, 5, 6, 7, 8, 9, 10, 11, 12, 13, 14, 15, 16, 17, 18, 19, or 20 second containers that are equal in size to the first container, wherein in each second container the portion of the T-cells from first small scale culture transferred to such second container is cultured in a second small scale culture for a period of about 4 to 7 days. In some embodiments, the step of rapid expansion is split into a plurality of steps to achieve a scaling out and scaling up of the culture by: (a) performing the rapid second expansion by culturing T-cells in a small scale culture in a first container, e.g., a G-REX 100MCS container, for a period of about 3 to 4 days, and then (b) effecting the transfer and apportioning of the T-cells from the small scale culture into and amongst at least 2, 3, 4, 5, 6, 7, 8, 9, 10, 11, 12, 13, 14, 15, 16, 17, 18, 19, or 20 second containers that are larger in size than the first container, e.g., G-REX 500MCS containers, wherein in each second container the portion of the T-cells from the small scale culture transferred to such second container is cultured in a larger scale culture for a period of about 4 to 7 days. In some embodiments, the step of rapid expansion is split into a plurality of steps to achieve a scaling out and scaling up of the culture by: (a) performing the rapid second expansion by culturing T-cells in a small scale culture in a first container, e.g., a G-REX 100MCS container, for a period of about 4 days, and then (b) effecting the transfer and apportioning of the T-cells from the small scale culture into and amongst 2, 3 or 4 second containers that are larger in size than the first container, e.g., G-REX 500MCS containers, wherein in each second container the portion of the T-cells from the small scale culture transferred to such second container is cultured in a larger scale culture for a period of about 5 days.

An exemplary TIL process known as process 3 (also referred to herein as GEN3) containing some of these features is depicted in FIGS. 2A and 2C and/or FIG. 9, and some of the advantages of this embodiment of the present disclosure over process 2A are described in FIG. 2B. Two embodiments of process 3 are shown in FIG. 2C. Process 2A or Gen 2 is also described in U.S. Patent Publication No. 2018/.0280436, incorporated by reference herein in its entirety. Process 3 or Gen 3 is also described in International Patent Application No. PCT/US2019/059718, incorporated by reference herein in its entirety, as well as figures and FIGS. 5, 6, 8, 9, 10, and 11 as provided in the present application.

In some embodiments, the rapid second expansion is performed after the activation of T-cells effected by the priming first expansion begins to decrease, abate, decay or subside.

In some embodiments, the rapid second expansion is performed after the activation of T-cells effected by the priming first expansion has decreased by at or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%.

In some embodiments, the rapid second expansion is performed after the activation of T-cells effected by the priming first expansion has decreased by a percentage in the range of at or about 1% to 100%.

In some embodiments, the rapid second expansion is performed after the activation of T-cells effected by the priming first expansion has decreased by a percentage in the range of at or about 1% to 10%, 10% to 20%, 20% to 30%, 30% to 40%, 40% to 50%, 50% to 60%, 60% to 70%, 70% to 80%, 80% to 90%, or 90% to 100%.

In some embodiments, the rapid second expansion is performed after the activation of T-cells effected by the priming first expansion has decreased by at least at or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99%.

In some embodiments, the rapid second expansion is performed after the activation of T-cells effected by the priming first expansion has decreased by up to at or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%.

In some embodiments, the decrease in the activation of T-cells effected by the priming first expansion is determined by a reduction in the amount of interferon gamma released by the T-cells in response to stimulation with antigen. A reduction in the amount of interferon gamma released by the T-cells of about 5%, 10%, 15%, 20%, 25%, 30%, 35%, 40%, 45%, 45%, 50%, 55%, 60%, 65%, 70%, and/or 75% as compared to an initial or control level of interferon gamma is indicative of a decrease in the activation of the T-cells. A reduction in the amount of interferon gamma released by the T-cells to less than 200 pg/mL, less than 250 pg/mL, less than 300 pg/mL, less than 350 pg/mL, less than 400 pg/mL, less than 450 pg/mL, less than 500 pg/mL, less than 550 pg/mL, less than 600 pg/mL, less than 650 pg/mL, less than 700 pg/mL, less than 750 pg/mL, less than 800 pg/mL, less than 850 pg/mL, less than 900 pg/mL, less than 950 pg/mL, or less than 1000 pg/mL is indicative of a decrease in the activation of the T-cells.

In some embodiments, the priming first expansion of T-cells is performed during a period of up to at or about 7 days or about 8 days.

In some embodiments, the priming first expansion of T-cells is performed during a period of up to at or about 1 day, 2 days, 3 days, 4 days, 5 days, 6 days, 7 days, or 8 days.

In some embodiments, the priming first expansion of T-cells is performed during a period of 1 day, 2 days, 3 days, 4 days, 5 days, 6 days, 7 days, or 8 days.

In some embodiments, the rapid second expansion of T-cells is performed during a period of up to at or about 11 days.

In some embodiments, the rapid second expansion of T-cells is performed during a period of up to at or about 1 day, 2 days, 3 days, 4 days, 5 days, 6 days, 7 days, 8 days, 9 days, 10 days or 11 days.

In some embodiments, the rapid second expansion of T-cells is performed during a period of 1 day, 2 days, 3 days, 4 days, 5 days, 6 days, 7 days, 8 days, 9 days, 10 days or 11 days.

In some embodiments, the priming first expansion of T-cells is performed during a period of from at or about 1 day to at or about 7 days and the rapid second expansion of T-cells is performed during a period of from at or about 1 day to at or about 11 days.

In some embodiments, the priming first expansion of T-cells is performed during a period of up to at or about 1 day, 2 days, 3 days, 4 days, 5 days, 6 days, 7 days, or 8 days and the rapid second expansion of T-cells is performed during a period of up to at or about 1 day, 2 days, 3 days, 4 days, 5 days, 6 days, 7 days, 8 days, 9 days, 10 days or 11 days.

In some embodiments, the priming first expansion of T-cells is performed during a period of from at or about 1 day to at or about 8 days and the rapid second expansion of T-cells is performed during a period of from at or about 1 day to at or about 9 days.

In some embodiments, the priming first expansion of T-cells is performed during a period of 8 days and the rapid second expansion of T-cells is performed during a period of 9 days.

In some embodiments, the priming first expansion of T-cells is performed during a period of from at or about 1 day to at or about 7 days and the rapid second expansion of T-cells is performed during a period of from at or about 1 day to at or about 9 days.

In some embodiments, the priming first expansion of T-cells is performed during a period of 7 days and the rapid second expansion of T-cells is performed during a period of 9 days.

In some embodiments, the T-cells are tumor infiltrating lymphocytes (TILs).

In some embodiments, the T-cells are marrow infiltrating lymphocytes (MILs).

In some embodiments, the T-cells are peripheral blood lymphocytes (PBLs).

In some embodiments, the T-cells are obtained from a donor suffering from a cancer.

In some embodiments, the T-cells are TILs obtained from a tumor excised from a patient suffering from a cancer.

In some embodiments, the T-cells are MILs obtained from bone marrow of a patient suffering from a hematologic malignancy.

In some embodiments, the T-cells are PBLs obtained from peripheral blood mononuclear cells (PBMCs) from a donor. In some embodiments, the donor is suffering from a cancer. In some embodiments, the cancer is the cancer is selected from the group consisting of melanoma, ovarian cancer, endometrial cancer, thyroid cancer, colorectal cancer, cervical cancer, non-small-cell lung cancer (NSCLC), lung cancer, bladder cancer, breast cancer, cancer caused by human papilloma virus, head and neck cancer (including head and neck squamous cell carcinoma (HNSCC)), glioblastoma (including GBM), gastrointestinal cancer, renal cancer, and renal cell carcinoma. In some embodiments, the cancer is selected from the group consisting of melanoma, ovarian cancer, cervical cancer, non-small-cell lung cancer (NSCLC), lung cancer, bladder cancer, breast cancer, cancer caused by human papilloma virus, head and neck cancer (including head and neck squamous cell carcinoma (HNSCC)), glioblastoma (including GBM), gastrointestinal cancer, renal cancer, and renal cell carcinoma. In some embodiments, the donor is suffering from a tumor. In some embodiments, the tumor is a liquid tumor. In some embodiments, the tumor is a solid tumor. In some embodiments, the donor is suffering from a hematologic malignancy.

In certain aspects of the present disclosure, immune effector cells, e.g., T-cells, can be obtained from a unit of blood collected from a subject using any number of techniques known to the skilled artisan, such as FICOLL separation. In one preferred aspect, cells from the circulating blood of an individual are obtained by apheresis. The apheresis product typically contains lymphocytes, including T-cells, monocytes, granulocytes, B cells, other nucleated white blood cells, red blood cells, and platelets. In one aspect, the cells collected by apheresis may be washed to remove the plasma fraction and, optionally, to place the cells in an appropriate buffer or media for subsequent processing steps. In one embodiment, the cells are washed with phosphate buffered saline (PBS). In an alternative embodiment, the wash solution lacks calcium and may lack magnesium or may lack many if not all divalent cations. In one aspect, T-cells are isolated from peripheral blood lymphocytes by lysing the red blood cells and depleting the monocytes, for example, by centrifugation through a PERCOLL gradient or by counterflow centrifugal elutriation.

In some embodiments, the T-cells are PBLs separated from whole blood or apheresis product enriched for lymphocytes from a donor. In some embodiments, the donor is suffering from a cancer. In some embodiments, the cancer is the cancer is selected from the group consisting of melanoma, ovarian cancer, endometrial cancer, thyroid cancer, colorectal cancer, cervical cancer, non-small-cell lung cancer (NSCLC), lung cancer, bladder cancer, breast cancer, cancer caused by human papilloma virus, head and neck cancer (including head and neck squamous cell carcinoma (HNSCC)), glioblastoma (including GBM), gastrointestinal cancer, renal cancer, and renal cell carcinoma. In some embodiments, the cancer is selected from the group consisting of melanoma, ovarian cancer, cervical cancer, non-small-cell lung cancer (NSCLC), lung cancer, bladder cancer, breast cancer, cancer caused by human papilloma virus, head and neck cancer (including head and neck squamous cell carcinoma (HNSCC)), glioblastoma (including GBM), gastrointestinal cancer, renal cancer, and renal cell carcinoma. In some embodiments, the donor is suffering from a tumor. In some embodiments, the tumor is a liquid tumor. In some embodiments, the tumor is a solid tumor. In some embodiments, the donor is suffering from a hematologic malignancy. In some embodiments, the PBLs are isolated from whole blood or apheresis product enriched for lymphocytes by using positive or negative selection methods, i.e., removing the PBLs using a marker(s), e.g., CD3+ CD45+, for T-cell phenotype, or removing non-T-cell phenotype cells, leaving PBLs. In other embodiments, the PBLs are isolated by gradient centrifugation. Upon isolation of PBLs from donor tissue, the priming first expansion of PBLs can be initiated by seeding a suitable number of isolated PBLs (in some embodiments, approximately $1 \times 10^7$ PBLs) in the priming first expansion culture according to the priming first expansion step of any of the methods described herein.

As discussed and generally outlined herein, TILs are taken from a patient sample and manipulated to expand their number prior to transplant into a patient using the TIL expansion process described herein. In some embodiments, the TILs may be optionally genetically manipulated as discussed below. In some embodiments, the TILs may be cryopreserved prior to or after expansion. Once thawed, they may also be restimulated to increase their metabolism prior to infusion into a patient.

In some embodiments, the priming first expansion (including processes referred herein as the pre-Rapid Expansion (Pre-REP), as well as processes shown in FIG. 2A as Step B) is shortened to 1 to 8 days and the rapid second expansion (including processes referred to herein as Rapid Expansion Protocol (REP) as well as processes shown in FIG. 2A as Step D) is shortened to 1 to 9 days, as discussed in detail below as well as in the examples and figures. In some embodiments, the priming first expansion (including processes referred herein as the pre-Rapid Expansion (Pre-REP), as well as processes shown in FIG. 2A as Step B) is shortened to 1 to 8 days and the rapid second expansion (including processes referred to herein as Rapid Expansion Protocol (REP) as well as processes shown in FIG. 2A as Step D) is shortened to 1 to 8 days, as discussed in detail below as well as in the examples and figures. In some embodiments, the priming first expansion (including processes referred herein as the pre-Rapid Expansion (Pre-REP), as well as processes shown in FIG. 2A as Step B) is shortened to 1 to 7 days and the rapid second expansion (including processes referred to herein as Rapid Expansion Protocol (REP) as well as processes shown in FIG. 2A as Step D) is shortened to 1 to 9 days, as discussed in detail below as well as in the examples and figures. In some embodiments, the priming first expansion (including processes referred herein as the pre-Rapid Expansion (Pre-REP), as well as processes shown in FIG. 2A as Step B) is 1 to 7 days and the rapid second expansion (including processes referred to herein as Rapid Expansion Protocol (REP) as well as processes shown in FIG. 2A as Step D is 1 to 10 days, as discussed in detail below as well as in the examples and figures. In some embodiments, the priming first expansion (for example, an expansion described as Step B in FIG. 2A) is shortened to 8 days and the rapid second expansion (for example, an expansion as described in Step D in FIG. 2A) is 7 to 9 days. In some embodiments, the priming first expansion (for example, an expansion described as Step B in FIG. 2A) is 8 days and the rapid second expansion (for example, an expansion as described in Step D in FIG. 2A) is 8 to 9 days. In some embodiments, the priming first expansion (for example, an expansion described as Step B in FIG. 2A is shortened to 7 days and the rapid second expansion (for example, an expansion as described in Step D in FIG. 2A) is 7 to 8 days. In some embodiments, the priming first expansion (for example, an expansion described as Step B in FIG. 2A) is shortened to 8 days and the rapid second expansion (for example, an expansion as described in Step D in FIG. 2A) is 8 days. In some embodiments, the priming first expansion (for example, an expansion described as Step B in FIG. 2A) is 8 days and the rapid second expansion (for example, an expansion as described in Step D in FIG. 2A) is 9 days. In some embodiments, the priming first expansion (for example, an expansion described as Step B in FIG. 2A) is 8 days and the rapid second expansion (for example, an expansion as described in Step D in FIG. 2A) is 10 days. In some embodiments, the priming first expansion (for example, an expansion described as Step B in FIG. 2A) is 7 days and the rapid second expansion (for example, an expansion as described in Step D in FIG. 2A) is 7 to 10 days. In some embodiments, the priming first expansion (for example, an expansion described as Step B in FIG. 2A) is 7 days and the rapid second expansion (for example, an expansion as described in Step D in FIG. 2A) is 8 to 10 days. In some embodiments, the priming first expansion (for example, an expansion described as Step B in FIG. 2A) is 7 days and the rapid second expansion (for example, an expansion as described in Step D in FIG. 2A is 9 to 10 days. In some embodiments, the priming first expansion (for example, an expansion described as Step B in FIG. 2A) is shortened to 7 days and the rapid second expansion (for example, an expansion as described in Step D in FIG. 2A) is 7 to 9 days. In some embodiments, the combination of the priming first expansion and rapid second expansion (for example, expansions described as Step B and Step D in FIG. 2A) is 14-16 days, as discussed in detail below and in the examples and figures. Particularly, it is considered that certain embodiments of the present invention comprise a priming first expansion step in which TILs are activated by exposure to an anti-CD3 antibody, e.g., OKT-3 in the presence of IL-2 or exposure to an antigen in the presence of at least IL-2 and an anti-CD3 antibody e.g., OKT-3. In certain embodiments, the TILs which are activated in the priming first expansion step as described above are a first population of TILs i.e., which are a primary cell population.

In some embodiments, the TILs are not stored after the first expansion and prior to the second expansion, and the TILs proceed directly to the second expansion (for example, in some embodiments, there is no storage during the transition from Step B to Step D as shown in FIG. 2A). In some embodiments, the transition occurs in closed system, as described herein. In some embodiments, the TILs from the first expansion, the second population of TILs, proceeds directly into the second expansion with no transition period.

In some embodiments, the first expansion, for example, Step B according to FIG. 2A, is performed in a closed system bioreactor. In some embodiments, a closed system is employed for the TIL expansion, as described herein. In some embodiments, a single bioreactor is employed. In some embodiments, the single bioreactor employed is for example a G-REX-10 or a G-REX-100. In some embodiments, the closed system bioreactor is a single bioreactor.

The "Step" Designations A, B, C, etc., referred to herein are in reference to the non-limiting example in FIG. 2A and in reference to certain non-limiting embodiments described herein. The ordering of the Steps below and in FIG. 2A is exemplary and any combination or order of steps, as well as additional steps, repetition of steps, and/or omission of steps is contemplated by the present application and the methods disclosed herein.

A. Cell Viability Analyses

A cell viability assay can be performed after the priming first expansion (sometimes referred to as the initial bulk expansion), using standard assays known in the art. Thus, in certain embodiments, the method comprises performing a cell viability assay subsequent to the priming first expansion. In some embodiments, a cell viability assay can be performed after the second expansion (e.g., after REP), as well as after the final harvest. For example, a trypan blue exclusion assay can be done on a sample of the bulk TILs, which selectively labels dead cells and allows a viability assessment. Other assays for use in testing viability can include but are not limited to the Alamar blue assay; and the MTT assay.

1. Cell Counts, Viability, Flow Cytometry

In some embodiments, cell counts and/or viability are measured. The expression of markers such as but not limited CD3, CD4, CD8, and CD56, as well as any other disclosed or described herein, can be measured by flow cytometry with antibodies, for example but not limited to those commercially available from BD Bio-sciences (BD Biosciences, San Jose, CA) using a FACSCantom flow cytometer (BD Bio-sciences). The cells can be counted manually using a disposable c-chip hemocytometer (VWR, Batavia, IL) and viability can be assessed using any method known in the art, including but not limited to trypan blue staining. The cell viability can also be assayed based on U.S. Ser. No. 15/863,634, incorporated by reference herein in its entirety. Cell viability can also be assayed based on U.S. Patent Publication No. 2018/0280436 or International Patent Publication No. WO/2018/081473, both of which are incorporate herein in their entireties for all purposes.

In some cases, the bulk TIL population can be cryopreserved immediately, using the protocols discussed below. Alternatively, the bulk TIL population can be subjected to REP and then cryopreserved as discussed below. Similarly, in the case where genetically modified TILs will be used in therapy, the bulk or REP TIL populations can be subjected to genetic modifications for suitable treatments.

III. TIL Manufacturing Processes (Embodiments of Process 2A)

Figure 5:
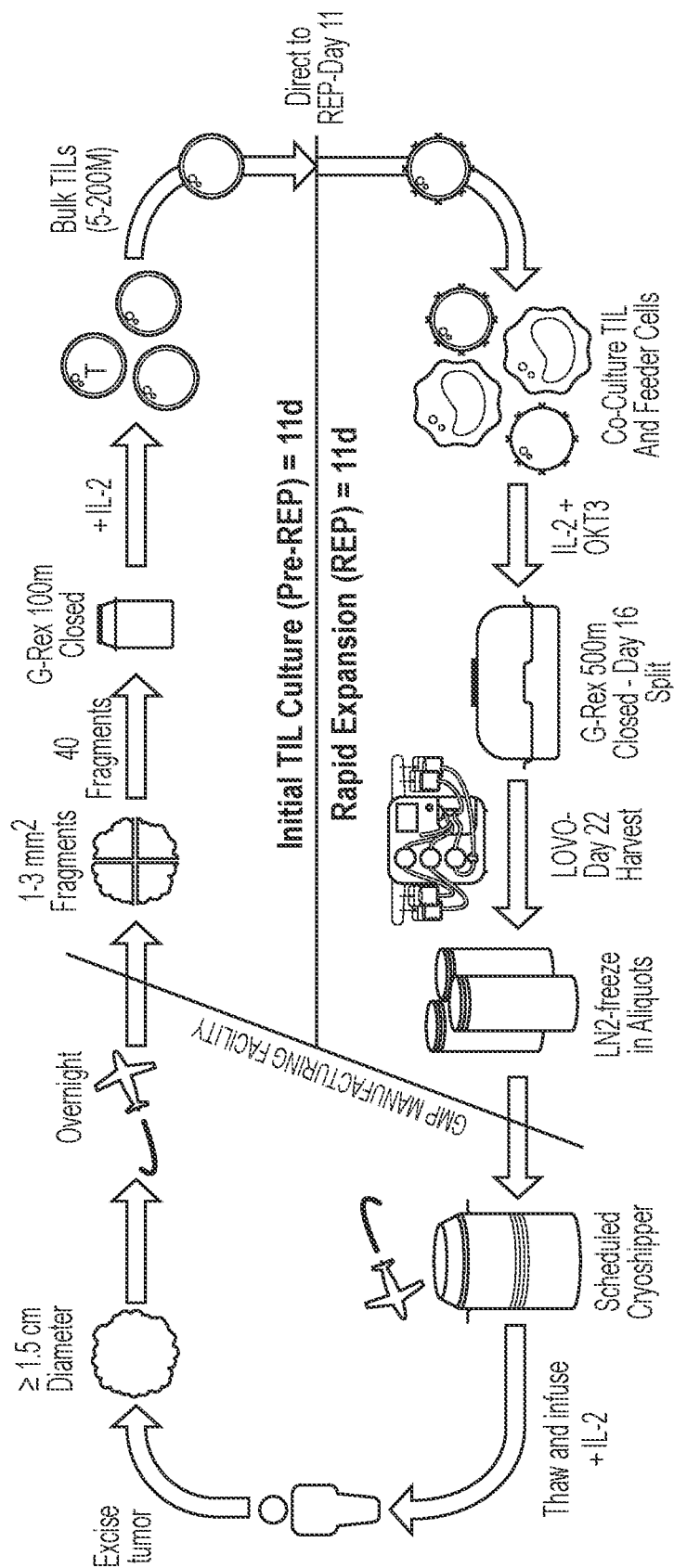
FIG. 5 shows a diagram of an embodiment of process 2A, a 22-day process for TIL manufacturing.
Figure 7:
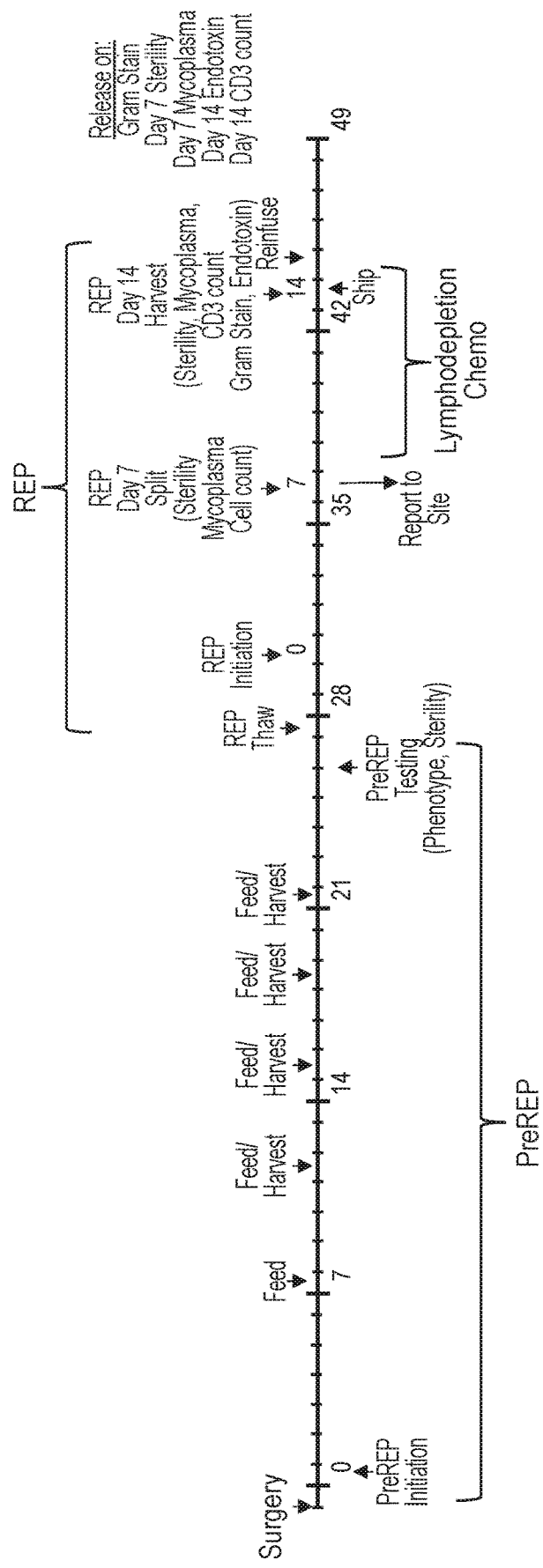
FIG. 7 shows the 1C process timeline.
Figure 8:
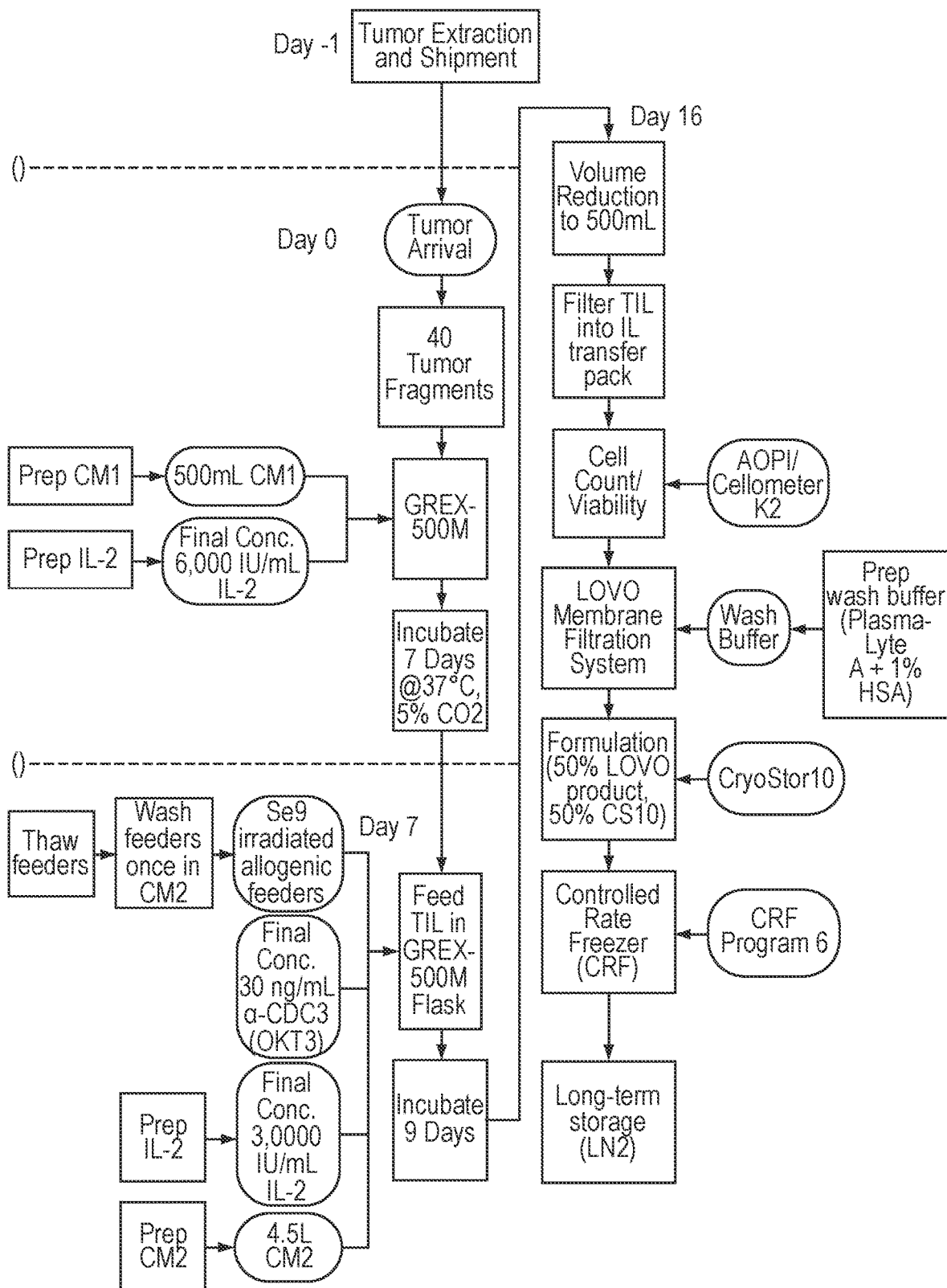
FIG. 8 shows a detailed schematic for an embodiment of the 2A process.

An exemplary TIL process known as process 2A containing some of these features is depicted in FIG. 5, and some of the differences and advantages of this embodiment of the present invention over process 1C are described in FIG. 6 as well FIG. 11. Process 1C is shown for comparison in FIGS. 6, 7, and 10. An embodiment of process 2A is shown in FIG. 6 as well as FIGS. 5, 9, 10, and 11. FIGS. 10 and 11 further provides an exemplary 2A process compared to an exemplary 1C process.

As discussed herein, the present invention can include a step relating to the restimulation of cryopreserved TTLs to increase their metabolic activity and thus relative health prior to transplant into a patient, and methods of testing said metabolic health. As generally outlined herein, TILs are generally taken from a patient sample and manipulated to expand their number prior to transplant into a patient. In some embodiments, the TILs may be optionally genetically manipulated as discussed below.

In some embodiments, the TILs may be cryopreserved. Once thawed, they may also be restimulated to increase their metabolism prior to infusion into a patient.

In some embodiments, the first expansion (including processes referred to as the preREP as well as processes shown in FIG. 9 as Step A) is shortened to 3 to 14 days and the second expansion (including processes referred to as the REP as well as processes shown in FIG. 9 as Step B) is shorted to 7 to 14 days, as discussed in detail below as well as in the examples and figures. In some embodiments, the first expansion (for example, an expansion described as Step B in FIG. 9) is shortened to 11 days and the second expansion (for example, an expansion as described in Step D in FIG. 9) is shortened to 11 days, as discussed in the Examples and shown in FIGS. 5, 6, 8, 9, 10, and 11. In some embodiments, the combination of the first expansion and second expansion (for example, expansions described as Step B and Step D in FIG. 9) is shortened to 22 days, as discussed in detail below and in the examples and figures.

The "Step" Designations A, B, C, etc., below are in reference to FIG. 9 and in reference to certain embodiments described herein. The ordering of the Steps below and in FIG. 9 is exemplary and any combination or order of steps, as well as additional steps, repetition of steps, and/or omission of steps is contemplated by the present application and the methods disclosed herein.

A. Step A: Obtain Patient Tumor Sample

In general, TILs are initially obtained from a patient tumor sample and then expanded into a larger population for further manipulation as described herein, optionally cryopreserved, restimulated as outlined herein and optionally evaluated for phenotype and metabolic parameters as an indication of TIL health.

A patient tumor sample may be obtained using methods known in the art, generally via surgical resection, needle biopsy, core biopsy, small biopsy, or other means for obtaining a sample that contains a mixture of tumor and TIL cells. In some embodiments, multilesional sampling is used. In some embodiments, surgical resection, needle biopsy, core biopsy, small biopsy, or other means for obtaining a sample that contains a mixture of tumor and TIL cells includes multilesional sampling (i.e., obtaining samples from one or more tumor cites and/or locations in the patient, as well as one or more tumors in the same location or in close proximity). In general, the tumor sample may be from any solid tumor, including primary tumors, invasive tumors or metastatic tumors. The tumor sample may also be a liquid tumor, such as a tumor obtained from a hematological malignancy. The solid tumor may be of lung tissue. In some embodiments, useful TTLs are obtained from non-small cell lung carcinoma (NSCLC).

Once obtained, the tumor sample is generally fragmented using sharp dissection into small pieces of between 1 to about 8 mm3, with from about 2-3 mm3 being particularly useful. In some embodiments, the TILs are cultured from these fragments using enzymatic tumor digests. Such tumor digests may be produced by incubation in enzymatic media (e.g., Roswell Park Memorial Institute (RPMI) 1640 buffer, 2 mM glutamate, 10 mcg/mL gentamicine, 30 units/mL of DNase and 1.0 mg/mL of collagenase) followed by mechanical dissociation (e.g., using a tissue dissociator). Tumor digests may be produced by placing the tumor in enzymatic media and mechanically dissociating the tumor for approximately 1 minute, followed by incubation for 30 minutes at 37° C. in 5% CO2, followed by repeated cycles of mechanical dissociation and incubation under the foregoing conditions until only small tissue pieces are present. At the end of this process, if the cell suspension contains a large number of red blood cells or dead cells, a density gradient separation using FICOLL branched hydrophilic polysaccharide may be performed to remove these cells. Alternative methods known in the art may be used, such as those described in U.S. Patent Application Publication No. 2012/0244133 A1, the disclosure of which is incorporated by reference herein. Any of the foregoing methods may be used in any of the embodiments described herein for methods of expanding TTLs or methods treating a cancer.

Tumor dissociating enzyme mixtures can include one or more dissociating (digesting) enzymes such as, but not limited to, collagenase (including any blend or type of collagenase), Accutase™, Accumax™, hyaluronidase, neutral protease (dispase), chymotrypsin, chymopapain, trypsin, caseinase, elastase, papain, protease type XIV (pronase), deoxyribonuclease I (DNase), trypsin inhibitor, any other dissociating or proteolytic enzyme, and any combination thereof.

In some embodiments, the dissociating enzymes are reconstituted from lyophilized enzymes. In some embodiments, lyophilized enzymes are reconstituted in an amount of sterile buffer such as HBSS.

In some instances, collagenase (such as animal free-type 1 collagenase) is reconstituted in 10 mL of sterile HBSS or another buffer. The lyophilized stock enzyme may be at a concentration of 2892 PZ U/vial. In some embodiments, collagenase is reconstituted in 5 mL to 15 mL buffer. In some embodiment, after reconstitution the collagenase stock ranges from about 100 PZ U/mL-about 400 PZ U/mL, e.g., about 100 PZ U/mL-about 400 PZ U/mL, about 100 PZ U/mL-about 350 PZ U/mL, about 100 PZ U/mL-about 300 PZ U/mL, about 150 PZ U/mL-about 400 PZ U/mL, about 100 PZ U/mL, about 150 PZ U/mL, about 200 PZ U/mL, about 210 PZ U/mL, about 220 PZ U/mL, about 230 PZ U/mL, about 240 PZ U/mL, about 250 PZ U/mL, about 260 PZ U/mL, about 270 PZ U/mL, about 280 PZ U/mL, about 289.2 PZ U/mL, about 300 PZ U/mL, about 350 PZ U/mL, or about 400 PZ U/mL.

In some embodiments, neutral protease is reconstituted in 1 mL of sterile HBSS or another buffer. The lyophilized stock enzyme may be at a concentration of 175 DMC U/vial. In some embodiments, after reconstitution the neutral protease stock ranges from about 100 DMC/mL-about 400 DMC/mL, e.g., about 100 DMC/mL-about 400 DMC/mL, about 100 DMC/mL-about 350 DMC/mL, about 100 DMC/mL-about 300 DMC/mL, about 150 DMC/mL-about 400 DMC/mL, about 100 DMC/mL, about 110 DMC/mL, about 120 DMC/mL, about 130 DMC/mL, about 140 DMC/mL, about 150 DMC/mL, about 160 DMC/mL, about 170 DMC/mL, about 175 DMC/mL, about 180 DMC/mL, about 190 DMC/mL, about 200 DMC/mL, about 250 DMC/mL, about 300 DMC/mL, about 350 DMC/mL, or about 400 DMC/mL.

In some embodiments, DNAse I is reconstituted in 1 mL of sterile HBSS or another buffer. The lyophilized stock enzyme was at a concentration of 4 KU/vial. In some embodiments, after reconstitution the DNase I stock ranges from about 1 KU/mL-10 KU/mL, e.g., about 1 KU/mL, about 2 KU/mL, about 3 KU/mL, about 4 KU/mL, about 5 KU/mL, about 6 KU/mL, about 7 KU/mL, about 8 KU/mL, about 9 KU/mL, or about 10 KU/mL.

In some embodiments, the stock of enzymes is variable and the concentrations may need to be determined. In some embodiments, the concentration of the lyophilized stock can be verified. In some embodiments, the final amount of enzyme added to the digest cocktail is adjusted based on the determined stock concentration.

In some embodiment, the enzyme mixture includes about 10.2-ul of neutral protease (0.36 DMC U/mL), 21.3 µL of collagenase (1.2 PZ/mL) and 250-ul of DNAse I (200 U/mL) in about 4.7 mL of sterile HBSS.

As indicated above, in some embodiments, the TILs are derived from solid tumors. In some embodiments, the solid tumors are not fragmented. In some embodiments, the solid tumors are not fragmented and are subjected to enzymatic digestion as whole tumors. In some embodiments, the tumors are digested in in an enzyme mixture comprising collagenase, DNase, and hyaluronidase. In some embodiments, the tumors are digested in in an enzyme mixture comprising collagenase, DNase, and hyaluronidase for 1-2 hours. In some embodiments, the tumors are digested in in an enzyme mixture comprising collagenase, DNase, and hyaluronidase for 1-2 hours at 37° C., 5% CO2. In some embodiments, the tumors are digested in in an enzyme mixture comprising collagenase, DNase, and hyaluronidase for 1-2 hours at 37° C., 5% CO2 with rotation. In some embodiments, the tumors are digested overnight with constant rotation. In some embodiments, the tumors are digested overnight at 37° C., 5% CO2 with constant rotation. In some embodiments, the whole tumor is combined with the enzymes to form a tumor digest reaction mixture.

In some embodiments, the tumor is reconstituted with the lyophilized enzymes in a sterile buffer. In some embodiments, the buffer is sterile HBSS.

In some embodiments, the enzyme mixture comprises collagenase. In some embodiments, the collagenase is collagenase IV. In some embodiments, the working stock for the collagenase is a 100 mg/mL 10× working stock.

In some embodiments, the enzyme mixture comprises DNAse. In some embodiments, the working stock for the DNAse is a 10,000 IU/mL 10× working stock.

In some embodiments, the enzyme mixture comprises hyaluronidase. In some embodiments, the working stock for the hyaluronidase is a 10-mg/mL 10× working stock.

In some embodiments, the enzyme mixture comprises 10 mg/mL collagenase, 1000 IU/mL DNAse, and 1 mg/mL hyaluronidase.

In some embodiments, the enzyme mixture comprises 10 mg/mL collagenase, 500 IU/mL DNAse, and 1 mg/mL hyaluronidase.

In general, the harvested cell suspension is called a "primary cell population" or a "freshly harvested" cell population.

In some embodiments, fragmentation includes physical fragmentation, including for example, dissection as well as digestion. In some embodiments, the fragmentation is physical fragmentation. In some embodiments, the fragmentation is dissection. In some embodiments, the fragmentation is by digestion. In some embodiments, TILs can be initially cultured from enzymatic tumor digests and tumor fragments obtained from patients. In an embodiment, TILs can be initially cultured from enzymatic tumor digests and tumor fragments obtained from patients.

In some embodiments, where the tumor is a solid tumor, the tumor undergoes physical fragmentation after the tumor sample is obtained in, for example, Step A (as provided in FIG. 1). In some embodiments, the fragmentation occurs before cryopreservation. In some embodiments, the fragmentation occurs after cryopreservation. In some embodiments, the fragmentation occurs after obtaining the tumor and in the absence of any cryopreservation. In some embodiments, the tumor is fragmented and 10, 20, 30, 40 or more fragments or pieces are placed in each container for the first expansion. In some embodiments, the tumor is fragmented and 30 or 40 fragments or pieces are placed in each container for the first expansion. In some embodiments, the tumor is fragmented and 40 fragments or pieces are placed in each container for the first expansion. In some embodiments, the multiple fragments comprise about 4 to about 50 fragments, wherein each fragment has a volume of about 27 mm3. In some embodiments, the multiple fragments comprise about 30 to about 60 fragments with a total volume of about 1300 mm3 to about 1500 mm3. In some embodiments, the multiple fragments comprise about 50 fragments with a total volume of about 1350 mm3. In some embodiments, the multiple fragments comprise about 50 fragments with a total mass of about 1 gram to about 1.5 grams. In some embodiments, the multiple fragments comprise about 4 fragments.

In some embodiments, the TILs are obtained from tumor fragments. In some embodiments, the tumor fragment is obtained by sharp dissection. In some embodiments, the tumor fragment is between about 1 mm3 and 10 mm3. In some embodiments, the tumor fragment is between about 1 mm3 and 8 mm3. In some embodiments, the tumor fragment is about 1 mm3. In some embodiments, the tumor fragment is about 2 mm3. In some embodiments, the tumor fragment is about 3 mm3. In some embodiments, the tumor fragment is about 4 mm3. In some embodiments, the tumor fragment is about 5 mm3. In some embodiments, the tumor fragment is about 6 mm3. In some embodiments, the tumor fragment is about 7 mm3. In some embodiments, the tumor fragment is about 8 mm3. In some embodiments, the tumor fragment is about 9 mm3. In some embodiments, the tumor fragment is about 10 mm3. In some embodiments, the tumors are 1-4 mm×1-4 mm×1-4 mm. In some embodiments, the tumors are 1 mm×1 mm×1 mm. In some embodiments, the tumors are 2 mm×2 mm×2 mm. In some embodiments, the tumors are 3 mm×3 mm×3 mm. In some embodiments, the tumors are 4 mm×4 mm×4 mm.

In some embodiments, the tumors are resected in order to minimize the amount of hemorrhagic, necrotic, and/or fatty tissues on each piece. In some embodiments, the tumors are resected in order to minimize the amount of hemorrhagic tissue on each piece. In some embodiments, the tumors are resected in order to minimize the amount of necrotic tissue on each piece. In some embodiments, the tumors are resected in order to minimize the amount of fatty tissue on each piece.

In some embodiments, the tumor fragmentation is performed in order to maintain the tumor internal structure. In some embodiments, the tumor fragmentation is performed without preforming a sawing motion with a scalpel. In some embodiments, the TILs are obtained from tumor digests. In some embodiments, tumor digests were generated by incubation in enzyme media, for example but not limited to RPMI 1640, 2 mM GlutaMAX, 10 mg/mL gentamicin, 30 U/mL DNase, and 1.0 mg/mL collagenase, followed by mechanical dissociation (GentleMACS, Miltenyi Biotec, Auburn, CA). After placing the tumor in enzyme media, the tumor can be mechanically dissociated for approximately 1 minute. The solution can then be incubated for 30 minutes at 37° C. in 5% CO2 and it then mechanically disrupted again for approximately 1 minute. After being incubated again for 30 minutes at 37° C. in 5% CO2, the tumor can be mechanically disrupted a third time for approximately 1 minute. In some embodiments, after the third mechanical disruption if large pieces of tissue were present, 1 or 2 additional mechanical dissociations were applied to the sample, with or without 30 additional minutes of incubation at 37° C. in 5% CO2. In some embodiments, at the end of the final incubation if the cell suspension contained a large number of red blood cells or dead cells, a density gradient separation using Ficoll can be performed to remove these cells.

In some embodiments, the harvested cell suspension prior to the first expansion step is called a "primary cell population" or a "freshly harvested" cell population.

In some embodiments, cells can be optionally frozen after sample harvest and stored frozen prior to entry into the expansion described in Step B, which is described in further detail below, as well as exemplified in FIG. 9.

1. Pleural Effusion T-Cells and TILs

In some embodiments, the sample is a pleural fluid sample. In some embodiments, the source of the T-cells TILs for expansion according to the processes described herein is a pleural fluid sample. In some embodiments, the sample is a pleural effusion derived sample. In some embodiments, the source of the T-cells or TILs for expansion according to the processes described herein is a pleural effusion derived sample. See, for example, methods described in U.S. Patent Publication US 2014/0295426, incorporated herein by reference in its entirety for all purposes.

In some embodiments, any pleural fluid or pleural effusion suspected of and/or containing TILs can be employed. Such a sample may be derived from a primary or metastatic lung cancer, such as NSCLC or SCLC. In some embodiments, the sample may be secondary metastatic cancer cells which originated from another organ, e.g., breast, ovary, colon or prostate. In some embodiments, the sample for use in the expansion methods described herein is a pleural exudate. In some embodiments, the sample for use in the expansion methods described herein is a pleural transudate. Other biological samples may include other serous fluids containing TILs, including, e.g., ascites fluid from the abdomen or pancreatic cyst fluid. Ascites fluid and pleural fluids involve very similar chemical systems; both the abdomen and lung have mesothelial lines and fluid forms in the pleural space and abdominal spaces in the same matter in malignancies and such fluids in some embodiments contain TILs. In some embodiments, wherein the disclosure exemplifies pleural fluid, the same methods may be performed with similar results using ascites or other cyst fluids containing TILs.

In some embodiments, the pleural fluid is in unprocessed form, directly as removed from the patient. In some embodiments, the unprocessed pleural fluid is placed in a standard blood collection tube, such as an EDTA or Heparin tube, prior to the contacting step. In some embodiments, the unprocessed pleural fluid is placed in a standard CellSave® tube (Veridex) prior to the contacting step. In some embodiments, the sample is placed in the CellSave tube immediately after collection from the patient to avoid a decrease in the number of viable TILs. The number of viable TILs can decrease to a significant extent within 24 hours, if left in the untreated pleural fluid, even at 4° C. In some embodiments, the sample is placed in the appropriate collection tube within 1 hour, 5 hours, 10 hours, 15 hours, or up to 24 hours after removal from the patient. In some embodiments, the sample is placed in the appropriate collection tube within 1 hour, 5 hours, 10 hours, 15 hours, or up to 24 hours after removal from the patient at 4° C.

In some embodiments, the pleural fluid sample from the chosen subject may be diluted. In one embodiment, the dilution is 1:10 pleural fluid to diluent. In another embodiment, the dilution is 1:9 pleural fluid to diluent. In another embodiment, the dilution is 1:8 pleural fluid to diluent. In another embodiment, the dilution is 1:5 pleural fluid to diluent. In another embodiment, the dilution is 1:2 pleural fluid to diluent. In another embodiment, the dilution is 1:1 pleural fluid to diluent. In some embodiments, diluents include saline, phosphate buffered saline, another buffer or a physiologically acceptable diluent. In some embodiments, the sample is placed in the CellSave tube immediately after collection from the patient and dilution to avoid a decrease in the viable TILs, which may occur to a significant extent within 24-48 hours, if left in the untreated pleural fluid, even at 4° C. In some embodiments, the pleural fluid sample is placed in the appropriate collection tube within 1 hour, 5 hours, 10 hours, 15 hours, 24 hours, 36 hours, up to 48 hours after removal from the patient, and dilution. In some embodiments, the pleural fluid sample is placed in the appropriate collection tube within 1 hour, 5 hours, 10 hours, 15 hours, 24 hours, 36 hours, up to 48 hours after removal from the patient, and dilution at 4° C.

In still another embodiment, pleural fluid samples are concentrated by conventional means prior further processing steps. In some embodiments, this pre-treatment of the pleural fluid is preferable in circumstances in which the pleural fluid must be cryopreserved for shipment to a laboratory performing the method or for later analysis (e.g., later than 24-48 hours post-collection). In some embodiments, the pleural fluid sample is prepared by centrifuging the pleural fluid sample after its withdrawal from the subject and resuspending the centrifugate or pellet in buffer. In some embodiments, the pleural fluid sample is subjected to multiple centrifugations and resuspensions, before it is cryopreserved for transport or later analysis and/or processing.

In some embodiments, pleural fluid samples are concentrated prior to further processing steps by using a filtration method. In some embodiments, the pleural fluid sample used in the contacting step is prepared by filtering the fluid through a filter containing a known and essentially uniform pore size that allows for passage of the pleural fluid through the membrane but retains the tumor cells. In some embodiments, the diameter of the pores in the membrane may be at least 4 µM. In another embodiment the pore diameter may be 5 µM or more, and in other embodiment, any of 6, 7, 8, 9, or 10 µM. After filtration, the cells, including TILs, retained by the membrane may be rinsed off the membrane into a suitable physiologically acceptable buffer. Cells, including TILs, concentrated in this way may then be used in the contacting step of the method.

In some embodiments, pleural fluid sample (including, for example, the untreated pleural fluid), diluted pleural fluid, or the resuspended cell pellet, is contacted with a lytic reagent that differentially lyses non-nucleated red blood cells present in the sample. In some embodiments, this step is performed prior to further processing steps in circumstances in which the pleural fluid contains substantial numbers of RBCs. Suitable lysing reagents include a single lytic reagent or a lytic reagent and a quench reagent, or a lytic agent, a quench reagent and a fixation reagent. Suitable lytic systems are marketed commercially and include the BD Pharm Lyse™ system (Becton Dickenson). Other lytic systems include the Versalyse™ system, the FACSlyse™ system (Becton Dickenson), the Immunoprep™ system or Erythrolyse II system (Beckman Coulter, Inc.), or an ammonium chloride system. In some embodiments, the lytic reagent can vary with the primary requirements being efficient lysis of the red blood cells, and the conservation of the TILs and phenotypic properties of the TILs in the pleural fluid. In addition to employing a single reagent for lysis, the lytic systems useful in methods described herein can include a second reagent, e.g., one that quenches or retards the effect of the lytic reagent during the remaining steps of the method, e.g., Stabilyse™ reagent (Beckman Coulter, Inc.). A conventional fixation reagent may also be employed depending upon the choice of lytic reagents or the preferred implementation of the method.

In some embodiments, the pleural fluid sample, unprocessed, diluted or multiply centrifuged or processed as described herein above is cryopreserved at a temperature of about −140° C. prior to being further processed and/or expanded as provided herein.

B. Step B: First Expansion

1. Young TILs

In some embodiments, the present methods provide for obtaining young TILs, which are capable of increased replication cycles upon administration to a subject/patient and as such may provide additional therapeutic benefits over older TTLs (i.e., TILs which have further undergone more rounds of replication prior to administration to a subject/patient). Features of young TILs have been described in the literature, for example Donia, at al., *Scandinavian Journal of Immunology*, 75:157-167 (2012); Dudley et al., *Clin Cancer Res*, 16:6122-6131 (2010); Huang et al., *J Immunother*, 28(3):258-267 (2005); Besser et al., *Clin Cancer Res*, 19(17):OF1-OF9 (2013); Besser et al., *J Immunother* 32:415-423 (2009); Robbins, et al., *J Immunol* 2004; 173: 7125-7130; Shen et al., *J Immunother*, 30:123-129 (2007); Zhou, et al., *J Immunother*, 28:53-62 (2005); and Tran, et al., *J Immunother*, 31:742-751 (2008), all of which are incorporated herein by reference in their entireties.

The diverse antigen receptors of T and B lymphocytes are produced by somatic recombination of a limited, but large number of gene segments. These gene segments: V (variable), D (diversity), J (joining), and C (constant), determine the binding specificity and downstream applications of immunoglobulins and T-cell receptors (TCRs). The present invention provides a method for generating TILs which exhibit and increase the T-cell repertoire diversity. In some embodiments, the TILs obtained by the present method exhibit an increase in the T-cell repertoire diversity. In some embodiments, the TILs obtained by the present method exhibit an increase in the T-cell repertoire diversity as compared to freshly harvested TILs and/or TILs prepared using other methods than those provide herein including for example, methods other than those embodied in FIG. 9. In some embodiments, the TILs obtained by the present method exhibit an increase in the T-cell repertoire diversity as compared to freshly harvested TILs and/or TILs prepared using methods referred to as process 1C, as exemplified in FIG. 10. In some embodiments, the TILs obtained in the first expansion exhibit an increase in the T-cell repertoire diversity. In some embodiments, the increase in diversity is an increase in the immunoglobulin diversity and/or the T-cell receptor diversity. In some embodiments, the diversity is in the immunoglobulin is in the immunoglobulin heavy chain. In some embodiments, the diversity is in the immunoglobulin is in the immunoglobulin light chain. In some embodiments, the diversity is in the T-cell receptor. In some embodiments, the diversity is in one of the T-cell receptors selected from the group consisting of alpha, beta, gamma, and delta receptors. In some embodiments, there is an increase in the expression of T-cell receptor (TCR) alpha and/or beta. In some embodiments, there is an increase in the expression of T-cell receptor (TCR) alpha. In some embodiments, there is an increase in the expression of T-cell receptor (TCR) beta. In some embodiments, there is an increase in the expression of TCRab (i.e., TCR$\alpha/\beta$).

After dissection or digestion of tumor fragments, for example such as described in Step A of FIG. 9, the resulting cells are cultured in serum containing IL-2 under conditions that favor the growth of TILs over tumor and other cells. In some embodiments, the tumor digests are incubated in 2 mL wells in media comprising inactivated human AB serum with 6000 IU/mL of IL-2. This primary cell population is cultured for a period of days, generally from 3 to 14 days, resulting in a bulk TIL population, generally about $1\times10^8$ bulk TIL cells. In some embodiments, this primary cell population is cultured for a period of 7 to 14 days, resulting in a bulk TIL population, generally about $1\times10^8$ bulk TIL cells. In some embodiments, this primary cell population is cultured for a period of 10 to 14 days, resulting in a bulk TIL population, generally about $1\times10^8$ bulk TIL cells. In some embodiments, this primary cell population is cultured for a period of about 11 days, resulting in a bulk TIL population, generally about $1\times10^8$ bulk TIL cells.

In a preferred embodiment, expansion of TILs may be performed using an initial bulk TIL expansion step (for example such as those described in Step B of FIG. 9, which can include processes referred to as pre-REP) as described below and herein, followed by a second expansion (Step D, including processes referred to as rapid expansion protocol (REP) steps) as described below under Step D and herein, followed by optional cryopreservation, and followed by a second Step D (including processes referred to as restimulation REP steps) as described below and herein. The TILs obtained from this process may be optionally characterized for phenotypic characteristics and metabolic parameters as described herein.

In embodiments where TIL cultures are initiated in 24-well plates, for example, using Costar 24-well cell culture cluster, flat bottom (Corning Incorporated, Corning, NY, each well can be seeded with $1\times10^6$ tumor digest cells or one tumor fragment in 2 mL of complete medium (CM) with IL-2 (6000 IU/mL; Chiron Corp., Emeryville, CA). In some embodiments, the tumor fragment is between about 1 mm$^3$ and 10 mm$^3$.

In some embodiments, the first expansion culture medium is referred to as "CM", an abbreviation for culture media. In some embodiments, CM for Step B consists of RPMI 1640 with GlutaMAX, supplemented with 10% human AB serum, 25 mM HEPES, and 10 mg/mL gentamicin. In embodiments where cultures are initiated in gas-permeable flasks with a 40 mL capacity and a 10 cm$^2$ gas-permeable silicon bottom (for example, G-Rex10; Wilson Wolf Manufacturing, New Brighton, MN) (FIG. 1), each flask was loaded with 10-40×10$^6$ viable tumor digest cells or 5-30 tumor fragments in 10-40 mL of CM with IL-2. Both the G-Rex10 and 24-well plates were incubated in a humidified incubator at 37° C. in 5% CO2 and 5 days after culture initiation, half the media was removed and replaced with fresh CM and IL-2 and after day 5, half the media was changed every 2-3 days.

After preparation of the tumor fragments, the resulting cells (i.e., fragments) are cultured in serum containing IL-2 under conditions that favor the growth of TILs over tumor and other cells. In some embodiments, the tumor digests are incubated in 2 mL wells in media comprising inactivated human AB serum (or, in some cases, as outlined herein, in the presence of aAPC cell population) with 6000 IU/mL of IL-2. This primary cell population is cultured for a period of days, generally from 10 to 14 days, resulting in a bulk TIL population, generally about $1\times10^8$ bulk TIL cells. In some embodiments, the growth media during the first expansion comprises IL-2 or a variant thereof. In some embodiments, the IL is recombinant human IL-2 (rhIL-2). In some embodiments the IL-2 stock solution has a specific activity of $20\text{-}30\times10^6$ IU/mg for a 1 mg vial. In some embodiments the IL-2 stock solution has a specific activity of $20\times10^6$ IU/mg for a 1 mg vial. In some embodiments the IL-2 stock solution has a specific activity of $25\times10^6$ IU/mg for a 1 mg vial. In some embodiments the IL-2 stock solution has a specific activity of $30\times10^6$ IU/mg for a 1 mg vial. In some embodiments, the IL-2 stock solution has a final concentration of $4\text{-}8\times10^6$ IU/mg of IL-2. In some embodiments, the IL-2 stock solution has a final concentration of $5\text{-}7\times10^6$ IU/mg of IL-2. In some embodiments, the IL-2 stock solution has a final concentration of $6\times10^6$ IU/mg of IL-2. In some embodiments, the IL-2 stock solution is prepare as described in Example 4. In some embodiments, the first expansion culture media comprises about 10,000 IU/mL of IL-2, about 9,000 IU/mL of IL-2, about 8,000 IU/mL of IL-2, about 7,000 IU/mL of IL-2, about 6000 IU/mL of IL-2 or about 5,000 IU/mL of IL-2. In some embodiments, the first expansion culture media comprises about 9,000 IU/mL of IL-2 to about 5,000 IU/mL of IL-2. In some embodiments, the first expansion culture media comprises about 8,000 IU/mL of IL-2 to about 6,000 IU/mL of IL-2. In some embodiments, the first expansion culture media comprises about 7,000 IU/mL of IL-2 to about 6,000 IU/mL of IL-2. In some embodiments, the first expansion culture media comprises about 6,000 IU/mL of IL-2. In an embodiment, the cell culture medium further comprises IL-2. In some embodiments, the cell culture medium comprises about 3000 IU/mL of IL-2. In an embodiment, the cell culture medium further comprises IL-2. In a preferred embodiment, the cell culture medium comprises about 3000 IU/mL of IL-2. In an embodiment, the cell culture medium comprises about 1000 IU/mL, about 1500 IU/mL, about 2000 IU/mL, about 2500 IU/mL, about 3000 IU/mL, about 3500 IU/mL, about 4000 IU/mL, about 4500 IU/mL, about 5000 IU/mL, about 5500 IU/mL, about 6000 IU/mL, about 6500 IU/mL, about 7000 IU/mL, about 7500 IU/mL, or about 8000 IU/mL of IL-2. In an embodiment, the cell culture medium comprises between 1000 and 2000 IU/mL, between 2000 and 3000 IU/mL, between 3000 and 4000 IU/mL, between 4000 and 5000 IU/mL, between 5000 and 6000 IU/mL, between 6000 and 7000 IU/mL, between 7000 and 8000 IU/mL, or about 8000 IU/mL of IL-2.

In some embodiments, first expansion culture media comprises about 500 IU/mL of IL-15, about 400 IU/mL of IL-15, about 300 IU/mL of IL-15, about 200 IU/mL of IL-15, about 180 IU/mL of IL-15, about 160 IU/mL of IL-15, about 140 IU/mL of IL-15, about 120 IU/mL of IL-15, or about 100 IU/mL of IL-15. In some embodiments, the first expansion culture media comprises about 500 IU/mL of IL-15 to about 100 IU/mL of IL-15. In some embodiments, the first expansion culture media comprises about 400 IU/mL of IL-15 to about 100 IU/mL of IL-15. In some embodiments, the first expansion culture media comprises about 300 IU/mL of IL-15 to about 100 IU/mL of IL-15. In some embodiments, the first expansion culture media comprises about 200 IU/mL of IL-15. In some embodiments, the cell culture medium comprises about 180 IU/mL of IL-15. In an embodiment, the cell culture medium further comprises IL-15. In a preferred embodiment, the cell culture medium comprises about 180 IU/mL of IL-15.

In some embodiments, first expansion culture media comprises about 20 IU/mL of IL-21, about 15 IU/mL of IL-21, about 12 IU/mL of IL-21, about 10 IU/mL of IL-21, about 5 IU/mL of IL-21, about 4 IU/mL of IL-21, about 3 IU/mL of IL-21, about 2 IU/mL of IL-21, about 1 IU/mL of IL-21, or about 0.5 IU/mL of IL-21. In some embodiments, the first expansion culture media comprises about 20 IU/mL of IL-21 to about 0.5 IU/mL of IL-21. In some embodiments, the first expansion culture media comprises about 15 IU/mL of IL-21 to about 0.5 IU/mL of IL-21. In some embodiments, the first expansion culture media comprises about 12 IU/mL of IL-21 to about 0.5 IU/mL of IL-21. In some embodiments, the first expansion culture media comprises about 10 IU/mL of IL-21 to about 0.5 IU/mL of IL-21. In some embodiments, the first expansion culture media comprises about 5 IU/mL of IL-21 to about 1 IU/mL of IL-21. In some embodiments, the first expansion culture media comprises about 2 IU/mL of IL-21. In some embodiments, the cell culture medium comprises about 1 IU/mL of IL-21. In some embodiments, the cell culture medium comprises about 0.5 IU/mL of IL-21. In an embodiment, the cell culture medium further comprises IL-21. In a preferred embodiment, the cell culture medium comprises about 1 IU/mL of IL-21.

In an embodiment, the cell culture medium comprises OKT-3 antibody. In some embodiments, the cell culture medium comprises about 30 ng/mL of OKT-3 antibody. In an embodiment, the cell culture medium comprises about 0.1 ng/mL, about 0.5 ng/mL, about 1 ng/mL, about 2.5 ng/mL, about 5 ng/mL, about 7.5 ng/mL, about 10 ng/mL, about 15 ng/mL, about 20 ng/mL, about 25 ng/mL, about 30 ng/mL, about 35 ng/mL, about 40 ng/mL, about 50 ng/mL, about 60 ng/mL, about 70 ng/mL, about 80 ng/mL, about 90 ng/mL, about 100 ng/mL, about 200 ng/mL, about 500 ng/mL, and about 1 pg/mL of OKT-3 antibody. In an embodiment, the cell culture medium comprises between 0.1 ng/mL and 1 ng/mL, between 1 ng/mL and 5 ng/mL, between 5 ng/mL and 10 ng/mL, between 10 ng/mL and 20 ng/mL, between 20 ng/mL and 30 ng/mL, between 30 ng/mL and 40 ng/mL, between 40 ng/mL and 50 ng/mL, and between 50 ng/mL and 100 ng/mL of OKT-3 antibody. In some embodiments, the cell culture medium does not comprise OKT-3 antibody. In some embodiments, the OKT-3 antibody is muromonab.

In some embodiments, the cell culture medium comprises one or more TNFRSF agonists in a cell culture medium. In some embodiments, the TNFRSF agonist comprises a 4-1BB agonist. In some embodiments, the TNFRSF agonist is a 4-1BB agonist, and the 4-1BB agonist is selected from the group consisting of urelumab, utomilumab, EU-101, a fusion protein, and fragments, derivatives, variants, biosimilars, and combinations thereof. In some embodiments, the TNFRSF agonist is added at a concentration sufficient to achieve a concentration in the cell culture medium of between 0.1 µg/mL and 100 µg/mL. In some embodiments, the TNFRSF agonist is added at a concentration sufficient to achieve a concentration in the cell culture medium of between 20 µg/mL and 40 µg/mL.

In some embodiments, in addition to one or more TNFRSF agonists, the cell culture medium further comprises IL-2 at an initial concentration of about 3000 IU/mL and OKT-3 antibody at an initial concentration of about 30 ng/mL, and wherein the one or more TNFRSF agonists comprises a 4-1BB agonist.

In some embodiments, the first expansion culture medium is referred to as "CM", an abbreviation for culture media. In some embodiments, it is referred to as CM1 (culture medium 1). In some embodiments, CM consists of RPMI 1640 with GlutaMAX, supplemented with 10% human AB serum, 25 mM HEPES, and 10 mg/mL gentamicin. In embodiments where cultures are initiated in gas-permeable flasks with a 40 mL capacity and a 10 cm$^2$ gas-permeable silicon bottom (for example, G-Rex10; Wilson Wolf Manufacturing, New Brighton, MN) (FIG. 1), each flask was loaded with 10-40× 10$^6$ viable tumor digest cells or 5-30 tumor fragments in 10-40 mL of CM with IL-2. Both the G-Rex10 and 24-well plates were incubated in a humidified incubator at 37° C. in 5% CO2 and 5 days after culture initiation, half the media was removed and replaced with fresh CM and IL-2 and after day 5, half the media was changed every 2-3 days. In some embodiments, the CM is the CM1 described in the Examples, see, Example 5. In some embodiments, the first expansion occurs in an initial cell culture medium or a first cell culture medium. In some embodiments, the initial cell culture medium or the first cell culture medium comprises IL-2.

In some embodiments, the first expansion (including processes such as for example those described in Step B of FIG. 9, which can include those sometimes referred to as the pre-REP) process is shortened to 3-14 days, as discussed in the examples and figures. In some embodiments, the first expansion (including processes such as for example those described in Step B of FIG. 9, which can include those sometimes referred to as the pre-REP) is shortened to 7 to 14 days, as shown in FIGS. 5, 6, 8, 9, 10, and 11, as well as including for example, an expansion as described in Step B of FIG. 9. In some embodiments, the first expansion of Step B is shortened to 10-14 days, as shown in FIGS. 5, 6, 8, 9, 10, and 11. In some embodiments, the first expansion is shortened to 11 days, as shown in FIGS. 5, 6, 8, 9, 10, and 11, as well as including for example, an expansion as described in Step B of FIG. 9.

In some embodiments, the first TIL expansion can proceed for 1 day, 2 days, 3 days, 4 days, 5 days, 6 days, 7 days, 8 days, 9 days, 10 days, 11 days, 12 days, 13 days, or 14 days. In some embodiments, the first TIL expansion can proceed for 1 day to 14 days. In some embodiments, the first TIL expansion can proceed for 2 days to 14 days. In some embodiments, the first TIL expansion can proceed for 3 days to 14 days. In some embodiments, the first TIL expansion can proceed for 4 days to 14 days. In some embodiments, the first TIL expansion can proceed for 5 days to 14 days. In some embodiments, the first TIL expansion can proceed for 6 days to 14 days. In some embodiments, the first TIL expansion can proceed for 7 days to 14 days. In some embodiments, the first TIL expansion can proceed for 8 days to 14 days. In some embodiments, the first TIL expansion can proceed for 9 days to 14 days. In some embodiments, the first TIL expansion can proceed for 10 days to 14 days. In some embodiments, the first TIL expansion can proceed for 11 days to 14 days. In some embodiments, the first TIL expansion can proceed for 12 days to 14 days. In some embodiments, the first TIL expansion can proceed for 13 days to 14 days. In some embodiments, the first TIL expansion can proceed for 14 days. In some embodiments, the first TIL expansion can proceed for 1 day to 11 days. In some embodiments, the first TIL expansion can proceed for 2 days to 11 days. In some embodiments, the first TIL expansion can proceed for 3 days to 11 days. In some embodiments, the first TIL expansion can proceed for 4 days to 11 days. In some embodiments, the first TIL expansion can proceed for 5 days to 11 days. In some embodiments, the first TIL expansion can proceed for 6 days to 11 days. In some embodiments, the first TIL expansion can proceed for 7 days to 11 days. In some embodiments, the first TIL expansion can proceed for 8 days to 11 days. In some embodiments, the first TIL expansion can proceed for 9 days to 11 days. In some embodiments, the first TIL expansion can proceed for 10 days to 11 days. In some embodiments, the first TIL expansion can proceed for 11 days.

In some embodiments, a combination of IL-2, IL-7, IL-15, and/or IL-21 are employed as a combination during the first expansion. In some embodiments, IL-2, IL-7, IL-15, and/or IL-21 as well as any combinations thereof can be included during the first expansion, including for example during a Step B processes according to FIG. 9, as well as described herein. In some embodiments, a combination of IL-2, IL-15, and IL-21 are employed as a combination during the first expansion. In some embodiments, IL-2, IL-15, and IL-21 as well as any combinations thereof can be included during Step B processes according to FIG. 9 and as described herein.

In some embodiments, the first expansion (including processes referred to as the pre-REP; for example, Step B according to FIG. 9) process is shortened to 3 to 14 days, as discussed in the figures. In some embodiments, the first expansion of Step B is shortened to 7 to 14 days, as shown in FIGS. 5, 6, 8, 9, 10, and 11. In some embodiments, the first expansion of Step B is shortened to 10 to 14 days, as shown in FIGS. 5, 6, 8, 9, 10, and 11. In some embodiments, the first expansion is shortened to 11 days, as shown in FIGS. 5, 6, 8, 9, 10, and 11.

In some embodiments, the first expansion, for example, Step B according to FIG. 9, is performed in a closed system bioreactor. In some embodiments, a closed system is employed for the TIL expansion, as described herein. In some embodiments, a single bioreactor is employed. In some embodiments, the single bioreactor employed is for example a G-REX-10 or a G-REX-100. In some embodiments, the closed system bioreactor is a single bioreactor.

1. Cytokines and Other Additives

The expansion methods described herein generally use culture media with high doses of a cytokine, in particular IL-2, as is known in the art.

Alternatively, using combinations of cytokines for the rapid expansion and or second expansion of TILs is additionally possible, with combinations of two or more of IL-2, IL-15 and IL-21 as is described in U.S. Patent Application Publication No. US 2017/0107490 A1, the disclosure of which is incorporated by reference herein. Thus, possible combinations include IL-2 and IL-15, IL-2 and IL-21, IL-15 and IL-21 and IL-2, or IL-15 and IL-21, with the latter finding particular use in many embodiments. The use of combinations of cytokines specifically favors the generation of lymphocytes, and in particular T-cells as described therein.

In an embodiment, Step B may also include the addition of OKT-3 antibody or muromonab to the culture media, as described elsewhere herein. In an embodiment, Step B may also include the addition of a 4-1BB agonist to the culture media, as described elsewhere herein. In an embodiment, Step B may also include the addition of an OX-40 agonist to the culture media, as described elsewhere herein. In other embodiments, additives such as peroxisome proliferator-activated receptor gamma coactivator I-alpha agonists, including proliferator-activated receptor (PPAR)-gamma agonists such as a thiazolidinedione compound, may be used in the culture media during Step B, as described in U.S. Patent Application Publication No. US 2019/0307796 A1, the disclosure of which is incorporated by reference herein.

C. Step C: First Expansion to Second Expansion Transition

In some cases, the bulk TIL population obtained from the first expansion, including for example the TIL population obtained from for example, Step B as indicated in FIG. 9, can be cryopreserved immediately, using the protocols discussed herein below. Alternatively, the TIL population obtained from the first expansion, referred to as the second TIL population, can be subjected to a second expansion (which can include expansions sometimes referred to as REP) and then cryopreserved as discussed below. Similarly, in the case where genetically modified TILs will be used in therapy, the first TIL population (sometimes referred to as the bulk TIL population) or the second TIL population (which can in some embodiments include populations referred to as the REP TIL populations) can be subjected to genetic modifications for suitable treatments prior to expansion or after the first expansion and prior to the second expansion.

In some embodiments, the TILs obtained from the first expansion (for example, from Step B as indicated in FIG. 9) are stored until phenotyped for selection. In some embodiments, the TILs obtained from the first expansion (for example, from Step B as indicated in FIG. 9) are not stored and proceed directly to the second expansion. In some embodiments, the TILs obtained from the first expansion are not cryopreserved after the first expansion and prior to the second expansion. In some embodiments, the transition from the first expansion to the second expansion occurs at about 3 days, 4, days, 5 days, 6 days, 7 days, 8 days, 9 days, 10 days, 11 days, 12 days, 13 days, or 14 days from when fragmentation occurs. In some embodiments, the transition from the first expansion to the second expansion occurs at about 3 days to 14 days from when fragmentation occurs. In some embodiments, the transition from the first expansion to the second expansion occurs at about 4 days to 14 days from when fragmentation occurs. In some embodiments, the transition from the first expansion to the second expansion occurs at about 4 days to 10 days from when fragmentation occurs. In some embodiments, the transition from the first expansion to the second expansion occurs at about 7 days to 14 days from when fragmentation occurs. In some embodiments, the transition from the first expansion to the second expansion occurs at about 14 days from when fragmentation occurs.

In some embodiments, the transition from the first expansion to the second expansion occurs at 1 day, 2 days, 3 days, 4 days, 5 days, 6 days, 7 days, 8 days, 9 days, 10 days, 11 days, 12 days, 13 days, or 14 days from when fragmentation occurs. In some embodiments, the transition from the first expansion to the second expansion occurs 1 day to 14 days from when fragmentation occurs. In some embodiments, the first TIL expansion can proceed for 2 days to 14 days. In some embodiments, the transition from the first expansion to the second expansion occurs 3 days to 14 days from when fragmentation occurs. In some embodiments, the transition from the first expansion to the second expansion occurs 4 days to 14 days from when fragmentation occurs. In some embodiments, the transition from the first expansion to the second expansion occurs 5 days to 14 days from when fragmentation occurs. In some embodiments, the transition from the first expansion to the second expansion occurs 6 days to 14 days from when fragmentation occurs. In some embodiments, the transition from the first expansion to the second expansion occurs 7 days to 14 days from when fragmentation occurs. In some embodiments, the transition from the first expansion to the second expansion occurs 8 days to 14 days from when fragmentation occurs. In some embodiments, the transition from the first expansion to the second expansion occurs 9 days to 14 days from when fragmentation occurs. In some embodiments, the transition from the first expansion to the second expansion occurs 10 days to 14 days from when fragmentation occurs. In some embodiments, the transition from the first expansion to the second expansion occurs 11 days to 14 days from when fragmentation occurs. In some embodiments, the transition from the first expansion to the second expansion occurs 12 days to 14 days from when fragmentation occurs. In some embodiments, the transition from the first expansion to the second expansion occurs 13 days to 14 days from when fragmentation occurs. In some embodiments, the transition from the first expansion to the second expansion occurs 14 days from when fragmentation occurs. In some embodiments, the transition from the first expansion to the second expansion occurs 1 day to 11 days from when fragmentation occurs. In some embodiments, the transition from the first expansion to the second expansion occurs 2 days to 11 days from when fragmentation occurs. In some embodiments, the transition from the first expansion to the second expansion occurs 3 days to 11 days from when fragmentation occurs. In some embodiments, the transition from the first expansion to the second expansion occurs 4 days to 11 days from when fragmentation occurs. In some embodiments, the transition from the first expansion to the second expansion occurs 5 days to 11 days from when fragmentation occurs. In some embodiments, the transition from the first expansion to the second expansion occurs 6 days to 11 days from when fragmentation occurs. In some embodiments, the transition from the first expansion to the second expansion occurs 7 days to 11 days from when fragmentation occurs. In some embodiments, the transition from the first expansion to the second expansion occurs 8 days to 11 days from when fragmentation occurs. In some embodiments, the transition from the first expansion to the second expansion occurs 9 days to 11 days from when fragmentation occurs. In some embodiments, the transition from the first expansion to the second expansion occurs 10 days to 11 days from when fragmentation occurs. In some embodiments, the transition from the first expansion to the second expansion occurs 11 days from when fragmentation occurs.

In some embodiments, the TILs are not stored after the first expansion and prior to the second expansion, and the TILs proceed directly to the second expansion (for example, in some embodiments, there is no storage during the transition from Step B to Step D as shown in FIG. 9). In some embodiments, the transition occurs in closed system, as described herein. In some embodiments, the TILs from the first expansion, the second population of TILs, proceeds directly into the second expansion with no transition period.

In some embodiments, the transition from the first expansion to the second expansion, for example, Step C according to FIG. 9, is performed in a closed system bioreactor. In some embodiments, a closed system is employed for the TIL expansion, as described herein. In some embodiments, a single bioreactor is employed. In some embodiments, the single bioreactor employed is for example a G-REX-10 or a G-REX-100. In some embodiments, the closed system bioreactor is a single bioreactor.

D. Step D: Second Expansion

In some embodiments, the TIL cell population is expanded in number after harvest and initial bulk processing for example, after Step A and Step B, and the transition referred to as Step C, as indicated in FIG. 9). This further expansion is referred to herein as the second expansion, which can include expansion processes generally referred to in the art as a rapid expansion process (REP; as well as processes as indicated in Step D of FIG. 9). The second expansion is generally accomplished using a culture media comprising a number of components, including feeder cells, a cytokine source, and an anti-CD3 antibody, in a gas-permeable container.

In some embodiments, the second expansion or second TIL expansion (which can include expansions sometimes referred to as REP; as well as processes as indicated in Step D of FIG. 9) of TIL can be performed using any TIL flasks or containers known by those of skill in the art. In some embodiments, the second TIL expansion can proceed for 7 days, 8 days, 9 days, 10 days, 11 days, 12 days, 13 days, or 14 days. In some embodiments, the second TIL expansion can proceed for about 7 days to about 14 days. In some embodiments, the second TIL expansion can proceed for about 8 days to about 14 days. In some embodiments, the second TIL expansion can proceed for about 9 days to about 14 days. In some embodiments, the second TIL expansion can proceed for about 10 days to about 14 days. In some embodiments, the second TIL expansion can proceed for about 11 days to about 14 days. In some embodiments, the second TIL expansion can proceed for about 12 days to about 14 days. In some embodiments, the second TIL expansion can proceed for about 13 days to about 14 days. In some embodiments, the second TIL expansion can proceed for about 14 days.

In an embodiment, the second expansion can be performed in a gas permeable container using the methods of the present disclosure (including for example, expansions referred to as REP; as well as processes as indicated in Step D of FIG. 9). For example, TILs can be rapidly expanded using non-specific T-cell receptor stimulation in the presence of interleukin-2 (IL-2) or interleukin-15 (IL-15). The non-specific T-cell receptor stimulus can include, for example, an anti-CD3 antibody, such as about 30 ng/ml of OKT3, a mouse monoclonal anti-CD3 antibody (commercially available from Ortho-McNeil, Raritan, NJ or Miltenyi Biotech, Auburn, CA) or UHCT-1 (commercially available from BioLegend, San Diego, CA, USA). TILs can be expanded to induce further stimulation of the TILs in vitro by including one or more antigens during the second expansion, including antigenic portions thereof, such as epitope(s), of the cancer, which can be optionally expressed from a vector, such as a human leukocyte antigen A2 (HLA-A2) binding peptide, e.g., 0.3 µM MART-1:26-35 (27 L) or gpl 00:209-217 (210M), in the presence of a T-cell growth factor, such as 300 IU/mL IL-2 or IL-15. Other suitable antigens may include, e.g., NY-ESO-1, TRP-1, TRP-2, tyrosinase cancer antigen, MAGE-A3, SSX-2, and VEGFR2, or antigenic portions thereof. TIL may also be rapidly expanded by re-stimulation with the same antigen(s) of the cancer pulsed onto HLA-A2-expressing antigen-presenting cells. Alternatively, the TTLs can be further restimulated with, e.g., example, irradiated, autologous lymphocytes or with irradiated HLA-A2+ allogeneic lymphocytes and IL-2. In some embodiments, the re-stimulation occurs as part of the second expansion. In some embodiments, the second expansion occurs in the presence of irradiated, autologous lymphocytes or with irradiated HLA-A2+ allogeneic lymphocytes and IL-2.

In an embodiment, the cell culture medium further comprises IL-2. In a some embodiments, the cell culture medium comprises about 3000 IU/mL of IL-2. In an embodiment, the cell culture medium comprises about 1000 IU/mL, about 1500 IU/mL, about 2000 IU/mL, about 2500 IU/mL, about 3000 IU/mL, about 3500 IU/mL, about 4000 IU/mL, about 4500 IU/mL, about 5000 IU/mL, about 5500 IU/mL, about 6000 IU/mL, about 6500 IU/mL, about 7000 IU/mL, about 7500 IU/mL, or about 8000 IU/mL of IL-2. In an embodiment, the cell culture medium comprises between 1000 and 2000 IU/mL, between 2000 and 3000 IU/mL, between 3000 and 4000 IU/mL, between 4000 and 5000 IU/mL, between 5000 and 6000 IU/mL, between 6000 and 7000 IU/mL, between 7000 and 8000 IU/mL, or between 8000 IU/mL of IL-2.

In an embodiment, the cell culture medium comprises OKT3 antibody. In a some embodiments, the cell culture medium comprises about 30 ng/mL of OKT3 antibody. In an embodiment, the cell culture medium comprises about 0.1 ng/mL, about 0.5 ng/mL, about 1 ng/mL, about 2.5 ng/mL, about 5 ng/mL, about 7.5 ng/mL, about 10 ng/mL, about 15 ng/mL, about 20 ng/mL, about 25 ng/mL, about 30 ng/mL, about 35 ng/mL, about 40 ng/mL, about 50 ng/mL, about 60 ng/mL, about 70 ng/mL, about 80 ng/mL, about 90 ng/mL, about 100 ng/mL, about 200 ng/mL, about 500 ng/mL, and about 1 µg/mL of OKT3 antibody. In an embodiment, the cell culture medium comprises between 0.1 ng/mL and 1 ng/mL, between 1 ng/mL and 5 ng/mL, between 5 ng/mL and 10 ng/mL, between 10 ng/mL and 20 ng/mL, between 20 ng/mL and 30 ng/mL, between 30 ng/mL and 40 ng/mL, between 40 ng/mL and 50 ng/mL, and between 50 ng/mL and 100 ng/mL of OKT3 antibody.

In some embodiments, a combination of IL-2, IL-7, IL-15, and/or IL-21 are employed as a combination during the second expansion. In some embodiments, IL-2, IL-7, IL-15, and/or IL-21 as well as any combinations thereof can be included during the second expansion, including for example during a Step D processes according to FIG. 9, as well as described herein. In some embodiments, a combination of IL-2, IL-15, and IL-21 are employed as a combination during the second expansion. In some embodiments, IL-2, IL-15, and IL-21 as well as any combinations thereof can be included during Step D processes according to FIG. 9 and as described herein.

In some embodiments, the second expansion can be conducted in a supplemented cell culture medium comprising IL-2, OKT-3, and antigen-presenting feeder cells. In some embodiments, the second expansion occurs in a supplemented cell culture medium. In some embodiments, the supplemented cell culture medium comprises IL-2, OKT-3, and antigen-presenting feeder cells. In some embodiments, the second cell culture medium comprises IL-2, OKT-3, and antigen-presenting cells (APCs; also referred to as antigen-presenting feeder cells). In some embodiments, the second expansion occurs in a cell culture medium comprising IL-2, OKT-3, and antigen-presenting feeder cells (i.e., antigen presenting cells).

In some embodiments, the second expansion culture media comprises about 500 IU/mL of IL-15, about 400 IU/mL of IL-15, about 300 IU/mL of IL-15, about 200 IU/mL of IL-15, about 180 IU/mL of IL-15, about 160 IU/mL of IL-15, about 140 IU/mL of IL-15, about 120 IU/mL of IL-15, or about 100 IU/mL of IL-15. In some embodiments, the second expansion culture media comprises about 500 IU/mL of IL-15 to about 100 IU/mL of IL-15. In some embodiments, the second expansion culture media comprises about 400 IU/mL of IL-15 to about 100 IU/mL of IL-15. In some embodiments, the second expansion culture media comprises about 300 IU/mL of IL-15 to about 100 IU/mL of IL-15. In some embodiments, the second expansion culture media comprises about 200 IU/mL of IL-15. In some embodiments, the cell culture medium comprises about 180 IU/mL of IL-15. In an embodiment, the cell culture medium further comprises IL-15. In a preferred embodiment, the cell culture medium comprises about 180 IU/mL of IL-15.

In some embodiments, the second expansion culture media comprises about 20 IU/mL of IL-21, about 15 IU/mL of IL-21, about 12 IU/mL of IL-21, about 10 IU/mL of IL-21, about 5 IU/mL of IL-21, about 4 IU/mL of IL-21, about 3 IU/mL of IL-21, about 2 IU/mL of IL-21, about 1 IU/mL of IL-21, or about 0.5 IU/mL of IL-21. In some embodiments, the second expansion culture media comprises about 20 IU/mL of IL-21 to about 0.5 IU/mL of IL-21. In some embodiments, the second expansion culture media comprises about 15 IU/mL of IL-21 to about 0.5 IU/mL of IL-21. In some embodiments, the second expansion culture media comprises about 12 IU/mL of IL-21 to about 0.5 IU/mL of IL-21. In some embodiments, the second expansion culture media comprises about 10 IU/mL of IL-21 to about 0.5 IU/mL of IL-21. In some embodiments, the second expansion culture media comprises about 5 IU/mL of IL-21 to about 1 IU/mL of IL-21. In some embodiments, the second expansion culture media comprises about 2 IU/mL of IL-21. In some embodiments, the cell culture medium comprises about 1 IU/mL of IL-21. In some embodiments, the cell culture medium comprises about 0.5 IU/mL of IL-21. In an embodiment, the cell culture medium further comprises IL-21. In a preferred embodiment, the cell culture medium comprises about 1 IU/mL of IL-21.

In some embodiments the antigen-presenting feeder cells (APCs) are PBMCs. In an embodiment, the ratio of TILs to PBMCs and/or antigen-presenting cells in the rapid expansion and/or the second expansion is about 1 to 25, about 1 to 50, about 1 to 100, about 1 to 125, about 1 to 150, about 1 to 175, about 1 to 200, about 1 to 225, about 1 to 250, about 1 to 275, about 1 to 300, about 1 to 325, about 1 to 350, about 1 to 375, about 1 to 400, or about 1 to 500. In an embodiment, the ratio of TILs to PBMCs in the rapid expansion and/or the second expansion is between 1 to 50 and 1 to 300. In an embodiment, the ratio of TILs to PBMCs in the rapid expansion and/or the second expansion is between 1 to 100 and 1 to 200.

In an embodiment, REP and/or the second expansion is performed in flasks with the bulk TILs being mixed with a 100- or 200-fold excess of inactivated feeder cells, 30 mg/mL OKT3 anti-CD3 antibody and 3000 IU/mL IL-2 in 150 ml media. Media replacement is done (generally ⅔ media replacement via respiration with fresh media) until the cells are transferred to an alternative growth chamber. Alternative growth chambers include G-REX flasks and gas permeable containers as more fully discussed below.

In some embodiments, the second expansion (which can include processes referred to as the REP process) is shortened to 7-14 days, as discussed in the examples and figures. In some embodiments, the second expansion is shortened to 11 days.

In an embodiment, REP and/or the second expansion may be performed using T-175 flasks and gas permeable bags as previously described (Tran, et al., *J. Immunother.* 2008, 31, 742-51; Dudley, et al., *J. Immunother.* 2003, 26, 332-42) or gas permeable cultureware (G-Rex flasks). In some embodiments, the second expansion (including expansions referred to as rapid expansions) is performed in T-175 flasks, and about $1 \times 10^6$ TILs suspended in 150 mL of media may be added to each T-175 flask. The TILs may be cultured in a 1 to 1 mixture of CM and AIM-V medium, supplemented with 3000 IU per mL of IL-2 and 30 ng per ml of anti-CD3. The T-175 flasks may be incubated at 37° C. in 5% CO2. Half the media may be exchanged on day 5 using 50/50 medium with 3000 IU per mL of IL-2. In some embodiments, on day 7 cells from two T-175 flasks may be combined in a 3 L bag and 300 mL of AIM V with 5% human AB serum and 3000 IU per mL of IL-2 was added to the 300 ml of TIL suspension. The number of cells in each bag was counted every day or two and fresh media was added to keep the cell count between 0.5 and $2.0 \times 10^6$ cells/mL.

In an embodiment, the second expansion (which can include expansions referred to as REP, as well as those referred to in Step D of FIG. 9) may be performed in 500 mL capacity gas permeable flasks with 100 cm gas-permeable silicon bottoms (G-Rex 100, commercially available from Wilson Wolf Manufacturing Corporation, New Brighton, MN, USA), $5 \times 10^6$ or $10 \times 10^6$ TIL may be cultured with PBMCs in 400 mL of 50/50 medium, supplemented with 5% human AB serum, 3000 IU per mL of IL-2 and 30 ng per ml of anti-CD3 (OKT3). The G-Rex 100 flasks may be incubated at 37° C. in 5% $CO_2$. On day 5, 250 mL of supernatant may be removed and placed into centrifuge bottles and centrifuged at 1500 rpm (491×g) for 10 minutes. The TIL pellets may be re-suspended with 150 mL of fresh medium with 5% human AB serum, 3000 IU per mL of IL-2, and added back to the original G-Rex 100 flasks. When TIL are expanded serially in G-Rex 100 flasks, on day 7 the TIL in each G-Rex 100 may be suspended in the 300 mL of media present in each flask and the cell suspension may be divided into 3 100 mL aliquots that may be used to seed 3 G-Rex 100 flasks. Then 150 mL of AIM-V with 5% human AB serum and 3000 IU per mL of IL-2 may be added to each flask. The G-Rex 100 flasks may be incubated at 37° C. in 5% $CO_2$ and after 4 days 150 mL of AIM-V with 3000 IU per mL of IL-2 may be added to each G-REX 100 flask. The cells may be harvested on day 14 of culture.

In an embodiment, the second expansion (including expansions referred to as REP) is performed in flasks with the bulk TILs being mixed with a 100- or 200-fold excess of inactivated feeder cells, 30 mg/mL OKT3 anti-CD3 antibody and 3000 IU/mL IL-2 in 150 ml media. In some embodiments, media replacement is done until the cells are transferred to an alternative growth chamber. In some embodiments, ⅔ of the media is replaced by respiration with fresh media. In some embodiments, alternative growth chambers include G-REX flasks and gas permeable containers as more fully discussed below.

In an embodiment, the second expansion (including expansions referred to as REP) is performed and further comprises a step wherein TILs are selected for superior tumor reactivity. Any selection method known in the art may be used. For example, the methods described in U.S. Patent Application Publication No. 2016/0010058 A1, the disclosures of which are incorporated herein by reference, may be used for selection of TILs for superior tumor reactivity.

Optionally, a cell viability assay can be performed after the second expansion (including expansions referred to as the REP expansion), using standard assays known in the art. For example, a trypan blue exclusion assay can be done on a sample of the bulk TILs, which selectively labels dead cells and allows a viability assessment. In some embodiments, TIL samples can be counted and viability determined using a Cellometer K2 automated cell counter (Nexcelom Bioscience, Lawrence, MA). In some embodiments, viability is determined according to the Cellometer K2 Image Cytometer Automatic Cell Counter protocol described, for example, in Example 15.

In some embodiments, the second expansion (including expansions referred to as REP) of TIL can be performed using T-175 flasks and gas-permeable bags as previously described (Tran K Q, Zhou J, Durflinger K H, et al., 2008, *J Immunother.*, 31:742-751, and Dudley M E, Wunderlich J R, Shelton T E, et al. 2003, *J Immunother.*, 26:332-342) or gas-permeable G-Rex flasks. In some embodiments, the second expansion is performed using flasks. In some embodiments, the second expansion is performed using gas-permeable G-Rex flasks. In some embodiments, the second expansion is performed in T-175 flasks, and about $1 \times 10^6$ TIL are suspended in about 150 mL of media and this is added to each T-175 flask. The TIL are cultured with irradiated (50 Gy) allogeneic PBMC as "feeder" cells at a ratio of 1 to 100 and the cells were cultured in a 1 to 1 mixture of CM and AIM-V medium (50/50 medium), supplemented with 3000 IU/mL of IL-2 and 30 ng/mL of anti-CD3. The T-175 flasks are incubated at 37° C. in 5% $CO_2$. In some embodiments, half the media is changed on day 5 using 50/50 medium with 3000 IU/mL of IL-2. In some embodiments, on day 7, cells from 2 T-175 flasks are combined in a 3 L bag and 300 mL of AIM-V with 5% human AB serum and 3000 IU/mL of IL-2 is added to the 300 mL of TIL suspension. The number of cells in each bag can be counted every day or two and fresh media can be added to keep the cell count between about 0.5 and about $2.0 \times 10^6$ cells/mL.

In some embodiments, the second expansion (including expansions referred to as REP) are performed in 500 mL capacity flasks with 100 cm² gas-permeable silicon bottoms (G-Rex 100, Wilson Wolf) (FIG. 1), about $5 \times 10^6$ or $10 \times 10^6$ TIL are cultured with irradiated allogeneic PBMC at a ratio of 1 to 100 in 400 mL of 50/50 medium, supplemented with 3000 IU/mL of IL-2 and 30 ng/mL of anti-CD3. The G-Rex 100 flasks are incubated at 37° C. in 5% $CO_2$. In some embodiments, on day 5, 250 mL of supernatant is removed and placed into centrifuge bottles and centrifuged at 1500 rpm (491 g) for 10 minutes. The TIL pellets can then be resuspended with 150 mL of fresh 50/50 medium with 3000 IU/mL of IL-2 and added back to the original G-Rex 100 flasks. In embodiments where TILs are expanded serially in G-Rex 100 flasks, on day 7 the TIL in each G-Rex 100 are suspended in the 300 mL of media present in each flask and the cell suspension was divided into three 100 mL aliquots that are used to seed 3 G-Rex 100 flasks. Then 150 mL of AIM-V with 5% human AB serum and 3000 IU/mL of IL-2 is added to each flask. The G-Rex 100 flasks are incubated at 37° C. in 5% CO2 and after 4 days 150 mL of AIM-V with 3000 IU/mL of IL-2 is added to each G-Rex 100 flask. The cells are harvested on day 14 of culture.

The diverse antigen receptors of T and B lymphocytes are produced by somatic recombination of a limited, but large number of gene segments. These gene segments: V (variable), D (diversity), J (joining), and C (constant), determine the binding specificity and downstream applications of immunoglobulins and T-cell receptors (TCRs). The present invention provides a method for generating TILs which exhibit and increase the T-cell repertoire diversity. In some embodiments, the TILs obtained by the present method exhibit an increase in the T-cell repertoire diversity. In some embodiments, the TILs obtained in the second expansion exhibit an increase in the T-cell repertoire diversity. In some embodiments, the increase in diversity is an increase in the immunoglobulin diversity and/or the T-cell receptor diversity. In some embodiments, the diversity is in the immunoglobulin is in the immunoglobulin heavy chain. In some embodiments, the diversity is in the immunoglobulin is in the immunoglobulin light chain. In some embodiments, the diversity is in the T-cell receptor. In some embodiments, the diversity is in one of the T-cell receptors selected from the group consisting of alpha, beta, gamma, and delta receptors. In some embodiments, there is an increase in the expression of T-cell receptor (TCR) alpha and/or beta. In some embodiments, there is an increase in the expression of T-cell receptor (TCR) alpha. In some embodiments, there is an increase in the expression of T-cell receptor (TCR) beta. In some embodiments, there is an increase in the expression of TCRab (i.e., TCRα/β).

In some embodiments, the second expansion culture medium (e.g., sometimes referred to as CM2 or the second cell culture medium), comprises IL-2, OKT-3, as well as the antigen-presenting feeder cells (APCs), as discussed in more detail below.

In some embodiments, the second expansion, for example, Step D according to FIG. 9, is performed in a closed system bioreactor. In some embodiments, a closed system is employed for the TIL expansion, as described herein. In some embodiments, a single bioreactor is employed. In some embodiments, the single bioreactor employed is for example a G-REX-10 or a G-REX-100. In some embodiments, the closed system bioreactor is a single bioreactor.

1. Feeder Cells and Antigen Presenting Cells

In an embodiment, the second expansion procedures described herein (for example including expansion such as those described in Step D from FIG. 9, as well as those referred to as REP) require an excess of feeder cells during REP TIL expansion and/or during the second expansion. In many embodiments, the feeder cells are peripheral blood mononuclear cells (PBMCs) obtained from standard whole blood units from healthy blood donors. The PBMCs are obtained using standard methods such as Ficoll-Paque gradient separation.

In general, the allogenic PBMCs are inactivated, either via irradiation or heat treatment, and used in the REP procedures, as described in the examples, in particular example 14, which provides an exemplary protocol for evaluating the replication incompetence of irradiate allogeneic PBMCs.

In some embodiments, PBMCs are considered replication incompetent and accepted for use in the TIL expansion procedures described herein if the total number of viable cells on day 14 is less than the initial viable cell number put into culture on day 0 of the REP and/or day 0 of the second expansion (i.e., the start day of the second expansion). See, for example, Example 14.

In some embodiments, PBMCs are considered replication incompetent and accepted for use in the TIL expansion procedures described herein if the total number of viable cells, cultured in the presence of OKT3 and IL-2, on day 7 and day 14 has not increased from the initial viable cell number put into culture on day 0 of the REP and/or day 0 of the second expansion (i.e., the start day of the second expansion). In some embodiments, the PBMCs are cultured in the presence of 30 ng/ml OKT3 antibody and 3000 IU/ml IL-2. See, for example, Example 13.

In some embodiments, PBMCs are considered replication incompetent and accepted for use in the TIL expansion procedures described herein if the total number of viable cells, cultured in the presence of OKT3 and IL-2, on day 7 and day 14 has not increased from the initial viable cell number put into culture on day 0 of the REP and/or day 0 of the second expansion (i.e., the start day of the second expansion). In some embodiments, the PBMCs are cultured in the presence of 5-60 ng/ml OKT3 antibody and 1000-6000 IU/ml IL-2. In some embodiments, the PBMCs are cultured in the presence of 10-50 ng/ml OKT3 antibody and 2000-5000 IU/ml IL-2. In some embodiments, the PBMCs are cultured in the presence of 20-40 ng/ml OKT3 antibody and 2000-4000 IU/ml IL-2. In some embodiments, the PBMCs are cultured in the presence of 25-35 ng/ml OKT3 antibody and 2500-3500 IU/ml IL-2.

In some embodiments, the antigen-presenting feeder cells are PBMCs. In some embodiments, the antigen-presenting feeder cells are artificial antigen-presenting feeder cells. In an embodiment, the ratio of TILs to antigen-presenting feeder cells in the second expansion is about 1 to 25, about 1 to 50, about 1 to 100, about 1 to 125, about 1 to 150, about 1 to 175, about 1 to 200, about 1 to 225, about 1 to 250, about 1 to 275, about 1 to 300, about 1 to 325, about 1 to 350, about 1 to 375, about 1 to 400, or about 1 to 500. In an embodiment, the ratio of TILs to antigen-presenting feeder cells in the second expansion is between 1 to 50 and 1 to 300. In an embodiment, the ratio of TILs to antigen-presenting feeder cells in the second expansion is between 1 to 100 and 1 to 200.

In an embodiment, the second expansion procedures described herein require a ratio of about $2.5 \times 10^9$ feeder cells to about $100 \times 10^6$ TILs. In another embodiment, the second expansion procedures described herein require a ratio of about $2.5 \times 10^9$ feeder cells to about $50 \times 10^6$ TILs. In yet another embodiment, the second expansion procedures described herein require about $2.5 \times 10^9$ feeder cells to about $25 \times 10^6$ TILs.

In an embodiment, the second expansion procedures described herein require an excess of feeder cells during the second expansion. In many embodiments, the feeder cells are peripheral blood mononuclear cells (PBMCs) obtained from standard whole blood units from healthy blood donors. The PBMCs are obtained using standard methods such as Ficoll-Paque gradient separation. In an embodiment, artificial antigen-presenting (aAPC) cells are used in place of PBMCs.

In general, the allogenic PBMCs are inactivated, either via irradiation or heat treatment, and used in the TIL expansion procedures described herein, including the exemplary procedures as described in FIGS. 5, 6, 8, 9, 10, and 11.

In an embodiment, artificial antigen presenting cells are used in the second expansion as a replacement for, or in combination with, PBMCs.

2. Cytokines

The expansion methods described herein generally use culture media with high doses of a cytokine, in particular IL-2, as is known in the art.

Alternatively, using combinations of cytokines for the rapid expansion and or second expansion of TILS is additionally possible, with combinations of two or more of IL-2, IL-15 and IL-21 as is generally outlined in International Publication No. WO 2015/189356 and W International Publication No. WO 2015/189357, hereby expressly incorporated by reference in their entirety. Thus, possible combinations include IL-2 and IL-15, IL-2 and IL-21, IL-15 and IL-21 and IL-2, IL-15 and IL-21, with the latter finding particular use in many embodiments. The use of combinations of cytokines specifically favors the generation of lymphocytes, and in particular T-cells as described therein.

3. Anti-CD3 Antibodies

In some embodiments, the culture media used in expansion methods described herein (including those referred to as REP, see for example, FIG. 9) also includes an anti-CD3 antibody. An anti-CD3 antibody in combination with IL-2 induces T-cell activation and cell division in the TIL population. This effect can be seen with full length antibodies as well as Fab and F(ab')2 fragments, with the former being generally preferred; see, e.g., Tsoukas et al., *J. Immunol.* 1985, 135, 1719, hereby incorporated by reference in its entirety.

As will be appreciated by those in the art, there are a number of suitable anti-human CD3 antibodies that find use in the invention, including anti-human CD3 polyclonal and monoclonal antibodies from various mammals, including, but not limited to, murine, human, primate, rat, and canine antibodies. In particular embodiments, the OKT3 anti-CD3 antibody is used (commercially available from Ortho-Mc-Neil, Raritan, NJ or Miltenyi Biotech, Auburn, CA).

E. Step E: Harvest TILS

After the second expansion step, cells can be harvested. In some embodiments the TILs are harvested after one, two, three, four or more expansion steps, for example as provided in FIG. 9. In some embodiments the TILs are harvested after two expansion steps, for example as provided in FIG. 9.

TILs can be harvested in any appropriate and sterile manner, including for example by centrifugation. Methods for TIL harvesting are well known in the art and any such know methods can be employed with the present process. In some embodiments, TILS are harvest using an automated system.

Cell harvesters and/or cell processing systems are commercially available from a variety of sources, including, for example, Fresenius Kabi, Tomtec Life Science, Perkin Elmer, and Inotech Biosystems International, Inc. Any cell based harvester can be employed with the present methods. In some embodiments, the cell harvester and/or cell processing systems is a membrane-based cell harvester. In some embodiments, cell harvesting is via a cell processing system, such as the LOVO system (manufactured by Fresenius Kabi). The term "LOVO cell processing system" also refers to any instrument or device manufactured by any vendor that can pump a solution comprising cells through a membrane or filter such as a spinning membrane or spinning filter in a sterile and/or closed system environment, allowing for continuous flow and cell processing to remove supernatant or cell culture media without pelletization. In some embodiments, the cell harvester and/or cell processing system can perform cell separation, washing, fluid-exchange, concentration, and/or other cell processing steps in a closed, sterile system.

In some embodiments, the harvest, for example, Step E according to FIG. 9, is performed from a closed system bioreactor. In some embodiments, a closed system is employed for the TIL expansion, as described herein. In some embodiments, a single bioreactor is employed. In some embodiments, the single bioreactor employed is for example a G-REX-10 or a G-REX-100. In some embodiments, the closed system bioreactor is a single bioreactor.

F. Step F: Final Formulation/Transfer to Infusion Bag

After Steps A through E as provided in an exemplary order in FIG. 9 and as outlined in detailed above and herein are complete, cells are transferred to a container for use in administration to a patient. In some embodiments, once a therapeutically sufficient number of TILs are obtained using the expansion methods described above, they are transferred to a container for use in administration to a patient.

In an embodiment, TILs expanded using APCs of the present disclosure are administered to a patient as a pharmaceutical composition. In an embodiment, the pharmaceutical composition is a suspension of TILs in a sterile buffer. TILs expanded using PBMCs of the present disclosure may be administered by any suitable route as known in the art. In some embodiments, the T-cells are administered as a single intra-arterial or intravenous infusion, which preferably lasts approximately 30 to 60 minutes. Other suitable routes of administration include intraperitoneal, intrathecal, and intralymphatic.

1. Pharmaceutical Compositions, Dosages, and Dosing Regimens

In an embodiment, TILs expanded using the methods of the present disclosure are administered to a patient as a pharmaceutical composition. In an embodiment, the pharmaceutical composition is a suspension of TILs in a sterile buffer. TILs expanded using PBMCs of the present disclosure may be administered by any suitable route as known in the art. In some embodiments, the T-cells are administered as a single intra-arterial or intravenous infusion, which preferably lasts approximately 30 to 60 minutes. Other suitable routes of administration include intraperitoneal, intrathecal, and intralymphatic administration.

Any suitable dose of TILs can be administered. In some embodiments, from about $2.3 \times 10^{10}$ to about $13.7 \times 10^{10}$ TILs are administered, with an average of around $7.8 \times 10^{10}$ TILs, particularly if the cancer is melanoma. In an embodiment, about $1.2 \times 10^{10}$ to about $4.3 \times 10^{10}$ of TILs are administered. In some embodiments, about $3 \times 10^{10}$ to about $12 \times 10^{10}$ TILs are administered. In some embodiments, about $4 \times 10^{10}$ to about $10 \times 10^{10}$ TILs are administered. In some embodiments, about $5 \times 10^{10}$ to about $8 \times 10^{10}$ TILs are administered. In some embodiments, about $6 \times 10^{10}$ to about $8 \times 10^{10}$ TILs are administered. In some embodiments, about $7 \times 10^{10}$ to about $8 \times 10^{10}$ TILs are administered. In some embodiments, the therapeutically effective dosage is about $2.3 \times 10^{10}$ to about $13.7 \times 10^{10}$. In some embodiments, the therapeutically effective dosage is about $7.8 \times 10^{10}$ TILs, particularly of the cancer is melanoma. In some embodiments, the therapeutically effective dosage is about $1.2 \times 10^{10}$ to about $4.3 \times 10^{10}$ of TILs. In some embodiments, the therapeutically effective dosage is about $3 \times 10^{10}$ to about $12 \times 10^{10}$ TILs. In some embodiments, the therapeutically effective dosage is about $4 \times 10^{10}$ to about $10 \times 10^{10}$ TILs. In some embodiments, the therapeutically effective dosage is about $5 \times 10^{10}$ to about $8 \times 10^{10}$ TILs. In some embodiments, the therapeutically effective dosage is about $6 \times 10^{10}$ to about $8 \times 10^{10}$ TILs. In some embodiments, the therapeutically effective dosage is about $7 \times 10^{10}$ to about $8 \times 10^{10}$ TILs.

In some embodiments, the number of the TILs provided in the pharmaceutical compositions of the invention is about $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, $1 \times 10^7$, $2 \times 10^7$, $3 \times 10^7$, $4 \times 10^7$, $5 \times 10^7$, $6 \times 10^7$, $7 \times 10^7$, $8 \times 10^7$, $9 \times 10^7$, $1 \times 10$, $2 \times 10$, $3 \times 10$, $4 \times 10^8$, $5 \times 10^8$, $6 \times 10^8$, $7 \times 10^8$, $8 \times 10$, $9 \times 10^8$, $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, $9 \times 10^{10}$, $1 \times 10^{11}$, $2 \times 10^{11}$, $3 \times 10^{11}$, $4 \times 10^{11}$, $5 \times 10^{11}$, $6 \times 10^{11}$, $7 \times 10^1$, $8 \times 10^{11}$, $9 \times 10^{11}$, $1 \times 10^{12}$, $2 \times 10^{12}$, $3 \times 10^{12}$, $4 \times 10^{12}$, $5 \times 10^{12}$, $6 \times 10^{12}$, $7 \times 10^{12}$ $8 \times 10^{12}$, $9 \times 10^{12}$, $1 \times 10^{13}$, $2 \times 10^{13}$, $3 \times 10^{13}$ $4 \times 10^{13}$, $5 \times 10^{13}$ $6 \times 10^{13}$, $7 \times 10^{13}$, $8 \times 10^{13}$, and $9 \times 10^{13}$. In an embodiment, the number of the TILs provided in the pharmaceutical compositions of the invention is in the range of $1 \times 10^6$ to $5 \times 10^6$, $5 \times 10^6$ to $1 \times 10^7$, $1 \times 10^7$ to $5 \times 10^7$, $5 \times 10^7$ to $1 \times 10^8$, $1 \times 10^8$ to $5 \times 10^8$, $5 \times 10^8$ to $1 \times 10^9$, $1 \times 10^9$ to $5 \times 10^9$, $5 \times 10^9$ to $1 \times 10^{10}$, $1 \times 10^{10}$ to $5 \times 10^{10}$, $5 \times 10^{10}$ to $1 \times 10^{11}$, $5 \times 10^{11}$ to $1 \times 10^{12}$, $1 \times 10^{12}$ to $5 \times 10^{12}$, and $5 \times 10^{12}$ to $1 \times 10^{13}$.

In some embodiments, the concentration of the TILs provided in the pharmaceutical compositions of the invention is less than, for example, 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v or v/v of the pharmaceutical composition.

In some embodiments, the concentration of the TILs provided in the pharmaceutical compositions of the invention is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v, or v/v of the pharmaceutical composition.

In some embodiments, the concentration of the TILs provided in the pharmaceutical compositions of the invention is in the range from about 0.0001% to about 50%, about 0.001% to about 40%, about 0.01% to about 30%, about 0.02% to about 29%, about 0.03% to about 28%, about 0.04% to about 27%, about 0.05% to about 26%, about 0.06% to about 25%, about 0.07% to about 24%, about 0.08% to about 23%, about 0.09% to about 22%, about 0.1% to about 21%, about 0.2% to about 20%, about 0.3% to about 19%, about 0.4% to about 18%, about 0.5% to about 17%, about 0.6% to about 16%, about 0.7% to about 15%, about 0.8% to about 14%, about 0.9% to about 12% or about 1% to about 10% w/w, w/v or v/v of the pharmaceutical composition.

In some embodiments, the concentration of the TILs provided in the pharmaceutical compositions of the invention is in the range from about 0.001% to about 10%, about 0.01% to about 5%, about 0.02% to about 4.5%, about 0.03% to about 4%, about 0.04% to about 3.5%, about 0.05% to about 3%, about 0.06% to about 2.5%, about 0.07% to about 2%, about 0.08% to about 1.5%, about 0.09% to about 1%, about 0.1% to about 0.9% w/w, w/v or v/v of the pharmaceutical composition.

In some embodiments, the amount of the TILs provided in the pharmaceutical compositions of the invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of the TILs provided in the pharmaceutical compositions of the invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

The TILs provided in the pharmaceutical compositions of the invention are effective over a wide dosage range. The exact dosage will depend upon the route of administration, the form in which the compound is administered, the gender and age of the subject to be treated, the body weight of the subject to be treated, and the preference and experience of the attending physician. The clinically-established dosages of the TILs may also be used if appropriate. The amounts of the pharmaceutical compositions administered using the methods herein, such as the dosages of TILs, will be dependent on the human or mammal being treated, the severity of the disorder or condition, the rate of administration, the disposition of the active pharmaceutical ingredients and the discretion of the prescribing physician.

In some embodiments, TILs may be administered in a single dose. Such administration may be by injection, e.g., intravenous injection. In some embodiments, TILs may be administered in multiple doses. Dosing may be once, twice, three times, four times, five times, six times, or more than six times per year. Dosing may be once a month, once every two weeks, once a week, or once every other day. Administration of TILs may continue as long as necessary.

In some embodiments, an effective dosage of TILs is about $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$, $1\times10^{13}$, $2\times10^{13}$, $3\times10^{13}$, $4\times10^{13}$, $5\times10^{13}$, $6\times10^{13}$, $7\times10^{13}$, $8\times10^{13}$, and $9\times10^{13}$. In some embodiments, an effective dosage of TILs is in the range of $1\times10^6$ to $5\times10^6$, $5\times10^6$ to $1\times10^7$, $1\times10^7$ to $5\times10^7$, $5\times10^7$ to $1\times10^8$, $1\times10^8$ to $5\times10^8$, $5\times10^8$ to $1\times10^9$, $1\times10^9$ to $5\times10^9$, $5\times10^9$ to $1\times10^{10}$, $1\times10^{10}$ to $5\times10^{10}$, $5\times10^{10}$ to $1\times10^{11}$, $5\times10^{11}$ to $1\times10^{12}$, $1\times10^{12}$ to $5\times10^{12}$, and $5\times10^{12}$ to $1\times10^{13}$.

In some embodiments, an effective dosage of TILs is in the range of about 0.01 mg/kg to about 4.3 mg/kg, about 0.15 mg/kg to about 3.6 mg/kg, about 0.3 mg/kg to about 3.2 mg/kg, about 0.35 mg/kg to about 2.85 mg/kg, about 0.15 mg/kg to about 2.85 mg/kg, about 0.3 mg to about 2.15 mg/kg, about 0.45 mg/kg to about 1.7 mg/kg, about 0.15 mg/kg to about 1.3 mg/kg, about 0.3 mg/kg to about 1.15 mg/kg, about 0.45 mg/kg to about 1 mg/kg, about 0.55 mg/kg to about 0.85 mg/kg, about 0.65 mg/kg to about 0.8 mg/kg, about 0.7 mg/kg to about 0.75 mg/kg, about 0.7 mg/kg to about 2.15 mg/kg, about 0.85 mg/kg to about 2 mg/kg, about 1 mg/kg to about 1.85 mg/kg, about 1.15 mg/kg to about 1.7 mg/kg, about 1.3 mg/kg mg to about 1.6 mg/kg, about 1.35 mg/kg to about 1.5 mg/kg, about 2.15 mg/kg to about 3.6 mg/kg, about 2.3 mg/kg to about 3.4 mg/kg, about 2.4 mg/kg to about 3.3 mg/kg, about 2.6 mg/kg to about 3.15 mg/kg, about 2.7 mg/kg to about 3 mg/kg, about 2.8 mg/kg to about 3 mg/kg, or about 2.85 mg/kg to about 2.95 mg/kg.

In some embodiments, an effective dosage of TILs is in the range of about 1 mg to about 500 mg, about 10 mg to about 300 mg, about 20 mg to about 250 mg, about 25 mg to about 200 mg, about 1 mg to about 50 mg, about 5 mg to about 45 mg, about 10 mg to about 40 mg, about 15 mg to about 35 mg, about 20 mg to about 30 mg, about 23 mg to about 28 mg, about 50 mg to about 150 mg, about 60 mg to about 140 mg, about 70 mg to about 130 mg, about 80 mg to about 120 mg, about 90 mg to about 110 mg, or about 95 mg to about 105 mg, about 98 mg to about 102 mg, about 150 mg to about 250 mg, about 160 mg to about 240 mg, about 170 mg to about 230 mg, about 180 mg to about 220 mg, about 190 mg to about 210 mg, about 195 mg to about 205 mg, or about 198 to about 207 mg.

An effective amount of the TILs may be administered in either single or multiple doses by any of the accepted modes of administration of agents having similar utilities, including intranasal and transdermal routes, by intra-arterial injection, intravenously, intraperitoneally, parenterally, intramuscularly, subcutaneously, topically, by transplantation, or by inhalation.

G. Optional Cell Viability Analyses

Optionally, a cell viability assay can be performed after the Step B first expansion, using standard assays known in the art. For example, a trypan blue exclusion assay can be done on a sample of the bulk TILs, which selectively labels dead cells and allows a viability assessment. Other assays for use in testing viability can include but are not limited to the Alamar blue assay; and the MTT assay.

1. Cell Counts, Viability, Flow Cytometry

In some embodiments, cell counts and/or viability are measured. The expression of markers such as but not limited CD3, CD4, CD8, and CD56, as well as any other disclosed or described herein, can be measured by flow cytometry with antibodies, for example but not limited to those commercially available from BD Bio-sciences (BD Biosciences, San Jose, CA) using a FACSCantom flow cytometer (BD Biosciences). The cells can be counted manually using a disposable c-chip hemocytometer (VWR, Batavia, IL) and viability can be assessed using any method known in the art, including but not limited to trypan blue staining.

In some cases, the bulk TIL population can be cryopreserved immediately, using the protocols discussed below. Alternatively, the bulk TIL population can be subjected to REP and then cryopreserved as discussed below. Similarly, in the case where genetically modified TILs will be used in therapy, the bulk or REP TIL populations can be subjected to genetic modifications for suitable treatments.

2. Cell Cultures

In an embodiment, a method for expanding TILs may include using about 5,000 mL to about 25,000 mL of cell medium, about 5,000 mL to about 10,000 mL of cell medium, or about 5,800 mL to about 8,700 mL of cell medium. In an embodiment, expanding the number of TILs uses no more than one type of cell culture medium. Any suitable cell culture medium may be used, e.g., AIM-V cell medium (L-glutamine, 50 µM streptomycin sulfate, and 10 µM gentamicin sulfate) cell culture medium (Invitrogen, Carlsbad CA). In this regard, the inventive methods advantageously reduce the amount of medium and the number of types of medium required to expand the number of TIL. In an embodiment, expanding the number of TIL may comprise adding fresh cell culture media to the cells (also referred to as feeding the cells) no more frequently than every third or fourth day. Expanding the number of cells in a gas permeable container simplifies the procedures necessary to expand the number of cells by reducing the feeding frequency necessary to expand the cells.

In an embodiment, the cell medium in the first and/or second gas permeable container is unfiltered. The use of unfiltered cell medium may simplify the procedures necessary to expand the number of cells. In an embodiment, the cell medium in the first and/or second gas permeable container lacks beta-mercaptoethanol (BME).

In an embodiment, the duration of the method comprising obtaining a tumor tissue sample from the mammal; culturing the tumor tissue sample in a first gas permeable container containing cell medium therein; obtaining TILs from the tumor tissue sample; expanding the number of TILs in a second gas permeable container containing cell medium therein using aAPCs for a duration of about 14 to about 42 days, e.g., about 28 days.

In an embodiment, TILs are expanded in gas-permeable containers. Gas-permeable containers have been used to expand TILs using PBMCs using methods, compositions, and devices known in the art, including those described in U.S. Patent Application Publication No. 2005/0106717 A1, the disclosures of which are incorporated herein by reference. In an embodiment, TILs are expanded in gas-permeable bags. In an embodiment, TILs are expanded using a cell expansion system that expands TILs in gas permeable bags, such as the Xuri Cell Expansion System W25 (GE Healthcare). In an embodiment, TILs are expanded using a cell expansion system that expands TILs in gas permeable bags, such as the WAVE Bioreactor System, also known as the Xuri Cell Expansion System W5 (GE Healthcare). In an embodiment, the cell expansion system includes a gas permeable cell bag with a volume selected from the group consisting of about 100 mL, about 200 mL, about 300 mL, about 400 mL, about 500 mL, about 600 mL, about 700 mL, about 800 mL, about 900 mL, about 1 L, about 2 L, about 3 L, about 4 L, about 5 L, about 6 L, about 7 L, about 8 L, about 9 L, and about 10 L. In an embodiment, TILs can be expanded in G-Rex flasks (commercially available from Wilson Wolf Manufacturing). Such embodiments allow for cell populations to expand from about $5 \times 10^5$ cells/cm$^2$ to between $10 \times 10^6$ and $30 \times 10^6$ cells/cm$^2$. In an embodiment this expansion is conducted without adding fresh cell culture media to the cells (also referred to as feeding the cells). In an embodiment, this is without feeding so long as medium resides at a height of about 10 cm in the G-Rex flask. In an embodiment this is without feeding but with the addition of one or more cytokines. In an embodiment, the cytokine can be added as a bolus without any need to mix the cytokine with the medium. Such containers, devices, and methods are known in the art and have been used to expand TILs, and include those described in U.S. Patent Application Publication No. US 2014/0377739A1, International Publication No. WO 2014/210036 A1, U.S. Patent Application Publication No. us 2013/0115617 A1, International Publication No. WO 2013/188427 A1, U.S. Patent Application Publication No. US 2011/0136228 A1, U.S. Pat. No. 8,809,050 B2, International publication No. WO 2011/072088 A2, U.S. Patent Application Publication No. US 2016/0208216 A1, U.S. Patent Application Publication No. US 2012/0244133 A1, International Publication No. WO 2012/129201 A1, U.S. Patent Application Publication No. US 2013/0102075 A1, U.S. Pat. No. 8,956,860 B2, International Publication No. WO 2013/173835 A1, U.S. Patent Application Publication No. US 2015/0175966 A1, the disclosures of which are incorporated herein by reference. Such processes are also described in Jin et al., *J. Immunotherapy*, 2012, 35:283-292.

Optional Genetic Engineering of TILs

In some embodiments, the TILs are optionally genetically engineered to include additional functionalities, including, but not limited to, a high-affinity T-cell receptor (TCR), e.g., a TCR targeted at a tumor-associated antigen such as MAGE-1, HER2, or NY-ESO-1, or a chimeric antigen receptor (CAR) which binds to a tumor-associated cell surface molecule (e.g., mesothelin) or lineage-restricted cell surface molecule (e.g., CD19).

H. Optional Cryopreservation of TILs

As discussed above, and exemplified in Steps A through E as provided in FIG. 9, cryopreservation can occur at numerous points throughout the TIL expansion process. In some embodiments, the expanded population of TILs after the second expansion (as provided for example, according to Step D of FIG. 9) can be cryopreserved. Cryopreservation can be generally accomplished by placing the TIL population into a freezing solution, e.g., 85% complement inactivated AB serum and 15% dimethyl sulfoxide (DMSO). The cells in solution are placed into cryogenic vials and stored for 24 hours at −80° C., with optional transfer to gaseous nitrogen freezers for cryopreservation. See Sadeghi, et al., *Acta Oncologica* 2013, 52, 978-986. In some embodiments, the TILs are cryopreserved in 5% DMSO. In some embodiments, the TILs are cryopreserved in cell culture media plus 5% DMSO. In some embodiments, the TILs are cryopreserved according to the methods provided in Examples 8 and 9.

When appropriate, the cells are removed from the freezer and thawed in a 37° C. water bath until approximately ⅘ of the solution is thawed. The cells are generally resuspended in complete media and optionally washed one or more times. In some embodiments, the thawed TILs can be counted and assessed for viability as is known in the art.

I. Phenotypic Characteristics of Expanded TILs

In some embodiment, the TILs are analyzed for expression of numerous phenotype markers after expansion, including those described herein and in the Examples. In an embodiment, expression of one or more phenotypic markers is examined. In some embodiments, the phenotypic characteristics of the TILs are analyzed after the first expansion in Step B. In some embodiments, the phenotypic characteristics of the TILs are analyzed during the transition in Step C. In some embodiments, the phenotypic characteristics of the TILs are analyzed during the transition according to Step C and after cryopreservation. In some embodiments, the phenotypic characteristics of the TILs are analyzed after the second expansion according to Step D. In some embodiments, the phenotypic characteristics of the TILs are analyzed after two or more expansions according to Step D. In some embodiments, the marker is selected from the group consisting of TCRab (i.e., TCRα/β), CD57, CD28, CD4, CD27, CD56, CD8a, CD45RA, CD8a, CCR7, CD4, CD3, CD38, and HLA-DR. In some embodiments, the marker is selected from the group consisting of TCRab (i.e., TCRα/β), CD57, CD28, CD4, CD27, CD56, and CD8a. In an embodiment, the marker is selected from the group consisting of CD45RA, CD8a, CCR7, CD4, CD3, CD38, and HLA-DR. In some embodiments, expression of one, two, three, four, five, six, seven, eight, nine, ten, eleven, twelve, thirteen, or fourteen markers is examined. In some embodiments, the expression from one or more markers from each group is examined. In some embodiments, one or more of HLA-DR, CD38, and CD69 expression is maintained (i.e., does not exhibit a statistically significant difference) in fresh TILs as compared to thawed TILs. In some embodiments, the activation status of TILs is maintained in the thawed TILs.

In an embodiment, expression of one or more regulatory markers is measured. In some embodiments, the regulatory marker is selected from the group consisting of CD137, CD8a, Lag3, CD4, CD3, PD-1, TIM-3, CD69, CD8a, TIGIT, CD4, CD3, KLRG1, and CD154. In some embodiments, the regulatory marker is selected from the group consisting of CD137, CD8a, Lag3, CD4, CD3, PD-1, and TIM-3. In some embodiments, the regulatory marker is selected from the group consisting of CD69, CD8a, TIGIT, CD4, CD3, KLRG1, and CD154. In some embodiments, regulatory molecule expression is decreased in thawed TILs as compared to fresh TILs. In some embodiments, expression of regulatory molecules LAG-3 and TIM-3 is decreased in thawed TILs as compared to fresh TILs. In some embodiments, there is no significant difference in CD4, CD8, NK, TCRαβ expression. In some embodiments, there is no significant difference in CD4, CD8, NK, TCRαβ expression, and/or memory markers in fresh TILs as compared to thawed TILs. In some embodiments, there is no significant difference in CD4, CD8, NK, TCRαβ expression between the TILs produced by the methods provided herein, as exemplified for example in FIG. 9, and/or TILs prepared using other methods than those provide herein including for example, methods other than those embodied in FIG. 9.

In some embodiments, no selection of the first population of TILs, second population of TILs, third population of TILs, harvested TIL population, and/or the therapeutic TIL population based on CD4, CD8, and/or NK, TCRαβ expression is performed during any of steps, including those discussed above or as provided for example in FIG. 9. In some embodiments, no selection of the first population of TILs based on CD4, CD8, and/or NK, TCRαβ is performed. In some embodiments, no selection of the second population of TILs based on CD4, CD8, and/or NK, TCRαβ expression is performed. In some embodiments, no selection of the third population of TILs based on CD4, CD8, and/or NK, TCRαβ expression is performed. In some embodiments, no selection of the harvested population of TILs based on CD4, CD8, and/or NK, TCRαβ expression is performed. In some embodiments, no selection of the therapeutic population of TILs based on CD4, CD8, and/or NK, TCRαβ expression is performed.

In an embodiment, no selection of the first population of TILs, second population of TILs, third population of TILs, or harvested TIL population based on CD4, CD8, and/or NK, TCRαβ expression is performed during any of steps (a) to (f) of the method for expanding tumor infiltrating lymphocytes (TILs) into a therapeutic population of TILs comprising:

(a) obtaining a first population of TILs from a tumor resected from a patient by processing a tumor sample obtained from the patient into multiple tumor fragments;

(b) adding the tumor fragments into a closed system;

(c) performing a first expansion by culturing the first population of TILs in a cell culture medium comprising IL-2 to produce a second population of TILs, wherein the first expansion is performed in a closed container providing a first gas-permeable surface area, wherein the first expansion is performed for about 3-14 days to obtain the second population of TILs, wherein the second population of TILs is at least 50-fold greater in number than the first population of TILs, and wherein the transition from step (b) to step (c) occurs without opening the system;

(d) performing a second expansion by supplementing the cell culture medium of the second population of TILs with additional IL-2, OKT-3, and antigen presenting cells (APCs), to produce a third population of TILs, wherein the second expansion is performed for about 7-14 days to obtain the third population of TILs, wherein the third population of TILs is a therapeutic population of TILs which comprises an increased subpopulation of effector T-cells and/or central memory T-cells relative to the second population of TILs, wherein the second expansion is performed in a closed container providing a second gas-permeable surface area, and wherein the transition from step (c) to step (d) occurs without opening the system;

(e) harvesting the therapeutic population of TILs obtained from step (d), wherein the transition from step (d) to step (e) occurs without opening the system; and (f) transferring the harvested TIL population from step (e) to an infusion bag, wherein the transfer from step (e) to (f) occurs without opening the system.

In an embodiment, no selection of the first population of TILs, second population of TILs, third population of TILs, or harvested TIL population based on CD4, CD8, and/or NK, TCRαβ expression is performed during any of steps (a) to (h) of the method for treating a subject with cancer, the method comprising administering expanded tumor infiltrating lymphocytes (TILs) comprising:

(a) obtaining a first population of TILs from a tumor resected from a subject by processing a tumor sample obtained from the patient into multiple tumor fragments;

(b) adding the tumor fragments into a closed system;

(c) performing a first expansion by culturing the first population of TILs in a cell culture medium comprising IL-2 to produce a second population of TILs, wherein the first expansion is performed in a closed container providing a first gas-permeable surface area, wherein the first expansion is performed for about 3-14 days to obtain the second population of TILs, wherein the second population of TILs is at least 50-fold greater in number than the first population of TILs, and wherein the transition from step (b) to step (c) occurs without opening the system;

(d) performing a second expansion by supplementing the cell culture medium of the second population of TILs with additional IL-2, OKT-3, and antigen presenting cells (APCs), to produce a third population of TILs, wherein the second expansion is performed for about 7-14 days to obtain the third population of TILs, wherein the third population of TILs is a therapeutic population of TILs which comprises an increased subpopulation of effector T-cells and/or central memory T-cells relative to the second population of TILs, wherein the second expansion is performed in a closed container providing a second gas-permeable surface area, and wherein the transition from step (c) to step (d) occurs without opening the system;

(e) harvesting the therapeutic population of TILs obtained from step (d), wherein the transition from step (d) to step (e) occurs without opening the system; and (f) transferring the harvested TIL population from step (e) to an infusion bag, wherein the transfer from step (e) to (f) occurs without opening the system;

(g) optionally cryopreserving the infusion bag comprising the harvested TIL population from step (f) using a cryopreservation process; and (h) administering a therapeutically effective dosage of the third population of TILs from the infusion bag in step (g) to the patient.

In some embodiments the memory marker is selected from the group consisting of CCR7 and CD62L In some embodiments, the viability of the fresh TILs as compared to the thawed TILs is at least 70%, at least 75%, at least 80%, at least 85%, at least 90%, at least 95%, or at least 98%. In some embodiments, the viability of both the fresh and thawed TILs is greater than 70%, greater than 75%, greater than 80%, greater than 85%, greater than 90%, greater than 95%, or greater than 98%. In some embodiments, the viability of both the fresh and thawed product is greater than 80%, greater than 81%, greater than 82%, greater than 83%, greater than 84%, greater than 85%, greater than 86%, greater than 87%, greater than 88%, greater than 89%, or greater than 90%. In some embodiments, the viability of both the fresh and thawed product is greater than 86%.

In an embodiment, restimulated TILs can also be evaluated for cytokine release, using cytokine release assays. In some embodiments, TILs can be evaluated for interferon-γ (IFN-γ) secretion in response to stimulation either with OKT3 or co-culture with autologous tumor digest. For example, in embodiments employing OKT3 stimulation, TILs are washed extensively, and duplicate wells are prepared with $1\times10^5$ cells in 0.2 mL CM in 96-well flat-bottom plates precoated with 0.1 or 1.0 μg/mL of OKT3 diluted in phosphate-buffered saline. After overnight incubation, the supernatants are harvested and IFN-7 in the supernatant is measured by ELISA (Pierce/Endogen, Woburn, MA). For the co-culture assay, $1 \times 10^5$ TIL cells are placed into a 96-well plate with autologous tumor cells. (1:1 ratio). After a 24-hour incubation, supernatants are harvested and IFN-7 release can be quantified, for example by ELISA.

Flow cytometric analysis of cell surface biomarkers: TIL samples were aliquoted for flow cytometric analysis of cell surface markers see, for Example see Examples 7, 8, and 9.

In some embodiments, the TTLs are being evaluated for various regulatory markers. In some embodiments, the regulatory marker is selected from the group consisting of TCR α/β, CD56, CD27, CD28, CD57, CD45RA, CD45RO, CD25, CD127, CD95, IL-2R-, CCR7, CD62L, KLRG1, and CD122. In some embodiments, the regulatory marker is TCR α/β. In some embodiments, the regulatory marker is CD56. In some embodiments, the regulatory marker is CD27. In some embodiments, the regulatory marker is CD28. In some embodiments, the regulatory marker is CD57. In some embodiments, the regulatory marker is CD45RA. In some embodiments, the regulatory marker is CD45RO. In some embodiments, the regulatory marker is CD25. In some embodiments, the regulatory marker is CD127. In some embodiments, the regulatory marker is CD95. In some embodiments, the regulatory marker is IL-2R-. In some embodiments, the regulatory marker is CCR7. In some embodiments, the regulatory marker is CD62L. In some embodiments, the regulatory marker is KLRG1. In some embodiments, the regulatory marker is CD122.

In an embodiment, the expanded TTLs are analyzed for expression of numerous phenotype markers, including those described herein and in the Examples. In an embodiment, expression of one or more phenotypic markers is examined. In some embodiments, the marker is selected from the group consisting of TCRab (i.e., TCRα/β), CD57, CD28, CD4, CD27, CD56, CD8a, CD45RA, CD8a, CCR7, CD4, CD3, CD38, and HLA-DR. In some embodiments, the marker is selected from the group consisting of TCRab (i.e., TCRα/β), CD57, CD28, CD4, CD27, CD56, and CD8a. In an embodiment, the marker is selected from the group consisting of CD45RA, CD8a, CCR7, CD4, CD3, CD38, and HLA-DR. In some embodiments, expression of one, two, three, four, five, six, seven, eight, nine, ten, eleven, twelve, thirteen, or fourteen markers is examined. In some embodiments, the expression from one or more markers from each group is examined. In some embodiments, one or more of HLA-DR, CD38, and CD69 expression is maintained (i.e., does not exhibit a statistically significant difference) in fresh TILs as compared to thawed TILs. In some embodiments, the activation status of TILs is maintained in the thawed TILs.

In an embodiment, expression of one or more regulatory markers is measured. In some embodiments, the regulatory marker is selected from the group consisting of CD137, CD8a, Lag3, CD4, CD3, PD1, TIM-3, CD69, CD8a, TIGIT, CD4, CD3, KLRG1, and CD154. In some embodiments, the regulatory marker is selected from the group consisting of CD137, CD8a, Lag3, CD4, CD3, PD1, and TIM-3. In some embodiments, the regulatory marker is selected from the group consisting of CD69, CD8a, TIGIT, CD4, CD3, KLRG1, and CD154. In some embodiments, regulatory molecule expression is decreased in thawed TILs as compared to fresh TILs. In some embodiments, expression of regulatory molecules LAG-3 and TIM-3 is decreased in thawed TILs as compared to fresh TILs. In some embodiments, there is no significant difference in CD4, CD8, NK, TCRαβ expression. In some embodiments, there is no significant difference in CD4, CD8, NK, TCRαβ expression, and/or memory markers in fresh TILs as compared to thawed TILs.

In some embodiments the memory marker is selected from the group consisting of CCR7 and CD62L.

In some embodiments, the viability of the fresh TILs as compared to the thawed TILs is at least 70%, at least 75%, at least 80%, at least 85%, at least 90%, at least 95%, or at least 98%. In some embodiments, the viability of both the fresh and thawed TILs is greater than 70%, greater than 75%, greater than 80%, greater than 85%, greater than 90%, greater than 95%, or greater than 98%. In some embodiments, the viability of both the fresh and thawed product is greater than 80%, greater than 81%, greater than 82%, greater than 83%, greater than 84%, greater than 85%, greater than 86%, greater than 87%, greater than 88%, greater than 89%, or greater than 90%. In some embodiments, the viability of both the fresh and thawed product is greater than 86%.

In an embodiment, restimulated TILs can also be evaluated for cytokine release, using cytokine release assays. In some embodiments, TILs can be evaluated for interferon-7 (IFN-7) secretion in response to stimulation either with OKT3 or coculture with autologous tumor digest. For example, in embodiments employing OKT3 stimulation, TILs are washed extensively, and duplicate wells are prepared with $1 \times 10^5$ cells in 0.2 mL CM in 96-well flat-bottom plates precoated with 0.1 or 1.0 μg/mL of OKT3 diluted in phosphate-buffered saline. After overnight incubation, the supernatants are harvested and IFN-7 in the supernatant is measured by ELISA (Pierce/Endogen, Woburn, MA). For the coculture assay, $1 \times 10^5$ TIL cells are placed into a 96-well plate with autologous tumor cells. (1:1 ratio). After a 24-hour incubation, supernatants are harvested and IFN-7 release can be quantified, for example by ELISA.

In some embodiments, TILs that exhibit greater than 3000 pg/$10^6$ TILs to 300000 pg/$10^6$ TILs or more Granzyme B secretion are TILs produced by the expansion methods of the present invention, including for example FIG. 2A and/or FIG. 2B and/or FIG. 2C and/or FIG. 9. In some embodiments, TILS that exhibit greater than 3000 pg/$10^6$ TILs greater than 5000 pg/$10^6$ TILs, greater than 7000 pg/$10^6$ TILs, greater than 9000 pg/$10^6$ TILs, greater than 11000 pg/$10^6$ TILs, greater than 13000 pg/$10^6$ TILs, greater than 15000 pg/$10^6$ TILs, greater than 17000 pg/$10^6$ TILs, greater than 19000 pg/$10^6$ TILs, greater than 20000 pg/$10^6$ TILs, greater than 40000 pg/$10^6$ TILs, greater than 60000 pg/$10^6$ TILs, greater than 80000 pg/$10^6$ TILs, greater than 100000 pg/$10^6$ TILs, greater than 120000 pg/$10^6$ TILs, greater than 140000 pg/$10^6$ TILs, greater than 160000 pg/$10^6$ TILs, greater than 180000 pg/$10^6$ TILs, greater than 200000 pg/$10^6$ TILs, greater than 220000 pg/$10^6$ TILs, greater than 240000 pg/$10^6$ TILs, greater than 260000 pg/106 TILs, greater than 280000 pg/$10^6$ TILs, greater than 300000 pg/$10^6$ TILs or more Granzyme B secretion are TILs produced by the expansion methods of the present invention, including for example FIG. 2A and/or FIG. 2B and/or FIG. 2C and/or FIG. 9. In some embodiments, TILs that exhibit greater than 3000 pg/$10^6$ TILs Granzyme B secretion are TILs produced by the expansion methods of the present invention, including for example FIG. 2A and/or FIG. 2B and/or FIG. 2C and/or FIG. 9. In some embodiments, TILs that exhibit greater than 5000 pg/$10^6$ TILs Granzyme B secretion are TILs produced by the expansion methods of the present invention, including for example FIG. 2A and/or FIG. 2B and/or FIG. 2C and/or FIG. 9. In some embodiments, TILs that exhibit greater than 7000 pg/10⁶ TILs Granzyme B secretion are TILs produced by the expansion methods of the present invention, including for example FIG. 2A and/or FIG. 2B and/or FIG. 2C and/or FIG. 9. In some embodiments, TILs that exhibit greater than 9000 pg/10⁶ TILs Granzyme B secretion are TILs produced by the expansion methods of the present invention, including for example FIG. 2A and/or FIG. 2B and/or FIG. 2C and/or FIG. 9. In some embodiments, TILs that exhibit greater than 11000 pg/106 TILs Granzyme B secretion are TILs produced by the expansion methods of the present invention, including for example FIG. 2A and/or FIG. 2B and/or FIG. 2C and/or FIG. 9. In some embodiments, TILs that exhibit greater than 13000 pg/10⁶ TILs Granzyme B secretion are TILs produced by the expansion methods of the present invention, including for example FIG. 2A and/or FIG. 2B and/or FIG. 2C and/or FIG. 9. In some embodiments, TILs that exhibit greater than 15000 pg/10⁶ TILs Granzyme B secretion are TILs produced by the expansion methods of the present invention, including for example FIG. 2A and/or FIG. 2B and/or FIG. 2C and/or FIG. 9. In some embodiments, TILs that exhibit greater than 17000 pg/10⁶ TILs Granzyme B secretion are TILs produced by the expansion methods of the present invention, including for example FIG. 2A and/or FIG. 2B and/or FIG. 2C and/or FIG. 9. In some embodiments, TILs that exhibit greater than 19000 pg/10⁶ TILs Granzyme B secretion are TILs produced by the expansion methods of the present invention, including for example FIG. 2A and/or FIG. 2B and/or FIG. 2C and/or FIG. 9. In some embodiments, TILs that exhibit greater than 20000 pg/10⁶ TILs Granzyme B secretion are TILs produced by the expansion methods of the present invention, including for example FIG. 2A and/or FIG. 2B and/or FIG. 2C and/or FIG. 9. In some embodiments, TILs that exhibit greater than 40000 pg/10⁶ TILs Granzyme B secretion are TILs produced by the expansion methods of the present invention, including for example FIG. 2A and/or FIG. 2B and/or FIG. 2C and/or FIG. 9. In some embodiments, TILs that exhibit greater than 60000 pg/10⁶ TILs Granzyme B secretion are TILs produced by the expansion methods of the present invention, including for example FIG. 2A and/or FIG. 2B and/or FIG. 2C and/or FIG. 9. In some embodiments, TILs that exhibit greater than 80000 pg/10⁶ TILs Granzyme B secretion are TILs produced by the expansion methods of the present invention, including for example FIG. 2A and/or FIG. 2B and/or FIG. 2C and/or FIG. 9. In some embodiments, TILs that exhibit greater than 100000 pg/10⁶ TILs Granzyme B secretion are TILs produced by the expansion methods of the present invention, including for example FIG. 2A and/or FIG. 2B and/or FIG. 2C and/or FIG. 9. In some embodiments, TILs that exhibit greater than 120000 pg/10⁶ TILs Granzyme B secretion are TILs produced by the expansion methods of the present invention, including for example FIG. 2A and/or FIG. 2B and/or FIG. 2C and/or FIG. 9. In some embodiments, TILs that exhibit greater than 140000 pg/10⁶ TILs Granzyme B secretion are TILs produced by the expansion methods of the present invention, including for example FIG. 2A and/or FIG. 2B and/or FIG. 2C and/or FIG. 9. In some embodiments, TILs that exhibit greater than 160000 pg/10⁶ TILs Granzyme B secretion are TILs produced by the expansion methods of the present invention, including for example FIG. 2A and/or FIG. 2B and/or FIG. 2C and/or FIG. 9. In some embodiments, TILs that exhibit greater than 180000 pg/10⁶ TILs Granzyme B secretion are TILs produced by the expansion methods of the present invention, including for example FIG. 2A and/or FIG. 2B and/or FIG. 2C and/or FIG. 9. In some embodiments, TILs that exhibit greater than 200000 pg/10⁶ TILs Granzyme B secretion are TILs produced by the expansion methods of the present invention, including for example FIG. 2A and/or FIG. 2B and/or FIG. 2C and/or FIG. 9. In some embodiments, TILs that exhibit greater than 220000 pg/10⁶ TILs Granzyme B secretion are TILs produced by the expansion methods of the present invention, including for example FIG. 2A and/or FIG. 2B and/or FIG. 2C and/or FIG. 9. In some embodiments, TILs that exhibit greater than 240000 pg/10⁶ TILs Granzyme B secretion are TILs produced by the expansion methods of the present invention, including for example FIG. 2A and/or FIG. 2B and/or FIG. 2C and/or FIG. 9. In some embodiments, TILs that exhibit greater than 260000 pg/10⁶ TILs Granzyme B secretion are TILs produced by the expansion methods of the present invention, including for example FIG. 2A and/or FIG. 2B and/or FIG. 2C and/or FIG. 9. In some embodiments, TILs that exhibit greater than 280000 pg/10⁶ TILs Granzyme B secretion are TILs produced by the expansion methods of the present invention, including for example FIG. 2A and/or FIG. 2B and/or FIG. 2C and/or FIG. 9. In some embodiments, TILs that exhibit greater than 300000 pg/10⁶ TILs Granzyme B secretion are TILs produced by the expansion methods of the present invention, including for example FIG. 2A and/or FIG. 2B and/or FIG. 2C and/or FIG. 9. In some embodiments, TILs that exhibit greater than 3000 pg/10⁶ TILs to 300000 pg/10⁶ TILs or more Granzyme B secretion are TILs produced by the expansion methods of the present invention, including for example FIG. 2A and/or FIG. 2B and/or FIG. 2C and/or FIG. 9. In some embodiments, TILS that exhibit greater than 3000 pg/10⁶ TILs greater than 5000 pg/10⁶ TILs, greater than 7000 pg/10⁶ TILs, greater than 9000 pg/10⁶ TILs, greater than 11000 pg/10⁶ TILs, greater than 13000 pg/10⁶ TILs, greater than 15000 pg/10⁶ TILs, greater than 17000 pg/10⁶ TILs, greater than 19000 pg/10⁶ TILs, greater than 20000 pg/10⁶ TILs, greater than 40000 pg/10⁶ TILs, greater than 60000 pg/10⁶ TILs, greater than 80000 pg/10⁶ TILs, greater than 100000 pg/10⁶ TILs, greater than 120000 pg/106 TILs, greater than 140000 pg/10⁶ TILs, greater than 160000 pg/10⁶ TILs, greater than 180000 pg/10⁶ TILs, greater than 200000 pg/10⁶ TILs, greater than 220000 pg/10⁶ TILs, greater than 240000 pg/10⁶ TILs, greater than 260000 pg/10⁶ TILs, greater than 280000 pg/10⁶ TILs, greater than 300000 pg/10⁶ TILs or more Granzyme B secretion are TILs produced by the expansion methods of the present invention, including for example FIG. 2A and/or FIG. 2B and/or FIG. 2C and/or FIG. 9. In some embodiments, TILs that exhibit greater than 3000 pg/106 TILs Granzyme B secretion are TILs produced by the expansion methods of the present invention, including for example FIG. 2A and/or FIG. 2B and/or FIG. 2C and/or FIG. 9. In some embodiments, TILs that exhibit greater than 5000 pg/10⁶ TILs Granzyme B secretion are TILs produced by the expansion methods of the present invention, including for example FIG. 2A and/or FIG. 2B and/or FIG. 2C and/or FIG. 9. In some embodiments, TILs that exhibit greater than 7000 pg/10⁶ TILs Granzyme B secretion are TILs produced by the expansion methods of the present invention, including for example FIG. 2A and/or FIG. 2B and/or FIG. 2C and/or FIG. 9. In some embodiments, TILs that exhibit greater than 9000 pg/106 TILs Granzyme B secretion are TILs produced by the expansion methods of the present invention, including for example FIG. 2A and/or FIG. 2B and/or FIG. 2C and/or FIG. 9. In some embodiments, TILs that exhibit greater than 11000 pg/10⁶ TILs Granzyme B secretion are TILs produced by the expansion methods of the present invention, including for example FIG. 2A and/or FIG. 2B and/or FIG. 2C and/or FIG. 9. In some embodiments, TILs that exhibit greater than 13000 pg/10$^6$ TILs Granzyme B secretion are TILs produced by the expansion methods of the present invention, including for example FIG. 2A and/or FIG. 2B and/or FIG. 2C and/or FIG. 9. In some embodiments, TILs that exhibit greater than 15000 pg/10$^6$ TILs Granzyme B secretion are TILs produced by the expansion methods of the present invention, including for example FIG. 2A and/or FIG. 2B and/or FIG. 2C and/or FIG. 9. In some embodiments, TILs that exhibit greater than 17000 pg/10$^6$ TILs Granzyme B secretion are TILs produced by the expansion methods of the present invention, including for example FIG. 2A and/or FIG. 2B and/or FIG. 2C and/or FIG. 9. In some embodiments, TILs that exhibit greater than 19000 pg/10$^6$ TILs Granzyme B secretion are TILs produced by the expansion methods of the present invention, including for example FIG. 2A and/or FIG. 2B and/or FIG. 2C and/or FIG. 9. In some embodiments, TILs that exhibit greater than 20000 pg/10$^6$ TILs Granzyme B secretion are TILs produced by the expansion methods of the present invention, including for example FIG. 2A and/or FIG. 2B and/or FIG. 2C and/or FIG. 9. In some embodiments, TILs that exhibit greater than 40000 pg/10$^6$ TILs Granzyme B secretion are TILs produced by the expansion methods of the present invention, including for example FIG. 2A and/or FIG. 2B and/or FIG. 2C and/or FIG. 9. In some embodiments, TILs that exhibit greater than 60000 pg/10$^6$ TILs Granzyme B secretion are TILs produced by the expansion methods of the present invention, including for example FIG. 2A and/or FIG. 2B and/or FIG. 2C and/or FIG. 9. In some embodiments, TILs that exhibit greater than 80000 pg/10$^6$ TILs Granzyme B secretion are TILs produced by the expansion methods of the present invention, including for example FIG. 2A and/or FIG. 2B and/or FIG. 2C and/or FIG. 9. In some embodiments, TILs that exhibit greater than 100000 pg/10$^6$ TILs Granzyme B secretion are TILs produced by the expansion methods of the present invention, including for example FIG. 2A and/or FIG. 2B and/or FIG. 2C and/or FIG. 9. In some embodiments, TILs that exhibit greater than 120000 pg/10$^6$ TILs Granzyme B secretion are TILs produced by the expansion methods of the present invention, including for example FIG. 2A and/or FIG. 2B and/or FIG. 2C and/or FIG. 9. In some embodiments, TILs that exhibit greater than 140000 pg/10$^6$ TILs Granzyme B secretion are TILs produced by the expansion methods of the present invention, including for example FIG. 2A and/or FIG. 2B and/or FIG. 2C and/or FIG. 9. In some embodiments, TILs that exhibit greater than 160000 pg/10$^6$ TILs Granzyme B secretion are TILs produced by the expansion methods of the present invention, including for example FIG. 2A and/or FIG. 2B and/or FIG. 2C and/or FIG. 9. In some embodiments, TILs that exhibit greater than 180000 pg/10$^6$ TILs Granzyme B secretion are TILs produced by the expansion methods of the present invention, including for example FIG. 2A and/or FIG. 2B and/or FIG. 2C and/or FIG. 9. In some embodiments, TILs that exhibit greater than 200000 pg/10$^6$ TILs Granzyme B secretion are TILs produced by the expansion methods of the present invention, including for example FIG. 2A and/or FIG. 2B and/or FIG. 2C and/or FIG. 9. In some embodiments, TILs that exhibit greater than 220000 pg/10$^6$ TILs Granzyme B secretion are TILs produced by the expansion methods of the present invention, including for example FIG. 2A and/or FIG. 2B and/or FIG. 2C and/or FIG. 9. In some embodiments, TILs that exhibit greater than 240000 pg/10$^6$ TILs Granzyme B secretion are TILs produced by the expansion methods of the present invention, including for example FIG. 2A and/or FIG. 2B and/or FIG. 2C and/or FIG. 9. In some embodiments, TILs that exhibit greater than 260000 pg/10$^6$ TILs Granzyme B secretion are TILs produced by the expansion methods of the present invention, including for example FIG. 2A and/or FIG. 2B and/or FIG. 2C and/or FIG. 9. In some embodiments, TILs that exhibit greater than 280000 pg/10$^6$ TILs Granzyme B secretion are TILs produced by the expansion methods of the present invention, including for example FIG. 2A and/or FIG. 2B and/or FIG. 2C and/or FIG. 9. In some embodiments, TILs that exhibit greater than 300000 pg/10$^6$ TILs Granzyme B secretion are TILs produced by the expansion methods of the present invention, including for example FIG. 2A and/or FIG. 2B and/or FIG. 2C and/or FIG. 9.

In some embodiments, TILs that exhibit greater than 1000 pg/ml to 300000 pg/ml or more Granzyme B secretion are TTLs produced by the expansion methods of the present invention, including for example FIG. 2A and/or FIG. 2B and/or FIG. 2C and/or FIG. 9. In some embodiments, TILs that exhibit greater than 1000 pg/ml, greater than 2000 pg/ml, greater than 3000 pg/ml, greater than 4000 pg/ml, greater than 5000 pg/ml, greater than 6000 pg/ml, greater than 7000 pg/ml, greater than 8000 pg/ml, greater than 9000 pg/ml, greater than 10000 pg/ml, greater than 20000 pg/ml, greater than 30000 pg/ml, greater than 40000 pg/ml, greater than 50000 pg/ml, greater than 60000 pg/ml, greater than 70000 pg/ml, greater than 80000 pg/ml, greater than 90000 pg/ml, greater than 100000 pg/ml or more Granzyme B secretion are TILs produced by the expansion methods of the present invention, including for example FIG. 2A and/or FIG. 2B and/or FIG. 2C and/or FIG. 9. In some embodiments, TILS that exhibit greater than 1000 pg/ml Granzyme B are TILs produced by the expansion methods of the present invention, including for example FIG. 2A and/or FIG. 2B and/or FIG. 2C and/or FIG. 9. In some embodiments, TILs that exhibit greater than 2000 pg/ml Granzyme B are TILs produced by the expansion methods of the present invention, including for example FIG. 2A and/or FIG. 2B and/or FIG. 2C and/or FIG. 9. In some embodiments, TILs that exhibit greater than 3000 pg/ml Granzyme B are TILs produced by the expansion methods of the present invention, including for example FIG. 2A and/or FIG. 2B and/or FIG. 2C and/or FIG. 9. In some embodiments, TILs that exhibit greater than 4000 pg/ml Granzyme B are TILs produced by the expansion methods of the present invention, including for example FIG. 2A and/or FIG. 2B and/or FIG. 2C and/or FIG. 9. In some embodiments, TILs that exhibit greater than 5000 pg/ml Granzyme B are TILs produced by the expansion methods of the present invention, including for example FIG. 2A and/or FIG. 2B and/or FIG. 2C and/or FIG. 9. In some embodiments, TILs that exhibit greater than 6000 pg/ml Granzyme B are TILs produced by the expansion methods of the present invention, including for example FIG. 2A and/or FIG. 2B and/or FIG. 2C and/or FIG. 9. In some embodiments, TILs that exhibit greater than 7000 pg/ml Granzyme B are TILs produced by the expansion methods of the present invention, including for example FIG. 2A and/or FIG. 2B and/or FIG. 2C and/or FIG. 9. In some embodiments, TILs that exhibit greater than 8000 pg/ml Granzyme B are TILs produced by the expansion methods of the present invention, including for example FIG. 2B and/or FIG. 2C and/or FIG. 9. In some embodiments, TILs that exhibit greater than 9000 pg/ml Granzyme B are TILs produced by the expansion methods of the present invention, including for example FIG. 2A and/or FIG. 2B and/or FIG. 2C and/or FIG. 9. In some embodiments, TILs that exhibit greater than 10000 pg/ml Granzyme B are TILs produced by the expansion methods of the present invention, including for example FIG. 2A and/or FIG. 2B and/or FIG. 2C and/or FIG. 9. In some embodiments, TILS that exhibit greater than 20000 pg/ml Granzyme B are TILs produced by the expansion methods of the present invention, including for example FIG. 2A and/or FIG. 2B and/or FIG. 2C and/or FIG. 9. In some embodiments, TILs that exhibit greater than 30000 pg/ml Granzyme B are TILs produced by the expansion methods of the present invention, including for example FIG. 2A and/or FIG. 2B and/or FIG. 2C and/or FIG. 9. In some embodiments, TILs that exhibit greater than 40000 pg/ml Granzyme B are TILs produced by the expansion methods of the present invention, including for example FIG. 2A and/or FIG. 2B and/or FIG. 2C and/or FIG. 9. In some embodiments, TILs that exhibit greater than 50000 pg/ml Granzyme B are TILs produced by the expansion methods of the present invention, including for example FIG. 2A and/or FIG. 2B and/or FIG. 2C and/or FIG. 9. In some embodiments, TILs that exhibit greater than 60000 pg/ml Granzyme B are TILs produced by the expansion methods of the present invention, including for example FIG. 2A and/or FIG. 2B and/or FIG. 2C and/or FIG. 9. In some embodiments, TILs that exhibit greater than 70000 pg/ml Granzyme B are TILs produced by the expansion methods of the present invention, including for example FIG. 2A and/or FIG. 2B and/or FIG. 2C and/or FIG. 9. In some embodiments, TILs that exhibit greater than 80000 pg/ml Granzyme B are TILs produced by the expansion methods of the present invention, including for example FIG. 2A and/or FIG. 2B and/or FIG. 2C and/or FIG. 9. In some embodiments, TILs that exhibit greater than 90000 pg/ml Granzyme B are TILs produced by the expansion methods of the present invention, including for example FIG. 2A and/or FIG. 2B and/or FIG. 2C and/or FIG. 9. In some embodiments, TILs that exhibit greater than 100000 pg/ml Granzyme B are TILs produced by the expansion methods of the present invention, including for example FIG. 2A and/or FIG. 2B and/or FIG. 2C and/or FIG. 9. In some embodiments, TILs that exhibit greater than 120000 pg/ml Granzyme B secretion are TILs produced by the expansion methods of the present invention, including for example FIG. 2A and/or FIG. 2B and/or FIG. 2C and/or FIG. 9. In some embodiments, TILs that exhibit greater than 140000 pg/ml Granzyme B are TILs Granzyme B secretion are TILs produced by the expansion methods of the present invention, including for example FIG. 2A and/or FIG. 2B and/or FIG. 2C and/or FIG. 9. In some embodiments, TILs that exhibit greater than 160000 pg/ml Granzyme B secretion are TILs produced by the expansion methods of the present invention, including for example FIG. 2A and/or FIG. 2B and/or FIG. 2C and/or FIG. 9. In some embodiments, TILs that exhibit greater than 180000 pg/ml Granzyme B secretion are TILs produced by the expansion methods of the present invention, including for example FIG. 2A and/or FIG. 2B and/or FIG. 2C and/or FIG. 9. In some embodiments, TILs that exhibit greater than 200000 pg/ml Granzyme B secretion are TILs produced by the expansion methods of the present invention, including for example FIG. 2A and/or FIG. 2B and/or FIG. 2C and/or FIG. 9. In some embodiments, TILs that exhibit greater than 220000 pg/ml Granzyme B secretion are TTLs produced by the expansion methods of the present invention, including for example FIG. 2A and/or FIG. 2B and/or FIG. 2C and/or FIG. 9. In some embodiments, TILs that exhibit greater than 240000 pg/ml Granzyme B secretion are TILs produced by the expansion methods of the present invention, including for example FIG. 2A and/or FIG. 2B and/or FIG. 2C and/or FIG. 9. In some embodiments, TILs that exhibit greater than 260000 pg/ml Granzyme B secretion are TILs produced by the expansion methods of the present invention, including for example FIG. 2A and/or FIG. 2B and/or FIG. 2C and/or FIG. 9. In some embodiments, TILs that exhibit greater than 280000 pg/ml Granzyme B secretion are TILs produced by the expansion methods of the present invention, including for example FIG. 2A and/or FIG. 2B and/or FIG. 2C and/or FIG. 9. In some embodiments, TILs that exhibit greater than 300000 pg/ml Granzyme B secretion are TILs produced by the expansion methods of the present invention, including for example FIG. 2A and/or FIG. 2B and/or FIG. 2C and/or FIG. 9.

In some embodiments, the expansion methods of the present invention produce an expanded population of TILs that exhibits increased Granzyme B secretion in vitro including for example TILs as provided in FIG. 2A and/or FIG. 2B and/or FIG. 2C and/or FIG. 9, as compared to non-expanded population of TILs. In some embodiments, Granzyme B secretion of the expanded population of TILs of the present invention is increased by at least one-fold to fifty-fold or more as compared to non-expanded population of TILs. In some embodiments, IFN-γ secretion is increased by at least one-fold, at least two-fold, at least three-fold, at least four-fold, at least five-fold, at least six-fold, at least seven-fold, at least eight-fold, at least nine-fold, at least ten-fold, at least twenty-fold, at least thirty-fold, at least forty-fold, at least fifty-fold or more as compared to non-expanded population of TILs. In some embodiments, Granzyme B secretion of the expanded population of TILs of the present invention is increased by at least one-fold as compared to non-expanded population of TILs. In some embodiments, Granzyme B secretion of the expanded population of TILs of the present invention is increased by at least two-fold as compared to non-expanded population of TILs. In some embodiments, Granzyme B secretion of the expanded population of TILs of the present invention is increased by at least three-fold as compared to non-expanded population of TILs. In some embodiments, Granzyme B secretion of the expanded population of TILs of the present invention is increased by at least four-fold as compared to non-expanded population of TILs. In some embodiments, Granzyme B secretion of the expanded population of TILs of the present invention is increased by at least five-fold as compared to non-expanded population of TILs. In some embodiments, Granzyme B secretion of the expanded population of TILs of the present invention is increased by at least six-fold as compared to non-expanded population of TILs. In some embodiments, Granzyme B secretion of the expanded population of TILs of the present invention is increased by at least seven-fold as compared to non-expanded population of TILs. In some embodiments, Granzyme B secretion of the expanded population of TILs of the present invention is increased by at least eight-fold as compared to non-expanded population of TILs. In some embodiments, Granzyme B secretion of the expanded population of TILs of the present invention is increased by at least nine-fold as compared to non-expanded population of TILs. In some embodiments, Granzyme B secretion of the expanded population of TILs of the present invention is increased by at least ten-fold as compared to non-expanded population of TILs. In some embodiments, Granzyme B secretion of the expanded population of TILs of the present invention is increased by at least twenty-fold as compared to non-expanded population of TILs. In some embodiments, Granzyme B secretion of the expanded population of TILs of the present invention is increased by at least thirty-fold as compared to non-expanded population of TILs. In some embodiments, Granzyme B secretion of the expanded population of TILs of the present invention is increased by at least forty-fold as compared to non-expanded population of TILs. In some embodiments, Granzyme B secretion of the expanded population of TILs of the present invention is increased by at least fifty-fold as compared to non-expanded population of TILs.

In some embodiments, the phenotypic characterization is examined after cryopreservation.

J. Metabolic Health of Expanded TILs

The restimulated TILs are characterized by significant enhancement of basal glycolysis as compared to either freshly harvested TILs and/or post-thawed TILs. In an embodiment, no selection of the first population of TILs, second population of TILs, third population of TILs, harvested TIL population, and/or the therapeutic TIL population based on CD8 expression is performed during any of steps, including those discussed above or as provided for example in FIG. 9. In some embodiments, no selection of the first population of TILs based on CD8 expression is performed. In some embodiments, no selection of the second population of TILs based on CD8 expression is performed. In some embodiments, no selection of the third population of TILs based on CD8 expression is performed. In some embodiments, no selection of the harvested population of TILs based on CD8 expression is performed. In some embodiments, no selection of the therapeutic population of TILs based on CD8 expression is performed.

In an embodiment, no selection of the first population of TILs, second population of TILs, third population of TILs, or harvested TIL population based on CD8 expression is performed during any of steps (a) to (f) of the method for expanding tumor infiltrating lymphocytes (TILs) into a therapeutic population of TILs comprising:

(a) obtaining a first population of TILs from a tumor resected from a patient by processing a tumor sample obtained from the patient into multiple tumor fragments;

(b) adding the tumor fragments into a closed system;

(c) performing a first expansion by culturing the first population of TILs in a cell culture medium comprising IL-2 to produce a second population of TILs, wherein the first expansion is performed in a closed container providing a first gas-permeable surface area, wherein the first expansion is performed for about 3-14 days to obtain the second population of TILs, wherein the second population of TILs is at least 50-fold greater in number than the first population of TILs, and wherein the transition from step (b) to step (c) occurs without opening the system;

(d) performing a second expansion by supplementing the cell culture medium of the second population of TILs with additional IL-2, OKT-3, and antigen presenting cells (APCs), to produce a third population of TILs, wherein the second expansion is performed for about 7-14 days to obtain the third population of TILs, wherein the third population of TILs is a therapeutic population of TILs which comprises an increased sub-population of effector T-cells and/or central memory T-cells relative to the second population of TILs, wherein the second expansion is performed in a closed container providing a second gas-permeable surface area, and wherein the transition from step (c) to step (d) occurs without opening the system;

(e) harvesting the therapeutic population of TILs obtained from step (d), wherein the transition from step (d) to step (e) occurs without opening the system; and (f) transferring the harvested TIL population from step (e) to an infusion bag, wherein the transfer from step (e) to (f) occurs without opening the system.

In an embodiment, no selection of the first population of TILs, second population of TILs, third population of TILs, or harvested TIL population based on CD8 expression is performed during any of steps (a) to (h) of the method for treating a subject with cancer, the method comprising administering expanded tumor infiltrating lymphocytes (TILs) comprising:

(a) obtaining a first population of TILs from a tumor resected from a subject by processing a tumor sample obtained from the patient into multiple tumor fragments;

(b) adding the tumor fragments into a closed system;

(c) performing a first expansion by culturing the first population of TILs in a cell culture medium comprising IL-2 to produce a second population of TILs, wherein the first expansion is performed in a closed container providing a first gas-permeable surface area, wherein the first expansion is performed for about 3-14 days to obtain the second population of TILs, wherein the second population of TILs is at least 50-fold greater in number than the first population of TILs, and wherein the transition from step (b) to step (c) occurs without opening the system;

(d) performing a second expansion by supplementing the cell culture medium of the second population of TILs with additional IL-2, OKT-3, and antigen presenting cells (APCs), to produce a third population of TILs, wherein the second expansion is performed for about 7-14 days to obtain the third population of TILs, wherein the third population of TILs is a therapeutic population of TILs which comprises an increased sub-population of effector T-cells and/or central memory T-cells relative to the second population of TILs, wherein the second expansion is performed in a closed container providing a second gas-permeable surface area, and wherein the transition from step (c) to step (d) occurs without opening the system;

(e) harvesting the therapeutic population of TILs obtained from step (d), wherein the transition from step (d) to step (e) occurs without opening the system; and (f) transferring the harvested TIL population from step (e) to an infusion bag, wherein the transfer from step (e) to (f) occurs without opening the system;

(g) optionally cryopreserving the infusion bag comprising the harvested TIL population from step (f) using a cryopreservation process; and (h) administering a therapeutically effective dosage of the third population of TILs from the infusion bag in step (g) to the patient.

The TILs prepared by the methods described herein are characterized by significant enhancement of basal glycolysis as compared to, for example, freshly harvested TILs and/or TILs prepared using other methods than those provide herein including for example, methods other than those embodied in FIG. 9. In an embodiment, no selection of the first population of TILs, second population of TILs, third population of TILs, harvested TIL population, and/or the therapeutic TIL population based on CD8 expression is performed during any of steps, including those discussed above or as provided for example in FIG. 9. In some embodiments, no selection of the first population of TILs based on CD8 expression is performed. In some embodiments, no selection of the second population of TILs based on CD8 expression is performed. In some embodiments, no selection of the third population of TILs based on CD8 expression is performed. In some embodiments, no selection of the harvested population of TILs based on CD8 expression is performed. In some embodiments, no selection of the therapeutic population of TILs based on CD8 expression is performed. In an embodiment, no selection of the first population of TILs, second population of TILs, third population of TILs, or harvested TIL population based on CD8 expression is performed during any of steps (a) to (h).

Spare respiratory capacity (SRC) and glycolytic reserve can be evaluated for TILs expanded with different methods of the present disclosure. The Seahorse XF Cell Mito Stress Test measures mitochondrial function by directly measuring the oxygen consumption rate (OCR) of cells, using modulators of respiration that target components of the electron transport chain in the mitochondria. The test compounds (oligomycin, FCCP, and a mix of rotenone and antimycin A, described below) are serially injected to measure ATP production, maximal respiration, and non-mitochondrial respiration, respectively. Proton leak and spare respiratory capacity are then calculated using these parameters and basal respiration. Each modulator targets a specific component of the electron transport chain. Oligomycin inhibits ATP synthase (complex V) and the decrease in OCR following injection of oligomycin correlates to the mitochondrial respiration associated with cellular ATP production. Carbonyl cyanide-4 (trifluoromethoxy) phenylhydrazone (FCCP) is an uncoupling agent that collapses the proton gradient and disrupts the mitochondrial membrane potential. As a result, electron flow through the electron transport chain is uninhibited and oxygen is maximally consumed by complex IV. The FCCP-stimulated OCR can then be used to calculate spare respiratory capacity, defined as the difference between maximal respiration and basal respiration. Spare respiratory capacity (SRC) is a measure of the ability of the cell to respond to increased energy demand. The third injection is a mix of rotenone, a complex I inhibitor, and antimycin A, a complex III inhibitor. This combination shuts down mitochondrial respiration and enables the calculation of nonmitochondrial respiration driven by processes outside the mitochondria. In some embodiments, the comparison is to, for example, freshly harvested TILs and/or TILs prepared using other methods than those provide herein including for example, methods other than those embodied in FIG. 9.

In some embodiments, the metabolic assay is basal respiration. In general, second expansion TILs have a basal respiration rate that is at least 50%, at least 55%, at least 60%, at least 65%, at least 70%, at least 75%, at least 80%, at least 85%, at least 90%, at least 95%, at least 97%, at least 98%, or at least 99% of the basal respiration rate of freshly harvested TILs and/or TILs prepared using other methods than those provide herein including for example, methods other than those embodied in FIG. 9. In some embodiments, the basal respiration rate is from about 50% to about 99% of the basal respiration rate of freshly harvested TILs and/or TILs prepared using other methods than those provide herein including for example, methods other than those embodied in FIG. 9. In some embodiments, the basal respiration rate is from about 60% to about 99% of the basal respiration rate of freshly harvested TILs and/or TILs prepared using other methods than those provide herein including for example, methods other than those embodied in FIG. 9. In some embodiments, the basal respiration rate is from about 70% to about 99% of the basal respiration rate of freshly harvested TILs and/or TILs prepared using other methods than those provide herein including for example, methods other than those embodied in FIG. 9. In some embodiments, the basal respiration rate is from about 80% to about 99% of the basal respiration rate of freshly harvested TILs and/or TILs prepared using other methods than those provide herein including for example, methods other than those embodied in FIG. 9. In some embodiments, the basal respiration rate is from about 90% to about 99% of the basal respiration rate of freshly harvested TILs and/or TILs prepared using other methods than those provide herein including for example, methods other than those embodied in FIG. 9. In some embodiments, the basal respiration rate is from about 95% to about 99% of the basal respiration rate of freshly harvested TILs and/or TILs prepared using other methods than those provide herein including for example, methods other than those embodied in FIG. 9. In some embodiments, the second expansion TILs or second additional expansion TILs (such as, for example, those described in Step D of FIG. 9, including TILs referred to as reREP TILs) have a basal respiration rate that is not statistically significantly different than the basal respiration rate of freshly harvested TILs and/or TILs prepared using other methods than those provide herein including for example, methods other than those embodied in FIG. 9. In some embodiments, the comparison is to, for example, freshly harvested TILs and/or TILs prepared using other methods than those provide herein including for example, methods other than those embodied in FIG. 9.

In some embodiments, the metabolic assay is spare respiratory capacity. In general, the second expansion TILs or second additional expansion TILs (such as, for example, those described in Step D of FIG. 9, including TILs referred to as reREP TILs) have a spare respiratory capacity that is at least is at least 50%, at least 55%, at least 60%, at least 65%, at least 70%, at least 75%, at least 80%, at least 85%, at least 90%, at least 95%, at least 97%, at least 98%, or at least 99% of the basal respiration rate of freshly harvested TILs and/or TILs prepared using other methods than those provide herein including for example, methods other than those embodied in FIG. 9. In some embodiments, the spare respiratory capacity is from about 50% to about 99% of the basal respiration rate of freshly harvested TILs. In some embodiments, the spare respiratory capacity is from about 50% to about 99% of the basal respiration rate of freshly harvested TILs and/or TILs prepared using other methods than those provide herein including for example, methods other than those embodied in FIG. 9. In some embodiments, the spare respiratory capacity is from about 60% to about 99% of the basal respiration rate of freshly harvested TILs and/or TILs prepared using other methods than those provide herein including for example, methods other than those embodied in FIG. 9. In some embodiments, the spare respiratory capacity is from about 70% to about 99% of the basal respiration rate of freshly harvested TILs and/or TILs prepared using other methods than those provide herein including for example, methods other than those embodied in FIG. 9. In some embodiments, the spare respiratory capacity is from about 80% to about 99% of the basal respiration rate of freshly harvested TILs. In some embodiments, the spare respiratory capacity is from about 90% to about 99% of the basal respiration rate of freshly harvested TILs and/or TILs prepared using other methods than those provide herein including for example, methods other than those embodied in FIG. 9. In some embodiments, the spare respiratory capacity is from about 95% to about 99% of the basal respiration rate of freshly harvested TILs and/or TILs prepared using other methods than those provide herein including for example, methods other than those embodied in FIG. 9. In some embodiments, the second expansion TILs or second additional expansion TILs (such as, for example, those described in Step D of FIG. 9, including TILs referred to as reREP TILs) have a spare respiratory capacity that is not statistically significantly different than the basal respiration rate of freshly harvested TILs and/or TILs prepared using other methods than those provide herein including for example, methods other than those embodied in FIG. 9.

In general, second expansion TILs or second additional expansion TILs (such as, for example, those described in Step D of FIG. 9, including TILs referred to as reREP TILs) have a spare respiratory capacity that is at least is at least 50%, at least 55%, at least 60%, at least 65%, at least 70%, at least 75%, at least 80%, at least 85%, at least 90%, at least 95%, at least 97%, at least 98%, or at least 99% of the basal respiration rate of freshly harvested TILs and/or TILs prepared using other methods than those provide herein including for example, methods other than those embodied in FIG. 9. In some embodiments, the metabolic assay measured is glycolytic reserve. In some embodiments, the metabolic assay is spare respiratory capacity. To measure cellular (respiratory) metabolism cells were treated with inhibitors of mitochondrial respiration and glycolysis to determine a metabolic profile for the TIL consisting of the following measures: baseline oxidative phosphorylation (as measured by OCR), spare respiratory capacity, baseline glycolytic activity (as measured by ECAR), and glycolytic reserve. Metabolic profiles were performed using the Seahorse Combination Mitochondrial/Glycolysis Stress Test Assay (including the kit commercially available from Agilent®), which allows for determining a cells' capacity to perform glycolysis upon blockage of mitochondrial ATP production. In some embodiments, cells are starved of glucose, then glucose is injected, followed by a stress agent. In some embodiments, the stress agent is selected from the group consisting of oligomycin, FCCP, rotenone, antimycin A and/or 2-deoxyglucose (2-DG), as well as combinations thereof. In some embodiments, oligomycin is added at 10 mM. In some embodiments, FCCP is added at 10 mM. In some embodiments, rotenone is added at 2.5 mM. In some embodiments, antimycin A is added at 2.5 mM. In some embodiments, 2-deoxyglucose (2-DG) is added at 500 mM. In some embodiments, glycolytic capacity, glycolytic reserve, and/or non-glycolytic acidification are measured. In general, TTLs have a glycolytic reserve that is at least 50%, at least 55%, at least 60%, at least 65%, at least 70%, at least 75%, at least 80%, at least 85%, at least 90%, at least 95%, at least 97%, at least 98%, or at least 99% of the basal respiration rate of freshly harvested TILs and/or TILs prepared using other methods than those provide herein including for example, methods other than those embodied in FIG. 9. In some embodiments, the glycolytic reserve is from about 50% to about 99% of the basal respiration rate of freshly harvested TILs and/or TILs prepared using other methods than those provide herein including for example, methods other than those embodied in FIG. 9. In some embodiments, the glycolytic reserve is from about 60% to about 99% of the basal respiration rate of freshly harvested TILs and/or TILs prepared using other methods than those provide herein including for example, methods other than those embodied in FIG. 9. In some embodiments, the glycolytic reserve is from about 70% to about 99% of the basal respiration rate of freshly harvested TILs and/or TILs prepared using other methods than those provide herein including for example, methods other than those embodied in FIG. 9. In some embodiments, the glycolytic reserve is from about 80% to about 99% of the basal respiration rate of freshly harvested TILs and/or TILs prepared using other methods than those provide herein including for example, methods other than those embodied in FIG. 9. In some embodiments, the glycolytic reserve is from about 90% to about 99% of the basal respiration rate of freshly harvested TILs and/or TILs prepared using other methods than those provide herein including for example, methods other than those embodied in FIG. 9. In some embodiments, the glycolytic reserve is from about 95% to about 99% of the basal respiration rate of freshly harvested TILs and/or TILs prepared using other methods than those provide herein including for example, methods other than those embodied in FIG. 9.

In some embodiments, the metabolic assay is basal glycolysis. In some embodiments, second expansion TILs or second additional expansion TILs (such as, for example, those described in Step D of FIG. 9, including TILs referred to as reREP TILs) have an increase in basal glycolysis of at least two-fold, at least three-fold, at least four-fold, at least five-fold, at least six-fold, at least 7-fold, at least eight-fold, at least nine-fold, or at least ten-fold as compared to freshly harvested TILs and/or TILs prepared using other methods than those provide herein including for example, methods other than those embodied in FIG. 9. In some embodiments, the second expansion TILs or second additional expansion TILs (such as, for example, those described in Step D of FIG. 9, including TILs referred to as reREP TILs) have an increase in basal glycolysis of about two-fold to about ten-fold as compared to freshly harvested TILs and/or TILs prepared using other methods than those provide herein including for example, methods other than those embodied in FIG. 9. In some embodiments, the second expansion TILs or second additional expansion TILs (such as, for example, those described in Step D of FIG. 9, including TILs referred to as reREP TILs) have an increase in basal glycolysis of about two-fold to about eight-fold as compared to freshly harvested TILs and/or TILs prepared using other methods than those provide herein including for example, methods other than those embodied in FIG. 9. In some embodiments, second expansion TILs or second additional expansion TILs (such as, for example, those described in Step D of FIG. 9, including TILs referred to as reREP TILs) have an increase in basal glycolysis of about three-fold to about seven-fold as compared to freshly harvested TILs and/or TILs prepared using other methods than those provide herein including for example, methods other than those embodied in FIG. 9. In some embodiments, the second expansion TILs or second additional expansion TILs (such as, for example, those described in Step D of FIG. 9, including TILs referred to as reREP TILs) have an increase in basal glycolysis of about two-fold to about four-fold as compared to freshly harvested TILs and/or TILs prepared using other methods than those provide herein including for example, methods other than those embodied in FIG. 9. In some embodiments, the second expansion TILs or second additional expansion TILs (such as, for example, those described in Step D of FIG. 9, including TILs referred to as reREP TILs) have an increase in basal glycolysis of about two-fold to about three-fold as compared to freshly harvested TILs and/or TILs prepared using other methods than those provide herein including for example, methods other than those embodied in FIG. 9.

In general, the second expansion TILs or second additional expansion TILs (such as, for example, those described in Step D of FIG. 9, including TILs referred to as reREP TILs) have a glycolytic reserve that is at least 50%, at least 55%, at least 60%, at least 65%, at least 70%, at least 75%, at least 80%, at least 85%, at least 90%, at least 95%, at least 97%, at least 98%, or at least 99% of the basal respiration rate of freshly harvested TILs and/or TILs prepared using other methods than those provide herein including for example, methods other than those embodied in FIG. 9. In some embodiments, the glycolytic reserve is from about 50% to about 99% of the basal respiration rate of freshly harvested TILs. In some embodiments, the glycolytic reserve is from about 60% to about 99% of the basal respiration rate of freshly harvested TILs and/or TILs prepared using other methods than those provide herein including for example, methods other than those embodied in FIG. 9. In some embodiments, the glycolytic reserve is from about 70% to about 99% of the basal respiration rate of freshly harvested TILs and/or TILs prepared using other methods than those provide herein including for example, methods other than those embodied in FIG. 9. In some embodiments, the glycolytic reserve is from about 80% to about 99% of the basal respiration rate of freshly harvested TILs and/or TILs prepared using other methods than those provide herein including for example, methods other than those embodied in FIG. 9. In some embodiments, the glycolytic reserve is from about 90% to about 99% of the basal respiration rate of freshly harvested TILs and/or TILs prepared using other methods than those provide herein including for example, methods other than those embodied in FIG. 9. In some embodiments, the glycolytic reserve is from about 95% to about 99% of the basal respiration rate of freshly harvested TILs.

Granzyme B Production: Granzyme B is another measure of the ability of TIL to kill target cells. Media supernatants restimulated as described above using antibodies to CD3, CD28, and CD137/4-1BB were also evaluated for their levels of Granzyme B using the Human Granzyme B DuoSet ELISA Kit (R & D Systems, Minneapolis, MN) according to the manufacturer's instructions. In some embodiments, the second expansion TILs or second additional expansion TILs (such as, for example, those described in Step D of FIG. 9, including TILs referred to as reREP TILs) have increased Granzyme B production. In some embodiments, the second expansion TILs or second additional expansion TILs (such as, for example, those described in Step D of FIG. 9, including TILs referred to as reREP TILs) have increased cytotoxic activity.

In some embodiments, telomere length can be used as a measure of cell viability and/or cellular function. In some embodiments, the telomeres are surprisingly the same length in the TILs produced by the present invention as compared to TILs prepared using other methods than those provide herein including for example, methods other than those embodied in FIG. 9. Telomere length measurement: Diverse methods have been used to measure the length of telomeres in genomic DNA and cytological preparations. The telomere restriction fragment (TRF) analysis is the gold standard to measure telomere length (de Lange et al., 1990). However, the major limitation of TRF is the requirement of a large amount of DNA (1.5 ^g). Two widely used techniques for the measurement of telomere lengths namely, fluorescence in situ hybridization (FISH; Agilent Technologies, Santa Clara, CA) and quantitative PCR can be employed with the present invention. In some embodiments, there is no change in telomere length between the initially harvest TILs in Step A and the expanded TILs from for example Step D as provided in FIG. 9.

In some embodiments, the TILs express one more markers selected from the group consisting of granzyme B, perforin, and granulysin. In some embodiments, the TILs express granzyme B. In some embodiments, the TILs express perforin. In some embodiments, the TILs express granulysin.

In an embodiment, restimulated TILs can also be evaluated for cytokine release, using cytokine release assays. In some embodiments, TILs can be evaluated for interferon-γ (IFN-γ) secretion. In some embodiments, the IFN-γ secretion is measured by an ELISA assay. In some embodiments, the IFN-γ secretion is measured by an ELISA assay after the rapid second expansion step, after Step D as provided in for example, FIG. 2 (in particular, e.g., FIG. 2A and/or FIG. 2B and/or FIG. 2C and/or FIG. 9). In some embodiments, TIL health is measured by IFN-gamma (IFN-γ) secretion. In some embodiments, IFN-γ secretion is indicative of active TILs. In some embodiments, a potency assay for IFN-γ production is employed. IFN-γ production is another measure of cytotoxic potential. IFN-γ production can be measured by determining the levels of the cytokine IFN-γ in the media of TIL stimulated with antibodies to CD3, CD28, and CD137/4-1BB. IFN-γ levels in media from these stimulated TIL can be determined using by measuring IFN-γ release. In some embodiments, an increase in IFN-γ production in for example Step D in the Gen 3 process as provided in FIG. 2 (in particular, e.g., FIG. 2A and/or FIG. 2B and/or FIG. 2C and/or FIG. 9) TTLs as compared to for example Step D in the 2A process as provided in FIG. 2 (in particular, e.g., FIG. 2A) is indicative of an increase in cytotoxic potential of the Step D TILs. In some embodiments, IFN-γ secretion is increased one-fold, two-fold, three-fold, four-fold, or five-fold or more. In some embodiments, IFN-γ secretion is increased one-fold. In some embodiments, IFN-γ secretion is increased two-fold. In some embodiments, IFN-γ secretion is increased three-fold. In some embodiments, IFN-γ secretion is increased four-fold. In some embodiments, IFN-γ secretion is increased five-fold. In some embodiments, IFN-γ is measured using a Quantikine ELISA kit. In some embodiments, IFN-γ is measured in TTLs ex vivo. In some embodiments, IFN-γ is measured in TILs ex vivo, including TILs produced by the methods of the present invention, including, for example FIG. 2B methods.

In some embodiments, TILs capable of at least one-fold, two-fold, three-fold, four-fold, or five-fold or more IFN-γ secretion are TILs produced by the expansion methods of the present invention, including, for example FIG. 2A and/or FIG. 2B and/or FIG. 2C and/or FIG. 9 methods. In some embodiments, TILs capable of at least one-fold more IFN-γ secretion are TILs produced by the expansion methods of the present invention, including, for example FIG. 2A and/or FIG. 2B and/or FIG. 2C and/or FIG. 9 methods. In some embodiments, TILs capable of at least two-fold more IFN-γ secretion are TILs produced by the expansion methods of the present invention, including, for example FIG. 2A and/or FIG. 2B and/or FIG. 2C and/or FIG. 9 methods. In some embodiments, TILs capable of at least three-fold more IFN-γ secretion are TILs produced by the expansion methods of the present invention, including, for example FIG. 2A and/or FIG. 2B and/or FIG. 2C and/or FIG. 9 methods. In some embodiments, TILs capable of at least four-fold more IFN-γ secretion are TILs produced by the expansion methods of the present invention, including, for example FIG. 2A and/or FIG. 2B and/or FIG. 2C and/or FIG. 9 methods. In some embodiments, TILs capable of at least five-fold more IFN-γ secretion are TILs produced by the expansion methods of the present invention, including, for example FIG. 2A and/or FIG. 2B and/or FIG. 2C and/or FIG. 9 methods.

In some embodiments, TILs capable of at least 100 pg/ml to about 1000 pg/mL or more IFN-γ secretion are TILs produced by the expansion methods of the present invention, including, for example FIG. 2A and/or FIG. 2B and/or FIG. 2C and/or FIG. 9 methods. In some embodiments, TILs capable of at least 200 pg/ml, at least 250 pg/ml, at least 300 pg/ml, at least 350 pg/ml, at least 400 pg/ml, at least 450 pg/ml, at least 500 pg/ml, at least 550 pg/ml, at least 600 pg/ml, at least 650 pg/ml, at least 700 pg/ml, at least 750 pg/ml, at least 800 pg/ml, at least 850 pg/ml, at least 900 pg/ml, at least 950 pg/ml, or at least 1000 pg/mL or more IFN-γ secretion are TILs produced by the expansion methods of the present invention, including, for example FIG. 2A and/or FIG. 2B and/or FIG. 2C and/or FIG. 9 methods. In some embodiments, TILs capable of at least 200 pg/ml IFN-γ secretion are TILs produced by the expansion methods of the present invention, including, for example FIG. 2A and/or FIG. 2B and/or FIG. 2C and/or FIG. 9 methods. In some embodiments, TILs capable of at least 200 pg/ml IFN-γ secretion are TILs produced by the expansion methods of the present invention, including, for example FIG. 2A and/or FIG. 2B and/or FIG. 2C and/or FIG. 9 methods. In some embodiments, TILs capable of at least 300 pg/ml IFN-γ secretion are TILs produced by the expansion methods of the present invention, including, for example FIG. 2A and/or FIG. 2B and/or FIG. 2C and/or FIG. 9 methods. In some embodiments, TILs capable of at least 400 pg/ml IFN-γ secretion are TILs produced by the expansion methods of the present invention, including, for example FIG. 2A and/or FIG. 2B and/or FIG. 2C and/or FIG. 9 methods. In some embodiments, TILs capable of at least 500 pg/ml IFN-γ secretion are TILs produced by the expansion methods of the present invention, including, for example FIG. 2A and/or FIG. 2B and/or FIG. 2C and/or FIG. 9 methods. In some embodiments, TILs capable of at least 600 pg/ml IFN-γ secretion are TILs produced by the expansion methods of the present invention, including, for example FIG. 2A and/or FIG. 2B and/or FIG. 2C and/or FIG. 9 methods. In some embodiments, TILs capable of at least 700 pg/ml IFN-γ secretion are TILs produced by the expansion methods of the present invention, including, for example FIG. 2A and/or FIG. 2B and/or FIG. 2C and/or FIG. 9 methods. In some embodiments, TILs capable of at least 800 pg/ml IFN-γ secretion are TILs produced by the expansion methods of the present invention, including, for example FIG. 2A and/or FIG. 2B and/or FIG. 2C and/or FIG. 9 methods. In some embodiments, TILs capable of at least 900 pg/ml IFN-γ secretion are TILs produced by the expansion methods of the present invention, including, for example FIG. 2A and/or FIG. 2B and/or FIG. 2C and/or FIG. 9 methods. In some embodiments, TILs capable of at least 1000 pg/ml IFN-γ secretion are TILs produced by the expansion methods of the present invention, including, for example FIG. 2A and/or FIG. 2B and/or FIG. 2C and/or FIG. 9 methods. In some embodiments, TILs capable of at least 2000 pg/ml IFN-γ secretion are TILs produced by the expansion methods of the present invention, including, for example FIG. 2A and/or FIG. 2B and/or FIG. 2C and/or FIG. 9 methods. In some embodiments, TILs capable of at least 3000 pg/ml IFN-γ secretion are TILs produced by the expansion methods of the present invention, including, for example FIG. 2A and/or FIG. 2B and/or FIG. 2C and/or FIG. 9 methods. In some embodiments, TILs capable of at least 4000 pg/ml IFN-γ secretion are TILs produced by the expansion methods of the present invention, including, for example FIG. 2A and/or FIG. 2B and/or FIG. 2C and/or FIG. 9 methods. In some embodiments, TILs capable of at least 5000 pg/ml IFN-γ secretion are TILs produced by the expansion methods of the present invention, including, for example FIG. 2A and/or FIG. 2B and/or FIG. 2C and/or FIG. 9 methods. In some embodiments, TILs capable of at least 6000 pg/ml IFN-γ secretion are TILs produced by the expansion methods of the present invention, including, for example FIG. 2A and/or FIG. 2B and/or FIG. 2C and/or FIG. 9 methods. In some embodiments, TILs capable of at least 7000 pg/ml IFN-γ secretion are TILs produced by the expansion methods of the present invention, including, for example FIG. 2A and/or FIG. 2B and/or FIG. 2C and/or FIG. 9 methods. In some embodiments, TILs capable of at least 8000 pg/ml IFN-γ secretion are TILs produced by the expansion methods of the present invention, including, for example FIG. 2A and/or FIG. 2B and/or FIG. 2C and/or FIG. 9 methods. In some embodiments, TILs capable of at least 9000 pg/ml IFN-γ secretion are TILs produced by the expansion methods of the present invention, including, for example FIG. 2A and/or FIG. 2B and/or FIG. 2C and/or FIG. 9 methods. In some embodiments, TILs capable of at least 10,000 pg/ml IFN-γ secretion are TILs produced by the expansion methods of the present invention, including, for example FIG. 2A and/or FIG. 2B and/or FIG. 2C and/or FIG. 9 methods. In some embodiments, TILs capable of at least 15,000 pg/ml IFN-γ secretion are TILs produced by the expansion methods of the present invention, including, for example FIG. 2A and/or FIG. 2B and/or FIG. 2C and/or FIG. 9 methods. In some embodiments, TILs capable of at least 20,000 pg/ml IFN-γ secretion are TILs produced by the expansion methods of the present invention, including, for example FIG. 2A and/or FIG. 2B and/or FIG. 2C and/or FIG. 9 methods. In some embodiments, TILs capable of at least 25,000 pg/ml IFN-γ secretion are TILs produced by the expansion methods of the present invention, including, for example FIG. 2A and/or FIG. 2B and/or FIG. 2C and/or FIG. 9 methods. In some embodiments, TILs capable of at least 30,000 pg/ml IFN-γ secretion are TILs produced by the expansion methods of the present invention, including, for example FIG. 2A and/or FIG. 2B and/or FIG. 2C and/or FIG. 9 methods. In some embodiments, TILs capable of at least 35,000 pg/ml IFN-γ secretion are TILs produced by the expansion methods of the present invention, including, for example FIG. 2A and/or FIG. 2B and/or FIG. 2C and/or FIG. 9 methods. In some embodiments, TILs capable of at least 40,000 pg/ml IFN-γ secretion are TILs produced by the expansion methods of the present invention, including, for example FIG. 2A and/or FIG. 2B and/or FIG. 2C and/or FIG. 9 methods. In some embodiments, TILs capable of at least 45,000 pg/ml IFN-γ secretion are TILs produced by the expansion methods of the present invention, including, for example FIG. 2A and/or FIG. 2B and/or FIG. 2C and/or FIG. 9 methods. In some embodiments, TILs capable of at least 50,000 pg/ml IFN-γ secretion are TILs produced by the expansion methods of the present invention, including, for example FIG. 2A and/or FIG. 2B and/or FIG. 2C and/or FIG. 9 methods.

In some embodiments, TILs capable of at least 100 pg/ml/5e5 cells to about 1000 pg/ml/5e5 cells or more IFN-γ secretion are TILs produced by the expansion methods of the present invention, including, for example FIG. 2A and/or FIG. 2B and/or FIG. 2C and/or FIG. 9 methods. In some embodiments, TILs capable of at least 200 pg/ml/5e5 cells, at least 250 pg/ml/5e5 cells, at least 300 pg/ml/5e5 cells, at least 350 pg/ml/5e5 cells, at least 400 pg/ml/5e5 cells, at least 450 pg/ml/5e5 cells, at least 500 pg/ml/5e5 cells, at least 550 pg/ml/5e5 cells, at least 600 pg/ml/5e5 cells, at least 650 pg/ml/5e5 cells, at least 700 pg/ml/5e5 cells, at least 750 pg/ml/5e5 cells, at least 800 pg/ml/5e5 cells, at least 850 pg/ml/5e5 cells, at least 900 pg/ml/5e5 cells, at least 950 pg/ml/5e5 cells, or at least 1000 pg/ml/5e5 cells or more IFN-γ secretion are TILs produced by the expansion methods of the present invention, including, for example FIG. 2A and/or FIG. 2B and/or FIG. 2C and/or FIG. 9 methods. In some embodiments, TILs capable of at least 200 pg/ml/5e5 cells IFN-γ secretion are TILs produced by the expansion methods of the present invention, including, for example FIG. 2A and/or FIG. 2B and/or FIG. 2C and/or FIG. 9 methods. In some embodiments, TILs capable of at least 200 pg/ml/5e5 cells IFN-γ secretion are TILs produced by the expansion methods of the present invention, including, for example FIG. 2A and/or FIG. 2B and/or FIG. 2C and/or FIG. 9 methods. In some embodiments, TILs capable of at least 300 pg/ml/5e5 cells IFN-γ secretion are TILs produced by the expansion methods of the present invention, including, for example FIG. 2A and/or FIG. 2B and/or FIG. 2C and/or FIG. 9 methods. In some embodiments, TILs capable of at least 400 pg/ml/5e5 cells IFN-γ secretion are TILs produced by the expansion methods of the present invention, including, for example FIG. 2A and/or FIG. 2B and/or FIG. 2C and/or FIG. 9 methods. In some embodiments, TILs capable of at least 500 pg/ml/5e5 cells IFN-γ secretion are TILs produced by the expansion methods of the present invention, including, for example FIG. 2A and/or FIG. 2B and/or FIG. 2C and/or FIG. 9 methods. In some embodiments, TILs capable of at least 600 pg/ml/5e5 cells IFN-γ secretion are TILs produced by the expansion methods of the present invention, including, for example FIG. 2A and/or FIG. 2B and/or FIG. 2C and/or FIG. 9 methods. In some embodiments, TILs capable of at least 700 pg/ml/5e5 cells IFN-γ secretion are TILs produced by the expansion methods of the present invention, including, for example FIG. 2A and/or FIG. 2B and/or FIG. 2C and/or FIG. 9 methods. In some embodiments, TILs capable of at least 800 pg/ml/5e5 cells IFN-γ secretion are TILs produced by the expansion methods of the present invention, including, for example FIG. 2A and/or FIG. 2B and/or FIG. 2C and/or FIG. 9 methods. In some embodiments, TILs capable of at least 900 pg/ml/5e5 cells IFN-γ secretion are TILs produced by the expansion methods of the present invention, including, for example FIG. 2A and/or FIG. 2B and/or FIG. 2C and/or FIG. 9 methods. In some embodiments, TILs capable of at least 1000 pg/ml/5e5 cells IFN-γ secretion are TILs produced by the expansion methods of the present invention, including, for example FIG. 2A and/or FIG. 2B and/or FIG. 2C and/or FIG. 9 methods. In some embodiments, TILs capable of at least 2000 pg/ml/5e5 cells IFN-γ secretion are TILs produced by the expansion methods of the present invention, including, for example FIG. 2A and/or FIG. 2B and/or FIG. 2C and/or FIG. 9 methods. In some embodiments, TILs capable of at least 3000 pg/ml/5e5 cells IFN-γ secretion are TILs produced by the expansion methods of the present invention, including, for example FIG. 2A and/or FIG. 2B and/or FIG. 2C and/or FIG. 9 methods. In some embodiments, TILs capable of at least 4000 pg/ml/5e5 cells IFN-γ secretion are TILs produced by the expansion methods of the present invention, including, for example FIG. 2A and/or FIG. 2B and/or FIG. 2C and/or FIG. 9 methods. In some embodiments, TILs capable of at least 5000 pg/ml/5e5 cells IFN-γ secretion are TILs produced by the expansion methods of the present invention, including, for example FIG. 2A and/or FIG. 2B and/or FIG. 2C and/or FIG. 9 methods. In some embodiments, TILs capable of at least 6000 pg/ml/5e5 cells IFN-γ secretion are TILs produced by the expansion methods of the present invention, including, for example FIG. 2A and/or FIG. 2B and/or FIG. 2C and/or FIG. 9 methods. In some embodiments, TILs capable of at least 7000 pg/ml/5e5 cells IFN-γ secretion are TILs produced by the expansion methods of the present invention, including, for example FIG. 2A and/or FIG. 2B and/or FIG. 2C and/or FIG. 9 methods. In some embodiments, TILs capable of at least 8000 pg/ml/5e5 cells IFN-γ secretion are TILs produced by the expansion methods of the present invention, including, for example FIG. 2A and/or FIG. 2B and/or FIG. 2C and/or FIG. 9 methods. In some embodiments, TILs capable of at least 9000 pg/ml/5e5 cells IFN-γ secretion are TILs produced by the expansion methods of the present invention, including, for example FIG. 2A and/or FIG. 2B and/or FIG. 2C and/or FIG. 9 methods. In some embodiments, TILs capable of at least 10,000 pg/ml/5e5 cells IFN-γ secretion are TILs produced by the expansion methods of the present invention, including, for example FIG. 2A and/or FIG. 2B and/or FIG. 2C and/or FIG. 9 methods. In some embodiments, TILs capable of at least 15,000 pg/ml/5e5 cells IFN-γ secretion are TILs produced by the expansion methods of the present invention, including, for example FIG. 2A and/or FIG. 2B and/or FIG. 2C and/or FIG. 9 methods. In some embodiments, TILs capable of at least 20,000 pg/ml/5e5 cells IFN-γ secretion are TILs produced by the expansion methods of the present invention, including, for example FIG. 2A and/or FIG. 2B and/or FIG. 2C and/or FIG. 9 methods. In some embodiments, TILs capable of at least 25,000 pg/ml/5e5 cells IFN-γ secretion are TILs produced by the expansion methods of the present invention, including, for example FIG. 2A and/or FIG. 2B and/or FIG. 2C and/or FIG. 9 methods. In some embodiments, TILs capable of at least 30,000 pg/ml/5e5 cells IFN-γ secretion are TILs produced by the expansion methods of the present invention, including, for example FIG. 2A and/or FIG. 2B and/or FIG. 2C and/or FIG. 9 methods. In some embodiments, TILs capable of at least 35,000 pg/ml/5e5 cells IFN-γ secretion are TILs produced by the expansion methods of the present invention, including, for example FIG. 2A and/or FIG. 2B and/or FIG. 2C and/or FIG. 9 methods. In some embodiments, TILs capable of at least 40,000 pg/ml/5e5 cells IFN-γ secretion are TILs produced by the expansion methods of the present invention, including, for example FIG. 2A and/or FIG. 2B and/or FIG. 2C and/or FIG. 9 methods. In some embodiments, TILs capable of at least 45,000 pg/ml/5e5 cells IFN-γ secretion are TILs produced by the expansion methods of the present invention, including, for example FIG. 2A and/or FIG. 2B and/or FIG. 2C and/or FIG. 9 methods. In some embodiments, TILs capable of at least 50,000 pg/ml/5e5 cells IFN-γ secretion are TILs produced by the expansion methods of the present invention, including, for example FIG. 2A and/or FIG. 2B and/or FIG. 2C and/or FIG. 9 methods.

In some embodiments, TILs capable of at least one-fold, two-fold, three-fold, four-fold, or five-fold or more lower levels of TNF-α (i.e., TNF-alpha) secretion as compared to IFN-γ secretion are TILs produced by the expansion methods of the present invention, including, for example FIG. 2A and/or FIG. 2B and/or FIG. 2C and/or FIG. 9 methods. In some embodiments, TILs capable of at least one-fold lower levels of TNF-α secretion as compared to IFN-γ secretion are TILs produced by the expansion methods of the present invention, including, for example FIG. 2A and/or FIG. 2B and/or FIG. 2C and/or FIG. 9 methods. In some embodiments, TILs capable of at least two-fold lower levels of TNF-α secretion as compared to IFN-γ secretion are TILs produced by the expansion methods of the present invention, including, for example FIG. 2A and/or FIG. 2B and/or FIG. 2C and/or FIG. 9 methods. In some embodiments, TILs capable of at least three-fold lower levels of TNF-α secretion as compared to IFN-γ secretion are TILs produced by the expansion methods of the present invention, including, for example FIG. 2A and/or FIG. 2B and/or FIG. 2C and/or FIG. 9 methods. In some embodiments, TILs capable of at least four-fold lower levels of TNF-α secretion as compared to IFN-γ secretion are TILs produced by the expansion methods of the present invention, including, for example FIG. 2A and/or FIG. 2B and/or FIG. 2C and/or FIG. 9 methods. In some embodiments, TILs capable of at least five-fold lower levels of TNF-α secretion as compared to IFN-γ secretion are TILs produced by the expansion methods of the present invention, including, for example FIG. 2A and/or FIG. 2B and/or FIG. 2C and/or FIG. 9 methods.

In some embodiments, TILs capable of at least 200 pg/ml/5e5 cells to about 10,000 pg/ml/5e5 cells or more TNF-α (i.e., TNF-alpha) secretion are TILs produced by the expansion methods of the present invention, including, for example FIG. 2A and/or FIG. 2B and/or FIG. 2C and/or FIG. 9 methods. In some embodiments, TILs capable of at least 500 pg/ml/5e5 cells to about 10,000 pg/ml/5e5 cells or more TNF-α secretion are TILs produced by the expansion methods of the present invention, including, for example FIG. 2A and/or FIG. 2B and/or FIG. 2C and/or FIG. 9 methods. In some embodiments, TILs capable of at least 1000 pg/ml/5e5 cells to about 10,000 pg/ml/5e5 cells or more TNF-α secretion are TILs produced by the expansion methods of the present invention, including, for example FIG. 2A and/or FIG. 2B and/or FIG. 2C and/or FIG. 9 methods. In some embodiments, TILs capable of at least 2000 pg/ml/5e5 cells to about 10,000 pg/ml/5e5 cells or more TNF-α secretion are TILs produced by the expansion methods of the present invention, including, for example FIG. 2A and/or FIG. 2B and/or FIG. 2C and/or FIG. 9 methods. In some embodiments, TILs capable of at least 3000 pg/ml/5e5 cells to about 10,000 pg/ml/5e5 cells or more TNF-α secretion are TILs produced by the expansion methods of the present invention, including, for example FIG. 2A and/or FIG. 2B and/or FIG. 2C and/or FIG. 9 methods. In some embodiments, TILs capable of at least 4000 pg/ml/5e5 cells to about 10,000 pg/ml/5e5 cells or more TNF-α secretion are TILs produced by the expansion methods of the present invention, including, for example FIG. 2A and/or FIG. 2B and/or FIG. 2C and/or FIG. 9 methods. In some embodiments, TILs capable of at least 5000 pg/ml/5e5 cells to about 10,000 pg/ml/5e5 cells or more TNF-α secretion are TILs produced by the expansion methods of the present invention, including, for example FIG. 2A and/or FIG. 2B and/or FIG. 2C and/or FIG. 9 methods. In some embodiments, TILs capable of at least 6000 pg/ml/5e5 cells to about 10,000 pg/ml/5e5 cells or more TNF-α secretion are TILs produced by the expansion methods of the present invention, including, for example FIG. 2A and/or FIG. 2B and/or FIG. 2C and/or FIG. 9 methods. In some embodiments, TILs capable of at least 7000 pg/ml/5e5 cells to about 10,000 pg/ml/5e5 cells or more TNF-α secretion are TILs produced by the expansion methods of the present invention, including, for example FIG. 2A and/or FIG. 2B and/or FIG. 2C and/or FIG. 9 methods. In some embodiments, TILs capable of at least 8000 pg/ml/5e5 cells to about 10,000 pg/ml/5e5 cells or more TNF-α secretion are TILs produced by the expansion methods of the present invention, including, for example FIG. 2A and/or FIG. 2B and/or FIG. 2C and/or FIG. 9 methods. In some embodiments, TILs capable of at least 9000 pg/ml/5e5 cells to about 10,000 pg/ml/5e5 cells or more TNF-α secretion are TILs produced by the expansion methods of the present invention, including, for example FIG. 2A and/or FIG. 2B and/or FIG. 2C and/or FIG. 9 methods.

In some embodiments, IFN-γ and granzyme B levels are measured to determine the phenotypic characteristics of the TILs produced by the expansion methods of the present invention, including, for example FIG. 2A and/or FIG. 2B and/or FIG. 2C and/or FIG. 9 methods. In some embodiments, IFN-γ and TNF-α levels are measured to determine the phenotypic characteristics of the TILs produced by the expansion methods of the present invention, including, for example FIG. 2A and/or FIG. 2B and/or FIG. 2C and/or FIG. 9 methods. In some embodiments, granzyme B and TNF-α levels are measured to determine the phenotypic characteristics of the TILs produced by the expansion methods of the present invention, including, for example FIG. 2A and/or FIG. 2B and/or FIG. 2C and/or FIG. 9 methods. In some embodiments, IFN-γ, granzyme B and TNF-α levels are measured to determine the phenotypic characteristics of the TILs produced by the expansion methods of the present invention, including, for example FIG. 2A and/or FIG. 2B and/or FIG. 2C and/or FIG. 9 methods.

In some embodiments, the cytotoxic potential of TIL to lyse target cells was assessed using a co-culture assay of TIL with the bioluminescent cell line, P815 (Clone G6), according to a bioluminescent redirected lysis assay (potency assay) for TIL assay which measures TIL cytotoxicity in a highly sensitive dose dependent manner.

In some embodiments, the present methods provide an assay for assessing TIL viability, using the methods as described above. In some embodiments, the TILs are expanded as discussed above, including for example as provided in FIG. 9. In some embodiments, the TILs are cryopreserved prior to being assessed for viability. In some embodiments, the viability assessment includes thawing the TILs prior to performing a first expansion, a second expansion, and an additional second expansion. In some embodiments, the present methods provide an assay for assessing cell proliferation, cell toxicity, cell death, and/or other terms related to viability of the TIL population. Viability can be measured by any of the TIL metabolic assays described above as well as any methods know for assessing cell viability that are known in the art. In some embodiments, the present methods provide as assay for assessment of cell proliferation, cell toxicity, cell death, and/or other terms related to viability of the TILs expanded using the methods described herein, including those exemplified in FIG. 9.

The present invention also provides assay methods for determining TIL viability. In some embodiments, the TILs have equal viability as compared to freshly harvested TILs and/or TILs prepared using other methods than those provide herein including for example, methods other than those embodied in FIG. 9. In some embodiments, the TILs have increased viability as compared to freshly harvested TILs and/or TILs prepared using other methods than those provide herein including for example, methods other than those embodied in FIG. 9. The present disclosure provides methods for assaying TILs for viability by expanding tumor infiltrating lymphocytes (TILs) into a larger population of TILs comprising:

(i) obtaining a first population of TILs which has been previously expanded;
(ii) performing a first expansion by culturing the first population of TILs in a cell culture medium comprising IL-2 to produce a second population of TILs; and
(iii) performing a second expansion by supplementing the cell culture medium of the second population of TILs with additional IL-2, OKT-3, and antigen presenting cells (APCs), to produce a third population of TILs, wherein the third population of TILs is at least 100-fold greater in number than the second population of TILs, and wherein the second expansion is performed for at least 14 days in order to obtain the third population of TILs, wherein the third population of TILs comprises an increased subpopulation of effector T-cells and/or central memory T-cells relative to the second population of TILs, and wherein the third population is further assayed for viability.

In some embodiments, the method further comprises:
(iv) performing an additional second expansion by supplementing the cell culture medium of the third population of TILs with additional IL-2, additional OKT-3, and additional APCs, wherein the additional second expansion is performed for at least 14 days to obtain a larger population of TILs than obtained in step (iii), wherein the larger population of TILs comprises an increased subpopulation of effector T-cells and/or central memory T-cells relative to the third population of TILs, and wherein the third population is further assayed for viability.

In some embodiments, prior to step (i), the cells are cryopreserved.

In some embodiments, the cells are thawed prior to performing step (i).

In some embodiments, step (iv) is repeated one to four times in order to obtain sufficient TILs for analysis.

In some embodiments, steps (i) through (iii) or (iv) are performed within a period of about 40 days to about 50 days.

In some embodiments, steps (i) through (iii) or (iv) are performed within a period of about 42 days to about 48 days.

In some embodiments, steps (i) through (iii) or (iv) are performed within a period of about 42 days to about 45 days.

In some embodiments, steps (i) through (iii) or (iv) are performed within about 44 days.

In some embodiments, the cells from steps (iii) or (iv) express CD4, CD8, and TCR α β at levels similar to freshly harvested cells.

In some embodiments, the antigen presenting cells are peripheral blood mononuclear cells (PBMCs).

In some embodiments, the PBMCs are added to the cell culture on any of days 9 through 17 in step (iii).

In some embodiments, the effector T-cells and/or central memory T-cells in the larger population of TILs in step (iv) exhibit one or more characteristics selected from the group consisting of expression of CD27, expression of CD28, longer telomeres, increased CD57 expression, and decreased CD56 expression, relative to effector T-cells, and/or central memory T-cells in the third population of cells.

In some embodiments, the effector T-cells and/or central memory T-cells exhibit increased CD57 expression and decreased CD56 expression.

In some embodiments, the APCs are artificial APCs (aAPCs).

In some embodiments, the method further comprises the step of transducing the first population of TILs with an expression vector comprising a nucleic acid encoding a high-affinity T-cell receptor.

In some embodiments, the step of transducing occurs before step (i).

In some embodiments, the method further comprises the step of transducing the first population of TILs with an expression vector comprising a nucleic acid encoding a chimeric antigen receptor (CAR) comprising a single chain variable fragment antibody fused with at least one endodomain of a T-cell signaling molecule.

In some embodiments, the step of transducing occurs before step (i).

In some embodiments, the TILs are assayed for viability.

In some embodiments, the TILs are assayed for viability after cryopreservation.

In some embodiments, the TILs are assayed for viability after cryopreservation and after step (iv).

The diverse antigen receptors of T and B lymphocytes are produced by somatic recombination of a limited, but large number of gene segments. These gene segments: V (variable), D (diversity), J (joining), and C (constant), determine the binding specificity and downstream applications of immunoglobulins and T-cell receptors (TCRs). The present invention provides a method for generating TILs which exhibit and increase the T-cell repertoire diversity (sometimes referred to as polyclonality). In some embodiments, the increase in T-cell repertoire diversity is as compared to freshly harvested TILs and/or TILs prepared using other methods than those provide herein including for example, methods other than those embodied in FIG. 9. In some embodiments, the TILs obtained by the present method exhibit an increase in the T-cell repertoire diversity. In some embodiments, the TILs obtained in the first expansion exhibit an increase in the T-cell repertoire diversity. In some embodiments, the increase in diversity is an increase in the immunoglobulin diversity and/or the T-cell receptor diversity. In some embodiments, the diversity is in the immunoglobulin is in the immunoglobulin heavy chain. In some embodiments, the diversity is in the immunoglobulin is in the immunoglobulin light chain. In some embodiments, the diversity is in the T-cell receptor. In some embodiments, the diversity is in one of the T-cell receptors selected from the group consisting of alpha, beta, gamma, and delta receptors. In some embodiments, there is an increase in the expression of T-cell receptor (TCR) alpha and/or beta. In some embodiments, there is an increase in the expression of T-cell receptor (TCR) alpha. In some embodiments, there is an increase in the expression of T-cell receptor (TCR) beta. In some embodiments, there is an increase in the expression of TCRab (i.e., TCRα/β).

According to the present disclosure, a method for assaying TILs for viability and/or further use in administration to a subject. In some embodiments, the method for assay tumor infiltrating lymphocytes (TILs) comprises:
(i) obtaining a first population of TILs;
(ii) performing a first expansion by culturing the first population of TILs in a cell culture medium comprising IL-2 to produce a second population of TILs; and
(iii) performing a second expansion by supplementing the cell culture medium of the second population of TILs with additional IL-2, OKT-3, and antigen presenting cells (APCs), to produce a third population of TILs, wherein the third population of TILs is at least 50-fold greater in number than the second population of TILs;
(iv) harvesting, washing, and cryopreserving the third population of TILs;
(v) storing the cryopreserved TILs at a cryogenic temperature;
(vi) thawing the third population of TILs to provide a thawed third population of TILs; and
(vii) performing an additional second expansion of a portion of the thawed third population of TILs by supplementing the cell culture medium of the third population with IL-2, OKT-3, and APCs for an additional expansion period (sometimes referred to as a reREP period) of at least 3 days, wherein the third expansion is performed to obtain a fourth population of TILs, wherein the number of TILs in the fourth population of TILs is compared to the number of TILs in the third population of TILs to obtain a ratio;

(viii) determining based on the ratio in step (vii) whether the thawed population of TILs is suitable for administration to a patient;

(ix) administering a therapeutically effective dosage of the thawed third population of TILs to the patient when the ratio of the number of TILs in the fourth population of TILs to the number of TILs in the third population of TILs is determined to be greater than 5:1 in step (viii).

In some embodiments, the additional expansion period (sometimes referred to as a reREP period) is performed until the ratio of the number of TILs in the fourth population of TILs to the number of TILs in the third population of TILs is greater than 50:1.

In some embodiments, the number of TILs sufficient for a therapeutically effective dosage is from about $2.3 \times 10^{10}$ to about $13.7 \times 10^{10}$.

In some embodiments, steps (i) through (vii) are performed within a period of about 40 days to about 50 days. In some embodiments, steps (i) through (vii) are performed within a period of about 42 days to about 48 days. In some embodiments, steps (i) through (vii) are performed within a period of about 42 days to about 45 days. In some embodiments, steps (i) through (vii) are performed within about 44 days.

In some embodiments, the cells from steps (iii) or (vii) express CD4, CD8, and TCR α β at levels similar to freshly harvested cells. In some embodiments the cells are TILs.

In some embodiments, the antigen presenting cells are peripheral blood mononuclear cells (PBMCs). In some embodiments, the PBMCs are added to the cell culture on any of days 9 through 17 in step (iii).

In some embodiments, the effector T-cells and/or central memory T-cells in the larger population of TILs in steps (iii) or (vii) exhibit one or more characteristics selected from the group consisting of expression of CD27, expression of CD28, longer telomeres, increased CD57 expression, and decreased CD56 expression, relative to effector T-cells, and/or central memory T-cells in the third population of cells.

In some embodiments, the effector T-cells and/or central memory T-cells exhibit increased CD57 expression and decreased CD56 expression.

In some embodiments, the APCs are artificial APCs (aAPCs).

In some embodiments, the step of transducing the first population of TILs with an expression vector comprising a nucleic acid encoding a high-affinity T-cell receptor.

In some embodiments, the step of transducing occurs before step (i).

In some embodiments, the step of transducing the first population of TILs with an expression vector comprising a nucleic acid encoding a chimeric antigen receptor (CAR) comprising a single chain variable fragment antibody fused with at least one endodomain of a T-cell signaling molecule.

In some embodiments, the step of transducing occurs before step (i).

In some embodiments, the TILs are assayed for viability after step (vii).

The present disclosure also provides further methods for assaying TILs. In some embodiments, the disclosure provides a method for assaying TILs comprising:

(i) obtaining a portion of a first population of cryopreserved TILs;

(ii) thawing the portion of the first population of cryopreserved TILs;

(iii) performing a first expansion by culturing the portion of the first population of TILs in a cell culture medium comprising IL-2, OKT-3, and antigen presenting cells (APCs) for an additional expansion period (sometimes referred to as a reREP period) of at least 3 days, to produce a second population of TILs, wherein the portion from the first population of TILs is compared to the second population of TILs to obtain a ratio of the number of TILs, wherein the ratio of the number of TILs in the second population of TILs to the number of TILs in the portion of the first population of TILs is greater than 5:1;

(iv) determining based on the ratio in step (iii) whether the first population of TILs is suitable for use in therapeutic administration to a patient;

(v) determining the first population of TILs is suitable for use in therapeutic administration when the ratio of the number of TILs in the second population of TILs to the number of TILs in the first population of TILs is determined to be greater than 5:1 in step (iv).

In some embodiments, the ratio of the number of TILs in the second population of TILs to the number of TILs in the portion of the first population of TILs is greater than 50:1.

In some embodiments, the method further comprises performing expansion of the entire first population of cryopreserved TILs from step (i) according to the methods as described in any of the embodiments provided herein.

In some embodiments, the method further comprises administering the entire first population of cryopreserved TILs from step (i) to the patient.

K. Closed Systems for TIL Manufacturing

The present invention provides for the use of closed systems during the TIL culturing process. Such closed systems allow for preventing and/or reducing microbial contamination, allow for the use of fewer flasks, and allow for cost reductions. In some embodiments, the closed system uses two containers.

Such closed systems are well-known in the art and can be found, for example, at http://www.fda.gov/cber/guidelines.htm and https://www.fda.gov/BiologicsBloodVaccines/GuidanceComplianceRegulatoryInformation/Guidances/Blood/ucm076779.htm.

As provided on the FDA website, closed systems with sterile methods are known and well described. See, https://www.fda.gov/BiologicsBloodVaccines/GuidanceComplianceRegulatoryInformation/Guidances/Blood/ucm076779.htm, as referenced above and provided in pertinent part below.

Introduction

Sterile connecting devices (STCDs) produce sterile welds between two pieces of compatible tubing. This procedure permits sterile connection of a variety of containers and tube diameters. This guidance describes recommended practices and procedures for use of these devices. This guidance does not address the data or information that a manufacturer of a sterile connecting device must submit to FDA in order to obtain approval or clearance for marketing. It is also important to note that the use of an approved or cleared sterile connecting device for purposes not authorized in the labeling may cause the device to be considered adulterated and misbranded under the Federal Food, Drug and Cosmetic Act.

1. FDA Recommendations

Manufacturers of blood products who propose to routinely use an FDA-cleared STCD should incorporate information regarding such use in standard operating procedure (SOP) manuals for each blood product. These entries should include record keeping, product tracking, tube weld quality control, lot numbers of software and disposables (including source(s) of elements to be added). Quality control procedures should include a test of the integrity of each weld.

2. Applications of the STCD

The user should be aware that use of the device may create a new product or significantly modify the configuration of a regulated product for which safety and efficacy have not been demonstrated. For those "new products" subject to licensure, applications, or application supplements must be submitted to FDA in addition to submission of a SOP. In general, pooling or mixing that involves cellular components represents a change in the product that requires submission and approval of a license application or application supplement. Such applications and application supplements should contain data and descriptions of manufacturing procedures that demonstrate that the "new product" is safe and effective for its intended use throughout the proposed dating period.

The following comments are provided as guidance on the more common uses of an FDA cleared or approved STCD:

L. Adding a New or Smaller Needle to a Blood Collection Set

Using the STCD to add a needle prior to the initiation of a procedure (whole blood collection, platelet pheresis or source plasma collection) is not considered to open a functionally closed system. If a needle is added during a procedure, only an STCD approved to weld liquid-filled tubing should be used. If the test of weld integrity is satisfactory, the use of an STCD is not considered to open a functionally closed system.

Platelets, Pheresis prepared in an open system should be labeled with a 24 hour outdate and Platelets, Pheresis products prepared in a functionally closed system should be labeled with a five day outdate (See Revised Guideline for Collection of Platelets, Pheresis, Oct. 7, 1988).

The source and specifications of added tubing and needles should be addressed in the blood center's SOP and records. Using the STCD to add needles does not represent a major change in manufacturing for which licensed establishments need preapproval.

M. Using the STCD to Prepare Components

When the STCD is used to attach additional component preparation bags, records should be properly maintained identifying the source of the transfer packs and the appropriate verification of blood unit number and ABO/Rh. All blood and blood components must be appropriately labeled (21 CFR 606.121).

EXAMPLES

Adding a fourth bag to a whole blood collection triple-pack for the production of Cryoprecipitated AHF from Fresh Frozen Plasma.

Connection of an additive solution to a red blood cell unit.

Addition of an in-line filter that has been FDA cleared for use in manufacturing components.

Addition of a third storage container to a platelet pheresis harness.

For the above stated uses, procedures should be developed and records maintained, but licensees need not have FDA approval in order to institute the procedures.

1. Using the STCD to Pool Blood Products

Appropriate use of an STCD to pool Platelets prepared from Whole Blood collection may obviate potential contamination from the spike and port entries commonly used. Pooling performed immediately before transfusion is an example of such appropriate use. Pooled Platelets should be administered not more than 4 hours after pooling (See 21 CFR 606.122(1)(2)).

However, pooling and subsequent storage may increase the risk compared to administration of random donor units; if one contaminated unit is pooled with others and stored before administration, the total bacterial inoculum administered may be increased as a result of replication in the additional volume. Accordingly, the proposed use of an STCD to pool and store platelets for more than 4 hours should be supported by data which satisfactorily addresses whether such pooling is associated with increased risk.

Such platelet pooling constitutes manufacture of a new product.

Pooling or mixing that involves platelets is considered the manufacture of a new product that requires submission and approval of a license application or application supplement if the storage period is to exceed four hours.

2. Using the STCD to Prepare an Aliquot for Pediatric Use and Divided Units

Pediatric units and divided units for Whole Blood, Red Blood Cells, and Fresh Frozen Plasma prepared using an STCD will not be considered a new product for which a biologics license application (BLA) supplement is required providing the following conditions are met:

The manufacturer should have an approved biologics license or license supplement, for the original (i.e., undivided) product, including approval for each anticoagulantused.

Labels should be submitted for review and approval before distribution. A notation should be made under the comments section of FDA Form 2567, Transmittal of Labels and Circulars.

Final product containers approved for storage of the component being prepared should be used.

Platelets manufactured under licensure must contain at least $5.5\times(10)^{10}$ platelets (21 CFR 640.24 (c)). Platelets, Pheresis manufactured under licensure should contain at least $3.0\times(10)^{11}$ platelets (See Revised Guideline for the Collection of Platelets, Pheresis, Oct. 7, 1988).

Procedures to be followed regarding the use of an STCD to prepare divided products from Whole Blood collections and from plasma and platelets prepared by automated hemapheresis procedures should include descriptions of:

How the apheresis harness or collection container will be modified with an FDA-cleared STCD;

the minimum volume of the split plasma or whole blood products;

the volume and platelet concentration of the split platelet pheresis products;

storage time of the product. The product should be in an approved container and should be consistent with the storage time on the label of such container;

method(s) to be used to label and track divided products in the blood center's records.

NOTE: Procedures for labeling the aliquots should be clearly stated in the procedure record keeping should be adequate to permit tracking and recall of all components, if necessary.

3. Using an STCD to Connect Additional Saline or Anticoagulant Lines During an Automated Plasmapheresis Procedure Procedures should be developed and records maintained consistent with the instrument manufacturer's directions for use, but licensees need not have FDA approval in order to institute the procedures.

4. Using the STCD to Attach Processing Solutions

When using an STCD to attach containers with processing solutions to washed or frozen red blood cell products, the dating period for the resulting products is 24 hours, unless data are provided in the form of license applications or application supplements to CBER to support a longer dating period (21 CFR 610.53(c)). Exemptions or modifications must be approved in writing from the Director, CBER (21 CFR 610.53(d)).

5. Using an STCD to Add an FDA-Cleared Leukocyte Reduction Filter

Some leuko-reduction filters are not integrally attached to the Whole Blood collection systems. Procedures for use of an STCD for pre-storage filtration should be consistent with filter manufacturers' directions for use.

Leukocyte reduction prior to issue constitutes a major manufacturing change. Therefore, for new leukocyte-reduced products prepared using an STCD, manufacturers must submit biologics license applications (21 CFR 601.2) or prior approval application supplements to FDA (21 CFR 601.12).

Using an STCD to remove samples from blood product containers for testing (e.g., using an STCD to obtain a sample of platelets from a container of Platelets or Platelets, Pheresis for cross matching).

If the volume and/or cell count of the product after sample withdrawal differ from what is stated on the original label or in the circular of information, the label on the product should be modified to reflect the new volume and/or cell count. For example, samples may not be removed that reduce the platelet count of a unit of Platelets to less than $5.5 \times (10)^{10}$ platelets (21 CFR 640.24 (c)).

6. Additional Information from FDA Guidance

The FDA guidance presents general guidance as well as specific information and examples concerning specifications for submission of applications and application supplements to FDA addressing use of an STCD. If further questions arise concerning appropriate use of an STCD, concerns should be directed to the Office of Blood Research and Review, Center for Biologics Evaluation and Research.

In some embodiments, the closed system uses one container from the time the tumor fragments are obtained until the TILs are ready for administration to the patient or cryopreserving. In some embodiments when two containers are used, the first container is a closed G-container and the population of TILs is centrifuged and transferred to an infusion bag without opening the first closed G-container. In some embodiments, when two containers are used, the infusion bag is a HypoThermosol-containing infusion bag. A closed system or closed TIL cell culture system is characterized in that once the tumor sample and/or tumor fragments have been added, the system is tightly sealed from the outside to form a closed environment free from the invasion of bacteria, fungi, and/or any other microbial contamination.

In some embodiments, the reduction in microbial contamination is between about 5% and about 100%. In some embodiments, the reduction in microbial contamination is between about 5% and about 95%. In some embodiments, the reduction in microbial contamination is between about 5% and about 90%. In some embodiments, the reduction in microbial contamination is between about 10% and about 90%. In some embodiments, the reduction in microbial contamination is between about 15% and about 85%. In some embodiments, the reduction in microbial contamination is about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 97%, about 98%, about 99%, or about 100%.

The closed system allows for TIL growth in the absence and/or with a significant reduction in microbial contamination.

Moreover, pH, carbon dioxide partial pressure and oxygen partial pressure of the TIL cell culture environment each vary as the cells are cultured. Consequently, even though a medium appropriate for cell culture is circulated, the closed environment still needs to be constantly maintained as an optimal environment for TIL proliferation. To this end, it is desirable that the physical factors of pH, carbon dioxide partial pressure and oxygen partial pressure within the culture liquid of the closed environment be monitored by means of a sensor, the signal whereof is used to control a gas exchanger installed at the inlet of the culture environment, and the that gas partial pressure of the closed environment be adjusted in real time according to changes in the culture liquid so as to optimize the cell culture environment. In some embodiments, the present invention provides a closed cell culture system which incorporates at the inlet to the closed environment a gas exchanger equipped with a monitoring device which measures the pH, carbon dioxide partial pressure and oxygen partial pressure of the closed environment, and optimizes the cell culture environment by automatically adjusting gas concentrations based on signals from the monitoring device.

In some embodiments, the pressure within the closed environment is continuously or intermittently controlled. That is, the pressure in the closed environment can be varied by means of a pressure maintenance device for example, thus ensuring that the space is suitable for growth of TILs in a positive pressure state, or promoting exudation of fluid in a negative pressure state and thus promoting cell proliferation. By applying negative pressure intermittently, moreover, it is possible to uniformly and efficiently replace the circulating liquid in the closed environment by means of a temporary shrinkage in the volume of the closed environment.

In some embodiments, optimal culture components for proliferation of the TILs can be substituted or added, and including factors such as IL-2 and/or OKT3, as well as combination, can be added.

N. Cell Cultures

In an embodiment, a method for expanding TILs, including those discuss above as well as exemplified in FIG. 9, may include using about 5,000 mL to about 25,000 mL of cell medium, about 5,000 mL to about 10,000 mL of cell medium, or about 5,800 mL to about 8,700 mL of cell medium. In some embodiments, the media is a serum free medium, as described for example in Example 21. In some embodiments, the media in the first expansion is serum free. In some embodiments, the media in the second expansion is serum free. In some embodiments, the media in the first expansion and the second are both serum free. In an embodiment, expanding the number of TILs uses no more than one type of cell culture medium. Any suitable cell culture medium may be used, e.g., AIM-V cell medium (L-glutamine, 50 µM streptomycin sulfate, and 10 µM gentamicin sulfate) cell culture medium (Invitrogen, Carlsbad CA). In this regard, the inventive methods advantageously reduce the amount of medium and the number of types of medium required to expand the number of TIL. In an embodiment, expanding the number of TIL may comprise feeding the cells no more frequently than every third or fourth day. Expanding the number of cells in a gas permeable container simplifies the procedures necessary to expand the number of cells by reducing the feeding frequency necessary to expand the cells.

In an embodiment, the cell medium in the first and/or second gas permeable container is unfiltered. The use of unfiltered cell medium may simplify the procedures necessary to expand the number of cells. In an embodiment, the cell medium in the first and/or second gas permeable container lacks beta-mercaptoethanol (BME).

In an embodiment, the duration of the method comprising obtaining a tumor tissue sample from the mammal; culturing the tumor tissue sample in a first gas permeable container containing cell medium therein; obtaining TILs from the tumor tissue sample; expanding the number of TTLs in a second gas permeable container containing cell medium for a duration of about 7 to 14 days, e.g., about 11 days. In some embodiments pre-REP is about 7 to 14 days, e.g., about 11 days. In some embodiments, REP is about 7 to 14 days, e.g., about 11 days.

In an embodiment, TILs are expanded in gas-permeable containers. Gas-permeable containers have been used to expand TILs using PBMCs using methods, compositions, and devices known in the art, including those described in U.S. Patent Application Publication No. 2005/0106717 A1, the disclosures of which are incorporated herein by reference. In an embodiment, TILs are expanded in gas-permeable bags. In an embodiment, TILs are expanded using a cell expansion system that expands TILs in gas permeable bags, such as the Xuri Cell Expansion System W25 (GE Healthcare). In an embodiment, TILs are expanded using a cell expansion system that expands TILs in gas permeable bags, such as the WAVE Bioreactor System, also known as the Xuri Cell Expansion System W5 (GE Healthcare). In an embodiment, the cell expansion system includes a gas permeable cell bag with a volume selected from the group consisting of about 100 mL, about 200 mL, about 300 mL, about 400 mL, about 500 mL, about 600 mL, about 700 mL, about 800 mL, about 900 mL, about 1 L, about 2 L, about 3 L, about 4 L, about 5 L, about 6 L, about 7 L, about 8 L, about 9 L, and about 10 L.

In an embodiment, TILs can be expanded in G-Rex flasks (commercially available from Wilson Wolf Manufacturing). Such embodiments allow for cell populations to expand from about $5 \times 10^5$ cells/cm$^2$ to between $10 \times 10^6$ and $30 \times 10^6$ cells/cm$^2$. In an embodiment this is without feeding. In an embodiment, this is without feeding so long as medium resides at a height of about 10 cm in the G-Rex flask. In an embodiment this is without feeding but with the addition of one or more cytokines. In an embodiment, the cytokine can be added as a bolus without any need to mix the cytokine with the medium. Such containers, devices, and methods are known in the art and have been used to expand TILs, and include those described in U.S. Patent Application Publication No. US 2014/0377739A1, International Publication No. WO 2014/210036 A1, U.S. Patent Application Publication No. us 2013/0115617 A1, International Publication No. WO 2013/188427 A1, U.S. Patent Application Publication No. US 2011/0136228 A1, U.S. Pat. No. 8,809,050 B2, International publication No. WO 2011/072088 A2, U.S. Patent Application Publication No. US 2016/0208216 A1, U.S. Patent Application Publication No. US 2012/0244133 A1, International Publication No. WO 2012/129201 A1, U.S. Patent Application Publication No. US 2013/0102075 A1, U.S. Pat. No. 8,956,860 B2, International Publication No. WO 2013/173835 A1, U.S. Patent Application Publication No. US 2015/0175966 A1, the disclosures of which are incorporated herein by reference. Such processes are also described in Jin et al., *J. Immunotherapy*, 2012, 35:283-292.

O. Optional Genetic Engineering of TILs

In some embodiments, the TILs are optionally genetically engineered to include additional functionalities, including, but not limited to, a high-affinity T-cell receptor (TCR), e.g., a TCR targeted at a tumor-associated antigen such as MAGE-1, HER2, or NY-ESO-1, or a chimeric antigen receptor (CAR) which binds to a tumor-associated cell surface molecule (e.g., mesothelin) or lineage-restricted cell surface molecule (e.g., CD19).

P. Optional Cryopreservation of TILs

Either the bulk TIL population or the expanded population of TILs can be optionally cryopreserved. In some embodiments, cryopreservation occurs on the therapeutic TIL population. In some embodiments, cryopreservation occurs on the TILs harvested after the second expansion. In some embodiments, cryopreservation occurs on the TILs in exemplary Step F of FIG. 9. In some embodiments, the TILs are cryopreserved in the infusion bag. In some embodiments, the TTLs are cryopreserved prior to placement in an infusion bag. In some embodiments, the TILs are cryopreserved and not placed in an infusion bag. In some embodiments, cryopreservation is performed using a cryopreservation medium. In some embodiments, the cryopreservation media contains dimethylsulfoxide (DMSO). This is generally accomplished by putting the TIL population into a freezing solution, e.g. 85% complement inactivated AB serum and 15% dimethyl sulfoxide (DMSO). The cells in solution are placed into cryogenic vials and stored for 24 hours at −80° C., with optional transfer to gaseous nitrogen freezers for cryopreservation. See, Sadeghi, et al., *Acta Oncologica* 2013, 52, 978-986.

When appropriate, the cells are removed from the freezer and thawed in a 37° C. water bath until approximately ⅘ of the solution is thawed. The cells are generally resuspended in complete media and optionally washed one or more times. In some embodiments, the thawed TILs can be counted and assessed for viability as is known in the art.

In a preferred embodiment, a population of TILs is cryopreserved using CS10 cryopreservation media (CryoStor 10, BioLife Solutions). In a preferred embodiment, a population of TILs is cryopreserved using a cryopreservation media containing dimethylsulfoxide (DMSO). In a preferred embodiment, a population of TILs is cryopreserved using a 1:1 (vol:vol) ratio of CS10 and cell culture media. In a preferred embodiment, a population of TILs is cryopreserved using about a 1:1 (vol:vol) ratio of CS10 and cell culture media, further comprising additional IL-2.

As discussed above in Steps A through E, cryopreservation can occur at numerous points throughout the TIL expansion process. In some embodiments, the bulk TIL population after the first expansion according to Step B or the expanded population of TILs after the one or more second expansions according to Step D can be cryopreserved. Cryopreservation can be generally accomplished by placing the TIL population into a freezing solution, e.g., 85% complement inactivated AB serum and 15% dimethyl sulfoxide (DMSO). The cells in solution are placed into cryogenic vials and stored for 24 hours at −80° C., with optional transfer to gaseous nitrogen freezers for cryopreservation. See Sadeghi, et al., *Acta Oncologica* 2013, 52, 978-986.

When appropriate, the cells are removed from the freezer and thawed in a 37° C. water bath until approximately ⅘ of the solution is thawed. The cells are generally resuspended in complete media and optionally washed one or more times. In some embodiments, the thawed TTLs can be counted and assessed for viability as is known in the art.

In some cases, the Step B TIL population can be cryopreserved immediately, using the protocols discussed below. Alternatively, the bulk TIL population can be subjected to Step C and Step D and then cryopreserved after Step D. Similarly, in the case where genetically modified TTLs will be used in therapy, the Step B or Step D TIL populations can be subjected to genetic modifications for suitable treatments.

Q. Optional Cell Viability Analyses

Optionally, a cell viability assay can be performed after the first expansion (sometimes referred to as the initial bulk expansion), using standard assays known in the art. For example, a trypan blue exclusion assay can be done on a sample of the bulk TILs, which selectively labels dead cells and allows a viability assessment. Other assays for use in testing viability can include but are not limited to the Alamar blue assay; and the MTT assay.

1. Cell Counts, Viability, Flow Cytometry

In some embodiments, cell counts and/or viability are measured. The expression of markers such as but not limited CD3, CD4, CD8, and CD56, as well as any other disclosed or described herein, can be measured by flow cytometry with antibodies, for example but not limited to those commercially available from BD Bio-sciences (BD Biosciences, San Jose, CA) using a FACSCantom flow cytometer (BD Biosciences). The cells can be counted manually using a disposable c-chip hemocytometer (VWR, Batavia, IL) and viability can be assessed using any method known in the art, including but not limited to trypan blue staining.

In some cases, the bulk TIL population can be cryopreserved immediately, using the protocols discussed below. Alternatively, the bulk TIL population can be subjected to REP and then cryopreserved as discussed below. Similarly, in the case where genetically modified TILs will be used in therapy, the bulk or REP TIL populations can be subjected to genetic modifications for suitable treatments.

2. Cell Cultures

In an embodiment, a method for expanding TILs may include using about 5,000 mL to about 25,000 mL of cell medium, about 5,000 mL to about 10,000 mL of cell medium, or about 5,800 mL to about 8,700 mL of cell medium. In an embodiment, expanding the number of TILs uses no more than one type of cell culture medium. Any suitable cell culture medium may be used, e.g., AIM-V cell medium (L-glutamine, 50 µM streptomycin sulfate, and 10 µM gentamicin sulfate) cell culture medium (Invitrogen, Carlsbad CA). In this regard, the inventive methods advantageously reduce the amount of medium and the number of types of medium required to expand the number of TIL. In an embodiment, expanding the number of TIL may comprise feeding the cells no more frequently than every third or fourth day. Expanding the number of cells in a gas permeable container simplifies the procedures necessary to expand the number of cells by reducing the feeding frequency necessary to expand the cells.

In an embodiment, the cell medium in the first and/or second gas permeable container is unfiltered. The use of unfiltered cell medium may simplify the procedures necessary to expand the number of cells. In an embodiment, the cell medium in the first and/or second gas permeable container lacks beta-mercaptoethanol (BME).

In an embodiment, the duration of the method comprising obtaining a tumor tissue sample from the mammal; culturing the tumor tissue sample in a first gas permeable container containing cell medium therein; obtaining TILs from the tumor tissue sample; expanding the number of TILs in a second gas permeable container containing cell medium therein using aAPCs for a duration of about 14 to about 42 days, e.g., about 28 days.

In an embodiment, TILs are expanded in gas-permeable containers. Gas-permeable containers have been used to expand TILs using PBMCs using methods, compositions, and devices known in the art, including those described in U.S. Patent Application Publication No. 2005/0106717 A1, the disclosures of which are incorporated herein by reference. In an embodiment, TILs are expanded in gas-permeable bags. In an embodiment, TILs are expanded using a cell expansion system that expands TILs in gas permeable bags, such as the Xuri Cell Expansion System W25 (GE Healthcare). In an embodiment, TILs are expanded using a cell expansion system that expands TILs in gas permeable bags, such as the WAVE Bioreactor System, also known as the Xuri Cell Expansion System W5 (GE Healthcare). In an embodiment, the cell expansion system includes a gas permeable cell bag with a volume selected from the group consisting of about 100 mL, about 200 mL, about 300 mL, about 400 mL, about 500 mL, about 600 mL, about 700 mL, about 800 mL, about 900 mL, about 1 L, about 2 L, about 3 L, about 4 L, about 5 L, about 6 L, about 7 L, about 8 L, about 9 L, and about 10 L.

In an embodiment, TILs can be expanded in G-Rex flasks (commercially available from Wilson Wolf Manufacturing). Such embodiments allow for cell populations to expand from about $5 \times 10^5$ cells/cm$^2$ to between $10 \times 10^6$ and $30 \times 10^6$ cells/cm$^2$. In an embodiment this is without feeding. In an embodiment, this is without feeding so long as medium resides at a height of about 10 cm in the G-Rex flask. In an embodiment this is without feeding but with the addition of one or more cytokines. In an embodiment, the cytokine can be added as a bolus without any need to mix the cytokine with the medium. Such containers, devices, and methods are known in the art and have been used to expand TILs, and include those described in U.S. Patent Application Publication No. US 2014/0377739A1, International Publication No. WO 2014/210036 A1, U.S. Patent Application Publication No. us 2013/0115617 A1, International Publication No. WO 2013/188427 A1, U.S. Patent Application Publication No. US 2011/0136228 A1, U.S. Pat. No. 8,809,050 B2, International publication No. WO 2011/072088 A2, U.S. Patent Application Publication No. US 2016/0208216 A1, U.S. Patent Application Publication No. US 2012/0244133 A1, International Publication No. WO 2012/129201 A1, U.S. Patent Application Publication No. US 2013/0102075 A1, U.S. Pat. No. 8,956,860 B2, International Publication No. WO 2013/173835 A1, U.S. Patent Application Publication No. US 2015/0175966 A1, the disclosures of which are incorporated herein by reference. Such processes are also described in Jin et al., *J. Immunotherapy,* 2012, 35:283-292.

Optional Genetic Engineering of TILs

In some embodiments, the TILs are optionally genetically engineered to include additional functionalities, including, but not limited to, a high-affinity T-cell receptor (TCR), e.g., a TCR targeted at a tumor-associated antigen such as MAGE-1, HER2, or NY-ESO-1, or a chimeric antigen receptor (CAR) which binds to a tumor-associated cell surface molecule (e.g., mesothelin) or lineage-restricted cell surface molecule (e.g., CD19).

IV. Methods of Treating Patients

Methods of treatment begin with the initial TIL collection and culture of TILs. Such methods have been both described in the art by, for example, Jin et al., *J. Immunotherapy*, 2012, 35(3):283-292, incorporated by reference herein in its entirety. Embodiments of methods of treatment are described throughout the sections below, including the Examples.

The expanded TILs produced according the methods described herein, including, for example as described in Steps A through F above or according to Steps A through F above (also as shown, for example, in FIG. 2A and/or FIG. 9 find particular use in the treatment of patients with cancer (for example, as described in Goff, et al., *J. Clinical Oncology*, 2016, 34(20):2389-239, as well as the supplemental content; incorporated by reference herein in its entirety. In some embodiments, TIL were grown from resected deposits of metastatic melanoma as previously described (see, Dudley, et al., *J Immunother.*, 2003, 26:332-342; incorporated by reference herein in its entirety). Fresh tumor can be dissected under sterile conditions. A representative sample can be collected for formal pathologic analysis. Single fragments of 2 $mm^3$ to 3 $mm^3$ may be used. In some embodiments, 5, 10, 15, 20, 25 or 30 samples per patient are obtained. In some embodiments, 20, 25, or 30 samples per patient are obtained. In some embodiments, 20, 22, 24, 26, or 28 samples per patient are obtained. In some embodiments, 24 samples per patient are obtained. Samples can be placed in individual wells of a 24-well plate, maintained in growth media with high-dose IL-2 (6,000 IU/mL), and monitored for destruction of tumor and/or proliferation of TIL. Any tumor with viable cells remaining after processing can be enzymatically digested into a single cell suspension and cryopreserved, as described herein.

In some embodiments, successfully grown TIL can be sampled for phenotype analysis (CD3, CD4, CD8, and CD56) and tested against autologous tumor when available. TIL can be considered reactive if overnight coculture yielded interferon-gamma (IFN-γ) levels>200 pg/mL and twice background. (Goff, et al., *J Immunother.*, 2010, 33:840-847; incorporated by reference herein in its entirety). In some embodiments, cultures with evidence of autologous reactivity or sufficient growth patterns can be selected for a second expansion (for example, a second expansion as provided in according to Step D of FIG. 2A and/or FIG. 9, including second expansions that are sometimes referred to as rapid expansion (REP). In some embodiments, expanded TILs with high autologous reactivity (for example, high proliferation during a second expansion), are selected for an additional second expansion. In some embodiments, TILs with high autologous reactivity (for example, high proliferation during second expansion as provided in Step D of FIG. 2A and/or FIG. 9, are selected for an additional second expansion according to Step D of FIG. 2A and/or FIG. 9.

In some embodiments, the patient is not moved directly to ACT (adoptive cell transfer), for example, in some embodiments, after tumor harvesting and/or a first expansion, the cells are not utilized immediately. In some embodiments, TILs can be cryopreserved and thawed 2 days before administration to a patient. In some embodiments, TILs can be cryopreserved and thawed 1 day before administration to a patient. In some embodiments, the TILs can be cryopreserved and thawed immediately before the administration to a patient.

Cell phenotypes of cryopreserved samples of infusion bag TIL can be analyzed by flow cytometry (e.g., FlowJo) for surface markers CD3, CD4, CD8, CCR7, and CD45RA (BD BioSciences), as well as by any of the methods described herein. Serum cytokines can be measured by using standard enzyme-linked immunosorbent assay techniques. A rise in serum IFN-γ can be defined as >100 pg/mL and at least 4-fold or at least 3-fold or at least 2-fold or at least 1-fold greater than baseline levels of serum IFN-γ. In some embodiments, a rise in serum IFN-γ is defined as >1000 pg/mL. In some embodiments, a rise in serum IFN-γ is defined as >200 pg/mL. In some embodiments, a rise in serum IFN-γ is defined as >250 pg/mL. In some embodiments, a rise in serum IFN-γ is defined as >300 pg/mL. In some embodiments, a rise in serum IFN-γ is defined as >350 pg/mL. In some embodiments, a rise in serum IFN-γ is defined as >400 pg/mL. In some embodiments, a rise in serum IFN-γ is defined as >450 pg/mL. In some embodiments, a rise in serum IFN-γ is defined as >500 pg/mL. In some embodiments, a rise in serum IFN-γ is defined as >550 pg/mL. In some embodiments, a rise in serum IFN-γ is defined as >600 pg/mL. In some embodiments, a rise in serum IFN-γ is defined as >650 pg/mL. In some embodiments, a rise in serum IFN-γ is defined as >700 pg/mL. In some embodiments, a rise in serum IFN-γ is defined as >750 pg/mL. In some embodiments, a rise in serum IFN-γ is defined as >800 pg/mL. In some embodiments, a rise in serum IFN-γ is defined as >850 pg/mL. In some embodiments, a rise in serum IFN-γ is defined as >900 pg/mL. In some embodiments, a rise in serum IFN-γ is defined as >950 pg/mL. In some embodiments, a rise in serum IFN-γ is defined as >1000 pg/mL.

In some embodiments, the TILs produced by the methods provided herein, for example those exemplified in FIG. 2A and/or FIG. 9, provide for a surprising improvement in clinical efficacy of the TILs. In some embodiments, the TILs produced by the methods provided herein, for example those exemplified in FIG. 2A and/or FIG. 9, exhibit increased clinical efficacy as compared to TILs produced by methods other than those described herein, including, for example, methods other than those exemplified in FIG. 2A and/or FIG. 9. In some embodiments, the methods other than those described herein include methods referred to as process 1C and/or Generation 1 (Gen 1). In some embodiments, the increased efficacy is measured by DCR, ORR, and/or other clinical responses. In some embodiments, the TILs produced by the methods provided herein, for example those exemplified in FIG. 2A and/or FIG. 9, exhibit a similar time to response and safety profile compared to TILs produced by methods other than those described herein, including, for example, methods other than those exemplified in FIG. 2A and/or FIG. 9, for example the Gen 1 process.

In some embodiments, IFN-gamma (IFN-γ) is indicative of treatment efficacy and/or increased clinical efficacy. In some embodiments, IFN-γ in the blood of subjects treated with TILs is indicative of active TILs. In some embodiments, a potency assay for IFN-γ production is employed. IFN-γ production is another measure of cytotoxic potential. IFN-γ production can be measured by determining the levels of the cytokine IFN-γ in the blood, serum, or TILs ex vivo of a subject treated with TILs prepared by the methods of the present invention, including those as described for example in FIG. 2A and/or FIG. 9. In some embodiments, an increase in IFN-γ is indicative of treatment efficacy in a patient treated with the TILs produced by the methods of the present invention. In some embodiments, IFN-γ is increased one-fold, two-fold, three-fold, four-fold, or five-fold or more as compared to an untreated patient and/or as compared to a patient treated with TILs prepared using other methods than those provide herein including, for example, methods other than those embodied in FIG. 2A and/or FIG. 9. In some embodiments, IFN-γ secretion is increased one-fold as compared to an untreated patient and/or as compared to a patient treated with TILs prepared using other methods than those provided herein including, for example, methods other than those embodied in FIG. 2A and/or FIG. 9. In some embodiments, IFN-γ secretion is increased two-fold as compared to an untreated patient and/or as compared to a patient treated with TILs prepared using other methods than those provide herein including, for example, methods other than those embodied in FIG. 2A and/or FIG. 9. In some embodiments, IFN-γ secretion is increased three-fold as compared to an untreated patient and/or as compared to a patient treated with TILs prepared using other methods than those provide herein including, for example, methods other than those embodied in FIG. 2A and/or FIG. 9. In some embodiments, IFN-γ secretion is increased four-fold as compared to an untreated patient and/or as compared to a patient treated with TILs prepared using other methods than those provide herein including, for example, methods other than those embodied in FIG. 2A and/or FIG. 9. In some embodiments, IFN-γ secretion is increased five-fold as compared to an untreated patient and/or as compared to a patient treated with TILs prepared using other methods than those provide herein including, for example, methods other than those embodied in FIG. 2A and/or FIG. 9. In some embodiments, IFN-γ is measured using a Quantikine ELISA kit. In some embodiments, IFN-γ is measured in TILs ex vivo of a subject treated with TILs prepared by the methods of the present invention, including those as described for example in FIG. 2A and/or FIG. 9. In some embodiments, IFN-γ is measured in blood of a subject treated with TILs prepared by the methods of the present invention, including those as described for example in FIG. 2A and/or FIG. 9. In some embodiments, IFN-γ is measured in TILs serum of a subject treated with TILs prepared by the methods of the present invention, including those as described for example in FIG. 2A and/or FIG. 9.

In some embodiments, the TILs prepared by the methods of the present invention, including those as described for example in FIG. 2A and/or FIG. 9, exhibit increased polyclonality as compared to TILs produced by other methods, including those not exemplified in FIG. 2A and/or FIG. 9, such as for example, methods referred to as process 1C methods. In some embodiments, significantly improved polyclonality and/or increased polyclonality is indicative of treatment efficacy and/or increased clinical efficacy. In some embodiments, polyclonality refers to the T-cell repertoire diversity. In some embodiments, an increase in polyclonality can be indicative of treatment efficacy with regard to administration of the TILs produced by the methods of the present invention. In some embodiments, polyclonality is increased one-fold, two-fold, ten-fold, 100-fold, 500-fold, or 1000-fold as compared to TILs prepared using methods than those provide herein including, for example, methods other than those embodied in FIG. 2A and/or FIG. 9. In some embodiments, polyclonality is increased one-fold as compared to an untreated patient and/or as compared to a patient treated with TILs prepared using other methods than those provide herein including, for example, methods other than those embodied in FIG. 2A and/or FIG. 9. In some embodiments, polyclonality is increased two-fold as compared to an untreated patient and/or as compared to a patient treated with TILs prepared using other methods than those provide herein including, for example, methods other than those embodied in FIG. 2A and/or FIG. 9. In some embodiments, polyclonality is increased ten-fold as compared to an untreated patient and/or as compared to a patient treated with TILs prepared using other methods than those provide herein including, for example, methods other than those embodied in FIG. 2A and/or FIG. 9. In some embodiments, polyclonality is increased 100-fold as compared to an untreated patient and/or as compared to a patient treated with TILs prepared using other methods than those provide herein including, for example, methods other than those embodied in FIG. 2A and/or FIG. 9. In some embodiments, polyclonality is increased 500-fold as compared to an untreated patient and/or as compared to a patient treated with TILs prepared using other methods than those provide herein including, for example, methods other than those embodied in FIG. 2A and/or FIG. 9. In some embodiments, polyclonality is increased 1000-fold as compared to an untreated patient and/or as compared to a patient treated with TILs prepared using other methods than those provide herein including, for example, methods other than those embodied in FIG. 2A and/or FIG. 9.

Measures of efficacy can include the disease control rate (DCR) as well as overall response rate (ORR), as known in the art as well as described herein.

A. Methods of Treating Cancers

The compositions and methods described herein can be used in a method for treating diseases. In an embodiment, they are for use in treating hyperproliferative disorders, such as cancer, in an adult patient or in a pediatric patient. They may also be used in treating other disorders as described herein and in the following paragraphs.

In some embodiments, the hyperproliferative disorder is cancer. In some embodiments, the hyperproliferative disorder is a solid tumor cancer. In some embodiments, the solid tumor cancer is selected from the group consisting of anal cancer, bladder cancer, breast cancer (including triple-negative breast cancer), bone cancer, cancer caused by human papilloma virus (HPV), central nervous system associated cancer (including ependymoma, medulloblastoma, neuroblastoma, pineoblastoma, and primitive neuroectodermal tumor), cervical cancer (including squamous cell cervical cancer, adenosquamous cervical cancer, and cervical adenocarcinoma), colon cancer, colorectal cancer, endometrial cancer, esophageal cancer, esophagogastric junction cancer, gastric cancer, gastrointestinal cancer, gastrointestinal stromal tumor, glioblastoma, glioma, head and neck cancer (including head and neck squamous cell carcinoma (HNSCC), hypopharynx cancer, larynx cancer, nasopharynx cancer, oropharynx cancer, and pharynx cancer), kidney cancer, liver cancer, lung cancer (including non-small-cell lung cancer (NSCLC) and small-cell lung cancer), melanoma (including uveal melanoma, choroidal melanoma, ciliary body melanoma, or iris melanoma), mesothelioma (including malignant pleural mesothelioma), ovarian cancer, pancreatic cancer (including pancreatic ductal adenocarcinoma), penile cancer, rectal cancer, renal cancer, renal cell carcinoma, sarcoma (including Ewing sarcoma, osteosarcoma, rhabdomyosarcoma, and other bone and soft tissue sarcomas), thyroid cancer (including anaplastic thyroid cancer), uterine cancer, and vaginal cancer.

In some embodiments, the hyperproliferative disorder is a hematological malignancy. In some embodiments, the hematological malignancy is selected from the group consisting of chronic lymphocytic leukemia, acute lymphoblastic leukemia, diffuse large B cell lymphoma, non-Hodgkin's lymphoma, Hodgkin's lymphoma, follicular lymphoma, mantle cell lymphoma, and multiple myeloma. In some embodiments, the present invention includes a method of treating a patient with a cancer, wherein the cancer is a hematological malignancy. In some embodiments, the present invention includes a method of treating a patient with a cancer using TILs, MILs, or PBLs modified to express one or more CCRs, wherein the cancer is a hematological malignancy. In some embodiments, the present invention includes a method of treating a patient with a cancer using MILs or PBLs modified to express one or more CCRs, wherein the cancer is a hematological malignancy.

In an embodiment, the cancer is one of the foregoing cancers, including solid tumor cancers and hematological malignancies, that is relapsed or refractory to treatment with at least one prior therapy, including chemotherapy, radiation therapy, or immunotherapy. In an embodiment, the cancer is one of the foregoing cancers that is relapsed or refractory to treatment with at least two prior therapies, including chemotherapy, radiation therapy, and/or immunotherapy. In an embodiment, the cancer is one of the foregoing cancers that is relapsed or refractory to treatment with at least three prior therapies, including chemotherapy, radiation therapy, and/or immunotherapy.

In some embodiments, the cancer is a microsatellite instability-high (MSI-H) or a mismatch repair deficient (dMMR) cancer. MSI-H and dMMR cancers and testing therefore have been described in Kawakami, et al., Curr. Treat. Options Oncol. 2015, 16, 30, the disclosures of which are incorporated by reference herein.

In some embodiments, the present invention includes a method of treating a patient with a cancer using TILs, MILs, or PBLs modified to express one or more CCRs, wherein the patient is a human. In some embodiments, the present invention includes a method of treating a patient with a cancer using TILs, MILs, or PBLs modified to express one or more CCRs, wherein the patient is a non-human. In some embodiments, the present invention includes a method of treating a patient with a cancer using TILs, MILs, or PBLs modified to express one or more CCRs, wherein the patient is a companion animal. In some embodiments, the present invention includes a method of treating a patient with a cancer using TILs, MILs, or PBLs modified to express one or more CCRs, wherein the patient is a primate, equine, canine, or feline animal.

In some embodiments, the present invention includes a method of treating a patient with a cancer, wherein the cancer is refractory to treatment with a BRAF inhibitor and/or a MEK inhibitor. In some embodiments, the present invention includes a method of treating a patient with a cancer, wherein the cancer is refractory to treatment with a BRAF inhibitor selected from the group consisting of vemurafenib, dabrafenib, encorafenib, sorafenib, and pharmaceutically acceptable salts or solvates thereof. In some embodiments, the present invention includes a method of treating a patient with a cancer, wherein the cancer is refractory to treatment with a MEK inhibitor selected from the group consisting of trametinib, cobimetinib, binimetinib, selumetinib, pimasertinib, refametinib, and pharmaceutically acceptable salts or solvates thereof. In some embodiments, the present invention includes a method of treating a patient with a cancer, wherein the cancer is refractory to treatment with a BRAF inhibitor selected from the group consisting of vemurafenib, dabrafenib, encorafenib, sorafenib, and pharmaceutically acceptable salts or solvates thereof, and a MEK inhibitor selected from the group consisting of trametinib, cobimetinib, binimetinib, selumetinib, pimasertinib, refametinib, and pharmaceutically acceptable salts or solvates thereof.

In some embodiments, the present invention includes a method of treating a patient with a cancer, wherein the cancer is a pediatric cancer.

In some embodiments, the present invention includes a method of treating a patient with a cancer wherein the cancer is uveal melanoma.

In some embodiments, the present invention includes a method of treating a patient with a cancer, wherein the uveal melanoma is choroidal melanoma, ciliary body melanoma, or iris melanoma.

In some embodiments, the present invention includes a method of treating a patient with a cancer, wherein the pediatric cancer is a neuroblastoma.

In some embodiments, the present invention includes a method of treating a patient with a cancer, wherein the pediatric cancer is a sarcoma.

In some embodiments, the present invention includes a method of treating a patient with a cancer, wherein the sarcoma is osteosarcoma.

In some embodiments, the present invention includes a method of treating a patient with a cancer, wherein the sarcoma is a soft tissue sarcoma.

In some embodiments, the present invention includes a method of treating a patient with a cancer, wherein the soft tissue sarcoma is rhabdomyosarcoma, Ewing sarcoma, or primitive neuroectodermal tumor (PNET).

In some embodiments, the present invention includes a method of treating a patient with a cancer, wherein the pediatric cancer is a central nervous system (CNS) associated cancer. In some embodiments, the pediatric cancer is refractory to treatment with chemotherapy. In some embodiments, the pediatric cancer is refractory to treatment with radiation therapy. In some embodiments, the pediatric cancer is refractory to treatment with dinutuximab.

In some embodiments, the present invention includes a method of treating a patient with a cancer, wherein the CNS associated cancer is medulloblastoma, pineoblastoma, glioma, ependymoma, or glioblastoma.

The compositions and methods described herein can be used in a method for treating cancer, wherein the cancer is refractory or resistant to prior treatment with an anti-PD-1 or anti-PD-L1 antibody. In some embodiments, the patient is a primary refractory patient to an anti-PD-1 or anti-PD-L1 antibody. In some embodiments, the patient shows no prior response to an anti-PD-1 or anti-PD-L1 antibody. In some embodiments, the patient shows a prior response to an anti-PD-1 or anti-PD-L1 antibody, follow by progression of the patient's cancer. In some embodiments, the cancer is refractory to an anti-CTLA-4 antibody and/or an anti-PD-1 or anti-PD-L1 antibody in combination with at least one chemotherapeutic agent. In some embodiments, the prior chemotherapeutic agent is carboplatin, paclitaxel, pemetrexed, and/or cisplatin. In some prior embodiments, the chemotherapeutic agent(s) is a platinum doublet chemotherapeutic agent. In some embodiments, the platinum doublet therapy comprises a first chemotherapeutic agent selected from the group consisting of cisplatin and carboplatin and a second chemotherapeutic agent selected from the group consisting of vinorelbine, gemcitabine and a taxane (including for example, paclitaxel, docetaxel or nab-paclitaxel). In some embodiments, the platinum doublet chemotherapeutic agent is in combination with pemetrexed.

In some embodiments, the NSCLC is PD-L1 negative and/or is from a patient with a cancer that expresses PD-L1 with a tumor proportion score (TPS) of <1%, as described elsewhere herein.

In some embodiments, the NSCLC is refractory to a combination therapy comprising an anti-PD-1 or the anti-PD-L1 antibody and a platinum doublet therapy, wherein the platinum doublet therapy comprises:
i) a first chemotherapeutic agent selected from the group consisting of cisplatin and carboplatin,
ii) and a second chemotherapeutic agent selected from the group consisting of vinorelbine, gemcitabine and a taxane (including for example, paclitaxel, docetaxel or nab-paclitaxel).

In some embodiments, the NSCLC is refractory to a combination therapy comprising an anti-PD-1 or the anti-PD-L1 antibody, pemetrexed, and a platinum doublet therapy, wherein the platinum doublet therapy comprises:
i) a first chemotherapeutic agent selected from the group consisting of cisplatin and carboplatin,
ii) and a second chemotherapeutic agent selected from the group consisting of vinorelbine, gemcitabine and a taxane (including for example, paclitaxel, docetaxel or nab-paclitaxel).

In some embodiments, the NSCLC has been treated with an anti-PD-1 antibody. In some embodiments, the NSCLC has been treated with an anti-PD-L1 antibody. In some embodiments, the NSCLC patient is treatment naïve. In some embodiments, the NSCLC has not been treated with an anti-PD-1 antibody. In some embodiments, the NSCLC has not been treated with an anti-PD-L1 antibody. In some embodiments, the NSCLC has been previously treated with a chemotherapeutic agent. In some embodiments, the NSCLC has been previously treated with a chemotherapeutic agent but is not longer being treated with the chemotherapeutic agent. In some embodiments, the NSCLC patient is anti-PD-1/PD-L1 naïve. In some embodiments, the NSCLC patient has low expression of PD-L1. In some embodiments, the NSCLC patient has treatment naïve NSCLC or is post-chemotherapeutic treatment but anti-PD-1/PD-L1 naïve. In some embodiments, the NSCLC patient is treatment naïve or post-chemotherapeutic treatment but anti-PD-1/PD-L1 naïve and has low expression of PD-L1. In some embodiments, the NSCLC patient has bulky disease at baseline. In some embodiments, the subject has bulky disease at baseline and has low expression of PD-L1. In some embodiments, the NSCLC patient has no detectable expression of PD-L1. In some embodiments, the NSCLC patient is treatment naïve or post-chemotherapeutic treatment but anti-PD-1/PD-L1 naïve and has no detectable expression of PD-L1. In some embodiments, the patient has bulky disease at baseline and has no detectable expression of PD-L1. In some embodiments, the NSCLC patient has treatment naïve NSCLC or post chemotherapy (e.g., post chemotherapeutic agent) but anti-PD-1/PD-L1 naïve who have low expression of PD-L1 and/or have bulky disease at baseline. In some embodiments, bulky disease is indicated where the maximal tumor diameter is greater than 7 cm measured in either the transverse or coronal plane. In some embodiments, bulky disease is indicated when there are swollen lymph nodes with a short-axis diameter of 20 mm or greater. In some embodiments, the chemotherapeutic includes a standard of care therapeutic for NSCLC.

In some embodiments, PD-L1 expression is determined by the tumor proportion score. In some embodiments, the subject with a refractory NSCLC tumor has a <1% tumor proportion score (TPS). In some embodiments, the subject with a refractory NSCLC tumor has a ≥1% TPS. In some embodiments, subject with the refractory NSCLC has been previously treated with an anti-PD-1 and/or anti-PD-L1 antibody and the tumor proportion score was determined prior to said anti-PD-1 and/or anti-PD-L1 antibody treatment. In some embodiments, subject with the refractory NSCLC has been previously treated with an anti-PD-L1 antibody and the tumor proportion score was determined prior to said anti-PD-L1 antibody treatment.

In some embodiments, the TILs prepared by the methods of the present invention, including those as described for example in FIG. 1, exhibit increased polyclonality as compared to TILs produced by other methods, including those not exemplified in FIG. 1, such as for example, methods referred to as process 1C methods. In some embodiments, significantly improved polyclonality and/or increased polyclonality is indicative of treatment efficacy and/or increased clinical efficacy for cancer treatment. In some embodiments, polyclonality refers to the T-cell repertoire diversity. In some embodiments, an increase in polyclonality can be indicative of treatment efficacy with regard to administration of the TILs produced by the methods of the present invention. In some embodiments, polyclonality is increased one-fold, two-fold, ten-fold, 100-fold, 500-fold, or 1000-fold as compared to TILs prepared using methods than those provide herein including for example, methods other than those embodied in FIG. 1. In some embodiments, polyclonality is increased one-fold as compared to an untreated patient and/or as compared to a patient treated with TILs prepared using other methods than those provide herein including for example, methods other than those embodied in FIG. 1. In some embodiments, polyclonality is increased two-fold as compared to an untreated patient and/or as compared to a patient treated with TILs prepared using other methods than those provide herein including for example, methods other than those embodied in FIG. 1. In some embodiments, polyclonality is increased ten-fold as compared to an untreated patient and/or as compared to a patient treated with TILs prepared using other methods than those provide herein including for example, methods other than those embodied in FIG. 1. In some embodiments, polyclonality is increased 100-fold as compared to an untreated patient and/or as compared to a patient treated with TILs prepared using other methods than those provide herein including for example, methods other than those embodied in FIG. 1. In some embodiments, polyclonality is increased 500-fold as compared to an untreated patient and/or as compared to a patient treated with TILs prepared using other methods than those provide herein including for example, methods other than those embodied in FIG. 1. In some embodiments, polyclonality is increased 1000-fold as compared to an untreated patient and/or as compared to a patient treated with TILs prepared using other methods than those provide herein including for example, methods other than those embodied in FIG. 1.

In some embodiments, PD-L1 expression is determined by the tumor proportion score using one more testing methods as described herein. In some embodiments, the subject or patient with a NSCLC tumor has a <1% tumor proportion score (TPS). In some embodiments, the NSCLC tumor has a ≥1% TPS. In some embodiments, the subject or patient with the NSCLC has been previously treated with an anti-PD-1 and/or anti-PD-L1 antibody and the tumor proportion score was determined prior to the anti-PD-1 and/or anti-PD-L1 antibody treatment. In some embodiments, the subject or patient with the NSCLC has been previously treated with an anti-PD-L1 antibody and the tumor proportion score was determined prior to the anti-PD-L1 antibody treatment. In some embodiments, the subject or patient with a refractory or resistant NSCLC tumor has a <1% tumor proportion score (TPS). In some embodiments, the subject or patient with a refractory or resistant NSCLC tumor has a ≥1% TPS. In some embodiments, the subject or patient with the refractory or resistant NSCLC has been previously treated with an anti-PD-1 and/or anti-PD-L1 antibody and the tumor proportion score was determined prior to the anti-PD-1 and/or anti-PD-L1 antibody treatment. In some embodiments, the subject or patient with the refractory or resistant NSCLC has been previously treated with an anti-PD-L1 antibody and the tumor proportion score was determined prior to the anti-PD-L1 antibody treatment.

In some embodiments, the NSCLC is an NSCLC that exhibits a tumor proportion score (TPS), or the percentage of viable tumor cells from a patient taken prior to anti-PD-1 or anti-PD-L1 therapy, showing partial or complete membrane staining at any intensity, for the PD-L1 protein that is less than 1% (TPS<1%). In an embodiment, the NSCLC is an NSCLC that exhibits a TPS selected from the group consisting of <50%, <45%, <40%, <35%, <30%, <25%, <20%, <15%, <10%, <9%, <8%, <7%, <6%, <5%, <4%, <3%, <2%, <1%, <0.9%, <0.8%, <0.7%, <0.6%, <0.5%, <0.4%, <0.3%, <0.2%, <0.1%, <0.09%, <0.08%, <0.07%, <0.06%, <0.05%, <0.04%, <0.03%, <0.02%, and <0.01%. In an embodiment, the NSCLC is an NSCLC that exhibits a TPS selected from the group consisting of about 50%, about 45%, about 40%, about 35%, about 30%, about 25%, about 20%, about 15%, about 10%, about 9%, about 8%, about 7%, about 6%, about 5%, about 4%, about 3%, about 2%, about 1%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, and about 0.01%. In an embodiment, the NSCLC is an NSCLC that exhibits a TPS between 0% and 1%. In an embodiment, the NSCLC is an NSCLC that exhibits a TPS between 0% and 0.9%. In an embodiment, the NSCLC is an NSCLC that exhibits a TPS between 0% and 0.8%. In an embodiment, the NSCLC is an NSCLC that exhibits a TPS between 0% and 0.7%. In an embodiment, the NSCLC is an NSCLC that exhibits a TPS between 0% and 0.6%. In an embodiment, the NSCLC is an NSCLC that exhibits a TPS between 0% and 0.5%. In an embodiment, the NSCLC is an NSCLC that exhibits a TPS between 0% and 0.4%. In an embodiment, the NSCLC is an NSCLC that exhibits a TPS between 0% and 0.3%. In an embodiment, the NSCLC is an NSCLC that exhibits a TPS between 0% and 0.2%. In an embodiment, the NSCLC is an NSCLC that exhibits a TPS between 0% and 0.1%. TPS may be measured by methods known in the art, such as those described in Hirsch, et al. *J. Thorac. Oncol.* 2017, 12, 208-222 or those used for the determination of TPS prior to treatment with pembrolizumab or other anti-PD-1 or anti-PD-L1 therapies. Methods for measurement of TPS that have been approved by the U.S. Food and Drug Administration may also be used. In some embodiments, the PD-L1 is exosomal PD-L1. In some embodiments, the PD-L1 is found on circulating tumor cells.

In some embodiments, the partial membrane staining includes 1%, 5%, 10%, 15%, 20%, 25%, 30%, 35%, 40%, 45%, 50%, 55%, 60%, 65%, 70%, 75%, 80%, 85%, 90%, 95%, 97%, 99%, or more. In some embodiments, the completed membrane staining includes approximately 100% membrane staining.

In some embodiments, testing for PD-L1 can involve measuring levels of PD-L1 in patient serum. In these embodiments, measurement of PD-L1 in patient serum removes the uncertainty of tumor heterogeneity and the patient discomfort of serial biopsies.

In some embodiments, elevated soluble PD-L1 as compared to a baseline or standard level correlates with worsened prognosis in NSCLC. See, for example, Okuma, et al., *Clinical Lung Cancer,* 2018, 19, 410-417; Vecchiarelli, et al., *Oncotarget,* 2018, 9, 17554-17563. In some embodiments, the PD-L1 is exosomal PD-L1. In some embodiments, the PD-L1 is expressed on circulating tumor cells.

In an embodiment, the invention provides a method of treating non-small cell lung carcinoma (NSCLC) by administering a population of tumor infiltrating lymphocytes (TILs) to a subject or patient in need thereof, wherein the subject or patient has at least one of:
 a predetermined tumor proportion score (TPS) of PD-L1<1%,
 a TPS score of PD-L1 of 1%-49%, or
 a predetermined absence of one or more driver mutations, wherein the driver mutation is selected from the group consisting of an EGFR mutation, an EGFR insertion, an EGFR exon 20 mutation, a KRAS mutation, a BRAF mutation, an ALK mutation, a c-ROS mutation (ROS1 mutation), a ROS1 fusion, a RET mutation, a RET fusion, an ERBB2 mutation, an ERBB2 amplification, a BRCA mutation, a MAP2K1 mutation, PIK3CA, CDKN2A, a PTEN mutation, an UMD mutation, an NRAS mutation, a KRAS mutation, an NF1 mutation, a MET mutation, a MET splice and/or altered MET signaling, a TP53 mutation, a CREBBP mutation, a KMT2C mutation, a KMT2D mutation, an ARID1A mutation, a RB1 mutation, an ATM mutation, a SETD2 mutation, a FLT3 mutation, a PTPN11 mutation, a FGFR1 mutation, an EP300 mutation, a MYC mutation, an EZH2 mutation, a JAK2 mutation, a FBXW7 mutation, a CCND3 mutation, and a GNA11 mutation, and wherein the method comprises:
 (a) obtaining and/or receiving a first population of TILs from a tumor resected from the subject or patient by processing a tumor sample obtained from the subject into multiple tumor fragments;
 (b) adding the first population of TILs into a closed system;
 (c) performing a first expansion by culturing the first population of TILs in a cell culture medium comprising IL-2 to produce a second population of TILs, wherein the first expansion is performed in a closed container providing a first gas-permeable surface area, wherein the first expansion is performed for about 3-14 days to obtain the second population of TILs, wherein the second population of TILs is at least 50-fold greater in number than the first population of TILs, and wherein the transition from step (b) to step (c) occurs without opening the system;
 (d) performing a second expansion by supplementing the cell culture medium of the second population of TILs with additional IL-2, OKT-3, and antigen presenting cells (APCs), to produce a third population of TILs, wherein the second expansion is performed for about 7-14 days to obtain the third population of TILs, wherein the third population of TILs is a therapeutic population of TILs, wherein the second expansion is performed in a closed container providing a second gas-permeable surface area, and wherein the transition from step (c) to step (d) occurs without opening the system;

(e) harvesting therapeutic population of TILs obtained from step (d), wherein the transition from step (d) to step (e) occurs without opening the system; and (f) transferring the harvested TIL population from step (e) to an infusion bag, wherein the transfer from step (e) to (f) occurs without opening the system;

(g) cryopreserving the infusion bag comprising the harvested TIL population from step (f) using a cryopreservation process; and (h) administering a therapeutically effective dosage of the third population of TILs from the infusion bag in step (g) to the subject or patient.

In an embodiment, the invention provides a method of treating non-small cell lung carcinoma (NSCLC) by administering a population of tumor infiltrating lymphocytes (TILs) to a patient in need thereof, wherein the method comprises:

(a) testing the patient's tumor for PD-L1 expression and tumor proportion score (TPS) of PD-L1, (b) testing the patient for the absence of one or more driver mutations, wherein the driver mutation is selected from the group consisting of an EGFR mutation, an EGFR insertion, an EGFR exon 20 mutation, a KRAS mutation, a BRAF mutation, an ALK mutation, a c-ROS mutation (ROS1 mutation), a ROS1 fusion, a RET mutation, a RET fusion, an ERBB2 mutation, an ERBB2 amplification, a BRCA mutation, a MAP2K1 mutation, PIK3CA, CDKN2A, a PTEN mutation, an UMD mutation, an NRAS mutation, a KRAS mutation, an NF1 mutation, a MET mutation, a MET splice and/or altered MET signaling, a TP53 mutation, a CREBBP mutation, a KMT2C mutation, a KMT2D mutation, an ARID1A mutation, a RB1 mutation, an ATM mutation, a SETD2 mutation, a FLT3 mutation, a PTPN11 mutation, a FGFR1 mutation, an EP300 mutation, a MYC mutation, an EZH2 mutation, a JAK2 mutation, a FBXW7 mutation, a CCND3 mutation, and a GNA11 mutation, (c) determining that the patient has a TPS score for PD-L1 of about 1% to about 49% and determining that the patient also has no driver mutations, (d) obtaining and/or receiving a first population of TILs from a tumor resected from the subject or patient by processing a tumor sample obtained from the subject into multiple tumor fragments;

(e) adding the first population of TILs into a closed system;

(f) performing a first expansion by culturing the first population of TILs in a cell culture medium comprising IL-2 to produce a second population of TILs, wherein the first expansion is performed in a closed container providing a first gas-permeable surface area, wherein the first expansion is performed for about 3-14 days to obtain the second population of TILs, wherein the second population of TILs is at least 50-fold greater in number than the first population of TILs, and wherein the transition from step (e) to step (f) occurs without opening the system;

(g) performing a second expansion by supplementing the cell culture medium of the second population of TILs with additional IL-2, OKT-3, and antigen presenting cells (APCs), to produce a third population of TILs, wherein the second expansion is performed for about 7-14 days to obtain the third population of TILs, wherein the third population of TILs is a therapeutic population of TILs, wherein the second expansion is performed in a closed container providing a second gas-permeable surface area, and wherein the transition from step (f) to step (g) occurs without opening the system;

(h) harvesting therapeutic population of TILs obtained from step (d), wherein the transition from step (d) to step (e) occurs without opening the system; and (i) transferring the harvested TIL population from step (e) to an infusion bag, wherein the transfer from step (e) to (f) occurs without opening the system;

(j) cryopreserving the infusion bag comprising the harvested TIL population from step (f) using a cryopreservation process; and (k) administering a therapeutically effective dosage of the third population of TILs from the infusion bag in step (g) to the subject or patient.

In an embodiment, the invention provides a method of treating non-small cell lung carcinoma (NSCLC) by administering a population of tumor infiltrating lymphocytes (TILs) to a patient in need thereof, wherein the method comprises:

(a) testing the patient's tumor for PD-L1 expression and tumor proportion score (TPS) of PD-L1, (b) testing the patient for the absence of one or more driver mutations, wherein the driver mutation is selected from the group consisting of an EGFR mutation, an EGFR insertion, an EGFR exon 20 mutation, a KRAS mutation, a BRAF mutation, an ALK mutation, a c-ROS mutation (ROS1 mutation), a ROS1 fusion, a RET mutation, a RET fusion, an ERBB2 mutation, an ERBB2 amplification, a BRCA mutation, a MAP2K1 mutation, PIK3CA, CDKN2A, a PTEN mutation, an UMD mutation, an NRAS mutation, a KRAS mutation, an NF1 mutation, a MET mutation, a MET splice and/or altered MET signaling, a TP53 mutation, a CREBBP mutation, a KMT2C mutation, a KMT2D mutation, an ARID1A mutation, a RB1 mutation, an ATM mutation, a SETD2 mutation, a FLT3 mutation, a PTPN11 mutation, a FGFR1 mutation, an EP300 mutation, a MYC mutation, an EZH2 mutation, a JAK2 mutation, a FBXW7 mutation, a CCND3 mutation, and a GNA11 mutation, (c) determining that the patient has a TPS score for PD-L1 of less than about 1% and determining that the patient also has no driver mutations, (d) obtaining and/or receiving a first population of TILs from a tumor resected from the subject or patient by processing a tumor sample obtained from the subject into multiple tumor fragments;

(e) adding the first population of TILs into a closed system;

(f) performing a first expansion by culturing the first population of TILs in a cell culture medium comprising IL-2 to produce a second population of TILs, wherein the first expansion is performed in a closed container providing a first gas-permeable surface area, wherein the first expansion is performed for about 3-14 days to obtain the second population of TILs, wherein the second population of TILs is at least 50-fold greater in number than the first population of TILs, and wherein the transition from step (e) to step (f) occurs without opening the system;

(g) performing a second expansion by supplementing the cell culture medium of the second population of TILs with additional IL-2, OKT-3, and antigen presenting cells (APCs), to produce a third population of TILs, wherein the second expansion is performed for about 7-14 days to obtain the third population of TILs, wherein the third population of TILs is a therapeutic population of TILs, wherein the second expansion is performed in a closed container providing a second gas-permeable surface area, and wherein the transition from step (f) to step (g) occurs without opening the system;
- (h) harvesting therapeutic population of TILs obtained from step (d), wherein the transition from step (d) to step (e) occurs without opening the system; and
- (i) transferring the harvested TIL population from step (e) to an infusion bag, wherein the transfer from step (e) to (f) occurs without opening the system;
- (j) cryopreserving the infusion bag comprising the harvested TIL population from step (f) using a cryopreservation process; and
- (k) administering a therapeutically effective dosage of the third population of TILs from the infusion bag in step (g) to the subject or patient.

In an embodiment, the invention provides a method of treating non-small cell lung carcinoma (NSCLC) by administering a population of tumor infiltrating lymphocytes (TILs) to a patient in need thereof, wherein the method comprises:

- (a) testing the patient's tumor for PD-L1 expression and tumor proportion score (TPS) of PD-L1,
- (b) testing the patient for the absence of one or more driver mutations, wherein the driver mutation is selected from the group consisting of an EGFR mutation, an EGFR insertion, a KRAS mutation, a BRAF mutation, an ALK mutation, a c-ROS mutation (ROS1 mutation), a ROS1 fusion, a RET mutation, or a RET fusion,
- (c) determining that the patient has a TPS score for PD-L1 of about 1% to about 49% and determining that the patient also has no driver mutations,
- (d) obtaining and/or receiving a first population of TILs from a tumor resected from the subject or patient by processing a tumor sample obtained from the subject into multiple tumor fragments;
- (e) adding the first population of TILs into a closed system;
- (f) performing a first expansion by culturing the first population of TTLs in a cell culture medium comprising IL-2 to produce a second population of TILs, wherein the first expansion is performed in a closed container providing a first gas-permeable surface area, wherein the first expansion is performed for about 3-14 days to obtain the second population of TILs, wherein the second population of TTLs is at least 50-fold greater in number than the first population of TILs, and wherein the transition from step (e) to step (f) occurs without opening the system;
- (g) performing a second expansion by supplementing the cell culture medium of the second population of TILs with additional IL-2, OKT-3, and antigen presenting cells (APCs), to produce a third population of TILs, wherein the second expansion is performed for about 7-14 days to obtain the third population of TILs, wherein the third population of TILs is a therapeutic population of TILs, wherein the second expansion is performed in a closed container providing a second gas-permeable surface area, and wherein the transition from step (f) to step (g) occurs without opening the system;
- (h) harvesting therapeutic population of TILs obtained from step (d), wherein the transition from step (d) to step (e) occurs without opening the system; and
- (i) transferring the harvested TIL population from step (e) to an infusion bag, wherein the transfer from step (e) to (f) occurs without opening the system;
- (j) cryopreserving the infusion bag comprising the harvested TIL population from step (f) using a cryopreservation process; and
- (k) administering a therapeutically effective dosage of the third population of TILs from the infusion bag in step (g) to the subject or patient.

In an embodiment, the invention provides a method of treating non-small cell lung carcinoma (NSCLC) by administering a population of tumor infiltrating lymphocytes (TILs) to a patient in need thereof, wherein the method comprises:

- (a) testing the patient's tumor for PD-L1 expression and tumor proportion score (TPS) of PD-L1,
- (b) testing the patient for the absence of one or more driver mutations, wherein the driver mutation is selected from the group consisting of an EGFR mutation, an EGFR insertion, a KRAS mutation, a BRAF mutation, an ALK mutation, a c-ROS mutation (ROS1 mutation), a ROS1 fusion, a RET mutation, or a RET fusion,
- (c) determining that the patient has a TPS score for PD-L1 of less than about 1% and determining that the patient also has no driver mutations,
- (d) obtaining and/or receiving a first population of TILs from a tumor resected from the subject or patient by processing a tumor sample obtained from the subject into multiple tumor fragments;
- (e) adding the first population of TILs into a closed system;
- (f) performing a first expansion by culturing the first population of TILs in a cell culture medium comprising IL-2 to produce a second population of TILs, wherein the first expansion is performed in a closed container providing a first gas-permeable surface area, wherein the first expansion is performed for about 3-14 days to obtain the second population of TILs, wherein the second population of TILs is at least 50-fold greater in number than the first population of TILs, and wherein the transition from step (e) to step (f) occurs without opening the system;
- (g) performing a second expansion by supplementing the cell culture medium of the second population of TILs with additional IL-2, OKT-3, and antigen presenting cells (APCs), to produce a third population of TILs, wherein the second expansion is performed for about 7-14 days to obtain the third population of TILs, wherein the third population of TILs is a therapeutic population of TILs, wherein the second expansion is performed in a closed container providing a second gas-permeable surface area, and wherein the transition from step (f) to step (g) occurs without opening the system;
- (h) harvesting therapeutic population of TILs obtained from step (d), wherein the transition from step (d) to step (e) occurs without opening the system; and
- (i) transferring the harvested TIL population from step (e) to an infusion bag, wherein the transfer from step (e) to (f) occurs without opening the system;
- (j) cryopreserving the infusion bag comprising the harvested TIL population from step (f) using a cryopreservation process; and
- (k) administering a therapeutically effective dosage of the third population of TILs from the infusion bag in step (g) to the subject or patient.

In another embodiment, the invention provides a method for treating a subject with cancer comprising administering to the subject a therapeutically effective dosage of the therapeutic TIL population described herein.

In another embodiment, the invention provides a method for treating a subject with cancer comprising administering to the subject a therapeutically effective dosage of the TIL composition described herein.

In another embodiment, the invention provides the method for treating a subject with cancer described herein modified such that prior to administering the therapeutically effective dosage of the therapeutic TIL population and the TIL composition described herein, respectively, a non-myeloablative lymphodepletion regimen has been administered to the subject.

In another embodiment, the invention provides the method for treating a subject with cancer described herein modified such that the non-myeloablative lymphodepletion regimen comprises the steps of administration of cyclophosphamide at a dose of 60 mg/m2/day for two days followed by administration of fludarabine at a dose of 25 mg/m2/day for five days.

In another embodiment, the invention provides the method for treating a subject with cancer described herein modified to further comprise the step of treating the subject with a high-dose IL-2 regimen starting on the day after administration of the TIL cells to the subject.

In another embodiment, the invention provides the method for treating a subject with cancer described herein modified such that the high-dose IL-2 regimen comprises 600,000 or 720,000 IU/kg administered as a 15-minute bolus intravenous infusion every eight hours until tolerance.

In another embodiment, the invention provides the method for treating a subject with cancer described herein modified such that the cancer is a solid tumor.

In another embodiment, the invention provides the method for treating a subject with cancer described herein modified such that the cancer is melanoma, ovarian cancer, cervical cancer, non-small-cell lung cancer (NSCLC), lung cancer, bladder cancer, breast cancer, cancer caused by human papilloma virus, head and neck cancer (including head and neck squamous cell carcinoma (HNSCC)), glioblastoma (including GBM), gastrointestinal cancer, renal cancer, or renal cell carcinoma.

In another embodiment, the invention provides the method for treating a subject with cancer described herein modified such that the cancer is melanoma, HNSCC, cervical cancers, NSCLC, glioblastoma (including GBM), and gastrointestinal cancer.

In another embodiment, the invention provides the method for treating a subject with cancer described herein modified such that the cancer is melanoma.

In another embodiment, the invention provides the method for treating a subject with cancer described herein modified such that the cancer is HNSCC.

In another embodiment, the invention provides the method for treating a subject with cancer described herein modified such that the cancer is a cervical cancer.

In another embodiment, the invention provides the method for treating a subject with cancer described herein modified such that the cancer is NSCLC.

In another embodiment, the invention provides the method for treating a subject with cancer described herein modified such that the cancer is glioblastoma (including GBM).

In another embodiment, the invention provides a method for treating a subject with cancer described herein modified such that the cancer is gastrointestinal cancer.

In another embodiment, the invention provides a method for treating a subject with cancer described herein modified such that the cancer is a hypermutated cancer.

In another embodiment, the invention provides a method for treating a subject with cancer described herein modified such that the cancer is a pediatric hypermutated cancer.

In another embodiment, the invention provides a therapeutic TIL population described herein for use in a method for treating a subject with cancer comprising administering to the subject a therapeutically effective dosage of the therapeutic TIL population.

In another embodiment, the invention provides a TIL composition described herein for use in a method for treating a subject with cancer comprising administering to the subject a therapeutically effective dosage of the TIL composition.

In another embodiment, the invention provides a therapeutic TIL population described herein or the TIL composition described herein modified such that prior to administering to the subject the therapeutically effective dosage of the therapeutic TIL population described herein or the TIL composition described herein, a non-myeloablative lymphodepletion regimen has been administered to the subject.

In another embodiment, the invention provides a therapeutic TIL population or the TIL composition described herein modified such that the non-myeloablative lymphodepletion regimen comprises the steps of administration of cyclophosphamide at a dose of 60 mg/m2/day for two days followed by administration of fludarabine at a dose of 25 mg/m2/day for five days.

In another embodiment, the invention provides a therapeutic TIL population or a TIL composition described herein modified to further comprise the step of treating patient with a high-dose IL-2 regimen starting on the day after administration of the TIL cells to the patient.

In another embodiment, the invention provides a therapeutic TIL population or a TIL composition described herein modified such that the high-dose IL-2 regimen comprises 600,000 or 720,000 IU/kg administered as a 15-minute bolus intravenous infusion every eight hours until tolerance.

In another embodiment, the invention provides a therapeutic TIL population or a TIL composition described herein modified such that the cancer is a solid tumor.

In another embodiment, the invention provides a therapeutic TIL population or a TIL composition described herein modified such that the cancer is melanoma, ovarian cancer, cervical cancer, non-small-cell lung cancer (NSCLC), lung cancer, bladder cancer, breast cancer, cancer caused by human papilloma virus, head and neck cancer (including head and neck squamous cell carcinoma (HNSCC)), glioblastoma (including GBM), gastrointestinal cancer, renal cancer, or renal cell carcinoma.

In another embodiment, the invention provides a therapeutic TIL population or a TIL composition described herein modified such that the cancer is melanoma, HNSCC, cervical cancers, NSCLC, glioblastoma (including GBM), and gastrointestinal cancer.

In another embodiment, the invention provides a therapeutic TIL population or a TIL composition described herein modified such that the cancer is melanoma.

In another embodiment, the invention provides a therapeutic TIL population or a TIL composition described herein modified such that the cancer is HNSCC.

In another embodiment, the invention provides a therapeutic TIL population or a TIL composition described herein modified such that the cancer is cervical cancer.

In another embodiment, the invention provides a therapeutic TIL population or a TIL composition described herein modified such that the cancer is NSCLC.

In another embodiment, the invention provides a therapeutic TIL population or a TIL composition described herein modified such that the cancer is glioblastoma.

In another embodiment, the invention provides a therapeutic TIL population or a TIL composition described herein modified such that the cancer is gastrointestinal cancer.

In another embodiment, the invention provides a therapeutic TIL population or a TIL composition described herein modified such that the cancer is a hypermutated cancer.

In another embodiment, the invention provides a therapeutic TIL population or a TIL composition described herein modified such that the cancer is a pediatric hypermutated cancer.

In another embodiment, the invention provides the use of a therapeutic TIL population described herein in a method of treating cancer in a subject comprising administering to the subject a therapeutically effective dosage of the therapeutic TIL population.

In another embodiment, the invention provides the use of a TIL composition described in any of the preceding paragraphs in a method of treating cancer in a subject comprising administering to the subject a therapeutically effective dosage of the TIL composition.

In another embodiment, the invention provides the use of a therapeutic TIL population described herein or a TIL composition described herein in a method of treating cancer in a patient comprising administering to the patient a non-myeloablative lymphodepletion regimen and then administering to the subject the therapeutically effective dosage of the therapeutic TIL population described in any of the preceding paragraphs or the therapeutically effective dosage of the TIL composition described herein.

1. Methods of Treating Cancers Based on Driver Mutations

As used herein, the phrases "driver mutation" and/or "actionable mutation" and/or "oncogenic driver mutation" refer to mutations that are typically considered oncogenic drivers (i.e., cancer drivers or cancer inducers). The presence of one or more of these mutations has traditionally been the utilized as the target for a targeted therapy. Often, driver mutations are examined and/or analyzed for treatment with targeted therapeutic moieties, including for example tyrosine kinase inhibitors (TKIs). Such driver mutations can, in some embodiments, impact or affect response to a first line therapeutic treatment. TIL therapy methods and compositions described herein are effective for treatment whether such driver mutations are present or absent in the patient or subject. Such driver mutations can be tested and determined by any method known in the art, including whole exome sequencing or methods targeted to the detection of a specific driver mutation.

In some embodiments, the cancer is a cancer that exhibits the presence or absence of one or more driver mutations. In some embodiments, the cancer exhibits the presence of one or more driver mutations. In some embodiments, a cancer exhibits the absence of one or more driver mutations. In some embodiments, a cancer has been analyzed for the absence or presence of one or more driver mutations. In some embodiments, the one or more driver mutations are not present. In some embodiments, a cancer treatment is independent of the presence or absence of one or more driver mutations. In some embodiments, the cancer exhibits one or more driver mutations selected from the group consisting of an EGFR mutation, an EGFR insertion, EGFR exon20, a KRAS mutation, a BRAF-mutation, a BRAF V600E mutation, a BRAF V600K mutation, a BRAF V600 mutation, an ALK mutation, a c-ROS mutation (ROS1-mutation), a ROS1 fusion, a RET mutation, a RET fusion, an ERBB2 mutation, an ERBB2 amplification, a BRCA mutation, a MAP2K1 mutation, PIK3CA, CDKN2A, a PTEN mutation, an UMD mutation, an NRAS mutation, a KRAS mutation, an NF1 mutation, a MET mutation, a MET splice and/or altered MET signaling, a TP53 mutation, a CREBBP mutation, a KMT2C mutation, a KMT2D mutation, an ARID1A mutation, a RB1 mutation, an ATM mutation, a SETD2 mutation, a FLT3 mutation, a PTPN11 mutation, a FGFR1 mutation, an EP300 mutation, a MYC mutation, an EZH2 mutation, a JAK2 mutation, a FBXW7 mutation, a CCND3 mutation, and a GNA11 mutation. In some embodiments, the cancer exhibits a PD-L1 TPS of <1% and has a predetermined absence of one or more driver mutations.

In some embodiments, a cancer is an cancer that is not indicated for treatment by an EGFR inhibitor, a BRAF inhibitor, an ALK inhibitor, a c-Ros inhibitor, a RET inhibitor, an ERBB2 inhibitor, BRCA inhibitor, a MAP2K1 inhibitor, PIK3CA inhibitor, CDKN2A inhibitor, a PTEN inhibitor, an UMD inhibitor, an NRAS inhibitor, a KRAS inhibitor, an NF1 inhibitor, MET inhibitor a TP53 inhibitor, a CREBBP inhibitor, a KMT2C inhibitor, a KMT2D mutation, an ARID1A mutation, a RB1 inhibitor, an ATM inhibitor, a SETD2 inhibitor, a FLT3 inhibitor, a PTPN11 inhibitor, a FGFR1 inhibitor, an EP300 inhibitor, a MYC inhibitor, an EZH2 inhibitor, a JAK2 inhibitor, a FBXW7 inhibitor, a CCND3 inhibitor, and a GNA11 inhibitor.

In some embodiments, a cancer exhibits a PD-L1 TPS of <1% and is not indicated for treatment by an EGFR inhibitor, a BRAF inhibitor, an ALK inhibitor, a c-Ros inhibitor, a RET inhibitor, an ERBB2 inhibitor, BRCA inhibitor, a MAP2K1 inhibitor, PIK3CA inhibitor, CDKN2A inhibitor, a PTEN inhibitor, an UMD inhibitor, an NRAS inhibitor, a KRAS inhibitor, an NF1 inhibitor, MET inhibitor a TP53 inhibitor, a CREBBP inhibitor, a KMT2C inhibitor, a KMT2D mutation, an ARID1A mutation, a RB1 inhibitor, an ATM inhibitor, a SETD2 inhibitor, a FLT3 inhibitor, a PTPN11 inhibitor, a FGFR1 inhibitor, an EP300 inhibitor, a MYC inhibitor, an EZH2 inhibitor, a JAK2 inhibitor, a FBXW7 inhibitor, a CCND3 inhibitor, and a GNA11 inhibitor In some embodiments, the cancer is NSCLC, and an EGFR mutation results in tumor transformation from NSCLC to small cell lung cancer (SCLC).

In some embodiments, a cancer (or a biopsy thereof) exhibits high-tumor mutational burden (high-TMB; >10 mut/kb) and/or microsatellite instability high (MSI-high). In some embodiments, the cancer (or a biopsy thereof) exhibits high-tumor mutational burden (high-TMB; >10 mut/kb). In some embodiments, a cancer (or a biopsy thereof) exhibits microsatellite instability high (MSI-high). Methods and systems for evaluating tumor mutational burden are known in the art. Exemplary disclosures of such methods and systems can be found in U.S. Pat. No. 9,792,403, U.S. Patent Application Publication No. US 2018/0363066 A1, International Patent Application Publication Nos. WO 2013/070634 A1 and WO 2018/106884 A1, and Metzker, Nature Biotechnol. Rev. 2010, 11, 31-46, each of which is incorporated by reference herein.

In some embodiments, an EGFR mutation includes, for example, but is not limited to T790M, Ex19Del, L858R, Exon 20 insertion, delE709-T710insD, I744_K745insKIPVAI, K745_E746insTPVAIK, E709X, E709K, E709A, Exon 18 deletion, G719X, G719A, G719S, L861Q, S768I, L747P, A763_764insFQEA, D770_N771insNPG, A763_764insFQEA, P772_H773insDNP exon 20 insertion, H773_V774insNPH exon 20 insertion, S768I, D770_N771insSVD, V769_D770InsASV, p.K745_E746insIPVAIK, p.K745_E746insTPVAIK, p.I744_K745insKIPVAI, D770_N771insNPG, P772_H773insPNP, A763_Y764insFQEA, and/or EGFR kinase domain duplication (EGFR-KDD). In some embodiments, an EGFR mutation is selected from the group consisting of T790M, Ex19Del, L858R, Exon 20 insertion, delE709-T710insD, I744_K745insKIPVAI, K745_E746insTPVAIK, E709X, E709K, E709A, Exon 18 deletion, G719X, G719A, G719S, L861Q, S768I, L747P, A763_764insFQEA, D770 N771insNPG, A763_764insFQEA, P772_H773insDNP exon 20 insertion, H773_V774insNPH exon 20 insertion, S768I, D770_N771insSVD, V769_D770InsASV, p.K745_E746insIPVAIK, p.K745_E746insTPVAIK, p.I744_K745insKIPVAI, D770_N771insNPG, P772_H773insPNP, A763_Y764insFQEA, and EGFR kinase domain duplication (EGFR-KDD).

In some embodiments, an EGFR mutation is a double mutation, including, but not limited to, L858R/T790M, Ex19Del/T790M, G719X/L861Q, G719X/S768I (or S768I/G719X), S768I/L858R, L858R/E709A, and/or E746_T751delinsA+T790M. In some embodiments, an EGFR mutation is a double mutation selected from group consisting of L858R/T790M, Ex19Del/T790M, G719X/L861Q, G719X/S768I (or S768I/G719X), S768I/L858R, L858R/E709A, and E746_T751delinsA+T790M. Additional properties and methods regarding EGFR mutations are provided in International Patent Application Publication No. WO 2010/020618 A1, which is incorporated by referenced herein.

In some embodiments, the ALK mutation includes, but not limited to, EML4-ALK Variant 1 (AB274722.1; BAF73611.1), EML4-ALK Variant 2 (AB275889.1; BAF73612.1), EML4-ALK Variant 3a (AB374361.1; BAG55003.1), EML4-ALK Variant 3b (AB374362.1; BAG55004.1), EML4-ALK Variant 4 (AB374363.1; BAG75147.1), EML4-ALK Variant 5a (AB374364.1; BAG75148.1), EML4-ALK Variant 5b (AB374365.1; BAG75149.1), EML4-ALK Variant 6 (AB462411.1; BAH57335.1), EML4-ALK Variant 7 (AB462412.1; BAH57336.1), KIF5B-ALK (AB462413.1; BAH57337.1), NPM-ALK, TPM3-ALK, TFGXL-ALK, TEGL-ALK, TFGS-ALK, A11C-ALK, CLTC-ALK, MSN-ALK, TPM4-ALK, MYH9-ALK, RANBP2-ALK, AL017-ALK, and CARS-ALK (see, for example. Pulford et al., (2004) J. Cell. Physiol. 199:330-358). In addition, a skilled artisan will understand that ALK kinase variants can arise depending upon the particular fusion event between an ALK kinase and its fusion partner (e.g., EML4 can fuse at least exon 2, 6a, 6b, 13, 14, and/or 15, as described, for example, in Horn and Pao, J. Clin. Oncol. 2009, 27, 4247-4253, the disclosure of which is incorporated by reference herein.

Additional examples of ALK mutations are described in U.S. Pat. Nos. 9,018,230 and 9,458,508, the disclosures of which are incorporated by reference herein.

In some embodiments, the ROS1 mutation of the present invention is a ROS1 fusion, where a portion of the ROS1 polypeptide that includes the kinase domain of the ROS1 protein (or polynucleotide encoding the same) fused to all or a portion of another polypeptide (or polynucleotide encoding the same) and where the name of that second polypeptide or polynucleotide is named in the fusion. In some embodiments, the ROS1 mutation is determined as ROS1-fusion protein (e.g., by IHC) and/or ROS-fusion gene (e.g. by FISH), and/or ROS1 mRNA (e.g. by qRT-PCR), preferably indicative of a ROS1-fusion protein selected from the group consisting of SLC34A2-ROS1 (SLC34A2 exons 13del2046 and 4 fused to ROS1 exons 32 and 34), CD74-ROS1 (CD74 exon 6 fused to ROS1 exons 32 and 34), EZR-ROS1 (EZR exon 10 fused to ROS1 exon 34), TPM3-ROS1 (TPM3 exon 8 fused to ROS1 exon 35), LRIG3-ROS1 (LRIG3 exon 16 fused to ROS1 exon 35), SDC4-ROS1 (SDC4 exon 2 and 4 fused to ROS1 exon 32 and SDC4 exon 4 fused to ROS1 exon 34), GOPC-ROS1, also known as FIG-ROS1, (GOPC exon 8 fused to ROS1 exon 35 and GOPC exon 4 fused to ROS1 exon 36), and G2032R, also known as ROS1G2032R.

Additional disclosures of ROS1 mutations and a ROS fusion have been provided in U.S. Patent Application Publication Nos. US 2010/0221737 A1, US 2015/0056193 A1, and US 2010/0143918 A1, and in International Patent Application Publication No WO 2010/093928 A1, each of which are incorporated by reference herein. In some embodiments, the RET mutation is a RET fusion or point mutation.

In some embodiments, a RET point mutation includes but is not limited to H6650, K666E, K666M, S686N, G691S, R694Q, M700L, V706M, V706A, E713K, G736R, G748C, A750P, S765P, P766S, E768Q, E768D, L769L, R770Q, D771N, N777S, V7781, Q781R, L790F, Y791F, Y791N, V804L, V804M, V804E, E805K, E806C, Y806E, Y806F, Y806S, Y806G, Y806C, E818K, S8191, G823E, Y826M, R833C, P841L, P841P, E843D, R844W, R844Q, R844L, M848T, 1852M A866W, R873W, A876V, L881V, A883F, A883S, A883T, E884K, R886W, S891A, R8970, D898V, E901K, 5904F, S904C2, K907E, K907M, R908K, G911D, R912P, R912Q M918T, M918V, M918L6, A919V, E921K, S922P, S922Y, T930M, F961L, R972G, R982C, M1009V, D1017N, V10416, and M1064T.

In some embodiments, a RET fusion is a fusion between RET and a fusion partner that is selected from the group consisting of BCR, BCR, CLIP 1, KIFSB, CCDC6, PTClex9, NCOA4, TRIM33, ERC1, FGFRIOP, MBD1, RAB61P2, PRKARIA, TRIM24, KTN1, GOLGA5, HOOK3, KIAA1468, TRIM27, AKAP13, FKBP15, SPECCIL, TBL1XR1, CEP55, CUX1, ACBD5, MYH13, PIBF1, KIAA1217, and MPRIP.

Additional disclosures of a RET mutations has been provided in U.S. patent Ser. No. 10/035,789, which is hereby incorporated by reference in their entirety.

In some embodiments, a BRAF mutation is BRAF V600E/K mutation. In other embodiments, the BRAF mutation is a non-V600E/K mutation.

In some embodiments, a non-V600E/K BRAF mutation is a kinase-activated mutation, a kinase-impaired mutation, or a kinase-unknown mutation, and combinations thereof.

In some embodiments, a kinase-activated mutation is selected from the group consisting of R4621, 1463S, G464E, G464R, G464V, G466A, G469A, N58 is, E586K, F595L, L597Q, L597R, L5975, L597V, A598V, T599E, V600R, K601E, 5602D, A728V, and combinations thereof. In some embodiments, a kinase-impaired mutation is selected from the group consisting of G466E, G466R, G466V, Y472C, K483M, D594A, D594E, D594G, D594H, D594N, D594V, G596R, T599A, 5602A, and combinations thereof. In some embodiments, a kinase-unknown mutation is selected from the group consisting of T4401, 5467L, G469E, G469R, G4695, G469V, L584F, L588F, V600 K6OldelinsE, 56051, Q609L, E611Q, and combinations thereof. In some embodiments, the non-V600E/K BRAF mutation is selected from the group consisting of D594, G469, K601E, L597, T599 duplication, L485W, F247L, G466V, BRAF fusion, BRAF-AGAP3 rearrangement, BRAF exon 15 slice variant, and combinations thereof.

In some embodiments, a Met mutation includes point mutation, deletion mutation, insertion mutation, inversion, aberrant splicing, missense mutation, or gene magnification that causes the increase of at least one bioactivity of c-Met protein, the tyrosine kinase activity such as improved, receptor homolog dimerization Ligand binding of formation, enhancing of body and heterodimer etc. The Met mutation can be located at any part of c-Met genes. In one embodiment, the mutation is in the kinase domain of c-Met protein encoded by the c-MET gene. In some embodiments, the c-Met mutations are point mutation at N375, V13, V923, R175, V136, L229, S323, R988, 51058/T1010 and E168.

In some embodiments, an ERBB2 mutation is a point mutation in the amino acid sequence of ERBB2. In some embodiments, the point mutation of ERBB2 is one that causes amino acid substitutions, causes mRNA splicing, or is a point mutation in the upstream region. Wherein the mutation comprises a nucleotide mutation causing at least one amino acid substitution selected from the group consisting of Q568E, P601R, I628M, P885S, R143Q, R434Q, and E874K.

In some embodiments, an ERBB2 mutation is ERBB2 amplification. In some embodiments, the ERBB2 amplification includes point mutation selected from the group consisting of V659E, G309A, G309E, S310F, D769H, D769Y, V777L, P780ins, P780-Y781insGSP, V842I, R896C, K753E, and L755S and can be detected by polymerase chain reaction or other sequencing techniques known in the art, such as those described in Bose, et al., Cancer Discov. 2013, 3(2), 224-237; and Zuo, et al. Clin Cancer Res. 2016, 22(19), 4859-4869, the disclosures of which are incorporated by reference herein.

In some embodiments, a BRCA mutation is a mutation in BRCA1 and/or BRCA2, preferably BRCA1, and/or in one or more other genes of which the protein product associates with BRCA1 and/or BRCA2 at DNA damage sites, including ATM, ATR, Chk2, H2AX, 53BP1, NFBD1, Mre11, Rad50, Nibrin, BRCA1-associated RING domain (BARD1), Abraxas, and MSH2. A mutation in one or more of these genes may result in a gene expression pattern that mimics a mutation in BRCA1 and/or BRCA2.

In certain embodiments, a BRCA mutation comprises a non-synonymous mutation. In some embodiments, a BRCA mutation comprises a nonsense mutation. In some embodiments, the BRCA mutation comprises a frameshift mutation. In some embodiments, the BRCA mutation comprises a splicing mutation. In some embodiments, a BRCA mutation is expressed as a mutant mRNA and ultimately a mutant protein. In some embodiments, a BRCA1/2 protein is functional. In other embodiments, a BRCA1/2 protein has reduced activity. In other embodiments, a BRCA1/2 protein is non-functional.

As used herein with regard to substitutions, the "=" sign with regard to mutations generally refers to synonymous substitutions, silent codons, and/or silent substitutions. In particular, a synonymous substitution (also called a silent substitution or silent codon) refers to the substitution of one nucleotide base for another in an exon of a gene encoding a protein, wherein the produced amino acid sequence is not modified. This is due to the fact that the genetic code is "degenerate", i.e., that some amino acids are coded for by more than one three-base-pair codon. Because some of the codons for a given amino acid vary by just one base pair from others coding for the same amino acid, a point mutation that replaces the wild-type base by one of the alternatives will result in incorporation of the same amino acid into the elongating polypeptide chain during translation of the gene. In some embodiments, synonymous substitutions and mutations affecting noncoding DNA are often considered silent mutations; however, it is not always the case that the mutation is silent and without any impact. For example, a synonymous mutation can affect transcription, splicing, mRNA transport, and translation, any of which could alter the resulting phenotype, rendering the synonymous mutation non-silent. The substrate specificity of the tRNA to the rare codon can affect the timing of translation, and in turn the co-translational folding of the protein. This is manifested in the codon usage bias that has been observed in many species. A nonsynonymous substitution/mutation results in a change in amino acid that may be arbitrarily classified as conservative (a change to an amino acid with similar physiochemical properties), semi-conservative (e.g. negatively to positively charged amino acid), or radical (vastly different amino acid). In some embodiments, the BRCA mutation is a BRCA1 mutation that includes, but is not limited to P871L, K1183R, D693N, S1634G, E1038G, S1040N, S694=(=: silence codon), M1673I, Q356R, S1436=, L771=, K654Sfs*47, S198N, R496H, R841W, R1347G, H619N, S1533I, L30=, A622V, Y655Vfs*18, R496C, E597K, R1443*, E23Vfs*17, L30F, E111Gfs*3, K339Rfs*2, L512F, D693N, P871S, S1140G, Q1240*, P1770S, R7=, L52F, T176M, A224S, L347=, S561F, E597*, K820E, K893Rfs*107, E962K, M1014I, R1028H, E1258D, E1346K, R1347T, L1439F, H1472R, Q1488*, S1572C, E1602K, R1610C, L1621=, Q1625*, Q1625=, D1754N, R1772Q, R1856*, and any combination thereof.

In some embodiments, a BRCA mutation is a BRCA2 mutation that includes, but is not limited to V2466A, N289H, N991D, S455=(=: silence codon), N372H, H743=, V1269=, S2414=, V2171=, L1521=, T3033Nfs*11, K1132=, T3033Lfs*29, R2842C, N1784Tfs*7, K3326*, K3326*, D1420Y, I605Yfs*9, I3412V, A2951T, T3085Nfs*26, R2645Nfs*3, S1013*, T1915M, F3090=, V3244I, A1393V, R2034C, L1356=, E2981Rfs*37, N1784Kfs*3, K3416Nfs*11, K1691Nfs*15, S1982Rfs*22, and any combination thereof.

In some embodiments, an NRAS mutation includes but is not limited to E63K, Q61R, Q61K, G12D, G13D, Q61R, Q61L, Q61K, G12S, G12C, G13R, Q61H, G12V, G12A, Q61L, G13V, Q61H, Q61H, G12R, G13C, Q61P, G13S, G12D, G13A, G13D, A18T, Q61X, G60E, G12S, Q61=(=: silence codon), Q61E, Q61R, A146T, A59T, A59D, Q61=, R68T, A146T, G12A, E62Q, G75=, A91V, and any combination thereof.

E132K In some embodiments, a PIK3CA mutation includes substitution mutations, deletion mutations, and insertion mutations. In some embodiments, mutations occur in PIK3CA's helical domain and in its kinase. In other embodiments, in PIK3CA's P85BD domain. In some embodiments, the PIK3CA mutation is in exon 1, 2, 4, 5, 7, 9, 13, 18, and 20. In some embodiments, the PIK3CA mutation is in exons 9 and 20. In yet other embodiments, the PIK3CA mutation is a combination of the any mutations listed above. Any combination of these exons can be tested, optionally in conjunction with testing other exons. Testing for mutations can be done along the whole coding sequence or can be focused in the areas where mutations have been found to cluster. Particular hotspots of mutations occur at nucleotide positions 1624, 1633, 1636, and 3140 of a PIK3CA coding sequence.

In some embodiments, the size of a PIK3CA mutation is small, ranging from 1 to 3 nucleotides. In some embodiments, the PIK3CA mutations include, but are not limited to G1624A, G1633A, C1636A, A3140G, G113A, T1258C, G3129T, C3139T, E542K, E545K, Q546R, H1047L, H1047R and G2702T.

In some embodiments, a MAP2K1 mutation is a somatic MAP2K1 mutation, optionally a MAP2K1 mutation that upregulates MEK1 levels. In some embodiments, the MAP2K1 mutation is a mutation in one or more genes associated with the RAS/MAPK pathway, comprising: HRAS, KRAS, NRAS, ARAF, BRAF, RAFI, MAP2K2, MAPK1, MAPK3, MAP3K3. In certain embodiments, the MAP2K1 mutation is in one or more genes selected from the group consisting of RASA, PTEN, ENG, ACVRL1, SMAD4, GDF2 or combinations thereof.

In some embodiments, a MAP2K1 mutation includes, but is not limited to, P124S, Q56P, K57N, E203K, G237*, P124L, G128D, D67N, K57E, E102_I103del, C121S, K57T, K57N, Q56P, P124L, K57N, G128V, Q58_E62del, F53L, I126=, I103_K104del, and any combination thereof.

In some embodiments, a KRAS mutation comprises a non-synonymous mutation. In some embodiments, a KRAS mutation comprises a nonsense mutation. In some embodiments, a KRAS mutation comprises a frameshift mutation. In some embodiments, a KRAS mutation comprises a splicing mutation. In some embodiments, a KRAS mutation is expressed as a mutant mRNA and ultimately a mutant protein. In some embodiments, a mutated KRAS protein is functional. In other embodiments, a mutated KRAS protein has reduced activity. In other embodiments, a mutated KRAS protein is non-functional.

In some embodiments, a KRAS mutation includes but is not limited to G12D, G12V, G13D, G12C, G12A, G12S, G12R, G13C, Q61H, A146T, Q61R, Q61H, Q61L, G13S, A146V, Q61K, G13R, G12F, K117N, G13A, G13V, A59T, V14I, K117N, Q22K, Q61P, A146P, G13D, L19F, L19F, Q61K, G12V, G60=, G12=, G13=, A18D, T58I, Q61E, E63K, G12L, G13V, A59G, G60D, G10R, G10dup, D57N, A59E, V14G, D33E, G12I, G13dup, and any combination thereof, wherein = is indicative of silence coding.

In some embodiments, a NF1 mutation includes substitution mutations, deletion mutations, missense mutations, aberrant splicing mutations, and insertion mutations. In some embodiments, the NF1 mutation is a loss of function (LOF) mutation. In some embodiments, the NF1 mutation is selected from the group consisting of R1947X (C5839T), R304X, exon 37 mutation, exon 4b mutation, exon 7 mutation, exon 10b mutation, and exon 10c mutation (e.g., 1570G→T, E524X).

In some embodiments, a CDKN2A mutation includes but is not limited to R24P, D108G, D108N, D108Y, G125R, P114L, R80*, R58*, H83Y, W110*, P114L, E88*, W110*, E120*, D108Y, D84Y, D84N, E69*, P81L, Q50*, L78Hfs*41, D108N, S12*, P48L, E61*, Y44*, E88K, R80*, D84G, L16Pfs*9, Y129*, D108H, A148T, A36G, A102V, W15*, H83R, A57V, E33*, D74Y, A76V, E153K, D74N, H83D, V82M, R58*, Y129*, E119*, Y44*, D74A, T18_A19dup, Y44Lfs*76, L32_L37del, V28_E33del, D14_L16del, A68T, or any combination thereof.

In some embodiments, a PTEN mutation comprises a non-synonymous mutation. In some embodiments, the PTEN mutation comprises a nonsense mutation. In some embodiments, the PTEN mutation comprises a frameshift mutation. In some embodiments, the PTEN mutation comprises a splicing mutation. In some embodiments, the mutated PTEN is expressed as an mRNA and ultimately a protein. In some embodiments, the mutated PTEN protein is functional. In other embodiments, the mutated PTEN protein has reduced activity. In other embodiments, the mutated PTEN protein is non-functional. In some embodiments, the PTEN mutation includes, but is not limited to, R130Q, R130G, T319*, R233*, R130*, K267Rfs*9, N323Mfs*21, N323Kfs*2, R173C, R173H, R335*, Q171*, Q245*, E7*, D268Gfs*30, R130Q, Q214*, R130L, C136R, Q298*, Q17*, H93R, P248Tfs*5, I33del, R233*, E299*, G132D, Y68H, T319Kfs*24, N329Kfs*14, V166Sfs*14, V290*, T319Nfs*6, R142W, P38S, A126T, H61R, F278L, S229*, R130P, G129R, R130Qfs*4, P246L, R130*, G165R, C136Y, R173C, I101T, Y155C, D92E, K164Rfs*3, N184Efs*6, G129E, R130G, G36R, F341V, H123Y, C124S, M35VG127E, G165E and any combination thereof.

In some embodiments, a TP53 mutation includes, but is not limited to, R175H, G245S, R248Q, R248W, R249S, R273C, R273H, R282W, C135Y, C141Y, P151S, V157F, R158L, Y163C, V173L, V173M, C176F, H179R, H179Y, H179Q, Y205C, Y220C, Y234C, M237I, C238Y, S241F, G245D, G245C, R248L, R249M, V272M, R273L, P278L, R280T, E285K, E286K, R158H, C176Y, I195T, G214R, G245V, G266R, G266E, P278S, R280K, or any combination thereof. In some further embodiments, the TP53 mutation is selected from the group consisting of: G245S; R249S; R273C; R273H; C141Y, V157F, R158L, Y163C, V173L, V173M, Y205C, Y220C, G245C, R249M, V272M, R273L, and E286K. In some embodiments, the TP53 mutation includes one or more of the mutations above.

In some embodiments, a CREBBP mutation includes, but is not limited to, R1446C, R1446H, S1680del, I1084Sfs*15, P1948L, I1084Nfs*3, ?R386*, S893L, R1341*, P1423Lfs*36, P1488L, Y1503H, R1664C, A1824T, R1173*, R1360*, Y1450C, H2228D, S71L, P928=, D1435N, W1502C, Y1503D, R483*, R601Q, S945L, R1103*, R1288W, R1392*, C1408Y, D1435G, R1446L, H1485Y, Q1491K, Q96*, L361M, L524Wfs*6, Q540*, Q1073*, A1100V, R1169C, C1237Y, R1347W, G1411E, W1472C, I1483F, P1488T, R1498*, Y1503F, Q1856*, R1985C, R2104C, S2328L, V2349=, S2377L, and any combination thereof.

In some embodiments, a KMT2C mutation includes, but is not limited to, D348N, P350=, R380L, C391*, P309S, C988F, Y987H, S990G, K2797Rfs*26, V346=, R894Q, R284Q, S806=, R1690=, P986=, A1685S, G315S, Q755*, R909K, T316S, S772L, G838S, L291F, P335=, C988F, Q2680=, E765G, K339N, Y816*, R526P, N729D, G845E, I817Nfs*11, G892R, C1103*, S3660L, F4496Lfs*21, G315C, R886C, D348N, S793=, V919L, R2481S, R2884*, R4549C, M305Dfs*28, T316S, P377=, I455M, T820I, S965=, S730Y, P860S, Q873Hfs*40, R904*, R2610Q, R4478*, and any combination thereof.

In some embodiments, a KMT2D mutation includes, but is not limited to, L1419P, E640D, E541D, E455D, T2131P, K1420R. P2354Lfs*30, G2493=, Q3612=, I942=, T1195Hfs*17, P4170=, P1194H, G1235Vfs*95, P4563=, P647Hfs*283, L449_P457del, P3557=, Q3603=, R1702*, P648Tfs*2, R5501*, R4198*, R4484*, R83Q, R1903*, R2685*, R4282*, L5326=, R5432W, R2734*, Q2800*, R2830*, Q3745dup, S4010P, R4904*, G5182Afs*61, R5214H, R1615*, Q2380*, R2687*, R2771*, V3089Wfs*30, Q3799Gfs*212, R4536*, R5030C, R5048C, R5432Q, A221Lfs*40, A476T, A2119Lfs*25, P2557L, R2801*, Q3913*, R4420W, G4641=, R5097*, and any combination thereof.

In some embodiments, a ARID1A mutation includes, but is not limited to, For example, subject has a mutation of ARID1A selected from the group consisting of a C884* (*: nonsense mutation), E966K, Q1411*, F1720fs (fs: frameshift), G1847fs, C1874fs, D1957E, Q1430, R1721fs, G1255E, G284fs, R1722*, M274fs, G1847fs, P559fs, R1276*, Q2176fs, H203fs, A591fs, Q1322*, S2264*, Q586*, Q548fs, and N756fs.

In some embodiments, a RB1 mutation includes, but is not limited to, R320X, R467X, R579X, R455X, R358X, R251X, R787X, R552X, R255X, R556X, Y790X, Q575X, E323X, R661W, R579*, R455*, R556*. R787*, R661W, R445*, R467*, Q217*, Q471*, W195*, Q395*, I680T, E137*, R255*, Q344*, Q62*, E440K, A488V, P777Lfs*33, E322K, R656W, G617Rfs*36, C221*, E440*, Q93*, Q504*, E125*, S834*, E323*, Q685*, S829*, W516*, G435*, Q257*, E79*, S567L, V654M, V654Sfs*14, G100Efs*11, K715*, and any combination thereof.

In some embodiments, an ATM mutation is a mutation in the ATM gene sequence including, but is not limited to, 10744A>G; 10744A>G; 11482G>A; IVS3-558A>T; 146C>G; 381delA; IVS8-3delGT; 1028delAAAA; 1120C>T; 1930ins16; IVS16+2T>C; 2572T>C; IVS21+1G>A; 3085delA; 3381delTGAC; 3602delTT; 4052delT; 4396C>T; 5188C>T; 5290delC; 5546delT; 5791G>CCT; 6047A>G; IVS44-1G>T; 6672delGC/6677delTACG; 6736del1 1/6749del7; 7159insAGCC; 7671delGTTT; 7705del14; 7865C>T; 7979delTGT; 8177C>T; 8545C>T; 8565T>A; IVS64+1G>T; and 9010del28.

In some embodiments of the present invention, a SETD2 mutation is an alteration in the gene sequence encoding the SETD2 protein, when the transcription initiation codon position of the mRNA sequence of NCBI accession number NM_014159 is set to 1. In some embodiments, the 7558th G (guanine) is substituted with T (thymine), the 4774th C (cytosine) is substituted by T, the 1210th A (adenine) is substituted by T, the 4883th T is substituted by G, the 5290th C is replaced by T, the 7072th C is replaced by T, the 4144th G is substituted by T, the 1297 C is replaced by T, the 755th T is replaced by G, the 7261 T is substituted by G, 6700 is replaced by T, the 2536th C is substituted by T, the 7438th C is replaced by T substitution, or there is an insertion of A at position 3866, insertion of T at position 6712, insertion of T at position 7572, deletion of the 913th A, deletion of the 5619th C, deletion of bases 4603-4604, deletion of the 1st base, deletion of the 1936th C, deletion of the 3094-3118 base, insertion of A in the 5289th position, and deletion of the 6323-6333 base.

In some embodiments, a FLT3 mutation includes, but is not limited to, (Q569_E648)ins, D835X, (Q569_E648)delins, (D835_I836), D835Y, D835V, D835Y, D835H, T227M, I836del, N676K, D835E, Y597_E598insDYVDFREY, D835E, D835del, F594_D600dup, A680V, D839G, D96=, D835H, V491L, D835E, Q989*, D835V, L561=, I836del, P986Afs*27, D7G, D324N, S451F, D835N, L576P, Y597 E598insDVDFREY, V491L, N841T, D324N, Y572C, R595_L601dup, K663R, N676K, F691L, D835A, I836H, N841K, S993L, L832F, I836M, A66V, and any combination thereof.

In some embodiments, a PTPN11 mutation includes, but is not limited to, c E76K, A72V, A72T, D61Y, D61V, G60V, E69K, E76G, G507V, S506L, G507A, T73I, E76A, E76Q, S506P, D61N, F71L, E76V, F71L, A72D, V432M, T472M, P495L, N58Y, F285S, S506A, S189A, A465T, R502W, G507R, T511K, D61H, D61G, G507E, G60R, G60A, Q514L, E139D, Y197*, N308D, Q514H, Q514H, N58S, E123D, L206=, A465G, P495S, G507R, and any combination thereof.

In some embodiments, a FGFR1 mutation includes, but is not limited to, N577K, K687E, N577K, D166del, T371M, R476W, T350=, E498K, N577D, D683G, R87C, A154D, N303=, A374V, D550=, S633=, V695L, G728=, R765W, P803S, W19C, P56=, R113C, V149I, S158L, D166dupR220C, N224Kfs*8, D249N, R281W, R281Q, A299S, S424L, S461F, S467F, R506Q, and any combination thereof.

In some embodiments, a EP300 mutation includes, but is not limited to, D1399N, Y1414C, M1470Cfs*26, Y1111*, H2324Pfs*55, R1627W, N2209_Q2213delinsK, Q2268del, L415P, M1470Nfs*3, E1514K, C1201Y, P1452L, S952*, C1164Y, D1399Y, S507G, Q824*, D1507N, H2324Tfs*29, P925T, P1440L, W1466C, P1502L, A1629V, R1645*, N1700Tfs*9, P1869L, Q65*, A171V, R202*, R580Q, A627V, Q1082*, N1236Kfs*2, N1286S, R1312*, R1356*, C1385F, H1451L, R1462*, Y1467N, Y1467H, R1478H, R1627Q, R86*, R370H, R397*, R754C, P842S, I997V, E1014*, and any combination thereof.

In some embodiments, a MYC mutation includes, but is limited to, E61T, E681, R74Q, R75N, W135E, W136E, V394D, L420P, W96E, V325D, L351P, a MYC protein with 41 amino acid deleted at the N-terminus (dN2MYC), N26S, S161L, P74L, V7M, F153S, E54D, P246, L164V, P74S, A59V, T73I, P72T, T73A, H374R, P17S, T73N, S264N, P72S, Q52del, S21T, P74A, S107N, P75S, S77P, P261S, P74Q, S190R, A59T, F153C, P75H, T73I, S77F, N11S, S21N, P78L, P72L, N9K, S190N, S267F, T73P, P78S, G105D, S187C, L71M, Q10H, L191x, Q50x, L191F, R25K, F130L, Y27S, D195N, D2G, V20A, V6G, V20I, D2H, P75A, G152D, P74T, C40Y, E8K, Q48x, and any combination thereof.

In some embodiments, a EZH2 mutation is associated with altered histone methylation patterns. In some embodiments, the EZH2 mutation leads to the conversion of amino acid Y641 (equivalent to Y646, catalytic domain), to either F, N, H, S or C resulting in hypertrimethylation of H3K27 and drives lymphomagenesis. In some embodiments, the EZH2 mutation includes EZH2 SET-domain mutations, overexpression of EZH2, overexpression of other PRC2 subunits, loss of function mutations of histone acetyl transferases (HATs), and loss of function of MLL2. Cells that are heterozygous for EZH2 Y646 mutations result in hypertrimethylation of H3K27 relative to cells that are homozygous wild-type (WT) for the EZH2 protein, or to cells that are homozygous for the Y646 mutation.

In some embodiments, a EZH2 mutation includes, but is not limited to, Y646F, Y646N, D185H, Y646F, Y646S, Y646H, R690H, Y646X, E745K, Y646C, V626M, V679M, R690H, R684H, A682G, E249K, G159R, R288Q, N322S, A692V, R690C, D730* (insertion frameshift), S695L, R684C, M667T, R288*, S644*, D192N, K550T, Q653E, D664G, R347Q, Y646C, G660R, R213C, A255T, S538L, N693K, I55M, R561H, A692V, K515R, Y733*, R63*, Q570*, Q328*, R25Q, T467P A656V, T573I, C571Y, E725K, R16W, P577L, F145S, V680M, G686D, G135R, K634E, S652F, R298C, G648E, R566H, L149R, R502Q, Y731D, R313W, N675K, S652C, T374Hfs*3, N152Ifs*15, E401Kfs*22, K406Mfs*17, E246*, S624C, 1146T, V626M, L674S, H694R, A581S, and any combination thereof.

In some embodiments, a JAK2 mutation is a mutation in the JAK2 gene includes, but is not limited to, T1923C mutation in combination with a G1920T mutation, a G1920T/C1922T mutation, or a G1920A mutation. In some embodiments, the JAK2 mutation is a mutant JAK2 protein comprising one or more substitutions include, but are not limited to, V617F, V617I, R683G, N542_E543del, E543_D544del, R683S, R683X, F537_K539delinsL (deletion in frame), K539L, N1108S, R1113H, R1063H, R487C, I540Mfs*3 (deletion-frameshift), R867Q, K539L, G571S, R1113C, R938Q, R228Q, L830*, E1080*, K539L, C618R, R564Q, D1036H, L1088S, H538Nfs*4, D873N, V392M, I682F, L393V, M535I, C618R, T875N, L611V, D319N, L611S, G921S, H538Y, S1035L, and any combination thereof.

In some embodiments, a FBXW7 mutation is a point mutation selected from the group consisting of W244* (*:stop codon), R222*, R278*, E192A, S282*, E113D, R465H/C, 726+1 G>A splice, R505C, R479Q, R465C, R367*, R499Vfs*25 (fs*: frameshift), R658*, D600Y, D520N, D520Y, and any combination thereof. In further embodiments, the FBXW7 mutation is double- or triple-mutation includes, but is not limited to, R479Q and S582L, R465H and S582L, D520N, D520Y and R14Q, and R367* and S582L.

In some embodiments, a CCND3 mutation includes, but is not limited to, S259A, R271Pfs*53 (insertion-caused frameshift), E51*, Q260*, P199S, T283A, T283P, V287D, D286_T288del, R271Gfs*33, Q276*, R241Q, D238G, R33P, I290K, I290T, I290R, P267fs, P284S, P284L, P100S, E253D, S262I, R14W, R114L, D238N, A266E, R167W, and any combination thereof.

In some embodiments, a GNA11 mutation includes, but is not limited to, Q209L, R183C, T257=, R183C, G208Afs*16, Q209H, R183C, Q209P, Q209R, Q209H, ?T96=, R210W, R256Q, T334=, G48D, S53G, Q209P, R213Q, and any combination thereof. In some embodiments, the GNA11 mutation has two mutations in exon 4, e.g., a mutation in V182 and a mutation in T175, or one or more mutations in exon 5.

2. Combinations with PD-1 and PD-L1 Inhibitors

In some embodiments, the TIL therapy provided to patients with cancer may include treatment with therapeutic populations of TILs alone or may include a combination treatment including TILs and one or more PD-1 and/or PD-L1 inhibitors.

Programmed death 1 (PD-1) is a 288-amino acid transmembrane immunocheckpoint receptor protein expressed by T cells, B cells, natural killer (NK) T cells, activated monocytes, and dendritic cells. PD-1, which is also known as CD279, belongs to the CD28 family, and in humans is encoded by the Pdcd1 gene on chromosome 2. PD-1 consists of one immunoglobulin (Ig) superfamily domain, a transmembrane region, and an intracellular domain containing an immunoreceptor tyrosine-based inhibitory motif (ITIM) and an immunoreceptor tyrosine-based switch motif (ITSM). PD-1 and its ligands (PD-L1 and PD-L2) are known to play a key role in immune tolerance, as described in Keir, et al., Annu. Rev. Immunol. 2008, 26, 677-704. PD-1 provides inhibitory signals that negatively regulate T cell immune responses. PD-L1 (also known as B7-H1 or CD274) and PD-L2 (also known as B7-DC or CD273) are expressed on tumor cells and stromal cells, which may be encountered by activated T cells expressing PD-1, leading to immunosuppression of the T cells. PD-L1 is a 290 amino acid transmembrane protein encoded by the Cd274 gene on human chromosome 9. Blocking the interaction between PD-1 and its ligands PD-L1 and PD-L2 by use of a PD-1 inhibitor, a PD-L1 inhibitor, and/or a PD-L2 inhibitor can overcome immune resistance, as demonstrated in recent clinical studies, such as that described in Topalian, et al., N. Eng. J. Med. 2012, 366, 2443-54. PD-L1 is expressed on many tumor cell lines, while PD-L2 is expressed is expressed mostly on dendritic cells and a few tumor lines. In addition to T cells (which inducibly express PD-1 after activation), PD-1 is also expressed on B cells, natural killer cells, macrophages, activated monocytes, and dendritic cells.

In an embodiment, the PD-1 inhibitor may be any PD-1 inhibitor or PD-1 blocker known in the art. In particular, it is one of the PD-1 inhibitors or blockers described in more detail in the following paragraphs. The terms "inhibitor," "antagonist," and "blocker" are used interchangeably herein in reference to PD-1 inhibitors. For avoidance of doubt, references herein to a PD-1 inhibitor that is an antibody may refer to a compound or antigen-binding fragments, variants, conjugates, or biosimilars thereof. For avoidance of doubt, references herein to a PD-1 inhibitor may also refer to a small molecule compound or a pharmaceutically acceptable salt, ester, solvate, hydrate, cocrystal, or prodrug thereof.

In a preferred embodiment, the PD-1 inhibitor is an antibody (i.e., an anti-PD-1 antibody), a fragment thereof, including Fab fragments, or a single-chain variable fragment (scFv) thereof. In some embodiments the PD-1 inhibitor is a polyclonal antibody. In a preferred embodiment, the PD-1 inhibitor is a monoclonal antibody. In some embodiments, the PD-1 inhibitor competes for binding with PD-1, and/or binds to an epitope on PD-1. In an embodiment, the antibody competes for binding with PD-1, and/or binds to an epitope on PD-1.

In some embodiments, the PD-1 inhibitor is one that binds human PD-1 with a KD of about 100 pM or lower, binds human PD-1 with a KD of about 90 pM or lower, binds human PD-1 with a KD of about 80 pM or lower, binds human PD-1 with a KD of about 70 pM or lower, binds human PD-1 with a KD of about 60 pM or lower, binds human PD-1 with a KD of about 50 pM or lower, binds human PD-1 with a KD of about 40 pM or lower, binds human PD-1 with a KD of about 30 pM or lower, binds human PD-1 with a KD of about 20 pM or lower, binds human PD-1 with a KD of about 10 pM or lower, or binds human PD-1 with a KD of about 1 pM or lower.

In some embodiments, the PD-1 inhibitor is one that binds to human PD-1 with a kassoc of about $7.5 \times 10^5$ 1/M·s or faster, binds to human PD-1 with a kassoc of about $7.5 \times 10^5$ 1/M·s or faster, binds to human PD-1 with a kassoc of about $8 \times 10^5$ 1/M·s or faster, binds to human PD-1 with a kassoc of about $8.5 \times 10^5$ 1/M·s or faster, binds to human PD-1 with a kassoc of about $9 \times 10^5$ 1/M·s or faster, binds to human PD-1 with a kassoc of about $9.5 \times 10^5$ 1/M·s or faster, or binds to human PD-1 with a kassoc of about $1 \times 10^6$ 1/M·s or faster.

In some embodiments, the PD-1 inhibitor is one that binds to human PD-1 with a kdissoc of about $2 \times 10^{-5}$ 1/s or slower, binds to human PD-1 with a kdissoc of about $2.1 \times 10^{-5}$ 1/s or slower, binds to human PD-1 with a kdissoc of about $2.2 \times 10^{-5}$ 1/s or slower, binds to human PD-1 with a kdissoc of about $2.3 \times 10^{-5}$ 1/s or slower, binds to human PD-1 with a kdissoc of about $2.4 \times 10^{-5}$ 1/s or slower, binds to human PD-1 with a kdissoc of about $2.5 \times 10^{-5}$ 1/s or slower, binds to human PD-1 with a kdissoc of about $2.6 \times 10^{-5}$ 1/s or slower or binds to human PD-1 with a kdissoc of about $2.7 \times 10^{-5}$ 1/s or slower, binds to human PD-1 with a kdissoc of about $2.8 \times 10^{-5}$ 1/s or slower, binds to human PD-1 with a kdissoc of about $2.9 \times 10^{-5}$ 1/s or slower, or binds to human PD-1 with a kdissoc of about $3 \times 10^{-5}$ 1/s or slower.

In some embodiments, the PD-1 inhibitor is one that blocks or inhibits binding of human PD-L1 or human PD-L2 to human PD-1 with an IC50 of about 10 nM or lower, blocks or inhibits binding of human PD-L1 or human PD-L2 to human PD-1 with an IC50 of about 9 nM or lower, blocks or inhibits binding of human PD-L1 or human PD-L2 to human PD-1 with an IC50 of about 8 nM or lower, blocks or inhibits binding of human PD-L1 or human PD-L2 to human PD-1 with an IC50 of about 7 nM or lower, blocks or inhibits binding of human PD-L1 or human PD-L2 to human PD-1 with an IC50 of about 6 nM or lower, blocks or inhibits binding of human PD-L1 or human PD-L2 to human PD-1 with an IC50 of about 5 nM or lower, blocks or inhibits binding of human PD-L1 or human PD-L2 to human PD-1 with an IC50 of about 4 nM or lower, blocks or inhibits binding of human PD-L1 or human PD-L2 to human PD-1 with an IC50 of about 3 nM or lower, blocks or inhibits binding of human PD-L1 or human PD-L2 to human PD-1 with an IC50 of about 2 nM or lower, or blocks or inhibits binding of human PD-L1 or human PD-L2 to human PD-1 with an IC50 of about 1 nM or lower.

In an embodiment, the PD-1 inhibitor is nivolumab (commercially available as OPDIVO from Bristol-Myers Squibb Co.), or biosimilars, antigen-binding fragments, conjugates, or variants thereof. Nivolumab is a fully human IgG4 antibody blocking the PD-1 receptor. In an embodiment, the anti-PD-1 antibody is an immunoglobulin G4 kappa, anti-(human CD274) antibody. Nivolumab is assigned Chemical Abstracts Service (CAS) registry number 946414-94-4 and is also known as 5C4, BMS-936558, MDX-1106, and ONO-4538. The preparation and properties of nivolumab are described in U.S. Pat. No. 8,008,449 and International Patent Publication No. WO 2006/121168, the disclosures of which are incorporated by reference herein. The clinical safety and efficacy of nivolumab in various forms of cancer has been described in Wang, et al., Cancer Immunol. Res. 2014, 2, 846-56; Page, et al., Ann. Rev. Med., 2014, 65, 185-202; and Weber, et al., J. Clin. Oncology, 2013, 31, 4311-4318, the disclosures of which are incorporated by reference herein. The amino acid sequences of nivolumab are set forth in Table 18. Nivolumab has intra-heavy chain disulfide linkages at 22-96, 140-196, 254-314, 360-418, 22"-96", 140"-196", 254"-314", and 360"-418"; intra-light chain disulfide linkages at 23'-88', 134'-194', 23'"-88'", and 134'"-194'"; inter-heavy-light chain disulfide linkages at 127-214', 127"-214'", inter-heavy-heavy chain disulfide linkages at 219-219" and 222-222"; and N-glycosylation sites (H CH2 84.4) at 290, 290".

In an embodiment, a PD-1 inhibitor comprises a heavy chain given by SEQ ID NO:158 and a light chain given by SEQ ID NO:159. In an embodiment, a PD-1 inhibitor comprises heavy and light chains having the sequences shown in SEQ ID NO:158 and SEQ ID NO:159, respectively, or antigen binding fragments, Fab fragments, single-chain variable fragments (scFv), variants, or conjugates thereof. In an embodiment, a PD-1 inhibitor comprises heavy and light chains that are each at least 99% identical to the sequences shown in SEQ ID NO:158 and SEQ ID NO:159, respectively. In an embodiment, a PD-1 inhibitor comprises heavy and light chains that are each at least 98% identical to the sequences shown in SEQ ID NO:158 and SEQ ID NO:159, respectively. In an embodiment, a PD-1 inhibitor comprises heavy and light chains that are each at least 97% identical to the sequences shown in SEQ ID NO:158 and SEQ ID NO:159, respectively. In an embodiment, a PD-1 inhibitor comprises heavy and light chains that are each at least 96% identical to the sequences shown in SEQ ID NO:158 and SEQ ID NO:159, respectively. In an embodiment, a PD-1 inhibitor comprises heavy and light chains that are each at least 95% identical to the sequences shown in SEQ ID NO:463 and SEQ ID NO:159, respectively.

In an embodiment, the PD-1 inhibitor comprises the heavy and light chain CDRs or variable regions (VRs) of nivolumab. In an embodiment, the PD-1 inhibitor heavy chain variable region (VH) comprises the sequence shown in SEQ ID NO:160, and the PD-1 inhibitor light chain variable region (VL) comprises the sequence shown in SEQ ID NO:161, or conservative amino acid substitutions thereof. In an embodiment, a PD-1 inhibitor comprises VH and VL regions that are each at least 99% identical to the sequences shown in SEQ ID NO:160 and SEQ ID NO:161, respectively. In an embodiment, a PD-1 inhibitor comprises VH and VL regions that are each at least 98% identical to the sequences shown in SEQ ID NO:160 and SEQ ID NO:161, respectively. In an embodiment, a PD-1 inhibitor comprises VH and VL regions that are each at least 97% identical to the sequences shown in SEQ ID NO:160 and SEQ ID NO:161, respectively. In an embodiment, a PD-1 inhibitor comprises VH and VL regions that are each at least 96% identical to the sequences shown in SEQ ID NO:160 and SEQ ID NO:161, respectively. In an embodiment, a PD-1 inhibitor comprises VH and VL regions that are each at least 95% identical to the sequences shown in SEQ ID NO:160 and SEQ ID NO:161, respectively.

In an embodiment, a PD-1 inhibitor comprises heavy chain CDR1, CDR2 and CDR3 domains having the sequences set forth in SEQ ID NO:162, SEQ ID NO:163, and SEQ ID NO:164, respectively, or conservative amino acid substitutions thereof, and light chain CDR1, CDR2 and CDR3 domains having the sequences set forth in SEQ ID NO:165, SEQ ID NO:166, and SEQ ID NO:167, respectively, or conservative amino acid substitutions thereof. In an embodiment, the antibody competes for binding with, and/or binds to the same epitope on PD-1 as any of the aforementioned antibodies.

In an embodiment, the PD-1 inhibitor is an anti-PD-1 biosimilar monoclonal antibody approved by drug regulatory authorities with reference to nivolumab. In an embodiment, the biosimilar comprises an anti-PD-1 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is nivolumab. In some embodiments, the one or more post-translational modifications are selected from one or more of: glycosylation, oxidation, deamidation, and truncation. In some embodiments, the biosimilar is an anti-PD-1 antibody authorized or submitted for authorization, wherein the anti-PD-1 antibody is provided in a formulation which differs from the formulations of a reference medicinal product or reference biological product, wherein the reference medicinal product or reference biological product is nivolumab. The anti-PD-1 antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is nivolumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is nivolumab.

IL-2 administration. In some embodiments, the nivolumab can also be administered 1, 2, 3, 4 or 5 weeks pre-resection (i.e., before obtaining a tumor sample from the subject or

TABLE 18

Amino acid sequences for PD-1 inhibitors related to nivolumab.

| Identifier | Sequence (One-Letter Amino Acid Symbols) | |
|---|---|---|
| SEQ ID NO: 158 nivolumab heavy chain | QVQLVESGGG VVQPGRSLRL DCKASGITFS NSGMHWVRQA PGKGLEWVAV IWYDGSKRYY<br>ADSVKGRFTI SRDNSKNTLF LQMNSLRAED TAVYYCATND DYWGQGTLVT VSSASTKGPS<br>VFPLAPCSRS TSESTAALGC LVKDYFPEPV TVSWNSGALT SGVHTFPAVL QSSGLYSLSS<br>VVTVPSSSLG TKTYTCNVDH KPSNTKVDKR VESKYGPPCP PCPAPEFLGG PSVFLFPPKP<br>KDTLMISRTP EVTCVVVDVS QEDPEVQFNW YVDGVEVHNA KTKPREEQFN STYRVVSVLT<br>VLHQDWLNGK EYKCKVSNKG LPSSIEKTIS KAKGQPREPQ VYTLPPSQEE MTKNQVSLTC<br>LVKGFYPSDI AVEWESNGQP ENNYKTTPPV LDSDGSFFLY SRLTVDKSRW QEGNVFSCSV<br>MHEALHNHYT QKSLSLSLGK | 60<br>120<br>180<br>240<br>300<br>360<br>420<br>440 |
| SEQ ID NO: 159 nivolumab light chain | EIVLTQSPAT LSLSPGERAT LSCRASQSVS SYLAWYQQKP GQAPRLLIYD ASNRATGIPA<br>RFSGSGSGTD FTLTISSLEP EDFAVYYCQQ SSNWPRTFGQ GTKVEIKRTV AAPSVFIFPP<br>SDEQLKSGTA SVVCLLNNFY PREAKVQWKV DNALQSGNSQ ESVTEQDSKD STYSLSSTLT<br>LSKADYEKHK VYACEVTHQG LSSPVTKSFN RGEC | 60<br>120<br>180<br>214 |
| SEQ ID NO: 160 nivolumab variable heavy chain | QVQLVESGGG VVQPGRSLRL DCKASGITFS NSGMHWVRQA PGKGLEWVAV IWYDGSKRYY<br>ADSVKGRFTI SRDNSKNTLF LQMNSLRAED TAVYYCATND DYWGQGTLVT VSS | 60<br>113 |
| SEQ ID NO: 161 nivolumab variable light chain | EIVLTQSPAT LSLSPGERAT LSCRASQSVS SYLAWYQQKP GQAPRLLIYD ASNRATGIPA<br>RFSGSGSGTD FTLTISSLEP EDFAVYYCQQ SSNWPRTFGQ GTKVEIK | 60<br>107 |
| SEQ ID NO: 162 nivolumab heavy chain CDR1 | NSGMH | 5 |
| SEQ ID NO: 163 nivolumab heavy chain CDR2 | VIWYDGSKRY YADSVKG | 17 |
| SEQ ID NO: 164 nivolumab heavy chain CDR3 | NDDY | 4 |
| SEQ ID NO: 165 nivolumab light chain CDR1 | RASQSVSSYL A | 11 |
| SEQ ID NO: 166 nivolumab light chain CDR2 | DASNRAT | 7 |
| SEQ ID NO: 167 nivolumab light chain CDR3 | QQSSNWPRT | 9 |

In some embodiments, the PD-1 inhibitor is nivolumab or a biosimilar thereof, and the nivolumab is administered at a dose of about 0.5 mg/kg to about 10 mg/kg. In some embodiments, the PD-1 inhibitor is nivolumab or a biosimilar thereof, and the nivolumab is administered at a dose of about 0.5 mg/kg, about 1 mg/kg, about 1.5 mg/kg, about 2 mg/kg, about 2.5 mg/kg, about 3 mg/kg, about 3.5 mg/kg, about 4 mg/kg, about 4.5 mg/kg, about 5 mg/kg, about 5.5 mg/kg, about 6 mg/kg, about 6.5 mg/kg, about 7 mg/kg, about 7.5 mg/kg, about 8 mg/kg, about 8.5 mg/kg, about 9 mg/kg, about 9.5 mg/kg, or about 10 mg/kg. In some embodiments, the nivolumab administration is begun 1, 2, 3, 4, or 5 days post IL-2 administration. In some embodiments, the nivolumab administration is begun 1, 2, or 3 days post patient). In some embodiments, the nivolumab can also be administered 1, 2, or 3 weeks pre-resection (i.e., before obtaining a tumor sample from the subject or patient).

In some embodiments, the PD-1 inhibitor is nivolumab or a biosimilar thereof, and the nivolumab is administered at a dose of about 200 mg to about 500 mg. In some embodiments, the PD-1 inhibitor is nivolumab or a biosimilar thereof, and the nivolumab is administered at a dose of about 200 mg, about 220 mg, about 240 mg, about 260 mg, about 280 mg, about 300 mg, about 320 mg, about 340 mg, about 360 mg, about 380 mg, about 400 mg, about 420 mg, about 440 mg, about 460 mg, about 480 mg, or about 500 mg. In some embodiments, the nivolumab administration is begun 1, 2, 3, 4, or 5 days post IL-2 administration. In some embodiments, the nivolumab administration is begun 1, 2, or 3 days post IL-2 administration. In some embodiments, the nivolumab can also be administered 1, 2, 3, 4 or 5 weeks pre-resection (i.e., before obtaining a tumor sample from the subject or patient). In some embodiments, the nivolumab can also be administered 1, 2, or 3 weeks pre-resection (i.e., before obtaining a tumor sample from the subject or patient).

In some embodiments, the PD-1 inhibitor is nivolumab or a biosimilar thereof, and the nivolumab is administered every 2 weeks, every 3 weeks, every 4 weeks, every 5 weeks, or every 6 weeks. In some embodiments, the nivolumab administration is begun 1, 2, 3, 4, or 5 days post IL-2 administration. In some embodiments, the nivolumab administration is begun 1, 2, or 3 days post IL-2 administration. In some embodiments, the nivolumab can also be administered 1, 2, 3, 4 or 5 weeks pre-resection (i.e., before obtaining a tumor sample from the subject or patient). In some embodiments, the nivolumab can also be administered 1, 2, or 3 weeks pre-resection (i.e., before obtaining a tumor sample from the subject or patient).

In some embodiments, the nivolumab is administered to treat unresectable or metastatic melanoma. In some embodiments, the nivolumab is administered to treat unresectable or metastatic melanoma and is administered at about 240 mg every 2 weeks. In some embodiments, the nivolumab is administered to treat unresectable or metastatic melanoma and is administered at about 480 mg every 4 weeks. In some embodiments, the nivolumab is administered to treat unresectable or metastatic melanoma and is administered at about 1 mg/kg followed by ipilimumab 3 mg/kg on the same day every 3 weeks for 4 doses, then 240 mg every 2 weeks or 480 mg every 4 weeks. In some embodiments, the nivolumab administration is begun 1, 2, 3, 4, or 5 days post IL-2 administration. In some embodiments, the nivolumab administration is begun 1, 2, or 3 days post IL-2 administration. In some embodiments, the nivolumab can also be administered 1, 2, 3, 4 or 5 weeks pre-resection (i.e., before obtaining a tumor sample from the subject or patient). In some embodiments, the nivolumab can also be administered 1, 2, or 3 weeks pre-resection (i.e., before obtaining a tumor sample from the subject or patient).

In some embodiments, the nivolumab is administered for the adjuvant treatment of melanoma. In some embodiments, the nivolumab is administered for the adjuvant treatment of melanoma at about 240 mg every 2 weeks. In some embodiments, the nivolumab is administered for the adjuvant treatment of melanoma at about 480 mg every 4 weeks. In some embodiments, the nivolumab administration is begun 1, 2, 3, 4, or 5 days post IL-2 administration. In some embodiments, the nivolumab administration is begun 1, 2, or 3 days post IL-2 administration. In some embodiments, the nivolumab can also be administered 1, 2, 3, 4 or 5 weeks pre-resection (i.e., before obtaining a tumor sample from the subject or patient). In some embodiments, the nivolumab can also be administered 1, 2, or 3 weeks pre-resection (i.e., before obtaining a tumor sample from the subject or patient).

In some embodiments, the nivolumab is administered to treat metastatic non-small cell lung cancer. In some embodiments, the nivolumab is administered to treat metastatic non-small cell lung cancer at about 3 mg/kg every 2 weeks along with ipilimumab at about 1 mg/kg every 6 weeks. In some embodiments, the nivolumab is administered to treat metastatic non-small cell lung cancer at about 360 mg every 3 weeks with ipilimumab 1 mg/kg every 6 weeks and 2 cycles of platinum-doublet chemotherapy. In some embodiments, the nivolumab is administered to treat metastatic non-small cell lung cancer at about 240 mg every 2 weeks or 480 mg every 4 weeks. In some embodiments, the nivolumab administration is begun 1, 2, 3, 4, or 5 days post IL-2 administration. In some embodiments, the nivolumab administration is begun 1, 2, or 3 days post IL-2 administration. In some embodiments, the nivolumab can also be administered 1, 2, 3, 4 or 5 weeks pre-resection (i.e., before obtaining a tumor sample from the subject or patient). In some embodiments, the nivolumab can also be administered 1, 2, or 3 weeks pre-resection (i.e., before obtaining a tumor sample from the subject or patient).

In some embodiments, the nivolumab is administered to treat small cell lung cancer. In some embodiments, the nivolumab is administered to treat small cell lung cancer at about 240 mg every 2 weeks. In some embodiments, the nivolumab administration is begun 1, 2, 3, 4, or 5 days post IL-2 administration. In some embodiments, the nivolumab administration is begun 1, 2, or 3 days post IL-2 administration. In some embodiments, the nivolumab can also be administered 1, 2, 3, 4 or 5 weeks pre-resection (i.e., before obtaining a tumor sample from the subject or patient). In some embodiments, the nivolumab can also be administered 1, 2, or 3 weeks pre-resection (i.e., before obtaining a tumor sample from the subject or patient).

In some embodiments, the nivolumab is administered to treat malignant pleural mesothelioma at about 360 mg every 3 weeks with ipilimumab 1 mg/kg every 6 weeks. In some embodiments, the nivolumab administration is begun 1, 2, 3, 4, or 5 days post IL-2 administration. In some embodiments, the nivolumab administration is begun 1, 2, or 3 days post IL-2 administration. In some embodiments, the nivolumab can also be administered 1, 2, 3, 4 or 5 weeks pre-resection (i.e., before obtaining a tumor sample from the subject or patient). In some embodiments, the nivolumab can also be administered 1, 2, or 3 weeks pre-resection (i.e., before obtaining a tumor sample from the subject or patient).

In some embodiments, the nivolumab is administered to treat advanced renal cell carcinoma. In some embodiments, the nivolumab is administered to treat advanced renal cell carcinoma at about 240 mg every 2 weeks. In some embodiments, the nivolumab is administered to treat advanced renal cell carcinoma at about 480 mg every 4 weeks. In some embodiments, the nivolumab is administered to treat advanced renal cell carcinoma at about 3 mg/kg followed by ipilimumab at about 1 mg/kg on the same day every 3 weeks for 4 doses, then 240 mg every 2 weeks. In some embodiments, the nivolumab is administered to treat advanced renal cell carcinoma at about 3 mg/kg followed by ipilimumab at about 1 mg/kg on the same day every 3 weeks for 4 doses, then 240 mg every 2 weeks 480 mg every 4 weeks. In some embodiments, the nivolumab administration is begun 1, 2, 3, 4, or 5 days post IL-2 administration. In some embodiments, the nivolumab administration is begun 1, 2, or 3 days post IL-2 administration. In some embodiments, the nivolumab can also be administered 1, 2, 3, 4 or 5 weeks pre-resection (i.e., before obtaining a tumor sample from the subject or patient). In some embodiments, the nivolumab can also be administered 1, 2, or 3 weeks pre-resection (i.e., before obtaining a tumor sample from the subject or patient).

In some embodiments, the nivolumab is administered to treat classical Hodgkin lymphoma. In some embodiments, the nivolumab is administered to treat classical Hodgkin lymphoma at about 240 mg every 2 weeks. In some embodiments, the nivolumab is administered to treat classical Hodgkin lymphoma at about 480 mg every 4 weeks. In some embodiments, the nivolumab administration is begun 1, 2, 3, 4, or 5 days post IL-2 administration. In some embodiments, the nivolumab administration is begun 1, 2, or 3 days post IL-2 administration. In some embodiments, the nivolumab can also be administered 1, 2, 3, 4 or 5 weeks pre-resection (i.e., before obtaining a tumor sample from the subject or patient). In some embodiments, the nivolumab can also be administered 1, 2, or 3 weeks pre-resection (i.e., before obtaining a tumor sample from the subject or patient).

In some embodiments, the nivolumab is administered to treat Recurrent or metastatic squamous cell carcinoma of the head and neck. In some embodiments, the nivolumab is administered to treat recurrent or metastatic squamous cell carcinoma of the head and neck at about 240 mg every 2 weeks. In some embodiments, the nivolumab is administered to treat recurrent or metastatic squamous cell carcinoma of the head and neck at about 480 mg every 4 weeks. In some embodiments, the nivolumab administration is begun 1, 2, 3, 4, or 5 days post IL-2 administration. In some embodiments, the nivolumab administration is begun 1, 2, or 3 days post IL-2 administration. In some embodiments, the nivolumab can also be administered 1, 2, 3, 4 or 5 weeks pre-resection (i.e., before obtaining a tumor sample from the subject or patient). In some embodiments, the nivolumab can also be administered 1, 2, or 3 weeks pre-resection (i.e., before obtaining a tumor sample from the subject or patient).

In some embodiments, the nivolumab is administered to treat locally advanced or metastatic urothelial carcinoma at about 240 mg every 2 weeks. In some embodiments, the nivolumab is administered to treat locally advanced or metastatic urothelial carcinoma at about 480 mg every 4 weeks. In some embodiments, the nivolumab administration is begun 1, 2, 3, 4, or 5 days post IL-2 administration. In some embodiments, the nivolumab administration is begun 1, 2, or 3 days post IL-2 administration. In some embodiments, the nivolumab can also be administered 1, 2, 3, 4 or 5 weeks pre-resection (i.e., before obtaining a tumor sample from the subject or patient). In some embodiments, the nivolumab can also be administered 1, 2, or 3 weeks pre-resection (i.e., before obtaining a tumor sample from the subject or patient).

In some embodiments, the nivolumab is administered to treat microsatellite instability-high (MSI-H) or mismatch repair deficient (dMMR) metastatic colorectal cancer. In some embodiments, the nivolumab is administered to treat microsatellite instability-high (MSI-H) or mismatch repair deficient (dMMR) metastatic colorectal cancer in adult and pediatric patients. In some embodiments, the nivolumab is administered to treat microsatellite instability-high (MSI-H) or mismatch repair deficient (dMMR) metastatic colorectal cancer in adult and pediatric patients≥40 kg at about 240 mg every 2 weeks. In some embodiments, the nivolumab is administered to treat microsatellite instability-high (MSI-H) or mismatch repair deficient (dMMR) metastatic colorectal cancer in adult and pediatric patients≥40 kg at about 480 mg every 4 weeks. In some embodiments, the nivolumab administration is begun 1, 2, 3, 4, or 5 days post IL-2 administration. In some embodiments, the nivolumab administration is begun 1, 2, or 3 days post IL-2 administration. In some embodiments, the nivolumab can also be administered 1, 2, 3, 4 or 5 weeks pre-resection (i.e., before obtaining a tumor sample from the subject or patient). In some embodiments, the nivolumab can also be administered 1, 2, or 3 weeks pre-resection (i.e., before obtaining a tumor sample from the subject or patient).

In some embodiments, the nivolumab is administered to treat microsatellite instability-high (MSI-H) or mismatch repair deficient (dMMR) metastatic colorectal cancer in pediatric patients<40 kg at about 3 mg/kg every 2 weeks. In some embodiments, the nivolumab is administered to treat microsatellite instability-high (MSI-H) or mismatch repair deficient (dMMR) metastatic colorectal cancer in adult and pediatric patients≥40 kg at about 3 mg/kg followed by ipilimumab 1 mg/kg on the same day every 3 weeks for 4 doses, then 240 mg every 2 weeks. In some embodiments, the nivolumab is administered to treat microsatellite instability-high (MSI-H) or mismatch repair deficient (dMMR) metastatic colorectal cancer in adult and pediatric patients≥40 kg at about 3 mg/kg followed by ipilimumab 1 mg/kg on the same day every 3 weeks for 4 doses, then 480 mg every 4 weeks. In some embodiments, the nivolumab administration is begun 1, 2, 3, 4, or 5 days post IL-2 administration. In some embodiments, the nivolumab administration is begun 1, 2, or 3 days post IL-2 administration. In some embodiments, the nivolumab can also be administered 1, 2, 3, 4 or 5 weeks pre-resection (i.e., before obtaining a tumor sample from the subject or patient). In some embodiments, the nivolumab can also be administered 1, 2, or 3 weeks pre-resection (i.e., before obtaining a tumor sample from the subject or patient).

In some embodiments, the nivolumab is administered to treat hepatocellular carcinoma. In some embodiments, the nivolumab is administered to treat hepatocellular carcinoma at about 240 mg every 2 weeks. In some embodiments, the nivolumab is administered to treat hepatocellular carcinoma at about 480 mg every 4 weeks. In some embodiments, the nivolumab is administered to treat hepatocellular carcinoma at about 1 mg/kg followed by ipilimumab 3 mg/kg on the same day every 3 weeks for 4 doses, then 240 mg every 2 weeks. In some embodiments, the nivolumab is administered to treat hepatocellular carcinoma at about 1 mg/kg followed by ipilimumab 3 mg/kg on the same day every 3 weeks for 4 doses, then 480 mg every 4 weeks. In some embodiments, the nivolumab administration is begun 1, 2, 3, 4, or 5 days post IL-2 administration. In some embodiments, the nivolumab administration is begun 1, 2, or 3 days post IL-2 administration. In some embodiments, the nivolumab can also be administered 1, 2, 3, 4 or 5 weeks pre-resection (i.e., before obtaining a tumor sample from the subject or patient). In some embodiments, the nivolumab can also be administered 1, 2, or 3 weeks pre-resection (i.e., before obtaining a tumor sample from the subject or patient).

In some embodiments, the nivolumab is administered to treat esophageal squamous cell carcinoma. In some embodiments, the nivolumab is administered to treat esophageal squamous cell carcinoma at about 240 mg every 2 weeks. In some embodiments, the nivolumab is administered to treat esophageal squamous cell carcinoma at about 480 mg every 4 weeks. In some embodiments, the nivolumab administration is begun 1, 2, 3, 4, or 5 days post IL-2 administration. In some embodiments, the nivolumab administration is begun 1, 2, or 3 days post IL-2 administration. In some embodiments, the nivolumab can also be administered 1, 2, 3, 4 or 5 weeks pre-resection (i.e., before obtaining a tumor sample from the subject or patient). In some embodiments, the nivolumab can also be administered 1, 2, or 3 weeks pre-resection (i.e., before obtaining a tumor sample from the subject or patient).

In another embodiment, the PD-1 inhibitor comprises pembrolizumab (commercially available as KEYTRUDA from Merck & Co., Inc., Kenilworth, NJ, USA), or antigen-binding fragments, conjugates, or variants thereof. Pembrolizumab is assigned CAS registry number 1374853-91-4 and is also known as lambrolizumab, MK-3475, and SCH-900475. Pembrolizumab has an immunoglobulin G4, anti-(human protein PDCD1 (programmed cell death 1)) (human-*Mus musculus* monoclonal heavy chain), disulfide with human-*Mus musculus* monoclonal light chain, dimer structure. The structure of pembrolizumab may also be described as immunoglobulin G4, anti-(human programmed cell death 1); humanized mouse monoclonal [228-L-proline(H10-S>P)]γ4 heavy chain (134-218')-disulfide with humanized mouse monoclonal κ light chain dimer (226-226":229-229")-bisdisulfide. The properties, uses, and preparation of pembrolizumab are described in International Patent Publication No. WO 2008/156712 A1, U.S. Pat. No. 8,354,509 and U.S. Patent Application Publication Nos. US 2010/0266617 A1, US 2013/0108651 A1, and US 2013/0109843 A2, the disclosures of which are incorporated herein by reference. The clinical safety and efficacy of pembrolizumab in various forms of cancer is described in Fuerst, *Oncology Times,* 2014, 36, 35-36; Robert, et al., *Lancet,* 2014, 384, 1109-17; and Thomas, et al., *Exp. Opin. Biol. Ther.,* 2014, 14, 1061-1064. The amino acid sequences of pembrolizumab are set forth in Table 19. Pembrolizumab includes the following disulfide bridges: 22-96, 22"-96", 23'-92', 23'''-92''', 134-218', 134"-218''', 138'-198', 138'''-198''', 147-203, 147-203", 226-226", 229-229", 261-321, 261"-321", 367-425, and 367"-425", and the following glycosylation sites (N): Asn-297 and Asn-297". Pembrolizumab is an IgG4/kappa isotype with a stabilizing S228P mutation in the Fc region; insertion of this mutation in the IgG4 hinge region prevents the formation of half molecules typically observed for IgG4 antibodies. Pembrolizumab is heterogeneously glycosylated at Asn297 within the Fc domain of each heavy chain, yielding a molecular weight of approximately 149 kDa for the intact antibody. The dominant glycoform of pembrolizumab is the fucosylated agalacto diantennary glycan form (G0F).

In an embodiment, a PD-1 inhibitor comprises a heavy chain given by SEQ ID NO:168 and a light chain given by SEQ ID NO:169. In an embodiment, a PD-1 inhibitor comprises heavy and light chains having the sequences shown in SEQ ID NO:168 and SEQ ID NO:169, respectively, or antigen binding fragments, Fab fragments, single-chain variable fragments (scFv), variants, or conjugates thereof. In an embodiment, a PD-1 inhibitor comprises heavy and light chains that are each at least 99% identical to the sequences shown in SEQ ID NO:168 and SEQ ID NO:169, respectively. In an embodiment, a PD-1 inhibitor comprises heavy and light chains that are each at least 98% identical to the sequences shown in SEQ ID NO:168 and SEQ ID NO:169, respectively. In an embodiment, a PD-1 inhibitor comprises heavy and light chains that are each at least 97% identical to the sequences shown in SEQ ID NO:168 and SEQ ID NO:169, respectively. In an embodiment, a PD-1 inhibitor comprises heavy and light chains that are each at least 96% identical to the sequences shown in SEQ ID NO:168 and SEQ ID NO:169, respectively. In an embodiment, a PD-1 inhibitor comprises heavy and light chains that are each at least 95% identical to the sequences shown in SEQ ID NO:168 and SEQ ID NO:169, respectively.

In an embodiment, the PD-1 inhibitor comprises the heavy and light chain CDRs or variable regions (VRs) of pembrolizumab. In an embodiment, the PD-1 inhibitor heavy chain variable region ($V_H$) comprises the sequence shown in SEQ ID NO:170, and the PD-1 inhibitor light chain variable region ($V_L$) comprises the sequence shown in SEQ ID NO:171, or conservative amino acid substitutions thereof. In an embodiment, a PD-1 inhibitor comprises $V_H$ and $V_L$ regions that are each at least 99% identical to the sequences shown in SEQ ID NO:170 and SEQ ID NO:171, respectively. In an embodiment, a PD-1 inhibitor comprises $V_H$ and $V_L$ regions that are each at least 98% identical to the sequences shown in SEQ ID NO:170 and SEQ ID NO:171, respectively. In an embodiment, a PD-1 inhibitor comprises $V_H$ and $V_L$ regions that are each at least 97% identical to the sequences shown in SEQ ID NO:170 and SEQ ID NO:171, respectively. In an embodiment, a PD-1 inhibitor comprises $V_H$ and $V_L$ regions that are each at least 96% identical to the sequences shown in SEQ ID NO:170 and SEQ ID NO:171, respectively. In an embodiment, a PD-1 inhibitor comprises $V_H$ and $V_L$ regions that are each at least 95% identical to the sequences shown in SEQ ID NO:170 and SEQ ID NO:171, respectively.

In an embodiment, a PD-1 inhibitor comprises the heavy chain CDR1, CDR2 and CDR3 domains having the sequences set forth in SEQ ID NO:172, SEQ ID NO:173, and SEQ ID NO:174, respectively, or conservative amino acid substitutions thereof, and light chain CDR1, CDR2 and CDR3 domains having the sequences set forth in SEQ ID NO:175, SEQ ID NO:176, and SEQ ID NO:177, respectively, or conservative amino acid substitutions thereof. In an embodiment, the antibody competes for binding with, and/or binds to the same epitope on PD-1 as any of the aforementioned antibodies.

In an embodiment, the PD-1 inhibitor is an anti-PD-1 biosimilar monoclonal antibody approved by drug regulatory authorities with reference to pembrolizumab. In an embodiment, the biosimilar comprises an anti-PD-1 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is pembrolizumab. In some embodiments, the one or more post-translational modifications are selected from one or more of: glycosylation, oxidation, deamidation, and truncation. In some embodiments, the biosimilar is an anti-PD-1 antibody authorized or submitted for authorization, wherein the anti-PD-1 antibody is provided in a formulation which differs from the formulations of a reference medicinal product or reference biological product, wherein the reference medicinal product or reference biological product is pembrolizumab. The anti-PD-1 antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is pembrolizumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is pembrolizumab.

TABLE 19

Amino acid sequences for PD-1 inhibitors related to pembrolizumab.

| Identifier | Sequence (One-Letter Amino Acid Symbols) | |
|---|---|---|
| SEQ ID NO: 168 pembrolizumab heavy chain | QVQLVQSGVE VKKPGASVKV SCKASGYTFT NYYMYWVRQA PGQGLEWMGG INPSNGGTNF | 60 |
| | NEKFKNRVTL TTDSSTTTAY MELKSLQFDD TAVYYCARRD YRFDMGFDYW GQGTTVTVSS | 120 |
| | ASTKGPSVFP LAPCSRSTSE STAALGCLVK DYFPEPVTVS WNSGALTSGV HTFPAVLQSS | 180 |
| | GLYSLSSVVT VPSSSLGTKT YTCNVDHKPS NTKVDKRVES KYGPPCPPCP APEFLGGPSV | 240 |
| | FLFPPKPKDT LMISRTPEVT CVVVDVSQED PEVQFNWYVD GVEVHNAKTK PREEQFNSTY | 300 |
| | RVVSVLTVLH QDWLNGKEYK CKVSNKGLPS SIEKTISKAK GQPREPQVYT LPPSQEEMTK | 360 |
| | NQVSLTCLVK GFYPSDIAVE WESNGQPENN YKTTPPVLDS DGSFFLYSRL TVDKSRWQEG | 420 |
| | NVFSCSVMHE ALHNHYTQKS LSLSLGK | 447 |
| SEQ ID NO: 169 pembrolizumab light chain | EIVLTQSPAT LSLSPGERAT LSCRASKGVS TSGYSYLHWY QQKPGQAPRL LIYLASYLES | 60 |
| | GVPARFSGSG SGTDFTLTIS SLEPEDFAVY YCQHSRDLPL TFGGGTKVEI KRTVAAPSVF | 120 |
| | IFPPSDEQLK SGTASVVCLL NNFYPREAKV QWKVDNALQS GNSQESVTEQ DSKDSTYSLS | 180 |
| | STLTLSKADY EKHKVYACEV THQGLSSPVT KSFNRGEC | 218 |
| SEQ ID NO: 170 pembrolizumab variable heavy chain | QVQLVQSGVE VKKPGASVKV SCKASGYTFT NYYMYWVRQA PGQGLEWMGG INPSNGGTNF | 60 |
| | NEKFKNRVTL TTDSSTTTAY MELKSLQFDD TAVYYCARRD YRFDMGFDYW GQGTTVTVSS | 120 |
| SEQ ID NO: 171 pembrolizumab variable light chain | EIVLTQSPAT LSLSPGERAT LSCRASKGVS TSGYSYLHWY QQKPGQAPRL LIYLASYLES | 60 |
| | GVPARFSGSG SGTDFTLTIS SLEPEDFAVY YCQHSRDLPL TFGGGTKVEI K | 111 |
| SEQ ID NO: 172 pembrolizumab heavy chain CDR1 | NYYMY | 5 |
| SEQ ID NO: 173 pembrolizumab heavy chain CDR2 | GINPSNGGTN FNEKFK | 16 |
| SEQ ID NO: 174 pembrolizumab heavy chain CDR3 | RDYRFDMGFD Y | 11 |
| SEQ ID NO: 175 pembrolizumab light chain CDR1 | RASKGVSTSG YSYLH | 15 |
| SEQ ID NO: 176 pembrolizumab light chain CDR2 | LASYLES | 7 |
| SEQ ID NO: 177 pembrolizumab light chain CDR3 | QHSRDLPLT | 9 |

In some embodiments, the PD-1 inhibitor is pembrolizumab or a biosimilar thereof, and the pembrolizumab is administered at a dose of about 0.5 mg/kg to about 10 mg/kg. In some embodiments, the PD-1 inhibitor is pembrolizumab or a biosimilar thereof, and the pembrolizumab is administered at a dose of about 0.5 mg/kg, about 1 mg/kg, about 1.5 mg/kg, about 2 mg/kg, about 2.5 mg/kg, about 3 mg/kg, about 3.5 mg/kg, about 4 mg/kg, about 4.5 mg/kg, about 5 mg/kg, about 5.5 mg/kg, about 6 mg/kg, about 6.5 mg/kg, about 7 mg/kg, about 7.5 mg/kg, about 8 mg/kg, about 8.5 mg/kg, about 9 mg/kg, about 9.5 mg/kg, or about 10 mg/kg. In some embodiments, the pembrolizumab administration is begun 1, 2, 3, 4, or 5 days post IL-2 administration. In some embodiments, the pembrolizumab administration is begun 1, 2, or 3 days post IL-2 administration. In some embodiments, the pembrolizumab can also be administered 1, 2, 3, 4 or 5 weeks pre-resection (i.e., before obtaining a tumor sample from the subject or patient). In some embodiments, the pembrolizumab can also be administered 1, 2, or 3 weeks pre-resection (i.e., before obtaining a tumor sample from the subject or patient).

In some embodiments, the PD-1 inhibitor is pembrolizumab or a biosimilar thereof, wherein the pembrolizumab is administered at a dose of about 200 mg to about 500 mg. In some embodiments, the PD-1 inhibitor is pembrolizumab or a biosimilar thereof, and the nivolumab is administered at a dose of about 200 mg, about 220 mg, about 240 mg, about 260 mg, about 280 mg, about 300 mg, about 320 mg, about 340 mg, about 360 mg, about 380 mg, about 400 mg, about 420 mg, about 440 mg, about 460 mg, about 480 mg, or about 500 mg. In some embodiments, the pembrolizumab administration is begun 1, 2, 3, 4, or 5 days post IL-2 administration. In some embodiments, the pembrolizumab administration is begun 1, 2, or 3 days post IL-2 administration. In some embodiments, the pembrolizumab can also be administered 1, 2, 3, 4 or 5 weeks pre-resection (i.e., before obtaining a tumor sample from the subject or patient). In some embodiments, the pembrolizumab can also be administered 1, 2, or 3 weeks pre-resection (i.e., before obtaining a tumor sample from the subject or patient).

In some embodiments, the PD-1 inhibitor is pembrolizumab or a biosimilar thereof, wherein the pembrolizumab is administered every 2 weeks, every 3 weeks, every 4 weeks, every 5 weeks, or every 6 weeks. In some embodiments, the pembrolizumab administration is begun 1, 2, 3, 4, or 5 days post IL-2 administration. In some embodiments, the pembrolizumab administration is begun 1, 2, or 3 days post IL-2 administration. In some embodiments, the pembrolizumab can also be administered 1, 2, 3, 4 or 5 weeks pre-resection (i.e., before obtaining a tumor sample from the subject or patient). In some embodiments, the pembrolizumab can also be administered 1, 2, or 3 weeks pre-resection (i.e., before obtaining a tumor sample from the subject or patient).

In some embodiments, the pembrolizumab is administered to treat melanoma. In some embodiments, the pembrolizumab is administered to treat melanoma at about 200 mg every 3 weeks. In some embodiments, the pembrolizumab is administered to treat melanoma at about 400 mg every 6 weeks. In some embodiments, the pembrolizumab administration is begun 1, 2, 3, 4, or 5 days post IL-2 administration. In some embodiments, the pembrolizumab administration is begun 1, 2, or 3 days post IL-2 administration. In some embodiments, the pembrolizumab can also be administered 1, 2, 3, 4 or 5 weeks pre-resection (i.e., before obtaining a tumor sample from the subject or patient). In some embodiments, the pembrolizumab can also be administered 1, 2, or 3 weeks pre-resection (i.e., before obtaining a tumor sample from the subject or patient).

In some embodiments, the pembrolizumab is administered to treat NSCLC. In some embodiments, the pembrolizumab is administered to treat NSCLC at about 200 mg every 3 weeks. In some embodiments, the pembrolizumab is administered to treat NSCLC at about 400 mg every 6 weeks. In some embodiments, the pembrolizumab administration is begun 1, 2, 3, 4, or 5 days post IL-2 administration. In some embodiments, the pembrolizumab administration is begun 1, 2, or 3 days post IL-2 administration. In some embodiments, the pembrolizumab can also be administered 1, 2, 3, 4 or 5 weeks pre-resection (i.e., before obtaining a tumor sample from the subject or patient). In some embodiments, the pembrolizumab can also be administered 1, 2, or 3 weeks pre-resection (i.e., before obtaining a tumor sample from the subject or patient).

In some embodiments, the pembrolizumab is administered to treat small cell lung cancer (SCLC). In some embodiments, the pembrolizumab is administered to treat SCLC at about 200 mg every 3 weeks. In some embodiments, the pembrolizumab is administered to treat SCLC at about 400 mg every 6 weeks. In some embodiments, the pembrolizumab administration is begun 1, 2, 3, 4, or 5 days post IL-2 administration. In some embodiments, the pembrolizumab administration is begun 1, 2, or 3 days post IL-2 administration. In some embodiments, the pembrolizumab can also be administered 1, 2, 3, 4 or 5 weeks pre-resection (i.e., before obtaining a tumor sample from the subject or patient). In some embodiments, the pembrolizumab can also be administered 1, 2, or 3 weeks pre-resection (i.e., before obtaining a tumor sample from the subject or patient).

In some embodiments, the pembrolizumab is administered to treat head and neck squamous cell cancer (HNSCC). In some embodiments, the pembrolizumab is administered to treat HNSCC at about 200 mg every 3 weeks. In some embodiments, the pembrolizumab is administered to treat HNSCC at about 400 mg every 6 weeks. In some embodiments, the pembrolizumab administration is begun 1, 2, 3, 4, or 5 days post IL-2 administration. In some embodiments, the pembrolizumab administration is begun 1, 2, or 3 days post IL-2 administration. In some embodiments, the pembrolizumab can also be administered 1, 2, 3, 4 or 5 weeks pre-resection (i.e., before obtaining a tumor sample from the subject or patient). In some embodiments, the pembrolizumab can also be administered 1, 2, or 3 weeks pre-resection (i.e., before obtaining a tumor sample from the subject or patient).

In some embodiments, the pembrolizumab is administered to treat classical Hodgkin lymphoma (cHL) or primary mediastinal large B-cell lymphoma (PMBCL) at about 200 mg every 3 weeks. In some embodiments, the pembrolizumab is administered to treat classical Hodgkin lymphoma (cHL) or primary mediastinal large B-cell lymphoma (PMBCL) at about 400 mg every 6 weeks for adults. In some embodiments, the pembrolizumab is administered to treat classical Hodgkin lymphoma (cHL) or primary mediastinal large B-cell lymphoma (PMBCL) at about 2 mg/kg (up to 200 mg) every 3 weeks for pediatrics. In some embodiments, the pembrolizumab administration is begun 1, 2, 3, 4, or 5 days post IL-2 administration. In some embodiments, the pembrolizumab administration is begun 1, 2, or 3 days post IL-2 administration. In some embodiments, the pembrolizumab can also be administered 1, 2, 3, 4 or 5 weeks pre-resection (i.e., before obtaining a tumor sample from the subject or patient). In some embodiments, the pembrolizumab can also be administered 1, 2, or 3 weeks pre-resection (i.e., before obtaining a tumor sample from the subject or patient).

In some embodiments, the pembrolizumab is administered to treat urothelial carcinoma at about 200 mg every 3 weeks. In some embodiments, the pembrolizumab is administered to treat urothelial carcinoma at about 400 mg every 6 weeks. In some embodiments, the pembrolizumab administration is begun 1, 2, 3, 4, or 5 days post IL-2 administration. In some embodiments, the pembrolizumab administration is begun 1, 2, or 3 days post IL-2 administration. In some embodiments, the pembrolizumab can also be administered 1, 2, 3, 4 or 5 weeks pre-resection (i.e., before obtaining a tumor sample from the subject or patient). In some embodiments, the pembrolizumab can also be administered 1, 2, or 3 weeks pre-resection (i.e., before obtaining a tumor sample from the subject or patient).

In some embodiments, the pembrolizumab is administered to treat microsatellite instability-high (MSI-H) or mismatch repair deficient (dMMR) cancer at about 200 mg every 3 weeks. In some embodiments, the pembrolizumab is administered to treat MSI-H or dMMR cancer at about 400 mg every 6 weeks for adults. In some embodiments, the pembrolizumab is administered to treat MSI-H or dMMR cancer at about 2 mg/kg (up to 200 mg) every 3 weeks for pediatrics. In some embodiments, the pembrolizumab administration is begun 1, 2, 3, 4, or 5 days post IL-2 administration. In some embodiments, the pembrolizumab administration is begun 1, 2, or 3 days post IL-2 administration. In some embodiments, the pembrolizumab can also be administered 1, 2, 3, 4 or 5 weeks pre-resection (i.e., before obtaining a tumor sample from the subject or patient). In some embodiments, the pembrolizumab can also be administered 1, 2, or 3 weeks pre-resection (i.e., before obtaining a tumor sample from the subject or patient). In some embodiments, the pembrolizumab administration is begun 1, 2, 3, 4, or 5 days post IL-2 administration. In some embodiments, the pembrolizumab administration is begun 1, 2, or 3 days post IL-2 administration. In some embodiments, the pembrolizumab can also be administered 1, 2, 3, 4 or 5 weeks pre-resection (i.e., before obtaining a tumor sample from the subject or patient). In some embodiments, the pembrolizumab can also be administered 1, 2, or 3 weeks pre-resection (i.e., before obtaining a tumor sample from the subject or patient).

In some embodiments, the pembrolizumab is administered to treat microsatellite instability-high (MSI-H) or mismatch repair deficient colorectal cancer (dMMR CRC at about 200 mg every 3 weeks. In some embodiments, the pembrolizumab is administered to treat MSI-H or dMMR CRC at about 400 mg every 6 weeks. In some embodiments, the pembrolizumab administration is begun 1, 2, 3, 4, or 5 days post IL-2 administration. In some embodiments, the pembrolizumab administration is begun 1, 2, or 3 days post IL-2 administration. In some embodiments, the pembrolizumab can also be administered 1, 2, 3, 4 or 5 weeks pre-resection (i.e., before obtaining a tumor sample from the subject or patient). In some embodiments, the pembrolizumab can also be administered 1, 2, or 3 weeks pre-resection (i.e., before obtaining a tumor sample from the subject or patient).

In some embodiments, the pembrolizumab is administered to treat gastric cancer at about 200 mg every 3 weeks. In some embodiments, the pembrolizumab is administered to treat gastric cancer at about 400 mg every 6 weeks. In some embodiments, the pembrolizumab administration is begun 1, 2, 3, 4, or 5 days post IL-2 administration. In some embodiments, the pembrolizumab administration is begun 1, 2, or 3 days post IL-2 administration. In some embodiments, the pembrolizumab can also be administered 1, 2, 3, 4 or 5 weeks pre-resection (i.e., before obtaining a tumor sample from the subject or patient). In some embodiments, the pembrolizumab can also be administered 1, 2, or 3 weeks pre-resection (i.e., before obtaining a tumor sample from the subject or patient).

In some embodiments, the pembrolizumab is administered to treat Esophageal Cancer at about 200 mg every 3 weeks. In some embodiments, the pembrolizumab is administered to treat Esophageal Cancer at about 400 mg every 6 weeks. In some embodiments, the pembrolizumab administration is begun 1, 2, 3, 4, or 5 days post IL-2 administration. In some embodiments, the pembrolizumab administration is begun 1, 2, or 3 days post IL-2 administration. In some embodiments, the pembrolizumab can also be administered 1, 2, 3, 4 or 5 weeks pre-resection (i.e., before obtaining a tumor sample from the subject or patient). In some embodiments, the pembrolizumab can also be administered 1, 2, or 3 weeks pre-resection (i.e., before obtaining a tumor sample from the subject or patient).

In some embodiments, the pembrolizumab is administered to treat cervical cancer at about 200 mg every 3 weeks. In some embodiments, the pembrolizumab is administered to treat cervical cancer at about 400 mg every 6 weeks. In some embodiments, the pembrolizumab administration is begun 1, 2, 3, 4, or 5 days post IL-2 administration. In some embodiments, the pembrolizumab administration is begun 1, 2, or 3 days post IL-2 administration. In some embodiments, the pembrolizumab can also be administered 1, 2, 3, 4 or 5 weeks pre-resection (i.e., before obtaining a tumor sample from the subject or patient). In some embodiments, the pembrolizumab can also be administered 1, 2, or 3 weeks pre-resection (i.e., before obtaining a tumor sample from the subject or patient).

In some embodiments, the pembrolizumab is administered to treat hepatocellular carcinoma (HCC) at about 200 mg every 3 weeks. In some embodiments, the pembrolizumab is administered to treat HCC at about 400 mg every 6 weeks. In some embodiments, the pembrolizumab administration is begun 1, 2, 3, 4, or 5 days post IL-2 administration. In some embodiments, the pembrolizumab administration is begun 1, 2, or 3 days post IL-2 administration. In some embodiments, the pembrolizumab can also be administered 1, 2, 3, 4 or 5 weeks pre-resection (i.e., before obtaining a tumor sample from the subject or patient). In some embodiments, the pembrolizumab can also be administered 1, 2, or 3 weeks pre-resection (i.e., before obtaining a tumor sample from the subject or patient).

In some embodiments, the pembrolizumab is administered to treat Merkel cell carcinoma (MCC) at about 200 mg every 3 weeks for adults. In some embodiments, the pembrolizumab is administered to treat MCC at about 400 mg every 6 weeks for adults. In some embodiments, the pembrolizumab is administered to treat MCC at about 2 mg/kg (up to 200 mg) every 3 weeks for pediatrics. In some embodiments, the pembrolizumab administration is begun 1, 2, 3, 4, or 5 days post IL-2 administration. In some embodiments, the pembrolizumab administration is begun 1, 2, or 3 days post IL-2 administration. In some embodiments, the pembrolizumab can also be administered 1, 2, 3, 4 or 5 weeks pre-resection (i.e., before obtaining a tumor sample from the subject or patient). In some embodiments, the pembrolizumab can also be administered 1, 2, or 3 weeks pre-resection (i.e., before obtaining a tumor sample from the subject or patient). In some embodiments, the pembrolizumab administration is begun 1, 2, 3, 4, or 5 days post IL-2 administration. In some embodiments, the pembrolizumab administration is begun 1, 2, or 3 days post IL-2 administration. In some embodiments, the pembrolizumab can also be administered 1, 2, 3, 4 or 5 weeks pre-resection (i.e., before obtaining a tumor sample from the subject or patient). In some embodiments, the pembrolizumab can also be administered 1, 2, or 3 weeks pre-resection (i.e., before obtaining a tumor sample from the subject or patient).

In some embodiments, the pembrolizumab is administered to treat renal cell carcinoma (RCC) at about 200 mg every 3 weeks. In some embodiments, the pembrolizumab is administered to treat RCC at about 400 mg every 6 weeks with axitinib 5 mg orally twice daily. In some embodiments, the pembrolizumab administration is begun 1, 2, 3, 4, or 5 days post IL-2 administration. In some embodiments, the pembrolizumab administration is begun 1, 2, or 3 days post IL-2 administration. In some embodiments, the pembrolizumab can also be administered 1, 2, 3, 4 or 5 weeks pre-resection (i.e., before obtaining a tumor sample from the subject or patient). In some embodiments, the pembrolizumab can also be administered 1, 2, or 3 weeks pre-resection (i.e., before obtaining a tumor sample from the subject or patient).

In some embodiments, the pembrolizumab is administered to treat endometrial carcinoma at about 200 mg every 3 weeks. In some embodiments, the pembrolizumab is administered to treat endometrial carcinoma at about 400 mg every 6 weeks with lenvatinib 20 mg orally once daily for tumors that are not MSI-H or dMMR. In some embodiments, the pembrolizumab administration is begun 1, 2, 3, 4, or 5 days post IL-2 administration. In some embodiments, the pembrolizumab administration is begun 1, 2, or 3 days post IL-2 administration. In some embodiments, the pembrolizumab can also be administered 1, 2, 3, 4 or 5 weeks pre-resection (i.e., before obtaining a tumor sample from the subject or patient). In some embodiments, the pembrolizumab can also be administered 1, 2, or 3 weeks pre-resection (i.e., before obtaining a tumor sample from the subject or patient).

In some embodiments, the pembrolizumab is administered to treat tumor mutational burden-high (TMB-H) Cancer at about 200 mg every 3 weeks for adults. In some embodiments, the pembrolizumab is administered to treat TMB-H Cancer at about 400 mg every 6 weeks for adults. In some embodiments, the pembrolizumab is administered to treat TMB-H Cancer at about 2 mg/kg (up to 200 mg) every 3 weeks for pediatrics. In some embodiments, the pembrolizumab administration is begun 1, 2, 3, 4, or 5 days post IL-2 administration. In some embodiments, the pembrolizumab administration is begun 1, 2, or 3 days post IL-2 administration. In some embodiments, the pembrolizumab can also be administered 1, 2, 3, 4 or 5 weeks pre-resection (i.e., before obtaining a tumor sample from the subject or patient). In some embodiments, the pembrolizumab can also be administered 1, 2, or 3 weeks pre-resection (i.e., before obtaining a tumor sample from the subject or patient).

In some embodiments, the pembrolizumab is administered to treat cutaneous squamous cell carcinoma (cSCC) at about 200 mg every 3 weeks. In some embodiments, the pembrolizumab is administered to treat cSCC at about 400 mg every 6 weeks. In some embodiments, the pembrolizumab administration is begun 1, 2, 3, 4, or 5 days post IL-2 administration. In some embodiments, the pembrolizumab administration is begun 1, 2, or 3 days post IL-2 administration. In some embodiments, the pembrolizumab can also be administered 1, 2, 3, 4 or 5 weeks pre-resection (i.e., before obtaining a tumor sample from the subject or patient). In some embodiments, the pembrolizumab can also be administered 1, 2, or 3 weeks pre-resection (i.e., before obtaining a tumor sample from the subject or patient).

In some embodiments, the pembrolizumab is administered to treat triple-negative breast cancer (TNBC) at about 200 mg every 3 weeks. In some embodiments, the pembrolizumab is administered to treat TNBC at about 400 mg every 6 weeks. In some embodiments, the pembrolizumab administration is begun 1, 2, 3, 4, or 5 days post IL-2 administration. In some embodiments, the pembrolizumab administration is begun 1, 2, or 3 days post IL-2 administration. In some embodiments, the pembrolizumab can also be administered 1, 2, 3, 4 or 5 weeks pre-resection (i.e., before obtaining a tumor sample from the subject or patient). In some embodiments, the pembrolizumab can also be administered 1, 2, or 3 weeks pre-resection (i.e., before obtaining a tumor sample from the subject or patient).

In an embodiment, if the patient or subject is an adult, i.e., treatment of adult indications, and additional dosing regimen of 400 mg every 6 weeks can be employed. In some embodiments, the pembrolizumab administration is begun 1, 2, 3, 4, or 5 days post IL-2 administration. In some embodiments, the pembrolizumab administration is begun 1, 2, or 3 days post IL-2 administration. In some embodiments, the pembrolizumab can also be administered 1, 2, 3, 4 or 5 weeks pre-resection (i.e., before obtaining a tumor sample from the subject or patient). In some embodiments, the pembrolizumab can also be administered 1, 2, or 3 weeks pre-resection (i.e., before obtaining a tumor sample from the subject or patient).

In an embodiment, the PD-1 inhibitor is a commercially-available anti-PD-1 monoclonal antibody, such as anti-m-PD-1 clones J43 (Cat #BE0033-2) and RMP1-14 (Cat #BE0146) (Bio X Cell, Inc., West Lebanon, NH, USA). A number of commercially-available anti-PD-1 antibodies are known to one of ordinary skill in the art.

In an embodiment, the PD-1 inhibitor is an antibody disclosed in U.S. Pat. No. 8,354,509 or U.S. Patent Application Publication Nos. 2010/0266617 A1, 2013/0108651 A1, 2013/0109843 A2, the disclosures of which are incorporated by reference herein. In an embodiment, the PD-1 inhibitor is an anti-PD-1 antibody described in U.S. Pat. Nos. 8,287,856, 8,580,247, and 8,168,757 and U.S. Patent Application Publication Nos. 2009/0028857 A1, 2010/0285013 A1, 2013/0022600 A1, and 2011/0008369 A1, the teachings of which are hereby incorporated by reference. In another embodiment, the PD-1 inhibitor is an anti-PD-1 antibody disclosed in U.S. Pat. No. 8,735,553 B1, the disclosure of which is incorporated herein by reference. In an embodiment, the PD-1 inhibitor is pidilizumab, also known as CT-011, which is described in U.S. Pat. No. 8,686,119, the disclosure of which is incorporated by reference herein.

In an embodiment, the PD-1 inhibitor may be a small molecule or a peptide, or a peptide derivative, such as those described in U.S. Pat. Nos. 8,907,053; 9,096,642; and 9,044,442 and U.S. Patent Application Publication No. US 2015/0087581; 1,2,4-oxadiazole compounds and derivatives such as those described in U.S. Patent Application Publication No. 2015/0073024; cyclic peptidomimetic compounds and derivatives such as those described in U.S. Patent Application Publication No. US 2015/0073042; cyclic compounds and derivatives such as those described in U.S. Patent Application Publication No. US 2015/0125491; 1,3,4-oxadiazole and 1,3,4-thiadiazole compounds and derivatives such as those described in International Patent Application Publication No. WO 2015/033301; peptide-based compounds and derivatives such as those described in International Patent Application Publication Nos. WO 2015/036927 and WO 2015/04490, or a macrocyclic peptide-based compounds and derivatives such as those described in U.S. Patent Application Publication No. US 2014/0294898; the disclosures of each of which are hereby incorporated by reference in their entireties. In an embodiment, the PD-1 inhibitor is cemiplimab, which is commercially available from Regeneron, Inc.

In an embodiment, the PD-L1 or PD-L2 inhibitor may be any PD-L1 or PD-L2 inhibitor, antagonist, or blocker known in the art. In particular, it is one of the PD-L1 or PD-L2 inhibitors, antagonist, or blockers described in more detail in the following paragraphs. The terms "inhibitor," "antagonist," and "blocker" are used interchangeably herein in reference to PD-L1 and PD-L2 inhibitors. For avoidance of doubt, references herein to a PD-L1 or PD-L2 inhibitor that is an antibody may refer to a compound or antigen-binding fragments, variants, conjugates, or biosimilars thereof. For avoidance of doubt, references herein to a PD-L1 or PD-L2 inhibitor may refer to a compound or a pharmaceutically acceptable salt, ester, solvate, hydrate, cocrystal, or prodrug thereof.

In some embodiments, the compositions, processes and methods described herein include a PD-L1 or PD-L2 inhibitor. In some embodiments, the PD-L1 or PD-L2 inhibitor is a small molecule. In a preferred embodiment, the PD-L1 or PD-L2 inhibitor is an antibody (i.e., an anti-PD-1 antibody), a fragment thereof, including Fab fragments, or a single-chain variable fragment (scFv) thereof. In some embodiments the PD-L1 or PD-L2 inhibitor is a polyclonal antibody. In a preferred embodiment, the PD-L1 or PD-L2 inhibitor is a monoclonal antibody. In some embodiments, the PD-L1 or PD-L2 inhibitor competes for binding with PD-L1 or PD-L2, and/or binds to an epitope on PD-L1 or PD-L2. In an embodiment, the antibody competes for binding with PD-L1 or PD-L2, and/or binds to an epitope on PD-L1 or PD-L2.

In some embodiments, the PD-L1 inhibitors provided herein are selective for PD-L1, in that the compounds bind or interact with PD-L1 at substantially lower concentrations than they bind or interact with other receptors, including the PD-L2 receptor. In certain embodiments, the compounds bind to the PD-L1 receptor at a binding constant that is at least about a 2-fold higher concentration, about a 3-fold higher concentration, about a 5-fold higher concentration, about a 10-fold higher concentration, about a 20-fold higher concentration, about a 30-fold higher concentration, about a 50-fold higher concentration, about a 100-fold higher concentration, about a 200-fold higher concentration, about a 300-fold higher concentration, or about a 500-fold higher concentration than to the PD-L2 receptor.

In some embodiments, the PD-L2 inhibitors provided herein are selective for PD-L2, in that the compounds bind or interact with PD-L2 at substantially lower concentrations than they bind or interact with other receptors, including the PD-L1 receptor. In certain embodiments, the compounds bind to the PD-L2 receptor at a binding constant that is at least about a 2-fold higher concentration, about a 3-fold higher concentration, about a 5-fold higher concentration, about a 10-fold higher concentration, about a 20-fold higher concentration, about a 30-fold higher concentration, about a 50-fold higher concentration, about a 100-fold higher concentration, about a 200-fold higher concentration, about a 300-fold higher concentration, or about a 500-fold higher concentration than to the PD-L1 receptor.

Without being bound by any theory, it is believed that tumor cells express PD-L1, and that T cells express PD-1. However, PD-L1 expression by tumor cells is not required for efficacy of PD-1 or PD-L1 inhibitors or blockers. In an embodiment, the tumor cells express PD-L1. In another embodiment, the tumor cells do not express PD-L1. In some embodiments, the methods can include a combination of a PD-1 and a PD-L1 antibody, such as those described herein, in combination with a TIL. The administration of a combination of a PD-1 and a PD-L1 antibody and a TIL may be simultaneous or sequential.

In some embodiments, the PD-L1 and/or PD-L2 inhibitor is one that binds human PD-L1 and/or PD-L2 with a KD of about 100 µM or lower, binds human PD-L1 and/or PD-L2 with a KD of about 90 µM or lower, binds human PD-L1 and/or PD-L2 with a KD of about 80 µM or lower, binds human PD-L1 and/or PD-L2 with a KD of about 70 µM or lower, binds human PD-L1 and/or PD-L2 with a KD of about 60 µM or lower, a KD of about 50 µM or lower, binds human PD-L1 and/or PD-L2 with a KD of about 40 µM or lower, or binds human PD-L1 and/or PD-L2 with a KD of about 30 µM or lower, In some embodiments, the PD-L1 and/or PD-L2 inhibitor is one that binds to human PD-L1 and/or PD-L2 with a kassoc of about 7.5×105 l/M·s or faster, binds to human PD-L1 and/or PD-L2 with a kassoc of about 8×105 l/M·s or faster, binds to human PD-L1 and/or PD-L2 with a kassoc of about 8.5×105 l/M·s or faster, binds to human PD-L1 and/or PD-L2 with a kassoc of about 9×105 l/M·s or faster, binds to human PD-L1 and/or PD-L2 with a kassoc of about 9.5×105 l/M·s and/or faster, or binds to human PD-L1 and/or PD-L2 with a kassoc of about 1×106 l/M·s or faster.

In some embodiments, the PD-L1 and/or PD-L2 inhibitor is one that binds to human PD-L1 or PD-L2 with a kdissoc of about 2×10-5 l/s or slower, binds to human PD-1 with a kdissoc of about 2.1×10-5 l/s or slower, binds to human PD-1 with a kdissoc of about 2.2×10-5 l/s or slower, binds to human PD-1 with a kdissoc of about 2.3×10-5 l/s or slower, binds to human PD-1 with a kdissoc of about 2.4×10-5 l/s or slower, binds to human PD-1 with a kdissoc of about 2.5×10-5 l/s or slower, binds to human PD-1 with a kdissoc of about 2.6×10-5 l/s or slower, binds to human PD-L1 or PD-L2 with a kdissoc of about 2.7×10-5 l/s or slower, or binds to human PD-L1 or PD-L2 with a kdissoc of about 3×10-5 l/s or slower.

In some embodiments, the PD-L1 and/or PD-L2 inhibitor is one that blocks or inhibits binding of human PD-L1 or human PD-L2 to human PD-1 with an IC50 of about 10 nM or lower; blocks or inhibits binding of human PD-L1 or human PD-L2 to human PD-1 with an IC50 of about 9 nM or lower; blocks or inhibits binding of human PD-L1 or human PD-L2 to human PD-1 with an IC50 of about 8 nM or lower; blocks or inhibits binding of human PD-L1 or human PD-L2 to human PD-1 with an IC50 of about 7 nM or lower; blocks or inhibits binding of human PD-L1 or human PD-L2 to human PD-1 with an IC50 of about 6 nM or lower; blocks or inhibits binding of human PD-L1 or human PD-L2 to human PD-1 with an IC50 of about 5 nM or lower; blocks or inhibits binding of human PD-L1 or human PD-L2 to human PD-1 with an IC50 of about 4 nM or lower; blocks or inhibits binding of human PD-L1 or human PD-L2 to human PD-1 with an IC50 of about 3 nM or lower; blocks or inhibits binding of human PD-L1 or human PD-L2 to human PD-1 with an IC50 of about 2 nM or lower; or blocks human PD-1, or blocks binding of human PD-L1 or human PD-L2 to human PD-1 with an IC50 of about 1 nM or lower.

In an embodiment, the PD-L1 inhibitor is durvalumab, also known as MEDI4736 (which is commercially available from Medimmune, LLC, Gaithersburg, Maryland, a subsidiary of AstraZeneca plc.), or antigen-binding fragments, conjugates, or variants thereof. In an embodiment, the PD-L1 inhibitor is an antibody disclosed in U.S. Pat. No. 8,779,108 or U.S. Patent Application Publication No. 2013/0034559, the disclosures of which are incorporated by reference herein. The clinical efficacy of durvalumab has been described in Page, et al., Ann. Rev. Med., 2014, 65, 185-202; Brahmer, et al., J. Clin. Oncol. 2014, 32, 5s (supplement, abstract 8021); and McDermott, et al., Cancer Treatment Rev., 2014, 40, 1056-64. The preparation and properties of durvalumab are described in U.S. Pat. No. 8,779,108, the disclosure of which is incorporated by reference herein. The amino acid sequences of durvalumab are set forth in Table 20. The durvalumab monoclonal antibody includes disulfide linkages at 22-96, 22"-96", 23'-89', 23"'-89"', 135'-195', 135"'-195"', 148-204, 148"-204", 215'-224, 215"'-224", 230-230", 233-233", 265-325, 265"-325", 371-429, and 371"-429'; and N-glycosylation sites at Asn-301 and Asn-301".

In an embodiment, a PD-L1 inhibitor comprises a heavy chain given by SEQ ID NO:178 and a light chain given by SEQ ID NO:179. In an embodiment, a PD-L1 inhibitor comprises heavy and light chains having the sequences shown in SEQ ID NO:178 and SEQ ID NO:179, respectively, or antigen binding fragments, Fab fragments, single-chain variable fragments (scFv), variants, or conjugates thereof. In an embodiment, a PD-L1 inhibitor comprises heavy and light chains that are each at least 99% identical to the sequences shown in SEQ ID NO:178 and SEQ ID NO:179, respectively. In an embodiment, a PD-L1 inhibitor comprises heavy and light chains that are each at least 98% identical to the sequences shown in SEQ ID NO:178 and SEQ ID NO:179, respectively. In an embodiment, a PD-L1 inhibitor comprises heavy and light chains that are each at least 97% identical to the sequences shown in SEQ ID NO:178 and SEQ ID NO:179, respectively. In an embodiment, a PD-L1 inhibitor comprises heavy and light chains that are each at least 96% identical to the sequences shown in SEQ ID NO:178 and SEQ ID NO:179, respectively. In an embodiment, a PD-L1 inhibitor comprises heavy and light chains that are each at least 95% identical to the sequences shown in SEQ ID NO:178 and SEQ ID NO:179, respectively.

In an embodiment, the PD-L1 inhibitor comprises the heavy and light chain CDRs or variable regions (VRs) of durvalumab. In an embodiment, the PD-L1 inhibitor heavy chain variable region ($V_H$) comprises the sequence shown in SEQ ID NO:180, and the PD-L1 inhibitor light chain variable region ($V_L$) comprises the sequence shown in SEQ ID NO:181, or conservative amino acid substitutions thereof. In an embodiment, a PD-L1 inhibitor comprises $V_H$ and $V_L$ regions that are each at least 99% identical to the sequences shown in SEQ ID NO:180 and SEQ ID NO:181, respectively. In an embodiment, a PD-L1 inhibitor comprises $V_H$ and $V_L$ regions that are each at least 98% identical to the sequences shown in SEQ ID NO:180 and SEQ ID NO:181, respectively. In an embodiment, a PD-L1 inhibitor comprises $V_H$ and $V_L$ regions that are each at least 97% identical to the sequences shown in SEQ ID NO:180 and SEQ ID NO:181, respectively. In an embodiment, a PD-L1 inhibitor comprises $V_H$ and $V_L$ regions that are each at least 96% identical to the sequences shown in SEQ ID NO:180 and SEQ ID NO:181, respectively. In an embodiment, a PD-L1 inhibitor comprises $V_H$ and $V_L$ regions that are each at least 95% identical to the sequences shown in SEQ ID NO:180 and SEQ ID NO:181, respectively.

In an embodiment, a PD-L1 inhibitor comprises heavy chain CDR1, CDR2 and CDR3 domains having the sequences set forth in SEQ ID NO:182, SEQ ID NO:183, and SEQ ID NO:184, respectively, or conservative amino acid substitutions thereof, and light chain CDR1, CDR2 and CDR3 domains having the sequences set forth in SEQ ID NO:185, SEQ ID NO:186, and SEQ ID NO:187, respectively, or conservative amino acid substitutions thereof. In an embodiment, the antibody competes for binding with, and/or binds to the same epitope on PD-L1 as any of the aforementioned antibodies.

In an embodiment, the PD-L1 inhibitor is an anti-PD-L1 biosimilar monoclonal antibody approved by drug regulatory authorities with reference to durvalumab. In an embodiment, the biosimilar comprises an anti-PD-L1 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is durvalumab. In some embodiments, the one or more post-translational modifications are selected from one or more of: glycosylation, oxidation, deamidation, and truncation. In some embodiments, the biosimilar is an anti-PD-L1 antibody authorized or submitted for authorization, wherein the anti-PD-L1 antibody is provided in a formulation which differs from the formulations of a reference medicinal product or reference biological product, wherein the reference medicinal product or reference biological product is durvalumab. The anti-PD-L1 antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is durvalumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is durvalumab.

TABLE 20

Amino acid sequences for PD-L1 inhibitors related to durvalumab.

| Identifier | Sequence (One-Letter Amino Acid Symbols) | | | | | |
|---|---|---|---|---|---|---|
| SEQ ID NO: 178 durvalumab heavy chain | EVQLVESGGG | LVQPGGSLRL | SCAASGFTFS | RYWMSWVRQA | PGKGLEWVAN | IKQDGSEKYY | 60 |
| | VDSVKGRFTI | SRDNAKNSLY | LQMNSLRAED | TAVYYCAREG | GWFGELAFDY | WGQGTLVTVS | 120 |
| | SASTKGPSVF | PLAPSSKSTS | GGTAALGCLV | KDYFPEPVTV | SWNSGALTSG | VHTFPAVLQS | 180 |
| | SGLYSLSSVV | TVPSSSLGTQ | TYICNVNHKP | SNTKVDKRVE | PKSCDKTHTC | PPCPAPEFEG | 240 |
| | GPSVFLFPPK | PKDTLMISRT | PEVTCVVVDV | SHEDPEVKFN | WYVDGVEVHN | AKTKPREEQY | 300 |
| | NSTYRVVSVL | TVLHQDWLNG | KEYKCKVSNK | ALPASIEKTI | SKAKGQPREP | QVYTLPPSRE | 360 |
| | EMTKNQVSLT | CLVKGFYPSD | IAVEWESNGQ | PENNYKTTPP | VLDSDGSFFL | YSKLTVDKSR | 420 |
| | WQQGNVFSCS | VMHEALHNHY | TQKSLSLSPG | K | | | 451 |
| SEQ ID NO: 179 durvalumab light chain | EVQLVESGGG | LVQPGGSLRL | SCAASGFTFS | RYWMSWVRQA | PGKGLEWVAN | EIVLTQSPGT | 60 |
| | LSLSPGERAT | LSCRASQRVS | SSYLAWYQQK | PGQAPRLLIY | DASSRATGIP | DRFSGSGSGT | 120 |
| | DFTLTISRLE | PEDFAVYYCQ | QYGSLPWTFG | QGTKVEIKRT | VAAPSVFIFP | PSDEQLKSGT | 180 |
| | ASVVCLLNNF | YPREAKVQWK | VDNALQSGNS | QESVTEQDSK | DSTYSLSSTL | TLSKADYEKH | 240 |
| | KVYACEVTHQ | GLSSPVTKSF | NRGEC | | | | 265 |
| SEQ ID NO: 180 durvalumab variable heavy chain | EVQLVESGGG | LVQPGGSLRL | SCAASGFTFS | RYWMSWVRQA | PGKGLEWVAN | IKQDGSEKYY | 60 |
| | VDSVKGRFTI | SRDNAKNSLY | LQMNSLRAED | TAVYYCAREG | GWFGELAFDY | WGQGTLVTVS | 120 |
| | S | | | | | | 121 |
| SEQ ID NO: 181 durvalumab variable light chain | EIVLTQSPGT | LSLSPGERAT | LSCRASQRVS | SSYLAWYQQK | PGQAPRLLIY | DASSRATGIP | 60 |
| | DRFSGSGSGT | DFTLTISRLE | PEDFAVYYCQ | QYGSLPWTFG | QGTKVEIK | | 108 |

TABLE 20-continued

Amino acid sequences for PD-L1 inhibitors related to durvalumab.

| Identifier | Sequence (One-Letter Amino Acid Symbols) | |
|---|---|---|
| SEQ ID NO: 182 durvalumab heavy chain CDR1 | RYWMS | 5 |
| SEQ ID NO: 183 durvalumab heavy chain CDR2 | NIKQDGSEKY YVDSVKG | 17 |
| SEQ ID NO: 184 durvalumab heavy chain CDR3 | EGGWFGELAF DY | 12 |
| SEQ ID NO: 185 durvalumab light chain CDR1 | RASQRVSSSY LA | 12 |
| SEQ ID NO: 186 durvalumab light chain CDR2 | DASSRAT | 7 |
| SEQ ID NO: 187 durvalumab light chain CDR3 | QQYGSLPWT | 9 |

In an embodiment, the PD-L1 inhibitor is avelumab, also known as MSB0010718C (commercially available from Merck KGaA/EMD Serono), or antigen-binding fragments, conjugates, or variants thereof. The preparation and properties of avelumab are described in U.S. Patent Application Publication No. US 2014/0341917 A1, the disclosure of which is specifically incorporated by reference herein. The amino acid sequences of avelumab are set forth in Table 21. Avelumab has intra-heavy chain disulfide linkages (C23-C104) at 22-96, 147-203, 264-324, 370-428, 22"-96", 147-203", 264"-324", and 370"-428"; intra-light chain disulfide linkages (C23-C104) at 22'-90', 138'-197', 22'''-90''', and 138'''-197'''; intra-heavy-light chain disulfide linkages (h 5-CL 126) at 223-215' and 223"-215'''; intra-heavy-heavy chain disulfide linkages (h 11, h 14) at 229-229" and 232-232"; N-glycosylation sites (H CH2 N84.4) at 300, 300"; fucosylated complex bi-antennary CHO-type glycans; and H CHS K2 C-terminal lysine clipping at 450 and 450'.

In an embodiment, a PD-L1 inhibitor comprises a heavy chain given by SEQ ID NO:188 and a light chain given by SEQ ID NO:189. In an embodiment, a PD-L1 inhibitor comprises heavy and light chains having the sequences shown in SEQ ID NO:188 and SEQ ID NO:189, respectively, or antigen binding fragments, Fab fragments, single-chain variable fragments (scFv), variants, or conjugates thereof. In an embodiment, a PD-L1 inhibitor comprises heavy and light chains that are each at least 99% identical to the sequences shown in SEQ ID NO:188 and SEQ ID NO:189, respectively. In an embodiment, a PD-L1 inhibitor comprises heavy and light chains that are each at least 98% identical to the sequences shown in SEQ ID NO:188 and SEQ ID NO:189, respectively. In an embodiment, a PD-L1 inhibitor comprises heavy and light chains that are each at least 97% identical to the sequences shown in SEQ ID NO:188 and SEQ ID NO:189, respectively. In an embodiment, a PD-L1 inhibitor comprises heavy and light chains that are each at least 96% identical to the sequences shown in SEQ ID NO:188 and SEQ ID NO:189, respectively. In an embodiment, a PD-L1 inhibitor comprises heavy and light chains that are each at least 95% identical to the sequences shown in SEQ ID NO:188 and SEQ ID NO:189, respectively.

In an embodiment, the PD-L1 inhibitor comprises the heavy and light chain CDRs or variable regions (VRs) of avelumab. In an embodiment, the PD-L1 inhibitor heavy chain variable region (VH) comprises the sequence shown in SEQ ID NO:190, and the PD-L1 inhibitor light chain variable region (VL) comprises the sequence shown in SEQ ID NO:191, or conservative amino acid substitutions thereof. In an embodiment, a PD-L1 inhibitor comprises $V_H$ and $V_L$ regions that are each at least 99% identical to the sequences shown in SEQ ID NO:190 and SEQ ID NO:191, respectively. In an embodiment, a PD-L1 inhibitor comprises $V_H$ and $V_L$ regions that are each at least 98% identical to the sequences shown in SEQ ID NO:190 and SEQ ID NO:191, respectively. In an embodiment, a PD-L1 inhibitor comprises $V_H$ and $V_L$ regions that are each at least 97% identical to the sequences shown in SEQ ID NO:190 and SEQ ID NO:191, respectively. In an embodiment, a PD-L1 inhibitor comprises $V_H$ and $V_L$ regions that are each at least 96% identical to the sequences shown in SEQ ID NO:190 and SEQ ID NO:191, respectively. In an embodiment, a PD-L1 inhibitor comprises $V_H$ and $V_L$ regions that are each at least 95% identical to the sequences shown in SEQ ID NO:190 and SEQ ID NO:191, respectively.

In an embodiment, a PD-L1 inhibitor comprises heavy chain CDR1, CDR2 and CDR3 domains having the sequences set forth in SEQ ID NO:192, SEQ ID NO:193, and SEQ ID NO:194, respectively, or conservative amino acid substitutions thereof, and light chain CDR1, CDR2 and CDR3 domains having the sequences set forth in SEQ ID NO:195, SEQ ID NO:196, and SEQ ID NO:197, respectively, or conservative amino acid substitutions thereof. In an embodiment, the antibody competes for binding with, and/or binds to the same epitope on PD-L1 as any of the aforementioned antibodies.

In an embodiment, the PD-L1 inhibitor is an anti-PD-L1 biosimilar monoclonal antibody approved by drug regulatory authorities with reference to avelumab. In an embodiment, the biosimilar comprises an anti-PD-L1 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is avelumab. In some embodiments, the one or more post-translational modifications are selected from one or more of: glycosylation, oxidation, deamidation, and truncation. In some embodiments, the biosimilar is an anti-PD-L1 antibody authorized or submitted for authorization, wherein the anti-PD-L1 antibody is provided in a formulation which differs from the formulations of a reference medicinal product or reference biological product, wherein the reference medicinal product or reference biological product is avelumab. The anti-PD-L1 antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is avelumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is avelumab.

TABLE 21

Amino acid sequences for PD-L1 inhibitors related to avelumab.

| Identifier | Sequence (One-Letter Amino Acid Symbols) | |
|---|---|---|
| SEQ ID NO: 188 avelumab heavy chain | EVQLLESGGG LVQPGGSLRL SCAASGFTFS SYIMMWVRQA PKGLEWVSS IYPSGGITFY<br>ADTVKGRFTI SRDNSKNTLY LQMNSLRAED TAVYYCARIK LGTVTTVDYW GQGTLVTVSS<br>ASTKGPSVFP LAPSSKSTSG GTAALGCLVK DYFPEPVTVS WNSGALTSGV HTFPAVLQSS<br>GLYSLSSVVT VPSSSLGTQT YICNVNHKPS NTKVDKKVEP KSCDKTHTCP PCPAPELLGG<br>PSVFLFPPKP KDTLMISRTP EVTCVVVDVS HEDPEVKFNW YVDGVEVHNA KTKPREEQYN<br>STYRVVSVLT VLHQDWLNGK EYKCKVSNKA LPAPIEKTIS KAKGQPREPQ VYTLPPSRDE<br>LTKNQVSLTC LVKGFYPSDI AVEWESNGQP ENNYKTTPPV LDSDGSFFLY SKLTVDKSRW<br>QQGNVFSCSV MHEALHNHYT QKSLSLSPGK | 60<br>120<br>180<br>240<br>300<br>360<br>420<br>450 |
| SEQ ID NO: 189 avelumab light chain | QSALTQPASV SGSPGQSITI SCTGTSSDVG GYNYVSWYQQ HPGKAPKLMI YDVSNRPSGV<br>SNRFSGSKSG NTASLTISGL QAEDEADYYC SSYTSSSTRV FGTGTKVTVL GQPKANPTVT<br>LFPPSSEELQ ANKATLVCLI SDFYPGAVTV AWKADGSPVK AGVETTKPSK QSNNKYAASS<br>YLSLTPEQWK SHRSYSCQVT HEGSTVEKTV APTECS | 60<br>120<br>180<br>216 |
| SEQ ID NO: 190 avelumab variable heavy chain | EVQLLESGGG LVQPGGSLRL SCAASGFTFS SYIMMWVRQA PKGLEWVSS IYPSGGITFY<br>ADTVKGRFTI SRDNSKNTLY LQMNSLRAED TAVYYCARIK LGTVTTVDYW GQGTLVTVSS | 60<br>120 |
| SEQ ID NO: 191 avelumab variable light chain | QSALTQPASV SGSPGQSITI SCTGTSSDVG GYNYVSWYQQ HPGKAPKLMI YDVSNRPSGV<br>SNRFSGSKSG NTASLTISGL QAEDEADYYC SSYTSSSTRV FGTGTKVTVL | 60<br>110 |
| SEQ ID NO: 192 avelumab heavy chain CDR1 | SYIMM | 5 |
| SEQ ID NO: 193 avelumab heavy chain CDR2 | SIYPSGGITF YADTVKG | 17 |
| SEQ ID NO: 194 avelumab heavy chain CDR3 | IKLGTVTTVD Y | 11 |
| SEQ ID NO: 195 avelumab light chain CDR1 | TGTSSDVGGY NYVS | 14 |
| SEQ ID NO: 196 avelumab light chain CDR2 | DVSNRPS | 7 |

TABLE 21-continued

Amino acid sequences for PD-L1 inhibitors related to avelumab.

| Identifier | Sequence (One-Letter Amino Acid Symbols) | |
|---|---|---|
| SEQ ID NO: 197 avelumab light chain CDR3 | SSYTSSSTRV | 10 |

In an embodiment, the PD-L1 inhibitor is atezolizumab, also known as MPDL3280A or RG7446 (commercially available as TECENTRIQ from Genentech, Inc., a subsidiary of Roche Holding AG, Basel, Switzerland), or antigen-binding fragments, conjugates, or variants thereof. In an embodiment, the PD-L1 inhibitor is an antibody disclosed in U.S. Pat. No. 8,217,149, the disclosure of which is specifically incorporated by reference herein. In an embodiment, the PD-L1 inhibitor is an antibody disclosed in U.S. Patent Application Publication Nos. 2010/0203056 A1, 2013/0045200 A1, 2013/0045201 A1, 2013/0045202 A1, or 2014/0065135 A1, the disclosures of which are specifically incorporated by reference herein. The preparation and properties of atezolizumab are described in U.S. Pat. No. 8,217,149, the disclosure of which is incorporated by reference herein. The amino acid sequences of atezolizumab are set forth in Table 22. Atezolizumab has intra-heavy chain disulfide linkages (C23-C104) at 22-96, 145-201, 262-322, 368-426, 22"-96", 145"-201", 262"-322", and 368"-426"; intra-light chain disulfide linkages (C23-C104) at 23'-88', 134'-194', 23'''-88''', and 134'''-194'''; intra-heavy-light chain disulfide linkages (h 5-CL 126) at 221-214' and 221"-214'''; intra-heavy-heavy chain disulfide linkages (h 11, h 14) at 227-227" and 230-230"; and N-glycosylation sites (H CH2 N84.4>A) at 298 and 298'.

In an embodiment, a PD-L1 inhibitor comprises a heavy chain given by SEQ ID NO:198 and a light chain given by SEQ ID NO:199. In an embodiment, a PD-L1 inhibitor comprises heavy and light chains having the sequences shown in SEQ ID NO:198 and SEQ ID NO:199, respectively, or antigen binding fragments, Fab fragments, single-chain variable fragments (scFv), variants, or conjugates thereof. In an embodiment, a PD-L1 inhibitor comprises heavy and light chains that are each at least 99% identical to the sequences shown in SEQ ID NO:198 and SEQ ID NO:199, respectively. In an embodiment, a PD-L1 inhibitor comprises heavy and light chains that are each at least 98% identical to the sequences shown in SEQ ID NO:198 and SEQ ID NO:199, respectively. In an embodiment, a PD-L1 inhibitor comprises heavy and light chains that are each at least 97% identical to the sequences shown in SEQ ID NO:198 and SEQ ID NO:199, respectively. In an embodiment, a PD-L1 inhibitor comprises heavy and light chains that are each at least 96% identical to the sequences shown in SEQ ID NO:198 and SEQ ID NO:199, respectively. In an embodiment, a PD-L1 inhibitor comprises heavy and light chains that are each at least 95% identical to the sequences shown in SEQ ID NO:198 and SEQ ID NO:199, respectively.

In an embodiment, the PD-L1 inhibitor comprises the heavy and light chain CDRs or variable regions (VRs) of atezolizumab. In an embodiment, the PD-L1 inhibitor heavy chain variable region ($V_H$) comprises the sequence shown in SEQ ID NO:200, and the PD-L1 inhibitor light chain variable region ($V_L$) comprises the sequence shown in SEQ ID NO:201, or conservative amino acid substitutions thereof. In an embodiment, a PD-L1 inhibitor comprises $V_H$ and $V_L$ regions that are each at least 99% identical to the sequences shown in SEQ ID NO:200 and SEQ ID NO:201, respectively. In an embodiment, a PD-L1 inhibitor comprises $V_H$ and $V_L$ regions that are each at least 98% identical to the sequences shown in SEQ ID NO:200 and SEQ ID NO:201, respectively. In an embodiment, a PD-L1 inhibitor comprises $V_H$ and $V_L$ regions that are each at least 97% identical to the sequences shown in SEQ ID NO:200 and SEQ ID NO:201, respectively. In an embodiment, a PD-L1 inhibitor comprises $V_H$ and $V_L$ regions that are each at least 96% identical to the sequences shown in SEQ ID NO:200 and SEQ ID NO:201, respectively. In an embodiment, a PD-L1 inhibitor comprises $V_H$ and $V_L$ regions that are each at least 95% identical to the sequences shown in SEQ ID NO:200 and SEQ ID NO:201, respectively.

In an embodiment, a PD-L1 inhibitor comprises heavy chain CDR1, CDR2 and CDR3 domains having the sequences set forth in SEQ ID NO:202, SEQ ID NO:203, and SEQ ID NO:204, respectively, or conservative amino acid substitutions thereof, and light chain CDR1, CDR2 and CDR3 domains having the sequences set forth in SEQ ID NO:205, SEQ ID NO:206, and SEQ ID NO:207, respectively, or conservative amino acid substitutions thereof. In an embodiment, the antibody competes for binding with, and/or binds to the same epitope on PD-L1 as any of the aforementioned antibodies.

In an embodiment, the anti-PD-L1 antibody is an anti-PD-L1 biosimilar monoclonal antibody approved by drug regulatory authorities with reference to atezolizumab. In an embodiment, the biosimilar comprises an anti-PD-L1 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is atezolizumab. In some embodiments, the one or more post-translational modifications are selected from one or more of: glycosylation, oxidation, deamidation, and truncation. In some embodiments, the biosimilar is an anti-PD-L1 antibody authorized or submitted for authorization, wherein the anti-PD-L1 antibody is provided in a formulation which differs from the formulations of a reference medicinal product or reference biological product, wherein the reference medicinal product or reference biological product is atezolizumab. The anti-PD-L1 antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is atezolizumab. In some embodiments, the biosimilar is provided as a composition which further comprises one or more excipients, wherein the one or more excipients are the same as or different to the excipients comprised in a reference medicinal product or reference biological product, wherein the reference medicinal product or reference biological product is atezolizumab.

L1 antibodies disclosed in U.S. Pat. No. 7,943,743, which are incorporated by reference herein.

In an embodiment, the PD-L1 inhibitor is a commercially-available monoclonal antibody, such as INVIVOMAB anti-m-PD-L1 clone 10F.9G2 (Catalog #BE0101, Bio X Cell, Inc., West Lebanon, NH, USA). In an embodiment, the anti-PD-L1 antibody is a commercially-available monoclo-

TABLE 22

Amino acid sequences for PD-L1 inhibitors related to atezolizumab.

| Identifier | Sequence (One-Letter Amino Acid Symbols) | |
|---|---|---|
| SEQ ID NO: 198 atezolizumab heavy chain | EVQLVESGGG LVQPGGSLRL SCAASGFTFS DSWIHWVRQA PGKGLEWVAW ISPYGGSTYY<br>ADSVKGRFTI SADTSKNTAY LQMNSLRAED TAVYYCARRH WPGGFDYWGQ GTLVTVSSAS<br>TKGPSVFPLA PSSKSTSGGT AALGCLVKDY FPEPVTVSWN SGALTSGVHT FPAVLQSSGL<br>YSLSSVVTVP SSSLGTQTYI CNVNHKPSNT KVDKKVEPKS CDKTHTCPPC PAPELLGGPS<br>VFLFPPKPKD TLMISRTPEV TCVVVDVSHE DPEVKFNWYV DGVEVHNAKT KPREEQYAST<br>YRVVSVLTVL HQDWLNGKEY KCKVSNKALP APIEKTISKA KGQPREPQVY TLPPSREEMT<br>KNQVSLTCLV KGFYPSDIAV EWESNGQPEN NYKTTPPVLD SDGSFFLYSK LTVDKSRWQQ<br>GNVFSCSVMH EALHNHYTQK SLSLSPGK | 60<br>120<br>180<br>240<br>300<br>360<br>420<br>448 |
| SEQ ID NO: 199 atezolizumab light chain | DIQMTQSPSS LSASVGDRVT ITCRASQDVS TAVAWYQQKP GKAPKLLIYS ASFLYSGVPS<br>RFSGSGSGTD FTLTISSLQP EDFATYYCQQ YLYHPATFGQ GTKVEIKRTV AAPSVFIFPP<br>SDEQLKSGTA SVVCLLNNFY PREAKVQWKV DNALQSGNSQ ESVTEQDSKD STYSLSSTLT<br>LSKADYEKHK VYACEVTHQG LSSPVTKSFN RGEC | 60<br>120<br>180<br>214 |
| SEQ ID NO: 200 atezolizumab variable heavy chain | EVQLVESGGG LVQPGGSLRL SCAASGFTFS DSWIHWVRQA PGKGLEWVAW ISPYGGSTYY<br>ADSVKGRFTI SADTSKNTAY LQMNSLRAED TAVYYCARRH WPGGFDYWGQ GTLVTVSA | 60<br>118 |
| SEQ ID NO: 201 atezolizumab variable light chain | DIQMTQSPSS LSASVGDRVT ITCRASQDVS TAVAWYQQKP GKAPKLLIYS ASFLYSGVPS<br>RFSGSGSGTD FTLTISSLQP EDFATYYCQQ YLYHPATFGQ GTKVEIKR | 60<br>108 |
| SEQ ID NO: 202 atezolizumab heavy chain CDR1 | GFTFSDSWIH | 10 |
| SEQ ID NO: 203 atezolizumab heavy chain CDR2 | AWISPYGGST YYADSVKG | 18 |
| SEQ ID NO: 204 atezolizumab heavy chain CDR3 | RHWPGGFDY | 9 |
| SEQ ID NO: 205 atezolizumab light chain CDR1 | RASQDVSTAV A | 11 |
| SEQ ID NO: 206 atezolizumab light chain CDR2 | SASFLYS | 7 |
| SEQ ID NO: 207 atezolizumab light chain CDR3 | QQYLYHPAT | 9 |

In an embodiment, PD-L1 inhibitors include those antibodies described in U.S. Patent Application Publication No. US 2014/0341917 A1, the disclosure of which is incorporated by reference herein. In another embodiment, antibodies that compete with any of these antibodies for binding to PD-L1 are also included. In an embodiment, the anti-PD-L1 antibody is MDX-1105, also known as BMS-935559, which is disclosed in U.S. Pat. No. 7,943,743, the disclosures of which are incorporated by reference herein. In an embodiment, the anti-PD-L1 antibody is selected from the anti-PDnal antibody, such as AFFYMETRIX EBIOSCIENCE (MIH1). A number of commercially-available anti-PD-L1 antibodies are known to one of ordinary skill in the art.

In an embodiment, the PD-L2 inhibitor is a commercially-available monoclonal antibody, such as BIOLEGEND 24F.10C12 Mouse IgG2a, κ isotype (catalog #329602 Biolegend, Inc., San Diego, CA), SIGMA anti-PD-L2 antibody (catalog #SAB3500395, Sigma-Aldrich Co., St. Louis, MO), or other commercially-available anti-PD-L2 antibodies known to one of ordinary skill in the art.

In some embodiments, the present invention includes a method of treating a patient with a cancer comprising the steps of administering a TIL regimen, wherein the TIL regimen includes a TIL product genetically modified to express a CCR, further comprising the step of administering either a PD-1 inhibitor or a PD-L1 inhibitor. In some embodiments, the present invention includes a composition comprising (i) a TIL product genetically modified to express a CCR and (ii) either a PD-1 inhibitor or a PD-L1 inhibitor. In some embodiments, the present invention includes a kit comprising (i) a TIL product genetically modified to express a CCR and (ii) either a PD-1 inhibitor or a PD-L1 inhibitor.

3. Combinations with CTLA-4 Inhibitors

In some embodiments, the TIL therapy provided to patients with cancer may include treatment with therapeutic populations of TILs alone or may include a combination treatment including TILs and one or more CTLA-4 inhibitors.

Cytotoxic T lymphocyte antigen 4 (CTLA-4) is a member of the immunoglobulin superfamily and is expressed on the surface of helper T cells. CTLA-4 is a negative regulator of CD28-dependent T cell activation and acts as a checkpoint for adaptive immune responses. Similar to the T cell costimulatory protein CD28, the CTLA-4 binding antigen presents CD80 and CD86 on the cells. CTLA-4 delivers a suppressor signal to T cells, while CD28 delivers a stimulus signal. Human antibodies against human CTLA-4 have been described as immunostimulatory modulators in many disease conditions, such as treating or preventing viral and bacterial infections and for treating cancer (WO 01/14424 and WO 00/37504). A number of fully human anti-human CTLA-4 monoclonal antibodies (mAbs) have been studied in clinical trials for the treatment of various types of solid tumors, including, but not limited to, ipilimumab (MDX-010) and tremelimumab (CP-675,206).

In some embodiments, a CTLA-4 inhibitor may be any CTLA-4 inhibitor or CTLA-4 blocker known in the art. In particular, it is one of the CTLA-4 inhibitors or blockers described in more detail in the following paragraphs. The terms "inhibitor," "antagonist," and "blocker" are used interchangeably herein in reference to CTLA-4 inhibitors. For avoidance of doubt, references herein to a CTLA-4 inhibitor that is an antibody may refer to a compound or antigen-binding fragments, variants, conjugates, or biosimilars thereof. For avoidance of doubt, references herein to a CTLA-4 inhibitor may also refer to a small molecule compound or a pharmaceutically acceptable salt, ester, solvate, hydrate, cocrystal, or prodrug thereof.

Suitable CTLA-4 inhibitors for use in the methods of the invention, include, without limitation, anti-CTLA-4 antibodies, human anti-CTLA-4 antibodies, mouse anti-CTLA-4 antibodies, mammalian anti-CTLA-4 antibodies, humanized anti-CTLA-4 antibodies, monoclonal anti-CTLA-4 antibodies, polyclonal anti-CTLA-4 antibodies, chimeric anti-CTLA-4 antibodies, MDX-010 (ipilimumab), tremelimumab, anti-CD28 antibodies, anti-CTLA-4 adnectins, anti-CTLA-4 domain antibodies, single chain anti-CTLA-4 fragments, heavy chain anti-CTLA-4 fragments, light chain anti-CTLA-4 fragments, inhibitors of CTLA-4 that agonize the co-stimulatory pathway, the antibodies disclosed in PCT Publication No. WO 2001/014424, the antibodies disclosed in PCT Publication No. WO 2004/035607, the antibodies disclosed in U.S. Publication No. 2005/0201994, and the antibodies disclosed in granted European Patent No. EP 1212422 B1, the disclosures of each of which are incorporated herein by reference. Additional CTLA-4 antibodies are described in U.S. Pat. Nos. 5,811, 097, 5,855,887, 6,051,227, and 6,984,720; in PCT Publication Nos. WO 01/14424 and WO 00/37504; and in U.S. Publication Nos. 2002/0039581 and 2002/086014, the disclosures of each of which are incorporated herein by reference. Other anti-CTLA-4 antibodies that can be used in a method of the present invention include, for example, those disclosed in: WO 98/42752; U.S. Pat. Nos. 6,682,736 and 6,207,156; Hurwitz et al., Proc. Natl. Acad. Sci. USA, 95(17):10067-10071 (1998); Camacho et al., J. Clin. Oncology, 22(145): Abstract No. 2505 (2004) (antibody CP-675206); Mokyr et al., Cancer Res., 58: 5301-5304 (1998), and U.S. Pat. Nos. 5,977,318, 6,682,736, 7,109,003, and 7,132,281, the disclosures of each of which are incorporated herein by reference.

Additional CTLA-4 inhibitors include, but are not limited to, the following: any inhibitor that is capable of disrupting the ability of CD28 antigen to bind to its cognate ligand, to inhibit the ability of CTLA-4 to bind to its cognate ligand, to augment T cell responses via the co-stimulatory pathway, to disrupt the ability of B7 to bind to CD28 and/or CTLA-4, to disrupt the ability of B7 to activate the co-stimulatory pathway, to disrupt the ability of CD80 to bind to CD28 and/or CTLA-4, to disrupt the ability of CD80 to activate the co-stimulatory pathway, to disrupt the ability of CD86 to bind to CD28 and/or CTLA-4, to disrupt the ability of CD86 to activate the co-stimulatory pathway, and to disrupt the co-stimulatory pathway, in general from being activated. This necessarily includes small molecule inhibitors of CD28, CD80, CD86, CTLA-4, among other members of the co-stimulatory pathway; antibodies directed to CD28, CD80, CD86, CTLA-4, among other members of the co-stimulatory pathway; antisense molecules directed against CD28, CD80, CD86, CTLA-4, among other members of the co-stimulatory pathway; adnectins directed against CD28, CD80, CD86, CTLA-4, among other members of the co-stimulatory pathway, RNAi inhibitors (both single and double stranded) of CD28, CD80, CD86, CTLA-4, among other members of the co-stimulatory pathway, among other CTLA-4 inhibitors.

In some embodiments a CTLA-4 inhibitor binds to CTLA-4 with a $K_d$ of about $10^{-6}$ M or less, $10^{-7}$ M or less, $10^{-8}$ M or less, $10^{-9}$ M or less, $10^{-10}$ M or less, $10^{-11}$ M or less, $10^{-12}$ M or less, e.g., between $10^{-13}$ M and $10^{-16}$ M, or within any range having any two of the aforementioned values as endpoints. In some embodiments a CTLA-4 inhibitor binds to CTLA-4 with a Kd of no more than 10-fold that of ipilimumab, when compared using the same assay. In some embodiments a CTLA-4 inhibitor binds to CTLA-4 with a Kd of about the same as, or less (e.g., up to 10-fold lower, or up to 100-fold lower) than that of ipilimumab, when compared using the same assay. In some embodiments, the IC50 values for inhibition by a CTLA-4 inhibitor of CTLA-4 binding to CD80 or CD86 is no more than 10-fold greater than that of ipilimumab-mediated inhibition of CTLA-4 binding to CD80 or CD86, respectively, when compared using the same assay. In some embodiments, the IC50 values for inhibition by a CTLA-4 inhibitor of CTLA-4 binding to CD80 or CD86 is about the same or less (e.g., up to 10-fold lower, or up to 100-fold lower) than that of ipilimumab-mediated inhibition of CTLA-4 binding to CD80 or CD86, respectively, when compared using the same assay.

In some embodiments a CTLA-4 inhibitor is used in an amount sufficient to inhibit expression and/or decrease biological activity of CTLA-4 by at least 20%, 30%, 40%, 50%, 60%, 70%, 80%, 90%, 95%, or 100% relative to a suitable control, e.g., between 50% and 75%, 75% and 90%, or 90% and 100%. In some embodiments a CTLA-4 pathway inhibitor is used in an amount sufficient to decrease the biological activity of CTLA-4 by reducing binding of CTLA-4 to CD80, CD86, or both by at least 20%, 30%, 40%, 50%, 60%, 70%, 80%, 90%, 95%, or 100% relative to a suitable control, e.g., between 50% and 75%, 75% and 90%, or 90% and 100% relative to a suitable control. A suitable control in the context of assessing or quantifying the effect of an agent of interest is typically a comparable biological system (e.g., cells or a subject) that has not been exposed to or treated with the agent of interest, e.g., CTLA-4 pathway inhibitor (or has been exposed to or treated with a negligible amount). In some embodiments a biological system may serve as its own control (e.g., the biological system may be assessed before exposure to or treatment with the agent and compared with the state after exposure or treatment has started or finished. In some embodiments a historical control may be used.

In an embodiment, the CTLA-4 inhibitor is ipilimumab (commercially available as Yervoy from Bristol-Myers Squibb Co.), or biosimilars, antigen-binding fragments, conjugates, or variants thereof. As is known in the art, ipilimumab refers to an anti-CTLA-4 antibody, a fully human IgG 1κ antibody derived from a transgenic mouse with human genes encoding heavy and light chains to generate a functional human repertoire. is there. Ipilimumab can also be referred to by its CAS Registry Number 477202-00-9, and in PCT Publication Number WO 01/14424, which is incorporated herein by reference in its entirety for all purposes. It is disclosed as antibody 10DI. Specifically, ipilimumab contains a light chain variable region and a heavy chain variable region (having a light chain variable region comprising SEQ ID NO:211 and having a heavy chain variable region comprising SEQ ID NO:210). A pharmaceutical composition of ipilimumab includes all pharmaceutically acceptable compositions containing ipilimumab and one or more diluents, vehicles, or excipients. An example of a pharmaceutical composition containing ipilimumab is described in International Patent Application Publication No. WO 2007/67959. Ipilimumab can be administered intravenously (IV).

In an embodiment, a CTLA-4 inhibitor comprises a heavy chain given by SEQ ID NO:208 and a light chain given by SEQ ID NO:209. In an embodiment, a CTLA-4 inhibitor comprises heavy and light chains having the sequences shown in SEQ ID NO:208 and SEQ ID NO:209, respectively, or antigen binding fragments, Fab fragments, single-chain variable fragments (scFv), variants, or conjugates thereof. In an embodiment, a CTLA-4 inhibitor comprises heavy and light chains that are each at least 99% identical to the sequences shown in SEQ ID NO:208 and SEQ ID NO:209, respectively. In an embodiment, a CTLA-4 inhibitor comprises heavy and light chains that are each at least 98% identical to the sequences shown in SEQ ID NO:208 and SEQ ID NO:209, respectively. In an embodiment, a CTLA-4 inhibitor comprises heavy and light chains that are each at least 97% identical to the sequences shown in SEQ ID NO:208 and SEQ ID NO:209, respectively. In an embodiment, a CTLA-4 inhibitor comprises heavy and light chains that are each at least 96% identical to the sequences shown in SEQ ID NO:208 and SEQ ID NO:209, respectively. In an embodiment, a CTLA-4 inhibitor comprises heavy and light chains that are each at least 95% identical to the sequences shown in SEQ ID NO:208 and SEQ ID NO:209, respectively.

In an embodiment, the CTLA-4 inhibitor comprises the heavy and light chain CDRs or variable regions (VRs) of ipilimumab. In an embodiment, the CTLA-4 inhibitor heavy chain variable region ($V_H$) comprises the sequence shown in SEQ ID NO:210, and the CTLA-4 inhibitor light chain variable region ($V_L$) comprises the sequence shown in SEQ ID NO:211, or conservative amino acid substitutions thereof. In an embodiment, a CTLA-4 inhibitor comprises $V_H$ and $V_L$ regions that are each at least 99% identical to the sequences shown in SEQ ID NO:210 and SEQ ID NO:211, respectively. In an embodiment, a CTLA-4 inhibitor comprises $V_H$ and $V_L$ regions that are each at least 98% identical to the sequences shown in SEQ ID NO:210 and SEQ ID NO:211, respectively. In an embodiment, a CTLA-4 inhibitor comprises $V_H$ and $V_L$ regions that are each at least 97% identical to the sequences shown in SEQ ID NO:210 and SEQ ID NO:211, respectively. In an embodiment, a CTLA-4 inhibitor comprises $V_H$ and $V_L$ regions that are each at least 96% identical to the sequences shown in SEQ ID NO:210 and SEQ ID NO:211, respectively. In an embodiment, a CTLA-4 inhibitor comprises $V_H$ and $V_L$ regions that are each at least 95% identical to the sequences shown in SEQ ID NO:210 and SEQ ID NO:211, respectively.

In an embodiment, a CTLA-4 inhibitor comprises the heavy chain CDR1, CDR2 and CDR3 domains having the sequences set forth in SEQ ID NO:212, SEQ ID NO:213, and SEQ ID NO:214, respectively, or conservative amino acid substitutions thereof, and light chain CDR1, CDR2 and CDR3 domains having the sequences set forth in SEQ ID NO:215, SEQ ID NO:216, and SEQ ID NO:217, respectively, or conservative amino acid substitutions thereof. In an embodiment, the antibody competes for binding with, and/or binds to the same epitope on CTLA-4 as any of the aforementioned antibodies.

In an embodiment, the CTLA-4 inhibitor is a CTLA-4 biosimilar monoclonal antibody approved by drug regulatory authorities with reference to ipilimumab. In an embodiment, the biosimilar comprises an anti-CTLA-4 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is ipilimumab. In some embodiments, the one or more post-translational modifications are selected from one or more of: glycosylation, oxidation, deamidation, and truncation. The amino acid sequences of ipilimumab are set forth in Table 23. In some embodiments, the biosimilar is an anti-CTLA-4 antibody authorized or submitted for authorization, wherein the anti-CTLA-4 antibody is provided in a formulation which differs from the formulations of a reference medicinal product or reference biological product, wherein the reference medicinal product or reference biological product is ipilimumab. The anti-CTLA-4 antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is ipilimumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is ipilimumab.

In some embodiments, the CTLA-4 inhibitor is ipilimumab or a biosimilar thereof, and the ipilimumab is administered at a dose of about 200 mg to about 500 mg. In some

TABLE 23

Amino acid sequences for ipilimumab.

| Identifier | Sequence (One-Letter Amino Acid Symbols) | |
|---|---|---|
| SEQ ID NO: 208 ipilimumab heavy chain | QVQLVESGGG VVQPGRSLRL SCAASGFTFS SYTMHWVRQA PGKGLEWVTF ISYDGNNKYY<br>ADSVKGRFTI SRDNSKNTLY LQMNSLRAED TAIYYCARTG WLGPFDYWGQ GTLVTVSSAS<br>TKGPSVFPLA PSSKSTSGGT AALGCLVKDY FPEPVTVSWN SGALTSGVHT FPAVLQSSGL<br>YSLSSVVTVP SSSLGTQTYI CNVNHKPSNT KVDKRVEPKS CDKTH | 60<br>120<br>180<br>225 |
| SEQ ID NO: 209 ipilimumab light chain | EIVLTQSPGT LSLSPGERAT LSCRASQSVG SSYLAWYQQK PGQAPRLLIY GAFSRATGIP<br>DRFSGSGSGT DFTLTISRLE PEDFAVYYCQ QYGSSPWTFG QGTKVEIKRT VAAPSVFIFP<br>PSDEQLKSGT ASVVCLLNNF YPREAKVQWK VDNALQSGNS QESVTEQDSK DSTYSLSSTL<br>TLSKADYEKH KVYACEVTHQ GLSSPVTKSF NRGEC | 60<br>120<br>180<br>215 |
| SEQ ID NO: 210 ipilimumab variable heavy chain | QVQLVESGGG VVQPGRSLRL SCAASGFTFS SYTMHWVRQA PGKGLEWVTF ISYDGNNKYY<br>ADSVKGRFTI SRDNSKNTLY LQMNSLRAED TAIYYCARTG WLGPFDYWGQ GTLVTVSS | 60<br>118 |
| SEQ ID NO: 211 ipilimumab variable light chain | EIVLTQSPGT LSLSPGERAT LSCRASQSVG SSYLAWYQQK PGQAPRLLIY GAFSRATGIP<br>DRFSGSGSGT DFTLTISRLE PEDFAVYYCQ QYGSSPWTFG QGTKVEIK | 60<br>108 |
| SEQ ID NO: 212 ipilimumab heavy chain CDR1 | GFTFSSYT | 8 |
| SEQ ID NO: 213 ipilimumab heavy chain CDR2 | TFISYDGNNK | 10 |
| SEQ ID NO: 214 ipilimumab heavy chain CDR3 | ARTGWLGPFD Y | 11 |
| SEQ ID NO: 215 ipilimumab light chain CDR1 | QSVGSSY | 7 |
| SEQ ID NO: 216 ipilimumab light chain CDR2 | GAF | 3 |
| SEQ ID NO: 217 ipilimumab light chain CDR3 | QQYGSSPWT | 9 |

In some embodiments, the CTLA-4 inhibitor is ipilimumab or a biosimilar thereof, and the ipilimumab is administered at a dose of about 0.5 mg/kg to about 10 mg/kg. In some embodiments, the CTLA-4 inhibitor is ipilimumab or a biosimilar thereof, and the ipilimumab is administered at a dose of about 0.5 mg/kg, about 1 mg/kg, about 1.5 mg/kg, about 2 mg/kg, about 2.5 mg/kg, about 3 mg/kg, about 3.5 mg/kg, about 4 mg/kg, about 4.5 mg/kg, about 5 mg/kg, about 5.5 mg/kg, about 6 mg/kg, about 6.5 mg/kg, about 7 mg/kg, about 7.5 mg/kg, about 8 mg/kg, about 8.5 mg/kg, about 9 mg/kg, about 9.5 mg/kg, or about 10 mg/kg. In some embodiments, the ipilimumab administration is begun 1, 2, 3, 4, or 5 weeks pre-resection (i.e., prior to obtaining the tumor sample from the subject or patient). In some embodiments, the ipilimumab administration is begun 1, 2, or 3 weeks pre-resection (i.e., prior to obtaining the tumor sample from the subject or patient).

embodiments, the CTLA-4 inhibitor is ipilimumab or a biosimilar thereof, and the ipilimumab is administered at a dose of about 200 mg, about 220 mg, about 240 mg, about 260 mg, about 280 mg, about 300 mg, about 320 mg, about 340 mg, about 360 mg, about 380 mg, about 400 mg, about 420 mg, about 440 mg, about 460 mg, about 480 mg, or about 500 mg. In some embodiments, the ipilimumab administration is begun 1, 2, 3, 4, or 5 weeks pre-resection (i.e., prior to obtaining the tumor sample from the subject or patient). In some embodiments, the ipilimumab administration is begun 1, 2, or 3 weeks pre-resection (i.e., prior to obtaining the tumor sample from the subject or patient).

In some embodiments, the CTLA-4 inhibitor is ipilimumab or a biosimilar thereof, and the ipilimumab is administered every 2 weeks, every 3 weeks, every 4 weeks, every 5 weeks, or every 6 weeks. In some embodiments, the ipilimumab administration is begun 1, 2, 3, 4, or 5 weeks pre-resection (i.e., prior to obtaining the tumor sample from the subject or patient). In some embodiments, the ipilimumab administration is begun 1, 2, or 3 weeks pre-resection (i.e., prior to obtaining the tumor sample from the subject or patient).

In some embodiments, the ipilimumab is administered to treat unresectable or metastatic melanoma. In some embodiments, the ipilimumab is administered to treat Unresectable or Metastatic Melanoma at about mg/kg every 3 weeks for a maximum of 4 doses. In some embodiments, the ipilimumab administration is begun 1, 2, 3, 4, or 5 weeks pre-resection (i.e., prior to obtaining the tumor sample from the subject or patient). In some embodiments, the ipilimumab administration is begun 1, 2, or 3 weeks pre-resection (i.e., prior to obtaining the tumor sample from the subject or patient).

In some embodiments, the ipilimumab is administered for the adjuvant treatment of melanoma. In some embodiments, the ipilimumab is administered to for the adjuvant treatment of melanoma at about 10 mg/kg every 3 weeks for 4 doses, followed by 10 mg/kg every 12 weeks for up to 3 years. In some embodiments, the ipilimumab administration is begun 1, 2, 3, 4, or 5 weeks pre-resection (i.e., prior to obtaining the tumor sample from the subject or patient). In some embodiments, the ipilimumab administration is begun 1, 2, or 3 weeks pre-resection (i.e., prior to obtaining the tumor sample from the subject or patient).

In some embodiments, the ipilimumab is administered to treat advanced renal cell carcinoma. In some embodiments, the ipilimumab is administered to treat advanced renal cell carcinoma at about 1 mg/kg immediately following nivolumab 3 mg/kg on the same day, every 3 weeks for 4 doses. In some embodiments, after completing 4 doses of the combination, nivolumab can be administered as a single agent according to standard dosing regimens for advanced renal cell carcinoma and/or renal cell carcinoma. In some embodiments, the ipilimumab administration is begun 1, 2, 3, 4, or 5 weeks pre-resection (i.e., prior to obtaining the tumor sample from the subject or patient). In some embodiments, the ipilimumab administration is begun 1, 2, or 3 weeks pre-resection (i.e., prior to obtaining the tumor sample from the subject or patient).

In some embodiments, the ipilimumab is administered to treat microsatellite instability-high (MSI-H) or mismatch repair deficient (dMMR) metastatic colorectal cancer. In some embodiments, the ipilimumab is administered to treat microsatellite instability-high (MSI-H) or mismatch repair deficient (dMMR) metastatic colorectal cancer at about 1 mg/kg intravenously over 30 minutes immediately following nivolumab 3 mg/kg intravenously over 30 minutes on the same day, every 3 weeks for 4 doses. In some embodiments, after completing 4 doses of the combination, administer nivolumab as a single agent as recommended according to standard dosing regimens for microsatellite instability-high (MSI-H) or mismatch repair deficient (dMMR) metastatic colorectal cancer. In some embodiments, the ipilimumab administration is begun 1, 2, 3, 4, or 5 weeks pre-resection (i.e., prior to obtaining the tumor sample from the subject or patient). In some embodiments, the ipilimumab administration is begun 1, 2, or 3 weeks pre-resection (i.e., prior to obtaining the tumor sample from the subject or patient).

In some embodiments, the ipilimumab is administered to treat hepatocellular carcinoma. In some embodiments, the ipilimumab is administered to treat hepatocellular carcinoma at about 3 mg/kg intravenously over 30 minutes immediately following nivolumab 1 mg/kg intravenously over 30 minutes on the same day, every 3 weeks for 4 doses. In some embodiments, after completion 4 doses of the combination, administer nivolumab as a single agent according to standard dosing regimens for hepatocellular carcinoma. In some embodiments, the ipilimumab administration is begun 1, 2, 3, 4, or 5 weeks pre-resection (i.e., prior to obtaining the tumor sample from the subject or patient). In some embodiments, the ipilimumab administration is begun 1, 2, or 3 weeks pre-resection (i.e., prior to obtaining the tumor sample from the subject or patient).

In some embodiments, the ipilimumab is administered to treat metastatic non-small cell lung cancer. In some embodiments, the ipilimumab is administered to treat metastatic non-small cell lung cancer at about 1 mg/kg every 6 weeks with nivolumab 3 mg/kg every 2 weeks. In some embodiments, the ipilimumab is administered to treat metastatic non-small cell lung cancer at about 1 mg/kg every 6 weeks with nivolumab 360 mg every 3 weeks and 2 cycles of platinum-doublet chemotherapy. In some embodiments, the ipilimumab administration is begun 1, 2, 3, 4, or 5 weeks pre-resection (i.e., prior to obtaining the tumor sample from the subject or patient). In some embodiments, the ipilimumab administration is begun 1, 2, or 3 weeks pre-resection (i.e., prior to obtaining the tumor sample from the subject or patient).

In some embodiments, the ipilimumab is administered to treat malignant pleural mesothelioma. In some embodiments, the ipilimumab is administered to treat malignant pleural mesothelioma at about 1 mg/kg every 6 weeks with nivolumab 360 mg every 3 weeks. In some embodiments, the ipilimumab administration is begun 1, 2, 3, 4, or 5 weeks pre-resection (i.e., prior to obtaining the tumor sample from the subject or patient). In some embodiments, the ipilimumab administration is begun 1, 2, or 3 weeks pre-resection (i.e., prior to obtaining the tumor sample from the subject or patient).

Tremelimumab (also known as CP-675,206) is a fully human IgG2 monoclonal antibody and has the CAS number 745013-59-6. Tremelimumab is disclosed as antibody 11.2.1 in U.S. Pat. No. 6,682,736 (incorporated herein by reference). The amino acid sequences of the heavy chain and light chain of tremelimumab are set forth in SEQ ID NOs:218 and 219, respectively. Tremelimumab has been investigated in clinical trials for the treatment of various tumors, including melanoma and breast cancer; in which Tremelimumab was administered intravenously either as single dose or multiple doses every 4 or 12 weeks at the dose range of 0.01 and 15 mg/kg. In the regimens provided by the present invention, tremelimumab is administered locally, particularly intradermally or subcutaneously. The effective amount of tremelimumab administered intradermally or subcutaneously is typically in the range of 5-200 mg/dose per person. In some embodiments, the effective amount of tremelimumab is in the range of 10-150 mg/dose per person per dose. In some particular embodiments, the effective amount of tremelimumab is about 10, 25, 37.5, 40, 50, 75, 100, 125, 150, 175, or 200 mg/dose per person.

In an embodiment, a CTLA-4 inhibitor comprises a heavy chain given by SEQ ID NO:218 and a light chain given by SEQ ID NO:219. In an embodiment, a CTLA-4 inhibitor comprises heavy and light chains having the sequences shown in SEQ ID NO:218 and SEQ ID NO:219, respectively, or antigen binding fragments, Fab fragments, single-chain variable fragments (scFv), variants, or conjugates thereof. In an embodiment, a CTLA-4 inhibitor comprises heavy and light chains that are each at least 99% identical to the sequences shown in SEQ ID NO:218 and SEQ ID NO:219, respectively. In an embodiment, a CTLA-4 inhibitor comprises heavy and light chains that are each at least 98% identical to the sequences shown in SEQ ID NO:218 and SEQ ID NO:219, respectively. In an embodiment, a CTLA-4 inhibitor comprises heavy and light chains that are each at least 97% identical to the sequences shown in SEQ ID NO:218 and SEQ ID NO:219, respectively. In an embodiment, a CTLA-4 inhibitor comprises heavy and light chains that are each at least 96% identical to the sequences shown in SEQ ID NO:218 and SEQ ID NO:219, respectively. In an embodiment, a CTLA-4 inhibitor comprises heavy and light chains that are each at least 95% identical to the sequences shown in SEQ ID NO:218 and SEQ ID NO:219, respectively.

In an embodiment, the CTLA-4 inhibitor comprises the heavy and light chain CDRs or variable regions (VRs) of tremelimumab. In an embodiment, the CTLA-4 inhibitor heavy chain variable region ($V_H$) comprises the sequence shown in SEQ ID NO:220, and the CTLA-4 inhibitor light chain variable region ($V_L$) comprises the sequence shown in SEQ ID NO:221, or conservative amino acid substitutions thereof. In an embodiment, a CTLA-4 inhibitor comprises $V_H$ and $V_L$ regions that are each at least 99% identical to the sequences shown in SEQ ID NO:220 and SEQ ID NO:221, respectively. In an embodiment, a CTLA-4 inhibitor comprises $V_H$ and $V_L$ regions that are each at least 98% identical to the sequences shown in SEQ ID NO:220 and SEQ ID NO:221, respectively. In an embodiment, a CTLA-4 inhibitor comprises $V_H$ and $V_L$ regions that are each at least 97% identical to the sequences shown in SEQ ID NO:220 and SEQ ID NO:221, respectively. In an embodiment, a CTLA-4 inhibitor comprises $V_H$ and $V_L$ regions that are each at least 96% identical to the sequences shown in SEQ ID NO:220 and SEQ ID NO:221, respectively. In an embodiment, a CTLA-4 inhibitor comprises $V_H$ and $V_L$ regions that are each at least 95% identical to the sequences shown in SEQ ID NO:220 and SEQ ID NO:221, respectively.

In an embodiment, a CTLA-4 inhibitor comprises the heavy chain CDR1, CDR2 and CDR3 domains having the sequences set forth in SEQ ID NO:222, SEQ ID NO:223, and SEQ ID NO:224, respectively, or conservative amino acid substitutions thereof, and light chain CDR1, CDR2 and CDR3 domains having the sequences set forth in SEQ ID NO:225, SEQ ID NO:226, and SEQ ID NO:227, respectively, or conservative amino acid substitutions thereof. In an embodiment, the antibody competes for binding with, and/or binds to the same epitope on CTLA-4 as any of the aforementioned antibodies.

In an embodiment, the CTLA-4 inhibitor is an anti-CTLA-4 biosimilar monoclonal antibody approved by drug regulatory authorities with reference to tremelimumab. In an embodiment, the biosimilar comprises an anti-CTLA-4 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is tremelimumab. In some embodiments, the one or more post-translational modifications are selected from one or more of: glycosylation, oxidation, deamidation, and truncation. The amino acid sequences of tremelimumab are set forth in Table 24. In some embodiments, the biosimilar is an anti-CTLA-4 antibody authorized or submitted for authorization, wherein the anti-CTLA-4 antibody is provided in a formulation which differs from the formulations of a reference medicinal product or reference biological product, wherein the reference medicinal product or reference biological product is tremelimumab. The anti-CTLA-4 antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is tremelimumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is tremelimumab.

TABLE 24

Amino acid sequences for tremelimumab.

| Identifier | Sequence (One-Letter Amino Acid Symbols) | | | | | |
|---|---|---|---|---|---|---|
| SEQ ID NO: 218 tremelimumab heavy chain | QVQLVESGGG ADSVKGRFTI VTVSSASTKG VIQSSGLYSL GPSVFLFPPK NSTFRVVSVL EMTKNQVSLT WQQGNVFSCS | VVQPGRSLRL SRDNSKNTLY PSVFPLAPCS SSVVTVPSSN PKDTLMISRT TVVHQDWLNG CLVKGFYPSD VMHEALHNHY | SCAASGFTFS LQMNSLRAED RSTSESTAAL FGTQTYTCNV PEVTCVVVDV KEYKCKVSNK IAVEWESNGQ TQKSLSLSPG | SYGMHWVRQA TAVYYCARDP GCLVKDYFPE DHKPSNTKVD SHEDPEVQFN GLPAPIEKTI PENNYKTTPP K | PGKGLEWVAV RGATLYYYYY PVTVSWNSGA KTVERKCCVE WYVDGVEVHN SKTKGQPREP MLDSDGSFFL | IWYDGSNKYY GMDVWGQGTT LTSGVHTFPA CPPCPAPPVA AKTKPREEQF QVYTLPPSRE YSKLTVDKSR | 60 120 180 240 300 360 420 451 |
| SEQ ID NO: 219 tremelimumab light chain | DIQMTQSPSS RFSGSGSGTD SDEQLKSGTA LSKADYEKHK | LSASVGDRVT FTLTISSLQP SVVCLLNNFY VYACEVTHQG | ITCRASQSIN EDFATYYCQQ PREAKVQWKV LSSPVTKSFN | SYLDWYQQKP YYSTPFTFGP DNALQSGNSQ RGEC | GKAPKLLIYA GTKVEIKRTV ESVTEQDSKD | ASSLQSGVPS AAPSVFIFPP STYSLSSTLT | 60 120 180 214 |
| SEQ ID NO: 220 tremelimumab variable heavy chain | GVVQPGRSLR ISRDNSKNTL GPSVFPLAPC | LSCAASGFTF YLQMNSLRAE SRSTSESTAA | SSYGMHWVRQ DTAVYYCARD LGCLVKDYFP | APGKGLEWVA PRGATLYYYY EPVTVSWNSG | VIWYDGSNKY YGMDVWGQGT ALTSGVH | YADSVKGRFT TVTVSSASTK | 60 120 167 |

TABLE 24-continued

Amino acid sequences for tremelimumab.

| Identifier | Sequence (One-Letter Amino Acid Symbols) | |
|---|---|---|
| SEQ ID NO: 221 tremelimumab variable light chain | PSSLSASVGD RVTITCRASQ SINSYLDWYQ QKPGKAPKLL IYAASSLQSG VPSRFSGSGS<br>GTDFTLTISS LQPEDFATYY CQQYYSTPFT FGPGTKVEIK RTVAAPSVFI FPPSDEQLKS<br>GTASVVCLLN NFYPREAKV | 60<br>120<br>139 |
| SEQ ID NO: 222 tremelimumab heavy chain CDR1 | GFTFSSYGMH | 10 |
| SEQ ID NO: 223 tremelimumab heavy chain CDR2 | VIWYDGSNKY YADSV | 15 |
| SEQ ID NO: 224 tremelimumab heavy chain CDR3 | DPRGATLYYY YYGMDV | 16 |
| SEQ ID NO: 225 tremelimumab light chain CDR1 | RASQSINSYL D | 11 |
| SEQ ID NO: 226 tremelimumab light chain CDR2 | AASSLQS | 7 |
| SEQ ID NO: 227 tremelimumab light chain CDR3 | QQYYSTPFT | 9 |

In some embodiments, the CTLA-4 inhibitor is tremelimumab or a biosimilar thereof, and the tremelimumab is administered at a dose of about 0.5 mg/kg to about 10 mg/kg. In some embodiments, the CTLA-4 inhibitor is tremelimumab or a biosimilar thereof, and the tremelimumab is administered at a dose of about 0.5 mg/kg, about 1 mg/kg, about 1.5 mg/kg, about 2 mg/kg, about 2.5 mg/kg, about 3 mg/kg, about 3.5 mg/kg, about 4 mg/kg, about 4.5 mg/kg, about 5 mg/kg, about 5.5 mg/kg, about 6 mg/kg, about 6.5 mg/kg, about 7 mg/kg, about 7.5 mg/kg, about 8 mg/kg, about 8.5 mg/kg, about 9 mg/kg, about 9.5 mg/kg, or about 10 mg/kg. In some embodiments, the tremelimumab administration is begun 1, 2, 3, 4, or 5 weeks pre-resection (i.e., prior to obtaining the tumor sample from the subject or patient). In some embodiments, the tremelimumab administration is begun 1, 2, or 3 weeks pre-resection (i.e., prior to obtaining the tumor sample from the subject or patient).

In some embodiments, the CTLA-4 inhibitor is tremelimumab or a biosimilar thereof, and the tremelimumab is administered at a dose of about 200 mg to about 500 mg. In some embodiments, the CTLA-4 inhibitor is tremelimumab or a biosimilar thereof, and the tremelimumab is administered at a dose of about 200 mg, about 220 mg, about 240 mg, about 260 mg, about 280 mg, about 300 mg, about 320 mg, about 340 mg, about 360 mg, about 380 mg, about 400 mg, about 420 mg, about 440 mg, about 460 mg, about 480 mg, or about 500 mg.

In some embodiments, the tremelimumab administration is begun 1, 2, 3, 4, or 5 weeks pre-resection (i.e., prior to obtaining the tumor sample from the subject or patient). In some embodiments, the tremelimumab administration is begun 1, 2, or 3 weeks pre-resection (i.e., prior to obtaining the tumor sample from the subject or patient).

In some embodiments, the CTLA-4 inhibitor is tremelimumab or a biosimilar thereof, and the tremelimumab is administered every 2 weeks, every 3 weeks, every 4 weeks, every 5 weeks, or every 6 weeks. In some embodiments, the tremelimumab administration is begun 1, 2, 3, 4, or 5 weeks pre-resection (i.e., prior to obtaining the tumor sample from the subject or patient). In some embodiments, the tremelimumab administration is begun 1, 2, or 3 weeks pre-resection (i.e., prior to obtaining the tumor sample from the subject or patient).

In an embodiment, the CTLA-4 inhibitor is zalifrelimab from Agenus, or biosimilars, antigen-binding fragments, conjugates, or variants thereof. Zalifrelimab is a fully human monoclonal antibody. Zalifrelimab is assigned Chemical Abstracts Service (CAS) registry number 2148321-69-9 and is also known as also known as AGEN1884. The preparation and properties of zalifrelimab are described in U.S. Pat. No. 10,144,779 and US Patent Application Publication No. US2020/0024350 A1, the disclosures of which are incorporated by reference herein.

In an embodiment, a CTLA-4 inhibitor comprises a heavy chain given by SEQ ID NO:228 and a light chain given by SEQ ID NO:229. In an embodiment, a CTLA-4 inhibitor comprises heavy and light chains having the sequences shown in SEQ ID NO:228 and SEQ ID NO:229, respectively, or antigen binding fragments, Fab fragments, single-chain variable fragments (scFv), variants, or conjugates thereof. In an embodiment, a CTLA-4 inhibitor comprises heavy and light chains that are each at least 99% identical to the sequences shown in SEQ ID NO:228 and SEQ ID NO:229, respectively. In an embodiment, a CTLA-4 inhibitor comprises heavy and light chains that are each at least 98% identical to the sequences shown in SEQ ID NO:228 and SEQ ID NO:229, respectively. In an embodiment, a CTLA-4 inhibitor comprises heavy and light chains that are each at least 97% identical to the sequences shown in SEQ ID NO:228 and SEQ ID NO:229, respectively. In an embodiment, a CTLA-4 inhibitor comprises heavy and light chains that are each at least 96% identical to the sequences shown in SEQ ID NO:228 and SEQ ID NO:229, respectively. In an embodiment, a CTLA-4 inhibitor comprises heavy and light chains that are each at least 95% identical to the sequences shown in SEQ ID NO:228 and SEQ ID NO:229, respectively.

In an embodiment, the CTLA-4 inhibitor comprises the heavy and light chain CDRs or variable regions (VRs) of zalifrelimab. In an embodiment, the CTLA-4 inhibitor heavy chain variable region ($V_H$) comprises the sequence shown in SEQ ID NO:230, and the CTLA-4 inhibitor light chain variable region ($V_L$) comprises the sequence shown in SEQ ID NO:231, or conservative amino acid substitutions thereof. In an embodiment, a CTLA-4 inhibitor comprises $V_H$ and $V_L$ regions that are each at least 99% identical to the sequences shown in SEQ ID NO:230 and SEQ ID NO:231, respectively. In an embodiment, a CTLA-4 inhibitor comprises $V_H$ and $V_L$ regions that are each at least 98% identical to the sequences shown in SEQ ID NO:230 and SEQ ID NO:231, respectively. In an embodiment, a CTLA-4 inhibitor comprises $V_H$ and $V_L$ regions that are each at least 97% identical to the sequences shown in SEQ ID NO:230 and SEQ ID NO:231, respectively. In an embodiment, a CTLA-4 inhibitor comprises $V_H$ and $V_L$ regions that are each at least 96% identical to the sequences shown in SEQ ID NO:230 and SEQ ID NO:231, respectively. In an embodiment, a CTLA-4 inhibitor comprises $V_H$ and $V_L$ regions that are each at least 95% identical to the sequences shown in SEQ ID NO:230 and SEQ ID NO:231, respectively.

In an embodiment, a CTLA-4 inhibitor comprises the heavy chain CDR1, CDR2 and CDR3 domains having the sequences set forth in SEQ ID NO:231, SEQ ID NO:233, and SEQ ID NO:234, respectively, or conservative amino acid substitutions thereof, and light chain CDR1, CDR2 and CDR3 domains having the sequences set forth in SEQ ID NO:235, SEQ ID NO:236, and SEQ ID NO:237, respectively, or conservative amino acid substitutions thereof. In an embodiment, the antibody competes for binding with, and/or binds to the same epitope on CTLA-4 as any of the aforementioned antibodies.

In an embodiment, the CTLA-4 inhibitor is a CTLA-4 biosimilar monoclonal antibody approved by drug regulatory authorities with reference to zalifrelimab. In an embodiment, the biosimilar comprises an anti-CTLA-4 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is zalifrelimab. In some embodiments, the one or more post-translational modifications are selected from one or more of: glycosylation, oxidation, deamidation, and truncation. The amino acid sequences of zalifrelimab are set forth in Table 25. In some embodiments, the biosimilar is an anti-CTLA-4 antibody authorized or submitted for authorization, wherein the anti-CTLA-4 antibody is provided in a formulation which differs from the formulations of a reference medicinal product or reference biological product, wherein the reference medicinal product or reference biological product is zalifrelimab. The anti-CTLA-4 antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is zalifrelimab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is zalifrelimab.

TABLE 25

Amino acid sequences for zalifrelimab.

| Identifier | Sequence (One-Letter Amino Acid Symbols) | | | | | |
|---|---|---|---|---|---|---|
| SEQ ID NO: 228 zalifrelimab heavy chain | EVQLVESGGG | LVKPGGSLRL | SCAASGFTFS | SYSMNWVRQA | PGKGLEWVSS | ISSSSSYIYY | 60 |
| | ADSVKGRFTI | SRDNAKNSLY | LQMNSLRAED | TAVYYCARVG | LMGPFDIWGQ | GTMVTVSSAS | 120 |
| | TKGPSVFPLA | PSSKSTSGGT | AALGCLVKDY | FPEPVTVSWN | SGALTSGVHT | FPAVLQSSGL | 180 |
| | YSLSSVVTVP | SSSLGTQTYI | CNVNHKPSNT | KVDKRVEPKS | CDKTHTCPPC | PAPELLGGPS | 240 |
| | VFLFPPKPKD | TLMISRTPEV | TCVVVDVSHE | DPEVKFNWYV | DGVEVHNAKT | KPREEQYNST | 300 |
| | YRVVSVLTVL | HQDWLNGKEY | KCKVSNKALP | APIEKTISKA | KGQPREPQVY | TLPPSREEMT | 360 |
| | KNQVSLTCLV | KGFYPSDIAV | EWESNGQPEN | NYKTTPPVLD | SDGSFFLYSK | LTVDKSRWQQ | 420 |
| | GNVFSCSVMH | EALHNHYTQK | SLSLSPGK | | | | 448 |
| SEQ ID NO: 229 zalifrelimab light chain | EIVLTQSPGT | LSLSPGERAT | LSCRASQSVS | RYLGWYQQKP | GQAPRLLIYG | ASTRATGIPD | 60 |
| | RFSGSGSGTD | FTLTITRLEP | EDFAVYYCQQ | YGSSPWTFGQ | GTKVEIKRTV | AAPSVFIFPP | 120 |
| | SDEQLKSGTA | SVVCLLNNFY | PREAKVQWKV | DNALQSGNSQ | ESVTEQDSKD | STYSLSSTLT | 180 |
| | LSKADYEKHK | VYACEVTHQG | LSSPVTKSFN | RGEC | | | 214 |
| SEQ ID NO: 230 zalifrelimab variable heavy chain | EVOLVESGGG | LVKPGGSLRL | SCAASGFTFS | SYSMNWVROA | PGKGLEWVSS | ISSSSSYIYY | 60 |
| | ADSVKGRFTI | SRDNAKNSLY | LOMNSLRAED | TAVYYCARVG | LMGPFDIWGQ | GTMVTVSS | 118 |

TABLE 25-continued

Amino acid sequences for zalifrelimab.

| Identifier | Sequence (One-Letter Amino Acid Symbols) | |
| --- | --- | --- |
| SEQ ID NO: 231 zalifrelimab variable light chain | EIVLTQSPGT LSLSPGERAT LSCRASQSVS RYLGWYQQKP GQAPRLLIYG ASTRATGIPD<br>RFSGSGSGTD FTLTITRLEP EDFAVYYCQQ YGSSPWTFGQ GTKVEIK | 60<br>107 |
| SEQ ID NO: 232 zalifrelimab heavy chain CDR1 | GFTFSSYS | 8 |
| SEQ ID NO: 233 zalifrelimab heavy chain CDR2 | ISSSSSYI | 8 |
| SEQ ID NO: 234 zalifrelimab heavy chain CDR3 | ARVGLMGPFD I | 11 |
| SEQ ID NO: 235 zalifrelimab light chain CDR1 | QSVSRY | 6 |
| SEQ ID NO: 236 zalifrelimab light chain CDR2 | GAS | 3 |
| SEQ ID NO: 237 zalifrelimab light chain CDR3 | QQYGSSPWT | 9 |

Examples of additional anti-CTLA-4 antibodies includes, but are not limited to: AGEN1181, BMS-986218, BCD-145, ONC-392, CS1002, REGN4659, and ADG116, which are known to one of ordinary skill in the art.

In some embodiments, the anti-CTLA-4 antibody is an anti-CTLA-4 antibody disclosed in any of the following patent publications: US 2019/0048096 A1; US 2020/0223907; US 2019/0201334; US 2019/0201334; US 2005/0201994; EP 1212422 B1; WO 2018/204760; WO 2018/204760; WO 2001/014424; WO 2004/035607; WO 2003/086459; WO 2012/120125; WO 2000/037504; WO 2009/100140; WO 2006/09649; WO2005092380; WO 2007/123737; WO 2006/029219; WO 2010/0979597; WO 2006/12168; and WO1997020574, each of which is incorporated herein by reference. Additional CTLA-4 antibodies are described in U.S. Pat. Nos. 5,811,097, 5,855,887, 6,051,227, and 6,984,720; in PCT Publication Nos. WO 01/14424 and WO 00/37504; and in U.S. Publication Nos. 2002/0039581 and 2002/086014; and/or U.S. Pat. Nos. 5,977,318, 6,682,736, 7,109,003, and 7,132,281, each of which is incorporated herein by reference. In some embodiments, the anti-CTLA-4 antibody is, for example, those disclosed in: WO 98/42752; U.S. Pat. Nos. 6,682,736 and 6,207,156; Hurwitz, et al., Proc. Natl. Acad. Sci. USA, 1998, 95, 10067-10071 (1998); Camacho, et al., J. Clin. Oncol., 2004, 22, 145 (Abstract No. 2505 (2004) (antibody CP-675206); or Mokyr, et al., Cancer Res., 1998, 58, 5301-5304 (1998), each of which is incorporated herein by reference.

In some embodiments, the CTLA-4 inhibitor is a CTLA-4 ligand as disclosed in WO 1996/040915 (incorporated herein by reference).

In some embodiments, the CTLA-4 inhibitor is a nucleic acid inhibitor of CTLA-4 expression. For example, anti-CTLA-4 RNAi molecules may take the form of the molecules described in PCT Publication Nos. WO 1999/032619 and WO 2001/029058; U.S. Publication Nos. 2003/0051263, 2003/0055020, 2003/0056235, 2004/265839, 2005/0100913, 2006/0024798, 2008/0050342, 2008/0081373, 2008/0248576, and 2008/055443; and/or U.S. Pat. Nos. 6,506,559, 7,282,564, 7,538,095, and 7,560,438 (incorporated herein by reference). In some instances, the anti-CTLA-4 RNAi molecules take the form of double stranded RNAi molecules described in European Patent No. EP 1309726 (incorporated herein by reference). In some instances, the anti-CTLA-4 RNAi molecules take the form of double stranded RNAi molecules described in U.S. Pat. Nos. 7,056,704 and 7,078,196 (incorporated herein by reference). In some embodiments, the CTLA-4 inhibitor is an aptamer described in International Patent Application Publication No. WO 2004/081021 (incorporated herein by reference).

In other embodiments, the anti-CTLA-4 RNAi molecules of the present invention are RNA molecules described in U.S. Pat. Nos. 5,898,031, 6,107,094, 7,432,249, and 7,432,250, and European Application No. EP 0928290 (incorporated herein by reference).

In some embodiments, the present invention includes a method of treating a patient with a cancer comprising the steps of administering a TIL regimen, wherein the TIL regimen includes a TIL product genetically modified to express a CCR, and further comprising the step of administering a CTLA-4 inhibitor. In some embodiments, the present invention includes a composition comprising (i) a TIL product genetically modified to express a CCR and (ii) a CTLA-4 inhibitor. In some embodiments, the present invention includes a kit comprising (i) a TIL product genetically modified to express a CCR and (ii) a CTLA-4 inhibitor.

In some embodiments, the present invention includes a method of treating a patient with a cancer comprising the steps of administering a TIL regimen, wherein the TIL regimen includes a TIL product genetically modified to express a CCR, and further comprising the steps of administering a CTLA-4 inhibitor and either a PD-1 inhibitor or a PD-L1 inhibitor. In some embodiments, the present invention includes a composition comprising (i) a TIL product genetically modified to express a CCR, (ii) a CTLA-4 inhibitor, and (iii) either a PD-1 inhibitor or a PD-L1 inhibitor. In some embodiments, the present invention includes a kit comprising (i) a TIL product genetically modified to express a CCR, (ii) a CTLA-4 inhibitor, and (iii) either a PD-1 inhibitor or a PD-L1 inhibitor.

4. Lymphodelpetion Preconditioning of Patients

In an embodiment, the invention includes a method of treating a cancer with a population of TILs, wherein a patient is pre-treated with non-myeloablative chemotherapy prior to an infusion of TILs according to the present disclosure. In an embodiment, the invention includes a population of TILs for use in the treatment of cancer in a patient which has been pre-treated with non-myeloablative chemotherapy. In an embodiment, the population of TILs is for administration by infusion. In an embodiment, the non-myeloablative chemotherapy is cyclophosphamide 60 mg/kg/d for 2 days (days 27 and 26 prior to TIL infusion) and fludarabine 25 mg/m2/d for 5 days (days 27 to 23 prior to TIL infusion). In an embodiment, after non-myeloablative chemotherapy and TIL infusion (at day 0) according to the present disclosure, the patient receives an intravenous infusion of IL-2 (aldesleukin, commercially available as PROLEUKIN) intravenously at 720,000 IU/kg every 8 hours to physiologic tolerance. In certain embodiments, the population of TILs is for use in treating cancer in combination with IL-2, wherein the IL-2 is administered after the population of TILs.

Experimental findings indicate that lymphodepletion prior to adoptive transfer of tumor-specific T lymphocytes plays a key role in enhancing treatment efficacy by eliminating regulatory T cells and competing elements of the immune system ('cytokine sinks'). Accordingly, some embodiments of the invention utilize a lymphodepletion step (sometimes also referred to as "immunosuppressive conditioning") on the patient prior to the introduction of the TILs of the invention.

In general, lymphodepletion is achieved using administration of fludarabine or cyclophosphamide (the active form being referred to as mafosfamide) and combinations thereof. Such methods are described in Gassner, et al., Cancer Immunol. Immunother. 2011, 60, 75-85, Muranski, et al., Nat. Clin. Pract. Oncol., 2006, 3, 668-681, Dudley, et al., J. Clin. Oncol. 2008, 26, 5233-5239, and Dudley, et al., J. Clin. Oncol. 2005, 23, 2346-2357, all of which are incorporated by reference herein in their entireties.

In some embodiments, the fludarabine is administered at a concentration of 0.5 µg/mL to 10 µg/mL fludarabine. In some embodiments, the fludarabine is administered at a concentration of 1 µg/mL fludarabine. In some embodiments, the fludarabine treatment is administered for 1 day, 2 days, 3 days, 4 days, 5 days, 6 days, or 7 days or more. In some embodiments, the fludarabine is administered at a dosage of 10 mg/kg/day, 15 mg/kg/day, 20 mg/kg/day, 25 mg/kg/day, 30 mg/kg/day, 35 mg/kg/day, 40 mg/kg/day, or 45 mg/kg/day. In some embodiments, the fludarabine treatment is administered for 2-7 days at 35 mg/kg/day. In some embodiments, the fludarabine treatment is administered for 4-5 days at 35 mg/kg/day. In some embodiments, the fludarabine treatment is administered for 4-5 days at 25 mg/kg/day.

In some embodiments, the mafosfamide, the active form of cyclophosphamide, is obtained at a concentration of 0.5 µg/mL-10 µg/mL by administration of cyclophosphamide. In some embodiments, mafosfamide, the active form of cyclophosphamide, is obtained at a concentration of 1 µg/mL by administration of cyclophosphamide. In some embodiments, the cyclophosphamide treatment is administered for 1 day, 2 days, 3 days, 4 days, 5 days, 6 days, or 7 days or more. In some embodiments, the cyclophosphamide is administered at a dosage of 100 mg/m2/day, 150 mg/m2/day, 175 mg/m2/day, 200 mg/m2/day, 225 mg/m2/day, 250 mg/m2/day, 275 mg/m2/day, or 300 mg/m2/day. In some embodiments, the cyclophosphamide is administered intravenously (i.e., i.v.) In some embodiments, the cyclophosphamide treatment is administered for 2-7 days at 35 mg/kg/day. In some embodiments, the cyclophosphamide treatment is administered for 4-5 days at 250 mg/m2/day i.v. In some embodiments, the cyclophosphamide treatment is administered for 4 days at 250 mg/m2/day i.v.

In some embodiments, lymphodepletion is performed by administering the fludarabine and the cyclophosphamide together to a patient. In some embodiments, fludarabine is administered at 25 mg/m2/day i.v. and cyclophosphamide is administered at 250 mg/m2/day i.v. over 4 days.

In an embodiment, the lymphodepletion is performed by administration of cyclophosphamide at a dose of 60 mg/m2/day for two days followed by administration of fludarabine at a dose of 25 mg/m2/day for five days.

In an embodiment, the lymphodepletion is performed by administration of cyclophosphamide at a dose of 60 mg/m2/day for two days and administration of fludarabine at a dose of 25 mg/m2/day for five days, wherein cyclophosphamide and fludarabine are both administered on the first two days, and wherein the lymphodepletion is performed in five days in total.

In an embodiment, the lymphodepletion is performed by administration of cyclophosphamide at a dose of about 50 mg/m2/day for two days and administration of fludarabine at a dose of about 25 mg/m2/day for five days, wherein cyclophosphamide and fludarabine are both administered on the first two days, and wherein the lymphodepletion is performed in five days in total.

In an embodiment, the lymphodepletion is performed by administration of cyclophosphamide at a dose of about 50 mg/m2/day for two days and administration of fludarabine at a dose of about 20 mg/m2/day for five days, wherein cyclophosphamide and fludarabine are both administered on the first two days, and wherein the lymphodepletion is performed in five days in total.

In an embodiment, the lymphodepletion is performed by administration of cyclophosphamide at a dose of about 40 mg/m2/day for two days and administration of fludarabine at a dose of about 20 mg/m2/day for five days, wherein cyclophosphamide and fludarabine are both administered on the first two days, and wherein the lymphodepletion is performed in five days in total.

In an embodiment, the lymphodepletion is performed by administration of cyclophosphamide at a dose of about 40 mg/m2/day for two days and administration of fludarabine at a dose of about 15 mg/m2/day for five days, wherein cyclophosphamide and fludarabine are both administered on the first two days, and wherein the lymphodepletion is performed in five days in total.

In an embodiment, the lymphodepletion is performed by administration of cyclophosphamide at a dose of 60 mg/m2/day and fludarabine at a dose of 25 mg/m2/day for two days followed by administration of fludarabine at a dose of 25 mg/m2/day for three days.

In an embodiment, the cyclophosphamide is administered with mesna. In an embodiment, mesna is administered at 15 mg/kg. In an embodiment where mesna is infused, and if infused continuously, mesna can be infused over approximately 2 hours with cyclophosphamide (on Days −5 and/or −4), then at a rate of 3 mg/kg/hour for the remaining 22 hours over the 24 hours starting concomitantly with each cyclophosphamide dose.

In an embodiment, the lymphodepletion comprises the step of treating the patient with an IL-2 regimen starting on the day after administration of the third population of TILs to the patient.

In an embodiment, the lymphodepletion comprises the step of treating the patient with an IL-2 regimen starting on the same day as administration of the third population of TILs to the patient.

In some embodiments, the lymphodeplete comprises 5 days of preconditioning treatment. In some embodiments, the days are indicated as days −5 through −1, or Day 0 through Day 4. In some embodiments, the regimen comprises cyclophosphamide on days −5 and −4 (i.e., days 0 and 1). In some embodiments, the regimen comprises intravenous cyclophosphamide on days −5 and −4 (i.e., days 0 and 1). In some embodiments, the regimen comprises 60 mg/kg intravenous cyclophosphamide on days −5 and −4 (i.e., days 0 and 1). In some embodiments, the cyclophosphamide is administered with mesna. In some embodiments, the regimen further comprises fludarabine. In some embodiments, the regimen further comprises intravenous fludarabine. In some embodiments, the regimen further comprises 25 mg/m2 intravenous fludarabine. In some embodiments, the regimen further comprises 25 mg/m2 intravenous fludarabine on days −5 and −1 (i.e., days 0 through 4). In some embodiments, the regimen further comprises 25 mg/m2 intravenous fludarabine on days −5 and −1 (i.e., days 0 through 4).

In some embodiments, the non-myeloablative lymphodepletion regimen comprises the steps of administration of cyclophosphamide at a dose of 60 mg/m2/day and fludarabine at a dose of 25 mg/m2/day for two days followed by administration of fludarabine at a dose of 25 mg/m2/day for five days.

In some embodiments, the non-myeloablative lymphodepletion regimen comprises the steps of administration of cyclophosphamide at a dose of 60 mg/m2/day and fludarabine at a dose of 25 mg/m2/day for two days followed by administration of fludarabine at a dose of 25 mg/m2/day for three days.

In some embodiments, the non-myeloablative lymphodepletion regimen is administered according to Table 26.

TABLE 26

Exemplary lymphodepletion and treatment regimen.

| | Day | | | | | | | | | |
|---|---|---|---|---|---|---|---|---|---|---|
| | −5 | −4 | −3 | −2 | −1 | 0 | 1 | 2 | 3 | 4 |
| Cyclophosphamide 60 mg/kg | X | X | | | | | | | | |
| Mesna (as needed) | X | X | | | | | | | | |

TABLE 26-continued

Exemplary lymphodepletion and treatment regimen.

| | Day | | | | | | | | | |
|---|---|---|---|---|---|---|---|---|---|---|
| | −5 | −4 | −3 | −2 | −1 | 0 | 1 | 2 | 3 | 4 |
| Fludarabine 25 mg/m²/day | X | X | X | X | X | | | | | |
| TIL infusion | | | | | | X | | | | |

In some embodiments, the non-myeloablative lymphodepletion regimen is administered according to Table 27.

TABLE 27

Exemplary lymphodepletion and treatment regimen.

| | Day | | | | | | | | |
|---|---|---|---|---|---|---|---|---|---|
| | −4 | −3 | −2 | −1 | 0 | 1 | 2 | 3 | 4 |
| Cyclophosphamide 60 mg/kg | X | X | | | | | | | |
| Mesna (as needed) | X | X | | | | | | | |
| Fludarabine 25 mg/m²/day | X | X | X | X | | | | | |
| TIL infusion | | | | | X | | | | |

In some embodiments, the non-myeloablative lymphodepletion regimen is administered according to Table 28.

TABLE 28

Exemplary lymphodepletion and treatment regimen.

| | Day | | | | | | | |
|---|---|---|---|---|---|---|---|---|
| | −3 | −2 | −1 | 0 | 1 | 2 | 3 | 4 |
| Cyclophosphamide 60 mg/kg | X | X | | | | | | |
| Mesna (as needed) | X | X | | | | | | |
| Fludarabine 25 mg/m²/day | X | X | X | | | | | |
| TIL infusion | | | | X | | | | |

In some embodiments, the non-myeloablative lymphodepletion regimen is administered according to Table 29.

TABLE 29

Exemplary lymphodepletion and treatment regimen.

| | Day | | | | | | | | | |
|---|---|---|---|---|---|---|---|---|---|---|
| | −5 | −4 | −3 | −2 | −1 | 0 | 1 | 2 | 3 | 4 |
| Cyclophosphamide 60 mg/kg | X | X | | | | | | | | |
| Mesna (as needed) | X | X | | | | | | | | |
| Fludarabine 25 mg/m²/day | | | X | X | X | | | | | |
| TIL infusion | | | | | | X | | | | |

In some embodiments, the non-myeloablative lymphodepletion regimen is administered according to Table 30.

TABLE 30

Exemplary lymphodepletion and treatment regimen.

| | Day | | | | | | | | | |
|---|---|---|---|---|---|---|---|---|---|---|
| | −5 | −4 | −3 | −2 | −1 | 0 | 1 | 2 | 3 | 4 |
| Cyclophosphamide 300 mg/kg | X | X | | | | | | | | |
| Mesna (as needed) | X | X | | | | | | | | |
| Fludarabine 30 mg/m²/day | X | X | X | X | X | | | | | |
| TIL infusion | | | | | | X | | | | |

In some embodiments, the non-myeloablative lymphodepletion regimen is administered according to Table 31.

TABLE 31

Exemplary lymphodepletion and treatment regimen.

| | Day | | | | | | | | |
|---|---|---|---|---|---|---|---|---|---|
| | −4 | −3 | −2 | −1 | 0 | 1 | 2 | 3 | 4 |
| Cyclophosphamide 300 mg/kg | X | X | | | | | | | |
| Mesna (as needed) | X | X | | | | | | | |
| Fludarabine 30 mg/m$^2$/day | X | X | X | X | | | | | |
| TIL infusion | | | | | X | | | | |

In some embodiments, the non-myeloablative lymphodepletion regimen is administered according to Table 32.

TABLE 32

Exemplary lymphodepletion and treatment regimen.

| | Day | | | | | | | |
|---|---|---|---|---|---|---|---|---|
| | −3 | −2 | −1 | 0 | 1 | 2 | 3 | 4 |
| Cyclophosphamide 300 mg/kg | X | X | | | | | | |
| Mesna (as needed) | X | X | | | | | | |
| Fludarabine 30 mg/m$^2$/day | X | X | X | | | | | |
| TIL infusion | | | | X | | | | |

In some embodiments, the non-myeloablative lymphodepletion regimen is administered according to Table 33.

TABLE 33

Exemplary lymphodepletion and treatment regimen.

| | Day | | | | | | | | |
|---|---|---|---|---|---|---|---|---|---|
| | −5 | −4 | −3 | −2 | −1 | 0 | 1 | 2 | 3 | 4 |
| Cyclophosphamide 300 mg/kg | X | X | | | | | | | |
| Mesna (as needed) | X | X | | | | | | | |
| Fludarabine 30 mg/m$^2$/day | | | X | X | X | | | | |
| TIL infusion | | | | | | X | | | |

In some embodiments, the TIL infusion used with the foregoing embodiments of myeloablative lymphodepletion regimens may be any TIL composition described herein, including TIL products genetically modified to express a CCR as described herein, and may also include infusions of MILs and PBLs in place of the TIL infusion, as well as the addition of IL-2 regimens and administration of co-therapies (such as PD-1 and PD-L1 inhibitors) as described herein.

5. IL-2 Regimens

In an embodiment, the IL-2 regimen comprises a high-dose IL-2 regimen, wherein the high-dose IL-2 regimen comprises aldesleukin, or a biosimilar or variant thereof, administered intravenously starting on the day after administering a therapeutically effective portion of therapeutic population of TILs, wherein the aldesleukin or a biosimilar or variant thereof is administered at a dose of 0.037 mg/kg or 0.044 mg/kg IU/kg (patient body mass) using 15-minute bolus intravenous infusions every eight hours until tolerance, for a maximum of 14 doses. Following 9 days of rest, this schedule may be repeated for another 14 doses, for a maximum of 28 doses in total. In some embodiments, IL-2 is administered in 1, 2, 3, 4, 5, or 6 doses. In some embodiments, IL-2 is administered at a maximum dosage of up to 6 doses.

In an embodiment, the IL-2 regimen comprises a decrescendo IL-2 regimen. Decrescendo IL-2 regimens have been described in O'Day, et al., J. Clin. Oncol. 1999, 17, 2752-61 and Eton, et al., Cancer 2000, 88, 1703-9, the disclosures of which are incorporated herein by reference. In an embodiment, a decrescendo IL-2 regimen comprises 18×10$^6$ IU/m2 aldesleukin, or a biosimilar or variant thereof, administered intravenously over 6 hours, followed by 18×10$^6$ IU/m2 administered intravenously over 12 hours, followed by 18×10$^6$ IU/m2 administered intravenously over 24 hours, followed by 4.5×10$^6$ IU/m2 administered intravenously over 72 hours. This treatment cycle may be repeated every 28 days for a maximum of four cycles. In an embodiment, a decrescendo IL-2 regimen comprises 18,000,000 IU/m2 on day 1, 9,000,000 IU/m2 on day 2, and 4,500,000 IU/m2 on days 3 and 4.

In an embodiment, the IL-2 regimen comprises a low-dose IL-2 regimen. Any low-dose IL-2 regimen known in the art may be used, including the low-dose IL-2 regimens described in Dominguez-Villar and Hafler, Nat. Immunology 2000, 19, 665-673; Hartemann, et al., Lancet Diabetes Endocrinol. 2013, 1, 295-305; and Rosenzwaig, et al., Ann. Rheum. Dis. 2019, 78, 209-217, the disclosures of which are incorporated herein by reference. In an embodiment, a low-dose IL-2 regimen comprises 18×10$^6$ IU per m2 of aldesleukin, or a biosimilar or variant thereof, per 24 hours, administered as a continuous infusion for 5 days, followed by 2-6 days without IL-2 therapy, optionally followed by an additional 5 days of intravenous aldesleukin or a biosimilar or variant thereof, as a continuous infusion of 18×10$^6$ IU per m2 per 24 hours, optionally followed by 3 weeks without IL-2 therapy, after which additional cycles may be administered.

In an embodiment, the IL-2 regimen comprises administration of pegylated IL-2 every 1, 2, 4, 6, 7, 14 or 21 days at a dose of 0.10 mg/day to 50 mg/day. In an embodiment, the IL-2 regimen comprises administration of bempegaldesleukin, or a fragment, variant, or biosimilar thereof, every 1, 2, 4, 6, 7, 14 or 21 days at a dose of 0.10 mg/day to 50 mg/day.

In an embodiment, the IL-2 regimen comprises administration of THOR-707, or a fragment, variant, or biosimilar thereof, every 1, 2, 4, 6, 7, 14 or 21 days at a dose of 0.10 mg/day to 50 mg/day.

In an embodiment, the IL-2 regimen comprises administration of nemvaleukin alfa, or a fragment, variant, or biosimilar thereof, every 1, 2, 4, 6, 7, 14 or 21 days at a dose of 0.10 mg/day to 50 mg/day.

In an embodiment, the IL-2 regimen comprises administration of an IL-2 fragment engrafted onto an antibody backbone. In an embodiment, the IL-2 regimen comprises administration of an antibody-cytokine engrafted protein that binds the IL-2 low affinity receptor. In an embodiment, the antibody cytokine engrafted protein comprises a heavy chain variable region (VH), comprising complementarity determining regions HCDR1, HCDR2, HCDR3; a light chain variable region (VL), comprising LCDR1, LCDR2, LCDR3; and an IL-2 molecule or a fragment thereof engrafted into a CDR of the VH or the VL, wherein the antibody cytokine engrafted protein preferentially expands T effector cells over regulatory T cells. In an embodiment, the antibody cytokine engrafted protein comprises a heavy chain variable region (VH), comprising complementarity determining regions HCDR1, HCDR2, HCDR3; a light chain variable region (VL), comprising LCDR1, LCDR2, LCDR3; and an IL-2 molecule or a fragment thereof engrafted into a CDR of the VH or the VL, wherein the IL-2 molecule is a mutein, and wherein the antibody cytokine engrafted protein preferentially expands T effector cells over regulatory T cells. In an embodiment, the IL-2 regimen comprises administration of an antibody comprising a heavy chain selected from the group consisting of SEQ ID NO:29 and SEQ ID NO:38 and a light chain selected from the group consisting of SEQ ID NO:37 and SEQ ID NO:39, or a fragment, variant, or biosimilar thereof, every 1, 2, 4, 6, 7, 14 or 21 days at a dose of 0.10 mg/day to 50 mg/day.

In some embodiments, the antibody cytokine engrafted protein described herein has a longer serum half-life that a wild-type IL-2 molecule such as, but not limited to, aldesleukin (Proleukin®) or a comparable molecule.

In some embodiments, the TIL infusion used with the foregoing embodiments of myeloablative lymphodepletion regimens may be any TIL composition described herein and may also include infusions of MILs and PBLs in place of the TIL infusion, as well as the addition of IL-2 regimens and administration of co-therapies (such as PD-1 and PD-L1 inhibitors) as described herein.

In some embodiments, the present invention includes a method of treating a patient with a cancer comprising the step of administering a TIL regimen, wherein the TIL regimen includes a TIL product genetically modified to express a CCR, and further comprising the step of administering an IL-2 regimen. In some embodiments, the present invention includes a composition comprising (i) a TIL product genetically modified to express a CCR and (ii) an IL-2 regimen. In some embodiments, the present invention includes a kit comprising (i) a TIL product genetically modified to express a CCR and (ii) an IL-2 regimen.

In some embodiments, the present invention includes a method of treating a patient with a cancer comprising the steps of administering a TIL regimen, wherein the TIL regimen includes a TIL product genetically modified to express a CCR, and further comprising the steps of administering an IL-2 regimen and either a PD-1 inhibitor or a PD-L1 inhibitor. In some embodiments, the present invention includes a composition comprising (i) a TIL product genetically modified to express a CCR, (ii) an IL-2 regimen, and (iii) either a PD-1 inhibitor or a PD-L1 inhibitor. In some embodiments, the present invention includes a kit comprising (i) a TIL product genetically modified to express a CCR, (ii) an IL-2 regimen, and (iii) either a PD-1 inhibitor or a PD-L1 inhibitor.

In some embodiments, the present invention includes a method of treating a patient with a cancer comprising the steps of administering a TIL regimen, wherein the TIL regimen includes a TIL product genetically modified to express a CCR, and further comprising the steps of administering a CTLA-4 inhibitor and an IL-2 regimen. In some embodiments, the present invention includes a composition comprising (i) a TIL product genetically modified to express a CCR, (ii) a CTLA-4 inhibitor, and (iii) an IL-2 regimen. In some embodiments, the present invention includes a kit comprising (i) a TIL product genetically modified to express a CCR, (ii) a CTLA-4 inhibitor, and (iii) an IL-2 regimen.

In some embodiments, the present invention includes a method of treating a patient with a cancer comprising the steps of administering a TIL regimen, wherein the TIL regimen includes a TIL product genetically modified to express a CCR, and further comprising the steps of administering an IL-2 regimen, a CTLA-4 inhibitor, and either a PD-1 inhibitor or a PD-L1 inhibitor. In some embodiments, the present invention includes a composition comprising (i) a TIL product genetically modified to express a CCR, (ii) an IL-2 regimen, (iii) either a PD-1 inhibitor or a PD-L1 inhibitor, and (iv) a CTLA-4 inhibitor. In some embodiments, the present invention includes a kit comprising (i) a TIL product genetically modified to express a CCR, (ii) an IL-2 regimen, (iii) either a PD-1 inhibitor or a PD-L1 inhibitor, and (iv) a CTLA-4 inhibitor.

B. Adoptive Cell Transfer

Adoptive cell transfer (ACT) is an effective form of immunotherapy and involves the transfer of immune cells with antitumor activity into cancer patients. ACT is a treatment approach that involves the identification, in vitro, of lymphocytes with antitumor activity, the in vitro expansion of these cells to large numbers and their infusion into the cancer-bearing host. Lymphocytes used for adoptive transfer can be derived from the stroma of resected tumors (tumor infiltrating lymphocytes or TILs). TILs for ACT can be prepared as described herein. In some embodiments, the TILs are prepared, for example, according to a method as described in FIG. 2A and/or FIG. 9. They can also be derived or from blood if they are genetically engineered to express antitumor T-cell receptors (TCRs) or chimeric antigen receptors (CARs), enriched with mixed lymphocyte tumor cell cultures (MLTCs), or cloned using autologous antigen presenting cells and tumor derived peptides. ACT in which the lymphocytes originate from the cancer-bearing host to be infused is termed autologous ACT. U.S. Publication No. 2011/0052530 relates to a method for performing adoptive cell therapy to promote cancer regression, primarily for treatment of patients suffering from metastatic melanoma, which is incorporated by reference in its entirety for these methods. In some embodiments, TILs can be administered as described herein. In some embodiments, TILs can be administered in a single dose. Such administration may be by injection, e.g., intravenous injection. In some embodiments, TILs and/or cytotoxic lymphocytes may be administered in multiple doses. Dosing may be once, twice, three times, four times, five times, six times, or more than six times per year. Dosing may be once a month, once every two weeks, once a week, or once every other day. Administration of TILs and/or cytotoxic lymphocytes may continue as long as necessary.

V. Coordinating Manufacturing of Cell Expansion Product and Patient Treatment Events As discussed herein, the timing from tumor resection from the patient to completion of the TIL manufacturing varies depending on several factors including, for example, the size of the tumor obtainable from the patient, cell count at the end of various stage of manufacturing, number of days for which various stages of manufacturing are performed, etc. As a consequence, certain amount of flexibility is needed in scheduling various patient treatment events. In some embodiments, patient treatment event includes lymphodepletion. In some embodiments, patient treatment event includes TIL infusion. In some embodiments, the patient treatment event includes a leukapheresis procedure. In some embodiments, patient treatment event includes administration of an IL-2 regimen. In some embodiments, patient treatment event includes tumor resection. In some embodiments, patient treatment event includes inpatient stay for post-procedure treatments.

An aspect of the present disclosure provides for a system for implementing the methods disclosed herein. The system may include a patient portal, a manufacturing portal, a clinician portal and a logistics portal. The patient portal enables a patient or a person associated with the patient (e.g., a caregiver, a guardian or a legally authorized agent) (together referred to herein as "the patient" for convenient reference) can access the information relating to the schedule of the patient treatment events. The patient portal may require the patient to provide authentication information to access this information. The patient portal may also allow the patient to edit information relating to the patient such as, for example, address or other personal information.

The clinician portal, also referred to as the hospital-side interface, enables the clinic (i.e., the clinic personnel) to access and/or edit information relating to the patient, the manufacturing process, the manufacturing facilities, the logistics provider as well as the information relating to various patient treatment events performed or to be performed at the clinic.

The manufacturing portal communicates with the hospital-side interface and the logistics portal/logistics interface to determine and convey information relating to the manufacturing process and/or availability of the manufacturing slots. The manufacturing portal also enables generation of manufacturing labels including updated quality information at various manufacturing steps as disclosed herein.

The logistics portal, also referred to herein as the logistics interface, communicates with the manufacturing portal and the hospital-side interface exchange information relating to the schedule for shipping of material (i.e., the solid tumor, or the manufactured cell therapy product) between the clinic and the manufacturing facility including, for example, the manufacturing schedule, the availability of manufacturing slots and the schedule of patient treatment events to facilitate timely shipment of the material.

The system for implemented the various methods disclosed herein can be implemented on a computing system by either implementing a proprietary computer program or by suitably modifying a commercially available software platform such as, for example, one provided by Vineti, Salesforce.com, Salesforce Health Cloud, IQVIA, TracSel, and SAP.

The modification of commercially available software platform so as to suitably implement the system and perform one or more methods disclosed herein may cause the platform to perform processes that it was not originally designed for. In other words, the modification, in some embodiments, may be based on unconventional use of the various tools provided by the platform. In some embodiments, the system for implementation of various methods disclosed herein can include a software platform such as a framework program that integrates an enterprise resource planning (ERP) system that enables automation of logistical tasks and a manufacturing execution system (MES) that enables automation of manufacturing tasks. An example of such a framework program is described in U.S. Pat. No. 7,343,605, which is incorporated herein by reference in its entirety.

For example, alongside MES applications, applications from the enterprise control level (Enterprise Resource Planning level) and from the automation level (controls level) can also be integrated via a framework program and monitored or managed via a workstation (e.g., at the clinical facility, at the manufacturing facility or at the courier facility). The framework program may thus form an integration platform for the entire patient treatment process including registering the patient, procurement of the tumor, shipping the tumor to the manufacturing facility, manufacturing the therapeutic or expanded cell therapy product, shipping the therapeutic cell therapy product to the clinical facility, administering the therapy to the patient, and subsequent patient treatment events. Different applications from the enterprise control level, the MES level and the automation level can be integrated by the framework program simply and cost-effectively with the aid of adapters and/or wrappers. The framework program must therefore be regarded as a middleware platform and as a manufacturing application integration tool. An end user (e.g. a case manager) can see the respective status of the applications to be monitored via a workstation and can also access data and methods of the applications. Further the end user can connect applications to each other by means of this access.

The framework program therefore makes it possible firstly to achieve a vertical integration of applications from different enterprise levels and secondly the framework program enables a horizontal integration of applications on the MES level.

For instance, a software-based case object, that allows storage of information in the platform, is the overall definition of the type of information being stored. For example, a software-based case object in the off-the-shelf platform allows storage of information regarding customer inquiries. For such object, there may be multiple records that store the information about specific instances of that type of data. Thus, a case record to store the information about an individual's training inquiry and another case record to store the information about another individual's configuration issue. These objects may be customized to store information relating to, e.g., a patient, the patient treatment events for that patient and a corresponding schedule.

Similarly, automated actions such as notifications and alerts, and workflow rules such as business logic actions, provided within the off-the-shelf platform may be modified to trigger changes in schedules and process steps such as, e.g., changes in manufacturing processes and the consequent changes in manufacturing schedules, availability of manufacturing slots and schedules of patient treatment events based on results of a QA test.

In some embodiments, the system disclosed herein provides quality assurance features for determining probable points of failure during the manufacturing process such as those described in U.S. Pat. Nos. 10,747,209, and 7,799,273, which is incorporated herein by reference in its entirety.

In some embodiments, the system disclosed herein provides data systems configured to maintain integrity of electronic batch records created during the process of manufacturing a final cell therapy product from a solid tumor (or a fragment thereof) obtained from the patient such as those described in U.S. Pat. No. 8,491,839, which is incorporated herein by reference in its entirety. In some embodiments, the system disclosed herein includes an application software adapted for use in cell manufacturing process wherein the cell manufacturing process produces expanded cell therapy product such as a therapeutic population of T-cells. The application software is configured to control a plurality of devices included in a closed system for cell manufacturing such as gas permeable devices.

In some embodiments, the system disclosed herein integrates application software and cell manufacturing methods disclosed herein to provide a comprehensive validation and quality assurance protocol that is used by a plurality of end users whereby the data compiled from the system is analyzed and used to determine is quality assurance protocols and validation protocols are being achieved.

In some embodiments, the system applies the application software to multiple product lines and/or multiple cell manufacturing facilities, whereby multiple cell manufacturing lines and multiple product lines are monitored and controlled using the same system.

In some embodiments, the system implements the methods described herein into the batch optimization of cell culture systems of the cell manufacturing process whereby the data compiled by the cell culture system is tracked continuously overtime and the data is used to analyze the cell culture system. In addition, the said data is integrated and used to analyze the quality control process of the cell manufacturing process at-large.

In some embodiments, the system disclosed herein enables design of work stations for performing various steps of the process of manufacturing a final cell therapy product. The work stations may be configured to enable verification of data associated with a previous step to ensure integrity of the process being performed and enable a remedial action, where possible. Examples of such work station designs are provided in U.S. Pat. No. 8,041,444, which is incorporated herein by reference in its entirety.

In some embodiments, the system disclosed herein enables coordination between a hospital facility and various manufacturers capable of manufacturing the cell therapy product from the solid tumor obtained at the hospital facility by providing access to available manufacturing schedules at the various manufacturers. Examples of systems enabling such coordination are provided in U.S. Pat. No. 8,069,071, which is incorporated herein by reference in its entirety.

In some embodiments, the system disclosed herein is based on a cloud based architecture which enables various entities associated with the manufacturing of the cell therapy product real-time access (with appropriate permissions) to information relating to the manufacturing and transportation of the cell therapy product. Examples of such cloud-based architecture are provided in U.S. Pat. No. 9,965,562, which is incorporated herein by reference in its entirety.

In some embodiments, the system disclosed herein enables personnel associated with obtaining the tumor from the patient, manufacturing of the cell therapy product from the obtained tumor and transportation of the tumor and the cell therapy product, to identify and authenticate themselves using electronic signatures for process control and approval, such as described in US Patent Application Publication No. 2004/0243260, which is incorporated herein by reference in its entirety.

In some embodiments, the system may further include, or incorporate therein, a customer relationship management (CRM) subsystem. The CRM subsystem may archive information relating to various parties such as, for example, doctors, hospital sites, nurses, billers, business contacts, etc. The information is maintained with the CRM subsystem to enable maintenance of a single view of parties in one unified funnel, allowing sharing of platform-based, single-funnel views of prospects and parties in a privacy-compliant manner within the system. Information relating to relationship between parties can be shared in a distributed multi-master, multi-slave or peer-peer context, partially or fully anonymously by removal of personally identifiable information, to one or more distributed slave or peer CRM systems. One example of such a CRM subsystem is disclosed in US Patent Application Publication No. 2014/0244351, U.S. Pat. Nos. 8,489,451, and 9,342,292, each of which is incorporated herein by reference in its entirety.

In some embodiments, the system described herein may be operable to provide a network that includes a central event processing subsystem for receiving, processing, and routing messages triggered by real-time medical events and/or manufacturing events. The central event processing system, for example, may identify patient information associated with a medical event and match the patient information to one or more of a health plan, a clinical location, a TIL manufacturing facility, and/or a logistics provider. Upon matching the medical and/or manufacturing event with the interested parties, the central event processing subsystem may forward at least a portion of the information regarding the medical and/or manufacturing event to one or more interested parties within a short period of time of the triggering event (e.g., in near real-time). For example, based upon rules associated with each interested party, the central event processing system may forward information and/or issue an alert or notification to an interested party to make the interested party aware of the medical event. Example of such a central event processing subsystem is described in US Patent Application Publication No. 2014/0372147, and U.S. Pat. No. 10,242,060, each of which is incorporated herein by reference in its entirety.

In some embodiments, the system disclosed herein is operable to select a workflow for a cancer treatment regimen including patient treatment events such as, for example, tumor resection, lymphodelpetion, leukapheresis, infusion of TILs, and/or IL-2 regimen, or other patient treatment events disclosed herein. Upon selection of the workflow, the system may produce purchase order corresponding to the cell infusion therapy on behalf of a patient, wherein the order corresponding to the cell infusion therapy includes at least one of a cell order request and a request for specified treatment regimen corresponding to the cancer treatment. Examples of such workflow selection subsystem are disclosed in US Patent Application Publication No. US 2014/0088985, which is incorporated herein by reference in its entirety.

In some embodiments, the system may include a telephony subsystem that may include authentication of service requests including authentication of a remote access device prior to text or audio communication with a patient or a representative of the patient. In some embodiments, the authentication may be accomplished by automatically authenticating the remove access device or by asking questions to the patient (or the representative). Example of the such a telephony subsystem and authentication method is disclosed in US Patent Application Publication No. US 2019/0026747, which is incorporated herein by reference in its entirety.

A. System for Coordinating Manufacturing of Cell Expansion Product

Embodiments of the present disclosure include a method and a system for coordinating the manufacturing of a cell therapy product such as, for example, T-cells or TILs for a patient, and dynamically scheduling various stages of the manufacturing process as well as various patient treatment events based on the progress and success of various stages of the manufacturing process.

The methods and systems described herein are further operable to provide the specific technical advantage over existing systems of providing a continuous and automatic chain of custody and chain of identity for a patient-specific biological sample during an immunotherapy procedure, to create a computerized information portal that interested parties—such as the patient, physician, manufacturer, and other medical personnel—may use to quickly understand and track the current phase of the immunotherapy procedure and the status of the patient's biological sample during the procedure. A lack of ability to maintain a chain of custody and chain of identity—resulting in delays during the manufacturing process which, for a patient dealing with a life-threatening illness, may be immeasurably severe.

Embodiments of the present disclosure enable maintenance of the chain of custody of the biological material during the manufacturing process (including QA, manufacturing, release testing, and finalizing for shipment), and the chain of custody of the biological material during the final product delivery process (including shipment and delivery to the infusion site). Embodiments of the present disclosure further enable continuously and constantly associating chain of custody with the specific patient—thereby ensuring a complete chain of identity between the patient and the biological material during all phases of manufacturing.

The maintenance of COC and COI is performed by associating each event during the entire journey of the biological material from the patient through transportation, the manufacturing process, transportation and back to the patient with a cell order identifier and a patient-specific identifier (that is unique to the patient), and tracking each event during the entire journey.

In addition, the methods and systems described herein are operable to integrate and synchronize obtaining the living tissue from the patient with the manufacturing process, as well as provide capability for auditing each step from obtaining the living tissue to administering of the cell therapy product and subsequent treatment events for COC and COI.

The methods and systems described herein are further operable for coordinating logistics for obtaining the living tissue from the patient, delivery of the living tissue to a selected manufacturing facility, manufacturing of the cell therapy product at the selected manufacturing facility, and delivery of the cell therapy product from the manufacturing facility to the clinic for patient treatment.

Figure 3A:
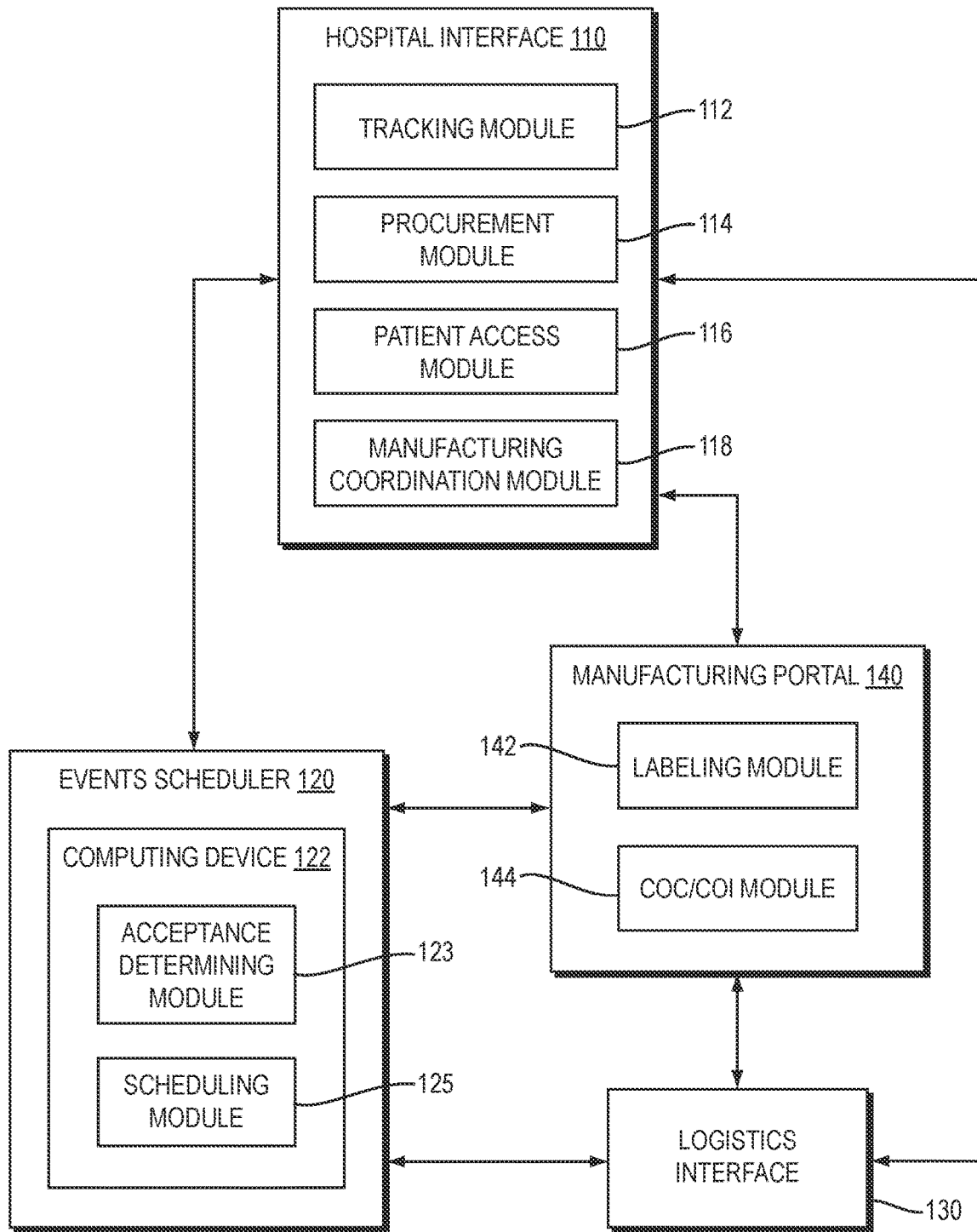
FIG. 3A shows a block diagram for a system for coordinating the manufacturing of TILs for a patient.

FIG. 3A shows a block diagram for a system for coordinating the manufacturing of a cell therapy product for a patient in accordance with an embodiment of the present disclosure. In some embodiments, functionality performed by the components in FIG. 3A may be integrated into a single component. Also, in some embodiments, functionality performed by one or more components in FIG. 3A may also be performed by other components in FIG. 3A.

Referring to FIG. 3A, the system 300 may include a hospital-side interface 110, an events scheduler 120, a logistics interface (also referred to herein as the courier portal) 130 and/or a manufacturing portal 140. Each of the hospital-side interface 110, the events scheduler 120, the logistics interface 130 and the manufacturing portal 140 communicates with the other three, e.g., using a communication network such as a LAN, a WAN (e.g., the Internet), and/or a cellular network.

In some embodiments, the hospital-side interface 110, the events scheduler 120, the logistics interface 130, the manufacturing portal 140, and corresponding modules (shown, e.g., in FIG. 3) suitably modify or build upon commercially available software platforms, such as, for example, those provided by Vineti, Salesforce.com, Salesforce Health Cloud, IQVIA, TracSel, and SAP.

The hospital-side interface 110 may be associated with or may interact with a hospital or other facility responsible for administration of a treating a patient, e.g., providing a therapy for cancer as disclosed herein. In some embodiments, the hospital-side interface 110 is associated with a clinical facility that performs a procedure for obtaining a solid tumor from a patient, and obtaining cell therapy product from the solid tumor or fragments thereof. In some embodiments, the clinical facility functions only to obtain the solid tumor while the process of obtaining the cell therapy product from the solid tumor or fragments thereof can be performed at a manufacturing facility.

In some embodiments, the hospital-side interface 110 is associated with a hospital that performs the infusion of an expanded cell therapy product obtained from a manufacturing facility and provides subsequent care and/or any prior or follow-on treatment to the patient. Clinicians or employees of the hospital or clinic may interact with the system 300 via the hospital-side interface 110.

In some embodiments, the hospital-side interface 110 includes one or more computing devices such as, for example, a desktop computer, a cloud server, a laptop computer, mobile devices, or any other computing device including hardware and software modules that execute on a processor and interact with a memory. The hospital-side interface 110 may be connected, via wired or wireless connection, to computing devices operated at, or associated with, the hospital or clinical facility.

In some embodiments, the hospital-side interface 110 may include a tracking module 112 configured for tracking the biological material (e.g., tumor from the patient, T-cells obtained from the patient, expanded T-cells at various stages of T-cell expansion process, etc.) from the patient from the time of extraction from the patient till the time of infusion into the patient.

In some embodiments, when a patient is enrolled for a TIL infusion treatment, a cell order request for manufacture of an expanded cell therapy product for the patient is created and a cell order identifier associated with the cell order request is generated. In some embodiments, a purchase order is generated in accordance with the cell order request and uploaded to the system from the hospital facility. In some embodiments, the system may include an interface for generating and/or uploading the purchase order.

In addition a patient-specific identifier unique to the patient is generated and associated with the cell order identifier. In some embodiments, the patient-specific identifier may include, for example, a patient ID # with sequential suffix, where the suffix is a single letter added in sequence per patient (A-Z). The patient-specific identifier is unique in the system. In some embodiments, the patient-specific identifier may be visible only to certain personas (described in detail elsewhere herein). In some embodiments, the patient-specific identifier is printed on every label printed through the journey of the patient biological material, as well as the manufactured biological material. In some embodiments, the patient-specific identifier is read only to all system users. In other words, the patient-specific identifier, in some embodiments, cannot be edited once generated.

In some embodiments, the cell order identifier may include information such as, for example, a unique patient identifier, a cell order identifier, an order code, a cell order lot number, values of one or more acceptance parameters at various time points, one or more indicators indicating whether acceptance criteria are met at various time points, or a combination thereof.

In some embodiments, the cell order identifier and the patient-specific identifier are scanned at each point where any biological material (e.g., solid tumor extracted from the patient, fragments thereof, cell therapy product extracted therefrom, or expanded cell therapy product obtained from expanding the cell therapy product) associated with the patient changes custody or undergoes processing. Each scanned may be logged and verified by the tracking module 112 during the entire process from the time of extraction from the patient till the time of infusion into the patient. The verification of patient-specific identifier at each step during the entire process ensures a chain of identity (COI) for the product, while the verification of the cell order identifier at each step during the entire process ensures a chain of custody (COC) for the product. The details relating to maintenance of COI and COC are described elsewhere herein.

In some embodiments, the scanned information is verified with the purchase order generated by the hospital facility. For example, when a shipment is received at the manufacturing facility, the label on the shipping container may be scanned and the information on the label may be verified with the purchase order to ensure accuracy. In some embodiments, the result of the verification is logged within the system.

It will be appreciated that while the tracking module 112 is shown in FIG. 3A, and described herein as being part of the hospital-side interface 110, the tracking module 112 can be implemented as a standalone computing device having a processor and a memory in some embodiments Similarly, the tracking module 112 can also be implemented as a standalone software module (e.g., stored on a cloud server) in some embodiments.

In some embodiments, the hospital-side interface 110 may provide limited access to a patient, via a patient access module 116, to enable the patient to obtain information relating to treatment procedures and corresponding schedules. The patient access module 116 may also enable the patient to provide information relating to oneself such as, for example, personal identifying information, insurance information, and information relating to one's health condition for clinicians.

The hospital-side interface 110 may further include a procurement module 114 operable to enable personnel at the clinical facility to obtain the solid tumor from the patient in accordance with a predetermined protocol, and enter information relating to the procedure for obtaining the solid tumor from the patient. The information relating to the procedure for obtaining the solid tumor may, in some embodiments, be archived to enable post-facto audit to ensure compliance with regulatory requirements.

In some embodiments, the procurement module 114 may further enable the personnel at the clinical facility to provide information to the manufacturing facility about the solid tumor and the processes used to obtain the solid tumor from the patient. In embodiments where the clinical facility is also operable to obtain cell therapy product from the solid tumor, the procurement module 114 may enable the personnel at clinical facility to provide information about the obtained cell therapy product such as, for example, the process or procedure used for obtaining the cell therapy product, and the results of quality control assays performed on the obtained cell therapy product to the manufacturing facility.

In some embodiments, the hospital-side interface 110 may further include a manufacturing coordination module 118. The manufacturing coordination module 118 is operable to enable users at the clinical facility to obtain information relating to one or more manufacturing facilities such as, for example, availability of manufacturing slots and capabilities available at each of the one or more manufacturing facilities. The manufacturing coordination module 118 further enables users at the clinical facility to coordinate the reservation of a manufacturing slot at a selected manufacturing facility, and coordinate with a logistics provider via the logistics interface 130 to arrange for transportation of the solid tumor, fragments thereof or cell therapy product obtained from the patient. The manufacturing coordination module 118 further enables users at the clinical facility to obtain information relating to the manufacturing process and/or quality control assays performed during the manufacturing process via the manufacturing portal 140.

The events scheduler 120 is operable to coordinate the scheduling of various activities performed at the clinical facility and the manufacturing facility. Additionally or alternately, the events scheduler 120 may provide the information relating to scheduling of various activities to a logistics provider so as to facilitate transportation of the cell therapy product between the clinical facility and the manufacturing facility. the facility for manufacturing the cell therapy product, e.g., facility where the cell therapy product expansion takes place. As described in more detail below, based on different events that occur during the manufacturing of the cell therapy product, the event scheduler is configured to dynamically schedule when other event(s) should occur.

In some embodiments, the events scheduler 120 includes a computing device 122 such as, for example, a desktop computer, a server, a laptop computer, mobile devices, or any other computing device including hardware and software modules that execute on a processor and interact with a memory. The hardware and/or software modules include an acceptance determining module 123 and a scheduling module 125. In some embodiments, the computing device 122 may be a cloud server accessible via the hospital interface 110, the manufacturing portal 140 and the logistics interface 130. The events scheduler 120 may be connected, via wired or wireless connection, to computing devices operated at, or associated with, the manufacturing facility and/or the hospital facility.

It will be appreciated that while the acceptance determination module 123 is shown in FIG. 3A as being part of the events scheduler 120, the acceptance determination module 123 may also be implemented as part of the manufacturing portal 140. Alternately, the acceptance determination module 123 may also be implemented as a standalone software module, e.g., hosted on a cloud server.

The logistics interface or courier portal 130 may be associated with or may interact with a logistics provider such as, for example, a courier service or a package handling service.

In some embodiments, the logistics interface 130 includes one or more computing devices such as, for example, a desktop computer, a cloud server, a laptop computer, mobile devices, or any other computing device including hardware and software modules that execute on a processor and interact with a memory. The logistics interface 130 may be connected, via wired or wireless connection via a network such as the Internet, to computing devices operated at, or associated with, the logistics provider.

The manufacturing portal 140 may be associated with the manufacturing facility that manufactures the expanded cell therapy product. The manufacturing portal 140 is operable to enable personnel at the manufacturing facility to control and record various processes during the manufacturing of the expanded cell product including, for example, maintaining a chain of identity and a chain of custody, recording information relating to quality control assays performed during the manufacturing, recording transition between various processes, and providing labels for containers of the cell therapy product during the expansion process.

In some embodiments, the manufacturing portal 140 includes one or more computing devices such as, for example, a desktop computer, a cloud server, a laptop computer, mobile devices, or any other computing device including hardware and software modules that execute on a processor and interact with a memory. The manufacturing portal 140 may be connected, via wired or wireless connection, to computing devices operated at, or associated with, the manufacturing facility.

In some embodiments, the manufacturing portal 140 includes a labeling module 142 and a COC/COI module 144. The labeling module 142 is operable to enable personnel at the manufacturing facility to generate labels for containers carrying the cell therapy product during the process of manufacturing the expanded cell therapy product (also referred to herein as the expansion process). The labels may include information such as, for example, a patient-specific identifier, an identifier relating to the personnel handling the container and/or performing the current and/or previous step of the expansion process, results of a quality control assay performed at a previous step, a reason code relating to the reason for generating the label, a barcode or a 2D code (e.g., a QR code) identifying the cell therapy product with the patient-specific identifier, and other suitable information.

The COC/COI module 144 is operable to enable users associated with the manufacturing facility to maintain an audit chain of custody during the expansion process. The COC/COI module 144 is further operable to enable users associated with manufacturing facility to maintain an audit chain of identity of the patient associated with the cell therapy product being expanded.

Figure 3B:
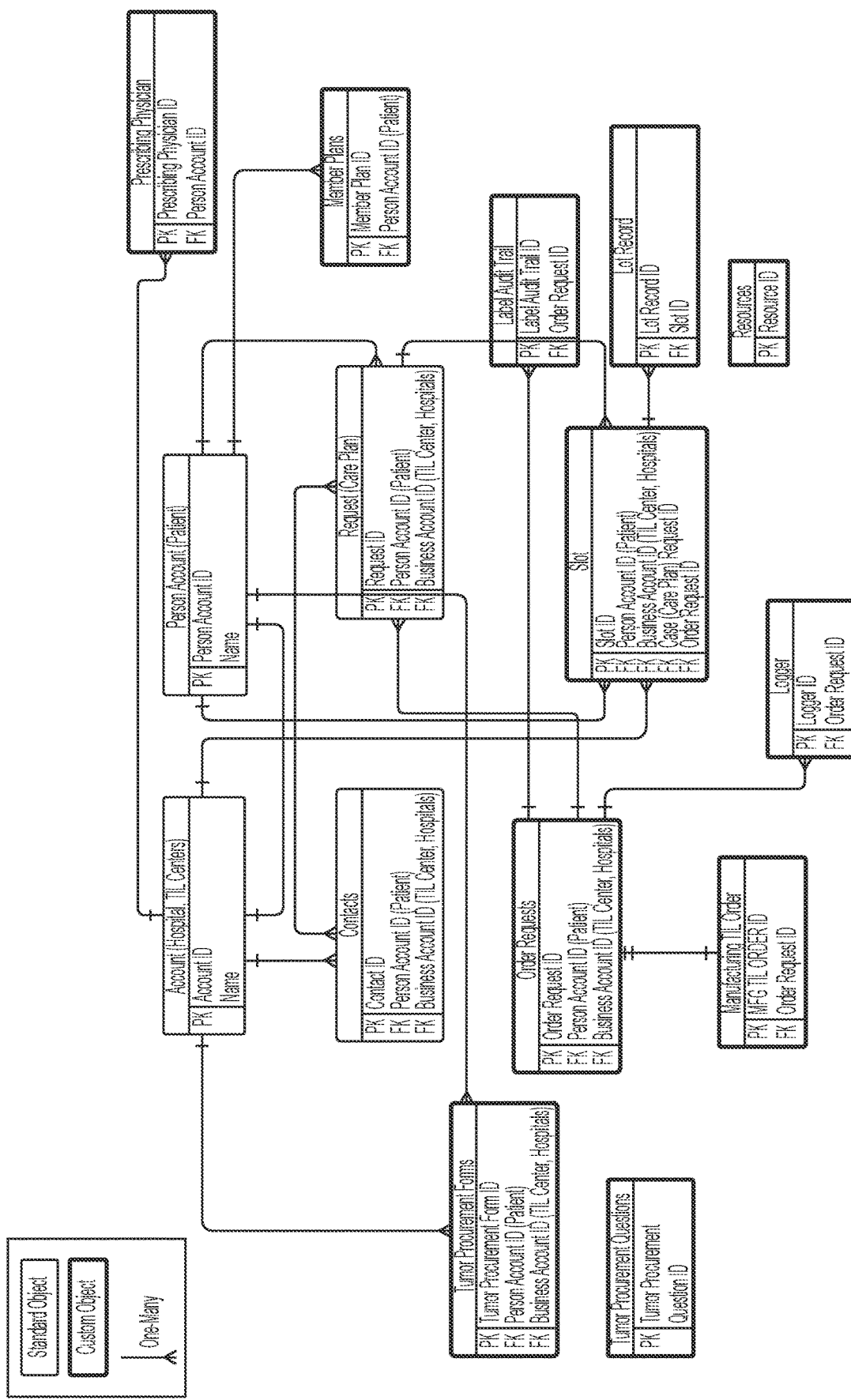
FIG. 3B illustrates the object schema for components of system 300 that are suitably modified or built upon commercially available software platforms in addition to those standard within those platforms in accordance with some embodiments.

FIG. 3B illustrates the object schema for components of system 300 that are suitably modified or built upon commercially available software platforms in addition to those standard within those platforms. For example, a commercially available software platform may have built-in objects corresponding to patient access (including, e.g., patient identifier, patient contact information, patient authentication information, etc.), treatment plan (including, e.g., an initial schedule of patient treatment events), clinician access (e.g., clinician identifier, and clinician authentication information), and a manufacturing access (e.g., contact information for the manufacturing facilities).

On the other hand, objects such as tumor procurement forms associated with the procedure for obtaining the solid tumor from the patient, manufacturing order including information relating to processes to be used for manufacturing the expanded cell therapy product and information relating to how the obtained solid tumor has been processed, schedule of manufacturing at one or more manufacturing facilities, label audit trail for enabling audit of the entire process, may be custom-built to interface with the built-in objects so as to provide the specific functionality associated with system 300.

The custom-built objects and the built-in objects are configured in the system 300 to interact with each other so as to enable maintaining and auditing COC and COI through all the events from obtaining the solid tumor from the patient to infusion of the expanded cell therapy product into the patient. The custom-built objects, in concert with the built-in objects, as well as schedule patient treatment events and associated logistics based on how the manufacturing processes progresses.

For example, in some embodiments, custom-built objects such as lot records and label audit trails may be provided in the system 300. These custom-built objects, in addition to custom-built workflow automation and custom-built user profiles, provide the commercially available software platform with functionality such as, for example, maintenance of COC/COI, audit capability, dynamic scheduling of patient treatment events based on manufacturing execution, label generation based on manufacturing execution, and/or interaction between manufacturing execution and procurement, that may not have been originally envisioned within the commercially available software platform. Additional details of the interaction between the custom-built objects and the built-in objects for tumor procurement procedure, maintenance of COC and COI, and generation of labels during the manufacturing process are provided elsewhere herein.

Figure 3C:
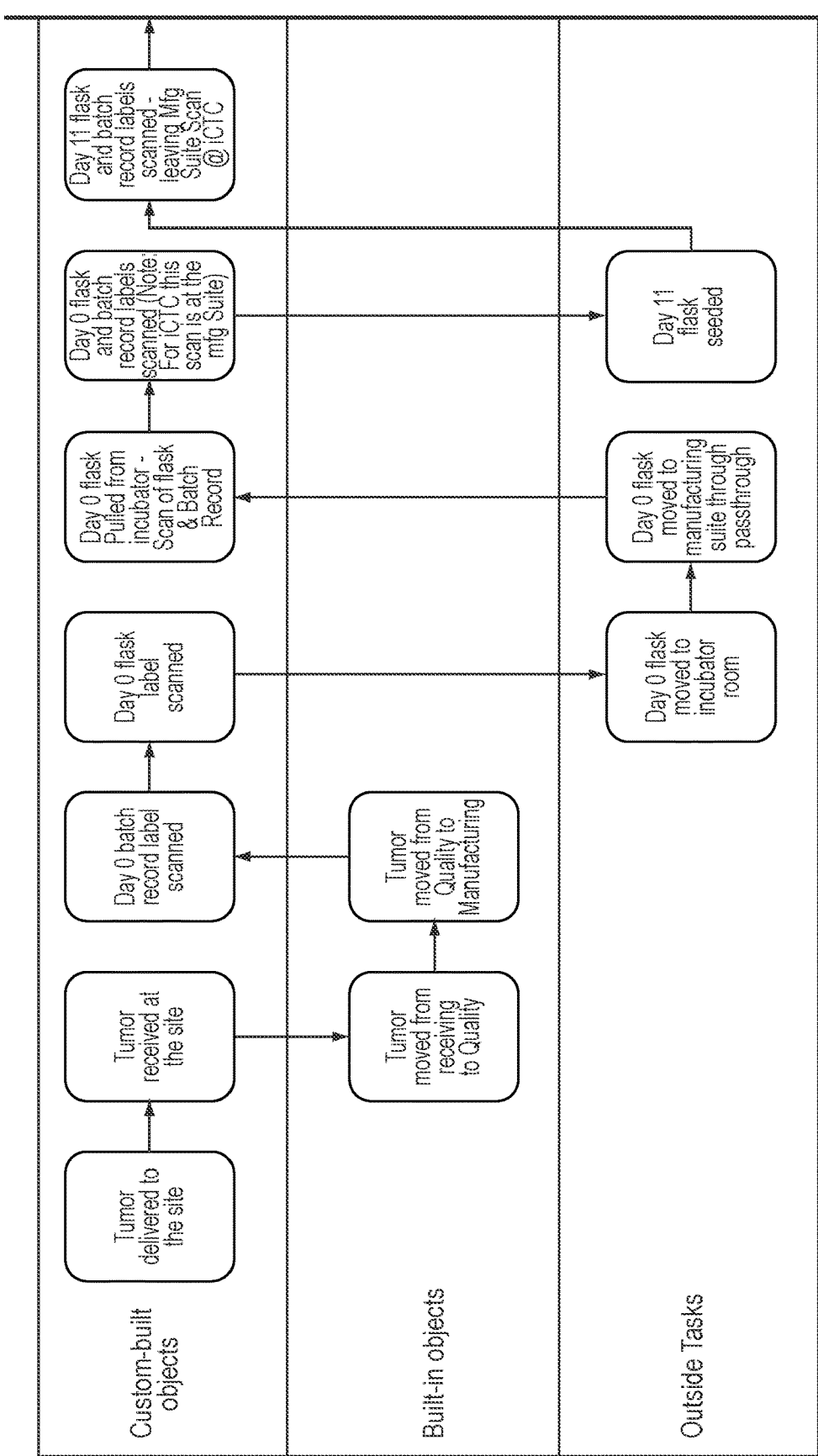
FIGS. 3C-3E schematically illustrate the tracking on biological material through the manufacturing process at a manufacturing facility in accordance with some embodiments.
Figure 3D:
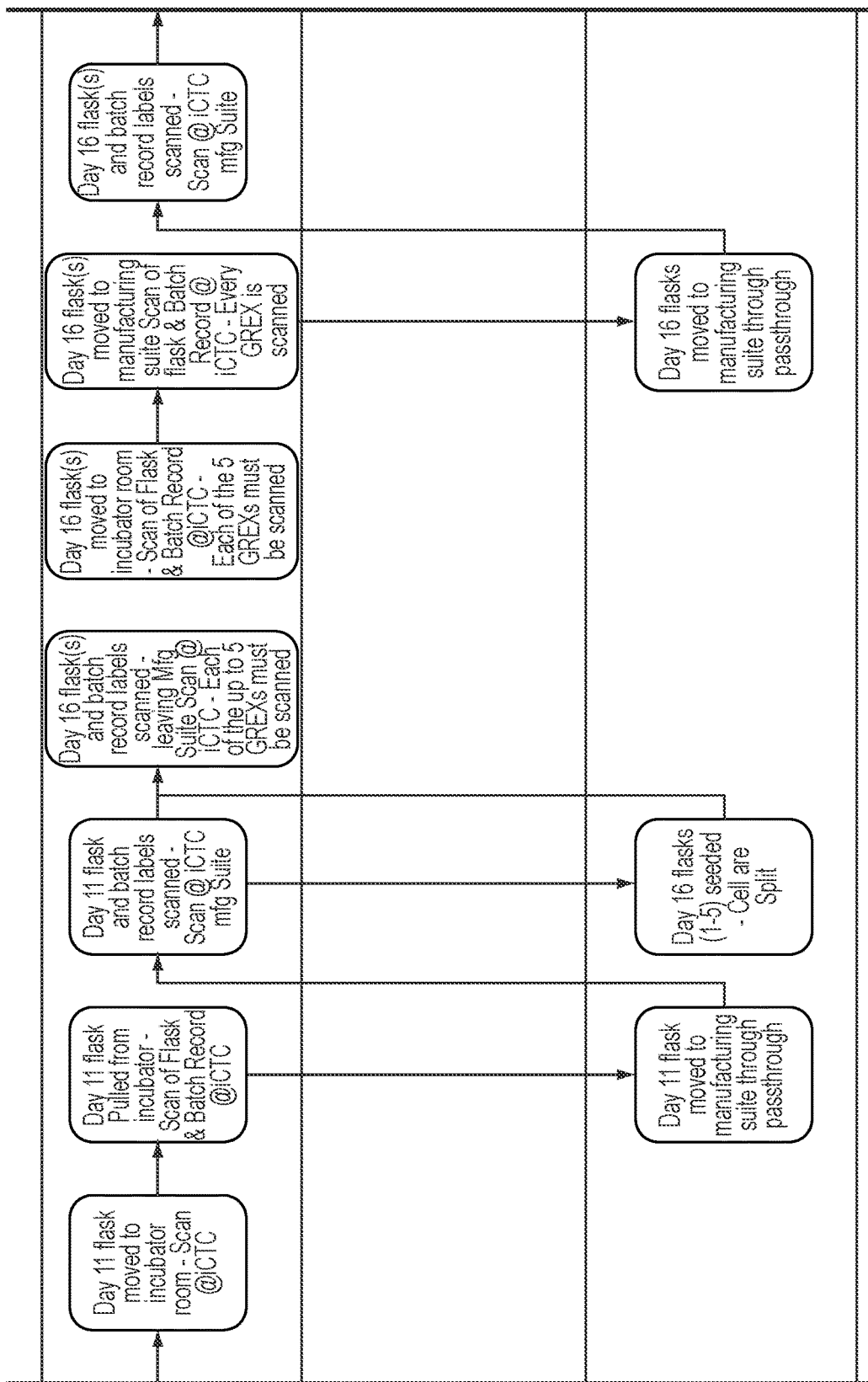
Figure 3E:
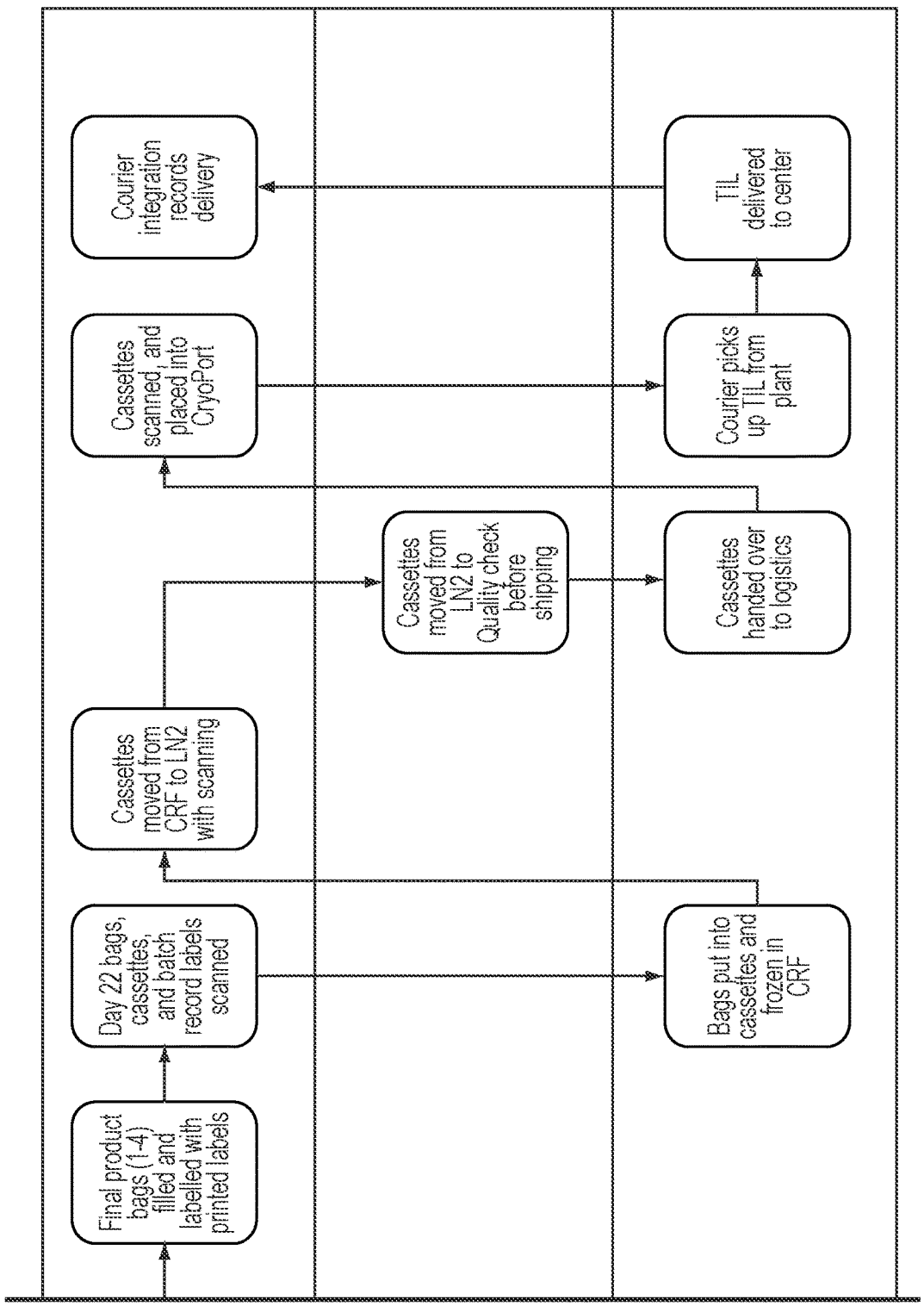

B. Interaction Between Custom-Built and Built-in Objects for Maintaining COC and COI FIGS. 3C-3E schematically illustrate the tracking on biological material through the manufacturing process at a manufacturing facility in accordance with some embodiments of the present disclosure. In some embodiments, initially, when the tumor sample obtained from the patient at the clinical facility is delivered to the manufacturing facility, the shipping label is scanned and the information obtained from the scan is associated with corresponding computer-based objects on the system. The information may include, but is not limited to, cell order identifier, patient-specific identifier, time of tumor resection, processes used for tumor resection, processes used for storing the tumor following resection, and expected processes to be used for expanding the cell therapy product from the tumor. Once patient-related information obtained from the scan is verified with the cell order request that is separately received at the manufacturing facility (e.g., via the manufacturing portal 140), the tumor is indicated in the system as received at the manufacturing facility, and the chain of custody passes to the manufacturing facility. Details about how the chain of custody and chain of identity are maintained through the manufacturing process are described elsewhere herein.

The tumor is then moved for checking quality. During the quality check, the tumor-related information received from the scan is further verified to ensure that the tumor sample meets the requisite quality criteria. The information verified in this process includes, for example, information relating to the processes used for tumor resection and the processes used for storing and shipping the tumor following resection. The information relating to the processes used for tumor resection may include, for example, various fields processed from a tumor procurement form which is further described in detail elsewhere herein. Once the tumor is deemed to meet the quality criteria, the corresponding label is scanned and the corresponding objects are updated. The updated information included in the objects is accessible throughout the system including, for example, at the hospital facility as well as the logistics provider (also referred to herein as the courier facility). In some embodiments, various processes associated with the hospital facility and the courier facility are updated based on the updated objects.

The tumor is then moved to manufacturing. A day zero batch record label is then scanned to verify that the appropriate tumor sample is being moved manufacturing is to be processed by the appropriate manufacturing processes. The tumor is then moved to the appropriate flask (which includes the media and reagents for the expansion process by which the tumor for the patient is to be processed), and the label of the flask is scanned. The corresponding objects are updated using the information obtained from the scans with appropriate time stamps.

The day zero flask is then manually moved to the incubator room from where it is moved to the manufacturing room. In the manufacturing room, the flask label is again scanned and the information contained therein recorded. The information from the flask label is also used ensure that the appropriate manufacturing processes are followed.

After a first requisite amount of time (e.g., 11 days shown in FIG. 3C) based on the particular manufacturing process being followed, the flask is seeded. During the seeding process, the flask may be required to be removed from the manufacturing room. In such instances, the flask label is scanned, and batch record is updated before and after the flask leaves the manufacturing room. The information from the before and after scans is matched before further processes is performed.

Following the seeding process, the flask is reintroduced into the manufacturing room. The flask label is scanned before and after reintroducing into the manufacturing room following the seeding process and the batch records are updated. The information from the before and after scans is matched to verify that the correct flask is being used and the appropriate subsequent processes are used for further processing the cell therapy product.

After a second requisite amount of time (e.g., at day 16 shown in FIG. 3C), the cells from the seeded flask are split into a plurality of bags (e.g., 5 bags shown in FIG. 3C). Labels for each of the bags are scanned before and after reintroducing into the manufacturing room and the batch records and corresponding objects are appropriately updated. The information from the before and after scans is used to verify that the cells from the flask are split in accordance with the cell order request, and that the bags are further processed using the appropriate manufacturing processes.

In some embodiments, a quality assay is performed at the first and second requite times to ensure that the manufacturing process is proceeding in accordance with the cell order request and following a predetermined schedule. In such embodiments, the results of the quality control assay may also be included in the scanned information. Upon obtaining such information from corresponding scans, if it is determined that the quality of the cell therapy product obtained at the corresponding time point does not meet certain quality criteria, the batch record and corresponding objects are updated accordingly. If necessary, the schedule of the manufacturing process is also updated. In some embodiments, the updated schedule may be communicated to the hospital facility as well as the courier so that the schedules for corresponding processes to be performed at the hospital facility and by the courier are suitable updated. The details of when and how the schedule of the manufacturing is updated are described elsewhere herein.

The manufacturing process is then continued (either as scheduled, or with a suitably modified schedule and/or intermediate steps) in the plurality of bags to a predetermined end point. In some embodiments, cells from one of the plurality of bags are used for performing quality assays on the final expanded cell therapy product. The bag selected from the quality assay as well as the bags containing cells to be released as the final product are then labeled, and the labels scanned for updating the batch records and the corresponding objects.

The bags to be released as the final product are then input into cassettes and frozen for transportation to the hospital facility. The labels for cassettes are scanned and the batch records updated along with the corresponding objects. The label for the bag to be used for performing quality control assays is then scanned, the batch record and the corresponding objects updated, and the bag is moved to quality control station. Upon obtaining the results of the quality control assay, the results are scanned and the batch records and corresponding objects are updated.

In some embodiments, the bags to be released as the final product may be released to the courier (and ultimately to the hospital facility) with a caveat that the product in the bags has not yet been approved for use in therapy with the patient because the results of the quality assays are not yet available. In such embodiments, the corresponding objects are updated in real-time when the results of the quality assay are obtained, thereby reducing the time for delivery of the final cell therapy product to the patient.

Once the results of quality assay indicate that the final cell therapy product is approved for therapeutic use with the patient, the cassettes are scanned and the batch records and corresponding objects are updated. The cassettes are then prepared processed for transportation, handed over to the logistics provider (i.e., the courier), and the scanned, indicating that the chain of custody has passed to the courier.

The courier then transports the final cell therapy product to the hospital facility where the labels are scanned again to indicate that the chain of custody has passed to the hospital facility. The batch records and corresponding objects are updated so that the manufacturing facility and the courier are notified that the final cell therapy product has been delivered to the hospital facility.

Figure 3F:
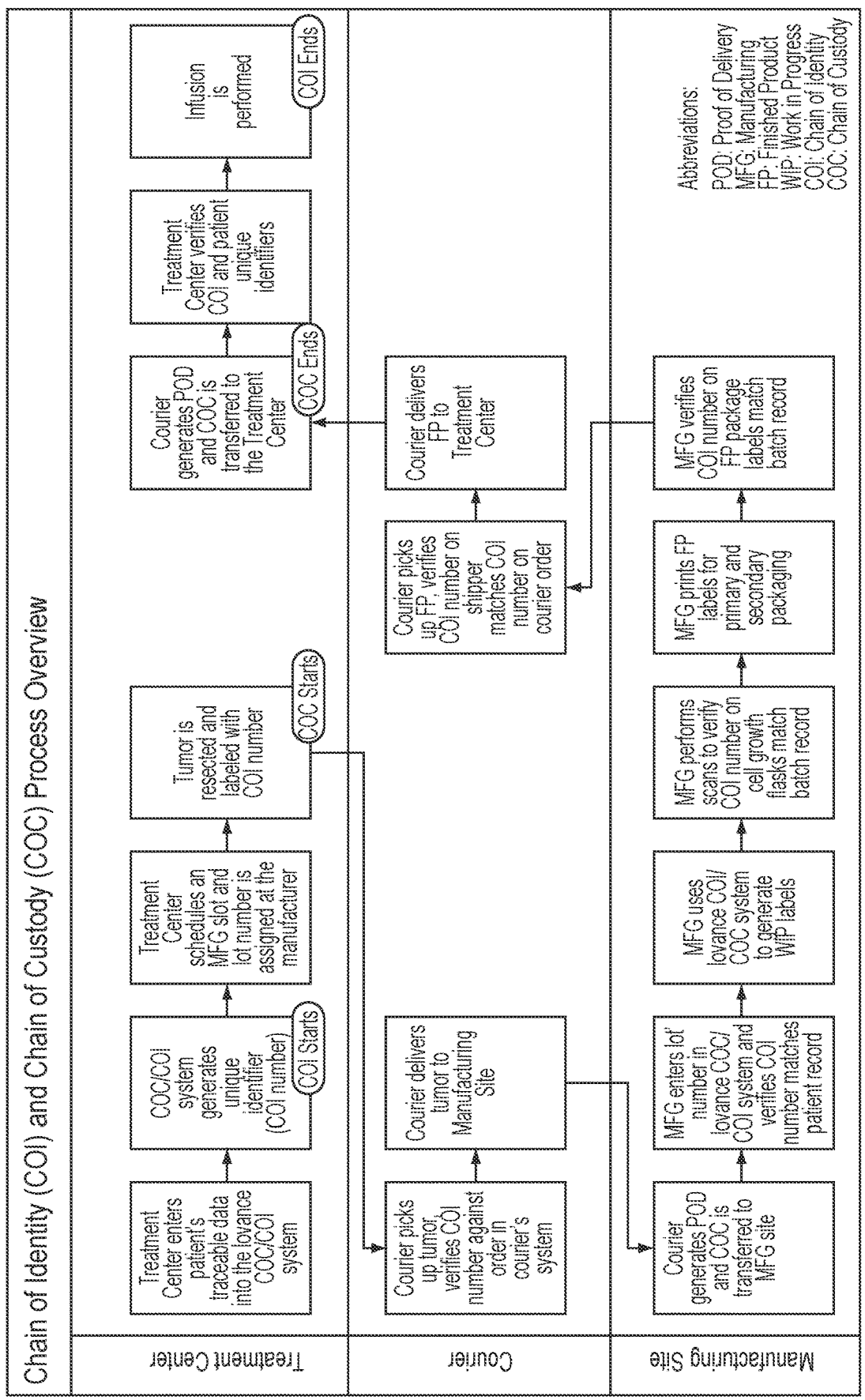
FIG. 3F schematically illustrates the process for maintaining COC and COI through the journey of the cell therapy product from obtaining the solid tumor through the manufacturing process to infusion into the patient in accordance with some embodiments of the manufacturing process (e.g., a GEN 3 process).

C. Labeling of Cell Therapy Product During Manufacturing Process and Maintenance of Chain of Custody and Chain of Identity FIG. 3F schematically illustrates the process for maintaining COC and COI through the journey of the cell therapy product from obtaining the solid tumor through the manufacturing process to infusion into the patient in accordance with some embodiments of the manufacturing process (e.g., a GEN 2 process, or a GEN 3 process). In some embodiments, initially, the hospital-side interface 110 receives information about the patient from an employee (e.g., registered nurse) at a hospital connected with the hospital-side interface 110. Information about the patient may include information about health insurance, personal identifying information, health-related information, patient enrollment information (e.g., consent forms) or any other information pertinent to the patient that may be helpful in identifying and caring for the patient.

After the employee, e.g., a clinician, of the hospital has determined a patient to be a candidate, for example, for a TIL infusion therapy, the patient may provide consent to proceed with the TIL infusion therapy through a computer connected to the hospital-side interface 110.

The employee of the hospital may then order TIL infusion therapy for the patient via the events scheduler 120. A billing department employee of the hospital may then place a purchase order for the TIL infusion therapy for the patient via the logistics interface 130. The TIL infusion therapy order and purchase order may be transmitted to the hospital-side interface 110. The hospital-side interface 110, may confirm receiving the order and purchase order as well as confirming patient enrollment and consent is complete before issuing a cell order request to the events scheduler 120. Likewise, the hospital-side interface may communicate with the insurance provider to notify that various patient treatment events have been scheduled and may also provide the schedule of the patient treatment events to the insurance provider for processing the payment.

A patient-specific identifier may then be associated with the cell order request and attached to the biological material associated with the patient at every processing and/or shipping step to enable uninterrupted chain-of-custody and chain-of-identity tracking of the biological material as detailed further herein. The patient-specific identifier may also be associated with the patient as well as the treatment equipment used for administering the different patient treatment processes so as to keep track of the patient through the entire treatment regimen.

The patient-specific identifier may also be communicated to an insurance provider through the hospital-side interface 110 so as to enable processing of payment following various patient treatment events. The patient-specific identifier may be further communicated to the courier through the courier portal 130 to enable the courier to verify the identity of the patient associated with the biological material being transported.

In various embodiments disclosed herein, any communication between the scheduling module 125 and the hospital-side interface 110, the manufacturing portal 140 or the logistics interface 130 relating to the schedule of manufacturing events and/or patient treatment events (whether changed or not) is accompanied with the patient-specific identifier associated with the cell order request being processed and scheduled. Such communication including the patient-specific identifier enables the hospital-side interface 110, the manufacturing portal 140 and the logistics interface 130 to accurately process, track and identify the biological material, thereby avoiding misidentification of the biological material or patient, and improving patient safety.

Additionally, as explained in detail herein, the patient-specific identifier is used for generating labels for the containers used during the expansion process for enabling maintenance of COC/COI through the expansion process and enabling a post-facto audit for compliance with regulatory requirements.

Figure 3G:
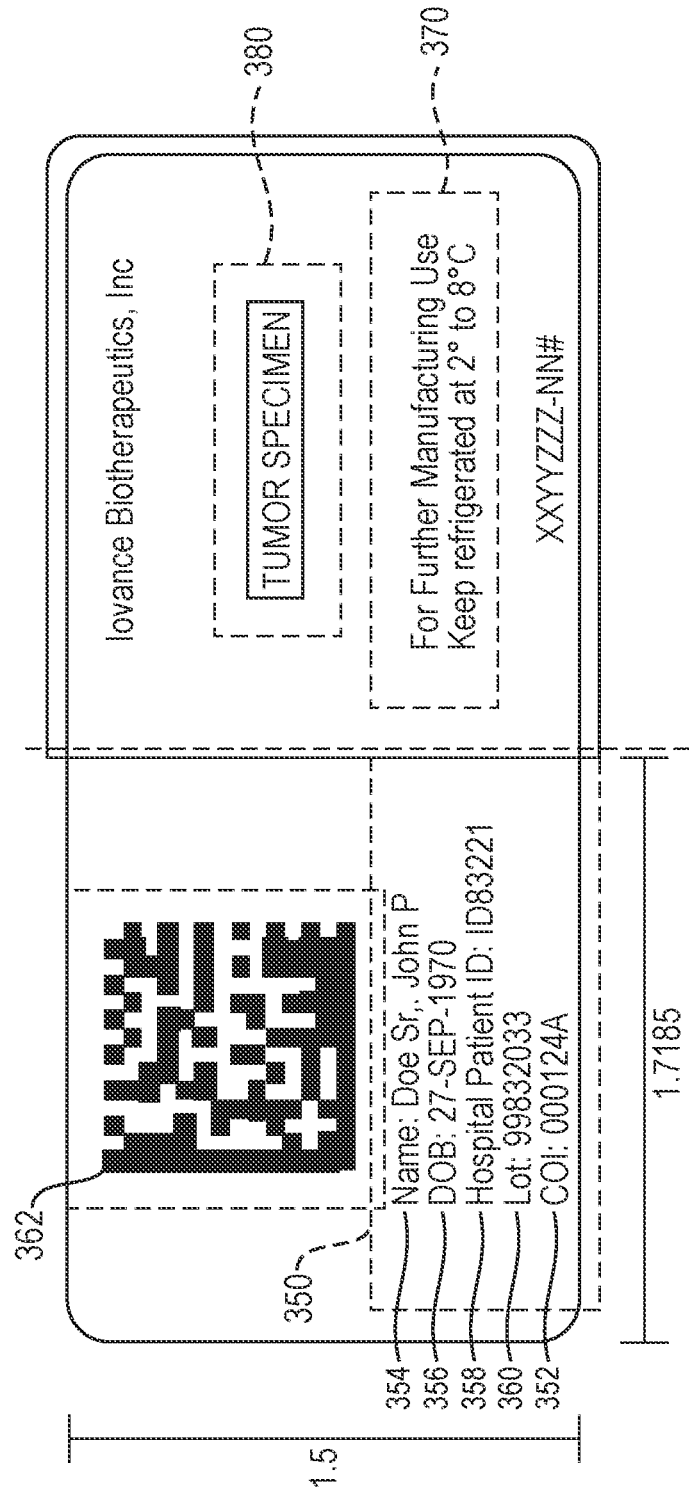
FIG. 3G is a representative image of a label for a cell therapy product in accordance with some embodiments.

In some embodiments, the patient-specific identifier may be included in the cell order identifier structured to also be used for tracking a chain of identity/chain of custody as well as for tracking event history. In some embodiments, the cell order identifier, in addition to the patient-specific identifier, may include several indicia or fields, each corresponding to the biological material from the patient having undergone a processing step. FIG. 3G is a representative image of a label for a cell therapy product in accordance with some embodiments. In some embodiments, the label includes a cell order identifier 350, a 2D code (e.g., a QR code) 362, a reason field 370 and a product field 380. The cell order identifier 350 may include various fields such as, for example, patient name 354, patient-specific identifier 352, patient's date of birth (e.g., for additional verification) 356, a hospital-associated patient identifier 358, and a manufacturing lot number 360.

Thus, the label enables maintenance of COI/COC and also enables tracking of materials from tumor resection at the clinical treatment center, shipment of tumor material to the manufacturing facility, manufacturing including testing of all in-process and finished product samples, shipment of drug product to the clinical treatment center, and infusion of the drug product.

In some embodiments, different labels may be generated at different time points during the journey of the cell therapy product from obtaining the solid tumor through the manufacturing process to infusion into the patient, such as those illustrated in FIG. 3H. The labels generated at different time points may include additional or different information that that included in the label illustrated in FIG. 3G. For example, in some embodiments, the labels generated during the cell expansion process, that are e.g., affixed to the containers used during the cell expansion process, may include a field corresponding to various time points and a result of a determination, made at the respective time point, of whether the acceptance parameters for the expansion cell therapy product meet certain acceptance criteria.

Thus, at any stage in the process, the label provides information about the patient (via the patient-specific identifier) thereby enabling the maintenance of chain of identity and chain of custody. The label may also provide information about the various processing steps the associated biological material has undergone, providing a record of the chain of custody as well as the event history, e.g., for audit purposes.

The system 300 may thus be configured to maintain COI and COC throughout the cell therapy product manufacturing process and supply chain. Additionally, the system 300 may be configured to include safeguards to meet 21 CFR Part 11, HIPAA (Health Insurance Portability and Accountability Act), and GDPR (General Data Protection Regulation) regulations and to ensure that the data is secured and protected.

To limit and restrict access to sensitive data, the system 300 implements users-based roles and access in some embodiments. In some embodiments, a time-stamp may be included on the label at the time of its generation.

In some embodiments, the cell order identifier being tracked through the tracking module may further include indicia or fields associated with, e.g., various shipping/transportation events, various manufacturing process events, and/or various steps in the treatment regimen. These indicia or fields may not be printed on a label, but generated or appended by the tracking module for tracking of the biological material associated with the patient as well as for tracking the progress of the therapy. In such embodiments, a time-stamp indicating a time of completion of a certain step may be associated or appended with the cell order identifier at every step where a given index or field is changed or updated. It will be appreciated that information included in such updated cell order identifier may also be used for dynamically rescheduling patient treatment events as discussed in detail elsewhere herein.

1. Labeling of Cell Therapy Product During Manufacturing Process

Referring back to FIG. 3F, in some embodiments, the cell order identifier is printed on readable labels and associated with barcodes or QR codes (or 2D codes), to allow adequate verification of identify from tumor resection to infusion of the autologous drug product. The label may be affixed to objects associated with the biological material as well as the treatment regimen. For example, the label including the patient-specific identifier may be affixed to a container carrying the resected tumor from the hospital or clinical facility to the TIL manufacturing facility, the TIL manufacturing equipment and containers during various steps of manufacturing, a shipping container for shipping the expanded TILs back to the hospital or clinical facility, equipment associated with various treatment events, or any combination thereof.

For example, in some implementations, a patient may enter the system via the patient access module 116 of the hospital-side interface 110 and is enrolled. Upon enrollment and capture within the system of the traceable patient information, a patient-specific identifier (COI number) may be assigned to the patient by the system. The assignment of the patient-specific identifier enables the scheduling of a resection date and a manufacturing slot.

Scheduling of the manufacturing slot within the system triggers generation of a cell order and assignment of a lot number at the manufacturing site.

Prior to tumor resection, the clinical facility may access the system, confirm the correct patient identification, and generate a tumor bottle label and a tumor shipper label. The label may include the patient-specific identifier in addition to the cell order identifier. In some embodiments, the patient-specific identifier may be a field within the cell order identifier Following tumor resection chain of custody is initiated at the tracking module 112. The labeled tumor bottle may then be placed in a shipper and handed off to the courier for transport to the manufacturing site. Chain of custody continues as the courier verifies the cell order number on the shipper label matches the cell order number on the shipping order in the courier's system which is integrated into the system 300, thereby providing real time tracking of the tumor between the treatment center and the manufacturing site.

Upon delivery of the tumor to the manufacturing site and a proof of delivery may be generated within the system. Upon receipt of the tumor, manufacturing personnel enter the manufacturing lot number into system at the manufacturing module 140 via the COC/COI module 144. Pulling up the patient record (made available via the manufacturing coordination module 118), the tumor bottle label is scanned into the system to verify that the patient-specific identifier is associated with the manufacturing lot number. Upon verification, COC passes to the manufacturing site.

Personnel at the manufacturing facility may enter the system, wherein the labeling module 142 enables generation of work in process (WIP) labels that contain the cell order request. In order to facilitate audit of records post-facto, the WIP labels may affixed to the batch record and cell growth flask. FIG. 3G is a representative image of a WIP label in accordance with an embodiment. FIG. 3H shows the different WIP types of labels and the information included in each type of label in accordance with an embodiment.

Manufacturing personnel may then scan the labels at key transition points during the manufacturing process to verify the cell order identifier number on the cell growth flask matches the batch record, ensuring COI is maintained throughout the manufacturing process.

Figure 3I:
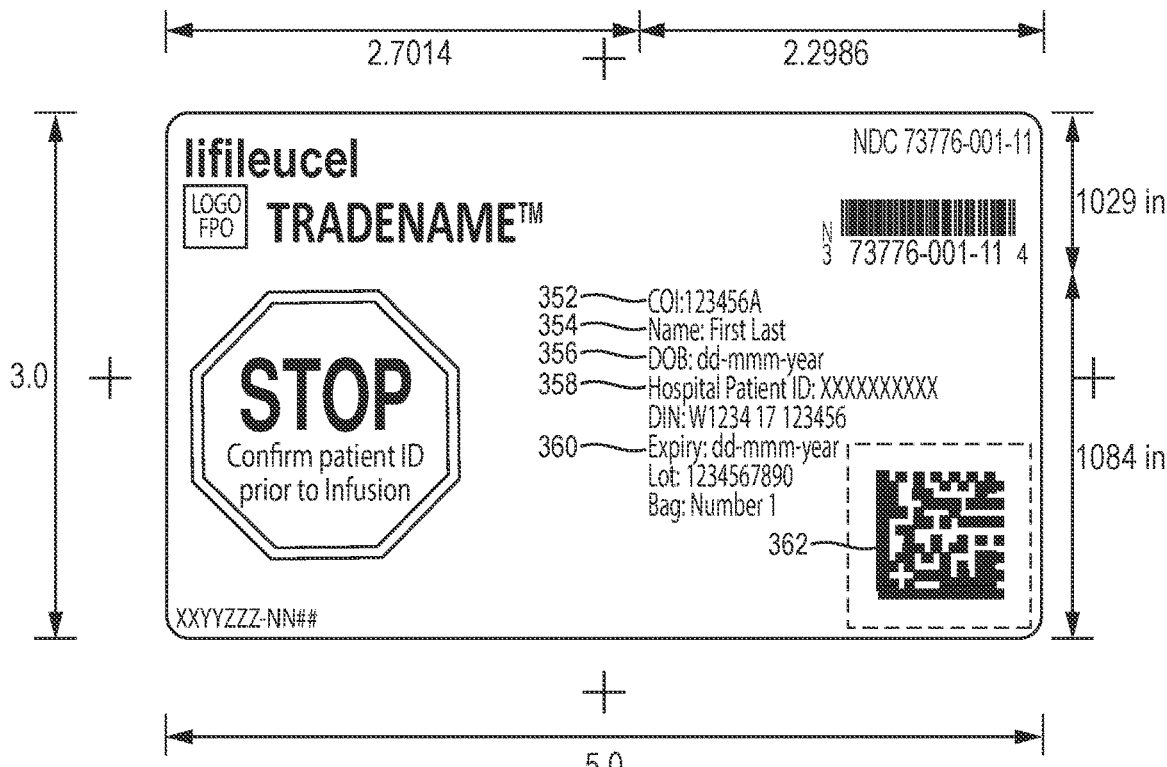
FIGS. 3I and 3J are representative images of a label for a finished product in accordance with some embodiments.
Figure 3J:
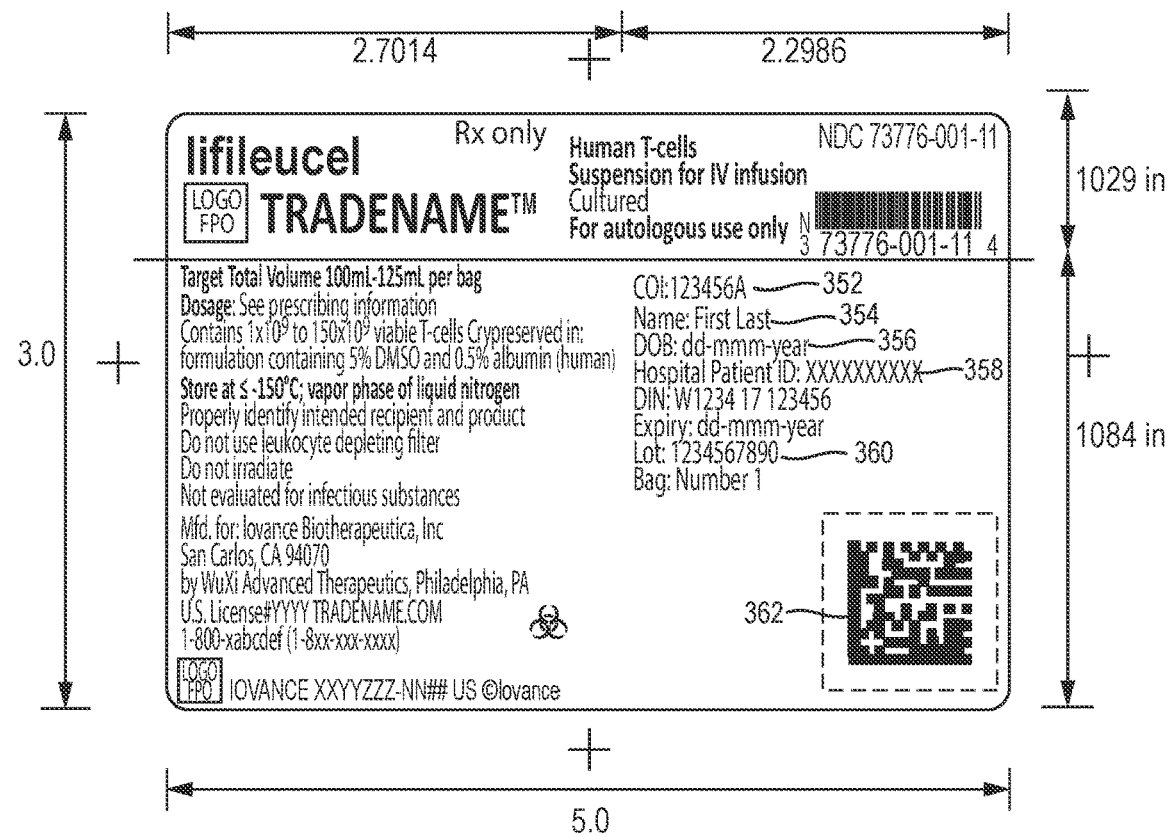

Additionally, each Quality Control (QC) sample will have its own label with the COI number to assure that the results generated are then linked to the corresponding batch record. Upon completion of the manufacturing process, the labeling module 142 may generate finished product labels. FIGS. 3I and 3J are examples of a finished product label.

As seen in FIGS. 3I-3J, these finished product labels contain unique patient identification including name 354, date of birth (DOB) 356, and the patient-specific identifier 352. Finished product labels are affixed to the final product and both batch record and labels are scanned to ensure COI and complete chain of custody within the manufacturing facility.

The finished product is placed in the shipper with the same cell order identifier including a matching patient-specific identifier, verified and transferred to the courier for delivery to the treatment center for infusion. The courier may then verifies that the cell order identifier and the patient-specific identifier on the shipping container matches the cell order and patient information in the courier's system received through the logistics interface 130, thereby providing near real time tracking of each drug product lot between the manufacturing site and the treatment center. At this time, COC is transferred from the manufacturing site to the courier.

The courier delivers the finished product to the treatment center for infusion into the patient. The courier may initiate proof of delivery (POD) through the logistics interface 130, and COC is passed from the courier to the treatment center. COI ends with infusion of the product to the patient at the treatment center.

As discussed herein, communicating the patient-specific identifier between the hospital-side interface 110, the events scheduler 120, the manufacturing portal 140 and the logistics interface 130 after each processing step ensures that all involved parties (e.g., the clinical facility, the manufacturing facility and the logistics provider) receive a record of the chain of custody as well as chain of identify of the biological material, and also receive a record of the various process steps the biological material has undergone.

The patient-specific identifier and the cell order request provided to the solid tumor via a label thus, enable tracking of the shipment so as to maintain chain of custody and chain of identification that is necessary for patient safety as well as for regulatory compliance (e.g., FDA audits).

2. Label Reconciliation in Case of Changes to Manufacturing Process

Once the solid tumor is received at the manufacturing facility, manufacturing of the cell therapy product is initiated in accordance with the cell order request. For example, at least a portion of the solid tumor may be used for manufacturing the cell therapy product using a cell expansion technique.

In some embodiments, a computer subsystem associated with the manufacturing facility, e.g., the labeling module 142, may cause a second label to be printed to be associated with the portion of the solid tumor being used for cell expansion. The second label may include the patient-specific identifier and the cell request identifier. The second label further enables the tracking of the cell therapy product for maintaining the chain of custody and chain of identification.

Subsequently, during the manufacturing of the cell therapy product acceptance parameters of for the manufactured cell therapy product at various time points are determined. The acceptance parameters are then compared, at the acceptance determining module 123, to determine whether the acceptance parameters determined at a particular time point meet acceptance criteria at the corresponding time point. The acceptance parameters may be determined by any suitable method or process disclosed herein. Additionally, the acceptance criteria may be any acceptance criteria disclosed herein.

In some embodiments, the result of the determination of the acceptance parameters and whether the acceptance parameters meet the acceptance criteria may be appended to the cell order identifier as disclosed elsewhere herein. In some embodiments, a third label may be generated based on the result of the determination of whether the acceptance parameters meet (or do not meet) the acceptance criteria.

For example, if the acceptance parameters at a second time point do not meet the acceptance criteria at the second time point, the third label is generated for the container used during the manufacturing process to include a "reason code" to convey the information that the acceptance parameters at the second time point do not meet the acceptance criteria at the second time point and why the acceptance criteria at the second time point are not met.

Further, if it is determined that the cell therapy product obtained at the second time point may be reprocessed from a first time point preceding the second time point to appropriately obtain a cell therapy product that meets the acceptance criteria at the second time point, the third label may include information such as, for example, a new or updated cell request identifier as disclosed elsewhere herein. In such instances, the third label may additionally include a "reason code" to convey the information relating to why the acceptance criteria at the second time point and why it was appropriate to reprocess the cell therapy product from the first time point.

Next, based on whether the acceptance criteria at one or more time points are met, as determined at the acceptance determination module 123, the manufacturing schedule for manufacturing of the cell therapy product is suitably modified to generate an updated manufacturing schedule as discussed elsewhere herein. In addition, the availability of manufacturing slots at the manufacturing facility is also suitably modified to reflect the changes, if any, in the current schedule of manufacturing of the cell therapy product. The changed or updated availability of manufacturing slots at that manufacturing facility may then be communicated to the computing device. Further, the preliminary schedule of patient treatment events may also be modified based on updated manufacturing schedule, and an updated schedule of patient treatment events may be communicated to the computing device.

The manufacturing of the cell therapy product is then completed in accordance with the updated manufacturing schedule.

In some embodiments, a manufacturing label corresponding to each of the plurality of time points at which the acceptance parameters are determined is generated. The manufacturing label at each time point may include updated information associated with quality of manufactured cell therapy product. The updated information may include the acceptance parameters at the corresponding time point and/or whether the acceptance parameters meet the acceptance criteria at that time point.

In addition, in some embodiments, a controller controlling the manufacturing process may be configured to read an updated manufacturing label and determine the subsequent processing step. For example, if an updated manufacturing label following QA test at a second time point indicates that the cell therapy product does not meet certain acceptance criteria, but the cell therapy product may be reprocessed from the first time point, the controller may cause suitable changes in the manufacturing process. In addition, suitable changes to the manufacturing schedule, the availability of manufacturing slots and the schedule of patient treatment events are also made based on the information on the updated label. Those of skill in the art will appreciate that the updated manufacturing label may include the cell order identifier and the patient-specific identifier in addition to the information relating to the quality of the manufactured cell therapy product and the reason code to facilitate chain of identification and chain of custody.

Those of skill in the art will further appreciate that the information relating to the changes to the manufacturing schedule, the availability of manufacturing slots and the schedule of patient treatment events, as obtained from reading the updated manufacturing labels may be communicated to the hospital-side interface and the logistics interface to enable corresponding computing devices to make corresponding changes to respective schedules associated with those entities.

Figure 4A:
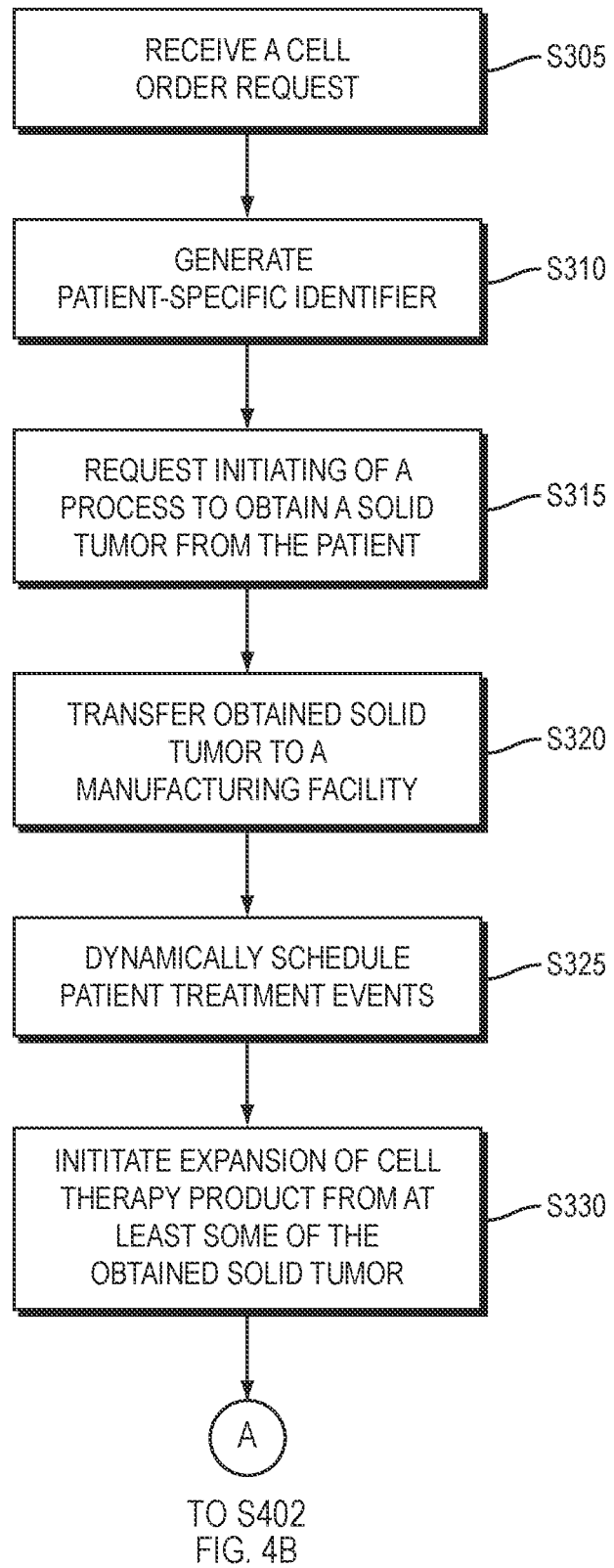
FIGS. 4A and 4B show a flow chart for determination of a schedule for patient treatment events based on success of the TIL manufacturing process.
Figure 4B:
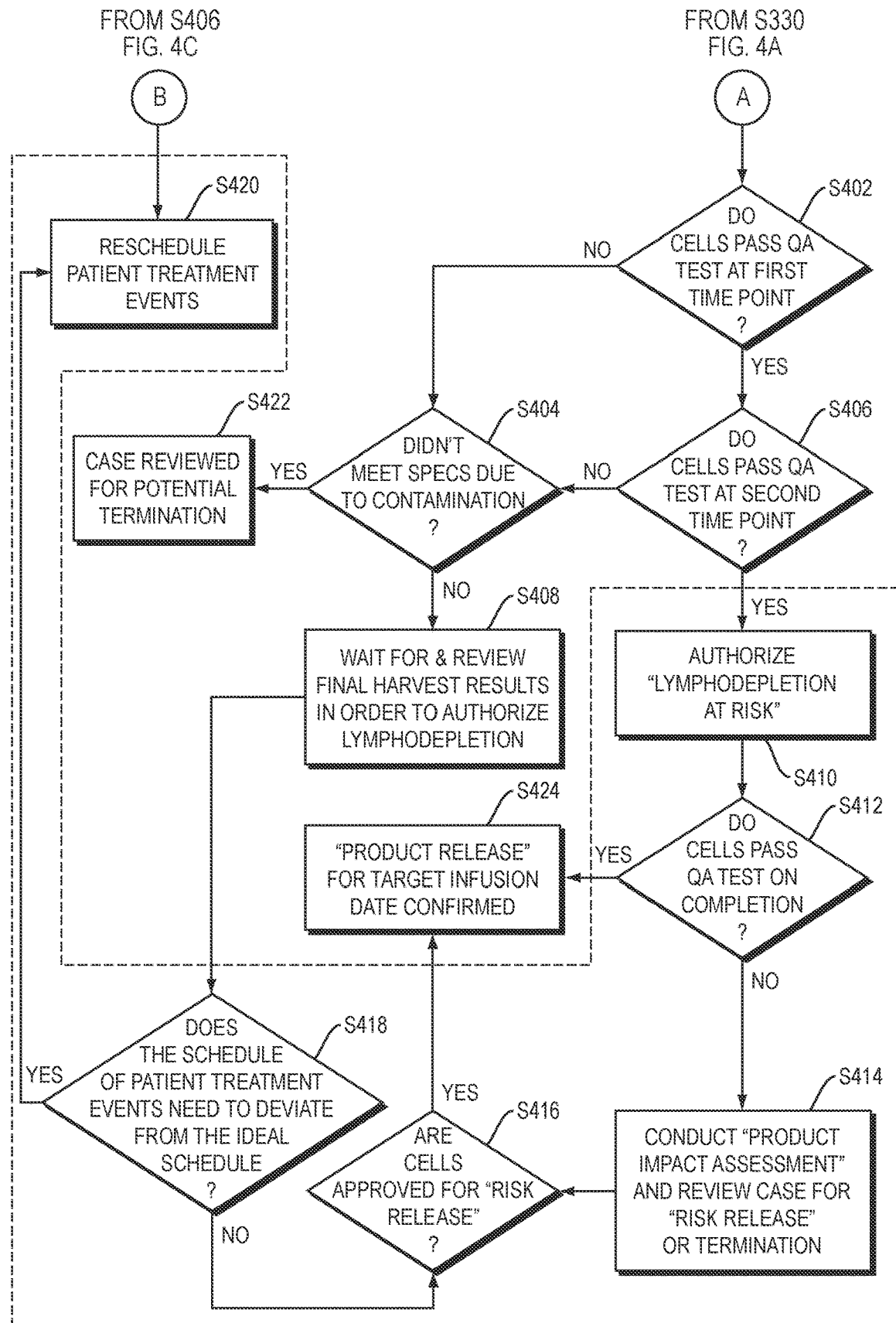

D. Coordinating Manufacturing of Cell Therapy Product with Patient Treatment Events FIGS. 4A and 4B show a flow chart for a method for coordinating the manufacturing of TILs for a patient in accordance with an embodiment of the present disclosure. In some embodiments, the method illustrated in FIGS. 4A and 4B is implemented on a system as a whole depicted in FIG. 3A, while in some embodiments, the method illustrated in FIGS. 4A and 4B is implemented by portions of the system depicted in FIG. 3A. In some embodiments, the events scheduler 120 receives, e.g., at S305, the cell order request to expand the cell therapy product, e.g., T-cells, for the patient from the hospital-side interface 110, and the patient-specific identifier associated with the cell order request.

In some embodiments, the patient-specific identifier or alternately a cell order identifier is generated by the events scheduler 120, e.g., at S310, rather than the tracking module 112.

The cell order request may include information such as, for example, patient identifying information, target dates for various patient treatment events, and/or target parameters for the final expanded TIL manufacturing product. Once the cell order request is received, the events scheduler 120 may transmit a confirmation to the hospital-side interface 110 indicating that the cell order request corresponding to the patient-specific identifier has been received. In embodiments where the patient-specific identifier is generated by the events scheduler 120, the events scheduler 120 may transmit the confirmation indicating that the cell order request for the patient has been received and provide the patient-specific identifier or the cell order identifier to the hospital-side interface 110. In addition, the events scheduler 120 may transmit a target schedule of patient treatment events based on the received cell order request.

In addition, the events scheduler 120 may transmit an initiation request including the patient specific identifier, e.g., at S315, to the hospital-side interface 110, e.g., to a clinical facility, to perform a procedure on the patient to obtain a solid tumor from the patient and schedule a courier pick-up time to transfer the obtained solid tumor to the manufacturing facility. As discussed herein, the procedure may include, but is not limited to, tumor biopsy for extracting a portion of a tumor from the patient. In some embodiments, the events scheduler 120 may receive a procedure date from the employee using the hospital-side interface 110. In response, the events scheduler 120 may prompt the employee to order supplies (e.g., tumor resection kit, tumor shipping container or cryo-shipping container) as needed and associate them with the patient-specific identifier.

After the procedure to obtain the solid tumor is performed and the solid tumor is shipped, e.g., at S320, and once the obtained solid tumor are received at the manufacturing facility, the scheduling module 125 dynamically schedules, e.g., at S325, various manufacturing events as well as various patient treatment events and associates each event with the patient-specific identifier. In some embodiments, the scheduling module 125 determines the schedule for manufacturing events and patient treatment events before receiving the obtained solid tumor such as, for example, upon receiving information about a scheduling of the procedure to obtain the solid tumor from the patient from the hospital-side interface 110, and associates each event with the patient-specific identifier.

The schedule for various manufacturing events is associated with the patient-specific identifier and may include corresponding target dates at which various manufacturing steps (e.g., steps A-F shown in FIG. 2A, 2B or 2C and/or FIG. 9) are performed as well as a corresponding target date for the completion of the TIL manufacturing process. As discussed herein, the target dates for various manufacturing steps may depend on factors such as the size of the tumor received, cell counts before initiating a given step, numerical folds at the end of a given step, number of days needed to achieve a certain numerical fold during a given step, and/or other factors.

The schedule for the various patient treatment events may include target dates for various patient treatment events associated with the patient-specific identifier such as, for example, target TIL infusion date, a lymphodepletion date, an inpatient stay duration, a schedule for IL-2 infusion regimen, and/or other similar treatment related dates. As discussed herein, the schedule for the patient treatment events is dependent on the schedule for the manufacturing events, and in particular on the TIL manufacturing completion date. The schedule for the various patient treatment events may be transmitted to the hospital-side interface 110 along with the patient-specific identifier in some embodiments.

The scheduling module 125 is configured to dynamically change the schedule for manufacturing events as well as the schedule for patient treatment events based on the progress and success of different manufacturing steps. For example, depending on whether the acceptance parameters associated with the expansion cell therapy product at different steps meet certain acceptance criteria, the dates at which subsequent manufacturing steps are initiated need to be changed, which, in turn, changes the target completion date, and as a consequence, the dates for the patient treatment events need to be changed using, for example, the methods depicted in FIG. 4B or 4C.

The acceptance determining module 123 determines whether the acceptance parameters associated with the expansion cell therapy product meet certain acceptance criteria. The acceptance parameters include, but are not limited to, cell count, cell viability, sterility, *mycoplasma* count, CD3 count, CD5 count, interferon γ (INF-γ) production, result of an endotoxin assay, result of a Gram stain assay, etc. Some or all of these acceptance parameters may need to meet acceptance criteria depending on the step at which the acceptance parameters are measured. For example, at the end of first priming expansion (also referred to herein as the first time point), e.g., at 11 days from initiation of the expansion, the acceptance criteria may be that the cell count should be at least $5 \times 10^6$ viable cells. The acceptance criteria at different steps also depend on the process (e.g., Gen 2, Gen 3, Gen 3.1, etc.) being used to perform the expansion.

Thus, the acceptance determining module 123 may determine whether the acceptance parameters meet certain acceptance criteria at more than one different time points following the initiation of expansion depending on the process being used to perform the expansion. In other words, the acceptance determining module 123 performs a quality test, also referred to herein as a QA test, at each of different specified time points to determine the next course of action, and the scheduling module 125 dynamically schedules subsequent manufacturing steps and patient treatment events based on the results of the QA tests obtained from the acceptance determining module 123.

One example of acceptance parameters and acceptance criteria for final product testing for Gen 2, Gen 2 like and Gen 3 process is provided in Table B.

TABLE B

Release Testing

| Test Type (Acceptance Parameter) | Method | Acceptance Criteria |
| --- | --- | --- |
| Cell viability | Fluorescence | ≥70% |
| Total Viable Cell Count | Fluorescence | 1e9 to 150e9 |

TABLE B-continued

Release Testing

| Test Type (Acceptance Parameter) | Method | Acceptance Criteria |
| --- | --- | --- |
| Identity (% CD45+/CD3+) | Flow Cytometry | Gen 2-like: ≥90% CD45+CD3+ TIL for all Indications Gen 3: ≥90% CD45+CD3+ TIL for Non-Ovarian ≥85% CD45+CD3+ TIL for Ovarian |
| Interferon-gamma production (Stimulated - Unstimulated) | Stimulation and ELISA | ≥500 pg/mL |

Referring to FIG. 4B, in an embodiment, following the initiation of expansion of the cell therapy product, the acceptance determining module 123 determines, e.g., at S402, whether the expanded cell therapy product at first time point pass a QA test associated with the first time point (e.g., following Step B shown in FIG. 2A and/or FIG. 9). Upon a determination that the cells do not pass the QA test at the first time point, e.g., at S404, the acceptance determining module 123 determines whether the cells did not pass the QA test because of contamination. If the cells did not pass the QA test because of contamination, the case is reviewed for potential termination, e.g., at S422.

On the other hand, if the cells did not pass the QA test because of reasons other than contamination, e.g., because of low cell count or low viability, the scheduling module 125 may extend the ongoing step for a time depending on the reasons due to which the cells did not pass the QA test, and review the results from the final harvest, e.g., at S408. In some embodiments, all subsequent manufacturing steps and patient treatment events may be rescheduled as a consequence of extending the ongoing step for a time.

Alternately, the scheduling module 125 may reschedule only the patient treatment events so as to account for a potential delay in completion of the manufacturing process or to account for a potential cryogenic freezing of the manufactured cell therapy product to allow for a time lag between completion of manufacturing and infusion of the cell therapy product. It will be appreciated that in some embodiments, the cell therapy product comprises T-cells of the patient. In some embodiments, the cell therapy product comprises tumor infiltrating lymphocytes (TILs). Thus, the discussion herein may, for the sake of simplicity, refer to the cell therapy product interchangeably as T-cells or TILs.

For example, in some cases, the cell therapy product may pass a final QA test despite not passing the QA test at the first time point. In such cases, it may be prudent to deviate from an ideal schedule for manufacturing events and patient treatment events, and delay lymphodepletion until the final QA test is performed so as to avoid unnecessary patient treatment. Thus, depending on the reasons for which the cells did not pass the QA test at the first time point, it is determined, at S418, whether the schedule of the patient treatment events needs to deviate from the ideal schedule for the patient treatment events. Upon a determination that the schedule of patient treatment events needs to deviate from the ideal schedule, the scheduling module 125 may reschedule (i.e., delay), e.g., at S420, lymphodepletion as well as subsequent patient treatment events, and further optionally schedule a cryogenic freezing step following the completion of manufacturing process.

Referring back to S402, if the cells pass the QA test at the first time point, no changes may be needed to the schedule of the manufacturing process or the patient treatment events. The acceptance determining module 123 then determines, e.g., at S406, whether the expanded T-cells at a second time point pass a QA test associated with the second time point (e.g., following Step C or Step D shown in FIG. 2A and/or FIG. 9).

If the cells do not pass the QA test at the second time point, the acceptance determining module 123 determines, e.g., at S404, whether the cells did not pass the QA test because of contamination. If the cells did not pass the QA test because of contamination, the case is reviewed for potential termination, e.g., at S422.

On the other hand, if the cells did not pass the QA test because of reasons other than contamination, e.g., because of low cell count or low viability, the scheduling module 125 may extend the ongoing step for a time depending on the reasons due to which the cells did not pass the QA test, and review the results from the final harvest, e.g., at S408. In some embodiments, all subsequent manufacturing steps and patient treatment events may be rescheduled as a consequence of extending the ongoing step for a time.

Alternately, the scheduling module 125 reschedule only the patient treatment events so as to account for a potential delay in completion of the manufacturing process or to account for a potential cryogenic freezing of the manufactured TILs to allow for a time lag between completion of manufacturing and infusion of the TILs.

For example, in some cases, the cells may pass a final QA test despite not passing the QA test at the second time point. In such cases, it may be prudent to deviate from an ideal pre-decided schedule (also referred to herein as of the golden path) of patient treatment events and delay lymphodepletion until the final QA test is performed so as to avoid unnecessary patient treatment. Thus, depending on the reasons for which the cells did not pass the QA test at the second time point, the scheduling module 125 may reschedule (i.e., delay), e.g., at S420, lymphodepletion as well as subsequent patient treatment events, and further schedule a cryogenic freezing step following the completion of manufacturing process.

In some embodiments, when the cells fail the QA test at the first or second time point, the patient-specific identifier may be updated to identify that the cells have failed the QA test at the respective time point, and the hospital-side interface 110 and the logistic interface 130 are notified that there is a possibility that the patient treatment events for the patient (associated with the patient-specific identifier) may have to be canceled or delayed. Where the schedule of patient treatment events has deviated from the pre-decided schedule (e.g., the golden path schedule) and the patient treatment events have been rescheduled, the hospital-side interface 110 and the logistics interface 130 are notified that the schedule corresponding to the patient-specific identifier has been updated, and the updated schedule is communicated to the hospital-side interface 110 and the logistics interface 130.

Such notification enables the clinical facility or the hospital to suitably adjust the various schedules for the patient treatment events as well as make necessary logistical arrangements relating to availability of appropriate personnel and availability of facilities and equipment needed for the respective patient treatment events. The notification may additionally facilitate the hospital or the clinical facility to inform the patient of the change in the schedule of the patient treatment events. Alternately, the events scheduler 120 and/or the hospital-side interface 110 may communicate with the patient directly to notify the patient of the change in the schedule of patient treatment events and enable the patient to coordinate with the hospital or the clinical facility for arranging the patient treatment events according to the changed schedule.

In some embodiments, the hospital-side interface 110 may additionally communicate the updated schedule to the insurance provider so that appropriate measures for processing the payment may be taken.

Similarly, the notification enables the logistics provider(s) to make necessary arrangements for rescheduling the shipment of the biological material such as, for example, arrangement of appropriate shipping boxes and availability of appropriate personnel for handling the biological material.

Referring back to S406, if the cells pass the QA test at the second time point, the scheduling module 125 may maintain the schedule for the patient treatment events. For example, in some embodiments, the scheduling module 125 may communicate, e.g., at S410, to the hospital-side interface 110 that a lymphodepletion treatment may be administered to the patient based on the pre-decided schedule with a caveat that there is a low but non-zero probability that the manufacturing process may yet be delayed or may not yield the desired final product. Such communication is designated in FIG. 4B as "lymphodepletion at risk." No changes are made to the schedule of the manufacturing process or the patient treatment events in such a situation.

The acceptance determining module 123 then determines, e.g., at S412, whether the expanded T-cells at a third time point pass a QA test associated with the third time point (e.g., following Step D or Step E shown in FIG. 2A and/or FIG. 9).

If the cells pass the QA test for the third time point, the expanded cells are deemed to be ready for product release at the target TIL infusion date. The scheduling module 125, in such cases, notifies, e.g., at S424, the hospital-side interface 110 that the patient treatment events are to continue at the target schedule. In other words, no change is made to the schedule.

On the other hand, if the cells do not pass the QA test for the third time point, a product impact assessment is performed (e.g., by the doctor or the chief medical officer administering the treatment), e.g., at S414, to determine whether the expanded cells can be provided for infusion or the treatment terminated depending on the reasons for which the cells did not pass the QA test for the third time point. If, upon the product impact assessment, it is determined, e.g., at S416, that the treatment can move forward with the caveat that there may be certain risk associated with continuing the treatment with the available product, the expanded cells are approved for release, e.g., at S424, without any change in the schedule of the patient treatment events.

Figure 4C:
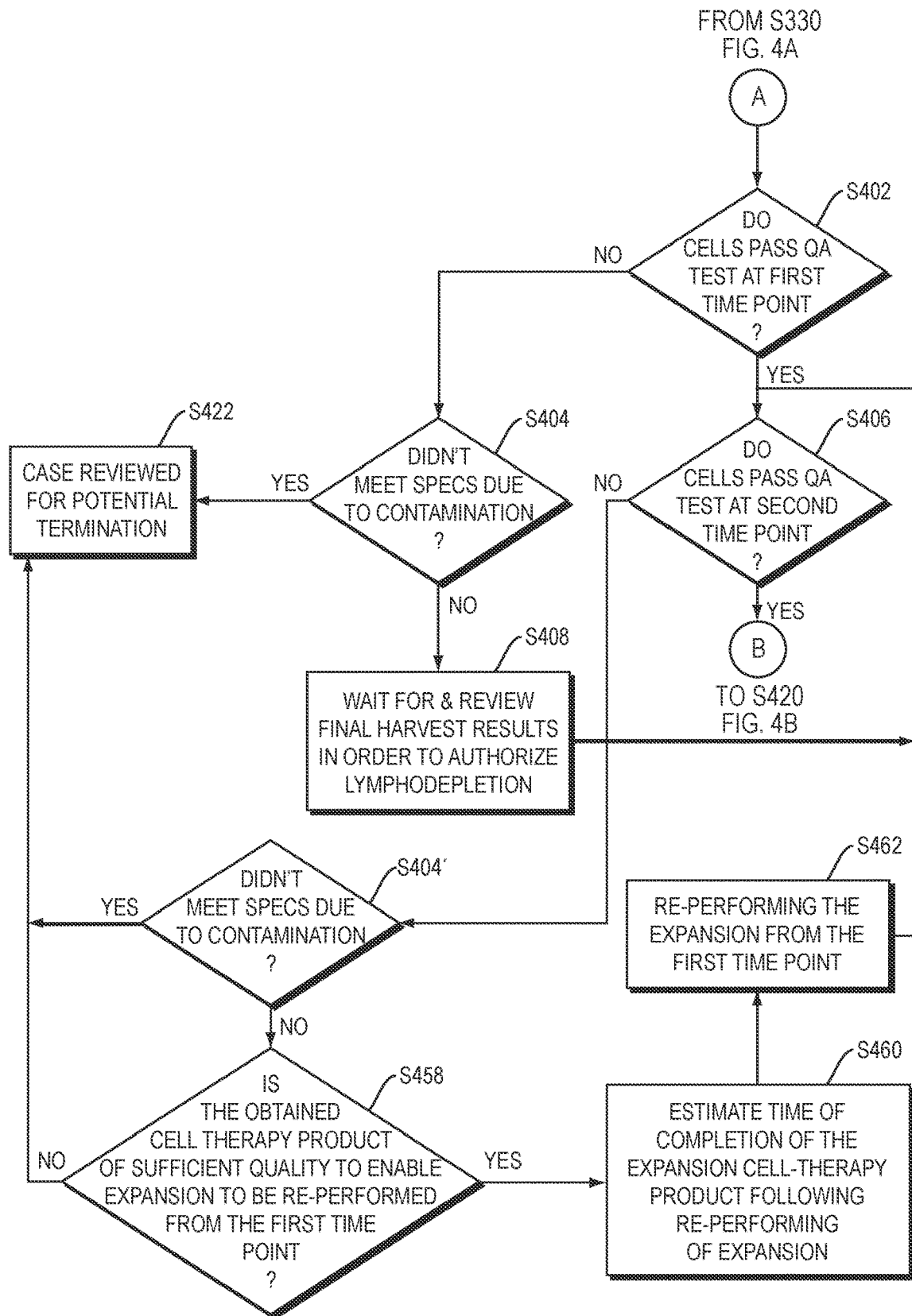
FIG. 4C shows a flow chart for an alternate embodiment for determination of a schedule for patient treatment events based on success of the TIL manufacturing process.

Referring to FIG. 4C, in an embodiment, following the initiation of expansion of the cell therapy product, the acceptance determining module 123 determines, e.g., at S402, whether the expanded cell therapy product at first time point passes a QA test associated with the first time point (e.g., following Step B shown in FIG. 2A and/or FIG. 9). Upon a determination that the cells do not pass the QA test at the first time point, e.g., at S404, the acceptance determining module 123 determines whether the cells did not pass the QA test because of contamination. If the cells did not pass the QA test because of contamination, the case is reviewed for potential termination, e.g., at S422.

On the other hand, if the cells did not pass the QA test because of reasons other than contamination, e.g., because of low cell count or low viability, the scheduling module 125 may extend the ongoing step for a time depending on the reasons due to which the cells did not pass the QA test, and review the results from the final harvest, e.g., at S408. In some embodiments, all subsequent manufacturing steps and patient treatment events may be rescheduled as a consequence of extending the ongoing step for a time.

Referring back to S402, if the cells pass the QA test at the first time point, no changes are made to the schedule of the manufacturing process or the patient treatment events. The acceptance determining module 123 then determines, e.g., at S406, whether the expanded T-cells at a second time point pass a QA test associated with the second time point (e.g., following Step C or Step D shown in FIG. 2A and/or FIG. 9).

If the cells do not pass the QA test a the second time point, the acceptance determining module 123 determines, e.g., at S404', whether the cells did not pass the QA test because of contamination. If the cells did not pass the QA test because of contamination, the case is reviewed for potential termination, e.g., at S422.

On the other hand, if the cells did not pass the QA test because of reasons other than contamination, e.g., because of low cell count or low viability, the acceptance determining module 123 determines, e.g., at S458, whether the cell therapy product obtained at the second time point is of sufficient quality to enable re-performing of the cell manufacturing process from first time point so as to result in the cell therapy product at the second time point with acceptance parameters that meet the acceptance criteria at the second time point. Such determination may be made based on the acceptance parameters of the cell therapy product obtained at the second time point. As an example, if the acceptance parameters at the second time point meet the all acceptance criteria at the second time point except the total viable cell count, it may be viable to re-perform the cell manufacturing process between the first and second time points to obtain the requisite viable cell count.

If it is determined that re-performing of the cell manufacturing process from the first time point is not viable, the case is reviewed for potential termination, e.g., at S422.

On the other hand, if it is determined that re-performing of the cell manufacturing process between the first and second time points is viable, the scheduling module 125 estimates a time of completion of the cell manufacturing process following the re-performing of the process between the first and second time points, e.g., at S460. It will be appreciated that the time needed to re-perform the cell manufacturing process between the first and second time points may be estimated based on the acceptance parameters of the cell therapy product obtained at the second time point. Thus, the time needed to complete the cell expansion process, including the re-performing of the process from the first time point, for manufacturing the cell therapy product may be dependent on the acceptance parameters of the cell therapy product obtained at the second time point.

The scheduling module 125 may then reschedule all subsequent manufacturing steps and patient treatment events as a consequence of re-performing the cell manufacturing process from the first time point based on the acceptance parameters of the cell therapy product obtained at the second time point. For example, the scheduling module 125 may reschedule the patient treatment events so as to account for the delay in completion of the manufacturing process or to account for a potential cryogenic freezing of the manufactured TILs to allow for a time lag between completion of manufacturing and infusion of the TILs.

On the other hand, if the acceptance parameters of the cell therapy product obtained at the second time point meet all the acceptance criteria, the cell manufacturing process may be continued as originally scheduled.

Those of skill in the art will appreciate that even after re-performing of the cell manufacturing process from the first time point upon determination that such re-performing is viable, the acceptance parameters of the cell therapy product obtained at the repeated second time point (also referred to herein as alternate second time point) are determined. It is then again determined if the acceptance parameters at the repeated second time point (which may be different from the original second time point in the cell manufacturing process) meet the acceptance criteria for the second time point before continuing the cell manufacturing process past the second time point.

The continued process then follows the same path "B" as that shown in FIG. 4B in some embodiments. For example, in some cases, the cells may pass a final QA test despite not passing the QA test at the second time point. In such cases, it may be prudent to deviate from an ideal pre-decided schedule (also referred to herein as of the golden path) of patient treatment events and delay lymphodepletion until the final QA test is performed so as to avoid unnecessary patient treatment. Thus, depending on the reasons for which the cells did not pass the QA test at the second time point, the scheduling module 125 may reschedule (i.e., delay), e.g., at S420, lymphodepletion as well as subsequent patient treatment events, and further schedule a cryogenic freezing step following the completion of manufacturing process.

Those of skill in the art will appreciate that when a cell manufacturing process has several time points for determining acceptance parameters and whether those acceptance parameters meet the acceptance criteria at those corresponding time points, it may be viable to re-perform the steps in the cell manufacturing process from an immediately prior time point. Thus, the terms "first time point" and "second time point" do not necessarily describe numerically first and numerically second time points at which acceptance parameters are determined. Instead, the "first time point" refers to a time point in the cell manufacturing process from which it may be viable to re-perform the steps of the cell manufacturing process if the acceptance parameters at a subsequent time point do not meet the acceptance criteria at that time point. For example, in a 1C-Process (see, FIG. 6), the first and second time points may be Day 27 and Day 30 respectively, Day 30 and Day 36 respectively, or Day 36 and Day 43 respectively. Similarly, in a 2A-Process (see, FIG. 6), the first and second time points may be Day 11 and Day 16 respectively, or Day 16 and Day 22 respectively.

In some embodiments, when the cells fail the QA test at the first or second time point, the patient-specific identifier may be updated to identify that the cells have failed the QA test at the respective time point, and the hospital-side interface 110 and the logistic interface 130 are notified that there is a possibility that the patient treatment events for the patient (associated with the patient-specific identifier) may have to be canceled or delayed.

Because the schedule of manufacturing of the cell therapy product may deviate from the ideal schedule if the re-performing of the cell manufacturing process at the first time point is viable, schedule of patient treatment events also deviates from the pre-decided schedule (e.g., the golden path schedule). Accordingly, the scheduling module reschedules the patient treatment events, and the hospital-side interface 110 and the logistics interface 130 are notified that the schedule corresponding to the patient-specific identifier has been updated. The updated schedule is communicated to the hospital-side interface 110 and the logistics interface 130.

As discussed herein, such notification about the change in schedule enables the clinical facility or the hospital to suitably adjust the various schedules for the patient treatment events. Additionally, necessary logistical arrangements relating to availability of appropriate personnel and availability of facilities and equipment needed for the respective patient treatment events can be made. The notification may further facilitate the hospital or the clinical facility to inform the patient of the change in the schedule of the patient treatment events. Alternately, the events scheduler 120 and/or the hospital-side interface 110 may communicate with the patient directly to notify the patient of the change in the schedule of patient treatment events and enable the patient to coordinate with the hospital or the clinical facility for arranging the patient treatment events according to the changed schedule.

In some embodiments, the hospital-side interface 110 may additionally communicate the updated schedule to the insurance provider so that appropriate measures for processing the payment may be taken.

Similarly, the notification enables the logistics provider(s) to make necessary arrangements for rescheduling the shipment of the biological material such as, for example, arrangement of appropriate shipping boxes and availability of appropriate personnel for handling the biological material.

In some embodiments, unless the treatment is terminated, the scheduling module 125 communicates with the logistics interface 130 to provide a pick-up order based on the completion date determined based on the results of the QA test at various time points. The logistics interface 130 then communicates with a logistics provider (not shown) to make suitable arrangements for timely collecting and shipping the expanded TILs to the hospital or clinical facility for subsequent patient treatment (e.g., infusion). For example, in some embodiments, the logistics provider may be required to ship a specialized container for handling a biological sample to the hospital or clinical facility a certain number of days before a scheduled patient treatment event.

Similarly, if it is determined that the expanded cells pass the QA test, the scheduling module 125 communicates the scheduled completion date and the schedule of patient treatment events (i.e., an updated schedule) to the hospital-side interface 110. On the other hand, if it is determined that the treatment is to be terminated, the scheduling module 125 communicates with the hospital-side interface 110 that the treatment is to be terminated.

In some embodiments, upon rescheduling the patient treatment event, an updated schedule for the patient treatment events is transmitted to the hospital-side interface 110 along with the associated patient-specific identifier.

In some embodiments, association between the cell order identifier and the patient-specific identifier may be updated if it is determined that re-performing the steps of the cell manufacturing process from the first time point viable. For example, upon determination that re-performing of the expansion of the cell therapy product from the first time point is viable, the cell order identifier is dissociated from the patient-specific identifier. A new cell order identifier associated with the cell order request may be generated and the patient-specific identifier is associated with the new cell order identifier. The new cell order identifier may be generated based on the acceptance parameters determined at the second time point, in some embodiments. The cell order identifier, in some embodiments, may include fields corresponding to each time point at which the acceptance parameters for the cell therapy product are determined. In addition, in some embodiments, the cell order identifier may also include the result of the determination of whether the acceptance parameters meet the acceptance criteria, including, for example, which acceptance parameters meet the acceptance criteria and the value of the acceptance parameters.

In some embodiments, the patient-specific identifier, the new cell order identifier and an estimated time of completion of the expansion of the cell therapy product is transmitted to the hospital-side interface to enable the hospital-side interface to track the cell therapy product and associate the cell therapy product with the patient.

The various fields included in the cell order identifier may enable the scheduling module 125 to determine a new schedule for the patient treatment events as well as the shipping and logistics events associated with the patient treatment events based on the updated or new cell order identifier generated at various time points. The new schedule is then transmitted to the logistics interface along with the associated patient-specific identifier. The patient-specific identifier and the updated or new cell order identifier may also be transmitted to the logistics interface along with the new schedule in some embodiments so as to maintain chain of custody and chain of identification for the cell therapy product.

In some embodiments, if it is determined that re-performing of the steps of the cell manufacturing process is not viable, e.g., because the acceptance parameters at the second time point do not meet a certain threshold for the acceptance criteria, the patient treatments subsequent to the second time point may be canceled. In such embodiments, the cancellation of the patient treatments is communicated to the hospital-side interface and the logistics interface. In some embodiments, the expanded cell therapy product may be destroyed upon determining that re-performing of the steps of the cell manufacturing process is not viable. For example, in instances where obtaining a viable expanded cell therapy product may not be possible if the steps of the cell manufacturing process cannot be re-performed, the infusion of the cell therapy product becomes impossible. Thus, it may be detrimental to the patient (e.g., either in terms of health outcomes, or in terms of financial outcomes or both) to continue patient treatment events subsequent to the second time point. Additionally, if it is determined based on the determined acceptance parameters at the second time that the expanded cell therapy product at the second time point cannot be further used (e.g., if the cell therapy product at the second time point is contaminated or does not meet certain other acceptance criteria), the cell therapy product may be destroyed. In such instances, the cell order identifier is dissociated from patient-specific identifier.

E. Coordinating Manufacturing Slots Between Manufacturing Facilities

In a further aspect of the present disclosure, a method of manufacturing a cell therapy product for a patient is disclosed. In some embodiments, the method includes receiving a cell order request to manufacture the cell therapy product for the patient. The cell order request may be received at a computing device associated with a clinical facility. The cell order request may be received via, e.g., a hospital-side interface 110. In some embodiments, the computing device may generate patient-specific identifier and a cell order identifier upon receiving the cell order request, and associate the patient-specific identifier and the cell order identifier with the cell order request.

In addition to the cell order request, the computing device may receive manufacturing slots at a plurality of manufacturing facilities for manufacturing the cell therapy product. For example, the computing device may be communicatively coupled to computer subsystems associated with the plurality of manufacturing facilities via, e.g., the Internet, such that the computing device may receive information relating to the manufacturing slots in response to a query by the computing device. The manufacturing slots for a respective manufacturing facility may be indicative of the availability of equipment and personnel at that manufacturing facility to enable that manufacturing facility to manufacturing the cell therapy product in accordance with the cell order request.

The computing device may further receive a preliminary schedule of patient treatment events for treating the patient with the cell therapy product. The preliminary schedule may be determined based on an ideal schedule of manufacturing the cell therapy product assuming that the cell therapy product meets the QA criteria at each manufacturing step during the manufacturing process as discussed elsewhere herein.

Upon receiving the cell order request, the manufacturing slots, and the preliminary schedule of patient treatment events, the computing device may determine and display, in a scheduling user interface, a plurality of available manufacturing slots for manufacturing the cell therapy product based on the preliminary schedule of patient treatment events. The available manufacturing slots are determined based on factors such as, for example, the location of the clinical facility, the location of the respective manufacturing facilities, the availability of logistics providers for shipping the cell therapy product between the respective manufacturing facility and the clinical facility, the availability of clinical personnel at the clinical facility so as to perform the necessary treatment procedures associated with the patient treatment events, and any other factors that may affect the timing of the arrival and/or use of the cell therapy product at a respective location.

One of the available manufacturing slots is then selected either by an operator of the computing device or automatically by the computing device. Upon selection of an available manufacturing slot, a solid tumor may be obtained from the patient, e.g., at the medical facility, by performing an appropriate procedure. The procedure may be performed in accordance with the preliminary schedule and based on the available manufacturing slot in consideration of the timing of shipping and availability of logistics provider the solid tumor to the respective manufacturing facility. In some embodiments, the computing device may initiate printing of a first shipper label (see e.g., row 1 of FIG. 3H) to be associated with the solid tumor. The first shipper label may include the patient-specific identifier and the cell order identifier. In some embodiments, the first label may additionally include information relating to the clinical facility, the selected manufacturing facility and the logistics provider. Additionally, a first product label (see, e.g., row 2 of FIG. 3H) to be associated with the product container. An example of the first product label is illustrated in FIG. 3G.

The solid tumor is then transferred to the selected manufacturing facility in accordance with the available manufacturing slot. Those of skill in the art will appreciate that because the solid tumor includes live cells, the timing of arrival of the solid tumor at the selected manufacturing facility should be carefully coordinated with the availability of the manufacturing slot so that the manufacturing steps may be initiated with an acceptable time window. Thus, the transfer of the solid tumor from the clinical facility to the selected manufacturing should be carefully coordinated based on the availability of the logistic provider, as well as other factors that may affect such transfer. For example, there may be weather-related or traffic delays that can be anticipated in some instances and thus, the transfer schedule may be adjusted accordingly. In other instances, the delays in transfer may not be foreseeable. However, even in such instances, the transfer of the solid tumor from the clinical facility to the selected manufacturing facility may be coordinated in other suitable ways.

F. Tumor Procurement Protocol

Referring back to FIG. 3A, the hospital-side interface of the system 300 includes a tumor procurement module 114 which enables personnel at the clinical facility to obtain the solid tumor from the patient in accordance with a predetermined protocol, and enter information relating to the procedure for obtaining the solid tumor from the patient.

In some embodiments, the procurement module 114 includes tumor procurement forms that are used by the personnel at the clinical facility to ensure that appropriate procedure is followed during the process of obtaining the solid tumor (or a fragment thereof) from the patient and preparing it for transportation to the manufacturing facility. FIGS. 3K-3P are representative screenshots of the tumor procurement forms according to some embodiments of the present disclosure. The tumor procurement forms may, in some embodiments, require a technician obtaining the tumor from the patient to enter information relating to the procedure being performed. The entered information may be used for updating batch records for post-facto audit if necessary.

Moreover, because the information included in the batch records is accessible throughout the system (with appropriate permissions), the information relating to the process followed for obtaining the tumor is also available to the personnel at the manufacturing facility. In some embodiments, the personnel at the manufacturing facility may access the information relating to the process for obtaining the tumor as a quality control measure to ensure that the biological material received at the manufacturing facility is suitable for further processing.

In some embodiments, the tumor procurement forms include smart form features that require that certain criteria are met before the technician can proceed to a subsequent step in the process. For example, the technician may be required to input information relating to the cell culture media, such as an expiry date, being used during the process, and if the expiry date is prior to current date, the tumor procurement module 114 may alert the technician. Further, the tumor procurement module 114 may not allow the technician to enter any further information relating to the process, thereby forcing the technician to abort the process.

Similarly, the tumor procurement forms may require that the technician has performed certain steps or procedures before enabling entry of information relating to a subsequent step or procedure. Thus, the procurement module 114 requires that the technician follow a certain protocol without missing or skipping certain steps.

In some embodiments, the procurement module 114 may require that the tumor procurement forms are verified before enabling the release of the obtained tumor to the courier for transportation to the manufacturing facility. The verification requirement functions as a fail-safe to ensure that appropriate protocols and procedures are followed when obtaining the tumor. In some embodiments, the procurement module 114 may require that the person verifying the tumor procurement forms is not the same as the person entering the information in the tumor procurement forms. Such verification requirement also ensures compliance with appropriate regulatory requirements.

G. Patient Support Services

Embodiments of the present disclosure are further operable to enable patient support services that interface with a patient or a patient's representative (collectively referred to herein as the patient) in support of travel, health management, health insurance, reimbursement, and other treatment related services. The patient support services may, in some embodiments, interface with a telephony interface and a persona from which the manufacturing process and the COC/COI process is accessible (with appropriate permissions). As used herein, the term persona refers to a user type. A given persona is provided with certain level of access to the system and the information within the system, and can access certain functions. The personas within the system include, but are not limited to, Community Persona, Tissue Procurement Persona, Manufacturer Persona, Patient Support Persona, Patient Persona, and Health System User persona.

The Community persona relates to community users, which is accessible to the personnel at the center providing the treatment procedures to the patient. Users of the Community persona may include, for example, cell therapy coordinators, bone marrow transplant nurses, hospital billing department, etc. Functions associated with the users of the Community persona include, but are not limited to, registering a new patient, updating patient enrollment data, creating and submitting a TIL order request for a patient, scheduling or changing a resection date, viewing Golden Path dates, view final product delivery dates, uploading hospital purchase orders, uploading patient consent forms, enrolling a patient for patient support options, viewing and updating caregiver records, completing and submitting tumor procurement forms for approval, approving tumor procurement forms, printing tumor procurement forms, uploading tumor procurement forms, and printing media bottle and tumor shipper labels.

Users associated with the Manufacturer persona include tumor receiving personnel, quality control personnel, manufacturing process personnel, and final product packaging personnel. Functions associated with the Manufacturer persona include, but are not limited to, entering lot numbers, viewing available and reserved manufacturing slots, printing and scanning in-process, final product and shipping labels.

Users associated with the tumor procurement persona include, for example, surgeons, and bone marrow transplant nurses. Functions associated with the tumor procurement persona may include, without limitation, completing tumor procurement forms, submitting tumor procurement forms for approval, approving tumor procurement forms, printing tumor procurement forms, and uploading tumor procurement forms.

Users of patient support persona may include, but are not limited to, patient support personnel, patient counsellors, hospital billing, hospital insurance managers, etc. Functions associated with the patient support persona may include, but are not limited to, viewing patient assistance services cases, uploading files to the cases, annotating the cases, transferring the cases to a case manager, etc.

In some embodiments of the system, certain types of information is accessible to certain personas. In some embodiments, the information may be accessible to users of certain personas only when performing certain types of functions, and not when performing other types of functions. For example, the some embodiments, the COC/COI and manufacturing process information may be accessible via patient support persona to hospital billing and/or hospital insurance managers, but not visible to patient counsellors. In some embodiments, the manufacturing and COC/COI information may be visible to, but not editable by patient support personnel who perform the functions of, e.g., scheduling patient treatment events, assisting the patient through the scheduling process and/or assisting the patient with transportation for patient treatment events.

For example, in some embodiments, a method for manufacturing a cell therapy product by expanding a population of cells obtained from a tumor from a patient into the cell therapy product may comprise:

receiving a population of cells from the patient at a manufacturing facility based on a cell order request to manufacture the cell therapy product for the patient;

generating, by a computing device, a patient-specific identifier including a cell order identifier associated with the cell order request;

initiating a process to manufacture the cell therapy product, the process comprising:

after receiving the population of cells at the manufacturing facility, scheduling, by the computing device, patient treatment events, initiating expansion of the cell therapy product from at least some of the population of cells using a cell expansion technique and determining acceptance parameters for the expansion cell therapy product at a first time point and at a second time point subsequent to the first time point, determining whether acceptance parameters for the expansion cell therapy product meet acceptance criteria associated with a corresponding time point, in response to a determination that the acceptance parameters for the expansion cell therapy product meet the acceptance criteria at the first time point, continuing the expansion of cell therapy product from the at least some of the obtained cell therapy product using the cell expansion technique up to the second time point, and in response to a determination that the acceptance parameters for the expansion cell therapy product do not meet the acceptance criteria at the second time point:

determining whether re-performing the expansion of the cell therapy product using the cell expansion technique is feasible from the first time point based on the acceptance parameters at the second time point, in response to a determination that the re-performing is feasible, re-performing the expansion of the cell therapy product from at least some of the cell therapy product obtained at the second time point using the cell expansion technique from the first time point to obtain the cell therapy product, estimating, by the computing device, a time of completion of the expansion of the cell therapy product following the re-performing of the expansion of the cell therapy product from the first time point, and rescheduling, by the computing device, the patient treatment events and completing a subsequent expansion of cell therapy product from the first time point, wherein the rescheduling of the patient treatment events is performed based on the estimated time of completion of the expansion of the cell therapy product and a timing of patient treatment events prior to or subsequent to an infusion of the expanded cell therapy product in the patient, and providing patient support services such as, for example, support for travel, health management, health insurance, reimbursement, and other treatment related services.

VI. Further Considerations

The examples set forth above are provided to give those of ordinary skill in the art a complete disclosure and description of how to make and use the embodiments of the compositions, systems and methods of the invention, and are not intended to limit the scope of what the inventors regard as their invention. Modifications of the above-described modes for carrying out the invention that are obvious to persons of skill in the art are intended to be within the scope of the following claims. All patents and publications mentioned in the specification are indicative of the levels of skill of those skilled in the art to which the invention pertains.

All headings and section designations are used for clarity and reference purposes only and are not to be considered limiting in any way. For example, those of skill in the art will appreciate the usefulness of combining various aspects from different headings and sections as appropriate according to the spirit and scope of the invention described herein.

All references cited herein are hereby incorporated by reference herein in their entireties and for all purposes to the same extent as if each individual publication or patent or patent application was specifically and individually indicated to be incorporated by reference in its entirety for all purposes.

Many modifications and variations of this application can be made without departing from its spirit and scope, as will be apparent to those skilled in the art. The specific embodiments and examples described herein are offered by way of example only, and the application is to be limited only by the terms of the appended claims, along with the full scope of equivalents to which the claims are entitled.

Various examples of aspects of the disclosure are described as numbered clauses (1, 2, 3, etc.) for convenience. These are provided as examples, and do not limit the subject technology. Identifications of the figures and reference numbers are provided below merely as examples and for illustrative purposes, and the clauses are not limited by those identifications.

Clause 1. A method for manufacturing a cell therapy product by expanding a population of cells obtained from a tumor from a patient into the cell therapy product, the method comprising:
receiving a population of cells from the patient at a manufacturing facility based on a cell order request to manufacture the cell therapy product for the patient;
generating, by a computing device, a patient-specific identifier including a cell order identifier associated with the cell order request;
initiating a process to manufacture the cell therapy product, the process comprising:
after receiving the population of cells at the manufacturing facility, scheduling, by the computing device, patient treatment events,
initiating expansion of the cell therapy product from at least some of the population of cells using a cell expansion technique and determining acceptance parameters for the expansion cell therapy product at a first time point and at a second time point subsequent to the first time point,
determining whether acceptance parameters for the expansion cell therapy product meet acceptance criteria associated with a corresponding time point,
in response to a determination that the acceptance parameters for the expansion cell therapy product meet the acceptance criteria at the first time point, continuing the expansion of cell therapy product from the at least some of the obtained cell therapy product using the cell expansion technique up to the second time point, and
in response to a determination that the acceptance parameters for the expansion cell therapy product do not meet the acceptance criteria at the second time point:
determining whether re-performing the expansion of the cell therapy product using the cell expansion technique is feasible from the first time point based on the acceptance parameters at the second time point,
in response to a determination that the re-performing is feasible, re-performing the expansion of the cell therapy product from at least some of the cell therapy product obtained at the second time point using the cell expansion technique from the first time point to obtain the cell therapy product,
estimating, by the computing device, a time of completion of the expansion of the cell therapy product following the re-performing of the expansion of the cell therapy product from the first time point, and
rescheduling, by the computing device, the patient treatment events and completing a subsequent expansion of cell therapy product from the first time point,
wherein the rescheduling of the patient treatment events is performed based on the estimated time of completion of the expansion of the cell therapy product and a timing of patient treatment events prior to or subsequent to an infusion of the expanded cell therapy product in the patient.

Clause 2. The method of clause 1, wherein the cell therapy product comprises T-cells.

Clause 3. The method of clause 1, wherein the cell therapy product comprises tumor infiltrating lymphocytes (TTLs).

Clause 4. The method of clause 1, wherein the patient treatment events include one or more of an inpatient stay time period, resection date, lymphodepletion date, infusion date for infusing the patient with the cell therapy product and IL-2 treatment date.

Clause 5. The method of clause 1, wherein the determining whether the acceptance parameters for the expansion cell therapy product meet the acceptance criteria comprises determining the acceptance parameters for the expansion cell therapy product at a plurality of time points following the initiation of the expansion of the obtained cell therapy product, the plurality of time points including the first and the second time points.

Clause 6. The method of clause 5, wherein the rescheduling of patient treatment events comprises rescheduling the patient treatment events in response to a determination that the acceptance parameters for the expansion cell therapy product do not meet the acceptance criteria at any of the plurality of time points.

Clause 7. The method of clause 5, wherein the rescheduling of patient treatment events comprises terminating the patient treatment events in response to a determination that the acceptance parameters for the expansion cell therapy product do not meet the acceptance criteria at any of the plurality of time points because of contamination.

Clause 8. The method of clause 5, wherein in response to a determination that the acceptance parameters for the expansion cell therapy product do not meet the acceptance criteria at any of the plurality of time points because of contamination, terminating the subsequent expansion of cell therapy product.

Clause 9. The method of clause 8, wherein determining acceptance parameters for the expansion cell therapy product comprise one or more of determination of viability, sterility, cell count, mycoplasma count, CD3 count, result of an Endotoxin assay, and a result of a Gram stain assay.

Clause 10. The method of clause 9, wherein the cell expansion technique comprises a rapid expansion step, and the method further comprises:
determining whether the acceptance parameters for the expansion cell therapy product meet the acceptance criteria prior to the rapid expansion step; and
in response to a determination that the acceptance parameters for the expansion cell therapy product meet the acceptance criteria, scheduling a lymphodepletion date at a date prior to the completion of the manufacturing of the expanded cell therapy product, scheduling an infusion date at a date following the completion of the manufacturing of the expanded cell therapy product, and scheduling an IL-2 treatment date following the infusion date.

Clause 11. The method of clause 1, wherein the cell expansion technique includes culturing the cell therapy product in a single closed container bioreactor.

Clause 12. The method of clause 1, wherein estimating the time of completion of the expansion of the cell therapy product following the re-performing of the expansion of the cell therapy product from the first time point comprises determining the time needed for completing the expansion process from the first time point based on one or both of the acceptance parameters at the second time point and the acceptance parameters associated with a population of cells used for re-performing the expansion of the cell therapy product from the first time point.

Clause 13. The method of clause 1, wherein cell order request to expand cell therapy product is received from a hospital-side interface, and the method further comprises transmitting, upon receiving the cell order request, a confirmation, including one or both of the patient-specific identifier and the cell order identifier, to the hospital-side interface that the cell order request associated with the patient has been received.

Clause 14. The method of clause 13, further comprising scheduling a set of dates corresponding to a plurality of time points, including the first and second time points, for determining whether acceptance parameters for the expansion cell therapy product meet the acceptance criteria during expansion of the cell therapy product depending on the cell expansion technique and when the cell order request is received.

Clause 15. The method of clause 13, further comprising transmitting, upon rescheduling the patient treatment events, to the hospital-side interface an updated schedule for the patient treatment events associated with the patient-specific identifier.

Clause 16. The method of clause 15, further comprising:
transmitting, to a logistics interface, a pick-up order associated with the patient-specific identifier based on the time of completion; and
transmitting, to a hospital-side interface, a schedule for the patient treatment events associated with the patient-specific identifier based on the time of completion.

Clause 17. The method of clause 16, further comprising:
in response to a determination that re-performing of the expansion of the cell therapy product from the first time point is feasible:
disassociating, by the computing device, the cell order identifier from the patient-specific identifier, and
generating, by the computing device, a new cell order identifier associated with the cell order request and associating the new cell order identifier with the patient-specific identifier.

Clause 18. The method of clause 17, wherein the cell order request to expand cell therapy product is received from a hospital-side interface, and the method further comprises transmitting the patient-specific identifier including the new cell order identifier and the estimated time of completion of the expansion of the cell therapy product to the hospital-side interface.

Clause 19. The method of clause 17, further comprising:
generating, by the computing device, a new schedule for shipping and logistics events associated with the patient treatment events based on the rescheduling of the patient treatment events, and
transmitting the new schedule of shipping and logistics events associated the patient-specific identifier including the new cell order identifier to a logistics interface based on the rescheduling of shipping and logistics events.

Clause 20. The method of clause 17, further comprising:
associating, by the computing device, with the patient-specific identifier at each time point at which the determination of whether acceptance parameters meet the certain acceptance criteria is made, the new cell order identifier including fields corresponding to each respective time point and a result of the determination.

Clause 21. The method of clause 20, wherein the scheduling comprises: scheduling, by the computing device, the patient treatment events based on the patient-specific identifier including the new cell order identifier.

Clause 22. The method of clause 21, further comprising, in response to a determination that the re-performing is not possible, canceling, by the computing device, the patient treatment events scheduled subsequent to the second time point.

Clause 23. The method of clause 22, further comprising transmitting the cancellation of patient treatment events to a hospital-side interface and a logistics interface.

Clause 24. The method of clause 23, further comprising, in response to a determination that the re-performing is not feasible, destroying the expanded cell therapy product and disassociating the patient-specific identifier from the cell order identifier.

Clause 25. A method of treating the patient with the expansion cell therapy product obtained by the method of clause 1 in accordance with the rescheduled patient treatment events.

Clause 26. A method of manufacturing a cell therapy product for a patient, the method comprising:
receiving, at a computing device, a cell order request to manufacture the cell therapy product for the patient, manufacturing slots at a plurality of manufacturing facilities for manufacturing the cell therapy product, wherein the manufacturing slots for a respective manufacturing facility are received at the computing device from a manufacturer computer subsystem associated with the respective manufacturing facility, and a preliminary schedule of patient treatment events for treating the patient with the cell therapy product;

determining and displaying in a scheduling user interface, by the computing device, a plurality of available manufacturing slots for manufacturing the cell therapy product based on the preliminary schedule of patient treatment events;

after selection of one of the available manufacturing slots, performing, at a medical facility, a procedure on the patient to obtain a solid tumor from the patient in accordance with the preliminary schedule of patient treatment events and the available manufacturing slot;

transferring the obtained solid tumor to a manufacturing facility corresponding to the available manufacturing slot in accordance with the available manufacturing slot;

initiating, upon receiving the obtained solid tumor at the manufacturing facility, manufacturing of the cell therapy product from at least a portion of the obtained solid tumor using a cell expansion technique;

determining, during the manufacturing of the cell therapy product, acceptance parameters for the manufactured cell therapy product at a first time point and a second time point subsequent to the first time point and whether the acceptance parameters meet acceptance criteria associated with a corresponding time point, the acceptance parameters being determined based on a result of an assay associated with the corresponding time point;

modifying, by the computing device, a manufacturing schedule for manufacturing of the cell therapy product, manufacturing slots corresponding to the manufacturing facility, and the preliminary schedule of patient treatment events based on whether the acceptance criteria at one or both of the first and second time points are met; and completing the manufacturing of the cell therapy product in accordance with the modified manufacturing schedule if the acceptance criteria at both the first and second time points are met.

Clause 27. The method of clause 26, further comprising transferring the manufactured cell therapy product to the medical facility.

Clause 28. The method of clause 26, further comprising, upon receiving the cell order request, generating, by the computing device, a patient-specific identifier associated with the patient and the cell order request.

Clause 29. The method of clause 28, further comprising automatically generating, by the computing device, a shipping label for a container for the obtained solid tumor, the shipping label comprising the patient-specific identifier, the cell order request, the manufacturing slot and the manufacturing facility corresponding to the available manufacturing slot.

Clause 30. The method of clause 29, further comprising automatically generating, by the computing device, a manufacturing label for the container for the obtained solid tumor, the manufacturing label comprising a time point corresponding to a manufacturing process being used for manufacturing the cell therapy product when the manufacturing label is generated, a container-identifying bar code, the patient-specific identifier, manufacturing steps completed at the time point, acceptance parameters associated with the completed processes, and a manufacturing process being performed at the time point.

Clause 31. The method of clause 26, wherein the cell therapy product comprises T-cells.

Clause 32. The method of clause 26, wherein the cell therapy product comprises tumor infiltrating lymphocytes (TILs).

Clause 33. The method of clause 26, wherein the patient treatment events include one or more of an inpatient stay time period, resection date, lymphodepletion date, infusion date for infusing the patient with the cell therapy product and IL-2 treatment date.

Clause 34. The method of clause 26, wherein the determining whether the acceptance parameters for the manufactured cell therapy product meet the acceptance criteria comprises determining the acceptance parameters for the manufactured cell therapy product at a plurality of time points following the initiation of the expansion of the received cell therapy product, the plurality of time points including the first and the second time points.

Clause 35. The method of clause 34, further comprising: rescheduling, by the computing device, the patient treatment events and completing a subsequent expansion of cell therapy product, wherein the rescheduling of patient treatment events comprises rescheduling the patient treatment events in response to a determination that the acceptance parameters for the manufactured cell therapy product do not meet the acceptance criteria at any of the plurality of time points.

Clause 36. The method of clause 34, wherein the rescheduling of patient treatment events comprises terminating the patient treatment events in response to a determination that the acceptance parameters for the manufactured cell therapy product do not meet the acceptance criteria at any of the plurality of time points because of contamination.

Clause 37. The method of clause 34, wherein in response to a determination that the acceptance parameters for the manufactured cell therapy product do not meet the acceptance criteria at any of the plurality of time points because of contamination, terminating the subsequent expansion of cell therapy product.

Clause 38. The method of clause 37, wherein determining acceptance parameters for the manufactured cell therapy product comprise one or more of determination of viability, sterility, cell count, *mycoplasma* count, CD3 count, result of an Endotoxin assay, and a result of a Gram stain assay.

Clause 39. The method of clause 38, wherein the cell expansion technique comprises a rapid expansion step, and the method further comprises:
  determining whether the acceptance parameters for the manufactured cell therapy product meet the acceptance criteria prior to the rapid expansion step; and
  in response to a determination that the acceptance parameters for the manufactured cell therapy product meet the acceptance criteria, scheduling a lymphodepletion date at a date prior to the completion of the manufacturing of the cell therapy product, scheduling an infusion date at a date following the completion of the manufacturing of the cell therapy product, and scheduling an IL-2 treatment date following the infusion date.

Clause 40. The method of clause 26, wherein the cell expansion technique includes culturing the cell therapy product in a single closed container bioreactor.

Clause 41. The method of clause 26, further comprising: estimating, by the computing device, a time of completion of the expansion of the cell therapy product, wherein estimating the time of completion of the expansion of the cell therapy product following a re-performing of the expansion of the cell therapy product from the first time point comprises determining the time needed for completing the expansion process from the first time point based on one or both of the acceptance parameters at the second time point and the acceptance parameters associated with a population of cells used for re-performing the expansion of the cell therapy product from the first time point.

Clause 42. The method of clause 29, wherein cell order request to expand cell therapy product is received from a hospital-side interface, and the method further comprises transmitting, upon receiving the cell order request, a confirmation, including one or both of the patient-specific identifier and the cell order identifier, to the hospital-side interface that the cell order request associated with the patient has been received.

Clause 43. The method of clause 42, further comprising scheduling a set of dates corresponding to a plurality of time points, including the first and second time points, for determining whether acceptance parameters for the manufactured cell therapy product meet the acceptance criteria during expansion of the cell therapy product depending on the cell expansion technique and when the cell order request is received.

Clause 44. The method of clause 43, further comprising transmitting, upon rescheduling the patient treatment events, to the hospital-side interface an updated schedule for the patient treatment events associated with the patient-specific identifier.

Clause 45. The method of clause 44, further comprising:
transmitting, to a logistics interface, a pick-up order associated with the patient-specific identifier based on the time of completion; and
transmitting, to a hospital-side interface, a schedule for the patient treatment events associated with the patient-specific identifier based on the time of completion.

Clause 46. The method of clause 45, further comprising: in response to a determination that re-performing of the expansion of the cell therapy product from the first time point is feasible:
disassociating, by the computing device, the cell order identifier from the patient-specific identifier, and
generating, by the computing device, a new cell order identifier associated with the cell order request and associating the new cell order identifier with the patient-specific identifier.

Clause 47. The method of clause 46, wherein the cell order request to expand cell therapy product is received from a hospital-side interface, and the method further comprises transmitting the patient-specific identifier including the new cell order identifier and an estimated time of completion of the expansion of the cell therapy product to the hospital-side interface.

Clause 48. The method of clause 47, further comprising:
generating, by the computing device, a new schedule for shipping and logistics events associated with the patient treatment events based on the rescheduling of the patient treatment events, and
transmitting the new schedule of shipping and logistics events associated the patient-specific identifier including the new cell order identifier to a logistics interface based on the rescheduling of shipping and logistics events.

Clause 49. The method of clause 48, further comprising:
associating, by the computing device, with the patient-specific identifier at each time point at which the determination of whether acceptance parameters meet the acceptance criteria is made, the new cell order identifier including fields corresponding to each respective time point and a result of the determination.

Clause 50. The method of clause 49, wherein the scheduling comprises:
scheduling, by the computing device, the patient treatment events based on the patient-specific identifier including the new cell order identifier.

Clause 51. The method of clause 50, further comprising, in response to a determination that the re-performing is not possible, canceling, by the computing device, the patient treatment events scheduled subsequent to the second time point.

Clause 52. The method of clause 51, further comprising transmitting the cancellation of patient treatment events to a hospital-side interface and a logistics interface.

Clause 53. The method of clause 52, further comprising, in response to a determination that the re-performing is not feasible, destroying the expanded cell therapy product and disassociating the patient-specific identifier from the cell order identifier.

Clause 54. A method of treating the patient with the manufactured cell therapy product obtained by the method of clause 26 in accordance with the rescheduled patient treatment events.

Clause 55. A method for manufacturing a cell therapy product, the method comprising:
receiving, at a manufacturing facility, a solid tumor obtained from a patient;
generating, by a computing device, a manufacturing label for a manufacturing container to be used in a process for manufacturing the cell therapy product from at least a portion of the obtained solid tumor using a cell expansion technique, the manufacturing label comprising information associated with the patient, the manufacturing process and quality of manufactured cell therapy product;
initiating a process to manufacture the cell therapy product, the process comprising:
performing, at a medical facility, a procedure on the patient to obtain a solid tumor from the patient,
transferring the obtained solid tumor to a manufacturing facility,
after receiving the obtained solid tumor at the manufacturing facility, dynamic scheduling, by the computing device, patient treatment events, the dynamic scheduling being dependent on acceptance parameters for subsequently obtained expansion cell therapy product,
initiating expansion of the cell therapy product from at least some of the obtained solid tumor using a cell expansion technique and determining acceptance parameters for the expansion cell therapy product at a plurality of time points,
performing a quality control assay to determine acceptance parameters for the manufactured cell therapy product at the plurality of time points;
receiving, at the computing device, the acceptance parameters for the manufactured cell therapy product;
generating, by the computing device, an updated manufacturing label corresponding to each of the plurality of time points, the updated manufacturing label comprising updated information associated with quality of manufactured cell therapy product, the updated information comprising the acceptance parameters at a corresponding time point;
reading, by the computing device, the updated manufacturing label at each of the plurality of time points; and
completing expansion of the cell therapy product based on information read from the updated manufacturing label at each of the plurality of time points.

Clause 56. The method of clause 55, further comprising providing, by the computing device, a warning signal if:
information relating to the patient on the updated manufacturing label for a subsequent manufacturing step does not match the information relating to the patient on the manufacturing label for an immediately preceding manufacturing step, or
acceptance parameters on the updated manufacturing label for a given time point in the manufacturing process do not meet acceptance criteria for that time point in the manufacturing process,
wherein the acceptance parameters comprise one or more of viability, sterility, cell count, *mycoplasma* count, CD3 count, a result of an endotoxin assay, and a result of a Gram stain assay.

Clause 57. The method of clause 55, wherein information relating to the patient comprises a patient-specific identifier and a cell order identifier associated with a cell order request to manufacture the cell therapy product for the patient.

Clause 58. The method of clause 55, wherein the cell expansion technique includes culturing the cell therapy product in a single closed container bioreactor.

Clause 59. The method of clause 55, wherein the manufacturing label comprises a barcode encoding the information associated with the patient, the manufacturing process and quality of manufactured cell therapy product.

Clause 60. The method of clause 56, further comprising scheduling a set of dates corresponding to a plurality of time points, including a first time point and a second time point subsequent to the first time point, for determining whether acceptance parameters for the manufactured cell therapy product meet the acceptance criteria during the manufacturing process depending on the cell expansion technique being used and when a cell order request is received at the manufacturing facility.

Clause 61. The method of clause 60, further comprising integrating with a logistics interface, receiving courier status information via a courier computing subsystem, wherein courier status information includes and in response to receiving the courier status information, determining shipping schedule for shipping the manufactured cell therapy product based on the determined schedule of manufacturing and generating a shipping label for a shipping container containing the manufactured cell therapy product.

Clause 62. The method of clause 60, further comprising transmitting a shipping request to a logistics facility based on the determined shipping schedule.

Clause 63. The method of clause 60, further comprising generating a shipping label for a shipping container containing the manufactured cell therapy product before performing a final quality control assay, the shipping label being indicative that the manufactured cell therapy product is not releasable unless a result of the final quality control assay indicates that the corresponding acceptance parameters meet the corresponding acceptance criteria.

Clause 64. The method of clause 56, further comprising:
upon determining that the acceptance parameters for the manufactured cell therapy product meet the acceptance criteria, determining a completion date for the manufacturing of the cell therapy;
generating, by the computing device, a schedule for patient treatment events corresponding to a use of the cell therapy product for treating a patient based on the completion date;
transmitting, to a logistics interface, a pick-up order based on the completion date; and
transmitting, to a hospital-side interface, the schedule for the patient treatment events.

Clause 65. The method of clause 55, wherein the cell therapy product comprises T-cells.

Clause 66. The method of clause 55, wherein the cell therapy product comprises tumor infiltrating lymphocytes (TTLs).

Clause 67. The method of clause 55, wherein the patient treatment events include one or more of an inpatient stay time period, resection date, lymphodepletion date, infusion date for infusing the patient with the cell therapy product and IL-2 treatment date.

Clause 68. The method of clause 56 wherein the determining whether the acceptance parameters for the expansion cell therapy product meet the acceptance criteria comprises determining the acceptance parameters for the expansion cell therapy product at a plurality of time points following the initiation of the expansion of the obtained cell therapy product, the plurality of time points including the first and the second time points.

Clause 69. The method of clause 68, further comprising: rescheduling, by the computing device, the patient treatment events and completing a subsequent expansion of cell therapy product, wherein the rescheduling of patient treatment events comprises rescheduling the patient treatment events in response to a determination that the acceptance parameters for the expansion cell therapy product do not meet the acceptance criteria at any of the plurality of time points.

Clause 70. The method of clause 68, wherein the rescheduling of patient treatment events comprises terminating the patient treatment events in response to a determination that the acceptance parameters for the expansion cell therapy product do not meet the acceptance criteria at any of the plurality of time points because of contamination.

Clause 71. The method of clause 68, wherein in response to a determination that the acceptance parameters for the expansion cell therapy product do not meet the acceptance criteria at any of the plurality of time points because of contamination, terminating the subsequent expansion of cell therapy product.

Clause 72. The method of clause 71, wherein determining acceptance parameters for the expansion cell therapy product comprise one or more of determination of viability, sterility, cell count, *mycoplasma* count, CD3 count, result of an Endotoxin assay, and a result of a Gram stain assay.

Clause 73. The method of clause 72, wherein the cell expansion technique comprises a rapid expansion step, and the method further comprises:
determining whether the acceptance parameters for the expansion cell therapy product meet the acceptance criteria prior to the rapid expansion step; and
in response to a determination that the acceptance parameters for the expansion cell therapy product meet the acceptance criteria, scheduling a lymphodepletion date at a date prior to the completion of the manufacturing of the cell therapy product, scheduling an infusion date at a date following the completion of the manufacturing of the cell therapy product, and scheduling an IL-2 treatment date following the infusion date.

Clause 74. The method of clause 55, wherein the cell expansion technique includes culturing the cell therapy product in a single closed container bioreactor.

Clause 75. The method of clause 55, wherein estimating the time of completion of the expansion of the cell therapy product following a re-performing of the expansion of the cell therapy product from the first time point comprises determining the time needed for completing the expansion process from the first time point based on one or both of the acceptance parameters at the second time point and the acceptance parameters associated with a population of cells used for re-performing the expansion of the cell therapy product from the first time point.

Clause 76. The method of clause 57, wherein cell order request to expand cell therapy product is received from a hospital-side interface, and the method further comprises transmitting, upon receiving the cell order request, a confirmation, including one or both of the patient-specific identifier and the cell order identifier, to the hospital-side interface that the cell order request associated with the patient has been received.

Clause 77. The method of clause 76, further comprising scheduling a set of dates corresponding to a plurality of time points, including the first and second time points, for determining whether acceptance parameters for the expansion cell therapy product meet the acceptance criteria during expansion of the cell therapy product depending on the cell expansion technique and when the cell order request is received.

Clause 78. The method of clause 76, further comprising transmitting, upon rescheduling the patient treatment events, to the hospital-side interface an updated schedule for the patient treatment events associated with the patient-specific identifier.

Clause 79. The method of clause 78, further comprising: transmitting, to a logistics interface, a pick-up order associated with the patient-specific identifier based on the time of completion; and transmitting, to a hospital-side interface, a schedule for the patient treatment events associated with the patient-specific identifier based on the time of completion.

Clause 80. The method of clause 79, further comprising:
in response to a determination that re-performing of the expansion of the cell therapy product from the first time point is feasible:
   disassociating, by the computing device, the cell order identifier from the patient-specific identifier, and
   generating, by the computing device, a new cell order identifier associated with the cell order request and associating the new cell order identifier with the patient-specific identifier.

Clause 81. The method of clause 80, wherein the cell order request to expand cell therapy product is received from a hospital-side interface, and the method further comprises transmitting the patient-specific identifier including the new cell order identifier and an estimated time of completion of the expansion of the cell therapy product to the hospital-side interface.

Clause 82. The method of clause 80, further comprising:
generating, by the computing device, a new schedule for shipping and logistics events associated with the patient treatment events based on the rescheduling of the patient treatment events, and
transmitting the new schedule of shipping and logistics events associated the patient-specific identifier including the new cell order identifier to a logistics interface based on the rescheduling of shipping and logistics events.

Clause 83. The method of clause 80, further comprising:
associating, by the computing device, with the patient-specific identifier at each time point at which the determination of whether acceptance parameters meet the certain acceptance criteria is made, the new cell order identifier including fields corresponding to each respective time point and a result of the determination.

Clause 84. The method of clause 83, wherein the scheduling comprises:
scheduling, by the computing device, the patient treatment events based on the patient-specific identifier including the new cell order identifier.

Clause 85. The method of clause 84, further comprising, in response to a determination that the re-performing is not possible, canceling, by the computing device, the patient treatment events scheduled subsequent to the second time point.

Clause 86. The method of clause 85, further comprising transmitting the cancellation of patient treatment events to a hospital-side interface and a logistics interface.

Clause 87. The method of clause 86, further comprising, in response to a determination that the re-performing is not feasible, destroying the expanded cell therapy product and disassociating the patient-specific identifier from the cell order identifier.

Clause 88. A method of treating the patient with the expansion cell therapy product obtained by the method of clause 55 in accordance with the rescheduled patient treatment events.

The invention claimed is:
1. A system for coordinating manufacturing of a cell therapy product for treating cancer in a patient, the system comprising:
at least one computing device and configured to:
receive and transmit patient information and a cell order request for manufacturing, using a multi-step cell expansion process, the cell therapy product from a population of cells obtained from a tumor resected from the patient, the patient information including a patient-specific identifier, and the cell order request including a cell order identifier, and
determine a schedule for patient treatment events including infusion of the cell therapy product in the patient based on an estimated completion date for obtaining of the cell therapy product manufactured by and received from a manufacturing facility using the multi-step cell expansion process;

generate a container label for a manufacturing container to be used in the multi-step cell expansion process for manufacturing the cell therapy product from at least a portion of the population of cells using a cell expansion technique, the container label comprising information associated with: (a) the cell order request including the cell order identifier, (b) the patient including the patient-specific identifier, and (c) the manufacturing facility where the cell therapy product is to be manufactured using the multi-step cell expansion process, wherein the multi-step cell expansion process comprises:
  (i) initiating the multi-step cell expansion process for manufacturing the cell therapy product, and
  (ii) initiating quality control assays to determine acceptance parameters at each of a plurality of time points during the multi-step cell expansion process,
receive the acceptance parameters obtained at the plurality of time points during the multi-step cell expansion process;
read the container label at each subsequent time point;
verify a chain of custody and a chain of identity based on the cell order identifier and the patient-specific identifier on the container label at corresponding subsequent time points;
generate a warning signal if:
  the patient-specific identifier on the container label for a subsequent manufacturing step does not match the patient-specific identifier on the container label for an immediately preceding manufacturing step; and
determine appropriate further processing steps of the multi-step cell expansion process based on information read from the container label for completing the manufacturing of the cell therapy product.

2. The system of claim 1, wherein the manufacturing subsystem is further configured to:
  determine a preliminary schedule of manufacturing including a set of dates corresponding to the plurality of time points, including a first time point and a second time point subsequent to the first time point, for determining whether the acceptance parameters meet acceptance criteria at the corresponding time point during the multi-step cell expansion process depending on a cell expansion technique being used and when the cell order request is received at the manufacturing facility; and
  determine a shipping schedule for shipping the cell therapy product based on the preliminary schedule of manufacturing.

3. The system of claim 1, further comprising a logistics subsystem comprising at least one computing device and configured to:
  transmit a shipping request to a logistics facility based on a shipping schedule received from the hospital-side subsystem and/or the manufacturing subsystem, and
  verify the chain of custody and the chain of identity based on the cell order identifier and the patient-specific identifier.

4. A method for manufacturing a cell therapy product for treating cancer in a patient, the method comprising:
  receiving, at a manufacturing facility, a population of cells from a tumor resected from the patient based on a cell order request;
  generating, by a computing device, a container label for a manufacturing container to be used in a multi-step cell expansion process used for manufacturing the cell therapy product from at least a portion of the population of tumor cells, the container label comprising information associated with: (a) the cell order request including a cell order identifier, (b) the patient including a patient-specific identifier, and (c) the manufacturing facility wherein the cell therapy product is to be manufactured, wherein the cell order identifier and the patient-specific identifier define a chain of custody and a chain of identity for the cell therapy product;
  initiating, at the manufacturing facility, the multi-step cell expansion process;
  performing, at the manufacturing facility, a quality control assay to determine acceptance parameters at a plurality of time points during the multi-step cell expansion process;
  receiving, at the computing device, the acceptance parameters at each of the plurality of time points;
  reading, by the computing device, the container label at each subsequent time point;
  providing, by the computing device, a warning signal if:
    information relating to the patient on the container label for a subsequent manufacturing step does not match the information relating to the patient on the container label for an immediately preceding manufacturing step; and
  determining appropriate further processing steps of the multi-step cell expansion process based on information read from the container label for completing the manufacturing of the cell therapy product.

5. The method of claim 4, further comprising:
  after receiving the population of the cells at the manufacturing facility, scheduling, by the computing device, patient treatment events including infusion of the cell therapy product in the patient, the scheduling being dependent on the acceptance parameters for subsequently obtained cell therapy product, and
  determining the acceptance parameters for the cell therapy product at a plurality of time points during the multi-step cell expansion process.

6. The method of claim 4, further comprising determining a preliminary schedule of manufacturing including a set of dates corresponding to the plurality of time points, including a first time point and a second time point subsequent to the first time point, for determining whether the acceptance parameters at a given of the plurality of time points meet acceptance criteria at the given time point depending on the cell expansion technique being used and when the cell order request is received at the manufacturing facility.

7. The method of claim 6, further comprising receiving courier status information via a logistics subsystem,
  in response to receiving the preliminary schedule, determining a shipping schedule for shipping the cell therapy product based on the preliminary schedule of manufacturing; and
  generating a shipping label for a shipping container containing the cell therapy product.

8. The method of claim 7, further comprising transmitting a shipping request to a logistics facility based on the determined shipping schedule.

9. The method of claim 6, wherein determining whether the acceptance parameters meet acceptance criteria comprises determining the acceptance parameters at the plurality of time points following the initiation of the process for manufacturing the cell therapy product, the plurality of time points including the first and second time points.

10. The method of claim 4, further comprising:
  upon determining that the acceptance parameters at a given time point meet acceptance criteria at the given time point, determining a completion date for the manufacturing of the cell therapy;

generating, by the computing device, a schedule for patient treatment events including infusion of the cell therapy product in the patient based on the completion date;

transmitting, to a logistics subsystem, a pick-up order based on the completion date; and transmitting, to a hospital-side subsystem, the schedule for the patient treatment events.

11. The method of claim 10, wherein the schedule for patient treatment events includes one or more of an inpatient stay time period, resection date, lymphodepletion date, infusion date for infusing the patient with the cell therapy product and IL-2 treatment date.

12. The method of claim 10, further comprising: scheduling, by the computing device, a provision of patient support services based on the schedule for patient treatment events, the provision of patient support services including provision of one or more of support for a patient's travel to and from a medical facility, transmission of requisite health insurance information, transmission of requisite financial reimbursement related information, and provision of treatment events-related services.

13. The method of claim 4, wherein the cell order request to perform the multi-step cell expansion process is received from a hospital-side subsystem, and the method further comprises transmitting, upon receiving the cell order request, a confirmation, including one or both of the patient-specific identifier and the cell order identifier, to the hospital-side subsystem that the cell order request associated with the patient has been received.

14. The method of claim 4, further comprising:
upon determining that the acceptance parameters at a given time point of the plurality of time points do not meet acceptance criteria at the given time point, determining an updated completion date for the process for manufacturing of the cell therapy;

rescheduling the patient treatment events based on the updated completion date; and transmitting, upon rescheduling the patient treatment events, to a hospital-side subsystem an updated schedule for the patient treatment events associated with the patient-specific identifier.

15. The method of claim 14, further comprising:
generating, by the computing device, an updated cell order identifier and an updated schedule for shipping and logistics events associated with the patient treatment events based on the rescheduling of the patient treatment events, and transmitting the updated schedule of shipping and logistics events, the updated cell order identifier, and the associated patient-specific identifier to a logistics subsystem based on the rescheduling of shipping and logistics events.

16. The method of claim 14, further comprising: scheduling, by the computing device, a provision of patient support services based on the updated schedule for the patient treatment events, the provision of patient support services including provision of one or more of support for a patient's travel to and from a medical facility, transmission of requisite health insurance information, transmission of requisite financial reimbursement related information, and provision of treatment events-related services.

17. The method of claim 4, further comprising:
associating, by the computing device, with the patient-specific identifier at each of the plurality of time points at which a determination of whether the acceptance parameters meet acceptance criteria is made, an updated cell order identifier including the acceptance parameters for each corresponding time point and a result of the determination.

18. The method of claim 4, wherein the container label comprises a graphical identification code encoding the cell order identifier, the patient-specific identifier, and information associated with the patient, the multi-step cell expansion process and quality of the cell therapy product, the graphical identification code being one of a 1-dimensional barcode and a 2-dimensional barcode.

19. The method of claim 4, further comprising generating a contingent shipping label for a shipping container containing the cell therapy product before performing a final quality control assay, the contingent shipping label being indicative that the cell therapy product is not releasable unless a result of the final quality control assay indicates that the acceptance parameters meet corresponding acceptance criteria.

* * * * *